(12) United States Patent
Fischer et al.

(10) Patent No.: US 8,536,202 B2
(45) Date of Patent: Sep. 17, 2013

(54) TRIAZOLE-SUBSTITUTED ANTHRANILAMIDES AS PESTICIDES

(75) Inventors: Rüdiger Fischer, Pulheim (DE); Christoph Grondal, Köln (DE); Ernst Rudolf Gesing, Erkrath (DE); Heinz-Juergen Wroblowsky, Langefeld (DE); Achim Hense, Leverkusen (DE); Eva-Maria Franken, Leverkusen (DE); Arnd Voerste, Köln (DE); Ulrich Görgens, Ratingen (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/087,105

(22) Filed: Apr. 14, 2011

(65) Prior Publication Data
US 2011/0275676 A1   Nov. 10, 2011

Related U.S. Application Data

(60) Provisional application No. 61/325,500, filed on Apr. 19, 2010.

(30) Foreign Application Priority Data

Apr. 16, 2010 (EP) .................................. 10160117

(51) Int. Cl.
*A61K 31/4439* (2006.01)
*A61K 31/4155* (2006.01)
*C07D 401/14* (2006.01)
*C07D 249/04* (2006.01)

(52) U.S. Cl.
USPC ........ 514/338; 514/341; 514/406; 546/275.4; 548/255

(58) Field of Classification Search
None
See application file for complete search history.

(56) References Cited

U.S. PATENT DOCUMENTS

| | | | |
|---|---|---|---|
| 5,705,476 A | 1/1998 | Hoffarth | |
| 6,602,823 B1 | 8/2003 | Roechling et al. | |
| 8,101,550 B2 * | 1/2012 | Alig et al. | 504/100 |
| 2010/0029478 A1 | 2/2010 | Alig et al. | |
| 2010/0256195 A1 * | 10/2010 | Fischer et al. | 514/341 |

FOREIGN PATENT DOCUMENTS

| | | |
|---|---|---|
| EP | 0 681 865 | 11/1995 |
| WO | 98/35553 | 8/1998 |
| WO | 00/35278 | 6/2000 |
| WO | 01/70671 | 9/2001 |
| WO | 03/015518 | 2/2003 |
| WO | 03/015519 | 2/2003 |
| WO | 03/016282 | 2/2003 |
| WO | 03/016283 | 2/2003 |
| WO | 03/016284 | 2/2003 |
| WO | 03/024222 | 3/2003 |
| WO | 03/027099 | 4/2003 |
| WO | 03/062226 | 7/2003 |
| WO | 2004/027042 | 4/2004 |
| WO | 2004/033468 | 4/2004 |
| WO | 2004/046129 | 6/2004 |
| WO | 2004/067528 | 8/2004 |
| WO | 2005/077934 | 8/2005 |
| WO | 2005/085234 | 9/2005 |
| WO | 2005/118552 | 12/2005 |
| WO | 2006/000336 | 1/2006 |
| WO | 2006/023783 | 3/2006 |
| WO | 2006/040113 | 4/2006 |
| WO | 2006/055922 | 5/2006 |
| WO | 2006/062978 | 6/2006 |
| WO | 2006/111341 | 10/2006 |
| WO | 2007/006670 | 1/2007 |
| WO | 2007/020877 | 2/2007 |
| WO | 2007/024833 | 3/2007 |
| WO | 2007/144100 | 12/2007 |
| WO | 2008/010897 | 1/2008 |
| WO | 2008/070158 | 6/2008 |

OTHER PUBLICATIONS

International Search Report Based on International Application No. PCT/EP2011/055693 Mailed May 19, 2011.
Von Gernot Reissenweber et al.; "Oxidation Von Isatinen Zu Anthranilsaeureestern"; Angew. Chem.; 91; 1981; pp. 914-915.
Lahm et al.; "Insecticidal Anthranilic Diamides: A New Class of Potent Ryanodine Receptor Activors"; Bioorganic & Medicinal Chemistry Letters 15 (2005) pp. 4898-4906.
Smallheer et al.; "Sar and Factor IXa Crystal Structure of a Dual Inhibitor of Factors IXa and Xa"; Bioorganic & Medicinal Chemistry Letters 14 (2004) pp. 5263-5267.
Baker et al.; "An Antimalarial Alkaloid From Hydrangea. XV. Synthesis of 5-. 6-, 7-, and 8- Derivatives With Two Identical Substituents"; J. Org. Chem; 3; 1938; pp. 149-153.
Sheibley; "6,8-Dichlorobenzoylene Urea, and the Interaction of 5,7-Dihalogen Isatoic Anhydrides With Ammonia.—A New Reagent for Sodium"; pp. 414-423.
Montoya-Pelaez et al.; "The Synthesis and Resolution of 2,2'-, 4,4'-, and 6,6'-Substituted Chiral Biphenyl Derivatives for Application in the Preparation of Chiral Materials"; J. Org. Chem. 2006; vol. 71; pp. 5921-5929.
Kornet; "Synthesis and Anticonvulsant Activity of 3-Alkyl-3, 4-Dihydro-2(1H)-Quinazolinones"; 1992; J. Heterocyclic Chem. 29; 103-105.
Baur et al.; "Polydisperse Ethoxylated Fatty Alcohol Surfactants as Accelerators of Cuticular Penetration. 1. Effects of Ethoxy Chain Length and the Size of the Penetrants"; Pestic. Sci. 1997; 51; pp. 131-152.

* cited by examiner

*Primary Examiner* — Alicia L Otton
(74) *Attorney, Agent, or Firm* — Baker Donelson Bearman Caldwell & Berkowitz, PC

(57) ABSTRACT

The present invention constitutes new, triazole-substituted anthranilamides of the general formula (I),

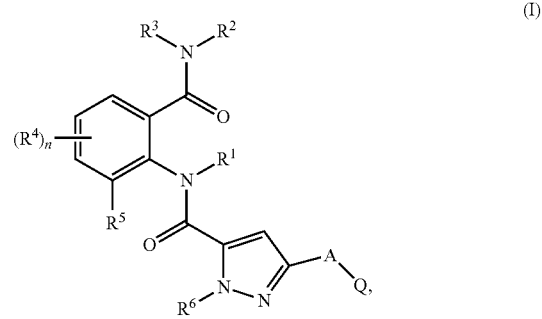

—in which $R^1$, $R^2$, $R^3$, $R^4$, $R^5$, $R^6$, Q, A and n have the definitions indicated in the description—, the application thereof as insecticides and acaricides for controlling animal pests, also in combination with further agents for activity boosting, and a number of processes for their preparation.

12 Claims, No Drawings

TRIAZOLE-SUBSTITUTED ANTHRANILAMIDES AS PESTICIDES

CROSS REFERENCE TO RELATED APPLICATIONS

This application claims priority to EP 10160117.7 filed Apr. 16, 2010 and U.S. Provisional Application No. 61/325,500 filed Apr. 19, 2010, the contents of which are incorporated herein by reference in their entireties.

BACKGROUND OF THE INVENTION

1. Field of the Invention

The present invention relates to triazole-substituted anthranilamides, to a number of processes for their preparation and to their use as active ingredients, also in combination with further agents for activity boosting, more particularly to their use as pesticides.

2. Description of Related Art

Already described in the literature is the possession by certain anthranilamides (e.g. WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO 2007/020877 and WO 07/144100) of insecticidal properties.

SUMMARY OF THE INVENTION

It has now been found that the new, triazole-containing anthranilamides represent advantages over the prior art, by means, for example, of better biological or environmental properties. Further advantages that may be mentioned include, by way of example, broader application methods, a better insecticidal and/or acaricidal activity, and also good tolerance by crop plants. The triazole-containing anthranilamides may be used in combination with other agents for improving activity, particularly against insects that are difficult to control.

The present invention provides anthranilamides of the general formula (I)

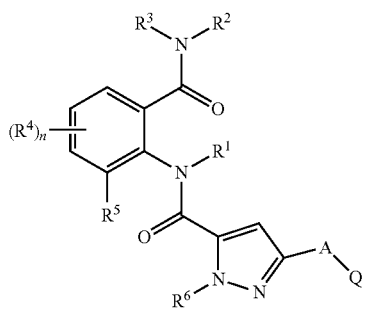

in which
$R^1$ is hydrogen, amino or hydroxyl or is $C_1$-$C_6$-alkyl, $C_2$-$C_6$-alkenyl, $C_2$-$C_6$-alkynyl or $C_3$-$C_6$-cyclo-alkyl each optionally substituted one or more times by identical or different substituents, the substituents being selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)-carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$-alkoxycarbonyl or $C_2$-$C_6$-alkylcarbonyl, $R^3$ is hydrogen or is $C_1$-$C_6$-alkyl, $C_1$-$C_6$-alkoxy, $C_2$-$C_6$-alkenyl or $C_2$-$C_6$-alkynyl each optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ additionally is $C_1$-$C_6$-alkyl, $C_1$-$C_6$-alkoxy, $C_2$-$C_6$-alkenyl, $C_2$-$C_6$-alkynyl each optionally substituted one or more times by identical or different substituents, the substituents being selectable independently of one another from amino, $C_3$-$C_6$-cycloalkylamino or a 5- or 6-membered heteroaromatic ring, $R^3$ likewise additionally is $C_3$-$C_{12}$-cycloalkyl, $C_3$-$C_{12}$-cycloalkyl-$C_1$-$C_6$-alkyl and $C_4$-$C_{13}$-bicycloalkyl, the substituents being selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, $R^2$ and $R^3$ may be joined to one another via two to six carbon atoms and form a ring which optionally further comprises another nitrogen, sulphur or oxygen atom and may optionally be substituted one to four times by $C_1$-$C_2$-alkyl, halogen, cyano, amino or $C_1$-$C_2$-alkoxy, $R^2$, $R^3$ additionally together are =S($C_1$-$C_4$-alkyl)$_2$, =S(O)($C_1$-$C_4$-alkyl)$_2$, $R^4$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, SF$_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two radicals $R^4$ form, via adjacent carbon atoms, a ring which is —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, two radicals $R^4$ additionally, via adjacent carbon atoms, form the fused-on rings below, which are optionally substituted one or more times by identical or different substituents, the substituents being selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

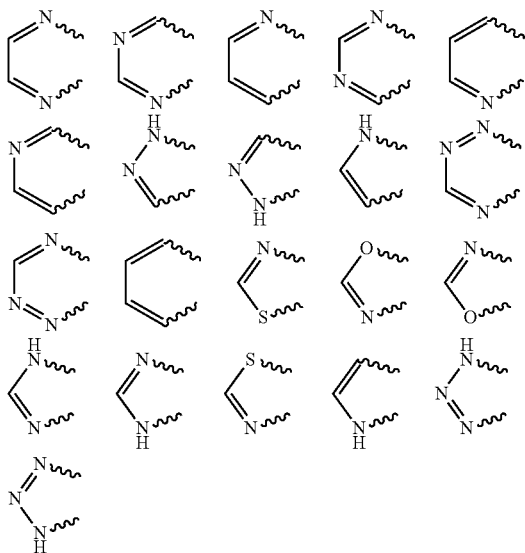

n is 0 to 3, $R^5$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

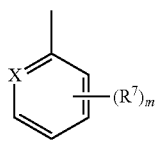

$R^6$ additionally is $C_3$-$C_6$-cycloalkoxy, $R^7$ independently at each occurrence is hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m is 0 to 4, X is N, CH, CF, CCl, CBr or CI, A is —$CH_2$—, —$CH_2O$—, —$CH_2OCH_2$—, —$CH_2S$—, —$CH_2SCH_2$—, —$CH_2N(C_1$-$C_6$-alkyl)-, —$CH_2N(C_1$-$C_6$-alkyl)$CH_2$—, —$CH[CO_2(C_1$-$C_6$-alkyl)]$—, —$CH(CN)$—, —$CH(C_1$-$C_6$-alkyl)-, —$C(di$-$C_1$-$C_6$-alkyl)-, —$CH_2CH_2$—, —$C$=$NO(C_1$-$C_6$-alkyl)-, Q is a 5- or 6-membered heteroaromatic ring or an aromatic 8-, 9- or 10-membered fused-on heterobicyclic ring system, the ring or the ring system comprising three nitrogens, the nitrogens in the ring or ring system occupying adjacent positions; the ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, ($C_1$-$C_4$-alkyl)($C_1$-$C_4$-alkoxy)imino, Q additionally is a 5- or 6-membered heteroaromatic or heterocyclic ring or an aromatic 8-, 9- or 10-membered fused-on heterobicyclic ring system, the ring or the ring system comprising three nitrogens, the nitrogens in the ring occupying adjacent positions; the ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, ($C_1$-$C_4$-alkyl)($C_1$-$C_4$-alkoxy)imino, or where the substituents are selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents;

the compounds of the general formula (I) further comprise N-oxides and salts.

Finally it has been found that the compounds of the formula (I) according to the invention possess very good insecticidal properties and can be used both in crop protection and in materials protection for controlling unwanted pests, such as insects.

DETAILED DESCRIPTION OF A PREFERRED EMBODIMENT

The compounds of the invention may optionally be present as mixtures of different possible isomeric forms, more particularly of stereoisomers, such as, for example, E- and Z-, threo- and erythro-, and also optical isomers, and also, optionally, of tautomers. The E- and the Z-isomers, and also the threo- and erythro-, and also the optical isomers, any desired mixtures of these isomers, and also the possible tautomeric forms are claimed.

A general definition of the anthranilamides of the invention is provided by the formula (I). Preferred definitions of radicals for the formulae given above and below are indicated below. The general elucidations and definitions of radicals, or those set out in preference ranges, may also be combined arbitrarily with one another, in other words combined arbitrarily between the respective ranges and preference ranges. The definitions apply equally to the end products of the formula (I) as to all intermediates.

$R^1$ preferably is hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl, $R^1$ more preferably is hydrogen, methyl, cyclopropyl, cyanomethyl, methoxymethyl, methylthiomethyl, methylsulphinylmethyl or methylsulphonylmethyl, $R^1$ very preferably is hydrogen.

$R^2$ preferably is hydrogen or $C_1$-$C_6$-alkyl, $R^2$ more preferably is hydrogen or methyl, $R^2$ very preferably is hydrogen.

$R^3$ preferably is hydrogen or is $C_1$-$C_6$-alkyl, $C_1$-$C_6$-alkoxy, $C_2$-$C_6$-alkenyl or $C_2$-$C_6$-alkynyl each optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ additionally preferably is $C_3$-$C_{12}$-cycloalkyl and $C_4$-$C_{10}$-bicycloalkyl, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ more preferably is hydrogen or is $C_1$-$C_6$-alkyl or $C_1$-$C_6$-alkoxy each optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ additionally more preferably is $C_3$-$C_6$-cycloalkyl optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ very preferably is methyl, ethyl, n-propyl, isopropyl, n-butyl, isobutyl, sec-butyl, tert-butyl, cyclopropyl, cyclobutyl, cyclopentyl, cyclohexyl, cyclopropylmethyl, cyclopropylethyl, cyclobutylmethyl, cyclobutylethyl, cyclopropylcyclopropyl, ethylcyclopropyl, cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl, $C_1$-$C_4$-alkylthio-($C_1$-$C_4$-alkyl), $C_1$-$C_4$-alkylsulphinyl-($C_1$-$C_4$-alkyl) or $C_1$-$C_4$-alkylsulphonyl-($C_1$-$C_4$-alkyl), $R^4$ preferably is hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

Preferably, moreover, two adjacent radicals $R^4$ are —$(CH_2)_3$—, —$(CH_2)_4$—, —$(CH_2)_5$—, —(CH=CH—)$_2$—, —OCH$_2$O—, —O(CH$_2$)$_2$O—, —OCF$_2$O—, —(CF$_2$)$_2$O—, —O(CF$_2$)$_2$—, —(CH=CH—CH=N)— or —(CH=CH—N=CH)—.

$R^4$ more preferably is hydrogen, $C_1$-$C_4$-alkyl, $C_1$-$C_2$-haloalkyl, halogen, cyano or $C_1$-$C_2$-haloalkoxy.

More preferably, moreover, two adjacent radicals $R^4$ are —$(CH_2)_4$—, —(CH=CH—)$_2$—, —O(CH$_2$)$_2$O—, —O(CF$_2$)$_2$O—, —(CH=CH—CH=N)— or —(CH=CH—N=CH)—.

$R^4$ very preferably is hydrogen, methyl, trifluoromethyl, cyano, fluorine, chlorine, bromine, iodine or trifluoromethoxy. Very preferably, moreover, two adjacent radicals $R^4$ are —$(CH_2)_4$—, or —(CH=CH—)$_2$—.

$R^4$ more particularly preferably is chlorine, bromine or fluorine, $R^4$ additionally more particularly preferably is iodine or cyano. More particularly preferably, moreover, two adjacent radicals $R^4$ are —(CH=CH—)$_2$—, n preferably is 1, 2 or 3, n more preferably is 1 or 2, n very preferably is 2, $R^5$ preferably is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^5$ more preferably is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^5$ very preferably is methyl, fluorine, chlorine, bromine or iodine.

$R^5$ more particularly preferably is methyl or chlorine.

$R^6$ preferably is $C_1$-$C_6$-alkyl or

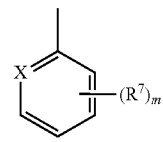

$R^6$ additionally preferably is $C_3$-$C_6$-cycloalkoxy, $R^6$ more preferably is methyl or

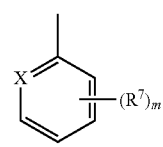

$R^7$ independently at each occurrence preferably is hydrogen, halogen, cyano, $C_1$-$C_4$-alkyl, $C_1$-$C_4$-alkoxy, $C_1$-$C_4$-haloalkyl or $C_1$-$C_4$-haloalkoxy $R^7$ independently at each occurrence more preferably is hydrogen, halogen or $C_1$-$C_4$-haloalkyl, $R^7$ very preferably is fluorine, chlorine or bromine, $R^7$ more particularly preferably is chlorine and bromine m preferably is 1, 2 or 3, m more preferably is 1 or 2, m very preferably is 1, X preferably is N, CH, CF, CCl, CBr or CI, X more preferably is N, CH, CF, CCl or CBr, X very preferably is N, CCl or CH.

A preferably is —$CH_2$—, —$CH_2O$—, —$CH_2OCH_2$—, —$CH_2S$—, —$CH_2SCH_2$—, —$CH_2N(C_1$-$C_6$-alkyl)-, —$CH_2N(C_1$-$C_6$-alkyl)$CH_2$—, —CH(CN)—, —CH($C_1$-$C_6$-alkyl)-, —C(di-$C_1$-$C_6$-alkyl)-, —$CH_2CH_2$—, —C=NO($C_1$-$C_6$-alkyl)-, A more preferably is —$CH_2$—, —CH($CH_3$), C($CH_3$)$_2$ or $CH_2CH_2$, A additionally more preferably is —CH(CN)—, A very preferably is $CH_2$ or CH($CH_3$), A more particularly preferably is $CH_2$.

Q preferably is a 5- or 6-membered heteroaromatic ring or an aromatic 8-, 9- or 10-membered fused-on heterobicyclic ring system, the ring or the ring system comprising three nitrogens and the nitrogens in the ring or ring system occupying adjacent positions, and the bond of the ring or ring system to the radical A in formula (I) being either via nitrogen or carbon. The ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, ($C_1$-$C_4$-alkyl)($C_1$-$C_4$-alkoxy)imino, or where the substituents may be selected independently of one another from phenyl or a 5- or 6-membered heteroaromatic ring, where phenyl or the ring may be optionally substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents, Q additionally preferably is a 5- or 6-membered heteroaromatic or heterocyclic ring or an aromatic 8-, 9- or 10-membered fused-on heterobicyclic ring system, the ring or the ring system comprising three nitrogens and the nitrogens in the ring or ring system occupying adjacent positions, and the bond of the ring or ring system to the radical A in formula (I) being either via nitrogen or carbon. The ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, ($C_1$-$C_4$-alkyl)($C_1$-$C_4$-alkoxy)imino, or where the substituents may be selected independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents, Q more preferably is a 5-membered heteroaromatic ring or an aromatic 9-membered fused-on heterobicyclic ring system, the ring or the ring system comprising three nitrogens and the nitrogens in the ring or ring system occupying adjacent positions, and the bond of the ring or ring system to the radical A in formula (I) being via nitrogen. The ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$) alkylsilyl, ($C_1$-$C_4$-alkyl)($C_1$-$C_4$-alkoxy)imino, or where the substituents may be selected independently of one another from phenyl or a 5- or 6-membered heteroaromatic ring, where phenyl or the ring may be optionally substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents, Q very preferably is a 5-membered heteroaromatic ring or an aromatic 9-membered fused-on heterobicyclic ring system, the ring or the ring system comprising three nitrogens, and the nitrogens in the ring or ring system occupying adjacent positions, and the bond of the ring or ring system to the radical A in formula (I) being via nitrogen. The ring or the ring system are optionally substituted one or more times by identical or different substituents, the substituents being selectable independently of one another from hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, CN, $NO_2$, $C_1$-$C_4$-alkoxy, $C_1$-$C_4$-haloalkoxy, or where the substituents may be selected independently of one another from phenyl which may be optionally substituted one or more times by identical or different $C_1$-$C_4$-alkyl, $C_2$-$C_6$-alkenyl, $C_2$-$C_6$-alkynyl, $C_3$-$C_6$-cycloalkyl, $C_1$-$C_4$-haloalkyl, halogen, CN, $NO_2$, $C_1$-$C_4$-alkoxy, $C_1$-$C_4$-haloalkoxy substituents.

Radicals substituted by halogen, haloalkyl for example, are halogenated singly or multiply up to the maximum possible number of substituents. In the case of multiple halogenations, the halogen atoms may be the same or different. Halogen here is fluorine, chlorine, bromine or iodine, more particularly fluorine, chlorine or bromine.

Preferred, more preferred, very preferred and more particularly preferred are compounds which in each case carry the substituents stated under preferably, more preferably, very preferably and more particularly preferably.

Saturated or unsaturated hydrocarbon radicals such as alkyl or alkenyl may in each case be straight-chain or branched, including in conjunction with heteroatoms, such as in alkoxy, for example, where possible.

Optionally substituted radicals may be substituted one or more times, and in the case of multiple substitutions the substituents may be the same or different.

The compounds of the formulae (I) may be present in the form of different isomers. The present invention therefore also provides the isomers of compounds of the formulae (I), and also mixtures of different isomeric forms.

More particularly, the compounds of the formulae (I) may be present in the form of different regioisomers: for example, in the form of mixtures of compounds where the bond of the ring or ring system Q to the radical (A) is in each case via different carbon atoms or nitrogen atoms.

Preparation of the Compounds of the General Formula (I) According to the Invention Anthranilamides of the formula (I) are obtained by one of the following processes:

Anthranilamides of the formula (I)

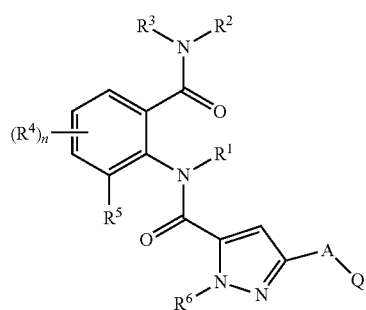

in which A, $R^1$, $R^2$, $R^3$, $R^4$, $R^5$, $R^6$, Q and n have the definitions indicated above are obtained by (A) reacting anilines of the formula (II)

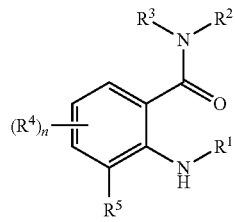

in which A, $R^1$, $R^2$, $R^3$, $R^4$, $R^5$ and n have the definitions indicated above with carbonyl chlorides of the formula (III)

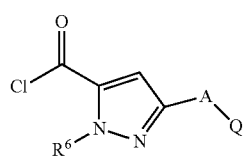

in which $R^6$, A and Q have the definitions indicated above, in the presence of an acid-binding agent, (B) reacting anilines of the formula (II)

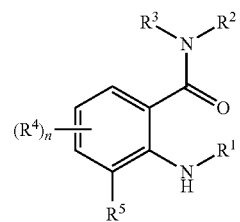

in which A, $R^1$, $R^2$, $R^3$, $R^4$, $R^5$ and n have the definitions indicated above
with a carboxylic acid of the formula (IV)

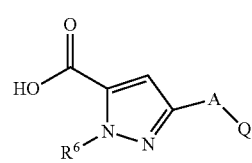

in which $R^6$, A and Q have the definitions indicated above, in the presence of a condensing agent, or by (C) for the synthesis of anthranilamides of the formula (I), in which $R^1$ is hydrogen, reacting benzoxazinones of the formula (V)

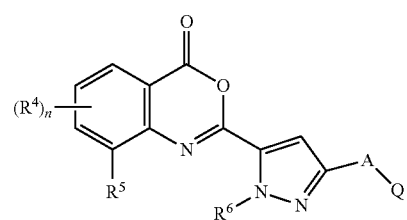

in which $R^4$, $R^5$, $R^6$, A, Q and n have the definitions indicated above
with an amine of the formula (VI)

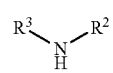

in which $R^2$ and $R^3$ have the definitions indicated above, in the presence of a diluent.

The active compounds according to the invention, in combination with good plant tolerance, favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The effectiveness of the compounds of the formula (I) can be increased by adding ammonium salts and phosphonium salts. The ammonium salts and phosphonium salts are defined by formula (XI)

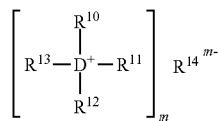

(XI)

in which
D is nitrogen or phosphorus,
D preferably is nitrogen,
$R^{10}$, $R^{11}$, $R^{12}$, and $R^{13}$ independently of one another are hydrogen or each optionally substituted $C_1$-$C_8$-alkyl or singly or unsaturated, optionally substituted $C_1$-$C_8$-alkylene, multiply the substituents being selectable from halogen, nitro and cyano,
$R^{10}$, $R^{11}$, $R^{12}$, and $R^{13}$ independently of one another preferably are hydrogen or each optionally substituted $C_1$-$C_4$-alkyl, the substituents being selectable from the group consisting of halogen, nitro and cyano,
$R^{10}$, $R^{11}$, $R^{12}$, and $R^{13}$ independently of one another particularly preferably are hydrogen, methyl, ethyl, n-propyl, isopropyl, n-butyl, isobutyl, s-butyl or t-butyl,
$R^{10}$, $R^{11}$, $R^{12}$ and $R^{13}$ very particularly preferably are hydrogen,
m is 1, 2, 3 or 4,
m preferably is 1 or 2,
$R^{14}$ is an inorganic or organic anion,
$R^{14}$ preferably is bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate,
$R^{14}$ particularly preferably is lactate, sulphate, monohydrogenphosphate, dihydrogenphosphate, nitrate, thiosulphate, thiocyanate, citrate, oxalate or formate,
$R^{14}$ very particularly preferably is sulphate.

The ammonium salts and phosphonium salts of the formula (XI) can be used in a wide concentration range for increasing the effect of crop protection compositions comprising compounds of the formula (I). In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not just an ammonium salt and/or phosphonium salt, but also a penetrant, that is added to the crop protection compositions to increase the activity. An activity increase can be observed even in these cases. The present invention thus also provides the use of a penetrant, and also the use of a combination of penetrant and ammonium salts and/or phosphonium salts for increasing the activity of crop protection compositions which comprise acaricidally/insecticidally active compounds of the formula (I) as active compound. Finally, the invention also provides the use of these compositions for controlling harmful insects.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, *Pesticide Science* 51, 131-152) can be used for determining this property.

Suitable penetrants are, for example, alkanol alkoxylates. Penetrants according to the invention are alkanol alkoxylates of the formula

(XII)

in which
R is straight-chain or branched alkyl having 4 to 20 carbon atoms,
R' is hydrogen, methyl, ethyl, n-propyl, isopropyl, n-butyl, isobutyl, tert-butyl, n-pentyl or n-hexyl,
AO is an ethylene oxide radical, a propylene oxide radical, or a butylene oxide radical or is mixtures of ethylene oxide and propylene oxide radicals or butylene oxide radicals, and
v stands for numbers from 2 to 30.

A preferred group of penetrants are alkanol alkoxylates of the formula $$R-O-(-EO-)_n-R' \quad \text{(XII-a)}$$

in which
R has the meaning given above,
R' has the meaning given above,
EO represents —CH$_2$—CH$_2$—O— and
n represents a number from 2 to 20.

A further preferred group of penetrants are alkanol alkoxylates of the formula $$R-O-(-EO-)_p-(-PO-)_q-R' \quad \text{(XII-b)}$$

in which
R has the meaning given above,
R' has the meaning given above,
EO represents —CH$_2$—CH$_2$—O—,
PO represents

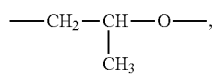

p represents a number from 1 to 10 and
q represents a number from 1 to 10.

A further preferred group of penetrants are alkanol alkoxylates of the formula $$R-O-(-PO-)_r-(EO-)_s-R' \quad \text{(XII-c)}$$

in which
R has the meaning given above,
R' has the meaning given above,
EO represents —CH$_2$—CH$_2$—O—,
PO represents

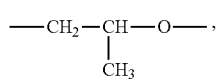

r represents a number from 1 to 10 and
s represents a number from 1 to 10.

A further preferred group of penetrants are alkanol alkoxylates of the formula $$R-O-(-EO-)_p-(-BO-)_q-R' \quad \text{(XII-d)}$$

in which
R and R' have the meanings given above,
EO represents —CH$_2$—CH$_2$—O—,
BO represents

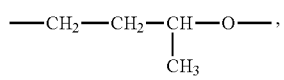

p represents a number from 1 to 10 and
q represents a number from 1 to 10.

A further preferred group of penetrants are alkanol alkoxylates of the formula $$R-O-(-BO-)_r-(-EO-)_s-R' \quad \text{(XII-e)}$$

in which
R and R' have the meanings given above,
BO represents

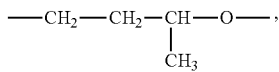

EO represents —CH$_2$—CH$_2$—O—,
r represents a number from 1 to 10 and
s represents a number from 1 to 10.

A further preferred group of penetrants are alkanol alkoxylates of the formula $$CH_3-(CH_2)_t-CH_2-O-(-CH_2-CH_2-O-)_u-R' \quad \text{(XII-f)}$$

in which
R' has the meaning given above,
t represents a number from 8 to 13,
u represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (XII-c), mention may be made of 2-ethylhexyl alkoxylate of the formula

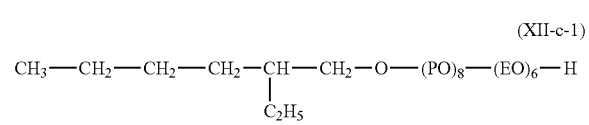

in which
EO represents —CH$_2$—CH$_2$—O—,
PO represents

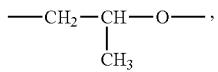

and
the numbers 8 and 6 represent average values.

As an example of an alkanol alkoxylate of the formula (XII-d), mention may be made of the formula $$CH_3-(CH_2)_{10}-O-(-EO-)_6-(-BO-)_2-CH_3 \quad \text{(XII-d-1)}$$

in which
EO represents —CH$_2$—CH$_2$—O—,
BO represents

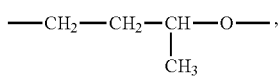

and
the numbers 10, 6 and 2 represent average values.

Particularly preferred alkanol alkoxylates of the formula (XII-f) are compounds of this formula in which
t represents a number from 9 to 12 and
u represents a number from 7 to 9.

With very particular preference, mention may be made of alkanol alkoxylate of the formula (XII-f-1)

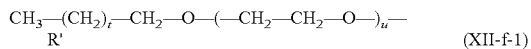
(XII-f-1)

in which
t represents the average value 10.5 and
u represents the average value 8.4.

The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865).

Suitable penetrants also include, for example, substances which promote the solubility of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentration is generally between 0.1 and 10 g/l, preferably between 0.5 and 5 g/l.

Inventively emphasized combinations of active ingredient, salt and penetrant are listed in the table below. Here, "according to test" means that any compound which acts as penetrant in the cuticle penetration test (Baur et al., 1997, *Pesticide Science* 51, 131-152) is suitable.

| Active # | compound | Salt | Penetrant |
|---|---|---|---|
| 1 | I | Ammonium sulphate | According to test |
| 2 | I | Ammonium lactate | According to test |
| 3 | I | Ammonium nitrate | According to test |
| 4 | I | Ammonium thiosulphate | According to test |
| 5 | I | Ammonium thiocyanate | According to test |
| 6 | I | Ammonium citrate | According to test |
| 7 | I | Ammonium oxalate | According to test |
| 8 | I | Ammonium formate | According to test |
| 9 | I | Ammonium hydrogenphosphate | According to test |
| 10 | I | Ammonium dihydrogenphosphate | According to test |
| 11 | I | Ammonium carbonate | According to test |
| 12 | I | Ammonium benzoate | According to test |
| 13 | I | Ammonium sulphite | According to test |
| 14 | I | Ammonium benzoate | According to test |
| 15 | I | Ammonium hydrogenoxalate | According to test |
| 16 | I | Ammonium hydrogencitrate | According to test |
| 17 | I | Ammonium acetate | According to test |
| 18 | I | Tetramethylammonium sulphate | According to test |
| 19 | I | Tetramethylammonium lactate | According to test |
| 20 | I | Tetramethylammonium nitrate | According to test |
| 21 | I | Tetramethylammonium thiosulphate | According to test |
| 22 | I | Tetramethylammonium thiocyanate | According to test |
| 23 | I | Tetramethylammonium citrate | According to test |
| 24 | I | Tetramethylammonium oxalate | According to test |
| 25 | I | Tetramethylammonium formate | According to test |
| 26 | I | Tetramethylammonium hydrogenphosphate | According to test |
| 27 | I | Tetramethylammonium dihydrogenphosphate | According to test |
| 28 | I | Tetraethylammonium sulphate | According to test |
| 29 | I | Tetraethylammonium lactate | According to test |
| 30 | I | Tetraethylammonium nitrate | According to test |
| 31 | I | Tetraethylammonium thiosulphate | According to test |
| 32 | I | Tetraethylammonium thiocyanate | According to test |
| 33 | I | Tetraethylammonium citrate | According to test |
| 34 | I | Tetraethylammonium oxalate | According to test |
| 35 | I | Tetraethylammonium formate | According to test |
| 36 | I | Tetraethylammonium hydrogenphosphate | According to test |
| 37 | I | Tetraethylammonium dihydrogenphosphate | According to test |

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural substances impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable Solid Carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of plant parts or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by varietal property rights. Plant parts are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injecting, and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions used according to the invention, better plant growth, increased tolerance to high or low temperatures, increased tolerance to drought or to water or soil salt content, increased flowering, easier harvesting, accelerated maturation, higher harvest yields, better quality and/or higher nutrient value of the harvested products, better storability and/or processability of the harvested products, which exceed the effects normally to be expected.

The transgenic plants or plant cultivars (those obtained by genetical engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutrient value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugarbeet, tomatoes, peas and other types of vegetable, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are the increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasised are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasised are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, non-energized, or passive, evaporation systems, moth papers, moth bags and moth gels, as granules or dusts, in baits for spreading or in bait stations.

Explanation of the Processes and Intermediates

Process (A)

Using, for example, 2-amino-N-ethyl-5-iodo-3-methylbenzamide and 1-(3-chloropyridin-2-yl)-3-{[4-trifluoromethyl)-1H-1,2,3-triazol-1-yl]methyl}-1H-pyrazole-5-carbonyl chloride as starting materials, the course of the process (A) can be illustrated by the formula scheme below.

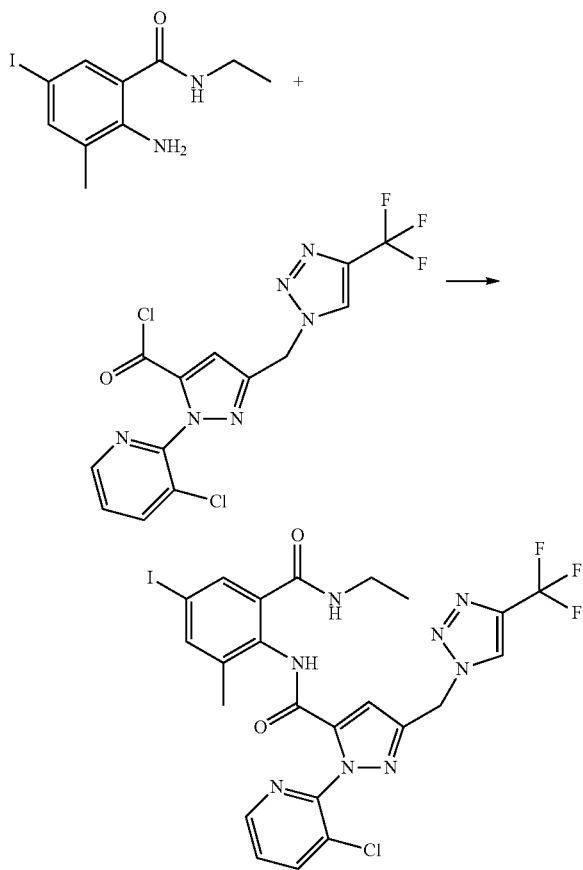

The formula (II) provides a general definition of the aminobenzamides required as starting materials for carrying out the process (A).

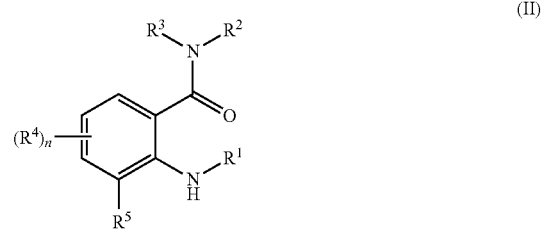

In this formula (II), $R^1$, $R^2$, $R^3$, $R^4$, $R^5$ and n have the definition indicated above.

The process (A) is carried out in the presence of an acid binding agent. Suitable for this purpose are all inorganic or organic bases customary for such coupling reactions. With preference it is possible to use the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU). It is also possible to use optionally polymer-supported acid binding agent, such as, for example, polymer-supported diisopropylamine and polymer-supported dimethylaminopyridine.

The process (A) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water, or pure water.

Aminobenzamides of the formula (II) are known or can be prepared by known methods (cf., for example, M. J. Kornet, *J. Heterocyl. Chem.* 1992, 29, 103-105; G. P. Lahm et al., *Bioorg. Med. Chem. Letters* 2005, 15, 4898-4906; WO 2003/016284, WO 2006/055922, WO 2006/062978, WO 2008/010897, WO 2008/070158).

The formula (III) provides a general definition of the pyrazolecarbonyl chlorides required as starting materials for carrying out the process (A).

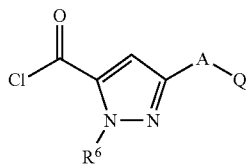

(III)

In this formula (III), Q, A and $R^6$ have the definition indicated above.

Pyrazolecarbonyl chlorides of the formula (III) are novel. They can be prepared, for example, by reacting pyrazolecarboxylic acid derivatives of the formula (IV)

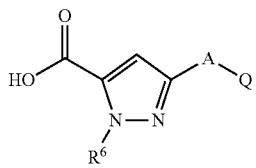

(IV)

in which Q, A and $R^6$ have the definition indicated above with a chlorinating agent (for example thionyl chloride and oxalyl chloride) in the presence of an inert diluent (for example toluene and dichloromethane) in the presence of a catalytic amount of N,N-dimethylformamide Pyrazolecarboxylic acid derivatives of the formula (IV) are novel. They can be prepared, for example, by reacting pyrazolecarboxylic esters of the formula (VII)

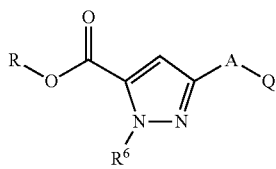

(VII)

in which Q, A and $R^6$ have the definitions indicated above and R represents $C_1$-$C_6$-alkyl, with an alkali metal hydroxide (for example sodium hydroxide or potassium hydroxide) in the presence of an inert diluent (for example dioxane/water or ethanol/water).

Pyrazolecarboxylic esters of the formula (VII) are known or can be obtained by known processes (cf., for example Smallheer, Joanne M.; Alexander, Richard S.; Wang, Jianmin; Wang, Shuaige; Nakajima, Suanne; Rossi, Karen A.; Smallwood, Angela; Barbera, Frank; Burdick, Debra; Luettgen, Joseph M.; Knabb, Robert M.; Wexler, Ruth R.; Jadhav, Prabhakar *Bioorganic & Medicinal Chemistry Letters* 2004, 14(21), 5263-5267).

Process (B)

Using, for example, 2-amino-N-ethyl-5-iodo-3-methylbenzamide and 1-(3-chloropyridin-2-yl)-3-{[4-(trifluoromethyl)-1H-1,2,3-triazol-1-yl]methyl}-1H-pyrazole-5-carboxylic acid as starting materials, the course of the process (B) can be illustrated by the formula scheme below.

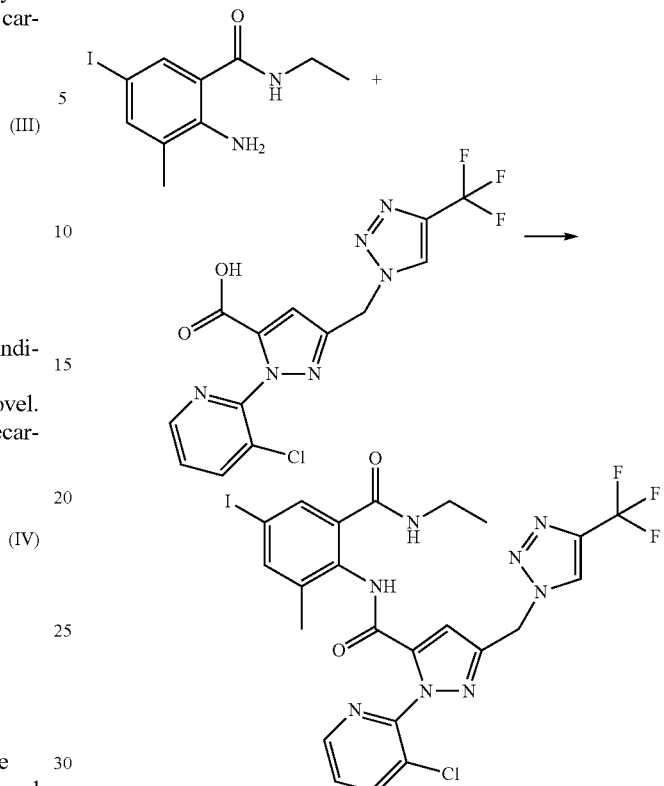

The anthranilamides of the formula (II) required as starting materials for carrying out the process (B) have already been described in connection with process (A).

The formula (IV) provides a general definition of the pyrazolecarboxylic acids furthermore required as starting materials for carrying out the process (B).

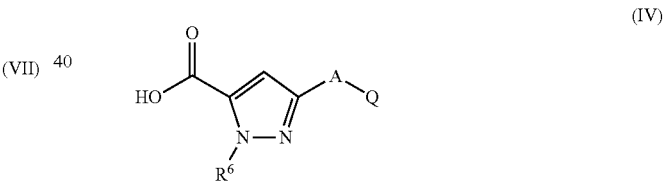

(IV)

In this formula (IV), Q, A and $R^6$ have the definition indicated above.

The process (B) is carried out in the presence of a condensing agent. Suitable for this purpose are all agents customary for such coupling reactions. Acid halide formers such as phosgene, phosphorus-tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris (dimethylamino)phosphonium hexafluorophosphate, may be mentioned by way of example. Polymer-supported reagents, such as, for example, polymer-supported cyclohexylcarbodiimide, may also be employed.

The process (B) is, if appropriate, carried out in the presence of a catalyst. 4-Dimethylaminopyridine, 1-hydroxybenzotriazole or dimethylformamide may be mentioned by way of example.

The process (B) can, if appropriate, be carried out in the presence of an inert organic diluent customary for such reactions. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; or mixtures thereof with water, or pure water.

Process (C)

Using 2-[1-(3-chloropyridin-2-yl)-3-{[4-(trifluoromethyl)-1H-1,2,3-triazol-1-yl]methyl}-1H-pyrazol-5-yl]-6-iodo-8-methyl-4H-3,1-benzoxazin-4-one and ethylamine, the course of the process (C) can be illustrated by the formula scheme below.

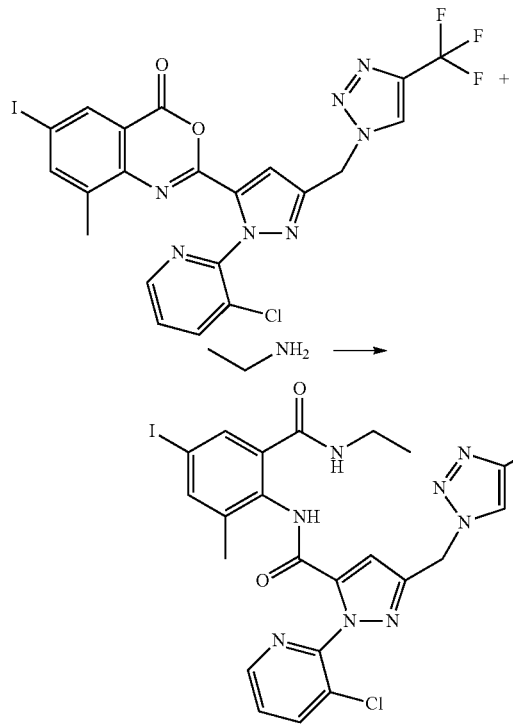

The formula (V) provides a general definition of the benzoxazinones required as starting materials for carrying out the process (C).

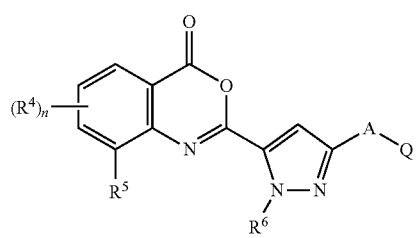

In this formula (V), $R^4$, $R^5$, $R^6$, A, Q and n have the definition indicated above.

Benzoxazinones of the formula (V) are novel. They are obtained, for example, by reacting pyrazolecarboxylic acid derivatives of the formula (IV)

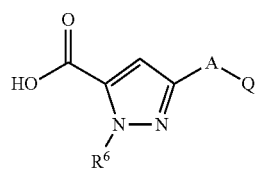

in which Q, A and $R^6$ have the definition indicated above with anthranilic acids of the formula (VIII)

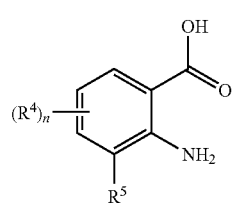

in which $R^4$ and $R^5$ and n have the definitions indicated above, in the presence of a base (for example triethylamine or pyridine) and in the presence of a sulphonyl chloride (for example methanesulphonyl chloride) and, if appropriate, in the presence of a diluent (for example acetonitrile).

The pyrazolecarboxylic acid derivatives of the formula (IV) required as starting materials for carrying out the process have already been described above in connection with process (A).

Anthranilic acids of the formula (VIII) are known or can be prepared by general synthesis methods (cf., for example, Baker et al. *J. Org. Chem.* 1952, 149-153; G. Reissenweber et al., *Angew. Chem* 1981, 93, 914-915, P. J. Montoya-Pelaez, *J. Org. Chem.* 2006, 71, 5921-5929; F. E. Sheibley, *J. Org. Chem.* 1938, 3, 414-423, WO 2006023783).

PREPARATION EXAMPLES

Compounds

Synthesis of 1-(3-chloropyridin-2-yl)-N-[2-(ethylcarbamoyl)-4-iodo-6-methylphenyl]-3-{[4-(trifluoromethyl)-1H-1,2,3-triazol-1-yl]methyl}-1H-pyrazole-5-carboxamide Example 1

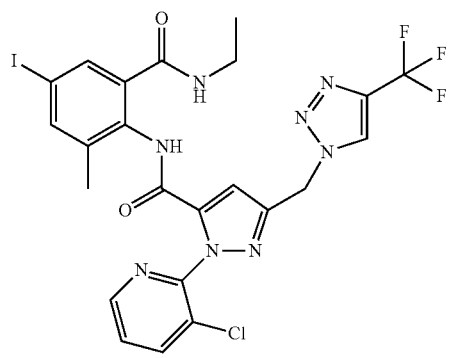 [SMILES: CCNC(=O)c1cc(I)cc(C)c1NC(=O)c1cc(Cn2cc(C(F)(F)F)nn2)nn1-c1ncccc1Cl]

An amount of 140 mg (0.228 mmol) of 2-[1-(3-chloropyridin-2-yl)-3-{[4-(trifluoromethyl)-1H-1,2,3-triazol-1-yl]methyl}-1H-pyrazol-5-yl]-6-iodo-8-methyl-4H-3,1-benzoxazin-4-one was introduced in 20 ml of tetrahydrofuran. Following introduction of 103 mg (2.281 mmol) of ethylamine, the resulting solution was stirred at room temperature for 12 hours, after which the solvent and the excess amine were distilled off at 40° C. under reduced pressure and the oily, pale yellow residue was recrystallized from petroleum ether. This gave 150 mg (99% of theory; purity 100%) of the desired product.

log P: 3.04; MH+: 659; $^1$H-NMR (400 MHz, DMSO-$d_6$, δ, ppm): 1.00 (t, 3H), 2.10 (s, 3H), 3.14 (m, 2H), 5.86 (s, 2H), 7.19 (s, 1H), 7.55 (dd, 1H), 7.59 (s, 1H), 7.69 (d, 1H), 7.98 (t, 1H), 8.09 (dd, 1H), 8.44 (dd, 1H), 8.93 (s, 1H), 10.06 (s, 1H).

The examples below can be obtained analogously. The compounds of the formula (I) may in some cases be present as different regioisomers. In the table below, in reference to the NMR data, the chemical shifts and the associated signal intensities are reported in each case; for example, for Compound 1:

Signal 1
10.081, 2.12; stands for 10.081 ppm (chemical shift), 2.12 (signal intensity);

Signal 2
8.795, 8.04; stands for 8.795 ppm (chemical shift), 8.04 (signal intensity).

| No. | Structure | logP | MH+ | NMR |
|---|---|---|---|---|
| 1 | 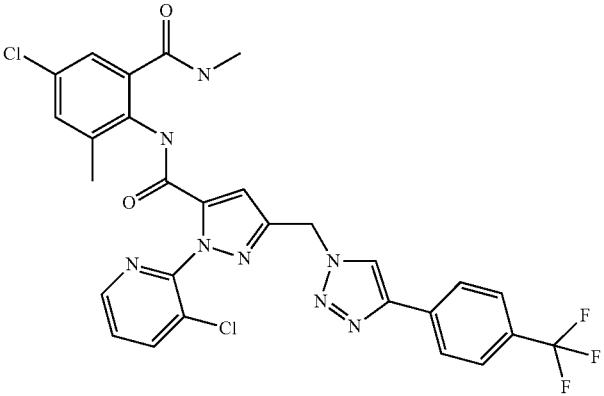 [SMILES: CNC(=O)c1cc(Cl)cc(C)c1NC(=O)c1cc(Cn2cc(-c3ccc(C(F)(F)F)cc3)nn2)nn1-c1ncccc1Cl] | 3.33 | 629 | 10.081, 2.12; 8.795, 8.04; 8.459, 2.93; 8.455, 3.12; 8.447, 3.23; 8.443, 3.13; 8.105, 5.93; 8.101, 5.64; 8.085, 6.31; 8.081, 6.43; 7.998, 0.89; 7.986, 0.88; 7.799, 4.11; 7.778, 3.57; 7.568, 3.52; 7.557, 3.29; 7.548, 3.18; 7.536, 3.17; 7.397, 2.42; 7.392, 2.74; 7.318, 2.88; 7.312, 2.55; 7.199, 3.39; 5.823, 10.94; 4.047, 0.41; 4.029, 0.41; 3.116, 382.94; 2.660, 10.66; 2.648, 10.54; 2.526, 2.90; 2.510, 1.47; 2.506, 2.07; 2.497, 29.05; 2.493, 59.87; 2.488, 84.36; 2.483, 58.88; 2.479, 28.02; 2.320, 0.35; 2.315, 0.51; 2.310, 0.38; 2.131, 16.00; 2.040, 0.82; 1.974, 1.95; 1.195, 0.55; 1.177, 1.15; 1.159, 0.59; 0.000, 5.68 |
| 2 | 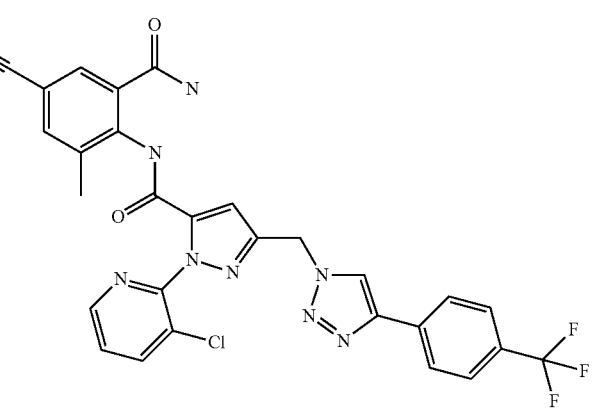 | 2.81 | 606 | 10.475, 2.54; 8.799, 8.72; 8.790, 0.96; 8.472, 2.92; 8.469, 3.13; 8.461, 3.17; 8.457, 3.09; 8.115, 3.23; 8.111, 3.98; 8.107, 3.45; 8.105, 3.80; 8.094, 3.80; 8.091, 4.53; 8.085, 4.25; 7.800, 9.14; 7.797, 6.50; 7.795, 5.64; 7.780, 3.86; 7.652, 0.47; 7.641, 0.46; 7.632, 0.42; 7.620, 0.40; 7.576, 3.43; 7.564, 3.28; 7.556, 3.17; 7.544, 3.18; 7.537, 0.83; 7.219, 7.89; 5.853, 1.12; 5.829, 11.54; 3.122, 126.62; 2.527, 0.91; 2.511, 0.50; 2.506, 0.73; 2.498, 9.68; 2.494, 19.80; 2.489, 27.73; 2.484, 19.34; 2.480, 9.21; 2.171, 16.00; 2.041, 0.55; 1.712, 1.38; 0.000, 1.85 |

| No. | Structure | logP | MH+ | NMR |
|---|---|---|---|---|
| 3 | 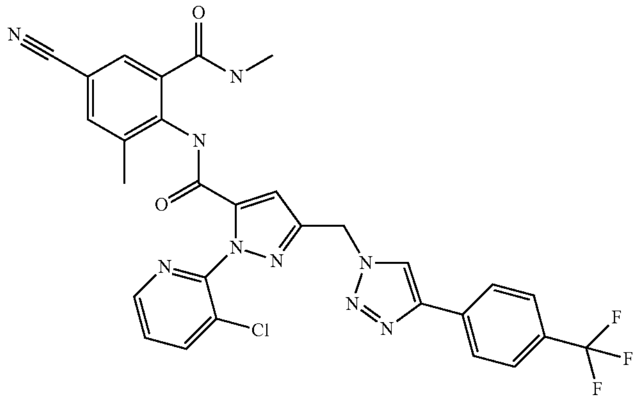 [SMILES: CNC(=O)c1cc(C#N)cc(C)c1NC(=O)c1cc(Cn2cc(-c3ccc(C(F)(F)F)cc3)nn2)nn1-c1ncccc1Cl] | 2.99 | 620 | 10.375, 2.88; 8.809, 0.73; 8.800, 8.79; 8.463, 3.02; 8.459, 3.23; 8.451, 3.24; 8.447, 3.25; 8.149, 0.97; 8.133, 1.07; 8.129, 0.85; 8.120, 0.50; 8.111, 3.42; 8.107, 4.62; 8.105, 3.58; 8.103, 3.90; 8.091, 4.00; 8.087, 4.98; 8.083, 4.34; 7.799, 4.55; 7.789, 2.97; 7.784, 3.66; 7.779, 4.20; 7.720, 3.08; 7.717, 2.82; 7.574, 3.40; 7.562, 3.31; 7.554, 3.18; 7.542, 3.12; 7.297, 0.60; 7.229, 6.02; 5.872, 0.89; 5.832, 11.47; 4.065, 0.32; 4.047, 0.95; 4.029, 0.98; 4.011, 0.33; 3.693, 1.87; 3.123, 621.12; 2.674, 10.89; 2.663, 11.15; 2.653, 0.71; 2.648, 0.36; 2.527, 3.11; 2.511, 1.65; 2.506, 2.34; 2.498, 31.82; 2.493, 65.45; 2.489, 92.15; 2.484, 64.30; 2.479, 30.62; 2.320, 0.41; 2.316, 0.52; 2.311, 0.36; 2.181, 16.00; 2.076, 0.52; 2.041, 2.02; 2.037, 0.40; 1.974, 4.44; 1.946, 1.08; 1.195, 1.34; 1.177, 2.62; 1.160, 1.28; 0.000, 3.84 |
| 4 | 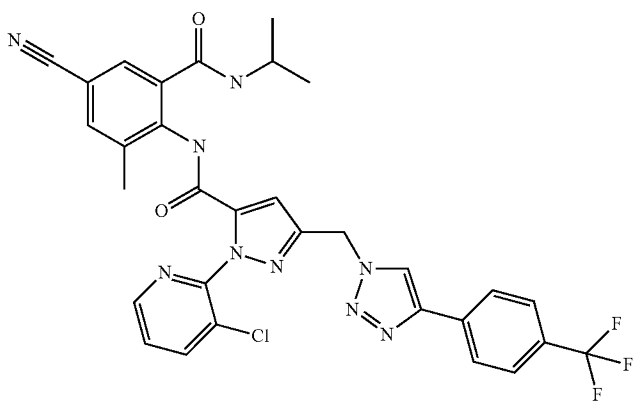 [SMILES: Cc1cc(C#N)cc(C(=O)NC(C)C)c1NC(=O)c1cc(Cn2cc(-c3ccc(C(F)(F)F)cc3)nn2)nn1-c1ncccc1Cl] | 3.39 | 648 | 10.307, 2.23; 8.790, 6.10; 8.451, 1.98; 8.448, 2.04; 8.440, 2.08; 8.436, 2.09; 8.101, 4.55; 8.097, 3.71; 8.081, 5.15; 8.077, 3.90; 7.975, 0.41; 7.944, 0.87; 7.926, 0.91; 7.800, 3.24; 7.780, 4.77; 7.694, 2.33; 7.690, 2.20; 7.570, 2.31; 7.558, 2.21; 7.550, 2.10; 7.538, 2.01; 7.221, 5.09; 5.831, 8.55; 3.920, 0.63; 3.903, 0.94; 3.885, 0.91; 3.868, 0.64; 3.115, 455.39; 3.056, 0.36; 2.667, 0.32; 2.662, 0.58; 2.657, 0.99; 2.652, 0.71; 2.545, 0.32; 2.526, 4.34; 2.510, 2.84; 2.505, 4.11; 2.497, 48.95; 2.493, 99.44; 2.488, 139.04; 2.483, 98.11; 2.479, 47.63; 2.319, 0.63; 2.315, 0.85; 2.310, 0.63; 2.286, 0.65; 2.185, 11.57; 2.137, 0.63; 2.040, 1.21; 2.037, 0.46; 1.363, 0.33; 1.245, 0.38; 1.110, 0.80; 1.092, 0.96; 1.076, 0.93; 1.029, 16.00; 1.013, 15.84; 0.008, 0.35; 0.000, 10.47; −0.008, 0.36 |
| 5 | 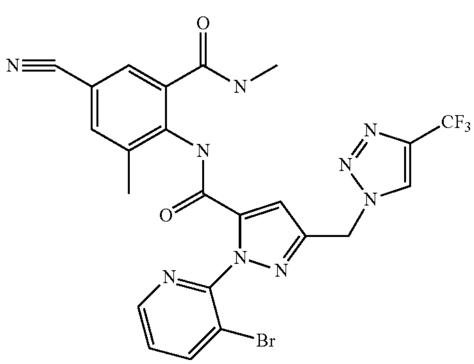 [SMILES: CNC(=O)c1cc(C#N)cc(C)c1NC(=O)c1cc(Cn2cc(C(F)(F)F)nn2)nn1-c1ncccc1Br] | 2.66 | 588 | 10.457, 4.01; 8.527, 4.52; 8.504, 2.68; 8.500, 2.85; 8.492, 2.87; 8.489, 2.77; 8.322, 0.64; 8.312, 1.61; 8.300, 1.62; 8.288, 0.66; 8.277, 2.77; 8.273, 2.73; 8.257, 2.97; 8.253, 2.69; 7.847, 3.21; 7.844, 3.34; 7.732, 3.65; 7.728, 3.40; 7.506, 2.72; 7.494, 2.69; 7.485, 2.61; 7.474, 2.56; 7.270, 5.04; 5.951, 10.45; 3.317, 750.60; 3.225, 0.32; 2.674, 0.76; 2.669, 1.15; 2.659, 9.92; 2.648, 9.68; 2.540, 2.74; 2.523, 2.68; 2.510, 34.26; 2.505, 62.69; 2.501, 80.56; 2.496, 55.46; 2.492, 26.90; 2.332, 0.45; 2.327, 0.58; 2.323, 0.43; 2.196, 15.00; 2.069, 0.35; 2.049, 0.50; 0.000, 3.20 |

| No. | Structure | logP | MH+ | NMR |
|---|---|---|---|---|
| 6 | 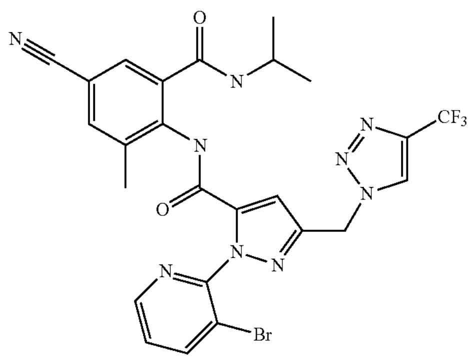 [SMILES: Cc1cc(C#N)cc(C(=O)NC(C)C)c1NC(=O)c1cc(Cn2cc(C(F)(F)F)nn2)nn1-c1ncccc1Br] | 3.11 | 616 | 10.389, 2.94; 8.525, 3.39; 8.488, 2.00; 8.485, 2.41; 8.477, 2.17; 8.473, 2.04; 8.395, 0.30; 8.387, 0.33; 8.264, 1.93; 8.260, 1.91; 8.244, 2.13; 8.240, 1.96; 8.109, 1.43; 8.090, 1.44; 7.839, 2.45; 7.836, 2.53; 7.696, 2.73; 7.692, 2.53; 7.665, 0.31; 7.500, 1.93; 7.488, 1.93; 7.480, 1.87; 7.468, 1.81; 7.422, 0.32; 7.413, 0.46; 7.402, 0.42; 7.265, 3.90; 6.629, 0.47; 5.950, 7.82; 5.778, 1.04; 3.911, 0.60; 3.894, 0.92; 3.875, 0.91; 3.859, 0.60; 3.307, 367.31; 2.674, 0.54; 2.669, 0.70; 2.664, 0.54; 2.660, 0.34; 2.539, 1.58; 2.509, 41.79; 2.504, 75.01; 2.500, 95.27; 2.496, 66.19; 2.331, 0.57; 2.327, 0.73; 2.322, 0.54; 2.207, 10.99; 2.069, 0.89; 1.464, 1.00; 1.235, 0.93; 1.205, 0.42; 1.191, 1.47; 1.175, 1.48; 1.015, 15.00; 0.998, 14.87; 0.066, 0.35; 0.008, 0.32; 0.000, 6.17 |
| 7 | 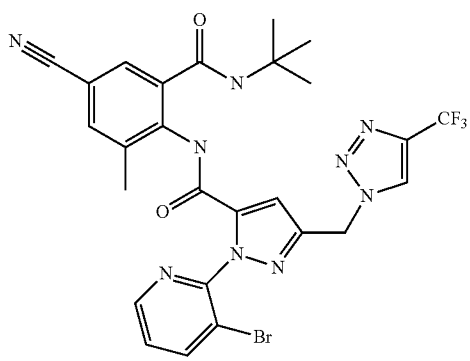 [SMILES: Cc1cc(C#N)cc(C(=O)NC(C)(C)C)c1NC(=O)c1cc(Cn2cc(C(F)(F)F)nn2)nn1-c1ncccc1Br] | 3.44 | 630 | 10.332, 0.89; 8.521, 1.06; 8.520, 1.04; 8.495, 0.63; 8.491, 0.68; 8.483, 0.68; 8.479, 0.66; 8.275, 0.64; 8.271, 0.63; 8.255, 0.70; 8.251, 0.63; 7.811, 0.75; 7.808, 0.78; 7.675, 1.29; 7.670, 0.90; 7.505, 0.65; 7.494, 0.64; 7.485, 0.62; 7.474, 0.60; 7.216, 1.20; 5.951, 2.39; 3.312, 138.73; 2.539, 0.66; 2.523, 0.62; 2.509, 8.16; 2.505, 15.06; 2.500, 19.49; 2.496, 13.37; 2.491, 6.45; 2.196, 3.41; 1.393, 0.51; 1.205, 15.00; 0.000, 0.80 |
| 8 | 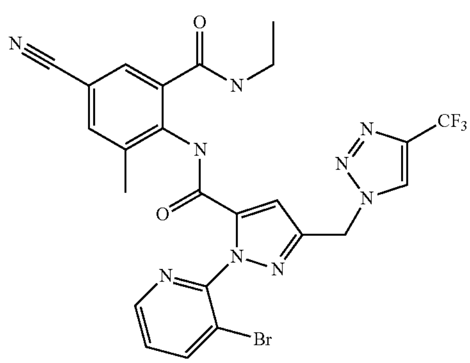 [SMILES: CCNC(=O)c1cc(C#N)cc(C)c1NC(=O)c1cc(Cn2cc(C(F)(F)F)nn2)nn1-c1ncccc1Br] | 2.88 | 602 | 10.426, 4.05; 8.524, 4.56; 8.523, 4.53; 8.496, 2.72; 8.493, 2.93; 8.485, 2.96; 8.481, 2.90; 8.304, 1.05; 8.290, 2.06; 8.271, 3.13; 8.268, 2.93; 8.251, 3.07; 8.248, 2.82; 7.844, 3.24; 7.841, 3.39; 7.722, 3.63; 7.718, 3.41; 7.503, 2.79; 7.491, 2.73; 7.483, 2.67; 7.471, 2.63; 7.263, 5.27; 5.949, 10.55; 3.321, 959.94; 3.166, 0.94; 3.148, 2.77; 3.134, 2.99; 3.130, 2.96; 3.116, 2.73; 3.098, 0.89; 2.674, 0.45; 2.670, 0.61; 2.665, 0.44; 2.540, 2.85; 2.523, 2.76; 2.510, 34.15; 2.505, 62.37; 2.501, 80.16; 2.497, 54.81; 2.492, 26.25; 2.332, 0.43; 2.328, 0.58; 2.323, 0.42; 2.202, 15.00; 2.069, 0.56; 2.049, 0.50; 0.998, 5.88; 0.980, 12.56; 0.962, 5.65; 0.000, 2.08 |
| 9 | 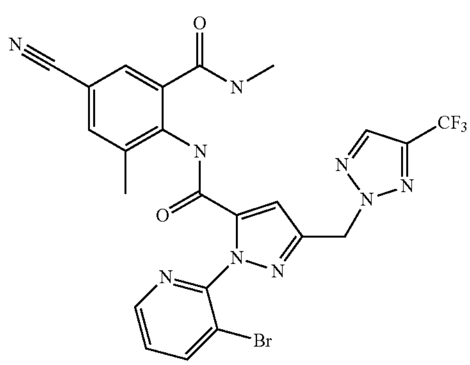 [SMILES: CNC(=O)c1cc(C#N)cc(C)c1NC(=O)c1cc(Cn2ncc(C(F)(F)F)n2)nn1-c1ncccc1Br] | 2.33 | 588 | 10.477, 4.28; 9.071, 7.72; 9.069, 7.61; 8.505, 4.67; 8.502, 5.23; 8.494, 5.19; 8.490, 5.17; 8.345, 1.65; 8.334, 1.66; 8.282, 3.10; 8.279, 3.16; 8.262, 3.35; 8.259, 3.24; 7.853, 3.52; 7.740, 4.03; 7.507, 2.97; 7.495, 2.96; 7.487, 2.94; 7.475, 2.78; 7.273, 4.12; 5.890, 13.39; 3.430, 1.16; 3.380, 0.48; 3.330, 966.97; 3.306, 6.77; 3.287, 0.74; 3.280, 0.76; 3.279, 0.78; 2.675, 1.26; 2.670, 2.02; 2.661, 13.43; 2.649, 13.20; 2.524, 3.97; 2.519, 5.54; 2.511, 57.76; 2.506, 127.82; 2.501, 179.99; 2.497, 131.86; 2.492, 61.89; 2.338, 0.44; 2.333, 0.88; 2.328, 1.21; 2.324, 0.92; 2.319, 0.44; 2.189, 16.00; 2.073, 3.39; 1.909, 0.71; 1.236, 0.53; 0.008, 0.52; −0.000, 16.37; 0.008, 0.56 |

-continued

| No. | Structure | logP | MH+ | NMR |
|---|---|---|---|---|
| 10 | 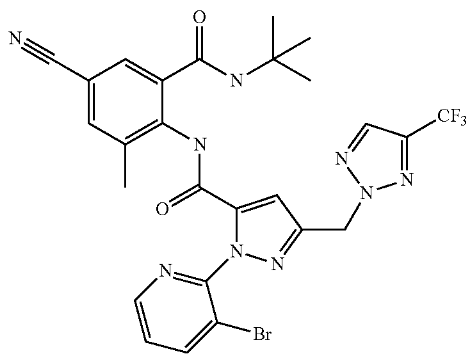 [SMILES: Cc1cc(C#N)cc(C(=O)NC(C)(C)C)c1NC(=O)c1cc(Cn2ncc(C(F)(F)F)n2)nn1-c1ncccc1Br] | 3.04 | 630 | 10.337, 0.85; 9.026, 1.10; 8.495, 0.66; 8.491, 0.72; 8.483, 0.70; 8.479, 0.69; 8.276, 0.54; 8.272, 0.55; 8.256, 0.60; 8.252, 0.56; 7.808, 0.76; 7.699, 0.86; 7.677, 0.80; 7.673, 0.75; 7.506, 0.56; 7.494, 0.55; 7.486, 0.55; 7.474, 0.53; 7.218, 1.08; 5.891, 2.35; 3.410, 0.33; 3.320, 489.18; 2.670, 0.32; 2.540, 1.25; 2.523, 1.44; 2.510, 18.55; 2.505, 34.09; 2.501, 44.03; 2.497, 30.25; 2.492, 14.64; 2.328, 0.31; 2.191, 3.15; 2.069, 0.66; 1.418, 0.35; 1.211, 15.00; 0.000, 1.66 |
| 11 | 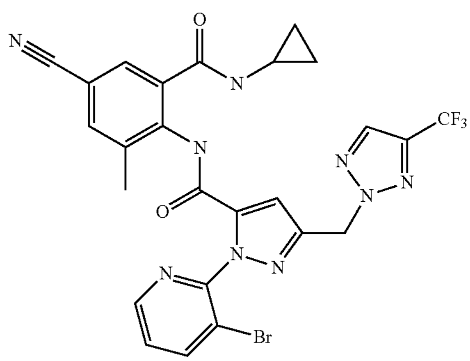 [SMILES: Cc1cc(C#N)cc(C(=O)NC2CC2)c1NC(=O)c1cc(Cn2ncc(C(F)(F)F)n2)nn1-c1ncccc1Br] | 2.55 | 614 | 10.413, 4.90; 9.055, 5.79; 8.505, 3.12; 8.502, 3.40; 8.494, 3.40; 8.490, 3.33; 8.350, 2.36; 8.340, 2.36; 8.276, 2.70; 8.272, 2.71; 8.255, 2.91; 8.252, 2.76; 7.835, 3.74; 7.693, 3.89; 7.506, 2.56; 7.495, 2.58; 7.486, 2.57; 7.475, 2.38; 7.273, 5.13; 5.895, 11.73; 3.310, 951.38; 3.247, 0.65; 3.216, 0.31; 2.707, 0.39; 2.697, 0.86; 2.687, 1.28; 2.679, 2.07; 2.674, 1.66; 2.669, 2.60; 2.660, 1.56; 2.651, 0.92; 2.641, 0.43; 2.539, 3.56; 2.522, 4.41; 2.509, 53.57; 2.505, 97.57; 2.500, 125.22; 2.496, 86.09; 2.491, 41.26; 2.332, 0.69; 2.327, 0.90; 2.322, 0.65; 2.194, 15.00; 2.069, 5.26; 2.049, 0.56; 0.619, 1.20; 0.607, 3.45; 0.601, 4.46; 0.589, 4.24; 0.584, 3.54; 0.572, 1.43; 0.444, 1.39; 0.433, 3.92; 0.427, 4.02; 0.418, 3.37; 0.406, 1.08; 0.008, 0.53; 0.000, 10.80; −0.008, 0.45 |
| 12 | 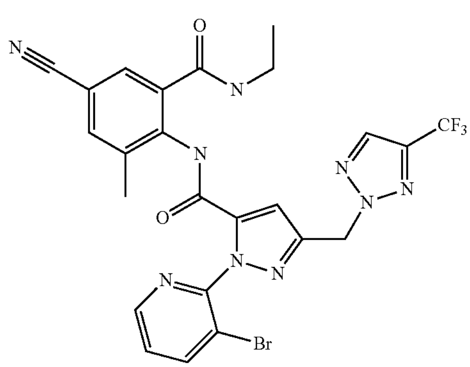 [SMILES: CCNC(=O)c1cc(C#N)cc(C)c1NC(=O)c1cc(Cn2ncc(C(F)(F)F)n2)nn1-c1ncccc1Br] | 2.53 | 602 | 10.438, 4.73; 9.047, 6.41; 8.496, 3.72; 8.492, 3.91; 8.484, 3.91; 8.480, 3.78; 8.305, 1.98; 8.292, 1.24; 8.272, 2.96; 8.269, 2.88; 8.252, 3.06; 8.248, 2.80; 7.843, 3.52; 7.728, 3.80; 7.502, 2.59; 7.490, 2.66; 7.482, 2.59; 7.470, 2.38; 7.262, 4.23; 5.887, 11.80; 3.429, 0.40; 3.306, 840.63; 3.172, 1.24; 3.154, 3.75; 3.140, 4.23; 3.136, 4.20; 3.122, 3.74; 3.104, 1.19; 2.674, 0.80; 2.669, 1.02; 2.664, 0.75; 2.539, 3.89; 2.522, 4.98; 2.509, 59.05; 2.504, 107.29; 2.500, 137.33; 2.496, 94.59; 2.491, 45.43; 2.331, 0.73; 2.327, 0.95; 2.322, 0.69; 2.195, 14.42; 2.069, 1.34; 2.049, 0.61; 1.237, 0.35; 1.031, 0.35; 1.004, 7.23; 0.986, 15.00; 0.968, 7.02; 0.008, 0.73; 0.000, 15.38; −0.008, 0.70 |

-continued

| No. | Structure | logP | MH+ | NMR |
|---|---|---|---|---|
| 13 | 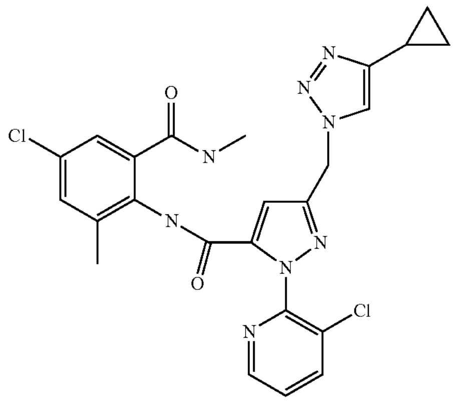 [SMILES: CNC(=O)c1cc(Cl)cc(C)c1NC(=O)c1cc(Cn2cc(C3CC3)nn2)nn1-c1ncccc1Cl] | 2.14 | 525/527 | 10.069, 2.33; 8.457, 2.63; 8.453, 2.77; 8.446, 2.78; 8.442, 2.61; 8.103, 2.08; 8.099, 2.09; 8.092, 1.10; 8.083, 2.37; 8.079, 2.31; 7.989, 1.16; 7.977, 1.37; 7.973, 0.88; 7.968, 0.91; 7.852, 5.27; 7.566, 2.14; 7.554, 2.37; 7.549, 1.92; 7.546, 2.60; 7.534, 2.01; 7.530, 1.01; 7.395, 3.44; 7.387, 2.21; 7.320, 2.94; 7.315, 3.33; 7.117, 3.38; 7.088, 0.97; 5.741, 3.57; 5.636, 10.05; 3.602, 1.52; 3.184, 1.07; 3.112, 552.58; 2.700, 1.46; 2.688, 1.72; 2.673, 8.50; 2.662, 9.94; 2.654, 4.24; 2.526, 1.93; 2.497, 66.54; 2.492, 124.14; 2.488, 165.13; 2.483, 119.27; 2.478, 60.66; 2.319, 0.80; 2.315, 1.02; 2.291, 0.66; 2.221, 2.08; 2.194, 0.80; 2.133, 16.00; 2.117, 2.46; 1.976, 0.85; 1.969, 0.88; 1.955, 1.53; 1.947, 0.86; 1.942, 1.13; 1.934, 0.96; 1.770, 0.82; 1.762, 1.57; 0.995, 0.96; 0.990, 1.00; 0.974, 0.96; 0.970, 0.92; 0.918, 0.89; 0.907, 2.51; 0.901, 2.91; 0.892, 1.60; 0.886, 2.64; 0.880, 2.68; 0.871, 1.24; 0.750, 1.20; 0.741, 2.97; 0.735, 3.05; 0.729, 3.04; 0.723, 2.73; 0.712, 0.94; 0.685, 1.11; 0.679, 1.08; 0.673, 1.05; 0.668, 1.04; −0.000, 3.04 |
| 14 | 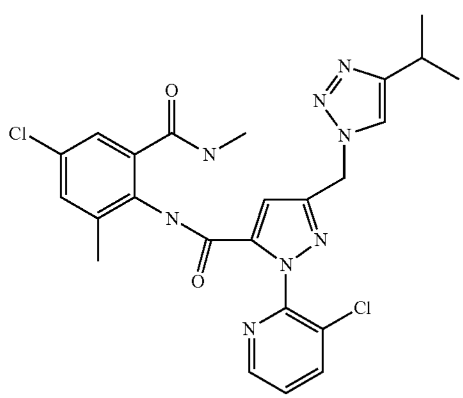 [SMILES: CNC(=O)c1cc(Cl)cc(C)c1NC(=O)c1cc(Cn2cc(C(C)C)nn2)nn1-c1ncccc1Cl] | 2.29 | 527/529 | 8.459, 1.50; 8.455, 1.70; 8.447, 1.55; 8.443, 1.59; 8.106, 1.38; 8.102, 1.36; 8.095, 0.57; 8.091, 0.57; 8.086, 1.56; 8.082, 1.51; 8.075, 0.46; 8.071, 0.47; 8.012, 0.38; 8.001, 0.57; 7.991, 0.56; 7.975, 0.66; 7.865, 2.88; 7.857, 0.44; 7.568, 1.63; 7.563, 1.23; 7.556, 1.59; 7.548, 1.61; 7.543, 0.76; 7.536, 1.51; 7.531, 0.49; 7.400, 1.43; 7.396, 1.88; 7.321, 1.71; 7.316, 1.54; 7.141, 1.93; 7.085, 0.46; 7.077, 0.36; 5.675, 1.68; 5.660, 6.39; 5.647, 0.76; 5.514, 0.50; 3.125, 325.05; 3.038, 0.84; 3.020, 1.05; 3.002, 1.16; 2.986, 0.94; 2.968, 0.46; 2.700, 0.49; 2.689, 0.55; 2.671, 5.38; 2.659, 6.64; 2.648, 1.74; 2.527, 0.86; 2.511, 2.30; 2.498, 37.10; 2.493, 72.76; 2.489, 99.82; 2.484, 70.87; 2.480, 34.91; 2.453, 0.41; 2.382, 9.36; 2.320, 0.43; 2.316, 0.58; 2.311, 0.45; 2.298, 3.74; 2.221, 0.67; 2.135, 8.94; 2.125, 2.56; 2.117, 0.85; 2.050, 0.78; 1.999, 0.58; 1.363, 0.34; 1.258, 16.00; 1.252, 2.65; 1.240, 15.95; 1.235, 3.38; 1.225, 0.63; 1.218, 1.69; 1.207, 3.57; 1.190, 3.48; 1.168, 0.52; 1.151, 0.52; −0.000, 0.66 |

| No. | Structure | logP | MH+ | NMR |
|---|---|---|---|---|
| 15 | 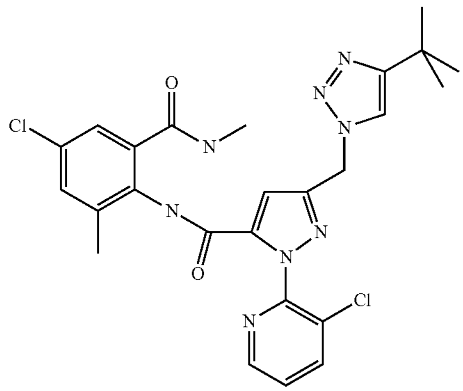 [SMILES: CNC(=O)c1cc(Cl)cc(C)c1NC(=O)c1cc(Cn2cc(C(C)(C)C)nn2)nn1-c1ncccc1Cl] | 2.53 | 541/543 | 8.484, 0.56; 8.480, 0.61; 8.472, 0.63; 8.469, 0.61; 8.133, 0.54; 8.129, 0.52; 8.113, 0.62; 8.109, 0.56; 7.893, 1.55; 7.594, 0.54; 7.582, 0.58; 7.574, 0.57; 7.562, 0.54; 7.425, 0.69; 7.420, 0.76; 7.347, 0.76; 7.341, 0.68; 7.173, 0.86; 5.679, 2.61; 3.627, 0.45; 3.152, 59.12; 2.694, 2.17; 2.683, 2.34; 2.522, 9.50; 2.518, 17.18; 2.513, 22.39; 2.509, 16.51; 2.504, 8.71; 2.405, 3.21; 2.326, 1.52; 2.162, 3.77; 2.148, 0.36; 1.786, 0.50; 1.383, 0.89; 1.342, 0.35; 1.321, 16.00; 1.300, 2.03 |
| 16 | 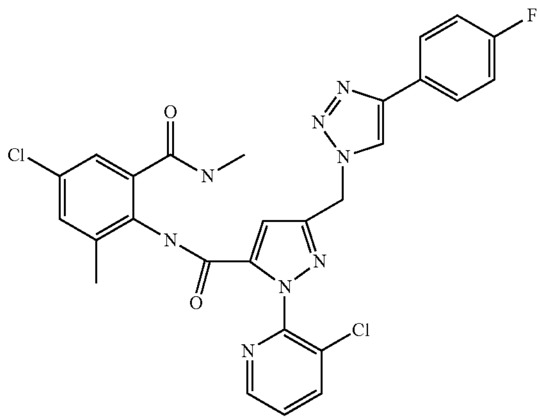 [SMILES: CNC(=O)c1cc(Cl)cc(C)c1NC(=O)c1cc(Cn2cc(-c3ccc(F)cc3)nn2)nn1-c1ncccc1Cl] | 2.84 | 579.581 | 10.077, 2.27; 8.605, 7.43; 8.458, 2.46; 8.454, 2.49; 8.446, 2.62; 8.442, 2.54; 8.104, 2.45; 8.101, 2.53; 8.084, 2.74; 8.080, 2.74; 8.055, 0.33; 7.992, 1.10; 7.980, 1.12; 7.974, 0.97; 7.919, 3.01; 7.913, 1.47; 7.905, 3.39; 7.896, 3.41; 7.888, 1.46; 7.883, 3.12; 7.632, 0.33; 7.567, 2.64; 7.555, 2.67; 7.547, 2.92; 7.535, 2.41; 7.529, 0.39; 7.451, 0.41; 7.396, 2.89; 7.391, 3.17; 7.316, 3.29; 7.310, 2.97; 7.302, 0.71; 7.277, 3.33; 7.254, 6.06; 7.237, 1.15; 7.232, 2.93; 7.182, 3.78; 5.785, 11.12; 5.732, 0.83; 3.402, 0.47; 3.385, 0.54; 3.367, 0.34; 3.279, 0.33; 3.264, 0.39; 3.228, 0.45; 3.208, 0.57; 3.198, 0.69; 3.113, 534.97; 3.031, 0.35; 2.700, 1.25; 2.688, 1.24; 2.671, 1.43; 2.660, 10.75; 2.648, 9.97; 2.622, 0.38; 2.611, 0.40; 2.550, 0.67; 2.526, 1.81; 2.497, 68.04; 2.492, 131.02; 2.488, 177.29; 2.483, 126.02; 2.478, 62.42; 2.433, 0.33; 2.388, 0.92; 2.319, 0.84; 2.315, 1.07; 2.310, 0.81; 2.305, 0.50; 2.291, 2.00; 2.221, 1.81; 2.129, 16.00; 2.117, 2.40; 2.040, 0.44; 1.363, 0.62; 1.247, 0.41; 1.109, 0.42; 1.091, 0.72; 1.074, 0.39; −0.000, 6.05 |
| 17 | 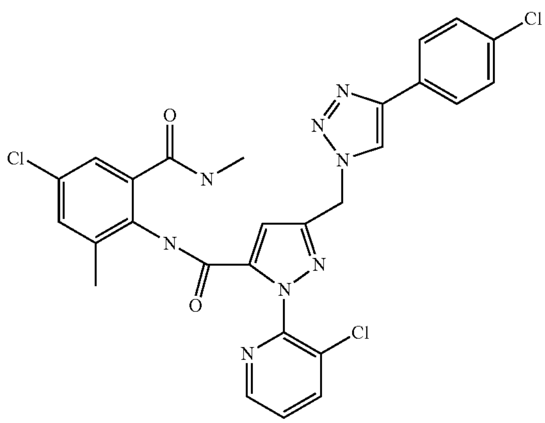 [SMILES: CNC(=O)c1cc(Cl)cc(C)c1NC(=O)c1cc(Cn2cc(-c3ccc(Cl)cc3)nn2)nn1-c1ncccc1Cl] | 3.57 | 595/597 | 8.659, 7.74; 8.555, 0.79; 8.457, 2.59; 8.453, 2.84; 8.445, 2.85; 8.441, 2.83; 8.436, 0.49; 8.103, 2.63; 8.099, 2.79; 8.083, 2.98; 8.079, 3.14; 8.006, 0.88; 7.994, 0.91; 7.981, 0.66; 7.977, 0.61; 7.974, 0.82; 7.941, 0.71; 7.903, 0.77; 7.897, 6.11; 7.892, 2.41; 7.880, 2.32; 7.875, 7.23; 7.869, 1.19; 7.861, 0.45; 7.855, 0.83; 7.606, 0.44; 7.584, 0.76; 7.566, 3.03; 7.554, 2.97; 7.546, 3.04; 7.538, 1.16; 7.534, 3.07; 7.528, 0.51; 7.516, 0.79; 7.506, 0.98; 7.499, 6.72; 7.494, 2.33; 7.483, 2.24; 7.478, 6.66; 7.471, 1.03; 7.456, 0.94; 7.395, 2.53; 7.394, 2.57; 7.389, 3.04; 7.317, 3.14; 7.312, 2.83; 7.185, 3.68; 5.791, 10.58; 5.755, 1.06; 5.604, 1.15; 3.402, 0.45; 3.384, 0.58; 3.113, 183.57; 2.671, 1.33; 2.659, 9.78; 2.648, 9.00; 2.633, 0.45; 2.619, 0.60; 2.526, 0.95; 2.510, 2.35; 2.497, 40.93; 2.492, 81.58; 2.488, 112.67; 2.483, 78.86; 2.478, 37.92; 2.367, 7.22; 2.319, 0.50; 2.315, 0.76; 2.310, 0.51; 2.294, 2.71; 2.173, 0.44; 2.128, 16.00; 1.761, 0.46; 1.364, 0.62; 1.109, 0.45; 1.091, 0.88; 1.074, 0.46; 0.008, 0.56; −0.000, 13.42; −0.008, 0.44 |

| No. | Structure | logP | MH+ | NMR |
|---|---|---|---|---|
| 18 | 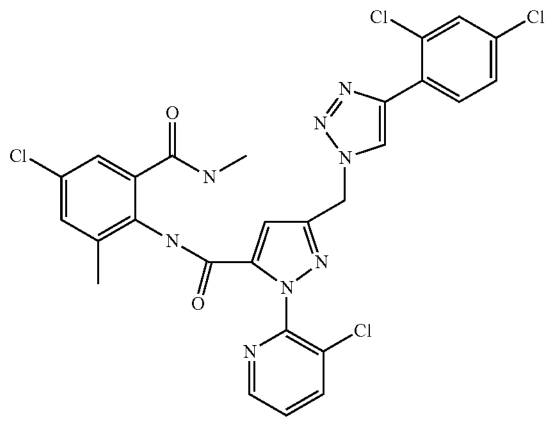 [SMILES: CNC(=O)c1cc(Cl)cc(C)c1NC(=O)c1cc(Cn2cc(-c3ccc(Cl)cc3Cl)nn2)nn1-c1ncccc1Cl] | 3.2 | 631 | 8.749, 7.43; 8.459, 2.54; 8.455, 2.71; 8.447, 2.91; 8.443, 2.81; 8.417, 0.43; 8.132, 4.37; 8.110, 4.91; 8.107, 3.14; 8.103, 3.00; 8.087, 3.11; 8.083, 2.94; 8.063, 0.43; 7.996, 0.97; 7.984, 1.06; 7.973, 0.50; 7.896, 0.63; 7.694, 3.62; 7.689, 3.73; 7.569, 2.98; 7.557, 2.94; 7.549, 3.57; 7.545, 3.80; 7.539, 3.71; 7.537, 3.46; 7.528, 0.63; 7.523, 2.93; 7.518, 2.76; 7.485, 0.50; 7.481, 0.90; 7.448, 0.65; 7.398, 2.68; 7.393, 3.14; 7.380, 0.77; 7.374, 0.61; 7.320, 3.10; 7.313, 2.82; 7.206, 3.20; 7.170, 0.61; 6.080, 0.64; 5.848, 10.53; 5.611, 0.94; 4.387, 0.48; 3.402, 0.48; 3.385, 0.52; 3.221, 0.51; 3.192, 0.75; 3.113, 911.31; 3.090, 9.58; 3.052, 0.57; 2.932, 0.43; 2.700, 2.57; 2.688, 2.54; 2.682, 1.30; 2.664, 10.06; 2.653, 10.55; 2.526, 2.17; 2.510, 4.63; 2.497, 82.88; 2.493, 165.95; 2.488, 230.13; 2.483, 161.87; 2.478, 78.28; 2.444, 0.37; 2.384, 3.08; 2.324, 0.48; 2.319, 1.02; 2.315, 1.41; 2.310, 0.95; 2.291, 1.55; 2.221, 3.56; 2.132, 16.00; 2.124, 2.65; 2.117, 3.78; 2.040, 0.52; 1.248, 0.47; 1.108, 0.47; 1.091, 0.92; 1.074, 0.46; −0.000, 12.20 |
| 19 | 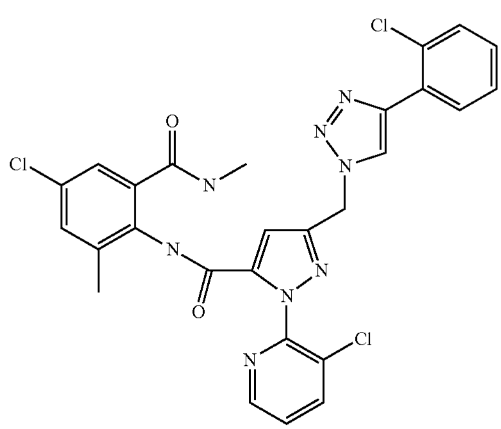 [SMILES: CNC(=O)c1cc(Cl)cc(C)c1NC(=O)c1cc(Cn2cc(-c3ccccc3Cl)nn2)nn1-c1ncccc1Cl] | 2.74 | 595/597 | 8.705, 6.50; 8.460, 2.28; 8.457, 2.50; 8.449, 2.56; 8.445, 2.51; 8.111, 2.54; 8.108, 2.93; 8.104, 2.93; 8.091, 2.42; 8.087, 4.54; 8.084, 2.94; 7.997, 0.88; 7.986, 0.90; 7.879, 0.70; 7.569, 2.84; 7.564, 2.05; 7.560, 2.51; 7.558, 3.33; 7.549, 3.06; 7.544, 2.82; 7.541, 3.00; 7.538, 3.32; 7.525, 0.69; 7.518, 0.76; 7.512, 0.70; 7.505, 0.75; 7.498, 0.58; 7.492, 0.62; 7.472, 1.47; 7.469, 1.55; 7.454, 2.69; 7.451, 2.56; 7.435, 2.28; 7.431, 1.84; 7.421, 0.58; 7.403, 2.23; 7.399, 4.19; 7.393, 3.06; 7.384, 2.16; 7.379, 2.18; 7.365, 1.06; 7.361, 0.90; 7.319, 2.87; 7.313, 2.58; 7.213, 3.10; 5.846, 10.03; 5.569, 1.05; 3.402, 0.68; 3.385, 0.77; 3.216, 0.61; 3.204, 0.75; 3.116, 242.93; 2.700, 0.97; 2.688, 1.05; 2.681, 1.24; 2.666, 9.04; 2.654, 9.02; 2.527, 1.11; 2.510, 2.80; 2.497, 46.15; 2.493, 91.85; 2.488, 126.72; 2.484, 89.04; 2.479, 43.11; 2.404, 0.74; 2.383, 16.00; 2.320, 0.57; 2.315, 0.75; 2.310, 0.54; 2.297, 6.12; 2.221, 1.34; 2.186, 0.67; 2.134, 14.33; 2.123, 2.18; 2.117, 2.08; 2.040, 0.95; 1.109, 0.67; 1.091, 1.29; 1.074, 0.65; −0.000, 5.97 |

-continued

| No. | Structure | logP | MH+ | NMR |
|---|---|---|---|---|
| 20 | 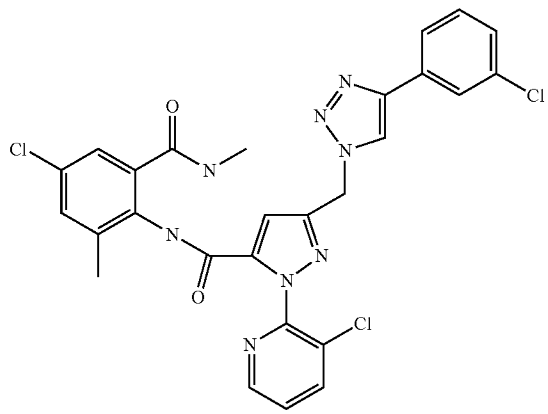 [SMILES: CNC(=O)c1cc(Cl)cc(C)c1NC(=O)c1cc(Cn2cc(-c3cccc(Cl)c3)nn2)nn1-c1ncccc1Cl] | 3.11 | 595/597 | 10.093, 0.41; 10.082, 0.60; 8.727, 7.81; 8.458, 2.61; 8.455, 2.83; 8.447, 2.78; 8.443, 2.73; 8.105, 2.59; 8.101, 2.75; 8.085, 3.00; 8.081, 3.05; 7.994, 0.97; 7.981, 1.24; 7.972, 0.56; 7.920, 2.09; 7.915, 3.38; 7.911, 2.34; 7.850, 1.56; 7.847, 2.03; 7.844, 1.50; 7.831, 1.78; 7.827, 2.25; 7.824, 1.70; 7.568, 3.03; 7.556, 3.11; 7.548, 3.04; 7.536, 3.05; 7.529, 0.41; 7.514, 0.54; 7.490, 1.76; 7.471, 3.96; 7.451, 2.60; 7.396, 2.74; 7.390, 4.50; 7.385, 2.26; 7.382, 2.28; 7.370, 1.49; 7.367, 1.44; 7.365, 1.36; 7.362, 1.25; 7.318, 3.02; 7.312, 2.80; 7.187, 3.48; 5.796, 10.82; 5.765, 0.74; 3.402, 0.42; 3.250, 0.42; 3.238, 0.48; 3.214, 0.56; 3.196, 0.80; 3.113, 911.79; 2.700, 0.78; 2.688, 0.77; 2.662, 10.84; 2.657, 3.93; 2.651, 10.14; 2.624, 0.46; 2.551, 0.63; 2.526, 2.08; 2.510, 5.34; 2.497, 91.86; 2.493, 183.58; 2.488, 254.22; 2.483, 178.01; 2.478, 85.73; 2.387, 4.21; 2.325, 0.56; 2.319, 1.06; 2.315, 1.58; 2.310, 1.10; 2.306, 0.52; 2.291, 1.79; 2.220, 0.94; 2.131, 16.00; 2.117, 1.31; 2.040, 0.61; 1.363, 0.52; 1.249, 0.49; 1.092, 0.79; −0.000, 12.11 |
| 21 | 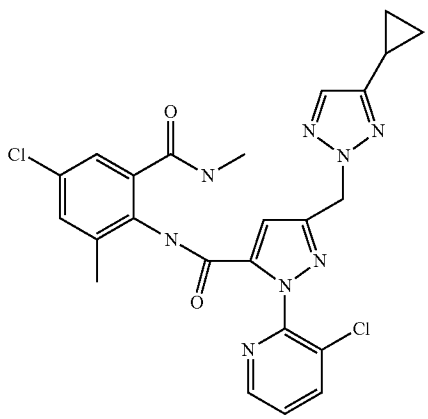 [SMILES: CNC(=O)c1cc(Cl)cc(C)c1NC(=O)c1cc(Cn2ncc(C3CC3)n2)nn1-c1ncccc1Cl] | 2.85 | 525/527 | 10.063, 0.33; 10.054, 0.36; 8.454, 2.58; 8.450, 2.74; 8.442, 2.78; 8.438, 2.73; 8.097, 2.59; 8.093, 2.68; 8.077, 2.89; 8.073, 2.74; 7.983, 0.90; 7.974, 1.11; 7.972, 0.82; 7.560, 2.93; 7.549, 3.08; 7.540, 9.31; 7.529, 2.77; 7.485, 0.45; 7.397, 2.44; 7.393, 2.76; 7.315, 2.83; 7.310, 2.53; 7.074, 2.78; 5.615, 12.05; 5.494, 0.42; 3.419, 0.42; 3.402, 1.07; 3.385, 1.10; 3.367, 0.40; 3.112, 174.23; 2.700, 0.71; 2.688, 0.75; 2.673, 9.77; 2.661, 10.07; 2.526, 0.99; 2.510, 1.76; 2.497, 30.38; 2.492, 60.42; 2.487, 83.76; 2.483, 59.00; 2.478, 28.67; 2.381, 1.02; 2.319, 0.39; 2.314, 0.52; 2.309, 0.36; 2.221, 0.95; 2.135, 16.00; 2.117, 1.05; 2.040, 0.62; 2.007, 0.45; 1.994, 0.88; 1.985, 0.97; 1.982, 0.63; 1.973, 1.91; 1.964, 0.64; 1.960, 1.00; 1.952, 1.02; 1.939, 0.51; 1.109, 1.13; 1.091, 2.18; 1.074, 1.06; 0.964, 1.23; 0.953, 3.22; 0.947, 3.56; 0.943, 1.65; 0.938, 1.88; 0.932, 3.63; 0.926, 3.39; 0.917, 1.66; 0.758, 1.56; 0.748, 3.51; 0.746, 2.38; 0.743, 3.53; 0.736, 3.40; 0.730, 3.41; 0.719, 1.19; 0.008, 0.40; −0.000, 10.13; −0.008, 0.38 |
| 22 | 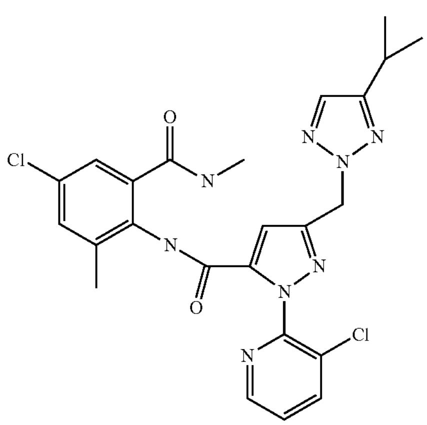 [SMILES: CNC(=O)c1cc(Cl)cc(C)c1NC(=O)c1cc(Cn2ncc(C(C)C)n2)nn1-c1ncccc1Cl] | 2.85 | 527/529 | 8.455, 1.42; 8.451, 1.49; 8.443, 1.44; 8.439, 1.42; 8.099, 1.40; 8.095, 1.42; 8.079, 1.51; 8.075, 1.44; 7.992, 0.57; 7.974, 0.55; 7.620, 3.14; 7.562, 1.62; 7.558, 0.68; 7.550, 1.70; 7.542, 1.46; 7.530, 1.36; 7.397, 1.35; 7.392, 1.53; 7.317, 1.60; 7.311, 1.38; 7.088, 1.47; 5.649, 6.45; 5.639, 0.55; 5.505, 0.58; 3.112, 66.06; 3.055, 0.75; 3.046, 0.43; 3.037, 1.02; 3.020, 1.22; 3.003, 0.93; 2.985, 0.43; 2.700, 0.75; 2.688, 0.76; 2.667, 5.08; 2.655, 5.20; 2.526, 0.63; 2.510, 1.62; 2.497, 25.50; 2.492, 50.07; 2.488, 68.70; 2.483, 48.38; 2.478, 23.57; 2.377, 5.36; 2.315, 0.42; 2.296, 3.40; 2.221, 1.07; 2.134, 8.74; 2.117, 1.13; 2.040, 0.56; 1.270, 16.00; 1.263, 1.84; 1.253, 15.96; 1.246, 1.80; 1.233, 1.78; −0.000, 5.79 |

-continued
| No. | Structure | logP | MH+ | NMR |
|---|---|---|---|---|
| 23 | 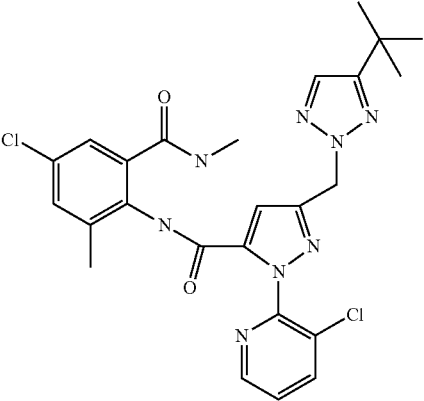 [SMILES: CNC(=O)c1cc(Cl)cc(C)c1NC(=O)c1cc(Cn2ncc(C(C)(C)C)n2)nn1-c1ncccc1Cl] | 3.2 | 541/543 | 8.456, 0.51; 8.452, 0.55; 8.444, 0.52; 8.440, 0.52; 8.101, 0.49; 8.097, 0.49; 8.080, 0.54; 8.077, 0.51; 7.645, 1.40; 7.563, 0.51; 7.551, 0.53; 7.543, 0.50; 7.531, 0.47; 7.398, 0.58; 7.393, 0.65; 7.318, 0.68; 7.312, 0.61; 7.078, 0.62; 5.650, 2.51; 3.116, 42.37; 2.666, 2.05; 2.655, 2.07; 2.497, 6.00; 2.492, 11.34; 2.488, 15.18; 2.483, 11.02; 2.479, 5.65; 2.379, 0.74; 2.134, 3.54; 1.310, 16.00; 1.289, 0.85; −0.000, 0.70 |
| 24 | 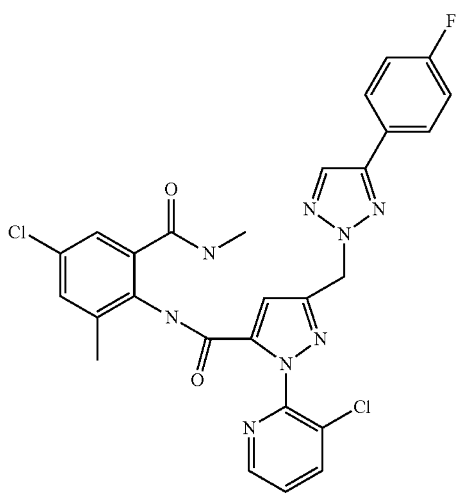 [SMILES: CNC(=O)c1cc(Cl)cc(C)c1NC(=O)c1cc(Cn2ncc(-c3ccc(F)cc3)n2)nn1-c1ncccc1Cl] | 3.23 | 579/581 | 10.057, 1.12; 8.455, 2.76; 8.451, 2.99; 8.444, 2.89; 8.440, 2.91; 8.265, 8.61; 8.211, 1.11; 8.100, 2.64; 8.096, 2.68; 8.080, 2.91; 8.076, 2.94; 7.983, 0.69; 7.974, 2.43; 7.965, 0.99; 7.922, 3.31; 7.917, 1.37; 7.908, 3.43; 7.900, 3.58; 7.892, 1.82; 7.886, 3.66; 7.879, 1.12; 7.871, 0.73; 7.857, 0.58; 7.563, 3.02; 7.551, 3.11; 7.543, 3.07; 7.531, 3.00; 7.392, 2.47; 7.386, 2.87; 7.308, 3.10; 7.303, 3.01; 7.298, 3.88; 7.293, 1.42; 7.275, 6.43; 7.270, 1.56; 7.262, 1.49; 7.253, 3.27; 7.239, 0.70; 7.158, 2.83; 5.789, 11.32; 5.691, 0.87; 3.273, 0.56; 3.265, 0.59; 3.243, 0.69; 3.227, 0.71; 3.111, 974.08; 3.049, 1.18; 2.887, 0.57; 2.734, 0.62; 2.699, 0.89; 2.688, 0.78; 2.666, 1.37; 2.661, 2.30; 2.657, 3.11; 2.649, 10.55; 2.637, 10.09; 2.581, 0.61; 2.526, 4.90; 2.510, 7.98; 2.497, 138.73; 2.492, 277.82; 2.488, 385.12; 2.483, 271.52; 2.478, 132.18; 2.385, 1.37; 2.324, 0.88; 2.319, 1.75; 2.315, 2.27; 2.310, 1.56; 2.305, 0.88; 2.290, 0.54; 2.220, 0.83; 2.129, 16.00; 2.040, 0.86; 1.363, 1.43; 1.296, 0.77; 1.250, 0.64; 0.008, 1.60; −0.000, 38.37; −0.009, 1.33 |
| 25 | 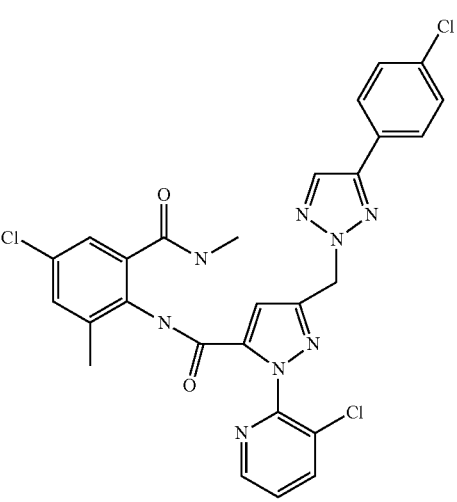 [SMILES: CNC(=O)c1cc(Cl)cc(C)c1NC(=O)c1cc(Cn2ncc(-c3ccc(Cl)cc3)n2)nn1-c1ncccc1Cl] | 3.62 | 597 | 8.454, 2.50; 8.450, 2.74; 8.442, 2.73; 8.438, 2.68; 8.307, 8.76; 8.288, 0.60; 8.233, 0.46; 8.097, 2.42; 8.093, 2.54; 8.077, 2.84; 8.073, 2.76; 8.051, 0.37; 8.025, 0.62; 7.901, 0.90; 7.895, 6.13; 7.890, 2.16; 7.878, 2.45; 7.873, 7.07; 7.867, 1.39; 7.860, 0.72; 7.845, 0.48; 7.561, 2.88; 7.549, 2.87; 7.541, 2.81; 7.529, 3.32; 7.522, 7.06; 7.516, 2.81; 7.505, 2.35; 7.500, 6.37; 7.480, 0.48; 7.457, 0.39; 7.384, 2.30; 7.379, 2.69; 7.314, 3.00; 7.308, 2.67; 7.151, 2.66; 7.104, 0.34; 5.797, 11.26; 5.758, 0.62; 5.615, 0.76; 3.301, 0.38; 3.227, 0.54; 3.212, 0.68; 3.113, 493.71; 2.700, 0.46; 2.688, 0.49; 2.666, 0.78; 2.662, 1.31; 2.657, 1.97; 2.649, 8.71; 2.638, 8.40; 2.623, 1.36; 2.597, 0.34; 2.589, 0.40; 2.579, 0.41; 2.526, 2.50; 2.510, 4.43; 2.497, 70.29; 2.493, 138.61; 2.488, 190.71; 2.483, 133.68; 2.478, 64.56; 2.325, 1.51; 2.319, 1.07; 2.315, 1.18; 2.310, 0.82; 2.305, 0.51; 2.292, 1.49; 2.275, 0.40; 2.221, 0.53; 2.214, 0.46; 2.184, 0.37; 2.167, 0.84; 2.125, 16.00; 2.040, 0.41; 2.004, 0.97; 1.885, 0.43; 1.363, 1.60; −0.000, 21.17; −0.008, 0.68 |

-continued

| No. | Structure | logP | MH+ | NMR |
|---|---|---|---|---|
| 26 | 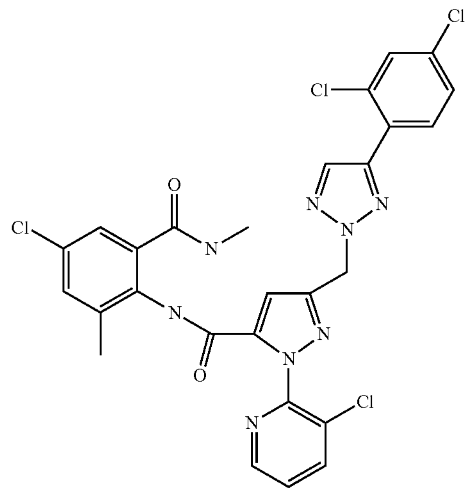 [SMILES: CNC(=O)c1cc(Cl)cc(C)c1NC(=O)c1cc(Cn2ncc(-c3ccc(Cl)cc3Cl)n2)nn1-c1ncccc1Cl] | 4.12 | 618 | 10.188, 0.40; 8.484, 2.81; 8.480, 2.93; 8.472, 3.22; 8.469, 2.85; 8.461, 0.34; 8.355, 8.73; 8.349, 1.01; 8.153, 2.77; 8.149, 2.73; 8.142, 0.48; 8.132, 3.05; 8.129, 2.78; 8.122, 0.34; 7.910, 4.34; 7.888, 4.85; 7.788, 4.29; 7.782, 4.38; 7.612, 2.93; 7.605, 3.63; 7.599, 3.19; 7.588, 2.95; 7.579, 3.31; 7.574, 3.56; 7.569, 4.58; 7.553, 4.74; 7.548, 4.08; 7.308, 0.34; 7.234, 6.03; 5.871, 9.85; 3.477, 0.39; 3.308, 486.81; 2.674, 0.84; 2.669, 1.13; 2.665, 0.85; 2.660, 0.46; 2.634, 1.03; 2.622, 1.03; 2.539, 5.87; 2.523, 4.61; 2.509, 65.38; 2.505, 121.73; 2.500, 157.95; 2.496, 107.33; 2.491, 50.53; 2.336, 0.43; 2.332, 0.81; 2.327, 1.09; 2.322, 0.80; 2.318, 0.41; 2.151, 15.00; 2.133, 1.75; 2.069, 3.16; 2.049, 0.45; 1.292, 0.32; 1.236, 1.03; 0.890, 0.47; 0.008, 0.41; −0.000, 10.20; −0.008, 0.42 |
| 27 | 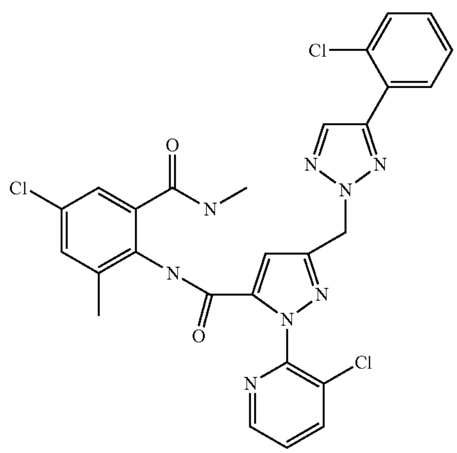 [SMILES: CNC(=O)c1cc(Cl)cc(C)c1NC(=O)c1cc(Cn2ncc(-c3ccccc3Cl)n2)nn1-c1ncccc1Cl] | 3.43 | 595/597 | 10.193, 2.91; 8.477, 2.82; 8.474, 2.90; 8.465, 2.96; 8.462, 2.83; 8.318, 8.40; 8.176, 1.31; 8.164, 1.30; 8.147, 2.81; 8.143, 2.65; 8.127, 2.89; 8.123, 2.63; 7.891, 2.09; 7.885, 1.85; 7.876, 1.45; 7.872, 1.66; 7.867, 2.28; 7.615, 2.07; 7.611, 1.59; 7.607, 1.44; 7.597, 2.11; 7.591, 4.91; 7.579, 2.82; 7.571, 2.62; 7.559, 2.51; 7.488, 0.52; 7.483, 0.95; 7.469, 2.91; 7.464, 3.18; 7.462, 3.24; 7.453, 5.71; 7.446, 2.93; 7.443, 3.18; 7.438, 4.80; 7.432, 2.99; 7.425, 1.14; 7.419, 0.54; 7.308, 3.23; 7.302, 2.95; 7.233, 5.14; 5.863, 10.02; 3.304, 441.53; 3.281, 20.73; 2.673, 0.60; 2.669, 0.81; 2.664, 0.60; 2.635, 9.37; 2.624, 9.80; 2.539, 1.32; 2.522, 3.10; 2.509, 42.18; 2.504, 77.83; 2.500, 100.60; 2.496, 69.03; 2.491, 32.99; 2.331, 0.49; 2.326, 0.70; 2.322, 0.50; 2.133, 15.00; 2.069, 0.60; 1.234, 0.34; 0.008, 0.56; −0.000, 12.85; −0.008, 0.54 |
| 28 | 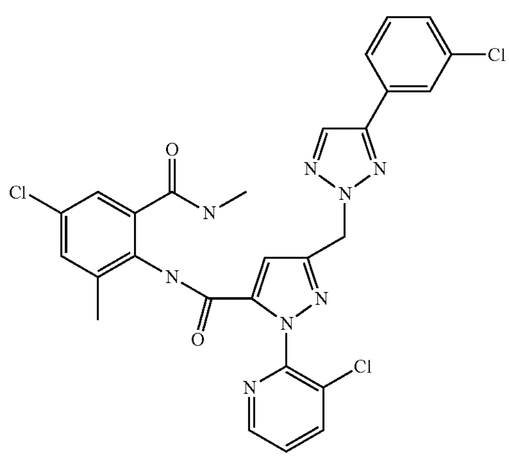 [SMILES: CNC(=O)c1cc(Cl)cc(C)c1NC(=O)c1cc(Cn2ncc(-c3cccc(Cl)c3)n2)nn1-c1ncccc1Cl] | 3.63 | 595/597 | 8.457, 2.20; 8.453, 2.42; 8.445, 2.39; 8.441, 2.28; 8.369, 7.04; 8.355, 0.44; 8.101, 2.27; 8.098, 2.29; 8.081, 2.52; 8.078, 2.50; 7.980, 1.11; 7.974, 1.73; 7.911, 3.47; 7.845, 2.06; 7.825, 2.32; 7.564, 2.23; 7.553, 2.55; 7.544, 2.71; 7.532, 2.03; 7.512, 1.59; 7.492, 3.45; 7.472, 2.39; 7.448, 0.66; 7.434, 2.30; 7.412, 1.33; 7.393, 2.84; 7.387, 3.18; 7.310, 3.24; 7.304, 2.89; 7.171, 3.47; 6.079, 0.50; 5.808, 10.94; 5.773, 0.41; 3.213, 0.46; 3.207, 0.45; 3.202, 0.51; 3.114, 366.17; 2.700, 1.58; 2.689, 1.57; 2.651, 9.51; 2.640, 9.15; 2.585, 0.35; 2.557, 0.57; 2.526, 1.36; 2.497, 43.69; 2.492, 80.33; 2.488, 105.69; 2.483, 77.25; 2.479, 40.06; 2.383, 2.57; 2.319, 0.58; 2.314, 0.67; 2.310, 0.55; 2.293, 1.52; 2.221, 2.48; 2.175, 0.52; 2.131, 16.00; 2.117, 2.88; 2.011, 0.47; −0.000, 2.90 |

-continued

| No. | Structure | logP | MH+ | NMR |
|---|---|---|---|---|
| 29 | 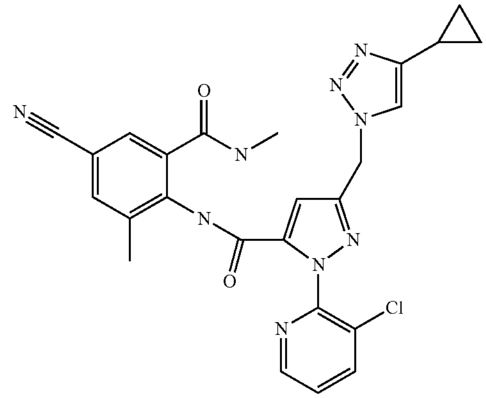 [SMILES: CNC(=O)c1cc(C#N)cc(C)c1NC(=O)c1cc(Cn2cc(C3CC3)nn2)nn1-c1ncccc1Cl] | 1.86 | 516 | 8.460, 3.02; 8.456, 3.15; 8.448, 3.08; 8.444, 2.98; 8.105, 2.13; 8.101, 2.24; 8.094, 1.00; 8.084, 2.31; 8.081, 2.35; 7.974, 1.31; 7.972, 0.93; 7.858, 6.19; 7.847, 0.94; 7.772, 3.16; 7.731, 3.01; 7.727, 3.19; 7.567, 2.44; 7.563, 1.19; 7.556, 2.36; 7.551, 1.20; 7.547, 2.27; 7.543, 1.10; 7.535, 2.18; 7.531, 1.03; 7.387, 1.53; 7.130, 3.76; 7.100, 1.18; 5.747, 3.70; 5.641, 10.48; 3.677, 1.65; 3.112, 577.79; 2.712, 2.70; 2.700, 2.95; 2.688, 8.50; 2.677, 9.05; 2.669, 3.78; 2.661, 1.27; 2.657, 1.41; 2.652, 1.06; 2.526, 1.55; 2.510, 4.30; 2.497, 65.28; 2.492, 128.61; 2.488, 177.14; 2.483, 125.68; 2.478, 61.82; 2.314, 1.05; 2.291, 1.10; 2.280, 4.19; 2.177, 16.00; 2.141, 3.93; 1.968, 0.92; 1.955, 2.13; 1.948, 1.72; 1.943, 1.16; 1.934, 1.29; 1.091, 1.29; 0.996, 1.05; 0.991, 1.13; 0.976, 1.07; 0.970, 1.02; 0.917, 1.10; 0.907, 2.60; 0.901, 3.35; 0.896, 1.57; 0.892, 1.71; 0.886, 3.02; 0.880, 3.20; 0.871, 1.47; 0.750, 1.40; 0.741, 3.30; 0.735, 3.09; 0.729, 3.41; 0.723, 3.13; 0.712, 1.24; 0.686, 1.13; 0.680, 1.17; 0.673, 1.02; 0.668, 1.23; −0.000, 12.56 |
| 30 | 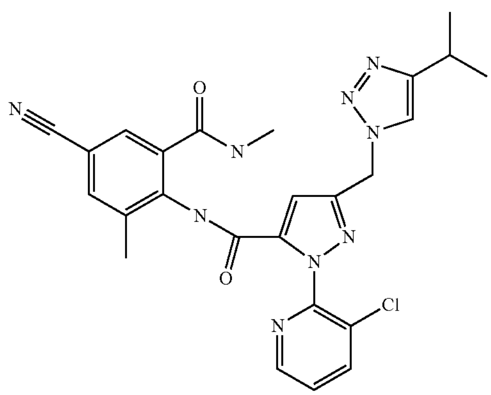 [SMILES: CNC(=O)c1cc(C#N)cc(C)c1NC(=O)c1cc(Cn2cc(C(C)C)nn2)nn1-c1ncccc1Cl] | 2.03 | 518 | 8.462, 1.38; 8.458, 1.63; 8.450, 1.59; 8.446, 1.60; 8.180, 0.46; 8.110, 1.35; 8.106, 1.35; 8.099, 0.47; 8.090, 1.46; 8.086, 1.40; 7.870, 3.18; 7.846, 0.34; 7.780, 2.06; 7.728, 1.78; 7.724, 1.72; 7.571, 1.53; 7.566, 1.25; 7.559, 1.51; 7.551, 1.48; 7.545, 0.55; 7.539, 1.35; 7.534, 0.44; 7.158, 3.05; 7.103, 0.62; 5.681, 1.68; 5.667, 6.83; 3.678, 0.36; 3.419, 0.47; 3.402, 1.29; 3.385, 1.37; 3.367, 0.52; 3.216, 0.34; 3.198, 0.45; 3.181, 0.69; 3.163, 0.99; 3.112, 470.97; 3.090, 6.26; 3.056, 0.55; 3.037, 0.52; 3.020, 0.84; 3.003, 1.07; 2.986, 0.81; 2.969, 0.40; 2.712, 0.90; 2.700, 0.98; 2.685, 5.44; 2.674, 6.12; 2.663, 1.76; 2.657, 1.04; 2.652, 0.75; 2.526, 1.11; 2.497, 44.85; 2.492, 87.30; 2.488, 119.35; 2.483, 85.32; 2.478, 42.59; 2.384, 1.35; 2.324, 0.32; 2.320, 0.62; 2.315, 0.80; 2.310, 0.62; 2.291, 1.08; 2.281, 1.33; 2.182, 8.91; 2.173, 2.46; 2.141, 1.33; 1.258, 16.00; 1.240, 15.68; 1.209, 3.25; 1.192, 3.20; 1.109, 1.39; 1.091, 2.81; 1.074, 1.42; −0.000, 6.75 |
| 31 | 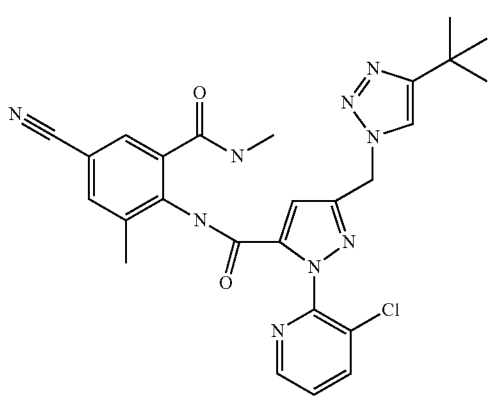 [SMILES: CNC(=O)c1cc(C#N)cc(C)c1NC(=O)c1cc(Cn2cc(C(C)(C)C)nn2)nn1-c1ncccc1Cl] | 2.25 | 532 | 8.463, 0.49; 8.460, 0.53; 8.451, 0.51; 8.448, 0.50; 8.114, 0.51; 8.111, 0.48; 8.094, 0.54; 8.090, 0.50; 7.875, 1.59; 7.787, 0.70; 7.726, 0.66; 7.722, 0.59; 7.574, 0.51; 7.562, 0.51; 7.554, 0.49; 7.542, 0.46; 7.172, 1.33; 5.662, 2.34; 3.619, 0.38; 3.608, 0.39; 3.602, 0.91; 3.586, 0.38; 3.145, 0.49; 3.111, 102.12; 2.700, 0.35; 2.684, 1.91; 2.673, 1.95; 2.526, 0.41; 2.497, 11.98; 2.492, 23.20; 2.488, 31.54; 2.483, 22.58; 2.478, 11.30; 2.387, 0.79; 2.291, 0.60; 2.281, 0.48; 2.186, 3.18; 2.142, 0.50; 1.778, 0.39; 1.770, 0.43; 1.762, 1.06; 1.753, 0.41; 1.745, 0.37; 1.360, 0.57; 1.297, 16.00; −0.000, 0.91 |

-continued

| No. | Structure | logP | MH+ | NMR |
|---|---|---|---|---|
| 32 | 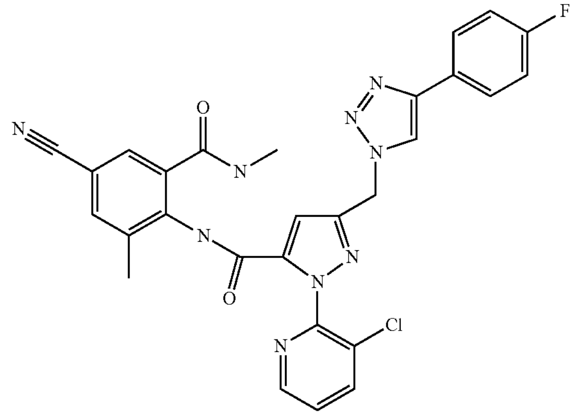 [SMILES: CNC(=O)c1cc(C#N)cc(C)c1NC(=O)c1cc(Cn2cc(-c3ccc(F)cc3)nn2)nn1-c1ncccc1Cl] | 2.41 | 570 | 10.453, 4.10; 10.174, 1.12; 8.710, 7.47; 8.478, 2.48; 8.474, 2.48; 8.466, 2.56; 8.463, 2.52; 8.424, 0.47; 8.411, 0.42; 8.307, 1.66; 8.295, 1.62; 8.150, 2.35; 8.147, 2.33; 8.130, 2.63; 8.127, 2.49; 7.993, 0.96; 7.975, 0.36; 7.944, 2.88; 7.939, 1.63; 7.930, 3.49; 7.922, 3.40; 7.908, 3.11; 7.838, 3.65; 7.802, 1.04; 7.727, 3.93; 7.595, 2.27; 7.583, 2.27; 7.575, 2.26; 7.563, 2.07; 7.513, 0.99; 7.313, 3.00; 7.291, 5.56; 7.269, 2.76; 7.238, 5.34; 6.967, 1.03; 5.819, 9.68; 5.772, 0.40; 3.440, 0.32; 3.421, 0.46; 3.303, 481.42; 3.181, 0.30; 2.696, 2.64; 2.684, 2.70; 2.669, 1.87; 2.665, 1.78; 2.649, 9.26; 2.638, 9.22; 2.576, 0.86; 2.504, 150.46; 2.500, 183.03; 2.496, 133.14; 2.411, 0.38; 2.327, 1.34; 2.277, 4.05; 2.177, 15.00; 2.131, 4.03; 2.069, 1.24; −0.000, 22.64 |
| 33 | 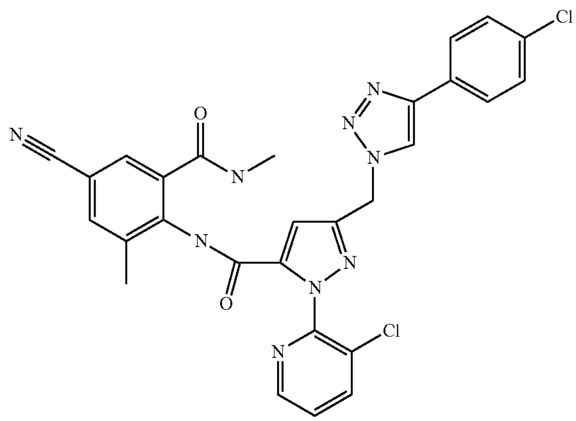 [SMILES: CNC(=O)c1cc(C#N)cc(C)c1NC(=O)c1cc(Cn2cc(-c3ccc(Cl)cc3)nn2)nn1-c1ncccc1Cl] | 2.75 | 586/588 | 8.672, 0.77; 8.660, 10.71; 8.455, 3.35; 8.451, 3.62; 8.443, 3.51; 8.439, 3.43; 8.093, 2.55; 8.089, 2.55; 8.073, 2.87; 8.069, 2.67; 7.979, 0.83; 7.974, 0.86; 7.940, 0.75; 7.896, 8.09; 7.891, 3.01; 7.879, 3.48; 7.874, 9.15; 7.868, 1.58; 7.837, 0.76; 7.789, 0.84; 7.748, 3.77; 7.725, 2.36; 7.587, 0.69; 7.556, 2.70; 7.544, 2.89; 7.536, 2.90; 7.524, 2.68; 7.505, 1.63; 7.498, 9.15; 7.493, 3.17; 7.482, 2.97; 7.477, 8.24; 7.470, 1.77; 7.149, 2.53; 6.874, 0.73; 5.842, 0.68; 5.785, 13.52; 5.755, 1.08; 3.688, 1.57; 3.619, 0.89; 3.602, 2.24; 3.585, 0.94; 3.402, 0.75; 3.385, 0.63; 3.222, 0.76; 3.203, 1.11; 3.113, 977.64; 2.712, 2.27; 2.700, 2.51; 2.679, 12.15; 2.668, 11.92; 2.657, 2.28; 2.652, 1.65; 2.563, 0.65; 2.526, 2.33; 2.510, 6.15; 2.497, 96.40; 2.493, 189.18; 2.488, 259.39; 2.483, 183.31; 2.478, 89.40; 2.363, 1.14; 2.319, 1.19; 2.315, 1.65; 2.310, 1.13; 2.292, 2.06; 2.276, 3.74; 2.207, 1.01; 2.155, 16.00; 2.141, 4.51; 2.040, 3.15; 1.946, 1.03; 1.778, 0.85; 1.770, 1.02; 1.762, 2.55; 1.753, 0.98; 1.745, 0.86; 1.363, 2.76; 1.091, 0.83; −0.000, 18.20 |
| 34 | 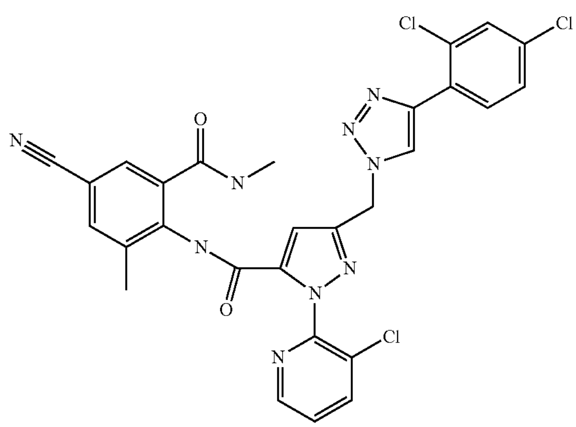 [SMILES: CNC(=O)c1cc(C#N)cc(C)c1NC(=O)c1cc(Cn2cc(-c3ccc(Cl)cc3Cl)nn2)nn1-c1ncccc1Cl] | 3.20 | 620/622 | 8.766, 0.51; 8.754, 8.22; 8.462, 2.72; 8.458, 2.75; 8.450, 2.82; 8.446, 2.91; 8.436, 0.44; 8.233, 0.42; 8.177, 0.98; 8.139, 0.45; 8.131, 4.44; 8.110, 6.19; 8.091, 2.91; 8.087, 2.94; 8.051, 0.46; 7.976, 0.71; 7.971, 0.95; 7.897, 0.75; 7.845, 0.79; 7.781, 3.54; 7.726, 3.72; 7.723, 3.26; 7.694, 3.67; 7.689, 3.98; 7.572, 2.96; 7.560, 2.80; 7.552, 2.83; 7.544, 3.43; 7.540, 4.31; 7.523, 3.03; 7.518, 2.82; 7.482, 0.88; 7.469, 0.86; 7.226, 6.09; 6.976, 0.46; 6.860, 0.75; 5.897, 0.53; 5.855, 11.25; 5.618, 0.89; 3.684, 0.93; 3.385, 0.42; 3.293, 0.42; 3.211, 0.90; 3.114, 1225.75; 3.090, 13.77; 2.712, 2.34; 2.700, 2.74; 2.679, 9.81; 2.668, 10.18; 2.657, 2.14; 2.652, .63; 2.648, 0.97; 2.615, 0.44; 2.603, 0.56; 2.564, 0.61; 2.526, 2.55; 2.510, 6.58; 2.497, 107.00; 2.493, 212.27; 2.488, 293.35; 2.483, 207.30; 2.479, 101.30; 2.384, 5.40; 2.325, 0.67; 2.319, 1.31; 2.315, 1.76; 2.310, 1.42; 2.306, 0.76; 2.292, 6.00; 2.281, 3.82; 2.211, 0.81; 2.179, 16.00; 2.142, 3.52; 2.040, 0.59; 1.951, 0.61; 1.363, 0.59; 1.247, 0.47; 1.091, 0.59; 0.008, 0.83; −0.000, 18.40 |

| No. | Structure | logP | MH+ | NMR |
|---|---|---|---|---|
| 35 | 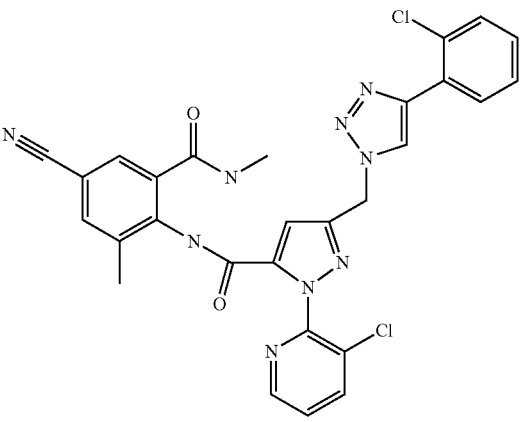 [SMILES: CNC(=O)c1cc(C#N)cc(C)c1NC(=O)c1cc(Cn2cc(-c3ccccc3Cl)nn2)nn1-c1ncccc1Cl] | 2.63 | 586/588 | 10.477, 3.26; 10.173, 0.78; 8.816, 7.66; 8.481, 2.56; 8.477, 2.53; 8.469, 2.60; 8.466, 2.48; 8.448, 0.37; 8.436, 0.40; 8.422, 0.39; 8.412, 0.41; 8.309, 1.61; 8.299, 1.63; 8.155, 2.54; 8.151, 2.39; 8.135, 4.61; 8.119, 2.34; 8.115, 2.17; 8.040, 0.43; 7.994, 0.88; 7.946, 0.69; 7.899, 0.84; 7.840, 3.71; 7.801, 0.95; 7.730, 4.14; 7.628, 0.41; 7.598, 2.87; 7.594, 2.67; 7.590, 2.71; 7.586, 2.75; 7.578, 2.90; 7.574, 3.17; 7.571, 3.01; 7.566, 2.65; 7.554, 0.43; 7.546, 0.34; 7.513, 1.06; 7.494, 1.25; 7.491, 1.19; 7.475, 2.58; 7.472, 2.52; 7.456, 1.95; 7.424, 1.75; 7.419, 1.78; 7.404, 2.01; 7.400, 1.92; 7.386, 0.88; 7.381, 0.75; 7.269, 5.14; 7.036, 0.49; 6.967, 0.88; 5.879, 9.84; 5.596, 0.81; 3.454, 0.42; 3.304, 802.83; 3.281, 17.17; 3.214, 0.64; 2.724, 0.34; 2.696, 2.23; 2.684, 2.45; 2.669, 3.03; 2.654, 9.25; 2.642, 9.18; 2.626, 0.77; 2.504, 197.10; 2.500, 244.99; 2.496, 176.07; 2.390, 0.62; 2.379, 0.69; 2.331, 1.46; 2.327, 1.76; 2.277, 3.56; 2.243, 0.68; 2.219, 0.46; 2.182, 15.00; 2.132, 3.81; 2.069, 2.29; 1.987, 0.61; 1.175, 0.41; −0.000, 31.84 |
| 36 | 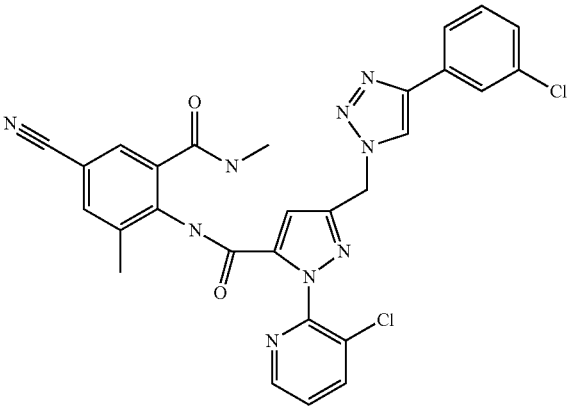 [SMILES: CNC(=O)c1cc(C#N)cc(C)c1NC(=O)c1cc(Cn2cc(-c3cccc(Cl)c3)nn2)nn1-c1ncccc1Cl] | 2.86 | 586/588 | 8.734, 6.61; 8.459, 2.62; 8.450, 2.56; 8.240, 0.49; 8.220, 0.47; 8.200, 0.46; 8.170, 1.42; 8.130, 0.68; 8.108, 2.38; 8.089, 2.59; 7.975, 0.92; 7.971, 0.71; 7.917, 3.80; 7.882, 0.48; 7.848, 3.05; 7.828, 2.58; 7.808, 0.54; 7.782, 4.53; 7.722, 4.06; 7.707, 0.55; 7.659, 0.45; 7.626, 0.49; 7.572, 2.13; 7.560, 2.14; 7.552, 2.27; 7.540, 2.19; 7.514, 0.91; 7.490, 1.77; 7.471, 4.25; 7.452, 2.26; 7.389, 2.37; 7.367, 1.54; 7.212, 5.78; 7.125, 0.48; 7.065, 0.51; 6.861, 0.92; 5.847, 0.59; 5.805, 10.65; 5.774, 1.01; 3.691, 1.06; 3.402, 0.56; 3.384, 0.56; 3.370, 0.47; 3.310, 0.47; 3.255, 0.58; 3.235, 0.57; 3.112, 318.79; 3.019, 0.55; 3.001, 0.58; 2.960, 0.45; 2.751, 0.54; 2.743, 0.53; 2.712, 2.06; 2.701, 2.32; 2.676, 9.37; 2.665, 9.90; 2.622, 0.63; 2.492, 141.18; 2.488, 176.92; 2.484, 136.67; 2.423, 0.87; 2.407, 0.65; 2.385, 2.03; 2.315, 1.14; 2.290, 1.95; 2.281, 3.26; 2.212, 0.68; 2.179, 16.00; 2.141, 3.30; 2.118, 0.85; 2.106, 0.73; 2.041, 1.02; 1.946, 0.95; 1.364, 1.19; 1.284, 0.45; 1.255, 1.13; 1.109, 0.55; 1.092, 0.85; 1.075, 0.50; −0.000, 13.60 |

-continued

| No. | Structure | logP | MH+ | NMR |
|---|---|---|---|---|
| 37 | 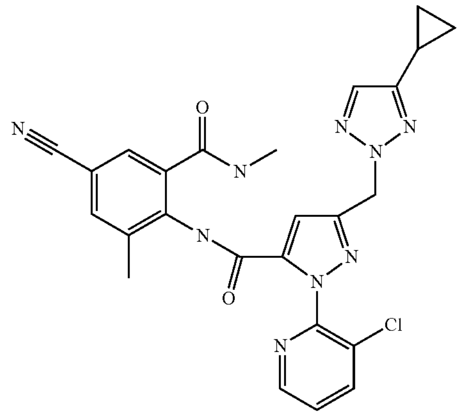 [SMILES: CNC(=O)c1cc(C#N)cc(C)c1NC(=O)c1cc(Cn2ncc(C3CC3)n2)nn1-c1ncccc1Cl] | 2.28 | 516 | 10.435, 3.97; 8.476, 2.74; 8.472, 3.02; 8.465, 3.05; 8.461, 3.06; 8.301, 1.55; 8.290, 1.58; 8.144, 2.44; 8.141, 2.55; 8.124, 2.71; 8.121, 2.66; 7.841, 3.44; 7.726, 3.62; 7.722, 3.53; 7.592, 10.19; 7.578, 2.71; 7.570, 2.54; 7.558, 2.45; 7.144, 4.51; 5.647, 11.98; 3.312, 1848.55; 3.288, 17.22; 3.193, 0.57; 2.674, 1.49; 2.669, 2.13; 2.659, 10.81; 2.648, 10.44; 2.618, 0.33; 2.598, 0.35; 2.539, 6.98; 2.522, 5.88; 2.509, 82.37; 2.505, 152.42; 2.500, 196.49; 2.496, 134.83; 2.492, 64.09; 2.332, 1.07; 2.327, 1.39; 2.322, 1.06; 2.187, 15.00; 2.085, 0.79; 2.069, 0.82; 2.049, 0.50; 2.017, 0.62; 2.005, 1.17; 1.996, 1.25; 1.993, 0.89; 1.984, 2.31; 1.975, 0.89; 1.972, 1.33; 1.963, 1.24; 1.951, 0.63; 1.292, 0.35; 1.238, 0.42; 0.975, 1.41; 0.964, 3.89; 0.958, 4.24; 0.954, 1.92; 0.949, 2.11; 0.943, 4.01; 0.937, 3.91; 0.928, 1.68; 0.890, 0.59; 0.762, 1.75; 0.752, 4.38; 0.750, 3.15; 0.747, 4.38; 0.740, 4.25; 0.734, 4.21; 0.724, 1.30; 0.008, 0.55; −0.000, 11.25; −0.008, 0.39 |
| 38 | 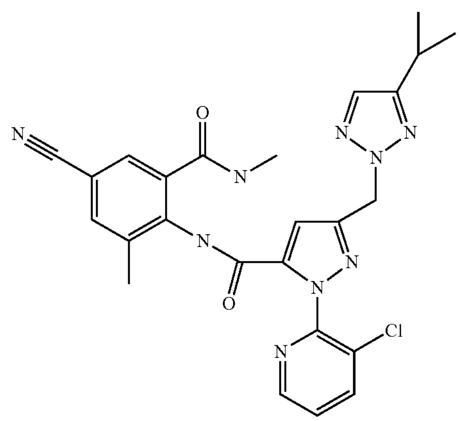 [SMILES: CNC(=O)c1cc(C#N)cc(C)c1NC(=O)c1cc(Cn2ncc(C(C)C)n2)nn1-c1ncccc1Cl] | 2.58 | 518/520 | 8.459, 1.27; 8.455, 1.39; 8.447, 1.40; 8.443, 1.39; 8.105, 1.22; 8.101, 1.29; 8.085, 1.36; 8.081, 1.34; 7.781, 1.49; 7.722, 1.47; 7.718, 1.36; 7.623, 2.88; 7.566, 1.39; 7.555, 1.33; 7.546, 1.32; 7.534, 1.30; 7.108, 1.87; 5.658, 6.22; 3.112, 126.45; 3.088, 3.59; 3.055, 0.41; 3.038, 0.75; 3.021, 0.96; 3.004, 0.77; 2.986, 0.36; 2.712, 0.93; 2.700, 0.99; 2.681, 4.77; 2.670, 4.94; 2.657, 0.49; 2.652, 0.34; 2.526, 0.52; 2.523, 0.41; 2.510, 1.26; 2.497, 20.90; 2.492, 41.53; 2.487, 57.31; 2.483, 40.43; 2.478, 19.68; 2.314, 0.34; 2.281, 1.47; 2.183, 7.55; 2.141, 1.39; 2.040, 0.53; 1.270, 16.00; 1.253, 15.84; 1.232, 0.44; 1.091, 0.38; −0.000, 6.58 |
| 39 | 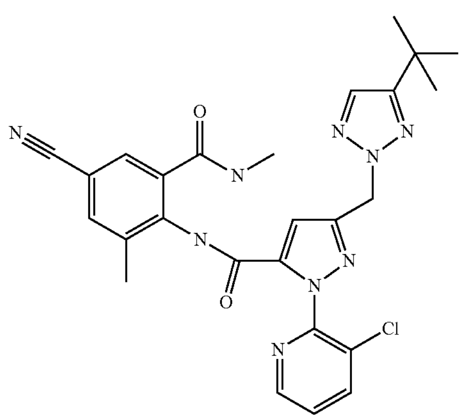 [SMILES: CNC(=O)c1cc(C#N)cc(C)c1NC(=O)c1cc(Cn2ncc(C(C)(C)C)n2)nn1-c1ncccc1Cl] | 2.89 | 532 | 8.456, 0.67; 8.449, 0.67; 8.142, 0.39; 8.107, 0.68; 8.087, 0.66; 7.975, 0.37; 7.850, 0.33; 7.787, 1.31; 7.721, 1.08; 7.650, 1.44; 7.569, 0.55; 7.557, 0.56; 7.549, 0.53; 7.537, 0.47; 7.104, 1.49; 5.660, 3.04; 3.113, 74.05; 2.712, 0.81; 2.700, 0.90; 2.681, 2.48; 2.669, 2.61; 2.488, 33.30; 2.386, 0.44; 2.290, 0.58; 2.281, 1.34; 2.184, 4.32; 2.141, 1.32; 1.340, 0.37; 1.310, 16.00; −0.000, 1.93 |

| No. | Structure | logP | MH+ | NMR |
|---|---|---|---|---|
| 40 | 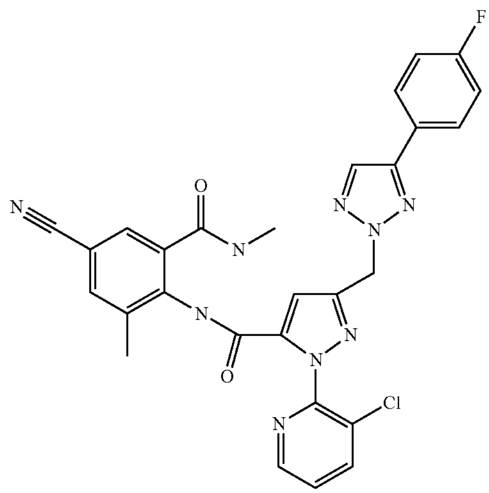 [SMILES: CNC(=O)c1cc(C#N)cc(C)c1NC(=O)c1cc(Cn2ncc(-c3ccc(F)cc3)n2)nn1-c1ncccc1Cl] | 2.96 | 570 | 8.460, 2.41; 8.456, 2.59; 8.448, 2.53; 8.444, 2.47; 8.269, 7.92; 8.252, 0.71; 8.242, 0.42; 8.142, 1.06; 8.128, 1.03; 8.106, 2.51; 8.103, 2.48; 8.086, 2.61; 8.082, 2.46; 8.033, 0.34; 8.016, 0.36; 7.975, 0.98; 7.972, 0.92; 7.923, 3.01; 7.917, 1.47; 7.909, 3.38; 7.900, 3.50; 7.892, 1.68; 7.887, 3.26; 7.847, 0.87; 7.782, 3.73; 7.713, 3.29; 7.709, 3.00; 7.569, 2.51; 7.557, 2.48; 7.549, 2.40; 7.537, 2.26; 7.473, 1.08; 7.299, 3.13; 7.293, 1.26; 7.281, 1.54; 7.276, 5.87; 7.271, 1.60; 7.259, 1.19; 7.254, 2.81; 7.222, 0.41; 7.186, 6.45; 6.860, 0.82; 5.846, 0.70; 5.799, 11.61; 3.678, 1.19; 3.402, 0.58; 3.384, 0.55; 3.113, 186.54; 2.712, 2.62; 2.701, 2.65; 2.664, 9.37; 2.652, 9.79; 2.526, 1.06; 2.497, 36.62; 2.492, 70.38; 2.488, 95.16; 2.483, 68.32; 2.478, 34.47; 2.387, 1.57; 2.318, 0.47; 2.315, 0.58; 2.309, 0.44; 2.292, 0.99; 2.281, 4.47; 2.219, 1.37; 2.180, 16.00; 2.141, 4.48; 2.041, 0.81; 1.945, 0.78; 1.255, 0.73; 1.109, 0.59; 1.091, 1.15; 1.074, 0.54; −0.000, 8.28 |
| 41 | 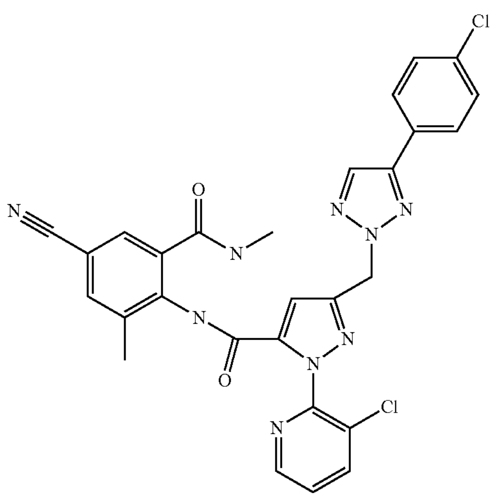 [SMILES: CNC(=O)c1cc(C#N)cc(C)c1NC(=O)c1cc(Cn2ncc(-c3ccc(Cl)cc3)n2)nn1-c1ncccc1Cl] | 3.34 | 586/588 | 8.459, 2.29; 8.456, 2.44; 8.448, 2.46; 8.444, 2.35; 8.313, 7.26; 8.295, 0.53; 8.138, 1.12; 8.125, 1.14; 8.106, 2.43; 8.102, 2.41; 8.086, 2.46; 8.082, 2.37; 7.974, 0.97; 7.896, 5.51; 7.891, 2.40; 7.879, 2.92; 7.874, 6.41; 7.858, 0.67; 7.847, 0.86; 7.781, 3.90; 7.713, 3.43; 7.709, 3.19; 7.569, 2.35; 7.557, 2.34; 7.549, 2.31; 7.537, 2.28; 7.522, 6.13; 7.517, 2.69; 7.501, 5.48; 7.474, 0.89; 7.226, 0.40; 7.191, 6.16; 6.861, 0.68; 5.855, 0.71; 5.809, 11.16; 3.678, 1.25; 3.402, 0.61; 3.384, 0.58; 3.233, 0.32; 3.114, 196.26; 2.712, 2.16; 2.701, 2.19; 2.663, 9.32; 2.652, 9.66; 2.579, 0.34; 2.497, 34.90; 2.492, 63.86; 2.488, 83.90; 2.483, 61.13; 2.479, 31.66; 2.386, 0.58; 2.315, 0.51; 2.282, 3.61; 2.221, 0.55; 2.180, 16.00; 2.141, 3.58; 2.041, 0.57; 1.945, 0.83; 1.363, 0.58; 1.256, 0.84; 1.109, 0.55; 1.091, 1.03; 1.074, 0.53; −0.000, 6.50 |
| 42 | 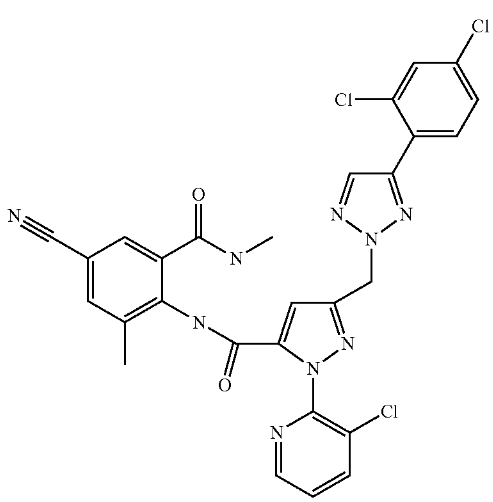 [SMILES: CNC(=O)c1cc(C#N)cc(C)c1NC(=O)c1cc(Cn2ncc(-c3ccc(Cl)cc3Cl)n2)nn1-c1ncccc1Cl] | 3.81 | 620/622 | 8.462, 2.60; 8.458, 2.78; 8.450, 2.77; 8.447, 2.76; 8.290, 8.19; 8.272, 0.51; 8.151, 0.92; 8.110, 2.68; 8.106, 2.74; 8.090, 2.95; 8.086, 2.81; 7.975, 1.53; 7.972, 0.70; 7.895, 4.19; 7.873, 4.70; 7.851, 0.83; 7.786, 3.61; 7.783, 3.66; 7.721, 6.47; 7.716, 6.89; 7.572, 2.88; 7.560, 2.72; 7.552, 2.66; 7.540, 2.99; 7.536, 3.30; 7.531, 2.94; 7.515, 2.60; 7.510, 2.59; 7.474, 0.86; 7.238, 0.37; 7.214, 6.17; 6.862, 0.64; 5.895, 0.63; 5.847, 11.63; 3.679, 1.00; 3.402, 0.56; 3.384, 0.48; 3.163, 0.65; 3.112, 205.25; 3.089, 6.56; 2.712, 2.52; 2.700, 2.58; 2.670, 9.37; 2.658, 10.04; 2.643, 0.36; 2.639, 0.35; 2.604, 0.53; 2.526, 1.26; 2.497, 45.61; 2.492, 89.33; 2.488, 121.99; 2.483, 85.96; 2.478, 41.93; 2.385, 0.59; 2.319, 0.55; 2.314, 0.79; 2.290, 0.58; 2.281, 4.00; 2.216, 0.72; 2.184, 16.00; 2.141, 3.79; 2.041, 0.94; 1.948, 0.67; 1.364, 0.54; 1.253, 0.57; 1.109, 0.52; 1.091, 1.05; 1.074, 0.46; 0.008, 0.66; −0.000, 12.90; −0.008, 0.60 |

-continued

| No. | Structure | logP | MH+ | NMR |
|---|---|---|---|---|
| 43 | 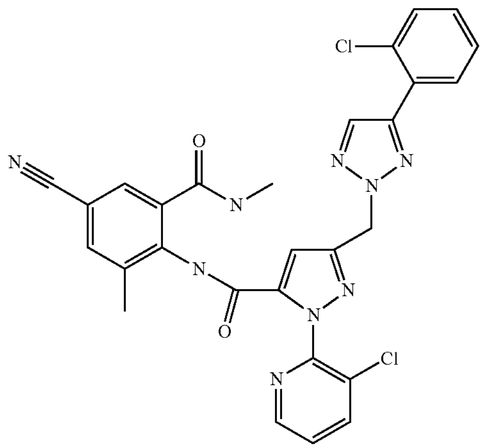 [SMILES: CNC(=O)c1cc(C#N)cc(C)c1NC(=O)c1cc(Cn2ncc(-c3ccccc3Cl)n2)nn1-c1ncccc1Cl] | 3.21 | 586/588 | 8.464, 2.48; 8.460, 2.61; 8.452, 2.57; 8.448, 2.54; 8.262, 6.75; 8.242, 0.52; 8.237, 0.39; 8.146, 0.95; 8.126, 0.71; 8.111, 2.46; 8.107, 2.42; 8.091, 2.62; 8.087, 2.42; 7.976, 0.66; 7.974, 0.76; 7.885, 0.41; 7.874, 2.05; 7.868, 1.55; 7.859, 1.42; 7.855, 1.66; 7.851, 2.71; 7.783, 3.68; 7.718, 3.22; 7.714, 3.01; 7.587, 1.74; 7.582, 1.44; 7.579, 1.35; 7.572, 3.52; 7.563, 2.77; 7.561, 2.91; 7.552, 2.63; 7.540, 2.33; 7.468, 0.82; 7.463, 0.85; 7.449, 2.61; 7.442, 3.26; 7.434, 4.92; 7.424, 2.54; 7.418, 1.96; 7.406, 0.51; 7.400, 0.36; 7.235, 0.41; 7.216, 5.98; 6.862, 0.64; 5.890, 0.46; 5.843, 11.78; 3.681, 0.85; 3.222, 0.35; 3.220, 0.38; 3.207, 0.40; 3.112, 305.08; 3.089, 9.50; 2.712, 2.12; 2.701, 2.22; 2.671, 9.34; 2.659, 9.99; 2.571, 0.37; 2.526, 1.45; 2.497, 52.59; 2.492, 100.72; 2.488, 136.09; 2.483, 97.63; 2.478, 49.07; 2.386, 0.90; 2.383, 0.36; 2.319, 0.66; 2.315, 0.88; 2.310, 0.61; 2.281, 3.35; 2.216, 0.52; 2.185, 16.00; 2.141, 3.30; 2.041, 1.46; 1.951, 0.56; 1.255, 0.58; −0.000, 10.64 |
| 44 | 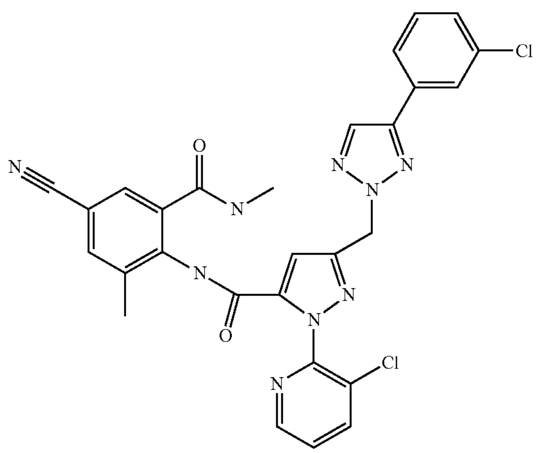 [SMILES: CNC(=O)c1cc(C#N)cc(C)c1NC(=O)c1cc(Cn2ncc(-c3cccc(Cl)c3)n2)nn1-c1ncccc1Cl] | 3.23 | 586/588 | 10.436, 3.08; 10.174, 1.14; 8.478, 3.02; 8.474, 3.25; 8.466, 3.52; 8.462, 4.07; 8.458, 11.31; 8.436, 0.39; 8.426, 0.53; 8.414, 0.48; 8.300, 1.21; 8.289, 1.23; 8.149, 2.59; 8.145, 2.58; 8.129, 2.78; 8.125, 2.72; 7.999, 1.35; 7.994, 1.40; 7.952, 2.88; 7.948, 4.76; 7.944, 3.09; 7.898, 1.39; 7.872, 2.87; 7.856, 2.42; 7.853, 3.33; 7.837, 3.50; 7.802, 1.44; 7.798, 1.37; 7.722, 3.67; 7.594, 2.57; 7.582, 2.62; 7.574, 2.48; 7.562, 2.41; 7.532, 2.04; 7.512, 5.81; 7.493, 3.35; 7.462, 2.99; 7.457, 2.49; 7.445, 1.36; 7.440, 1.57; 7.235, 3.99; 6.969, 1.07; 6.953, 0.52; 5.846, 11.16; 3.409, 0.34; 3.307, 696.21; 3.284, 68.08; 3.208, 0.48; 3.203, 0.35; 2.696, 3.23; 2.685, 3.82; 2.674, 1.26; 2.669, 1.50; 2.665, 1.22; 2.641, 9.47; 2.630, 11.09; 2.597, 0.41; 2.593, 0.41; 2.539, 2.52; 2.505, 130.84; 2.500, 166.16; 2.496, 116.74; 2.331, 0.94; 2.327, 1.13; 2.323, 0.88; 2.277, 5.91; 2.181, 15.00; 2.131, 6.07; 2.069, 1.01; 2.050, 0.31; 1.236, 0.33; 0.890, 0.40; −0.000, 11.36 |
| 45 | 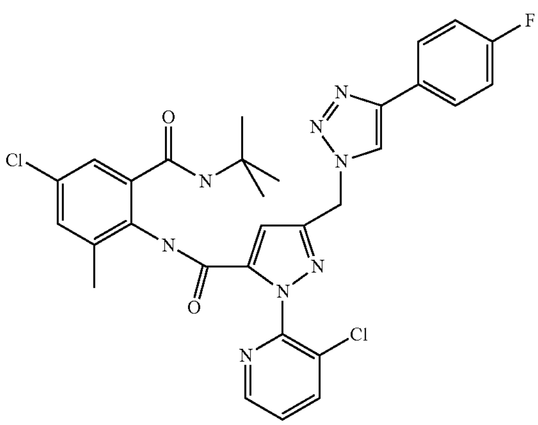 [SMILES: Cc1cc(Cl)cc(C(=O)NC(C)(C)C)c1NC(=O)c1cc(Cn2cc(-c3ccc(F)cc3)nn2)nn1-c1ncccc1Cl] | 3.63 | 621/623 | 8.574, 1.60; 8.451, 0.57; 8.447, 0.58; 8.439, 0.59; 8.435, 0.57; 8.105, 0.58; 8.101, 0.54; 8.085, 0.65; 8.081, 0.58; 7.908, 0.73; 7.903, 0.33; 7.894, 0.80; 7.886, 0.85; 7.878, 0.44; 7.872, 0.72; 7.570, 0.68; 7.558, 0.64; 7.550, 0.62; 7.538, 0.61; 7.364, 0.62; 7.359, 0.67; 7.287, 0.59; 7.279, 0.92; 7.273, 0.33; 7.261, 0.41; 7.256, 1.42; 7.251, 0.33; 7.234, 1.14; 7.230, 0.74; 7.149, 0.75; 5.789, 2.40; 3.402, 0.34; 3.385, 0.37; 3.112, 118.42; 2.529, 1.12; 2.510, 0.90; 2.497, 14.28; 2.493, 28.22; 2.488, 38.76; 2.483, 27.33; 2.478, 13.37; 2.211, 0.88; 2.123, 3.44; 1.251, 2.19; 1.205, 1.45; 1.196, 16.00; 1.109, 0.35; 1.091, 0.69; 1.074, 0.34; −0.000, 2.78 |

| No. | Structure | logP | MH+ | NMR |
|---|---|---|---|---|
| 46 | 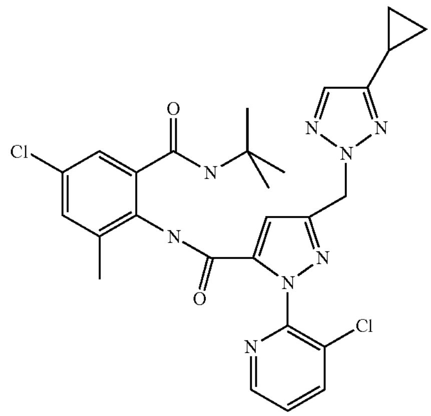 [SMILES: Cc1cc(Cl)cc(C(=O)NC(C)(C)C)c1NC(=O)c1cc(Cn2ncc(C3CC3)n2)nn1-c1ncccc1Cl] | 3.6 | 567/569 | 8.446, 0.57; 8.443, 0.62; 8.435, 0.59; 8.431, 0.59; 8.099, 0.54; 8.095, 0.56; 8.079, 0.64; 8.075, 0.54; 7.564, 0.67; 7.552, 0.65; 7.543, 0.66; 7.538, 0.39; 7.533, 1.63; 7.372, 0.58; 7.366, 0.65; 7.278, 0.40; 7.243, 0.65; 7.236, 0.61; 7.048, 0.62; 5.664, 0.43; 5.616, 2.64; 3.112, 120.38; 3.088, 3.49; 2.657, 0.34; 2.530, 0.90; 2.510, 1.15; 2.497, 18.54; 2.492, 36.54; 2.488, 50.08; 2.483, 35.15; 2.478, 17.04; 2.212, 0.64; 2.130, 3.39; 2.040, 0.67; 1.965, 0.42; 1.773, 0.56; 1.248, 1.40; 1.224, 16.00; 0.951, 0.80; 0.945, 0.87; 0.941, 0.42; 0.935, 0.52; 0.930, 0.89; 0.924, 0.82; 0.914, 0.37; 0.751, 0.35; 0.741, 0.87; 0.738, 0.56; 0.735, 0.88; 0.729, 0.91; 0.723, 0.78; 0.712, 0.38; −0.000, 4.71 |
| 47 | 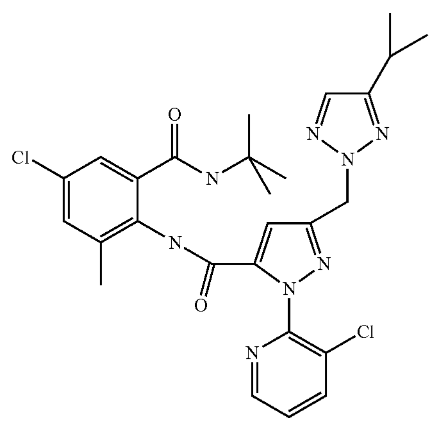 [SMILES: Cc1cc(Cl)cc(C(=O)NC(C)(C)C)c1NC(=O)c1cc(Cn2ncc(C(C)C)n2)nn1-c1ncccc1Cl] | 3.86 | 569/571 | 8.447, 0.57; 8.443, 0.59; 8.435, 0.60; 8.432, 0.57; 8.100, 0.53; 8.096, 0.54; 8.080, 0.60; 8.076, 0.58; 7.609, 1.24; 7.564, 0.61; 7.553, 0.60; 7.544, 0.57; 7.532, 0.53; 7.370, 0.57; 7.365, 0.60; 7.279, 0.36; 7.244, 0.62; 7.237, 0.57; 7.063, 0.56; 5.650, 2.56; 3.108, 78.62; 3.083, 1.93; 3.029, 0.35; 3.012, 0.42; 2.529, 0.90; 2.510, 0.71; 2.497, 12.30; 2.492, 24.52; 2.487, 33.87; 2.483, 23.90; 2.478, 11.70; 2.211, 0.77; 2.129, 3.32; 1.266, 6.76; 1.248, 6.79; 1.219, 16.00; −0.000, 1.25 |
| 48 | 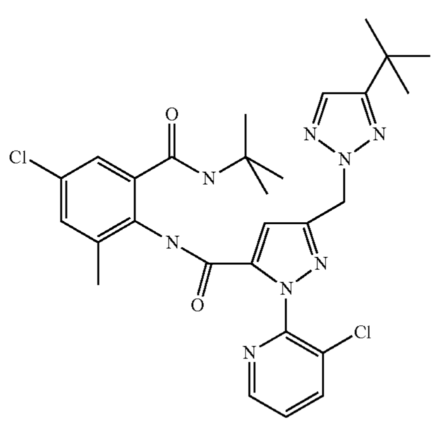 [SMILES: Cc1cc(Cl)cc(C(=O)NC(C)(C)C)c1NC(=O)c1cc(Cn2ncc(C(C)(C)C)n2)nn1-c1ncccc1Cl] | 4.25 | 583/585 | 8.448, 0.44; 8.444, 0.47; 8.437, 0.47; 8.433, 0.45; 8.101, 0.44; 8.097, 0.41; 8.081, 0.48; 8.077, 0.43; 7.635, 1.32; 7.565, 0.50; 7.554, 0.48; 7.545, 0.47; 7.534, 0.47; 7.373, 0.42; 7.371, 0.41; 7.366, 0.46; 7.245, 0.49; 7.240, 0.43; 7.058, 0.43; 5.650, 1.93; 3.112, 75.17; 3.088, 1.92; 2.529, 0.53; 2.510, 0.58; 2.497, 9.73; 2.492, 19.47; 2.488, 27.02; 2.483, 18.98; 2.478, 9.19; 2.211, 0.42; 2.128, 2.54; 1.303, 16.00; 1.259, 0.35; 1.217, 12.53; −0.000, 2.76 |

-continued

| No. | Structure | logP | MH+ | NMR |
|---|---|---|---|---|
| 49 | 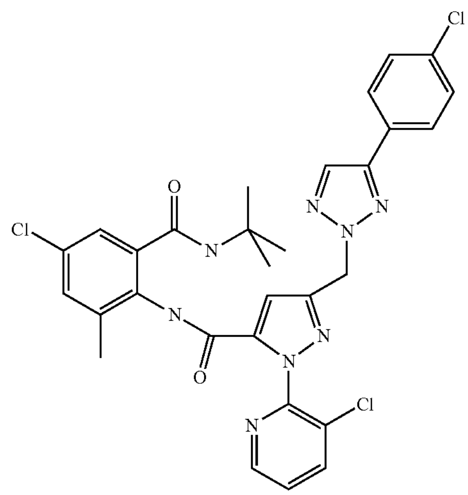 [SMILES: Cc1cc(Cl)cc(C(=O)NC(C)(C)C)c1NC(=O)c1cc(Cn2ncc(-c3ccc(Cl)cc3)n2)nn1-c1ncccc1Cl] | 4.58 | 637/639 | 8.449, 0.59; 8.445, 0.59; 8.437, 0.60; 8.433, 0.58; 8.302, 1.90; 8.102, 0.58; 8.098, 0.57; 8.082, 0.64; 8.078, 0.58; 7.890, 1.33; 7.885, 0.49; 7.873, 0.55; 7.868, 1.50; 7.567, 0.67; 7.555, 0.61; 7.547, 0.60; 7.535, 0.61; 7.522, 1.49; 7.516, 0.54; 7.505, 0.49; 7.500, 1.29; 7.362, 0.57; 7.357, 0.61; 7.262, 0.37; 7.231, 0.67; 7.225, 0.58; 7.127, 0.63; 5.800, 2.38; 3.109, 107.95; 3.085, 2.44; 2.526, 0.37; 2.510, 0.93; 2.497, 15.45; 2.492, 30.55; 2.488, 42.14; 2.483, 29.63; 2.478, 14.39; 2.123, 3.39; 1.250, 1.42; 1.183, 16.00; 1.091, 0.59; −0.000, 2.82 |
| 50 | 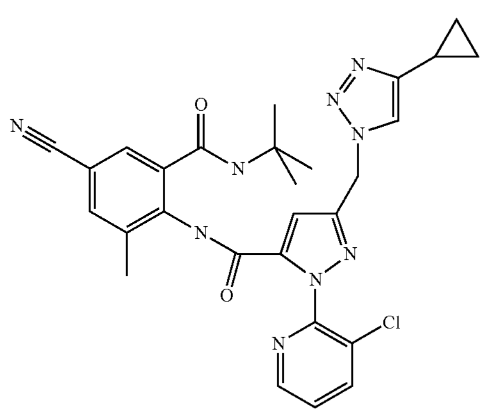 [SMILES: Cc1cc(C#N)cc(C(=O)NC(C)(C)C)c1NC(=O)c1cc(Cn2cc(C3CC3)nn2)nn1-c1ncccc1Cl] | 2.57 | 558 | 8.451, 0.75; 8.447, 0.78; 8.439, 0.77; 8.436, 0.78; 8.102, 0.51; 8.099, 0.53; 8.082, 0.55; 8.079, 0.56; 7.821, 1.44; 7.747, 0.67; 7.666, 0.67; 7.568, 0.64; 7.556, 0.67; 7.548, 0.61; 7.544, 0.32; 7.536, 0.63; 7.384, 0.35; 7.111, 0.83; 5.750, 0.77; 5.644, 2.47; 3.107, 90.26; 2.657, 0.39; 2.552, 0.55; 2.526, 0.51; 2.510, 1.17; 2.497, 20.35; 2.492, 40.80; 2.487, 56.58; 2.483, 39.83; 2.478, 19.30; 2.314, 0.33; 2.237, 0.41; 2.177, 3.18; 1.950, 0.38; 1.272, 1.19; 1.251, 3.58; 1.240, 16.00; 1.229, 5.15; 0.907, 0.64; 0.901, 0.76; 0.897, 0.39; 0.892, 0.43; 0.886, 0.72; 0.880, 0.73; 0.871, 0.38; 0.742, 0.34; 0.732, 0.75; 0.729, 0.53; 0.726, 0.77; 0.720, 0.71; 0.714, 0.72; −0.000, 8.13; −0.008, 0.33 |
| 51 | 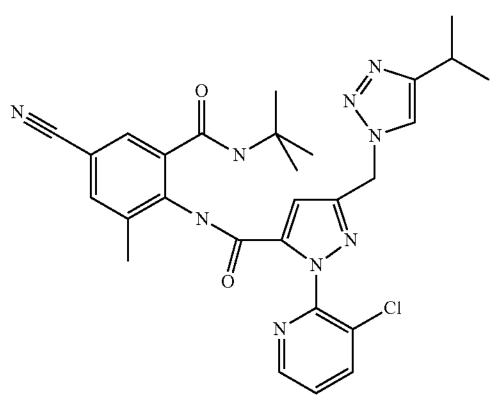 [SMILES: Cc1cc(C#N)cc(C(=O)NC(C)(C)C)c1NC(=O)c1cc(Cn2cc(C(C)C)nn2)nn1-c1ncccc1Cl] | 2.74 | 560/562 | 8.453, 0.47; 8.450, 0.50; 8.441, 0.50; 8.438, 0.50; 8.106, 0.41; 8.103, 0.41; 8.086, 0.45; 8.083, 0.41; 7.830, 1.05; 7.751, 0.64; 7.670, 0.59; 7.570, 0.47; 7.559, 0.69; 7.550, 0.48; 7.539, 0.45; 7.138, 0.76; 5.686, 0.52; 5.669, 2.11; 3.109, 67.79; 2.998, 0.37; 2.497, 11.43; 2.492, 21.24; 2.487, 28.16; 2.483, 20.60; 2.478, 10.69; 2.179, 2.77; 2.169, 0.80; 1.272, 0.68; 1.254, 5.58; 1.237, 16.00; 1.222, 2.87; 1.191, 0.93; 1.173, 0.89; −0.000, 2.35 |

-continued

| No. | Structure | logP | MH+ | NMR |
|---|---|---|---|---|
| 52 | 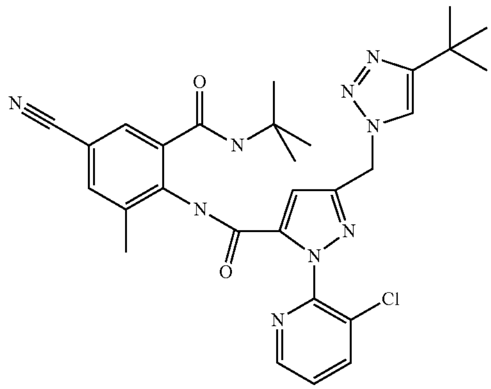 [SMILES: Cc1cc(C#N)cc(C(=O)NC(C)(C)C)c1NC(=O)c1cc(Cn2cc(C(C)(C)C)nn2)nn1-c1ncccc1Cl] | 3.02 | 574/576 | 8.454, 0.49; 8.450, 0.52; 8.442, 0.54; 8.439, 0.48; 8.107, 0.46; 8.104, 0.44; 8.087, 0.49; 8.083, 0.47; 7.829, 1.56; 7.746, 0.54; 7.674, 0.61; 7.571, 0.54; 7.559, 0.53; 7.550, 0.51; 7.539, 0.47; 7.140, 0.74; 5.661, 2.27; 3.110, 87.40; 3.086, 2.04; 2.497, 12.38; 2.492, 23.97; 2.488, 32.61; 2.483, 23.37; 2.478, 11.75; 2.178, 2.84; 1.340, 0.40; 1.292, 16.00; 1.272, 1.01; 1.252, 1.97; 1.235, 13.78; 1.217, 0.60; −0.000, 3.03 |
| 53 | 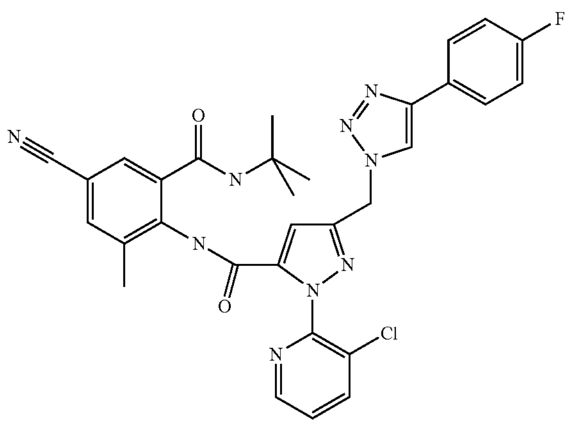 [SMILES: Cc1cc(C#N)cc(C(=O)NC(C)(C)C)c1NC(=O)c1cc(Cn2cc(-c3ccc(F)cc3)nn2)nn1-c1ncccc1Cl] | 3.17 | 612 | 8.581, 1.75; 8.453, 0.58; 8.449, 0.60; 8.441, 0.61; 8.437, 0.59; 8.105, 0.54; 8.101, 0.55; 8.085, 0.60; 8.081, 0.57; 7.909, 0.77; 7.896, 0.77; 7.887, 0.76; 7.879, 0.34; 7.873, 0.71; 7.744, 0.57; 7.662, 0.64; 7.570, 0.69; 7.559, 0.65; 7.550, 0.63; 7.538, 0.63; 7.278, 0.73; 7.256, 1.38; 7.233, 0.69; 7.169, 0.93; 5.793, 2.36; 3.109, 101.41; 3.087, 1.95; 2.552, 0.61; 2.526, 0.37; 2.510, 0.93; 2.497, 15.95; 2.492, 31.79; 2.488, 44.05; 2.483, 30.97; 2.478, 15.01; 2.290, 0.40; 2.236, 0.50; 2.172, 3.08; 1.272, 0.57; 1.254, 2.58; 1.224, 1.22; 1.212, 16.00; −0.000, 3.38 |
| 54 | 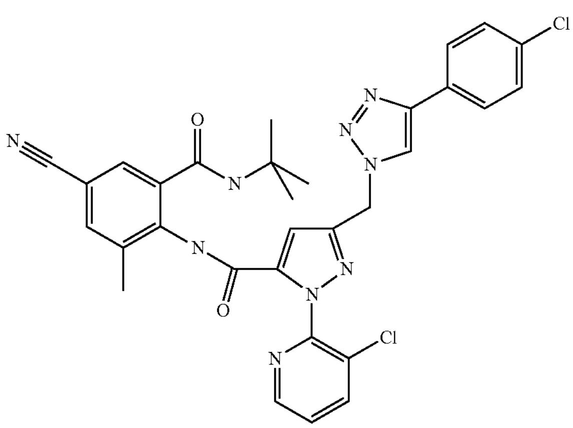 [SMILES: Cc1cc(C#N)cc(C(=O)NC(C)(C)C)c1NC(=O)c1cc(Cn2cc(-c3ccc(Cl)cc3)nn2)nn1-c1ncccc1Cl] | 3.54 | 628/630 | 8.637, 1.80; 8.452, 0.55; 8.448, 0.61; 8.440, 0.63; 8.436, 0.57; 8.104, 0.53; 8.100, 0.45; 8.084, 0.56; 8.080, 0.60; 7.887, 1.33; 7.882, 0.50; 7.871, 0.53; 7.866, 1.47; 7.743, 0.54; 7.660, 0.60; 7.570, 0.59; 7.558, 0.66; 7.549, 0.63; 7.538, 0.59; 7.508, 0.35; 7.502, 1.64; 7.497, 0.61; 7.485, 0.57; 7.480, 1.37; 7.170, 0.78; 5.800, 2.24; 3.109, 229.36; 3.085, 4.59; 2.661, 0.44; 2.657, 0.59; 2.652, 0.38; 2.552, 0.42; 2.526, 0.72; 2.510, 1.92; 2.497, 32.74; 2.492, 65.11; 2.487, 90.27; 2.483, 64.11; 2.478, 31.53; 2.319, 0.42; 2.314, 0.51; 2.310, 0.36; 2.171, 3.06; 2.040, 0.47; 1.272, 0.84; 1.252, 2.90; 1.222, 1.32; 1.212, 16.00; 0.008, 0.56; −0.000, 12.21; −0.009, 0.50 |

-continued
| No. | Structure | logP | MH+ | NMR |
|---|---|---|---|---|
| 55 | 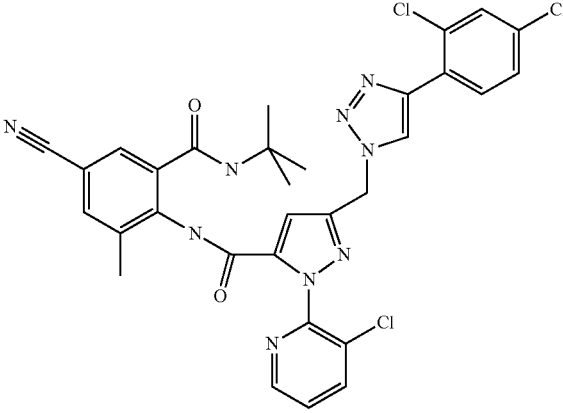 | 4.06 | 660/662 | 8.726, 1.70; 8.454, 0.56; 8.450, 0.59; 8.442, 0.65; 8.439, 0.57; 8.133, 1.02; 8.112, 1.12; 8.109, 0.63; 8.105, 0.64; 8.089, 0.62; 8.085, 0.59; 7.751, 0.68; 7.696, 0.81; 7.690, 0.87; 7.663, 0.76; 7.660, 0.68; 7.573, 0.68; 7.561, 0.65; 7.553, 0.68; 7.548, 0.79; 7.542, 0.98; 7.526, 0.76; 7.521, 0.71; 7.200, 1.21; 5.859, 2.40; 3.109, 121.75; 3.086, 2.76; 2.657, 0.36; 2.552, 0.47; 2.526, 0.48; 2.497, 19.54; 2.492, 38.41; 2.488, 52.73; 2.483, 37.61; 2.478, 18.69; 2.314, 0.33; 2.291, 1.27; 2.237, 0.38; 2.176, 3.37; 1.272, 0.69; 1.255, 4.99; 1.242, 1.38; 1.214, 16.00; −0.000, 4.41 |
| 56 | 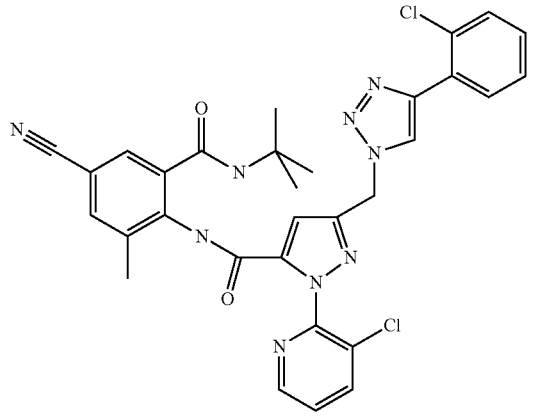 [SMILES: Cc1cc(C#N)cc(C(=O)NC(C)(C)C)c1NC(=O)c1cc(Cn2cc(-c3ccccc3Cl)nn2)nn1-c1ncccc1Cl] | 3.45 | 628/630 | 8.677, 1.63; 8.455, 0.55; 8.451, 0.65; 8.443, 0.61; 8.439, 0.55; 8.112, 0.53; 8.107, 0.89; 8.103, 0.63; 8.092, 0.54; 8.087, 0.80; 8.083, 0.57; 7.741, 0.52; 7.667, 0.63; 7.571, 0.63; 7.563, 0.51; 7.560, 1.02; 7.551, 0.64; 7.544, 0.62; 7.540, 1.00; 7.470, 0.41; 7.455, 0.58; 7.451, 0.54; 7.436, 0.45; 7.432, 0.41; 7.403, 0.58; 7.399, 0.51; 7.384, 0.49; 7.379, 0.47; 7.194, 0.64; 5.854, 2.28; 3.108, 220.20; 3.084, 4.99; 2.661, 0.46; 2.657, 0.59; 2.652, 0.41; 2.552, 0.55; 2.526, 0.77; 2.510, 1.96; 2.497, 34.13; 2.492, 68.35; 2.487, 94.95; 2.483, 67.13; 2.478, 32.74; 2.324, 0.33; 2.319, 0.43; 2.314, 0.52; 2.310, 0.38; 2.289, 0.40; 2.237, 0.37; 2.174, 2.89; 2.146, 0.38; 1.272, 0.73; 1.251, 4.33; 1.242, 2.01; 1.212, 16.00; 0.008, 0.35; −0.000, 8.93; −0.009, 0.35 |
| 57 | 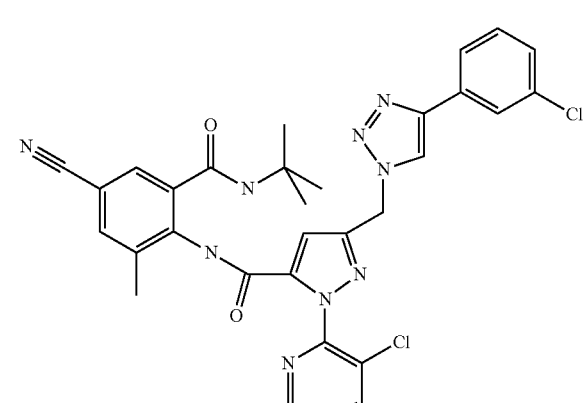 | 3.55 | 628/630 | 8.703, 1.85; 8.453, 0.55; 8.449, 0.60; 8.442, 0.63; 8.438, 0.57; 8.105, 0.51; 8.101, 0.51; 8.085, 0.56; 8.081, 0.55; 7.907, 0.48; 7.903, 0.81; 7.898, 0.53; 7.839, 0.47; 7.823, 0.41; 7.820, 0.50; 7.816, 0.40; 7.740, 0.55; 7.668, 0.62; 7.570, 0.62; 7.558, 0.62; 7.550, 0.61; 7.538, 0.59; 7.492, 0.48; 7.472, 0.92; 7.452, 0.54; 7.392, 0.40; 7.389, 0.44; 7.387, 0.43; 7.384, 0.41; 7.165, 0.77; 5.804, 2.34; 3.108, 103.30; 3.085, 2.41; 2.552, 0.33; 2.526, 0.44; 2.510, 1.02; 2.497, 17.15; 2.492, 33.79; 2.487, 46.46; 2.483, 32.80; 2.478, 16.04; 2.171, 3.05; 1.272, 0.55; 1.251, 2.07; 1.220, 2.01; 1.212, 16.00; −0.000, 3.52 |

-continued
| No. | Structure | logP | MH+ | NMR |
|---|---|---|---|---|
| 58 | 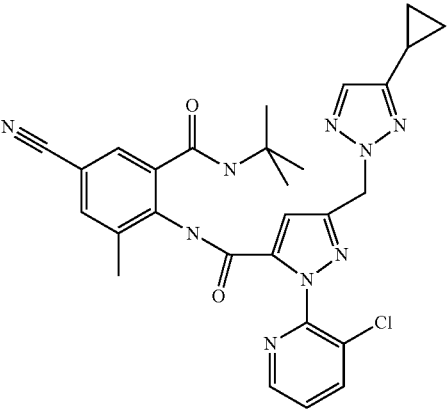 [SMILES: Cc1cc(C#N)cc(C(=O)NC(C)(C)C)c1NC(=O)c1cc(Cn2ncc(C3CC3)n2)nn1-c1ncccc1Cl] | 3.12 | 558 | 8.449, 0.57; 8.445, 0.56; 8.437, 0.57; 8.433, 0.57; 8.099, 0.50; 8.095, 0.52; 8.079, 0.57; 8.075, 0.55; 7.749, 0.56; 7.665, 0.61; 7.564, 0.57; 7.552, 0.59; 7.544, 0.59; 7.534, 1.71; 7.063, 0.67; 5.621, 2.66; 3.109, 110.27; 3.085, 2.19; 2.552, 0.37; 2.526, 0.33; 2.510, 0.88; 2.497, 15.21; 2.492, 30.14; 2.487, 41.69; 2.483, 29.72; 2.478, 14.69; 2.180, 3.04; 1.966, 0.40; 1.272, 0.99; 1.253, 1.17; 1.240, 16.00; 0.951, 0.72; 0.945, 0.78; 0.941, 0.38; 0.936, 0.42; 0.930, 0.76; 0.924, 0.72; 0.915, 0.33; 0.752, 0.35; 0.742, 0.77; 0.739, 0.55; 0.736, 0.82; 0.730, 0.80; 0.724, 0.76; −0.000, 4.54 |
| 59 | 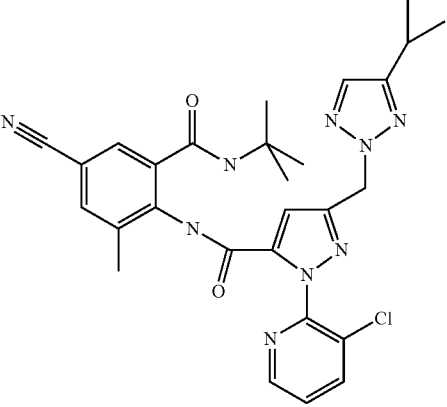 [SMILES: Cc1cc(C#N)cc(C(=O)NC(C)(C)C)c1NC(=O)c1cc(Cn2ncc(C(C)C)n2)nn1-c1ncccc1Cl] | 3.38 | 560 | 8.450, 0.57; 8.446, 0.60; 8.438, 0.59; 8.434, 0.54; 8.100, 0.46; 8.096, 0.50; 8.080, 0.50; 8.076, 0.48; 7.750, 0.46; 7.666, 0.55; 7.612, 1.37; 7.565, 0.54; 7.554, 0.50; 7.545, 0.48; 7.533, 0.47; 7.078, 0.41; 5.655, 2.53; 3.151, 0.45; 3.110, 181.39; 3.086, 3.62; 3.031, 0.38; 3.013, 0.49; 2.996, 0.37; 2.657, 0.38; 2.526, 0.45; 2.510, 1.30; 2.497, 21.73; 2.492, 42.74; 2.488, 58.76; 2.483, 42.04; 2.478, 21.04; 2.315, 0.35; 2.178, 2.64; 1.272, 1.33; 1.266, 6.70; 1.249, 6.95; 1.234, 16.00; −0.000, 6.07 |
| 60 | 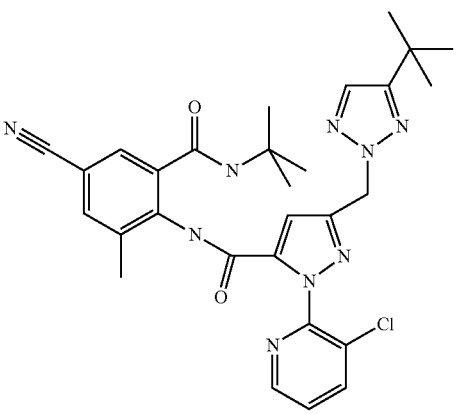 [SMILES: Cc1cc(C#N)cc(C(=O)NC(C)(C)C)c1NC(=O)c1cc(Cn2ncc(C(C)(C)C)n2)nn1-c1ncccc1Cl] | 3.74 | 574 | 8.451, 0.46; 8.447, 0.49; 8.439, 0.49; 8.436, 0.48; 8.102, 0.47; 8.099, 0.46; 8.082, 0.53; 8.078, 0.49; 7.755, 0.49; 7.752, 0.50; 7.668, 0.55; 7.664, 0.52; 7.636, 1.49; 7.567, 0.53; 7.556, 0.51; 7.547, 0.50; 7.535, 0.48; 7.074, 0.88; 5.656, 2.20; 3.111, 93.66; 2.552, 0.72; 2.510, 0.72; 2.497, 11.36; 2.492, 22.46; 2.488, 30.96; 2.483, 21.89; 2.478, 10.69; 2.291, 0.69; 2.236, 0.61; 2.179, 2.70; 1.304, 16.00; 1.272, 0.74; 1.256, 2.32; 1.234, 13.05; −0.000, 2.81 |

-continued

| No. | Structure | logP | MH+ | NMR |
|---|---|---|---|---|
| 61 | 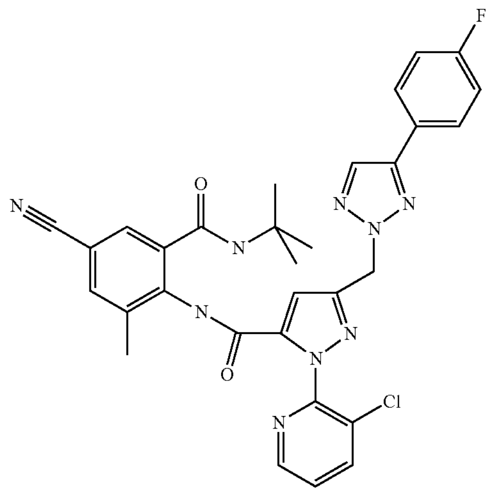 [SMILES: Cc1cc(C#N)cc(C(=O)NC(C)(C)C)c1NC(=O)c1cc(Cn2ncc(-c3ccc(F)cc3)n2)nn1-c1ncccc1Cl] | 3.72 | 612 | 8.447, 0.78; 8.435, 0.71; 8.257, 1.94; 8.091, 0.49; 8.072, 0.55; 7.917, 1.03; 7.907, 0.74; 7.903, 1.12; 7.896, 1.10; 7.882, 0.97; 7.678, 0.33; 7.667, 0.33; 7.579, 0.36; 7.559, 0.48; 7.547, 0.47; 7.539, 0.47; 7.528, 0.42; 7.296, 1.02; 7.274, 1.81; 7.253, 0.86; 5.786, 1.94; 3.217, 0.32; 3.111, 299.95; 2.657, 0.54; 2.553, 1.41; 2.538, 0.44; 2.526, 0.82; 2.497, 30.84; 2.493, 58.33; 2.488, 78.61; 2.484, 58.94; 2.316, 0.47; 2.237, 1.20; 2.159, 1.55; 1.269, 0.54; 1.229, 0.41; 1.195, 16.00; −0.000, 0.93 |
| 62 | 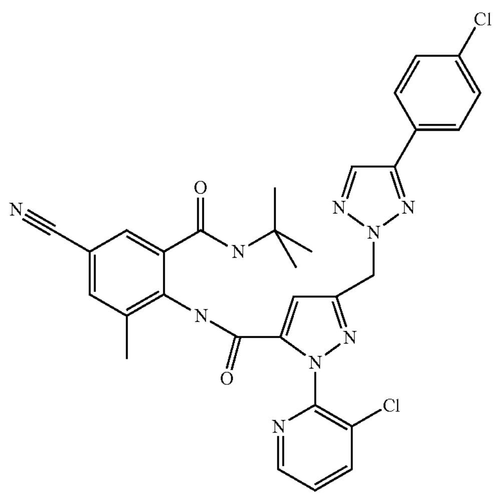 [SMILES: Cc1cc(C#N)cc(C(=O)NC(C)(C)C)c1NC(=O)c1cc(Cn2ncc(-c3ccc(Cl)cc3)n2)nn1-c1ncccc1Cl] | 4.06 | | 10.203, 0.60; 8.452, 0.56; 8.448, 0.60; 8.440, 0.61; 8.436, 0.57; 8.305, 1.90; 8.105, 0.55; 8.101, 0.58; 8.085, 0.59; 8.081, 0.58; 7.891, 1.33; 7.886, 0.48; 7.874, 0.51; 7.870, 1.47; 7.748, 0.67; 7.651, 0.71; 7.646, 0.66; 7.570, 0.63; 7.558, 0.61; 7.550, 0.55; 7.538, 0.55; 7.522, 1.43; 7.516, 0.49; 7.505, 0.49; 7.500, 1.27; 7.466, 0.51; 7.152, 1.37; 5.808, 2.52; 3.113, 145.87; 2.551, 0.76; 2.526, 0.38; 2.510, 0.99; 2.497, 15.31; 2.493, 29.94; 2.488, 41.00; 2.483, 29.15; 2.478, 14.41; 2.236, 0.63; 2.176, 3.33; 1.273, 0.40; 1.258, 0.40; 1.201, 16.00; −0.000, 0.93 |
| 63 | 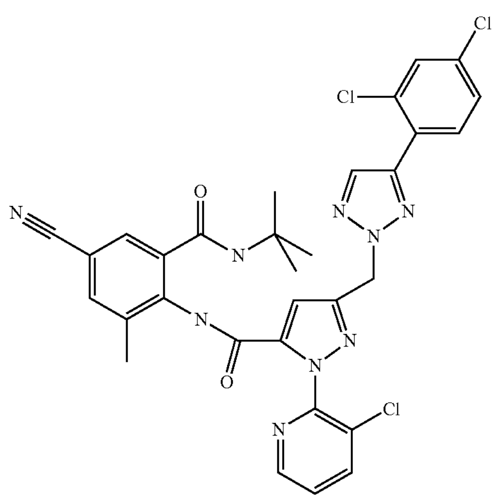 [SMILES: Cc1cc(C#N)cc(C(=O)NC(C)(C)C)c1NC(=O)c1cc(Cn2ncc(-c3ccc(Cl)cc3Cl)n2)nn1-c1ncccc1Cl] | 4.67 | 660/662 | 8.446, 0.75; 8.443, 0.75; 8.434, 0.74; 8.431, 0.75; 8.277, 2.05; 8.085, 0.45; 8.065, 0.50; 7.887, 1.58; 7.865, 1.78; 7.720, 1.58; 7.714, 1.64; 7.698, 0.39; 7.555, 0.47; 7.532, 1.44; 7.527, 1.33; 7.511, 1.07; 7.506, 0.96; 5.826, 1.65; 3.109, 157.99; 2.657, 0.36; 2.551, 1.17; 2.526, 0.66; 2.497, 22.10; 2.492, 42.26; 2.487, 57.13; 2.483, 40.96; 2.478, 20.55; 2.315, 0.35; 2.237, 1.02; 2.154, 1.28; 1.268, 0.78; 1.195, 16.00; −0.000, 2.63 |

-continued

| No. | Structure | logP | MH+ | NMR |
|---|---|---|---|---|
| 64 | 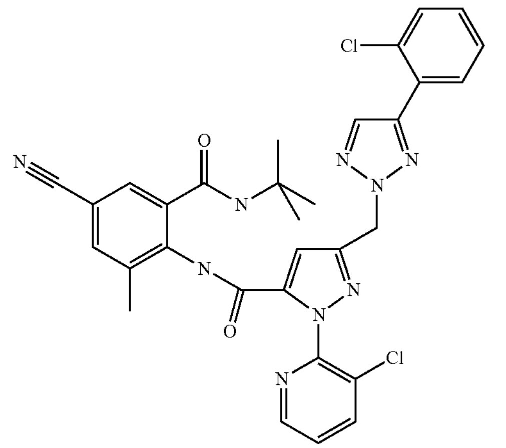 [SMILES: Cc1cc(C#N)cc(C(=O)NC(C)(C)C)c1NC(=O)c1cc(Cn2ncc(-c3ccccc3Cl)n2)nn1-c1ncccc1Cl] | 4.03 | 628/630 | |
| 65 | 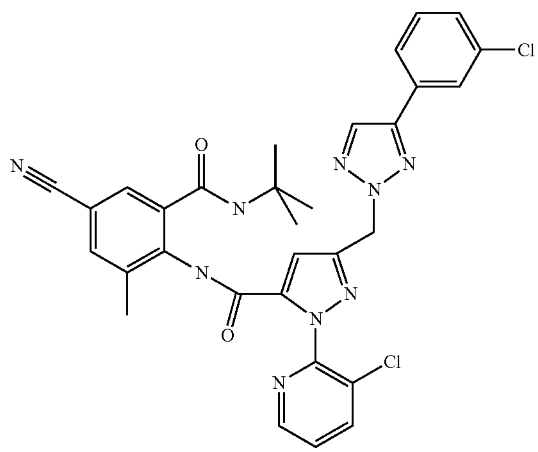 [SMILES: Cc1cc(C#N)cc(C(=O)NC(C)(C)C)c1NC(=O)c1cc(Cn2ncc(-c3cccc(Cl)c3)n2)nn1-c1ncccc1Cl] | 4.14 | 628/630 | 8.436, 0.84; 8.428, 0.82; 8.394, 0.39; 8.352, 1.83; 8.204, 0.46; 8.131, 0.43; 8.066, 0.60; 8.051, 0.65; 7.902, 1.37; 7.836, 0.89; 7.817, 0.96; 7.579, 0.53; 7.541, 0.48; 7.528, 0.54; 7.508, 0.88; 7.488, 1.32; 7.468, 0.90; 7.431, 0.97; 7.411, 0.50; 5.783, 1.63; 3.112, 253.40; 2.658, 0.53; 2.652, 0.40; 2.552, 2.25; 2.492, 55.71; 2.488, 72.75; 2.484, 54.80; 2.314, 0.44; 2.236, 2.04; 2.125, 1.25; 1.263, 0.51; 1.183, 16.00; 1.155, 0.36; −0.000, 0.96 |
| 66 | 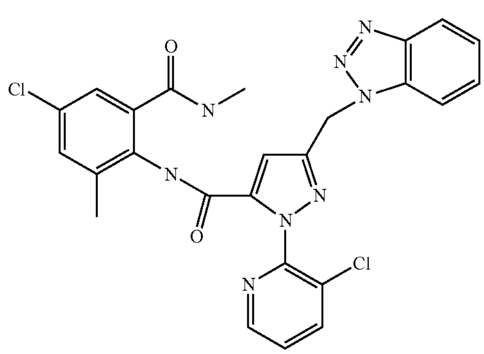 [SMILES: CNC(=O)c1cc(Cl)cc(C)c1NC(=O)c1cc(Cn2nnc3ccccc32)nn1-c1ncccc1Cl] | 2.38 | 535/537 | 10.01, 0.51; 8.44, 1.49; 8.44, 1.60; 8.43, 1.61; 8.43, 1.54; 8.09, 1.49; 8.09, 1.51; 8.07, 2.45; 8.07, 2.48; 8.05, 1.02; 8.05, 1.64; 8.04, 0.95; 7.95, 0.42; 7.87, 1.38; 7.85, 1.54; 7.58, 0.87; 7.57, 0.87; 7.56, 1.50; 7.56, 2.95; 7.55, 1.05; 7.54, 1.69; 7.54, 2.21; 7.52, 1.50; 7.44, 1.02; 7.43, 1.04; 7.42, 0.93; 7.42, 1.30; 7.41, 1.03; 7.40, 0.81; 7.40, 0.80; 7.38, 1.38; 7.37, 1.50; 7.30, 1.66; 7.29, 1.48; 7.12, 1.44; 6.09, 7.04; 3.60, 0.43; 3.11, 121.40; 2.66, 0.43; 2.65, 0.34; 2.63, 5.73; 2.62, 5.66; 2.53, 0.60; 2.51, 1.25; 2.50, 16.77; 2.49, 32.97; 2.49, 45.39; 2.48, 32.28; 2.48, 16.00; 2.10, 9.23; 1.76, 0.53; −0.00, 2.73 |

-continued

| No. | Structure | logP | MH+ | NMR |
|---|---|---|---|---|
| 67 | 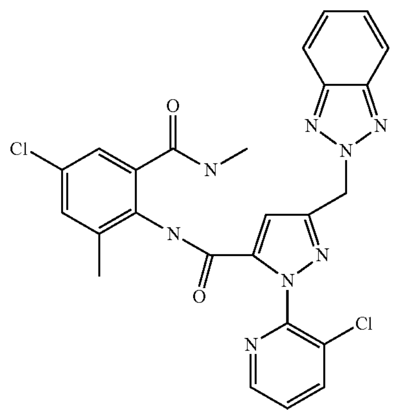 [SMILES: CNC(=O)c1cc(Cl)cc(C)c1NC(=O)c1cc(Cn2nc3ccccc3n2)nn1-c1ncccc1Cl] | 2.75 | 535/537 | 10.05, 0.67; 8.45, 0.77; 8.45, 0.80; 8.44, 0.80; 8.44, 0.77; 8.10, 0.79; 8.09, 0.81; 8.08, 0.86; 8.07, 0.78; 7.96, 0.42; 7.96, 0.45; 7.95, 1.69; 7.94, 1.21; 7.93, 1.09; 7.93, 1.55; 7.56, 0.86; 7.55, 0.93; 7.54, 0.85; 7.53, 0.77; 7.47, 1.63; 7.46, 1.13; 7.45, 1.18; 7.44, 1.48; 7.39, 0.73; 7.38, 0.87; 7.30, 0.88; 7.30, 0.76; 7.20, 1.02; 6.09, 3.67; 3.10, 85.78; 2.70, 0.33; 2.69, 0.37; 2.66, 0.43; 2.64, 3.00; 2.63, 2.94; 2.53, 0.63; 2.51, 1.23; 2.50, 16.99; 2.49, 33.45; 2.49, 45.98; 2.48, 32.54; 2.48, 16.00; 2.22, 0.46; 2.12, 4.71; 1.09, 0.48; −0.00, 5.63 |
| 68 | 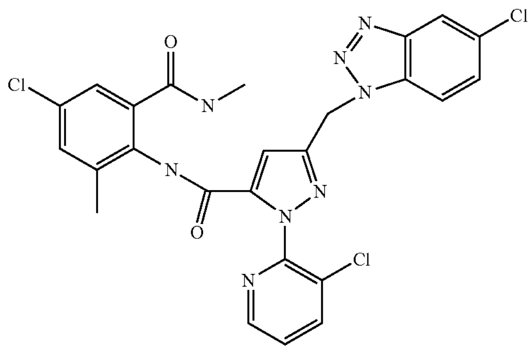 [SMILES: CNC(=O)c1cc(Cl)cc(C)c1NC(=O)c1cc(Cn2nnc3cc(Cl)ccc32)nn1-c1ncccc1Cl] | 2.9 | 567/569 | 10.03, 0.60; 8.45, 1.52; 8.44, 1.99; 8.44, 1.69; 8.44, 1.79; 8.43, 2.00; 8.43, 1.38; 8.18, 1.31; 8.18, 1.39; 8.17, 1.42; 8.17, 1.30; 8.10, 1.92; 8.10, 2.14; 8.10, 1.93; 8.10, 1.65; 8.09, 1.47; 8.09, 1.58; 8.08, 3.45; 8.08, 1.77; 8.07, 1.52; 8.07, 1.37; 8.03, 1.67; 8.03, 1.75; 7.96, 1.02; 7.95, 1.01; 7.93, 1.57; 7.91, 1.56; 7.60, 1.41; 7.60, 1.36; 7.58, 1.25; 7.58, 1.25; 7.56, 1.74; 7.56, 1.61; 7.55, 1.72; 7.55, 1.63; 7.54, 1.69; 7.54, 1.45; 7.53, 1.55; 7.53, 1.35; 7.45, 1.54; 7.44, 1.51; 7.42, 1.43; 7.42, 1.46; 7.38, 2.58; 7.38, 2.88; 7.30, 3.10; 7.30, 2.71; 7.14, 1.84; 7.13, 1.64; 6.11, 5.89; 6.10, 6.64; 3.11, 127.15; 2.66, 0.41; 2.66, 0.58; 2.64, 8.71; 2.63, 8.58; 2.53, 1.12; 2.50, 17.45; 2.49, 33.78; 2.49, 46.09; 2.48, 32.53; 2.48, 16.00; 2.39, 1.15; 2.29, 1.06; 2.18, 0.51; 2.11, 10.86; 2.08, 1.91; 1.36, 2.58; −0.00, 1.13 |
| 69 | 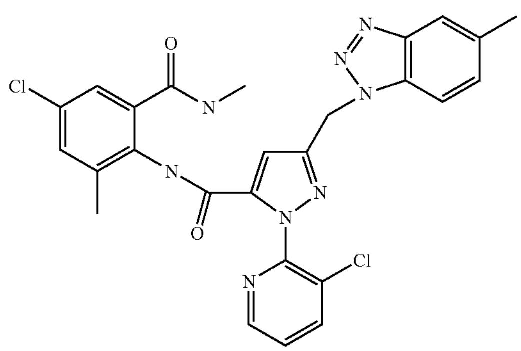 [SMILES: CNC(=O)c1cc(Cl)cc(C)c1NC(=O)c1cc(Cn2nnc3cc(C)ccc32)nn1-c1ncccc1Cl] | 2.63 | 549/551 | 10.02, 0.73; 8.45, 1.05; 8.44, 1.37; 8.44, 1.09; 8.44, 1.22; 8.43, 1.39; 8.43, 0.94; 8.10, 1.01; 8.09, 1.08; 8.09, 0.93; 8.09, 0.87; 8.08, 1.16; 8.07, 1.15; 8.07, 1.02; 8.07, 0.91; 7.95, 0.67; 7.94, 0.70; 7.93, 1.33; 7.91, 1.06; 7.81, 0.93; 7.74, 0.73; 7.72, 0.81; 7.62, 1.20; 7.56, 1.20; 7.56, 1.01; 7.55, 1.23; 7.55, 1.08; 7.54, 1.21; 7.54, 0.98; 7.53, 1.08; 7.53, 0.89; 7.40, 0.69; 7.39, 0.71; 7.38, 1.84; 7.38, 2.43; 7.30, 2.09; 7.29, 1.84; 7.26, 0.80; 7.25, 0.78; 7.24, 0.74; 7.23, 0.73; 7.10, 1.97; 6.04, 3.74; 6.02, 4.58; 3.60, 0.34; 3.11, 162.99; 2.66, 0.41; 2.65, 0.35; 2.63, 6.26; 2.62, 6.10; 2.53, 1.10; 2.51, 1.34; 2.50, 16.31; 2.49, 31.75; 2.49, 44.44; 2.48, 35.69; 2.48, 16.00; 2.47, 5.99; 2.12, 0.61; 2.10, 8.30; 1.76, 0.37; 1.60, 0.81; 1.09, 0.32; −0.00, 1.65 |
| 70 | 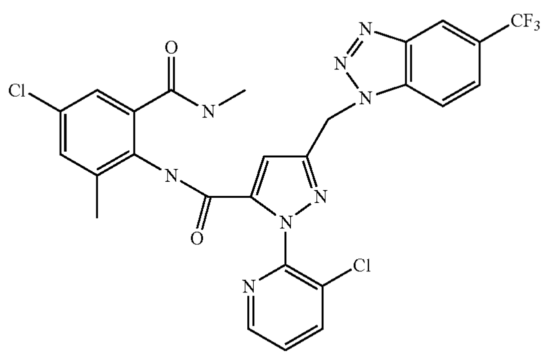 [SMILES: CNC(=O)c1cc(Cl)cc(C)c1NC(=O)c1cc(Cn2nnc3cc(C(F)(F)F)ccc32)nn1-c1ncccc1Cl] | 3.13 | 603/605 | 8.53, 0.52; 8.44, 0.65; 8.44, 0.72; 8.43, 0.65; 8.42, 0.67; 8.40, 0.51; 8.32, 0.35; 8.29, 0.38; 8.13, 0.38; 8.11, 0.41; 8.09, 0.53; 8.09, 0.71; 8.09, 0.57; 8.07, 0.58; 8.07, 0.76; 8.06, 0.58; 7.96, 0.34; 7.89, 0.37; 7.88, 0.36; 7.87, 0.33; 7.72, 0.32; 7.56, 0.97; 7.54, 0.97; 7.54, 0.92; 7.52, 0.88; 7.38, 0.88; 7.38, 0.98; 7.30, 1.06; 7.30, 0.91; 7.16, 0.60; 7.15, 0.59; 6.23, 1.90; 6.19, 2.03; 3.11, 185.62; 2.66, 0.39; 2.63, 3.24; 2.62, 3.19; 2.53, 1.07; 2.51, 1.32; 2.50, 17.12; 2.49, 33.40; 2.49, 45.75; 2.48, 32.41; 2.48, 16.00; 2.39, 0.74; 2.29, 0.46; 2.10, 5.50; 1.36, 0.69; −0.00, 1.08 |

-continued

| No. | Structure | logP | MH+ | NMR |
|---|---|---|---|---|
| 71 | 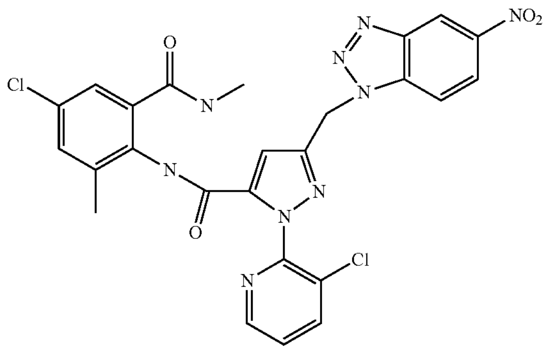 [SMILES: CNC(=O)c1cc(Cl)cc(C)c1NC(=O)c1cc(Cn2nnc3cc([N+](=O)[O-])ccc32)nn1-c1ncccc1Cl] | 2.64 | 580/582 | 10.04, 0.33; 9.02, 0.91; 9.02, 0.98; 8.96, 0.75; 8.96, 0.76; 8.44, 1.43; 8.43, 1.52; 8.42, 1.54; 8.42, 1.61; 8.41, 0.92; 8.40, 1.00; 8.39, 0.95; 8.33, 0.60; 8.33, 0.59; 8.31, 0.93; 8.31, 0.90; 8.24, 0.79; 8.23, 0.79; 8.22, 0.50; 8.21, 0.48; 8.14, 1.09; 8.11, 0.93; 8.09, 0.81; 8.09, 1.54; 8.08, 1.03; 8.07, 0.89; 8.07, 1.63; 8.06, 1.01; 7.97, 0.94; 7.97, 0.55; 7.55, 1.65; 7.54, 1.55; 7.53, 1.47; 7.52, 1.44; 7.39, 1.48; 7.38, 1.68; 7.31, 1.70; 7.30, 1.50; 7.19, 1.49; 6.29, 2.83; 6.22, 3.92; 5.69, 1.19; 4.05, 0.78; 4.03, 0.77; 3.60, 0.70; 3.40, 0.40; 3.38, 0.43; 3.11, 84.11; 2.66, 0.34; 2.66, 0.48; 2.65, 0.45; 2.64, 3.72; 2.63, 3.27; 2.63, 3.94; 2.62, 2.76; 2.53, 1.07; 2.51, 1.31; 2.50, 17.21; 2.49, 33.48; 2.49, 45.75; 2.48, 32.36; 2.48, 16.00; 2.39, 0.85; 2.29, 0.76; 2.18, 0.58; 2.11, 9.50; 1.97, 3.38; 1.76, 0.82; 1.36, 4.96; 1.19, 0.94; 1.18, 1.81; 1.16, 0.89; 1.11, 0.41; 1.09, 0.82; 1.07, 0.41; −0.00, 1.73 |
| 72 | 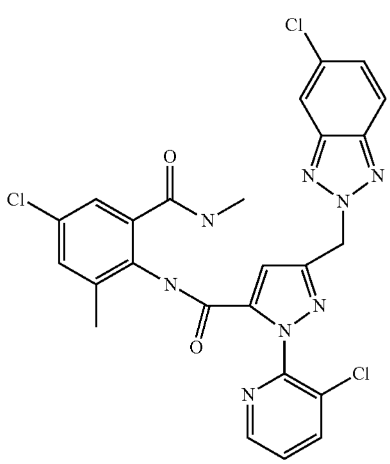 | 3.28 | 567/569 | 8.45, 0.93; 8.45, 0.95; 8.44, 0.98; 8.43, 0.92; 8.10, 0.92; 8.09, 0.99; 8.08, 1.12; 8.08, 1.97; 8.07, 1.08; 8.02, 1.13; 8.02, 1.07; 8.00, 1.32; 7.99, 1.26; 7.97, 0.44; 7.97, 0.35; 7.56, 1.01; 7.55, 1.00; 7.54, 0.97; 7.53, 0.93; 7.47, 1.02; 7.47, 1.02; 7.45, 0.93; 7.44, 0.92; 7.39, 0.93; 7.39, 1.01; 7.31, 1.06; 7.30, 0.95; 7.20, 1.11; 6.11, 4.18; 3.15, 0.79; 3.11, 180.29; 2.66, 0.37; 2.65, 3.63; 2.64, 3.56; 2.53, 1.25; 2.51, 1.18; 2.50, 16.67; 2.49, 32.84; 2.49, 45.15; 2.48, 32.14; 2.48, 16.00; 2.12, 5.81; 2.04, 0.42; −0.00, 3.02 |
| 73 | 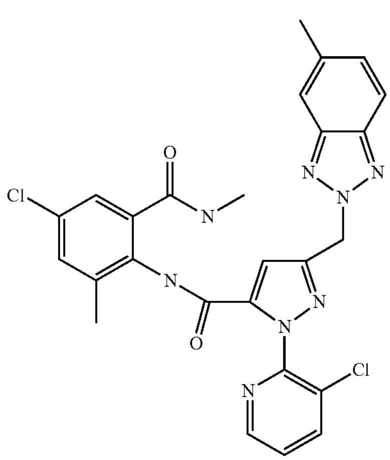 [SMILES: CNC(=O)c1cc(Cl)cc(C)c1NC(=O)c1cc(Cn2nc3ccc(C)cc3n2)nn1-c1ncccc1Cl] | 3.05 | 549/551 | 8.45, 0.64; 8.45, 0.66; 8.44, 0.67; 8.43, 0.65; 8.09, 0.61; 8.09, 0.61; 8.07, 0.67; 8.07, 0.62; 7.97, 0.33; 7.83, 0.61; 7.80, 0.66; 7.68, 0.76; 7.56, 0.69; 7.55, 0.70; 7.54, 0.60; 7.53, 0.62; 7.38, 0.58; 7.38, 0.68; 7.30, 1.12; 7.30, 1.17; 7.28, 0.50; 7.28, 0.49; 7.17, 0.67; 6.04, 2.91; 3.11, 169.92; 2.66, 0.32; 2.66, 0.42; 2.64, 2.52; 2.63, 2.44; 2.53, 1.28; 2.50, 17.24; 2.49, 33.51; 2.49, 45.83; 2.48, 32.39; 2.48, 16.00; 2.46, 3.86; 2.12, 4.07; −0.00, 0.73 |

-continued
| No. | Structure | logP | MH+ | NMR |
|---|---|---|---|---|
| 74 | 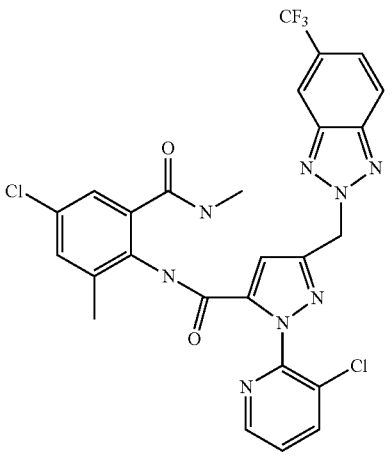 [SMILES: CNC(=O)c1cc(Cl)cc(C)c1NC(=O)c1cc(Cn2nc3ccc(C(F)(F)F)cc3n2)nn1-c1ncccc1Cl] | 3.48 | 603/605 | 10.05, 0.83; 8.47, 1.01; 8.45, 0.93; 8.45, 0.93; 8.44, 0.98; 8.44, 0.93; 8.22, 0.77; 8.20, 0.84; 8.10, 0.93; 8.10, 0.92; 8.08, 1.04; 8.08, 0.93; 7.98, 0.37; 7.97, 0.35; 7.97, 0.35; 7.72, 0.74; 7.71, 0.72; 7.69, 0.68; 7.69, 0.64; 7.56, 0.97; 7.55, 0.97; 7.54, 0.95; 7.53, 0.90; 7.39, 0.88; 7.39, 0.95; 7.31, 1.06; 7.30, 0.93; 7.22, 1.00; 6.20, 3.89; 3.57, 0.48; 3.11, 137.89; 2.66, 0.33; 2.66, 0.48; 2.65, 3.53; 2.63, 3.48; 2.53, 1.10; 2.51, 1.35; 2.50, 17.47; 2.49, 33.91; 2.49, 46.25; 2.48, 32.61; 2.48, 16.00; 2.18, 0.46; 2.12, 5.47; 1.60, 0.40; 1.36, 4.23; −0.00, 1.74 |
| 75 | 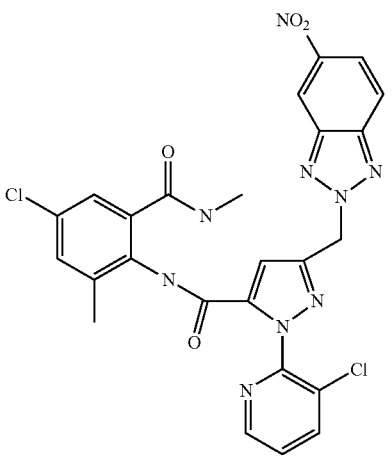 [SMILES: CNC(=O)c1cc(Cl)cc(C)c1NC(=O)c1cc(Cn2nc3ccc([N+](=O)[O-])cc3n2)nn1-c1ncccc1Cl] | 2.95 | 580/582 | 8.99, 0.33; 8.22, 0.75; 8.22, 0.90; 6.23, 0.98; 3.11, 180.54; 2.65, 1.03; 2.64, 0.90; 2.53, 0.84; 2.51, 1.30; 2.50, 16.97; 2.49, 33.06; 2.49, 45.30; 2.48, 32.21; 2.48, 16.00; 2.12, 1.36; 0.01, 0.47; −0.00, 9.18; −0.01, 0.36 |
| 76 | 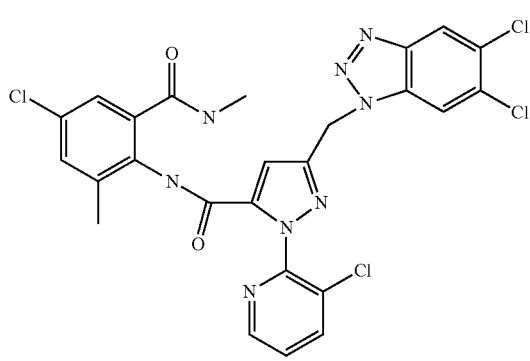 [SMILES: CNC(=O)c1cc(Cl)cc(C)c1NC(=O)c1cc(Cn2nnc3cc(Cl)c(Cl)cc32)nn1-c1ncccc1Cl] | 3.33 | | 10.155, 27.78; 8.535, 66.39; 8.464, 22.95; 8.460, 24.99; 8.452, 25.56; 8.448, 24.54; 8.404, 56.11; 8.196, 11.51; 8.184, 11.50; 8.147, 18.32; 8.144, 18.69; 8.127, 20.45; 8.124, 19.47; 7.588, 18.57; 7.577, 18.35; 7.568, 17.70; 7.556, 17.36; 7.434, 20.66; 7.429, 22.16; 7.301, 24.63; 7.295, 22.85; 7.180, 45.07; 6.167, 67.63; 3.422, 5.40; 3.322, 6683.80; 3.299, 23.30; 3.272, 14.21; 2.679, 3.23; 2.675, 6.56; 2.670, 9.17; 2.666, 6.87; 2.661, 3.47; 2.619, 76.86; 2.607, 77.50; 2.524, 20.14; 2.510, 509.60; 2.506, 1107.97; 2.501, 1541.83; 2.497, 1113.33; 2.492, 512.23; 2.455, 5.74; 2.451, 5.88; 2.333, 6.81; 2.328, 9.37; 2.323, 7.05; 2.319, 3.51; 2.105, 105.66; 2.074, 26.92; 0.008, 5.20; −0.000, 169.43; −0.008, 5.69 |

| No. | Structure | logP | MH+ | NMR |
|---|---|---|---|---|
| 77 | 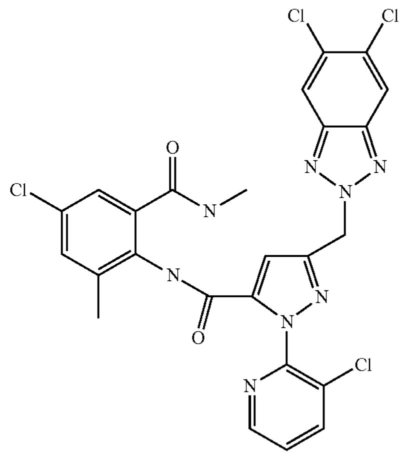 [SMILES: CNC(=O)c1cc(Cl)cc(C)c1NC(=O)c1cc(Cn2nc3cc(Cl)c(Cl)cc3n2)nn1-c1ncccc1Cl] | 3.73 | | |
| 78 | 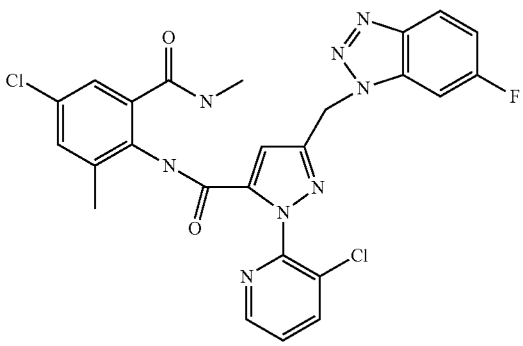 [SMILES: CNC(=O)c1cc(Cl)cc(C)c1NC(=O)c1cc(Cn2nnc3ccc(F)cc32)nn1-c1ncccc1Cl] | 2.57 | 553/555 | 10.025, 0.92; 8.446, 0.85; 8.442, 1.24; 8.439, 0.92; 8.434, 0.93; 8.431, 1.22; 8.427, 0.67; 8.130, 0.39; 8.120, 0.43; 8.109, 0.47; 8.095, 1.08; 8.091, 1.05; 8.087, 0.65; 8.075, 0.89; 8.071, 1.06; 8.067, 0.63; 7.956, 0.55; 7.946, 0.56; 7.940, 0.61; 7.928, 0.46; 7.916, 0.42; 7.905, 0.37; 7.871, 0.36; 7.866, 0.37; 7.848, 0.35; 7.844, 0.36; 7.730, 0.51; 7.725, 0.51; 7.708, 0.46; 7.703, 0.47; 7.560, 0.88; 7.558, 0.80; 7.549, 0.87; 7.547, 0.78; 7.540, 0.83; 7.538, 0.71; 7.529, 0.79; 7.526, 0.67; 7.477, 0.51; 7.471, 0.47; 7.384, 1.41; 7.379, 1.39; 7.323, 0.38; 7.317, 0.38; 7.304, 1.63; 7.299, 1.74; 7.277, 0.33; 7.144, 0.88; 7.135, 0.76; 6.106, 2.61; 6.087, 0.95; 6.072, 3.10; 3.113, 291.78; 2.657, 0.48; 2.649, 1.06; 2.638, 5.24; 2.626, 4.54; 2.526, 1.30; 2.510, 1.42; 2.497, 17.26; 2.493, 33.18; 2.488, 45.06; 2.483, 32.09; 2.479, 16.00; 2.123, 1.31; 2.108, 6.29; 2.039, 0.42; 1.762, 0.33; −0.000, 5.17 |
| 79 | 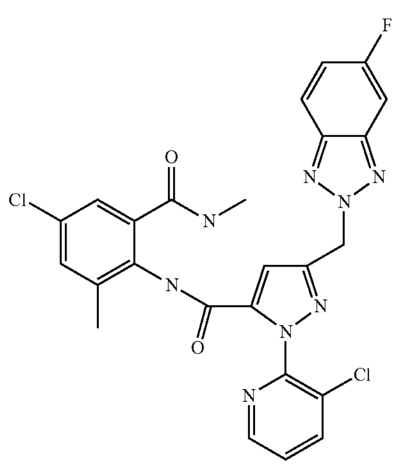 [SMILES: CNC(=O)c1cc(Cl)cc(C)c1NC(=O)c1cc(Cn2nc3ccc(F)cc3n2)nn1-c1ncccc1Cl] | 2.89 | | |

| No. | Structure | logP | MH+ | NMR |
|---|---|---|---|---|
| 80 | 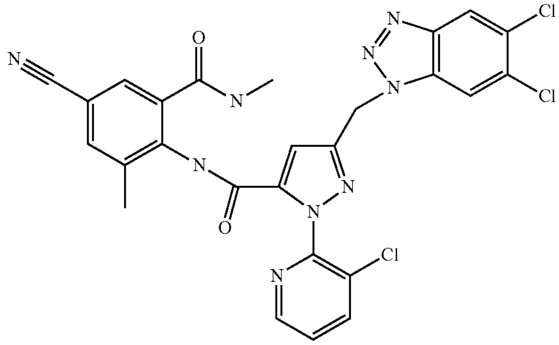 [SMILES: CNC(=O)c1cc(C#N)cc(C)c1NC(=O)c1cc(Cn2nnc3cc(Cl)c(Cl)cc32)nn1-c1ncccc1Cl] | 2.96 | 592/594 | 10.419, 4.17; 8.536, 8.12; 8.536, 9.11; 8.468, 3.29; 8.464, 3.73; 8.456, 3.67; 8.452, 3.62; 8.407, 8.79; 8.328, 0.57; 8.317, 1.77; 8.305, 1.73; 8.294, 0.55; 8.154, 3.21; 8.150, 3.40; 8.133, 3.62; 8.130, 3.48; 7.842, 3.31; 7.839, 3.52; 7.721, 3.83; 7.718, 3.63; 7.594, 3.52; 7.582, 3.30; 7.574, 3.32; 7.562, 3.28; 7.209, 5.02; 6.176, 10.63; 3.427, 0.78; 3.425, 0.91; 3.365, 0.52; 3.347, 2.48; 3.346, 2.59; 3.345, 2.84; 3.325, 1186.84; 3.306, 3.33; 3.304, 3.10; 3.304, 3.07; 3.303, 3.07; 3.302, 3.14; 3.302, 3.17; 3.286, 1.07; 3.275, 1.09; 2.675, 0.71; 2.670, 1.05; 2.666, 0.75; 2.630, 10.96; 2.618, 10.97; 2.524, 2.21; 2.519, 3.26; 2.510, 51.80; 2.506, 114.50; 2.501, 161.17; 2.497, 116.36; 2.492, 53.20; 2.333, 0.70; 2.328, 1.01; 2.324, 0.75; 2.158, 16.00; 0.008, 0.88; −0.000, 28.04; −0.008, 0.86 |
| 81 | 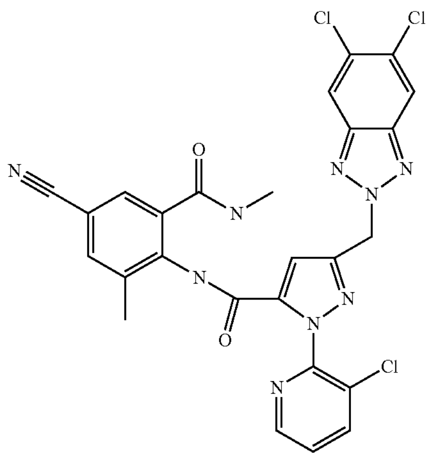 [SMILES: CNC(=O)c1cc(C#N)cc(C)c1NC(=O)c1cc(Cn2nc3cc(Cl)c(Cl)cc3n2)nn1-c1ncccc1Cl] | 3.35 | | |
| 82 | 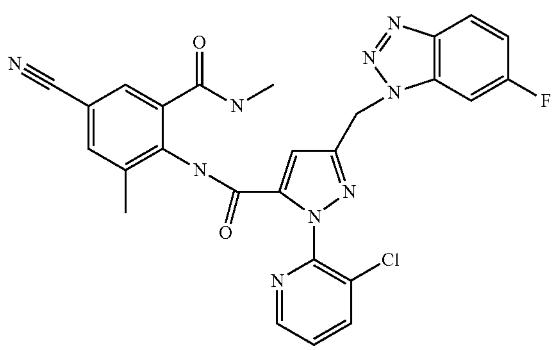 [SMILES: CNC(=O)c1cc(C#N)cc(C)c1NC(=O)c1cc(Cn2nnc3ccc(F)cc32)nn1-c1ncccc1Cl] | 2.24 | 544 | 10.416, 3.22; 8.469, 2.67; 8.465, 4.87; 8.461, 2.89; 8.457, 3.07; 8.453, 5.00; 8.449, 2.64; 8.310, 1.60; 8.300, 1.58; 8.180, 1.54; 8.168, 1.67; 8.156, 1.77; 8.149, 2.31; 8.145, 4.57; 8.141, 2.15; 8.129, 2.23; 8.125, 3.20; 8.120, 1.97; 8.002, 1.28; 7.991, 1.37; 7.979, 1.43; 7.968, 1.40; 7.955, 1.46; 7.950, 1.46; 7.932, 1.49; 7.927, 1.46; 7.839, 4.32; 7.835, 4.95; 7.819, 1.73; 7.813, 1.58; 7.719, 4.22; 7.592, 2.33; 7.590, 2.29; 7.580, 2.35; 7.578, 2.28; 7.572, 2.33; 7.570, 2.26; 7.565, 1.57; 7.560, 2.98; 7.542, 2.07; 7.536, 1.92; 7.519, 1.04; 7.513, 0.96; 7.374, 1.16; 7.368, 1.07; 7.351, 2.06; 7.345, 1.89; 7.328, 1.18; 7.322, 1.01; 7.212, 2.49; 7.204, 2.35; 6.163, 6.81; 6.123, 7.60; 3.320, 221.12; 3.296, 1.04; 2.670, 0.66; 2.665, 0.50; 2.626, 15.34; 2.615, 15.37; 2.523, 1.49; 2.510, 32.54; 2.506, 71.51; 2.501, 100.05; 2.496, 72.62; 2.492, 33.66; 2.332, 0.48; 2.328, 0.64; 2.323, 0.48; 2.154, 16.00; 2.074, 2.07; 0.008, 0.75; −0.000, 24.39; −0.008, 0.80 |

| No. | Structure | logP | MH+ | NMR |
|---|---|---|---|---|
| 83 | 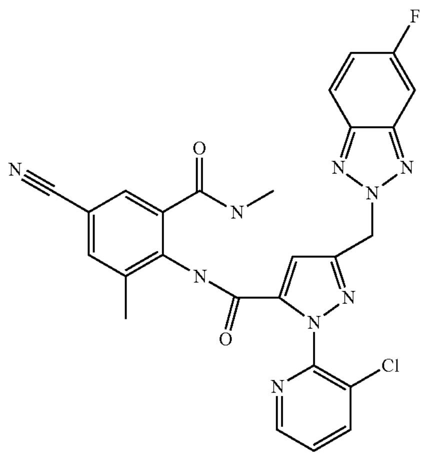 [SMILES: CNC(=O)c1cc(C#N)cc(C)c1NC(=O)c1cc(Cn2nc3ccc(F)cc3n2)nn1-c1ncccc1Cl] | 2.55 | | |
| 84 | 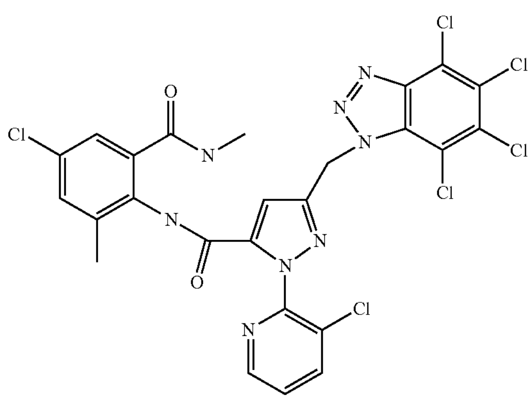 [SMILES: CNC(=O)c1cc(Cl)cc(C)c1NC(=O)c1cc(Cn2nnc3c(Cl)c(Cl)c(Cl)c(Cl)c32)nn1-c1ncccc1Cl] | 4.19 | 674 | 10.005, 0.53; 8.423, 0.72; 8.419, 0.89; 8.411, 0.91; 8.407, 0.82; 8.071, 0.73; 8.067, 0.80; 8.051, 0.79; 8.047, 0.80; 8.024, 0.57; 8.001, 0.60; 7.985, 0.34; 7.975, 1.03; 7.541, 0.89; 7.529, 0.76; 7.521, 0.75; 7.509, 0.78; 7.392, 0.64; 7.386, 0.74; 7.310, 0.84; 7.304, 0.73; 7.115, 0.81; 7.110, 0.66; 7.093, 0.63; 6.339, 3.18; 6.211, 0.87; 6.103, 0.79; 4.064, 0.52; 4.046, 1.47; 4.029, 1.46; 4.011, 0.47; 3.835, 2.70; 3.121, 880.11; 3.096, 49.70; 2.671, 0.88; 2.667, 0.57; 2.662, 1.31; 2.658, 1.51; 2.653, 1.08; 2.645, 2.68; 2.634, 2.81; 2.527, 1.74; 2.511, 3.12; 2.506, 4.56; 2.498, 65.14; 2.493, 133.94; 2.488, 188.76; 2.484, 132.78; 2.479, 64.15; 2.324, 0.37; 2.320, 0.82; 2.315, 1.09; 2.310, 0.74; 2.182, 0.93; 2.113, 4.40; 2.076, 0.64; 2.041, 16.00; 1.974, 6.34; 1.901, 1.58; 1.245, 0.90; 1.195, 1.84; 1.177, 3.62; 1.159, 1.90; 1.153, 0.82; 0.895, 0.35; 0.008, 0.45; −0.000, 12.07 |
| 85 | 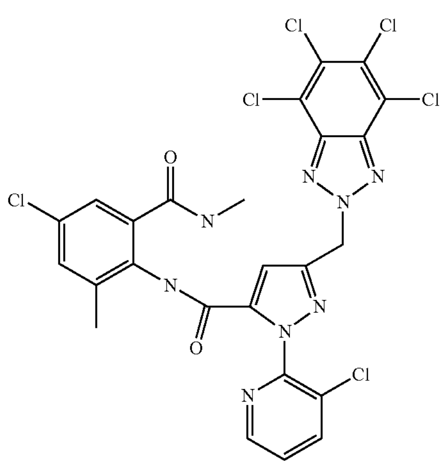 [SMILES: CNC(=O)c1cc(Cl)cc(C)c1NC(=O)c1cc(Cn2nc3c(Cl)c(Cl)c(Cl)c(Cl)c3n2)nn1-c1ncccc1Cl] | 4.66 | 670/672 | 10.087, 1.94; 8.453, 2.85; 8.450, 3.24; 8.442, 3.17; 8.438, 3.24; 8.105, 2.94; 8.101, 3.08; 8.085, 3.38; 8.081, 3.26; 7.994, 0.86; 7.983, 0.92; 7.974, 0.78; 7.970, 0.47; 7.571, 3.51; 7.559, 3.30; 7.551, 3.33; 7.539, 3.21; 7.398, 2.25; 7.393, 2.69; 7.315, 2.81; 7.309, 2.60; 7.280, 2.13; 6.227, 11.38; 6.211, 0.54; 3.370, 0.96; 3.251, 0.34; 3.236, 0.35; 3.231, 0.40; 3.221, 0.43; 3.120, 1030.74; 2.660, 10.91; 2.653, 2.37; 2.648, 10.87; 2.631, 0.67; 2.527, 4.65; 2.518, 1.69; 2.511, 3.52; 2.506, 4.73; 2.498, 66.89; 2.493, 138.44; 2.489, 195.63; 2.484, 135.67; 2.479, 64.01; 2.325, 0.34; 2.320, 0.78; 2.316, 1.16; 2.311, 0.76; 2.306, 0.35; 2.133, 16.00; 2.117, 0.37; 2.037, 0.40; 1.901, 0.74; 1.404, 0.77; 1.363, 1.50; 1.245, 0.63; 0.895, 0.38; −0.000, 2.44 |

| No. | Structure | logP | MH+ | NMR |
|---|---|---|---|---|
| 86 | 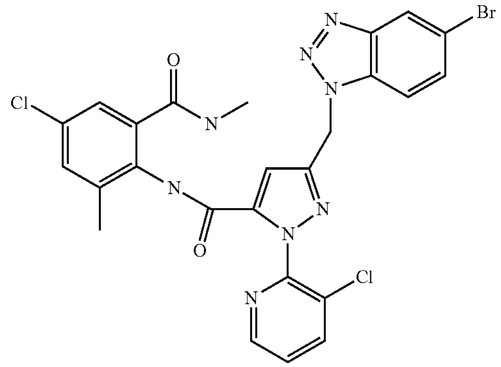 [SMILES: CNC(=O)c1cc(Cl)cc(C)c1NC(=O)c1cc(Cn2nnc3cc(Br)ccc32)nn1-c1ncccc1Cl] | 2.94 | 615 | 8.447, 2.61; 8.443, 2.83; 8.435, 3.01; 8.431, 2.89; 8.429, 1.14; 8.425, 0.84; 8.332, 0.73; 8.328, 0.74; 8.187, 2.94; 8.184, 3.04; 8.100, 2.50; 8.096, 2.60; 8.088, 0.83; 8.084, 0.88; 8.080, 2.82; 8.076, 2.76; 8.068, 0.86; 8.064, 0.79; 8.042, 3.08; 8.040, 3.17; 8.019, 3.54; 8.018, 3.53; 7.992, 0.64; 7.989, 0.67; 7.972, 0.41; 7.881, 0.70; 7.858, 0.82; 7.712, 0.83; 7.707, 0.79; 7.690, 0.65; 7.686, 0.63; 7.561, 3.59; 7.560, 3.71; 7.555, 3.71; 7.550, 2.99; 7.544, 1.19; 7.541, 3.03; 7.538, 3.12; 7.533, 2.96; 7.529, 2.89; 7.524, 0.91; 7.380, 2.62; 7.374, 2.99; 7.308, 3.47; 7.302, 2.99; 7.126, 2.45; 6.110, 3.36; 6.101, 11.49; 3.224, 0.40; 3.124, 337.98; 2.667, 0.35; 2.662, 0.56; 2.658, 0.73; 2.653, 0.68; 2.641, 8.76; 2.630, 8.99; 2.527, 0.77; 2.511, 1.73; 2.506, 2.49; 2.498, 33.58; 2.493, 68.55; 2.489, 95.97; 2.484, 67.13; 2.479, 32.12; 2.320, 0.38; 2.316, 0.54; 2.311, 0.34; 2.108, 16.00; 2.040, 0.89; 1.898, 0.32; 1.244, 0.43; 1.097, 0.84; 1.081, 0.90; −0.000, 1.35 |
| 87 | 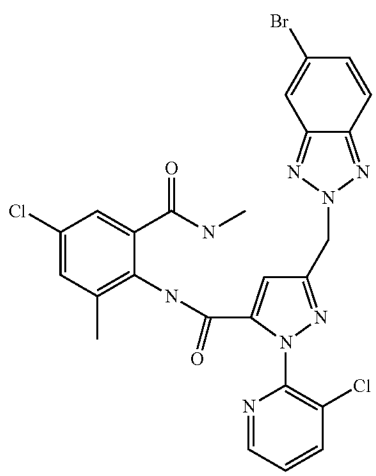 [SMILES: CNC(=O)c1cc(Cl)cc(C)c1NC(=O)c1cc(Cn2nc3ccc(Br)cc3n2)nn1-c1ncccc1Cl] | 3.39 | 614/616 | 10.045, 2.24; 8.450, 2.93; 8.446, 3.19; 8.438, 3.18; 8.434, 3.15; 8.252, 2.89; 8.250, 3.20; 8.247, 3.19; 8.245, 3.03; 8.097, 3.02; 8.093, 2.98; 8.077, 3.37; 8.073, 3.09; 7.972, 0.94; 7.957, 3.94; 7.955, 3.90; 7.935, 3.87; 7.933, 3.82; 7.580, 3.50; 7.575, 3.49; 7.563, 3.59; 7.557, 3.16; 7.553, 3.61; 7.551, 3.85; 7.543, 3.26; 7.531, 3.26; 7.390, 2.35; 7.385, 2.71; 7.307, 2.90; 7.301, 2.59; 7.197, 2.92; 6.104, 12.18; 3.602, 0.41; 3.112, 1012.80; 2.667, 0.43; 2.662, 0.91; 2.657, 1.41; 2.649, 10.92; 2.637, 10.74; 2.526, 4.79; 2.510, 2.71; 2.506, 3.72; 2.497, 60.03; 2.493, 124.72; 2.488, 176.69; 2.483, 123.03; 2.478, 58.52; 2.324, 0.34; 2.319, 0.73; 2.315, 1.04; 2.310, 0.72; 2.305, 0.34; 2.122, 16.00; 2.037, 0.45; 1.901, 0.33; 1.762, 0.49; 1.363, 2.16; 1.245, 0.50; 1.083, 0.32; 0.008, 0.44; −0.000, 14.11; −0.008, 0.41 |
| 88 | 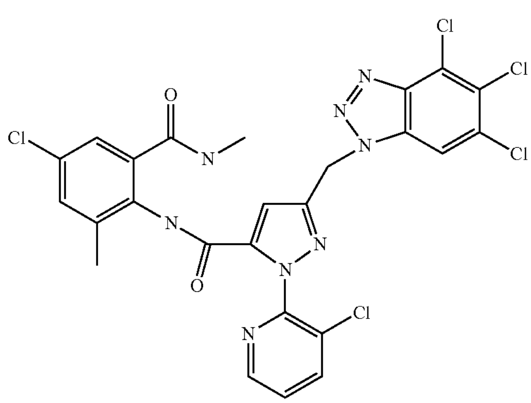 [SMILES: CNC(=O)c1cc(Cl)cc(C)c1NC(=O)c1cc(Cn2nnc3c(Cl)c(Cl)c(Cl)cc32)nn1-c1ncccc1Cl] | 3.75 | 637/639 | 10.157, 0.47; 8.608, 0.60; 8.455, 3.43; 8.448, 2.07; 8.444, 1.74; 8.199, 0.42; 8.137, 0.78; 8.119, 0.79; 7.580, 0.63; 7.570, 0.71; 7.563, 0.73; 7.550, 0.64; 7.426, 0.64; 7.311, 0.77; 7.183, 0.58; 6.330, 0.45; 6.195, 2.47; 3.417, 0.39; 3.367, 0.34; 3.317, 402.26; 3.293, 16.00; 3.267, 0.39; 2.674, 0.52; 2.670, 0.72; 2.665, 0.50; 2.626, 4.79; 2.615, 5.35; 2.510, 36.06; 2.505, 77.38; 2.501, 106.53; 2.496, 75.52; 2.492, 34.12; 2.332, 0.53; 2.328, 0.70; 2.323, 0.52; 2.132, 0.39; 2.125, 0.53; 2.098, 3.31; 1.890, 1.41; 1.696, 0.64; 1.689, 0.55; 1.673, 0.55; 1.657, 1.11; 1.615, 1.07; 1.588, 0.37; 1.351, 0.90; 1.336, 0.67; 1.298, 0.93; 1.281, 0.33; 1.258, 1.48; 1.235, 3.86; 1.225, 1.62; 1.211, 0.46; 1.179, 0.74; 1.175, 0.74; 1.147, 0.89; 1.118, 0.85; 1.091, 0.47; 1.059, 0.46; 1.040, 0.49; 1.016, 0.44; 1.010, 0.40; 0.972, 0.43; 0.948, 0.65; 0.945, 0.65; 0.917, 0.50; 0.884, 0.32; 0.868, 0.43; 0.854, 0.89; 0.836, 0.56; 0.008, 1.60; −0.000, 51.25; −0.008, 1.72 |

| No. | Structure | logP | MH+ | NMR |
|---|---|---|---|---|
| 89 | 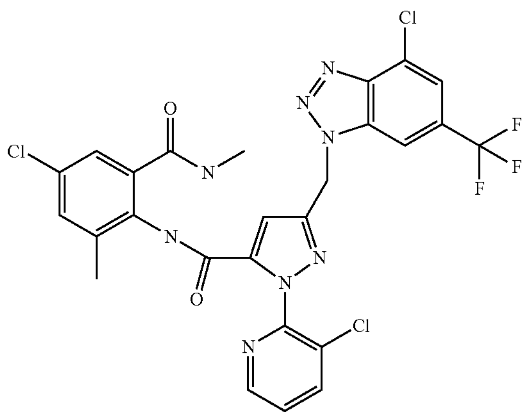 [SMILES: CNC(=O)c1cc(Cl)cc(C)c1NC(=O)c1cc(Cn2nnc3c(Cl)cc(C(F)(F)F)cc32)nn1-c1ncccc1Cl] | 3.59 | 637/639 | 8.577, 0.75; 8.575, 0.59; 8.438, 2.67; 8.434, 2.98; 8.426, 5.61; 8.422, 5.60; 8.418, 1.32; 8.410, 0.84; 8.406, 0.82; 8.090, 2.62; 8.087, 2.77; 8.070, 3.01; 8.066, 3.01; 8.061, 0.87; 8.045, 0.80; 8.041, 0.77; 7.998, 0.92; 7.996, 0.94; 7.976, 0.88; 7.974, 0.81; 7.964, 0.96; 7.856, 3.13; 7.853, 3.17; 7.557, 3.11; 7.545, 3.00; 7.537, 3.49; 7.525, 3.44; 7.517, 0.83; 7.505, 0.77; 7.387, 2.60; 7.382, 2.89; 7.381, 2.97; 7.309, 2.74; 7.304, 3.03; 7.168, 2.39; 7.102, 0.46; 6.350, 2.69; 6.270, 10.37; 3.126, 517.45; 2.663, 0.38; 2.658, 0.55; 2.654, 0.58; 2.640, 9.39; 2.636, 3.92; 2.628, 9.53; 2.624, 3.34; 2.528, 1.61; 2.512, 1.21; 2.507, 1.64; 2.499, 24.12; 2.494, 49.97; 2.489, 70.70; 2.485, 49.22; 2.480, 23.34; 2.384, 0.39; 2.316, 0.43; 2.297, 1.23; 2.128, 0.35; 2.108, 16.00; 1.248, 0.47; −0.000, 0.43 |
| 90 | 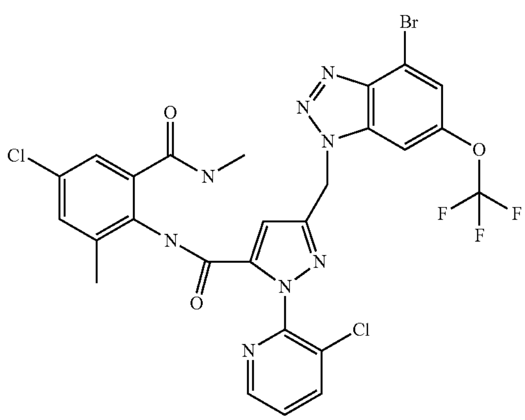 [SMILES: CNC(=O)c1cc(Cl)cc(C)c1NC(=O)c1cc(Cn2nnc3c(Br)cc(OC(F)(F)F)cc32)nn1-c1ncccc1Cl] | 3.74 | 698 | 8.438, 2.69; 8.434, 2.87; 8.426, 3.00; 8.423, 3.09; 8.420, 1.12; 8.412, 0.84; 8.408, 0.80; 8.222, 0.51; 8.220, 0.68; 8.217, 0.69; 8.215, 0.53; 8.090, 2.72; 8.087, 2.78; 8.070, 3.07; 8.066, 3.23; 8.062, 0.92; 8.045, 0.86; 8.042, 0.84; 8.017, 1.94; 8.014, 2.57; 8.012, 2.60; 8.010, 2.06; 7.976, 0.81; 7.963, 0.91; 7.918, 0.63; 7.916, 0.69; 7.913, 0.68; 7.911, 0.64; 7.735, 2.12; 7.734, 2.40; 7.731, 2.35; 7.729, 2.12; 7.557, 3.15; 7.545, 3.05; 7.537, 3.35; 7.525, 3.28; 7.518, 0.87; 7.506, 0.82; 7.388, 2.64; 7.383, 3.03; 7.382, 3.00; 7.310, 2.81; 7.305, 3.11; 7.299, 0.85; 7.159, 2.67; 7.077, 0.49; 6.336, 2.78; 6.175, 10.32; 3.129, 668.29; 2.664, 0.41; 2.659, 0.60; 2.654, 0.70; 2.645, 9.38; 2.638, 4.09; 2.634, 9.67; 2.627, 3.03; 2.528, 1.62; 2.512, 1.21; 2.507, 1.67; 2.499, 24.24; 2.494, 50.13; 2.490, 70.87; 2.485, 49.35; 2.480, 23.41; 2.316, 0.43; 2.297, 0.39; 2.113, 6.15; 2.108, 16.00; 1.902, 0.34; 1.762, 0.35; 1.092, 0.51; −0.000, 0.63 |
| 91 | 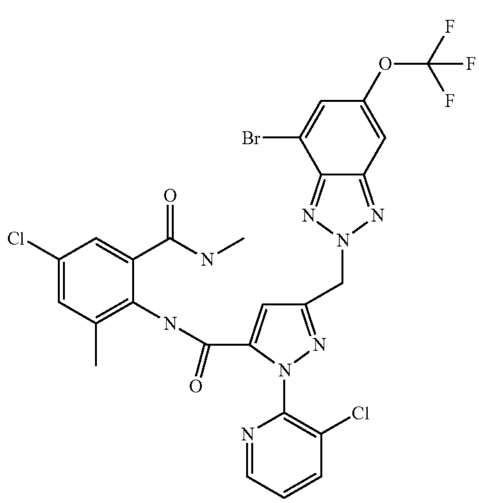 [SMILES: CNC(=O)c1cc(Cl)cc(C)c1NC(=O)c1cc(Cn2nc3cc(OC(F)(F)F)cc(Br)c3n2)nn1-c1ncccc1Cl] | 4.17 | 698 | 10.065, 0.54; 8.454, 2.81; 8.450, 3.12; 8.442, 3.05; 8.438, 3.04; 8.103, 2.88; 8.099, 2.94; 8.083, 3.53; 8.079, 4.75; 8.076, 2.78; 8.073, 2.71; 8.071, 2.17; 8.068, 0.95; 7.982, 0.83; 7.971, 0.87; 7.798, 2.22; 7.796, 2.45; 7.793, 2.40; 7.791, 2.21; 7.568, 3.35; 7.556, 3.32; 7.548, 3.14; 7.536, 3.07; 7.395, 2.21; 7.393, 2.34; 7.389, 2.66; 7.387, 2.56; 7.310, 2.81; 7.305, 2.47; 7.230, 2.61; 6.187, 10.67; 3.116, 230.54; 2.670, 0.33; 2.667, 0.36; 2.662, 0.65; 2.653, 10.42; 2.641, 10.01; 2.527, 2.51; 2.511, 1.39; 2.506, 1.90; 2.498, 31.37; 2.493, 65.20; 2.489, 92.45; 2.484, 64.37; 2.479, 30.67; 2.387, 1.12; 2.320, 0.40; 2.315, 0.55; 2.311, 0.38; 2.293, 0.60; 2.128, 16.00; 2.114, 0.98; 1.364, 0.43; −0.000, 3.22 |

| No. | Structure | logP | MH+ | NMR |
|---|---|---|---|---|
| 92 | 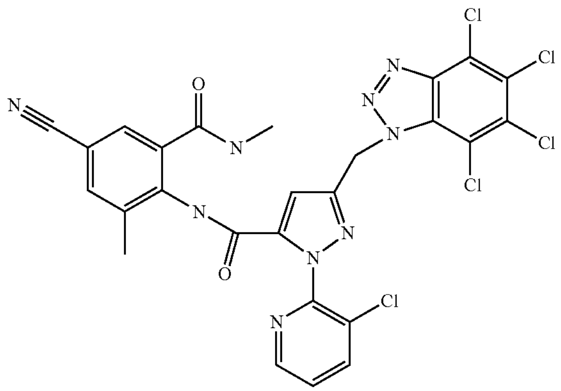 [SMILES: CNC(=O)c1cc(C#N)cc(C)c1NC(=O)c1cc(Cn2nnc3c(Cl)c(Cl)c(Cl)c(Cl)c32)nn1-c1ncccc1Cl] | 3.79 | 663 | 10.992, 0.33; 10.300, 1.97; 10.283, 0.55; 8.425, 3.64; 8.422, 4.10; 8.414, 4.12; 8.410, 4.06; 8.132, 0.84; 8.095, 0.42; 8.091, 0.43; 8.075, 2.82; 8.071, 2.95; 8.054, 3.07; 8.051, 3.14; 7.778, 2.24; 7.759, 0.39; 7.716, 3.31; 7.543, 3.18; 7.532, 3.03; 7.523, 3.07; 7.512, 2.96; 7.469, 0.33; 7.217, 0.48; 7.136, 2.51; 6.390, 0.77; 6.346, 15.36; 6.191, 0.33; 4.046, 0.49; 4.029, 0.50; 3.650, 1.75; 3.242, 0.32; 3.231, 0.33; 3.218, 0.35; 3.205, 0.42; 3.180, 0.65; 3.115, 721.60; 2.888, 0.46; 2.734, 0.53; 2.712, 0.37; 2.696, 0.32; 2.662, 15.53; 2.650, 14.64; 2.633, 0.43; 2.571, 0.39; 2.526, 3.33; 2.510, 4.38; 2.506, 6.25; 2.497, 76.98; 2.493, 156.22; 2.488, 217.83; 2.483, 150.79; 2.479, 71.09; 2.324, 0.47; 2.320, 1.00; 2.315, 1.34; 2.310, 0.91; 2.305, 0.36; 2.162, 16.00; 2.141, 0.48; 2.041, 0.96; 1.974, 2.32; 1.935, 1.00; 1.901, 0.39; 1.656, 0.38; 1.628, 0.32; 1.361, 0.48; 1.303, 0.68; 1.263, 1.27; 1.244, 2.56; 1.195, 1.08; 1.177, 1.59; 1.159, 0.80; 1.153, 0.33; 0.895, 1.87; 0.872, 0.33; 0.856, 0.56; 0.836, 0.33; 0.008, 0.62; −0.000, 17.62; −0.009, 0.39 |
| 93 | 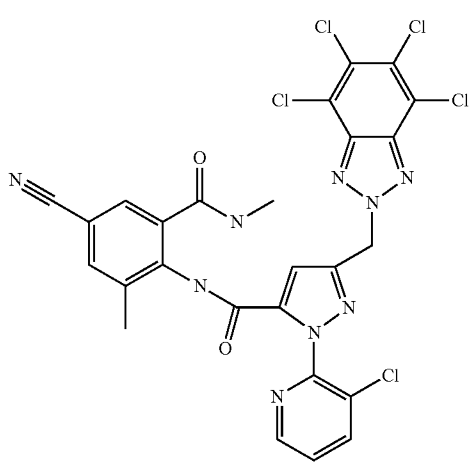 [SMILES: CNC(=O)c1cc(C#N)cc(C)c1NC(=O)c1cc(Cn2nc3c(Cl)c(Cl)c(Cl)c(Cl)c3n2)nn1-c1ncccc1Cl] | 4.24 | 663 | 16.654, 1.05; 10.546, 1.18; 9.741, 1.03; 8.453, 3.80; 8.450, 3.92; 8.441, 4.09; 8.438, 4.17; 8.146, 1.57; 8.101, 2.58; 8.080, 2.36; 7.975, 4.85; 7.760, 1.54; 7.748, 1.68; 7.737, 2.56; 7.568, 2.48; 7.555, 2.16; 7.546, 2.08; 7.536, 1.88; 7.278, 1.57; 7.271, 1.33; 6.228, 11.40; 3.567, 1.98; 3.498, 1.27; 3.415, 1.19; 3.394, 1.06; 3.324, 1.07; 3.306, 1.14; 3.289, 1.20; 3.260, 1.52; 3.241, 1.66; 3.226, 2.14; 3.116, 5453.91; 2.993, 1.10; 2.944, 1.17; 2.676, 14.52; 2.665, 16.00; 2.657, 8.22; 2.653, 6.16; 2.648, 3.41; 2.608, 1.41; 2.589, 1.14; 2.570, 1.91; 2.526, 9.28; 2.510, 21.92; 2.506, 32.04; 2.497, 436.15; 2.493, 889.52; 2.488, 1242.95; 2.483, 865.83; 2.479, 412.58; 2.324, 2.83; 2.320, 4.84; 2.315, 7.02; 2.310, 5.31; 2.305, 2.39; 2.169, 9.63; 2.040, 1.78; 2.037, 1.24; 1.404, 2.90; 1.349, 1.24; 1.298, 1.69; 1.296, 2.06; 1.246, 5.53; 1.153, 1.19; 1.082, 1.58; 0.855, 1.22; 0.008, 2.78; −0.000, 57.43; −0.008, 1.82; −2.105, 1.09 |

-continued
| No. | Structure | logP | MH+ | NMR |
|---|---|---|---|---|
| 94 | 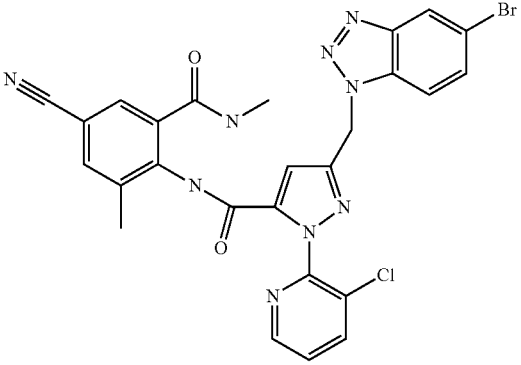 [SMILES: CNC(=O)c1cc(C#N)cc(C)c1NC(=O)c1cc(Cn2nnc3cc(Br)ccc32)nn1-c1ncccc1Cl] | 2.66 | 604/606 | 10.325, 1.57; 10.311, 2.67; 8.452, 1.58; 8.448, 2.06; 8.446, 2.92; 8.442, 3.30; 8.436, 2.10; 8.434, 2.93; 8.430, 2.78; 8.333, 2.87; 8.332, 3.01; 8.329, 3.06; 8.328, 2.74; 8.194, 1.84; 8.193, 1.92; 8.190, 1.89; 8.117, 1.69; 8.113, 1.63; 8.108, 2.82; 8.104, 2.90; 8.096, 3.43; 8.092, 3.36; 8.088, 2.18; 8.084, 1.89; 8.076, 3.17; 8.072, 2.85; 8.043, 1.83; 8.042, 1.70; 8.021, 1.92; 8.020, 1.83; 7.886, 2.95; 7.884, 2.78; 7.864, 3.86; 7.862, 3.47; 7.775, 4.19; 7.715, 3.49; 7.710, 4.07; 7.707, 4.87; 7.702, 4.26; 7.693, 2.89; 7.689, 2.58; 7.569, 1.83; 7.563, 3.61; 7.558, 3.15; 7.552, 3.32; 7.549, 1.96; 7.543, 3.00; 7.540, 1.99; 7.537, 2.30; 7.532, 2.84; 7.165, 3.50; 7.158, 6.11; 6.157, 1.01; 6.120, 12.00; 6.111, 6.93; 6.054, 0.81; 3.649, 2.20; 3.251, 1.28; 3.139, 1016.33; 2.657, 8.45; 2.654, 11.67; 2.645, 8.28; 2.642, 10.63; 2.528, 6.44; 2.512, 3.49; 2.507, 5.35; 2.500, 63.19; 2.495, 125.77; 2.490, 172.41; 2.485, 118.73; 2.481, 55.63; 2.321, 0.70; 2.317, 0.92; 2.312, 0.70; 2.161, 10.96; 2.157, 16.00; 2.041, 11.04; 1.927, 1.20; 1.245, 1.02; −0.000, 5.35 |
| 95 | 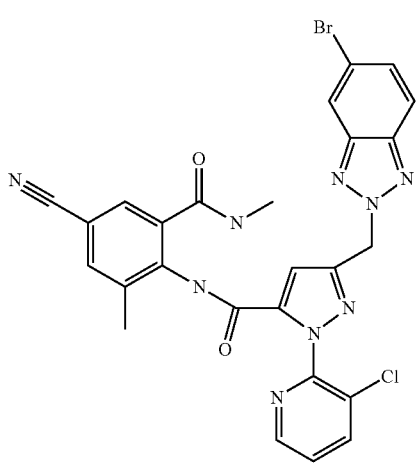 [SMILES: CNC(=O)c1cc(C#N)cc(C)c1NC(=O)c1cc(Cn2nc3ccc(Br)cc3n2)nn1-c1ncccc1Cl] | 3.01 | 604/606 | 14.012, 0.45; 10.969, 0.42; 10.370, 0.46; 10.324, 0.54; 8.450, 4.18; 8.446, 4.25; 8.438, 4.42; 8.434, 4.35; 8.253, 5.21; 8.251, 5.31; 8.248, 5.45; 8.247, 5.02; 8.167, 1.01; 8.094, 2.68; 8.090, 2.51; 8.073, 2.80; 7.957, 5.78; 7.956, 5.50; 7.935, 6.36; 7.933, 6.02; 7.772, 0.45; 7.742, 2.02; 7.730, 3.53; 7.670, 0.45; 7.580, 5.36; 7.575, 5.32; 7.557, 6.35; 7.552, 5.10; 7.547, 2.93; 7.538, 2.76; 7.527, 2.42; 7.519, 0.50; 7.189, 1.29; 7.184, 1.30; 6.892, 0.45; 6.120, 0.68; 6.105, 14.58; 3.626, 0.42; 3.322, 0.52; 3.287, 0.61; 3.274, 0.58; 3.247, 0.84; 3.231, 0.90; 3.120, 774.07; 3.096, 90.36; 3.036, 1.18; 3.019, 0.69; 3.001, 0.51; 2.823, 0.51; 2.687, 0.50; 2.665, 13.82; 2.654, 16.00; 2.587, 0.49; 2.556, 0.59; 2.527, 3.48; 2.511, 7.41; 2.506, 11.21; 2.498, 155.33; 2.493, 316.25; 2.488, 441.42; 2.484, 307.88; 2.479, 146.42; 2.449, 0.62; 2.324, 1.02; 2.320, 1.92; 2.315, 2.81; 2.310, 1.87; 2.306, 1.00; 2.156, 13.42; 2.041, 0.57; 2.037, 0.44; 1.298, 0.67; 1.245, 1.88; 1.081, 0.47; 0.830, 0.47; 0.008, 1.05; −0.000, 28.88; −0.008, 1.02; −0.593, 0.42; −3.446, 0.48 |

-continued
| No. | Structure | logP | MH+ | NMR |
|---|---|---|---|---|
| 96 | 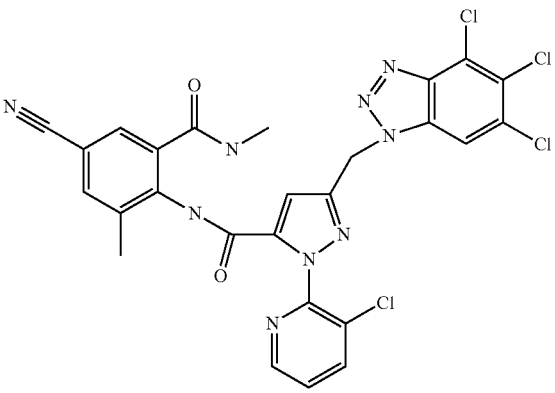 [SMILES: CNC(=O)c1cc(C#N)cc(C)c1NC(=O)c1cc(Cn2nnc3c(Cl)c(Cl)c(Cl)cc32)nn1-c1ncccc1Cl] | 3.42 | 628/630 | 12.815, 0.48; 10.322, 1.04; 10.297, 1.18; 8.510, 5.32; 8.449, 1.59; 8.445, 1.70; 8.438, 1.86; 8.434, 1.87; 8.426, 1.63; 8.422, 1.75; 8.414, 1.73; 8.410, 1.63; 8.351, 5.88; 8.121, 1.05; 8.106, 2.03; 8.102, 2.00; 8.086, 1.87; 8.082, 1.79; 8.074, 1.61; 8.070, 1.54; 8.054, 1.79; 8.050, 1.58; 7.976, 0.64; 7.780, 2.89; 7.709, 3.21; 7.568, 1.79; 7.557, 1.74; 7.548, 1.76; 7.544, 1.99; 7.536, 1.77; 7.532, 1.88; 7.524, 1.77; 7.512, 1.55; 7.186, 2.85; 7.118, 2.59; 6.321, 7.06; 6.169, 6.95; 4.047, 0.50; 4.029, 0.51; 3.309, 0.50; 3.299, 0.55; 3.289, 0.57; 3.268, 0.66; 3.261, 0.79; 3.251, 1.08; 3.240, 1.04; 3.233, 1.11; 3.184, 3.08; 3.137, 3338.32; 3.087, 1.29; 3.079, 0.85; 3.066, 0.46; 3.058, 0.51; 2.662, 7.65; 2.658, 8.01; 2.650, 7.81; 2.647, 6.80; 2.528, 9.61; 2.512, 4.98; 2.508, 7.31; 2.500, 91.24; 2.495, 184.23; 2.490, 255.53; 2.485, 177.31; 2.481, 83.61; 2.326, 0.67; 2.322, 1.17; 2.317, 1.42; 2.312, 1.03; 2.308, 0.54; 2.163, 16.00; 2.040, 0.60; 1.974, 2.24; 1.299, 0.89; 1.245, 1.06; 1.195, 0.69; 1.178, 1.29; 1.160, 0.66; 1.083, 0.60; −0.000, 9.86 |
| 97 | 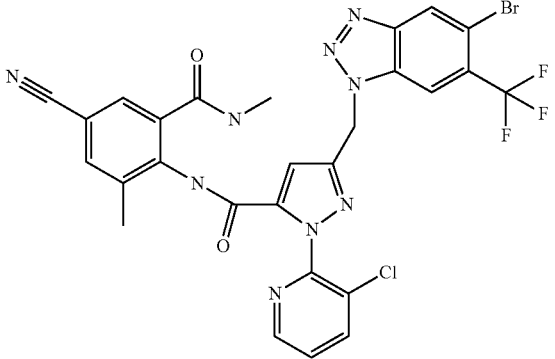 [SMILES: CNC(=O)c1cc(C#N)cc(C)c1NC(=O)c1cc(Cn2nnc3cc(Br)c(C(F)(F)F)cc32)nn1-c1ncccc1Cl] | 3.27 | 672/674 | 10.329, 3.88; 8.673, 3.61; 8.658, 4.74; 8.651, 1.82; 8.575, 3.46; 8.557, 1.58; 8.539, 5.03; 8.450, 2.69; 8.446, 3.03; 8.442, 2.36; 8.438, 4.67; 8.435, 3.18; 8.430, 2.76; 8.426, 2.58; 8.126, 1.95; 8.107, 3.39; 8.103, 3.29; 8.099, 2.51; 8.095, 2.50; 8.087, 2.85; 8.083, 2.84; 8.078, 2.44; 8.075, 2.33; 7.976, 1.53; 7.778, 4.80; 7.711, 5.08; 7.568, 2.37; 7.563, 2.33; 7.556, 3.15; 7.548, 2.98; 7.543, 2.51; 7.536, 2.74; 7.531, 2.19; 7.300, 2.11; 7.193, 5.69; 7.188, 5.24; 6.258, 8.52; 6.229, 3.01; 6.193, 10.86; 3.664, 6.39; 3.650, 2.67; 3.304, 1.40; 3.269, 1.82; 3.251, 3.01; 3.222, 2.66; 3.214, 3.04; 3.182, 6.86; 3.176, 9.10; 3.165, 12.98; 3.128, 7681.82; 3.076, 2.50; 2.663, 5.41; 2.658, 15.22; 2.654, 14.00; 2.646, 12.31; 2.642, 9.57; 2.528, 31.88; 2.512, 17.49; 2.507, 25.61; 2.499, 306.40; 2.494, 613.11; 2.489, 842.97; 2.485, 582.96; 2.480, 274.33; 2.326, 1.69; 2.321, 3.10; 2.316, 4.79; 2.312, 3.23; 2.307, 1.67; 2.163, 16.00; 2.158, 12.43; 1.974, 2.04; 1.938, 4.17; 1.299, 2.78; 1.296, 1.78; 1.245, 4.07; 1.082, 2.22; 0.008, 2.71; −0.000, 70.61; −0.009, 2.11 |

| No. | Structure | logP | MH+ | NMR |
|---|---|---|---|---|
| 98 | 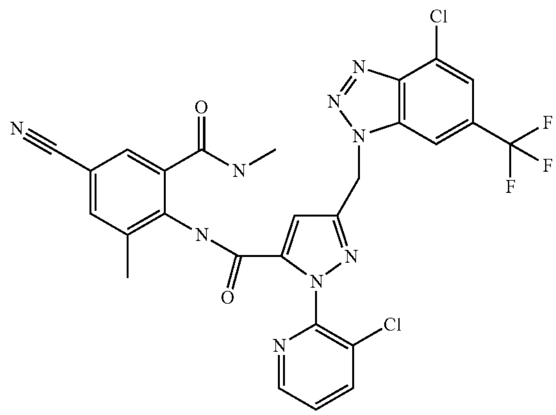 [SMILES: CNC(=O)c1cc(C#N)cc(C)c1NC(=O)c1cc(Cn2nnc3c(Cl)cc(C(F)(F)F)cc32)nn1-c1ncccc1Cl] | 3.24 | 628/630 | 10.328, 2.53; 10.303, 0.60; 8.581, 0.66; 8.441, 3.62; 8.437, 5.81; 8.429, 3.75; 8.425, 3.78; 8.421, 1.03; 8.413, 0.98; 8.409, 0.74; 8.125, 1.14; 8.117, 1.24; 8.098, 3.23; 8.094, 3.22; 8.077, 3.31; 8.074, 3.16; 8.068, 0.90; 8.051, 0.81; 8.048, 0.77; 8.002, 0.98; 7.857, 3.55; 7.778, 3.28; 7.712, 3.09; 7.707, 3.45; 7.562, 3.42; 7.550, 3.08; 7.542, 3.68; 7.530, 3.59; 7.522, 0.85; 7.510, 0.71; 7.200, 6.00; 7.135, 1.32; 6.358, 2.83; 6.279, 11.73; 3.312, 0.58; 3.243, 0.70; 3.211, 0.88; 3.201, 1.10; 3.115, 1429.39; 3.055, 0.64; 2.662, 2.35; 2.654, 11.59; 2.642, 11.00; 2.526, 3.07; 2.510, 7.23; 2.506, 10.59; 2.497, 143.03; 2.493, 291.51; 2.488, 407.54; 2.483, 282.82; 2.479, 133.75; 2.320, 1.62; 2.315, 2.36; 2.310, 1.76; 2.306, 0.62; 2.222, 0.63; 2.157, 16.00; 1.974, 0.90; 1.901, 2.64; 1.659, 1.06; 1.627, 0.81; 1.620, 0.80; 1.610, 0.56; 1.404, 14.68; 1.263, 0.98; 1.258, 0.90; 1.245, 2.62; 1.194, 0.63; 1.177, 0.89; 1.159, 0.83; 1.153, 0.93; 1.135, 0.66; 1.131, 0.76; 1.074, 0.70; 0.958, 0.62; 0.895, 0.95; 0.856, 0.64; 0.008, 0.83; −0.000, 20.62; −0.009, 0.68 |
| 99 | 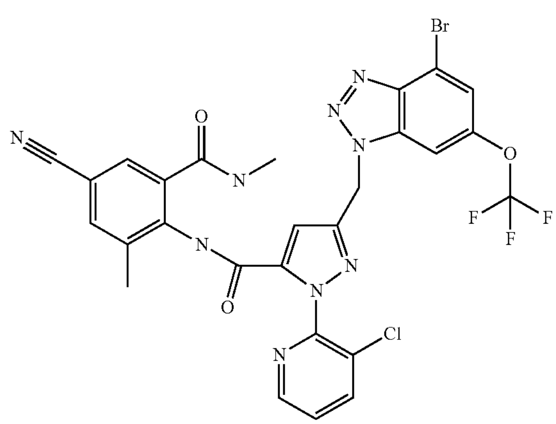 [SMILES: CNC(=O)c1cc(C#N)cc(C)c1NC(=O)c1cc(Cn2nnc3c(Br)cc(OC(F)(F)F)cc32)nn1-c1ncccc1Cl] | 3.37 | 688/690 | 10.324, 1.08; 8.441, 2.89; 8.438, 3.19; 8.430, 3.23; 8.426, 3.55; 8.415, 0.91; 8.412, 0.91; 8.224, 0.78; 8.222, 0.79; 8.219, 0.64; 8.130, 0.73; 8.097, 2.96; 8.093, 2.90; 8.077, 3.04; 8.073, 3.21; 8.068, 1.07; 8.052, 0.83; 8.048, 0.87; 8.028, 2.30; 8.025, 3.17; 8.023, 3.29; 8.021, 2.64; 7.920, 0.81; 7.917, 0.80; 7.777, 2.94; 7.738, 2.87; 7.735, 2.88; 7.733, 2.65; 7.715, 3.09; 7.710, 3.26; 7.562, 3.13; 7.550, 3.01; 7.542, 3.39; 7.530, 3.32; 7.522, 0.90; 7.511, 0.83; 7.188, 3.46; 7.108, 0.87; 6.344, 3.24; 6.185, 11.83; 4.064, 0.64; 4.047, 2.24; 4.029, 2.19; 4.011, 0.74; 3.119, 516.73; 3.095, 30.62; 2.659, 10.43; 2.653, 5.36; 2.648, 11.34; 2.642, 3.55; 2.527, 1.00; 2.511, 2.36; 2.506, 3.41; 2.498, 47.31; 2.493, 96.85; 2.489, 135.83; 2.484, 94.72; 2.479, 45.06; 2.320, 0.60; 2.315, 0.85; 2.311, 0.54; 2.157, 16.00; 2.041, 0.51; 1.996, 0.35; 1.985, 0.48; 1.974, 9.92; 1.901, 0.34; 1.245, 0.68; 1.195, 2.95; 1.177, 5.78; 1.160, 2.94; 1.031, 0.37; 0.892, 0.41; 0.008, 0.64; −0.000, 16.96; −0.009, 0.45 |

-continued

| No. | Structure | logP | MH+ | NMR |
|---|---|---|---|---|
| 100 | 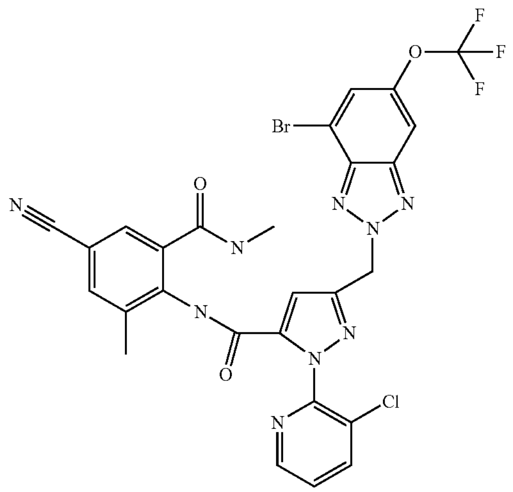 [SMILES: CNC(=O)c1cc(C#N)cc(C)c1NC(=O)c1cc(Cn2nc3cc(OC(F)(F)F)cc(Br)c3n2)nn1-c1ncccc1Cl] | 3.78 | 687/689 | 10.356, 2.81; 8.459, 2.93; 8.455, 2.96; 8.447, 3.17; 8.443, 2.99; 8.134, 1.01; 8.122, 1.06; 8.110, 3.33; 8.106, 3.09; 8.090, 3.35; 8.086, 3.29; 8.082, 2.38; 8.079, 2.93; 8.077, 2.78; 8.074, 2.22; 7.801, 2.60; 7.800, 2.85; 7.797, 2.81; 7.795, 2.66; 7.787, 2.87; 7.784, 3.05; 7.712, 3.20; 7.708, 2.83; 7.575, 3.17; 7.563, 3.05; 7.554, 2.90; 7.543, 2.91; 7.262, 6.12; 6.197, 11.52; 3.685, 0.43; 3.303, 0.34; 3.251, 0.69; 3.240, 0.65; 3.136, 1050.97; 2.666, 10.76; 2.655, 11.10; 2.528, 5.47; 2.512, 2.78; 2.507, 4.09; 2.499, 52.60; 2.495, 106.33; 2.490, 147.41; 2.485, 102.56; 2.481, 48.70; 2.322, 0.55; 2.317, 0.84; 2.312, 0.58; 2.180, 16.00; 2.041, 0.44; 1.403, 1.36; 1.299, 0.47; 1.245, 0.73; 1.083, 0.35; −0.000, 2.74 |
| 101 | 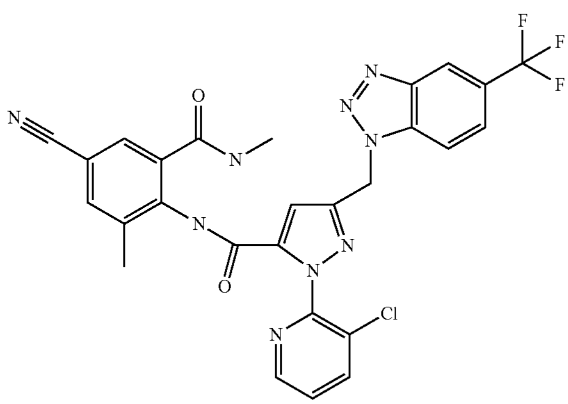 [SMILES: CNC(=O)c1cc(C#N)cc(C)c1NC(=O)c1cc(Cn2nnc3cc(C(F)(F)F)ccc32)nn1-c1ncccc1Cl] | 2.76 | 594 | 10.31, 1.250; 8.53, 1.830; 8.44, 1.930; 8.44, 2.260; 8.43, 2.100; 8.43, 2.220; 8.40, 1.530; 8.32, 1.050; 8.30, 1.270; 8.14, 1.540; 8.12, 0.870; 8.12, 2.670; 8.10, 1.900; 8.10, 2.710; 8.09, 1.980; 8.08, 1.580; 8.08, 2.610; 8.07, 1.960; 7.89, 1.340; 7.89, 1.390; 7.87, 1.320; 7.78, 2.660; 7.72, 1.180; 7.71, 3.220; 7.70, 3.520; 7.56, 3.150; 7.55, 2.970; 7.54, 2.990; 7.53, 2.700; 7.19, 2.290; 7.18, 2.800; 6.24, 5.690; 6.23, 1.310; 6.20, 7.080; 3.65, 2.170; 3.21, 0.810; 3.13, 2932.550; 3.04, 0.980; 2.66, 1.700; 2.66, 2.280; 2.65, 2.110; 2.65, 11.070; 2.64, 10.740; 2.53, 11.430; 2.51, 5.200; 2.51, 7.540; 2.50, 110.480; 2.49, 229.120; 2.49, 324.740; 2.49, 230.890; 2.48, 113.360; 2.33, 0.780; 2.32, 1.570; 2.32, 2.160; 2.31, 1.540; 2.31, 0.800; 2.16, 16.000; 2.13, 1.190; 1.97, 0.880; 1.93, 1.400; 1.30, 1.270; 1.25, 1.650; 1.08, 0.890; −0.00, 12.910 |
| 102 | 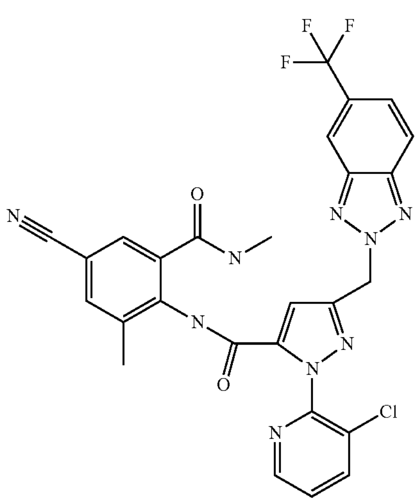 [SMILES: CNC(=O)c1cc(C#N)cc(C)c1NC(=O)c1cc(Cn2nc3ccc(C(F)(F)F)cc3n2)nn1-c1ncccc1Cl] | 3.19 | 594 | 10.341, 2.17; 8.473, 2.67; 8.471, 2.92; 8.469, 2.86; 8.455, 3.09; 8.451, 3.38; 8.443, 3.25; 8.439, 3.33; 8.219, 2.47; 8.217, 1.80; 8.196, 2.65; 8.194, 1.97; 8.122, 0.89; 8.106, 3.16; 8.102, 3.12; 8.086, 3.31; 8.082, 3.12; 7.781, 2.70; 7.719, 2.38; 7.712, 3.40; 7.707, 3.02; 7.696, 2.18; 7.692, 2.14; 7.570, 3.32; 7.558, 3.20; 7.550, 3.16; 7.538, 3.08; 7.252, 4.84; 6.248, 0.32; 6.207, 12.49; 3.675, 0.61; 3.180, 0.39; 3.114, 480.28; 3.090, 7.23; 2.888, 0.34; 2.733, 0.32; 2.660, 11.05; 2.648, 11.24; 2.635, 0.35; 2.546, 0.34; 2.526, 2.26; 2.510, 2.85; 2.506, 4.02; 2.497, 50.60; 2.493, 103.41; 2.488, 144.93; 2.483, 100.79; 2.479, 47.75; 2.320, 0.51; 2.315, 0.83; 2.310, 0.60; 2.173, 16.00; 2.041, 2.25; 1.938, 0.34; 1.901, 0.38; 1.263, 0.47; 1.245, 1.03; 0.895, 0.71; 0.008, 0.66; −0.000, 17.12; −0.009, 0.48 |

-continued
| No. | Structure | logP | MH+ | NMR |
|---|---|---|---|---|
| 103 | 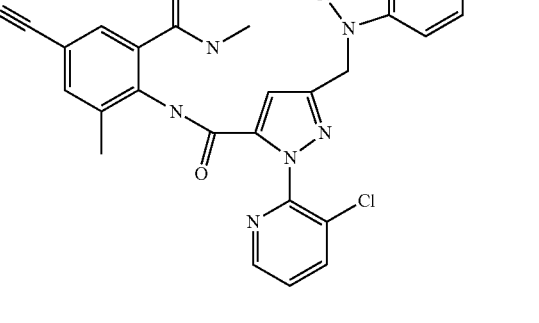 | 2.34 | 571 | 10.330, 2.68; 9.024, 2.20; 9.023, 2.34; 9.019, 2.40; 9.017, 2.40; 9.013, 0.39; 8.965, 0.65; 8.961, 0.66; 8.960, 0.65; 8.441, 2.74; 8.437, 2.91; 8.429, 2.98; 8.425, 3.08; 8.421, 2.48; 8.416, 2.27; 8.399, 2.67; 8.393, 2.59; 8.337, 0.69; 8.314, 0.87; 8.312, 0.88; 8.242, 0.79; 8.236, 0.84; 8.219, 0.49; 8.214, 0.49; 8.172, 0.33; 8.142, 3.47; 8.141, 3.52; 8.133, 1.17; 8.129, 1.16; 8.119, 3.58; 8.118, 3.46; 8.113, 0.94; 8.109, 0.75; 8.097, 0.89; 8.093, 2.97; 8.090, 2.45; 8.077, 0.87; 8.073, 3.20; 8.069, 2.48; 7.781, 2.70; 7.778, 2.92; 7.710, 3.13; 7.706, 2.79; 7.561, 3.18; 7.549, 3.06; 7.541, 2.96; 7.529, 2.92; 7.303, 0.59; 7.219, 6.46; 6.303, 2.67; 6.264, 0.99; 6.229, 10.17; 3.657, 2.00; 3.128, 425.53; 2.657, 9.12; 2.651, 3.63; 2.645, 9.02; 2.639, 2.87; 2.528, 2.55; 2.512, 1.33; 2.507, 1.84; 2.499, 23.67; 2.494, 48.43; 2.489, 67.97; 2.485, 47.49; 2.480, 22.67; 2.316, 0.42; 2.159, 16.00; 2.137, 0.55; 2.041, 5.63; 1.926, 1.17; 1.245, 0.47; −0.000, 6.33 |
| 104 | 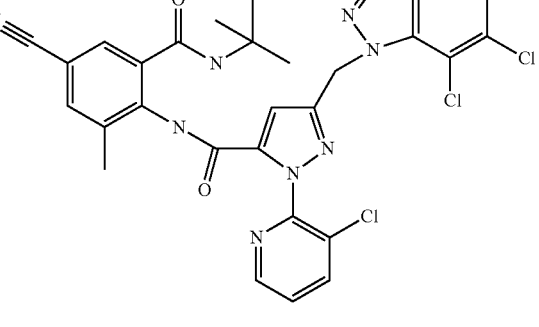 | 4.64 | 705 | 8.429, 0.57; 8.425, 0.61; 8.417, 0.59; 8.413, 0.59; 8.081, 0.50; 8.077, 0.51; 8.061, 0.57; 8.057, 0.53; 7.741, 0.49; 7.643, 0.59; 7.640, 0.58; 7.552, 0.59; 7.540, 0.56; 7.532, 0.54; 7.520, 0.53; 7.012, 0.67; 6.349, 2.43; 3.118, 226.12; 3.096, 1.98; 2.631, 0.34; 2.527, 2.67; 2.511, 0.80; 2.506, 1.12; 2.498, 13.99; 2.493, 28.40; 2.488, 39.71; 2.484, 27.90; 2.479, 13.46; 2.154, 2.93; 1.272, 0.90; 1.158, 16.00; −0.000, 3.05 |
| 105 | 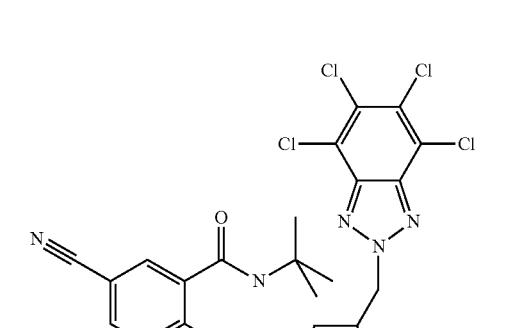 | 5.13 | 705 | 10.232, 0.55; 8.452, 0.56; 8.448, 0.61; 8.441, 0.61; 8.437, 0.61; 8.112, 0.56; 8.108, 0.57; 8.092, 0.64; 8.088, 0.61; 7.757, 0.56; 7.754, 0.56; 7.656, 0.61; 7.653, 0.58; 7.578, 0.67; 7.567, 0.63; 7.558, 0.61; 7.547, 0.61; 7.488, 0.45; 7.240, 1.24; 6.242, 2.30; 3.122, 259.49; 2.658, 0.34; 2.527, 0.44; 2.511, 0.87; 2.506, 1.31; 2.498, 17.53; 2.493, 35.86; 2.489, 50.22; 2.484, 34.96; 2.479, 16.57; 2.179, 3.01; 2.137, 0.65; 2.041, 0.48; 1.974, 0.54; 1.273, 1.04; 1.246, 0.39; 1.185, 16.00; 1.180, 1.57; −0.000, 4.10 |

US 8,536,202 B2

-continued

| No. | Structure | logP | MH+ | NMR |
|---|---|---|---|---|
| 106 | 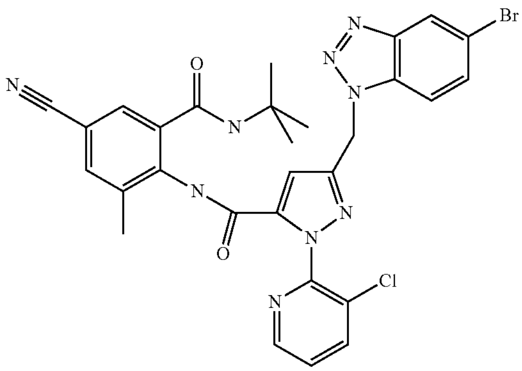 [SMILES: Cc1cc(C#N)cc(C(=O)NC(C)(C)C)c1NC(=O)c1cc(Cn2nnc3cc(Br)ccc32)nn1-c1ncccc1Cl] | 3.31 | 648 | 8.443, 0.40; 8.441, 0.64; 8.438, 0.70; 8.432, 0.44; 8.430, 0.68; 8.426, 0.63; 8.333, 0.55; 8.332, 0.64; 8.329, 0.64; 8.328, 0.62; 8.140, 0.39; 8.135, 0.41; 8.096, 0.54; 8.092, 0.57; 8.088, 0.35; 8.076, 0.59; 8.072, 0.57; 8.041, 0.37; 8.040, 0.37; 8.019, 0.46; 8.018, 0.45; 7.843, 0.61; 7.842, 0.61; 7.821, 0.83; 7.820, 0.86; 7.738, 0.72; 7.697, 0.68; 7.693, 0.70; 7.675, 0.54; 7.671, 0.53; 7.638, 0.87; 7.570, 0.36; 7.565, 0.65; 7.558, 0.70; 7.554, 0.80; 7.550, 0.41; 7.545, 0.62; 7.538, 0.44; 7.537, 0.46; 7.533, 0.76; 7.095, 0.50; 7.085, 0.85; 6.125, 2.45; 6.117, 1.40; 3.118, 178.14; 2.527, 0.44; 2.511, 0.91; 2.506, 1.34; 2.498, 17.64; 2.493, 35.99; 2.488, 50.38; 2.484, 35.06; 2.479, 16.63; 2.155, 1.94; 2.149, 3.12; 2.131, 0.79; 1.974, 0.75; 1.901, 0.49; 1.273, 1.08; 1.243, 0.37; 1.195, 0.33; 1.177, 0.73; 1.164, 16.00; 1.154, 8.88; −0.000, 1.48 |
| 107 | 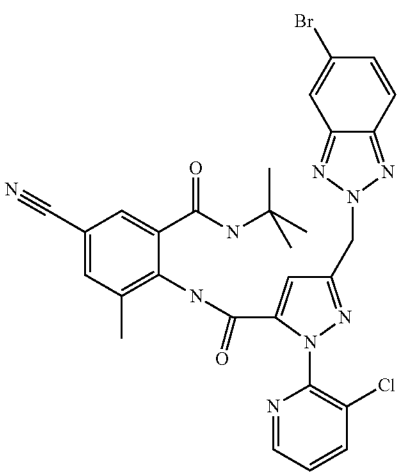 [SMILES: Cc1cc(C#N)cc(C(=O)NC(C)(C)C)c1NC(=O)c1cc(Cn2nc3ccc(Br)cc3n2)nn1-c1ncccc1Cl] | 3.85 | 648 | 8.446, 0.62; 8.442, 0.66; 8.434, 0.68; 8.430, 0.65; 8.239, 0.74; 8.237, 0.81; 8.234, 0.80; 8.233, 0.72; 8.098, 0.46; 8.094, 0.46; 8.078, 0.51; 8.074, 0.48; 7.947, 0.81; 7.945, 0.77; 7.925, 0.91; 7.923, 0.87; 7.728, 0.34; 7.661, 0.46; 7.583, 0.79; 7.578, 0.79; 7.565, 0.61; 7.560, 0.78; 7.556, 0.89; 7.554, 0.65; 7.545, 0.55; 7.534, 0.53; 7.153, 0.32; 6.109, 2.34; 3.118, 94.71; 2.527, 0.58; 2.511, 0.54; 2.506, 0.84; 2.498, 10.31; 2.493, 20.62; 2.488, 28.41; 2.484, 19.66; 2.479, 9.28; 2.160, 2.53; 1.182, 16.00; −0.000, 0.39 |
| 108 | 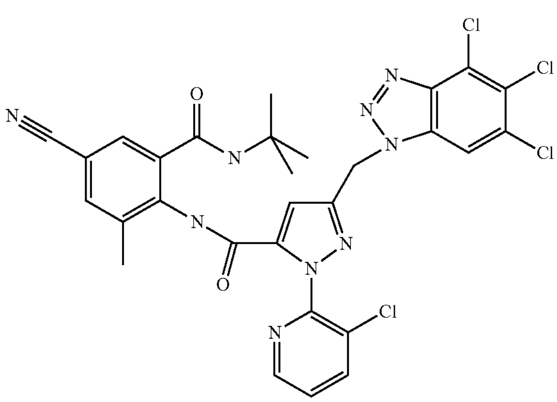 [SMILES: Cc1cc(C#N)cc(C(=O)NC(C)(C)C)c1NC(=O)c1cc(Cn2nnc3c(Cl)c(Cl)c(Cl)cc32)nn1-c1ncccc1Cl] | 4.18 | 670 | 10.154, 0.47; 10.134, 0.38; 8.524, 1.30; 8.448, 0.47; 8.444, 0.53; 8.436, 0.52; 8.432, 0.57; 8.428, 0.47; 8.424, 0.47; 8.416, 0.43; 8.412, 0.45; 8.306, 1.82; 8.109, 0.42; 8.106, 0.51; 8.089, 0.51; 8.085, 0.54; 8.080, 0.41; 8.076, 0.40; 8.060, 0.42; 8.056, 0.43; 7.745, 0.88; 7.638, 1.00; 7.573, 0.53; 7.561, 0.54; 7.551, 0.58; 7.540, 0.65; 7.530, 0.40; 7.519, 0.38; 7.451, 0.34; 7.089, 0.99; 7.005, 0.72; 6.320, 1.80; 6.183, 2.21; 4.028, 0.34; 3.116, 182.91; 2.662, 0.49; 2.657, 0.73; 2.653, 0.49; 2.632, 1.02; 2.527, 1.05; 2.510, 1.91; 2.506, 2.77; 2.497, 36.37; 2.493, 74.23; 2.488, 103.99; 2.483, 72.56; 2.479, 34.59; 2.320, 0.43; 2.315, 0.66; 2.310, 0.43; 2.155, 4.79; 2.108, 0.39; 1.974, 1.40; 1.391, 0.51; 1.263, 0.37; 1.244, 0.77; 1.230, 0.60; 1.195, 0.57; 1.184, 0.61; 1.177, 1.10; 1.157, 12.87; 1.153, 16.00; −0.000, 6.34 |

| No. | Structure | logP | MH+ | NMR |
|---|---|---|---|---|
| 109 | 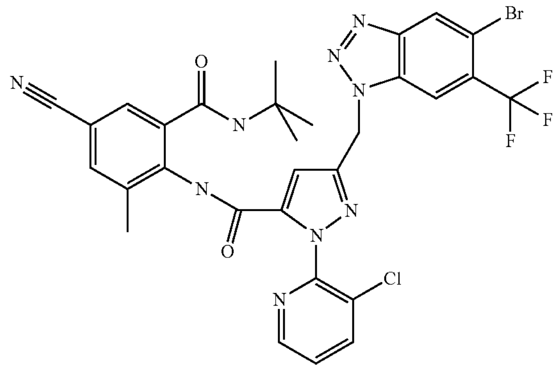 [SMILES: Cc1cc(C#N)cc(C(=O)NC(C)(C)C)c1NC(=O)c1cc(Cn2nnc3cc(Br)c(C(F)(F)F)cc32)nn1-c1ncccc1Cl] | 4.02 | | |
| 110 | 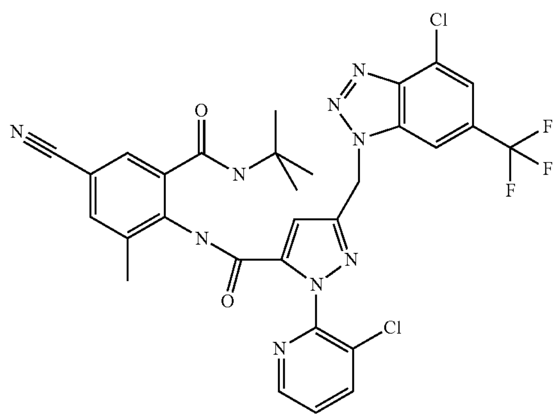 [SMILES: Cc1cc(C#N)cc(C(=O)NC(C)(C)C)c1NC(=O)c1cc(Cn2nnc3c(Cl)cc(C(F)(F)F)cc32)nn1-c1ncccc1Cl] | 3.96 | 670/672 | 10.158, 0.32; 8.439, 0.62; 8.435, 0.69; 8.427, 0.83; 8.423, 0.85; 8.385, 0.78; 8.099, 0.53; 8.095, 0.56; 8.079, 0.69; 8.075, 0.68; 7.864, 0.75; 7.862, 0.75; 7.741, 0.65; 7.641, 0.62; 7.636, 0.71; 7.565, 0.65; 7.553, 0.65; 7.545, 0.64; 7.533, 0.63; 7.113, 0.81; 6.357, 0.83; 6.290, 2.37; 4.047, 0.41; 4.029, 0.40; 3.114, 100.66; 3.092, 1.80; 2.510, 0.62; 2.506, 0.91; 2.497, 13.08; 2.493, 27.00; 2.488, 38.00; 2.483, 26.50; 2.479, 12.60; 2.152, 3.81; 1.974, 1.90; 1.195, 0.60; 1.177, 1.18; 1.169, 0.33; 1.159, 0.77; 1.148, 6.23; 1.141, 16.00; −0.000, 1.49 |
| 111 | 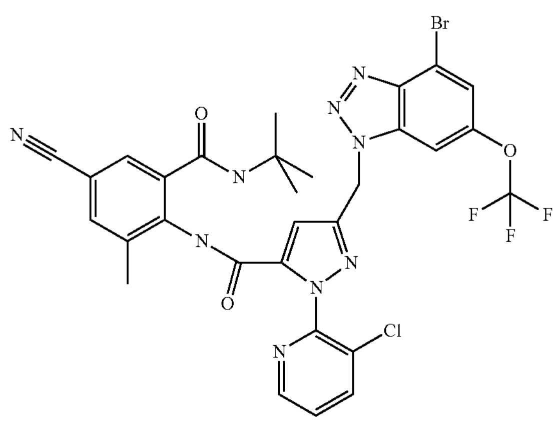 [SMILES: Cc1cc(C#N)cc(C(=O)NC(C)(C)C)c1NC(=O)c1cc(Cn2nnc3c(Br)cc(OC(F)(F)F)cc32)nn1-c1ncccc1Cl] | 4.09 | 730 | 10.162, 0.57; 8.438, 0.58; 8.434, 0.62; 8.427, 0.73; 8.423, 0.62; 8.099, 0.55; 8.095, 0.56; 8.079, 0.65; 8.075, 0.63; 7.978, 0.43; 7.976, 0.59; 7.974, 0.67; 7.971, 0.47; 7.743, 1.08; 7.642, 0.66; 7.639, 0.57; 7.565, 0.65; 7.554, 0.62; 7.545, 0.61; 7.533, 0.60; 7.446, 0.42; 7.111, 1.36; 6.343, 0.54; 6.195, 2.23; 3.115, 165.90; 2.526, 0.48; 2.510, 0.76; 2.506, 1.12; 2.497, 16.66; 2.493, 34.34; 2.488, 48.38; 2.483, 33.81; 2.479, 16.15; 2.154, 3.39; 2.137, 0.38; 1.974, 0.41; 1.273, 0.47; 1.156, 16.00; 1.146, 3.97; −0.000, 1.99 |

| No. | Structure | logP | MH+ | NMR |
|---|---|---|---|---|
| 112 | 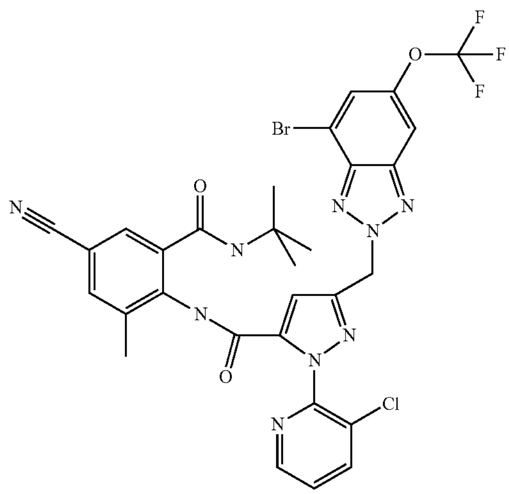 [SMILES: Cc1cc(C#N)cc(C(=O)NC(C)(C)C)c1NC(=O)c1cc(Cn2nc3cc(OC(F)(F)F)cc(Br)c3n2)nn1-c1ncccc1Cl] | 4.59 | 730 | 8.455, 0.40; 8.451, 0.43; 8.443, 0.42; 8.439, 0.43; 8.111, 0.40; 8.107, 0.41; 8.091, 0.45; 8.087, 0.43; 8.060, 0.37; 8.058, 0.37; 7.805, 0.35; 7.803, 0.40; 7.800, 0.39; 7.799, 0.37; 7.752, 0.47; 7.750, 0.50; 7.747, 0.54; 7.745, 0.51; 7.645, 0.48; 7.641, 0.47; 7.640, 0.46; 7.577, 0.47; 7.565, 0.45; 7.557, 0.44; 7.545, 0.43; 7.189, 1.01; 6.199, 1.59; 3.123, 77.62; 2.528, 0.38; 2.507, 0.38; 2.499, 6.11; 2.494, 12.69; 2.489, 17.97; 2.484, 12.55; 2.480, 5.97; 2.306, 3.56; 2.176, 2.21; 1.300, 0.38; 1.272, 0.40; 1.263, 16.00; 1.160, 11.56; 1.083, 0.35; −0.000, 0.48 |
| 113 | 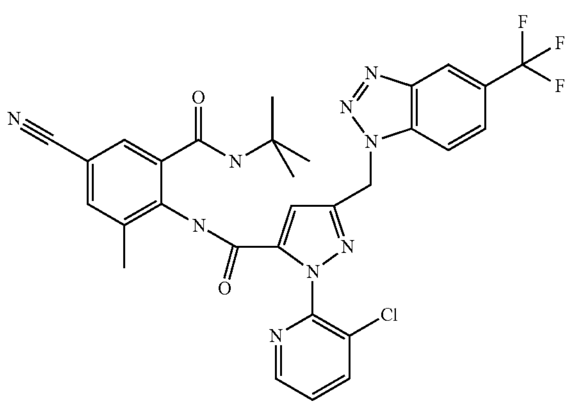 [SMILES: Cc1cc(C#N)cc(C(=O)NC(C)(C)C)c1NC(=O)c1cc(Cn2nnc3cc(C(F)(F)F)ccc32)nn1-c1ncccc1Cl] | 3.5 | 636 | 8.534, 0.66; 8.441, 0.64; 8.437, 0.97; 8.434, 0.54; 8.429, 0.69; 8.426, 0.98; 8.422, 0.52; 8.349, 0.48; 8.318, 0.33; 8.296, 0.35; 8.094, 1.13; 8.091, 1.08; 8.074, 1.10; 8.071, 1.34; 7.872, 0.44; 7.869, 0.47; 7.850, 0.39; 7.846, 0.40; 7.725, 0.85; 7.715, 0.41; 7.645, 0.93; 7.563, 0.77; 7.551, 0.76; 7.543, 0.72; 7.531, 0.72; 7.100, 0.52; 7.087, 0.72; 6.246, 1.78; 6.200, 2.48; 3.111, 208.73; 2.657, 0.36; 2.632, 0.39; 2.526, 1.33; 2.510, 0.98; 2.505, 1.35; 2.497, 20.62; 2.493, 42.84; 2.488, 60.66; 2.483, 42.45; 2.478, 20.36; 2.315, 0.37; 2.145, 5.15; 1.272, 0.81; 1.251, 1.68; 1.139, 16.00; 1.131, 11.67; 1.092, 0.59; −0.000, 2.92 |
| 114 | 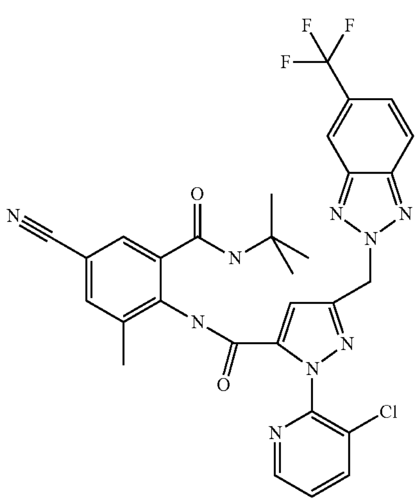 [SMILES: Cc1cc(C#N)cc(C(=O)NC(C)(C)C)c1NC(=O)c1cc(Cn2nc3ccc(C(F)(F)F)cc3n2)nn1-c1ncccc1Cl] | 3.94 | 636 | 10.189, 0.36; 8.454, 0.69; 8.450, 0.98; 8.447, 0.77; 8.439, 0.67; 8.435, 0.64; 8.210, 0.51; 8.187, 0.54; 8.107, 0.54; 8.103, 0.51; 8.087, 0.58; 8.083, 0.55; 7.746, 0.51; 7.723, 0.47; 7.719, 0.49; 7.701, 0.42; 7.696, 0.42; 7.647, 0.57; 7.643, 0.58; 7.573, 0.61; 7.561, 0.59; 7.553, 0.56; 7.541, 0.57; 7.473, 0.32; 7.185, 0.86; 6.207, 2.42; 3.123, 293.21; 2.632, 0.59; 2.527, 0.62; 2.511, 0.81; 2.506, 1.17; 2.498, 15.77; 2.493, 32.11; 2.489, 44.84; 2.484, 31.16; 2.480, 14.82; 2.168, 2.95; 2.041, 0.69; 1.273, 0.74; 1.170, 16.00; −0.000, 3.72 |

| No. | Structure | logP | MH+ | NMR |
|---|---|---|---|---|
| 115 | 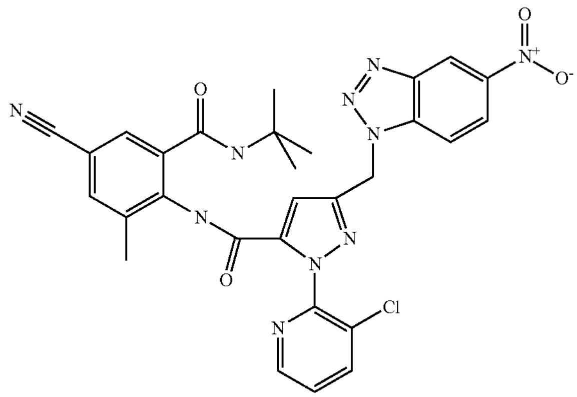 [SMILES: Cc1cc(C#N)cc(C(=O)NC(C)(C)C)c1NC(=O)c1cc(Cn2nnc3cc([N+](=O)[O-])ccc32)nn1-c1ncccc1Cl] | 3.03 | 613 | 10.173, 0.39; 9.029, 0.56; 9.028, 0.60; 9.024, 0.62; 9.023, 0.60; 8.437, 0.80; 8.433, 0.89; 8.425, 0.87; 8.421, 0.88; 8.409, 0.60; 8.404, 0.58; 8.386, 0.66; 8.381, 0.68; 8.318, 0.34; 8.316, 0.34; 8.111, 0.78; 8.109, 0.79; 8.094, 0.66; 8.088, 0.86; 8.087, 0.76; 8.073, 0.72; 8.070, 0.57; 7.742, 0.67; 7.647, 0.56; 7.642, 0.62; 7.563, 0.75; 7.551, 0.73; 7.543, 0.71; 7.531, 0.70; 7.155, 0.79; 7.146, 0.37; 6.310, 0.94; 6.235, 2.44; 3.113, 113.72; 3.090, 1.99; 2.526, 0.37; 2.510, 0.78; 2.505, 1.08; 2.497, 14.95; 2.493, 30.62; 2.488, 42.92; 2.483, 29.86; 2.478, 14.15; 2.152, 3.92; 1.404, 1.18; 1.273, 0.40; 1.245, 0.40; 1.169, 16.00; 1.143, 6.12; −0.000, 2.28 |
| 116 | 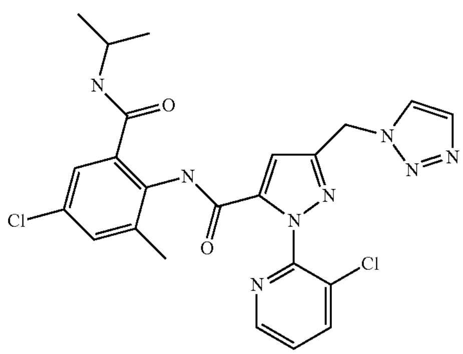 [SMILES: Cc1cc(Cl)cc(C(=O)NC(C)C)c1NC(=O)c1cc(Cn2ccnn2)nn1-c1ncccc1Cl] | 2.12 | 513 | 10.019, 1.54; 8.445, 2.03; 8.441, 2.18; 8.434, 2.17; 8.430, 2.16; 8.148, 3.39; 8.145, 3.39; 8.091, 2.10; 8.087, 2.19; 8.071, 2.39; 8.067, 2.27; 7.777, 0.70; 7.754, 3.63; 7.752, 3.42; 7.562, 2.50; 7.550, 2.40; 7.542, 2.32; 7.530, 2.28; 7.393, 1.75; 7.391, 1.80; 7.387, 2.01; 7.385, 1.92; 7.288, 2.01; 7.282, 1.81; 7.142, 2.41; 6.873, 0.61; 6.398, 0.32; 5.758, 9.56; 3.933, 0.57; 3.916, 0.85; 3.897, 0.83; 3.881, 0.58; 3.112, 86.52; 2.526, 0.58; 2.509, 0.41; 2.505, 0.58; 2.497, 9.09; 2.492, 18.86; 2.487, 26.67; 2.482, 18.55; 2.478, 8.82; 2.183, 1.05; 2.134, 11.45; 1.364, 11.63; 1.037, 16.00; 1.021, 15.84; −0.000, 1.17 |
| 117 | 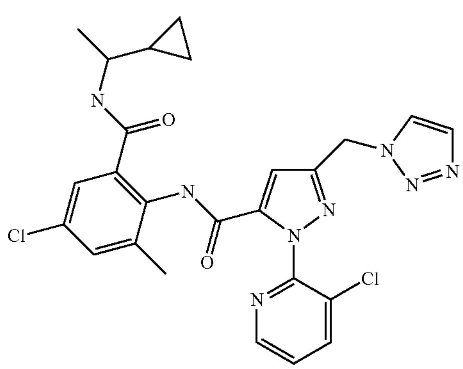 [SMILES: Cc1cc(Cl)cc(C(=O)NC(C)C2CC2)c1NC(=O)c1cc(Cn2ccnn2)nn1-c1ncccc1Cl] | 2.41 | 539 | 8.445, 2.09; 8.441, 2.25; 8.433, 2.26; 8.429, 2.25; 8.138, 3.33; 8.136, 3.36; 8.090, 2.02; 8.086, 2.11; 8.069, 2.30; 8.066, 2.17; 7.750, 3.15; 7.747, 3.13; 7.561, 2.44; 7.550, 2.31; 7.541, 2.26; 7.529, 2.19; 7.396, 1.65; 7.391, 1.88; 7.296, 1.91; 7.290, 1.74; 7.132, 2.21; 6.872, 0.86; 5.751, 9.44; 3.368, 0.45; 3.348, 0.86; 3.331, 0.86; 3.312, 0.46; 3.112, 136.29; 2.526, 1.16; 2.510, 0.84; 2.505, 1.15; 2.497, 17.34; 2.492, 35.95; 2.487, 50.85; 2.483, 35.38; 2.478, 16.82; 2.182, 1.57; 2.134, 11.49; 1.363, 16.00; 1.137, 0.38; 1.121, 0.37; 1.067, 7.07; 1.050, 6.96; 0.838, 0.47; 0.825, 0.89; 0.818, 0.52; 0.813, 0.58; 0.805, 0.90; 0.793, 0.53; 0.785, 0.37; 0.378, 0.37; 0.374, 0.40; 0.365, 0.90; 0.357, 0.71; 0.352, 0.69; 0.343, 0.81; 0.336, 0.41; 0.331, 0.50; 0.322, 0.46; 0.254, 0.35; 0.243, 0.55; 0.240, 0.50; 0.229, 0.74; 0.223, 0.72; 0.220, 0.64; 0.209, 1.15; 0.202, 0.45; 0.197, 0.62; 0.195, 0.59; 0.188, 0.66; 0.185, 0.80; 0.172, 1.09; 0.162, 0.90; 0.149, 0.97; 0.140, 0.65; 0.137, 0.85; 0.127, 0.87; 0.114, 0.63; 0.105, 0.36; −0.000, 1.69 |

| No. | Structure | logP | MH+ | NMR |
|---|---|---|---|---|
| 118 | 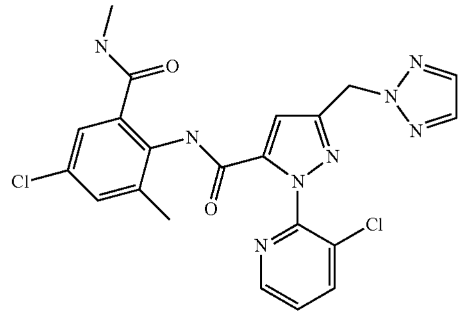 [SMILES: CNC(=O)c1cc(Cl)cc(C)c1NC(=O)c1cc(Cn2nccn2)nn1-c1ncccc1Cl] | 2.03 | 485 | 10.053, 1.70; 8.454, 2.68; 8.450, 2.85; 8.442, 2.88; 8.438, 2.83; 8.096, 2.72; 8.092, 2.75; 8.076, 3.05; 8.072, 2.85; 7.976, 0.81; 7.974, 0.89; 7.965, 0.83; 7.826, 13.59; 7.561, 3.12; 7.549, 3.14; 7.541, 2.95; 7.529, 2.86; 7.396, 2.34; 7.391, 2.66; 7.314, 2.80; 7.308, 2.44; 7.104, 2.81; 5.752, 13.35; 3.402, 0.65; 3.385, 0.64; 3.158, 0.36; 3.118, 346.54; 2.701, 0.56; 2.689, 0.63; 2.668, 10.25; 2.657, 10.50; 2.526, 1.07; 2.510, 0.87; 2.505, 1.25; 2.497, 18.01; 2.493, 37.26; 2.488, 52.62; 2.483, 36.98; 2.478, 17.81; 2.315, 0.35; 2.221, 0.84; 2.132, 16.00; 2.117, 0.98; 1.364, 0.91; 1.109, 0.66; 1.091, 1.35; 1.074, 0.64; −0.000, 2.35 |
| 119 | 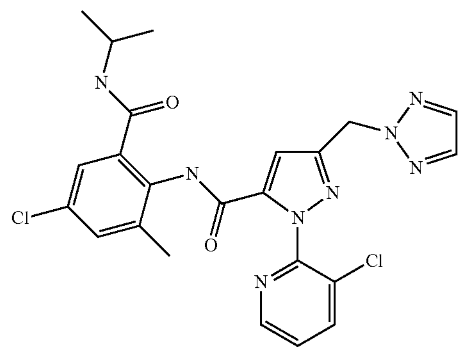 [SMILES: Cc1cc(Cl)cc(C(=O)NC(C)C)c1NC(=O)c1cc(Cn2nccn2)nn1-c1ncccc1Cl] | 2.5 | 513 | 9.992, 0.95; 8.443, 2.04; 8.439, 2.14; 8.427, 2.13; 8.087, 2.14; 8.083, 2.13; 8.066, 2.39; 8.062, 2.27; 7.821, 10.89; 7.762, 0.60; 7.743, 0.61; 7.558, 2.46; 7.546, 2.37; 7.538, 2.28; 7.526, 2.25; 7.390, 1.76; 7.389, 1.83; 7.384, 2.04; 7.383, 1.95; 7.283, 2.01; 7.277, 1.82; 7.106, 2.07; 5.751, 10.33; 3.928, 0.57; 3.911, 0.85; 3.892, 0.84; 3.876, 0.59; 3.114, 136.34; 2.526, 0.68; 2.510, 0.48; 2.505, 0.68; 2.497, 10.43; 2.492, 21.70; 2.487, 30.74; 2.483, 21.44; 2.478, 10.26; 2.221, 0.67; 2.182, 0.50; 2.135, 11.78; 2.114, 0.72; 1.364, 5.24; 1.078, 0.96; 1.061, 0.98; 1.035, 16.00; 1.018, 15.84; −0.000, 0.99 |
| 120 | 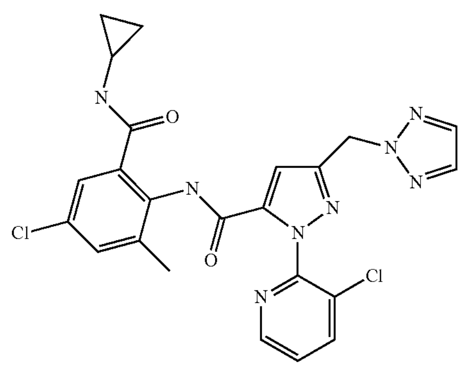 [SMILES: Cc1cc(Cl)cc(C(=O)NC2CC2)c1NC(=O)c1cc(Cn2nccn2)nn1-c1ncccc1Cl] | 2.26 | 511 | 9.993, 0.81; 8.584, 0.49; 8.580, 0.51; 8.573, 0.52; 8.569, 0.52; 8.455, 1.69; 8.451, 1.80; 8.443, 1.81; 8.439, 1.80; 8.269, 0.49; 8.265, 0.52; 8.248, 0.55; 8.245, 0.51; 8.094, 1.66; 8.090, 1.67; 8.074, 1.85; 8.070, 1.78; 8.019, 0.56; 8.010, 0.56; 7.865, 0.41; 7.864, 0.42; 7.859, 0.46; 7.858, 0.47; 7.828, 8.44; 7.823, 2.75; 7.729, 0.48; 7.727, 0.54; 7.723, 0.51; 7.721, 0.49; 7.711, 0.57; 7.699, 0.54; 7.691, 0.53; 7.679, 0.52; 7.562, 2.00; 7.550, 1.92; 7.542, 1.83; 7.530, 1.80; 7.387, 1.31; 7.386, 1.35; 7.381, 1.50; 7.268, 1.65; 7.263, 1.52; 7.120, 1.58; 7.112, 1.62; 6.873, 0.85; 5.801, 2.54; 5.757, 7.55; 3.609, 0.41; 3.115, 180.87; 3.094, 1.17; 2.692, 0.57; 2.682, 0.57; 2.674, 0.39; 2.529, 0.94; 2.526, 1.20; 2.510, 0.65; 2.505, 0.88; 2.497, 13.08; 2.493, 27.12; 2.488, 38.32; 2.483, 26.65; 2.478, 12.66; 2.211, 0.81; 2.183, 1.50; 2.129, 9.32; 1.774, 2.82; 1.364, 16.00; 1.112, 0.42; 0.609, 1.10; 0.604, 1.45; 0.592, 1.42; 0.586, 1.12; 0.574, 0.47; 0.446, 0.66; 0.435, 1.65; 0.429, 1.56; 0.425, 1.42; 0.419, 1.42; 0.407, 0.46; −0.000, 2.36 |
| 121 | 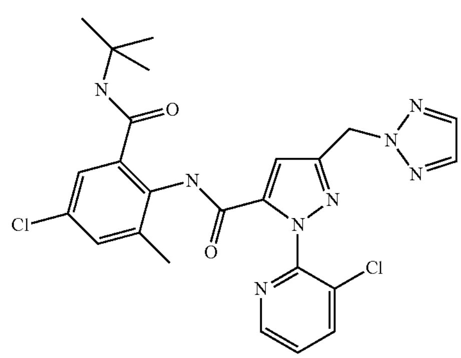 [SMILES: Cc1cc(Cl)cc(C(=O)NC(C)(C)C)c1NC(=O)c1cc(Cn2nccn2)nn1-c1ncccc1Cl] | 2.87 | 527 | 8.439, 0.44; 8.435, 0.45; 8.427, 0.44; .423, 0.45; 7.960, 0.49; 7.957, 0.49; 7.940, 0.54; 7.936, 0.50; 7.691, 1.57; 7.474, 0.55; 7.462, 0.54; 7.454, 0.52; 7.442, 0.48; 7.323, 0.76; 7.319, 0.69; 6.921, 0.54; 5.723, 2.70; 2.144, 3.03; 1.995, 123.96; 1.952, 0.38; 1.943, 1.70; 1.937, 1.34; 1.931, 15.06; 1.925, 28.90; 1.918, 41.73; 1.912, 28.41; 1.906, 14.41; 1.308, 16.00; −0.000, 3.04 |

-continued

| No. | Structure | logP | MH+ | NMR |
|---|---|---|---|---|
| 122 | 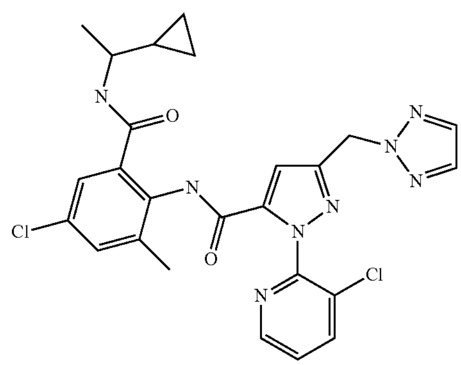 [SMILES: Cc1cc(Cl)cc(C(=O)NC(C)C2CC2)c1NC(=O)c1cc(Cn2nccn2)nn1-c1ncccc1Cl] | 2.81 | 539 | 9.99, 1.000; 8.44, 2.850; 8.44, 3.010; 8.43, 3.080; 8.43, 3.010; 8.09, 2.840; 8.08, 2.930; 8.07, 3.180; 8.06, 3.050; 7.83, 1.110; 7.82, 15.680; 7.56, 3.350; 7.55, 3.170; 7.54, 3.100; 7.53, 3.010; 7.40, 2.480; 7.40, 2.580; 7.39, 2.880; 7.39, 2.740; 7.29, 2.890; 7.28, 2.690; 7.10, 3.170; 5.75, 14.400; 3.34, 1.170; 3.33, 1.210; 3.11, 77.930; 2.53, 0.760; 2.53, 0.760; 2.50, 10.360; 2.49, 21.540; 2.49, 30.540; 2.48, 21.450; 2.48, 10.350; 2.14, 16.000; 1.36, 4.710; 1.07, 9.790; 1.05, 9.710; 0.82, 1.290; 0.82, 0.760; 0.81, 0.880; 0.80, 1.320; 0.79, 0.730; 0.36, 1.240; 0.36, 1.000; 0.35, 0.960; 0.34, 1.160; 0.24, 0.770; 0.24, 0.750; 0.23, 1.050; 0.22, 1.030; 0.22, 0.930; 0.21, 1.590; 0.20, 0.890; 0.19, 0.840; 0.19, 0.920; 0.18, 1.090; 0.17, 1.480; 0.16, 1.260; 0.15, 1.350; 0.14, 0.910; 0.14, 1.220; 0.13, 1.250; 0.11, 0.900; −0.00, 1.430 |
| 123 | 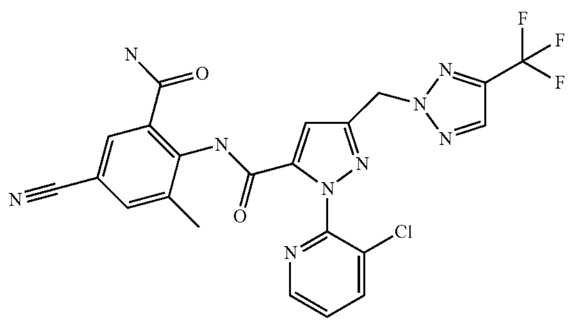 [SMILES: Cc1cc(C#N)cc(C(N)=O)c1NC(=O)c1cc(Cn2ncc(C(F)(F)F)n2)nn1-c1ncccc1Cl] | 2.41 | 530 | 10.473, 3.19; 8.469, 2.65; 8.465, 2.80; 8.457, 2.89; 8.453, 2.79; 8.434, 3.67; 8.111, 2.55; 8.108, 2.64; 8.091, 2.82; 8.087, 2.69; 7.801, 9.87; 7.707, 0.36; 7.689, 0.37; 7.653, 0.40; 7.635, 0.37; 7.614, 0.34; 7.597, 0.34; 7.576, 3.00; 7.564, 2.96; 7.556, 2.77; 7.544, 2.82; 7.446, 0.45; 7.425, 0.35; 7.358, 0.32; 7.216, 7.16; 5.912, 11.90; 3.285, 0.35; 3.234, 0.53; 3.115, 728.86; 3.070, 0.76; 3.057, 0.62; 2.661, 1.03; 2.657, 1.49; 2.653, 0.93; 2.575, 0.40; 2.526, 1.76; 2.510, 5.03; 2.497, 79.92; 2.493, 156.65; 2.488, 213.93; 2.483, 149.42; 2.479, 72.05; 2.428, 0.33; 2.320, 0.92; 2.315, 1.19; 2.310, 0.89; 2.176, 16.00; 2.040, 1.53; 1.404, 0.39; 1.246, 0.38; −0.000, 4.34 |
| 124 | 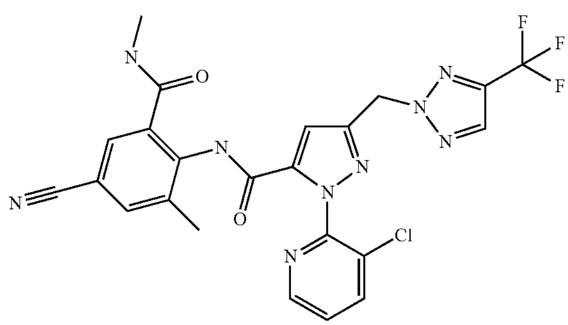 [SMILES: CNC(=O)c1cc(C#N)cc(C)c1NC(=O)c1cc(Cn2ncc(C(F)(F)F)n2)nn1-c1ncccc1Cl] | 2.68 | 544 | 10.381, 1.79; 8.462, 2.98; 8.458, 3.19; 8.450, 3.25; 8.446, 3.23; 8.438, 3.70; 8.436, 3.70; 8.423, 0.64; 8.390, 0.41; 8.387, 0.41; 8.379, 0.45; 8.375, 0.45; 8.313, 0.40; 8.308, 0.36; 8.151, 1.01; 8.147, 1.14; 8.131, 1.18; 8.127, 0.97; 8.111, 3.01; 8.107, 3.00; 8.090, 3.28; 8.087, 3.05; 7.975, 0.41; 7.888, 0.44; 7.795, 2.55; 7.792, 2.69; 7.723, 3.02; 7.719, 2.78; 7.575, 3.31; 7.564, 3.15; 7.555, 3.07; 7.543, 3.09; 7.533, 0.59; 7.521, 0.58; 7.512, 0.55; 7.501, 0.41; 7.259, 1.30; 7.223, 5.37; 5.961, 1.88; 5.918, 11.62; 3.677, 4.22; 3.171, 0.46; 3.115, 626.17; 2.712, 0.81; 2.700, 0.81; 2.683, 10.94; 2.671, 10.91; 2.662, 0.96; 2.657, 1.05; 2.652, 0.78; 2.648, 0.42; 2.526, 0.94; 2.510, 2.34; 2.506, 3.28; 2.497, 49.27; 2.493, 101.43; 2.488, 142.69; 2.483, 99.47; 2.479, 47.32; 2.319, 0.52; 2.315, 0.85; 2.310, 0.65; 2.305, 0.32; 2.281, 1.14; 2.190, 16.00; 2.141, 1.10; 2.040, 1.04; 1.949, 2.37; 1.404, 0.50; 1.363, 0.49; 1.258, 0.47; −0.000, 3.65 |

-continued
| No. | Structure | logP | MH+ | NMR |
|---|---|---|---|---|
| 125 | 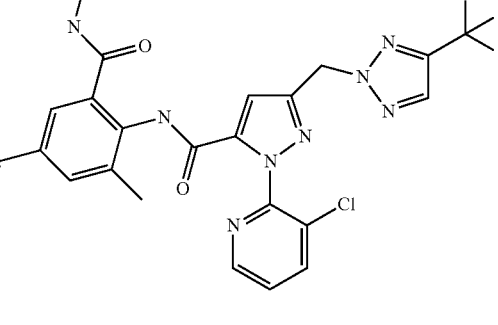 | 3.39 | 598 | 8.453, 2.99; 8.449, 3.25; 8.441, 3.35; 8.437, 3.40; 8.431, 3.96; 8.430, 3.89; 8.100, 3.06; 8.096, 3.13; 8.080, 3.36; 8.076, 3.22; 8.022, 0.76; 8.007, 0.93; 8.002, 0.96; 7.798, 2.57; 7.796, 2.82; 7.793, 3.04; 7.791, 2.72; 7.699, 3.12; 7.696, 2.88; 7.572, 3.45; 7.560, 3.30; 7.552, 3.19; 7.540, 3.12; 7.220, 6.47; 5.913, 12.04; 3.366, 0.65; 3.347, 1.25; 3.330, 1.28; 3.310, 0.67; 3.115, 38.16; 2.526, 0.96; 2.510, 0.64; 2.505, 0.89; 2.497, 12.29; 2.492, 25.38; 2.488, 35.75; 2.483, 24.96; 2.478, 11.88; 2.287, 1.03; 2.198, 16.00; 2.183, 0.69; 2.135, 1.00; 1.364, 5.17; 1.132, 0.68; 1.115, 0.70; 1.075, 10.19; 1.059, 10.09; 0.847, 0.69; 0.834, 1.29; 0.827, 0.83; 0.822, 0.83; 0.814, 1.32; 0.801, 0.75; 0.373, 0.60; 0.365, 1.20; 0.356, 1.10; 0.352, 1.02; 0.343, 1.21; 0.336, 0.65; 0.331, 0.71; 0.321, 0.65; 0.247, 0.84; 0.243, 0.86; 0.237, 0.69; 0.233, 1.10; 0.227, 1.11; 0.223, 0.99; 0.213, 1.53; 0.206, 0.80; 0.201, 1.19; 0.191, 1.65; 0.179, 1.54; 0.168, 1.31; 0.155, 1.16; 0.145, 0.95; 0.141, 1.21; 0.132, 1.29; 0.127, 0.70; 0.119, 0.89; −0.000, 2.10 |
| 126 | 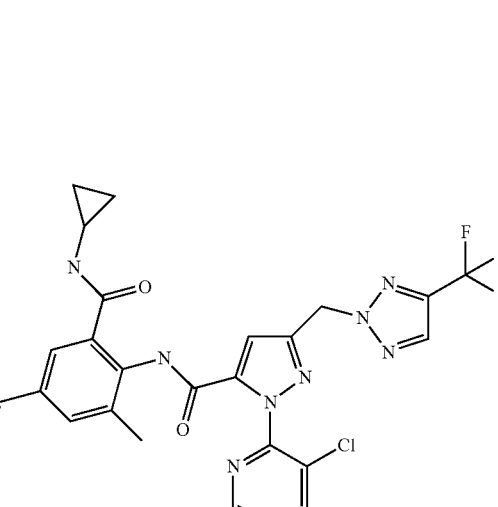 | 2.9 | 570 | 10.314, 2.21; 8.463, 3.01; 8.460, 3.26; 8.452, 3.33; 8.448, 3.29; 8.439, 3.74; 8.438, 3.78; 8.410, 0.40; 8.321, 0.36; 8.313, 0.33; 8.309, 0.33; 8.261, 0.33; 8.258, 0.33; 8.230, 0.34; 8.226, 0.33; 8.209, 0.38; 8.206, 0.35; 8.173, 1.16; 8.164, 1.18; 8.109, 2.94; 8.105, 3.01; 8.088, 3.26; 8.085, 3.11; 7.857, 0.32; 7.854, 0.34; 7.786, 2.73; 7.783, 2.90; 7.682, 2.77; 7.678, 2.55; 7.577, 3.46; 7.565, 3.34; 7.556, 3.19; 7.545, 3.19; 7.540, 0.47; 7.528, 0.33; 7.519, 0.33; 7.287, 0.89; 7.234, 6.93; 6.873, 0.69; 5.941, 1.30; 5.923, 11.11; 3.122, 365.56; 2.719, 0.55; 2.709, 0.76; 2.701, 1.17; 2.691, 1.17; 2.682, 0.78; 2.672, 0.59; 2.662, 0.48; 2.658, 0.46; 2.527, 0.42; 2.511, 1.06; 2.506, 1.52; 2.498, 22.66; 2.493, 46.69; 2.489, 65.61; 2.484, 45.64; 2.479, 21.64; 2.315, 0.39; 2.283, 1.05; 2.191, 16.00; 2.146, 1.05; 2.040, 0.52; 1.900, 1.57; 1.364, 10.78; 1.187, 0.35; 0.629, 0.81; 0.617, 2.17; 0.612, 2.81; 0.599, 2.70; 0.594, 2.11; 0.582, 0.96; 0.461, 1.11; 0.451, 2.96; 0.444, 2.78; 0.440, 2.48; 0.435, 2.42; 0.423, 0.81; −0.000, 2.84 |
| 127 | 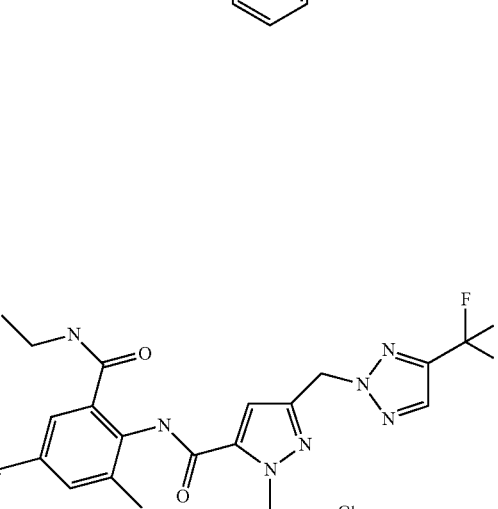 | 2.88 | 558 | 10.345, 0.47; 8.456, 2.96; 8.452, 3.24; 8.444, 3.29; 8.441, 3.34; 8.434, 3.70; 8.433, 3.65; 8.164, 0.35; 8.147, 0.70; 8.143, 0.77; 8.137, 0.72; 8.105, 2.99; 8.101, 3.07; 8.085, 3.28; 8.081, 3.11; 7.791, 2.54; 7.788, 2.81; 7.719, 2.99; 7.715, 2.71; 7.573, 3.36; 7.561, 3.27; 7.553, 3.15; 7.541, 3.13; 7.218, 5.56; 7.180, 0.48; 5.974, 0.64; 5.917, 11.49; 3.194, 1.00; 3.176, 2.88; 3.162, 3.05; 3.158, 3.09; 3.144, 3.16; 3.140, 1.72; 3.117, 167.86; 2.510, 0.77; 2.506, 1.13; 2.497, 16.17; 2.493, 33.37; 2.488, 46.95; 2.483, 32.83; 2.479, 15.70; 2.286, 1.06; 2.194, 16.00; 2.139, 1.08; 2.012, 0.87; 1.403, 1.12; 1.323, 0.60; 1.066, 0.40; 1.048, 0.84; 1.026, 5.82; 1.008, 12.33; 0.990, 5.64; −0.000, 2.72 |

-continued

| No. | Structure | logP | MH+ | NMR |
|---|---|---|---|---|
| 128 | 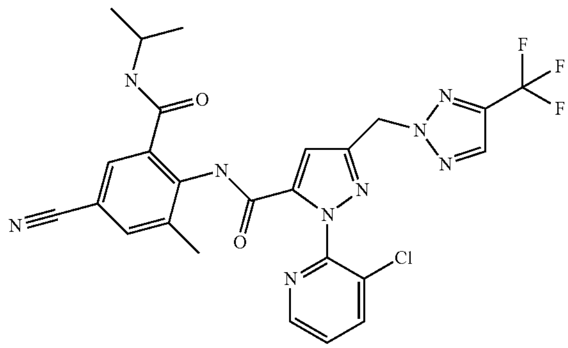 [SMILES: Cc1cc(C#N)cc(C(=O)NC(C)C)c1NC(=O)c1cc(Cn2ncc(C(F)(F)F)n2)nn1-c1ncccc1Cl] | 3.1 | 572 | 10.307, 1.02; 8.451, 1.75; 8.447, 1.82; 8.439, 2.17; 8.435, 4.08; 8.100, 1.68; 8.096, 1.66; 8.080, 1.83; 8.076, 1.72; 7.934, 0.60; 7.918, 0.61; 7.784, 2.20; 7.699, 2.33; 7.695, 2.19; 7.571, 1.84; 7.560, 1.83; 7.551, 1.75; 7.540, 1.69; 7.221, 3.68; 6.873, 1.13; 6.403, 0.53; 5.917, 8.77; 3.936, 0.65; 3.919, 0.96; 3.901, 0.95; 3.884, 0.62; 3.111, 105.24; 2.657, 0.32; 2.510, 0.86; 2.497, 18.01; 2.492, 36.17; 2.488, 50.57; 2.483, 35.89; 2.479, 17.80; 2.315, 0.32; 2.286, 0.74; 2.196, 11.81; 2.183, 2.06; 2.138, 0.79; 1.364, 15.66; 1.187, 1.15; 1.093, 1.03; 1.076, 1.03; 1.043, 16.00; 1.027, 15.90; −0.000, 1.77 |
| 129 | 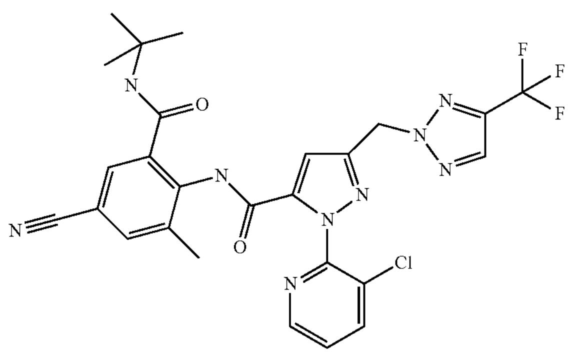 [SMILES: Cc1cc(C#N)cc(C(=O)NC(C)(C)C)c1NC(=O)c1cc(Cn2ncc(C(F)(F)F)n2)nn1-c1ncccc1Cl] | 3.46 | 586 | 10.236, 0.35; 8.455, 0.56; 8.451, 0.61; 8.443, 0.61; 8.439, 0.61; 8.431, 0.71; 8.429, 0.71; 8.108, 0.53; 8.104, 0.54; 8.088, 0.60; 8.084, 0.56; 7.763, 0.48; 7.760, 0.50; 7.665, 0.56; 7.661, 0.52; 7.576, 0.63; 7.564, 0.61; 7.555, 0.58; 7.544, 0.57; 7.186, 0.93; 5.918, 2.19; 3.112, 48.09; 2.505, 0.32; 2.497, 4.98; 2.492, 10.26; 2.488, 14.45; 2.483, 10.10; 2.478, 4.82; 2.187, 2.90; 1.273, 0.81; 1.228, 16.00; −0.000, 1.21 |
| 130 | 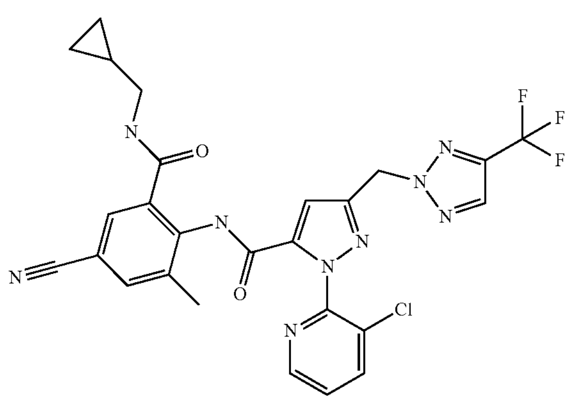 [SMILES: Cc1cc(C#N)cc(C(=O)NCC2CC2)c1NC(=O)c1cc(Cn2ncc(C(F)(F)F)n2)nn1-c1ncccc1Cl] | 3.17 | 584 | 10.345, 0.64; 8.526, 0.32; 8.521, 0.38; 8.450, 1.78; 8.438, 1.86; 8.434, 2.07; 8.431, 2.23; 8.429, 2.20; 8.198, 0.47; 8.192, 0.60; 8.188, 0.59; 8.183, 0.40; 8.172, 0.39; 8.168, 0.36; 8.101, 1.65; 8.097, 1.66; 8.081, 1.83; 8.077, 1.71; 7.800, 1.46; 7.797, 1.57; 7.726, 1.75; 7.722, 1.60; 7.571, 1.94; 7.559, 1.84; 7.550, 1.77; 7.539, 1.74; 7.314, 0.43; 7.222, 2.96; 6.003, 0.97; 5.968, 0.45; 5.911, 6.85; 3.203, 16.00; 3.111, 108.21; 3.036, 1.73; 3.022, 2.24; 3.020, 2.24; 3.005, 1.71; 2.588, 2.79; 2.584, 5.84; 2.579, 8.29; 2.574, 5.87; 2.569, 2.90; 2.510, 0.84; 2.505, 1.19; 2.497, 15.91; 2.492, 32.52; 2.488, 45.57; 2.483, 31.80; 2.478, 15.19; 2.288, 1.77; 2.197, 9.04; 2.183, 0.56; 2.134, 0.59; 2.023, 0.60; 1.455, 0.65; 1.364, 4.70; 0.891, 0.37; 0.888, 0.36; 0.884, 0.34; 0.872, 0.62; 0.859, 0.40; 0.855, 0.38; 0.851, 0.37; 0.345, 0.68; 0.335, 1.76; 0.330, 1.88; 0.325, 0.83; 0.320, 0.97; 0.314, 1.78; 0.310, 1.51; 0.300, 0.76; 0.142, 0.71; 0.131, 1.86; 0.128, 1.79; 0.119, 1.62; 0.116, 1.88; 0.104, 0.49; 0.091, 0.37; −0.000, 2.20 |

| No. | Structure | logP | MH+ | NMR |
|---|---|---|---|---|
| 131 | 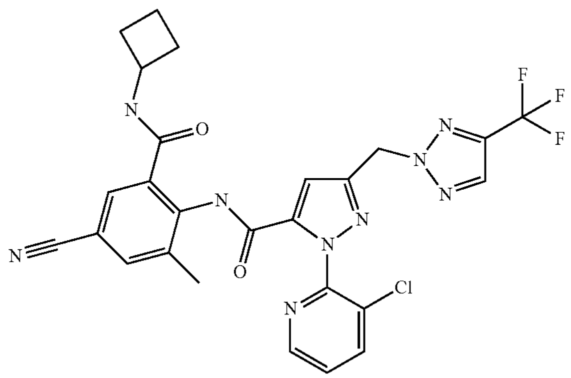 [SMILES: Cc1cc(C#N)cc(C(=O)NC2CCC2)c1NC(=O)c1cc(Cn2ncc(C(F)(F)F)n2)nn1-c1ncccc1Cl] | 3.23 | 584 | 10.302, 0.41; 8.457, 2.98; 8.453, 3.18; 8.446, 3.31; 8.442, 3.25; 8.433, 4.01; 8.432, 3.91; 8.345, 0.75; 8.342, 0.69; 8.334, 0.74; 8.330, 0.74; 8.102, 2.85; 8.099, 2.87; 8.082, 3.16; 8.079, 2.96; 7.791, 2.75; 7.788, 3.03; 7.731, 2.99; 7.727, 2.69; 7.574, 3.52; 7.562, 3.39; 7.554, 3.27; 7.542, 3.24; 7.218, 0.39; 7.206, 5.65; 5.916, 11.60; 5.783, 0.51; 4.252, 0.66; 4.233, 1.18; 4.213, 1.13; 4.193, 0.62; 3.176, 0.40; 3.119, 136.75; 2.657, 0.33; 2.527, 0.34; 2.510, 0.90; 2.506, 1.26; 2.498, 17.79; 2.493, 36.65; 2.488, 51.51; 2.484, 35.85; 2.479, 17.04; 2.289, 1.10; 2.191, 16.00; 2.169, 0.61; 2.161, 0.65; 2.150, 1.07; 2.139, 2.15; 2.130, 1.34; 2.121, 1.50; 2.112, 1.23; 2.101, 0.71; 2.092, 0.60; 1.960, 0.39; 1.954, 0.36; 1.937, 1.26; 1.931, 0.94; 1.914, 1.63; 1.907, 1.38; 1.891, 1.17; 1.884, 1.29; 1.868, 0.38; 1.862, 0.41; 1.671, 0.93; 1.660, 0.85; 1.652, 1.36; 1.647, 1.18; 1.639, 1.22; 1.633, 1.05; 1.627, 1.86; 1.620, 0.67; 1.616, 0.63; 1.607, 0.85; 1.602, 0.81; 1.583, 0.40; 1.557, 0.66; 1.008, 0.41; −0.000, 2.22 |
| 132 | 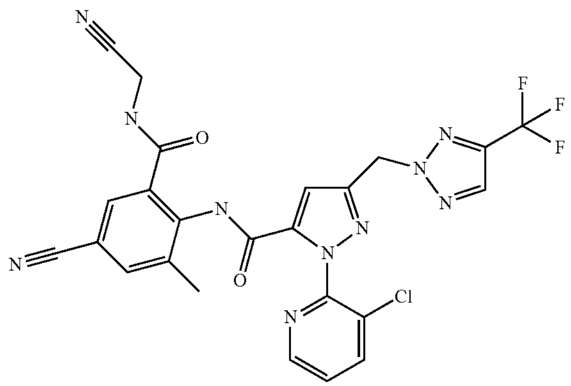 [SMILES: Cc1cc(C#N)cc(C(=O)NCC#N)c1NC(=O)c1cc(Cn2ncc(C(F)(F)F)n2)nn1-c1ncccc1Cl] | 2.76 | 569 | 10.322, 0.49; 8.956, 0.81; 8.469, 1.33; 8.464, 3.20; 8.460, 3.42; 8.457, 1.76; 8.452, 3.39; 8.448, 3.19; 8.431, 4.18; 8.417, 0.37; 8.114, 0.39; 8.111, 1.03; 8.107, 1.10; 8.102, 2.94; 8.098, 3.15; 8.094, 0.53; 8.091, 1.22; 8.087, 1.19; 8.082, 3.23; 8.078, 3.07; 8.003, 0.37; 7.862, 2.51; 7.860, 2.75; 7.857, 2.96; 7.801, 3.04; 7.764, 3.13; 7.760, 2.92; 7.582, 0.39; 7.576, 1.24; 7.569, 3.51; 7.564, 1.33; 7.557, 3.50; 7.549, 3.25; 7.544, 1.22; 7.537, 3.09; 7.253, 6.10; 7.217, 2.46; 7.162, 0.52; 6.000, 0.36; 5.909, 12.92; 5.224, 0.44; 4.215, 0.35; 4.201, 0.38; 4.170, 4.32; 4.156, 4.30; 4.138, 0.34; 4.062, 0.35; 3.995, 0.46; 3.980, 0.47; 3.686, 2.14; 3.674, 2.37; 3.622, 0.51; 3.492, 1.55; 3.213, 0.37; 3.120, 89.55; 3.004, 0.34; 2.662, 0.35; 2.657, 0.56; 2.653, 0.39; 2.527, 0.39; 2.511, 1.21; 2.506, 1.79; 2.498, 29.57; 2.493, 61.54; 2.488, 87.23; 2.484, 61.69; 2.479, 30.06; 2.320, 0.42; 2.315, 0.59; 2.307, 1.15; 2.237, 0.37; 2.216, 16.00; 2.177, 5.41; 2.137, 1.09; 2.123, 1.20; 1.969, 0.55; 1.404, 0.81; 1.364, 1.21; −0.000, 4.40 |
| 133 | Chiral | 3.33 | 619 | 8.454, 1.09; 8.450, 1.16; 8.443, 1.21; 8.439, 1.18; 8.429, 1.47; 8.428, 1.45; 8.098, 1.01; 8.095, 1.00; 8.078, 1.13; 8.074, 1.02; 7.789, 0.80; 7.718, 0.97; 7.714, 0.86; 7.571, 1.10; 7.559, 1.07; 7.551, 1.02; 7.539, 1.01; 7.219, 1.09; 6.873, 0.86; 6.403, 0.38; 5.910, 4.07; 3.978, 0.36; 3.113, 53.50; 2.601, 0.46; 2.585, 0.47; 2.568, 0.79; 2.552, 0.77; 2.510, 0.57; 2.505, 0.84; 2.497, 11.24; 2.492, 23.07; 2.488, 32.45; 2.483, 22.57; 2.478, 10.72; 2.468, 0.88; 2.450, 0.74; 2.434, 0.45; 2.417, 0.43; 2.196, 5.15; 2.182, 1.63; 2.137, 0.37; 2.089, 0.54; 2.040, 0.40; 2.005, 9.59; 1.997, 1.93; 1.364, 16.00; 1.174, 0.42; 1.128, 0.54; 1.107, 3.25; 1.090, 3.19; −0.000, 3.73 |

-continued

| No. | Structure | logP | MH+ | NMR |
|---|---|---|---|---|
| 134 | 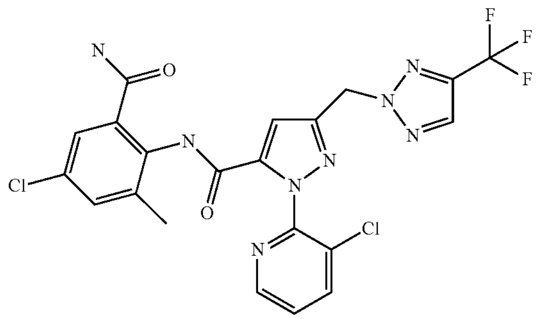 | 2.7 | 539 | 10.161, 1.04; 8.464, 1.47; 8.461, 1.60; 8.453, 1.60; 8.449, 1.60; 8.432, 1.83; 8.431, 1.78; 8.104, 1.47; 8.100, 1.53; 8.084, 1.66; 8.080, 1.58; 7.570, 1.77; 7.558, 1.72; 7.549, 1.67; 7.538, 1.66; 7.412, 0.96; 7.411, 1.00; 7.406, 2.04; 7.405, 1.97; 7.397, 2.21; 7.396, 2.15; 7.391, 1.06; 7.195, 1.44; 6.874, 0.89; 6.402, 0.46; 5.904, 5.82; 3.602, 0.39; 3.115, 46.59; 2.505, 0.38; 2.497, 5.43; 2.492, 11.17; 2.487, 15.71; 2.483, 10.98; 2.478, 5.23; 2.183, 1.48; 2.132, 8.11; 1.761, 0.49; 1.364, 16.00; −0.000, 0.33 |
| 135 | 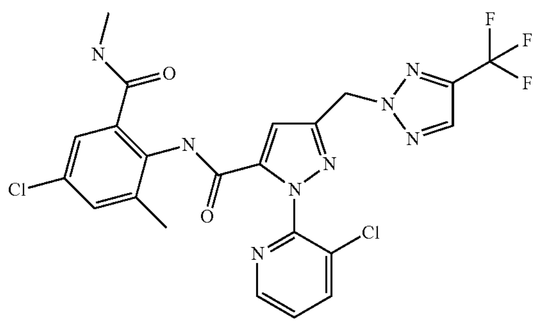 [SMILES: CNC(=O)c1cc(Cl)cc(C)c1NC(=O)c1cc(Cn2ncc(C(F)(F)F)n2)nn1-c1ncccc1Cl] | 2.99 | 553 | 10.093, 1.59; 10.005, 0.75; 8.460, 1.66; 8.458, 2.04; 8.456, 1.95; 8.454, 2.04; 8.448, 1.86; 8.446, 2.24; 8.444, 2.06; 8.443, 2.14; 8.435, 3.61; 8.372, 1.37; 8.368, 1.44; 8.360, 1.50; 8.356, 1.50; 8.348, 1.62; 8.347, 1.62; 8.106, 1.61; 8.104, 1.99; 8.102, 1.85; 8.100, 1.85; 8.086, 1.80; 8.084, 2.21; 8.082, 1.92; 8.080, 1.94; 8.018, 1.47; 8.014, 1.63; 7.998, 2.36; 7.994, 2.19; 7.571, 1.85; 7.570, 2.14; 7.560, 1.81; 7.558, 2.08; 7.551, 1.80; 7.549, 2.01; 7.539, 1.68; 7.538, 1.93; 7.483, 1.56; 7.472, 1.51; 7.463, 1.47; 7.451, 1.44; 7.405, 2.40; 7.399, 2.77; 7.322, 3.04; 7.316, 3.59; 7.236, 1.37; 7.230, 1.25; 7.195, 2.60; 7.108, 1.25; 5.911, 9.68; 5.824, 5.16; 3.117, 66.40; 3.115, 81.43; 3.028, 58.19; 2.670, 8.39; 2.659, 8.37; 2.584, 5.06; 2.572, 5.03; 2.510, 0.56; 2.498, 9.14; 2.497, 10.38; 2.494, 18.80; 2.492, 20.03; 2.489, 26.80; 2.488, 26.70; 2.484, 19.93; 2.483, 18.49; 2.480, 10.15; 2.411, 5.71; 2.406, 11.52; 2.401, 16.00; 2.397, 11.09; 2.392, 5.22; 2.141, 14.45; 2.054, 7.68; 1.366, 1.11; 1.364, 1.23; 1.278, 0.91; 0.002, 0.70; −0.000, 0.73 |
| 136 | 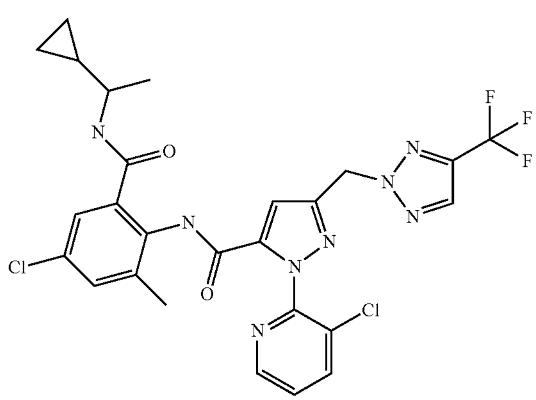 [SMILES: Cc1cc(Cl)cc(C(=O)NC(C)C2CC2)c1NC(=O)c1cc(Cn2ncc(C(F)(F)F)n2)nn1-c1ncccc1Cl] | 3.8 | 607 | 10.027, 2.11; 8.449, 3.11; 8.445, 3.34; 8.437, 3.50; 8.433, 3.93; 8.429, 3.97; 8.428, 3.88; 8.096, 3.17; 8.092, 3.15; 8.076, 3.54; 8.072, 3.28; 7.843, 1.09; 7.823, 1.12; 7.569, 3.65; 7.557, 3.46; 7.548, 3.34; 7.537, 3.34; 7.407, 2.59; 7.406, 2.61; 7.401, 2.96; 7.291, 2.96; 7.284, 2.66; 7.191, 2.97; 5.903, 12.00; 3.356, 0.65; 3.336, 1.25; 3.319, 1.30; 3.302, 0.61; 3.299, 0.66; 3.112, 229.64; 2.657, 0.71; 2.652, 0.54; 2.526, 2.86; 2.510, 1.79; 2.505, 2.50; 2.497, 36.54; 2.492, 75.63; 2.487, 106.79; 2.483, 74.50; 2.478, 35.45; 2.314, 0.65; 2.145, 16.00; 1.404, 0.72; 1.363, 0.72; 1.059, 10.35; 1.042, 10.21; 0.827, 0.68; 0.814, 1.27; 0.807, 0.72; 0.802, 0.85; 0.794, 1.28; 0.782, 0.74; 0.774, 0.55; 0.357, 0.54; 0.349, 1.11; 0.340, 1.07; 0.336, 1.01; 0.326, 1.33; 0.320, 0.62; 0.314, 0.70; 0.305, 0.67; 0.222, 0.83; 0.218, 0.69; 0.208, 1.06; 0.202, 1.14; 0.196, 1.19; 0.187, 1.62; 0.182, 1.27; 0.174, 1.09; 0.167, 1.19; 0.161, 1.55; 0.150, 1.27; 0.137, 1.12; 0.127, 0.93; 0.123, 1.13; 0.115, 1.25; 0.108, 0.65; 0.100, 0.79; 0.092, 0.52; −0.000, 4.50 |

| No. | Structure | logP | MH+ | NMR |
|---|---|---|---|---|
| 137 | 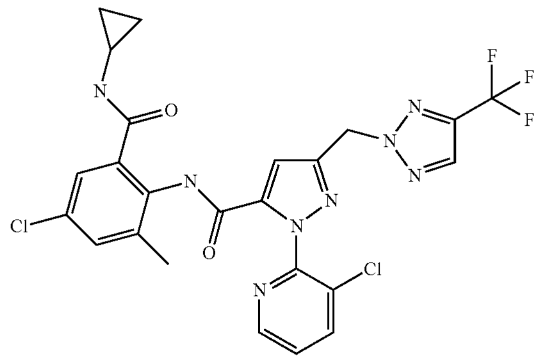 [SMILES: Cc1cc(Cl)cc(C(=O)NC2CC2)c1NC(=O)c1cc(Cn2ncc(C(F)(F)F)n2)nn1-c1ncccc1Cl] | 3.18 | 579 | 10.023, 2.25; 8.459, 2.83; 8.455, 3.05; 8.447, 3.14; 8.443, 3.13; 8.434, 3.64; 8.101, 2.76; 8.098, 2.81; 8.081, 3.00; 8.078, 2.93; 8.026, 1.16; 8.017, 1.21; 7.571, 3.22; 7.559, 3.09; 7.551, 3.00; 7.539, 2.97; 7.393, 2.45; 7.388, 2.65; 7.274, 2.99; 7.268, 2.74; 7.199, 2.69; 5.912, 10.86; 3.117, 759.98; 3.083, 1.07; 2.710, 0.49; 2.700, 0.73; 2.691, 1.13; 2.681, 1.09; 2.672, 0.73; 2.662, 0.99; 2.657, 0.83; 2.653, 0.74; 2.648, 0.34; 2.527, 2.31; 2.510, 2.18; 2.506, 3.07; 2.498, 40.97; 2.493, 83.84; 2.488, 117.71; 2.484, 82.42; 2.479, 39.55; 2.320, 0.55; 2.315, 0.72; 2.310, 0.44; 2.136, 16.00; 2.040, 1.43; 1.110, 1.23; 0.612, 0.72; 0.600, 2.04; 0.594, 2.62; 0.582, 2.56; 0.577, 1.99; 0.565, 0.88; 0.440, 1.26; 0.429, 3.13; 0.423, 2.96; 0.419, 2.72; 0.413, 2.66; 0.401, 0.83; −0.000, 1.02 |
| 138 | 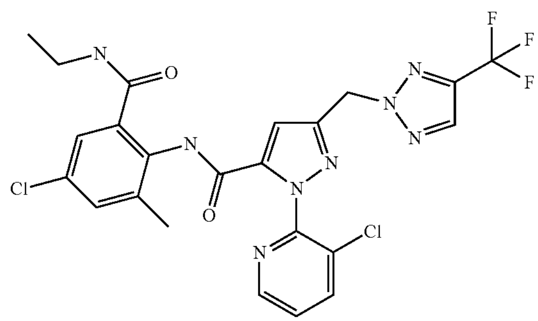 [SMILES: CCNC(=O)c1cc(Cl)cc(C)c1NC(=O)c1cc(Cn2ncc(C(F)(F)F)n2)nn1-c1ncccc1Cl] | 3.26 | 567 | 10.064, 2.31; 8.453, 2.37; 8.449, 2.47; 8.441, 2.58; 8.437, 2.66; 8.430, 3.89; 8.099, 2.31; 8.095, 2.30; 8.079, 2.55; 8.075, 2.40; 7.990, 0.67; 7.978, 1.15; 7.966, 0.68; 7.568, 2.58; 7.556, 2.50; 7.548, 2.38; 7.536, 2.33; 7.401, 2.59; 7.395, 2.88; 7.312, 3.03; 7.306, 2.67; 7.191, 2.89; 5.909, 11.35; 3.182, 0.85; 3.164, 2.63; 3.150, 2.95; 3.146, 2.92; 3.132, 2.98; 3.128, 1.79; 3.114, 54.00; 2.497, 5.43; 2.492, 10.87; 2.487, 15.08; 2.483, 10.63; 2.478, 5.16; 2.144, 16.00; 1.012, 5.22; 0.994, 10.72; 0.976, 5.02; −0.000, 1.57 |
| 139 | 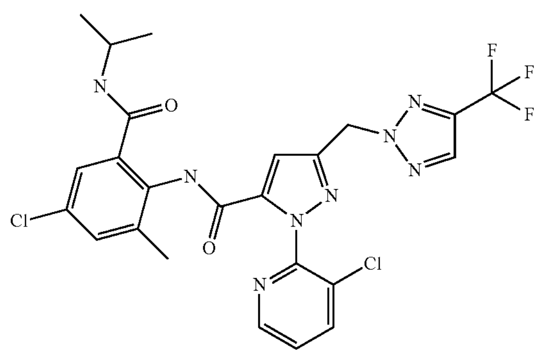 [SMILES: Cc1cc(Cl)cc(C(=O)NC(C)C)c1NC(=O)c1cc(Cn2ncc(C(F)(F)F)n2)nn1-c1ncccc1Cl] | 3.48 | 581 | 10.026, 1.51; 8.448, 2.04; 8.444, 2.20; 8.436, 2.82; 8.433, 4.54; 8.096, 2.10; 8.092, 2.13; 8.076, 2.38; 8.072, 2.25; 7.771, 0.72; 7.752, 0.74; 7.568, 2.46; 7.556, 2.39; 7.548, 2.28; 7.536, 2.26; 7.397, 1.78; 7.392, 1.96; 7.391, 1.90; 7.287, 1.97; 7.282, 1.82; 7.190, 1.91; 5.909, 8.11; 3.927, 0.57; 3.910, 0.84; 3.891, 0.84; 3.875, 0.58; 3.112, 136.76; 2.657, 0.43; 2.526, 1.53; 2.510, 0.93; 2.505, 1.31; 2.497, 19.30; 2.492, 40.21; 2.487, 56.87; 2.483, 39.76; 2.478, 19.00; 2.314, 0.34; 2.143, 11.16; 1.026, 16.00; 1.009, 15.83; −0.000, 3.01 |
| 140 | 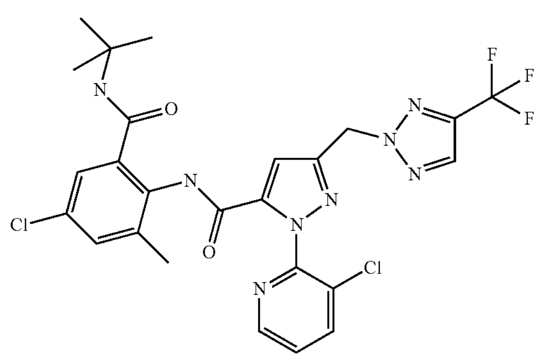 | 3.85 | 595 | 9.419, 0.42; 8.461, 0.52; 8.457, 0.62; 8.449, 0.62; 8.446, 0.65; 8.092, 0.89; 7.984, 0.50; 7.980, 0.57; 7.964, 0.60; 7.960, 0.63; 7.504, 0.56; 7.492, 0.60; 7.484, 0.59; 7.472, 0.55; 7.341, 0.59; 7.336, 0.99; 7.323, 0.96; 7.318, 0.72; 7.062, 1.37; 6.555, 0.42; 5.833, 2.75; 2.134, 7.54; 1.951, 3.51; 1.945, 6.62; 1.939, 9.45; 1.933, 7.30; 1.926, 4.36; 1.292, 16.00; −0.000, 3.44 |

| No. | Structure | logP | MH+ | NMR |
|---|---|---|---|---|
| 141 | 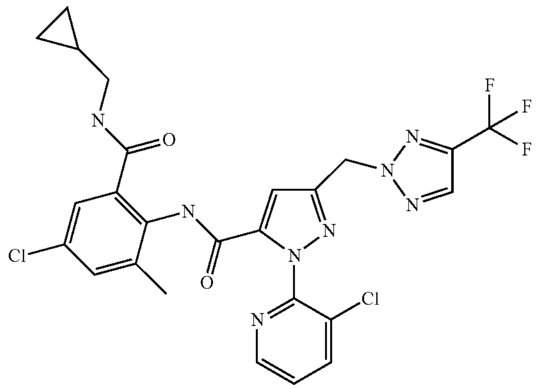 [SMILES: Cc1cc(Cl)cc(C(=O)NCC2CC2)c1NC(=O)c1cc(Cn2ncc(C(F)(F)F)n2)nn1-c1ncccc1Cl] | 3.55 | 593 | 10.07, 2.300; 8.45, 3.000; 8.44, 3.240; 8.44, 3.370; 8.43, 4.140; 8.43, 3.970; 8.43, 3.920; 8.10, 3.100; 8.09, 3.220; 8.08, 3.520; 8.07, 3.350; 8.05, 0.660; 8.04, 1.170; 8.02, 0.670; 7.57, 3.630; 7.56, 3.480; 7.55, 3.370; 7.54, 3.350; 7.41, 2.510; 7.41, 2.850; 7.32, 3.050; 7.31, 2.710; 7.19, 2.820; 5.90, 11.950; 3.12, 230.140; 3.02, 3.100; 3.01, 4.050; 2.99, 3.110; 2.53, 1.430; 2.51, 0.910; 2.51, 1.250; 2.50, 18.580; 2.49, 38.710; 2.49, 54.810; 2.48, 38.400; 2.48, 18.360; 2.15, 16.000; 2.08, 0.380; 1.40, 1.050; 0.88, 0.580; 0.88, 0.630; 0.87, 0.580; 0.87, 0.500; 0.86, 1.100; 0.85, 0.500; 0.85, 0.630; 0.84, 0.620; 0.84, 0.650; 0.83, 0.370; 0.32, 1.130; 0.31, 3.000; 0.31, 3.270; 0.30, 1.470; 0.30, 1.640; 0.29, 3.310; 0.29, 2.770; 0.28, 1.380; 0.13, 1.230; 0.12, 3.190; 0.11, 3.090; 0.10, 2.810; 0.10, 3.310; 0.09, 0.840; −0.00, 1.710 |
| 142 | 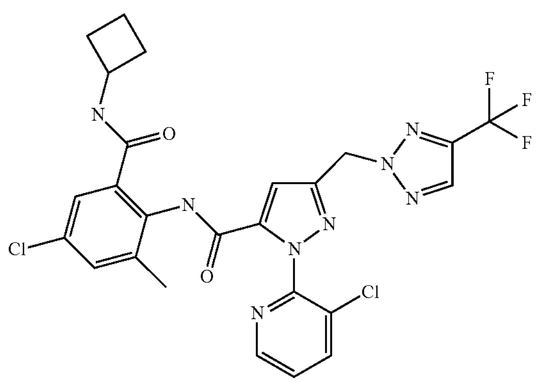 [SMILES: Cc1cc(Cl)cc(C(=O)NC2CCC2)c1NC(=O)c1cc(Cn2ncc(C(F)(F)F)n2)nn1-c1ncccc1Cl] | 3.64 | 593 | 10.024, 1.18; 8.454, 2.69; 8.450, 2.86; 8.442, 2.98; 8.438, 2.95; 8.431, 3.56; 8.429, 3.49; 8.188, 0.74; 8.170, 0.75; 8.097, 2.56; 8.094, 2.62; 8.077, 2.86; 8.073, 2.70; 7.569, 3.22; 7.557, 3.11; 7.549, 2.98; 7.537, 2.97; 7.402, 2.25; 7.401, 2.35; 7.396, 2.66; 7.395, 2.50; 7.314, 2.62; 7.308, 2.39; 7.177, 2.40; 5.907, 10.42; 4.245, 0.57; 4.226, 1.08; 4.205, 1.07; 4.186, 0.59; 3.115, 187.87; 2.526, 0.99; 2.510, 0.71; 2.505, 0.99; 2.497, 13.70; 2.492, 28.24; 2.488, 39.72; 2.483, 27.70; 2.478, 13.21; 2.152, 0.68; 2.139, 16.00; 2.127, 1.32; 2.125, 1.35; 2.119, 1.20; 2.113, 1.15; 2.105, 1.35; 2.101, 1.13; 2.095, 1.11; 2.085, 0.61; 2.077, 0.56; 1.940, 0.33; 1.917, 1.15; 1.911, 0.85; 1.894, 1.53; 1.886, 1.33; 1.871, 1.12; 1.864, 1.24; 1.848, 0.35; 1.843, 0.36; 1.653, 0.81; 1.642, 0.73; 1.636, 1.12; 1.630, 1.19; 1.619, 1.17; 1.611, 1.76; 1.603, 0.58; 1.596, 0.56; 1.591, 0.64; 1.586, 0.77; 1.364, 1.10; 0.992, 0.34; −0.000, 1.91 |
| 143 | 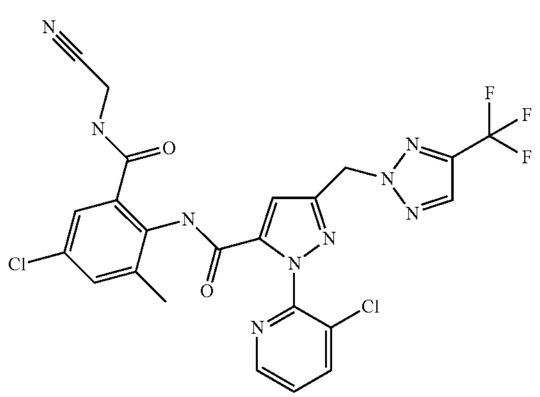 [SMILES: Cc1cc(Cl)cc(C(=O)NCC#N)c1NC(=O)c1cc(Cn2ncc(C(F)(F)F)n2)nn1-c1ncccc1Cl] | 2.97 | 578 | 10.072, 0.65; 8.849, 0.94; 8.459, 2.97; 8.455, 3.29; 8.447, 3.23; 8.443, 3.19; 8.427, 3.49; 8.426, 3.46; 8.095, 2.93; 8.091, 2.99; 8.085, 0.36; 8.080, 0.34; 8.075, 3.30; 8.071, 3..55; 7.472, 2.64; 7.468, 2.93; 7.466, 2.78; 7.359, 2.80; 7.354, 2.59; 7.224, 2.40; 5.898, 11.46; 4.156, 4.10; 4.143, 4.12; 3.994, 0.33; 3.980, 0.34; 3.672, 0.37; 3.480, 1.04; 3.115, 50.12; 2.657, 0.36; 2.510, 0.73; 2.505, 1.06; 2.497, 19.41; 2.492, 40.55; 2.488, 57.53; 2.483, 40.52; 2.478, 19.63; 2.319, 0.34; 2.315, 0.38; 2.162, 16.00; 2.140, 0.35; 2.131, 0.87; 2.082, 0.60; 1.364, 1.64; −0.000, 3.84 |

| No. | Structure | logP | MH+ | NMR |
|---|---|---|---|---|
| 144 | Chiral | 3.74 | 627 | 10.048, 0.40; 10.024, 1.32; 8.515, 0.47; 8.452, 1.73; 8.448, 1.88; 8.440, 1.92; 8.436, 1.95; 8.427, 2.68; 8.097, 1.62; 8.093, 1.56; 8.077, 1.78; 8.073, 1.61; 7.941, 0.68; 7.922, 0.71; 7.570, 1.82; 7.558, 1.76; 7.549, 1.70; 7.538, 1.66; 7.413, 1.68; 7.407, 1.70; 7.396, 0.42; 7.335, 0.41; 7.329, 0.37; 7.314, 1.89; 7.308, 1.69; 7.206, 1.72; 5.993, 1.08; 5.905, 7.51; 3.989, 0.56; 3.971, 0.65; 3.952, 0.57; 3.208, 16.00; 3.154, 0.38; 3.119, 106.35; 2.589, 0.88; 2.585, 1.53; 2.581, 3.08; 2.576, 4.58; 2.571, 3.53; 2.567, 1.74; 2.556, 1.34; 2.550, 0.39; 2.540, 1.26; 2.510, 0.40; 2.497, 7.75; 2.493, 15.87; 2.488, 22.44; 2.483, 16.26; 2.479, 8.13; 2.462, 1.35; 2.444, 1.28; 2.429, 0.80; 2.411, 0.77; 2.237, 1.54; 2.149, 10.59; 2.087, 2.10; 2.078, 0.50; 1.999, 14.31; 1.990, 3.33; 1.364, 1.04; 1.181, 0.83; 1.164, 0.83; 1.117, 1.36; 1.100, 1.65; 1.093, 5.65; 1.077, 5.53; 0.996, 0.39; 0.979, 0.39 |
| 145 | 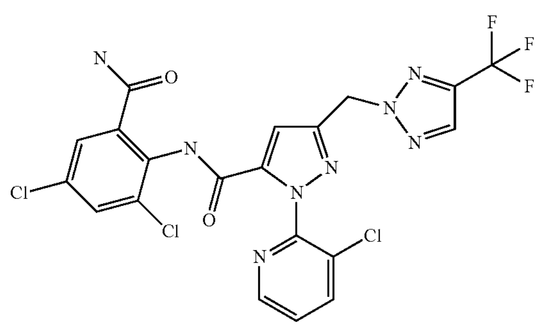 [SMILES: NC(=O)c1cc(Cl)cc(Cl)c1NC(=O)c1cc(Cn2ncc(C(F)(F)F)n2)nn1-c1ncccc1Cl] | 2.69 | 559 | 10.263, 4.41; 8.466, 3.60; 8.462, 3.74; 8.455, 3.95; 8.451, 3.82; 8.435, 5.29; 8.095, 3.50; 8.091, 3.49; 8.075, 3.88; 8.071, 3.60; 7.975, 0.54; 7.735, 5.17; 7.729, 5.37; 7.569, 3.99; 7.557, 4.01; 7.549, 3.95; 7.537, 3.92; 7.522, 7.31; 7.516, 6.98; 7.473, 0.68; 7.417, 0.66; 7.410, 0.67; 7.398, 0.55; 7.252, 8.16; 5.908, 16.00; 3.222, 0.33; 3.120, 496.19; 3.063, 0.35; 3.055, 0.36; 2.662, 0.50; 2.658, 0.75; 2.653, 0.56; 2.527, 0.98; 2.510, 2.68; 2.498, 43.49; 2.493, 84.17; 2.488, 113.38; 2.484, 78.74; 2.479, 37.72; 2.320, 0.51; 2.315, 0.69; 2.310, 0.51; 2.040, 0.78; 1.404, 0.47; −0.000, 3.02 |
| 146 | 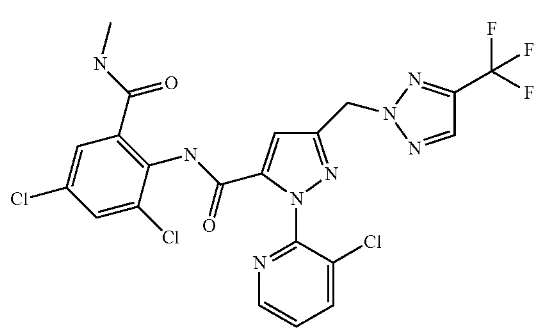 [SMILES: CNC(=O)c1cc(Cl)cc(Cl)c1NC(=O)c1cc(Cn2ncc(C(F)(F)F)n2)nn1-c1ncccc1Cl] | 2.98 | 573 | 10.254, 2.76; 8.459, 2.98; 8.456, 3.13; 8.448, 3.36; 8.444, 3.43; 8.437, 5.69; 8.419, 0.43; 8.097, 2.94; 8.095, 2.79; 8.094, 2.93; 8.077, 3.31; 8.075, 3.10; 8.074, 3.23; 8.034, 1.27; 8.014, 0.66; 8.009, 0.53; 7.730, 3.77; 7.724, 3.98; 7.700, 0.35; 7.570, 3.18; 7.559, 3.17; 7.550, 3.08; 7.539, 3.20; 7.461, 5.30; 7.455, 5.14; 7.259, 6.76; 7.239, 0.59; 6.873, 1.20; 6.404, 0.59; 5.959, 0.84; 5.912, 16.00; 3.654, 1.45; 3.115, 317.38; 3.079, 0.36; 2.704, 0.74; 2.692, 0.75; 2.656, 14.36; 2.645, 13.82; 2.527, 0.62; 2.497, 30.73; 2.493, 61.09; 2.488, 84.08; 2.483, 60.09; 2.319, 0.41; 2.315, 0.50; 2.183, 1.89; 2.040, 0.41; 1.404, 0.41; 1.364, 15.15; −0.000, 4.46 |

| No. | Structure | logP | MH+ | NMR |
|---|---|---|---|---|
| 147 | 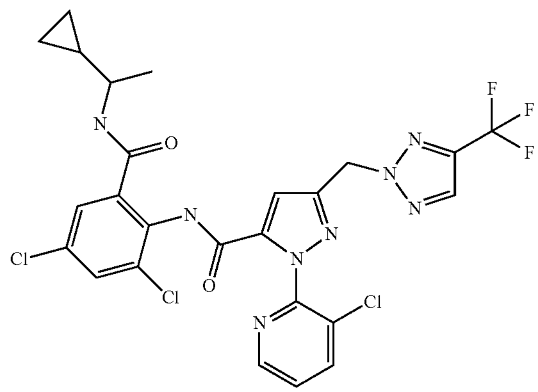 [SMILES: CC(NC(=O)c1cc(Cl)cc(Cl)c1NC(=O)c1cc(Cn2ncc(C(F)(F)F)n2)nn1-c1ncccc1Cl)C1CC1] | 3.73 | 627 | 10.185, 3.84; 8.447, 4.19; 8.443, 4.38; 8.435, 6.43; 8.431, 9.14; 8.088, 4.03; 8.085, 4.20; 8.068, 4.54; 8.064, 4.30; 7.893, 1.54; 7.873, 1.54; 7.736, 5.89; 7.730, 6.16; 7.568, 4.71; 7.556, 4.55; 7.548, 4.36; 7.536, 4.46; 7.422, 6.57; 7.416, 6.34; 7.267, 7.85; 5.907, 16.00; 3.327, 0.87; 3.306, 1.66; 3.290, 1.74; 3.270, 0.90; 3.112, 144.04; 2.526, 2.24; 2.510, 1.40; 2.505, 1.97; 2.497, 28.90; 2.492, 60.20; 2.487, 85.32; 2.483, 59.76; 2.478, 28.60; 2.314, 0.52; 1.363, 0.56; 1.123, 0.69; 1.107, 0.69; 1.044, 14.12; 1.027, 13.91; 0.820, 0.66; 0.812, 0.91; 0.800, 1.72; 0.792, 1.02; 0.787, 1.15; 0.779, 1.81; 0.767, 1.02; 0.759, 0.68; 0.365, 0.58; 0.357, 0.71; 0.353, 0.80; 0.344, 1.94; 0.336, 1.42; 0.332, 1.34; 0.323, 1.69; 0.316, 0.82; 0.310, 0.91; 0.301, 0.87; 0.229, 0.66; 0.219, 0.99; 0.215, 0.99; 0.205, 1.35; 0.198, 1.47; 0.195, 1.22; 0.184, 2.08; 0.173, 1.51; 0.164, 2.16; 0.160, 0.87; 0.152, 2.23; 0.142, 1.89; 0.138, 1.54; 0.135, 1.59; 0.129, 1.35; 0.127, 1.39; 0.122, 1.77; 0.114, 1.65; 0.108, 0.86; 0.101, 1.14; 0.092, 0.65; −0.000, 4.59 |
| 148 | 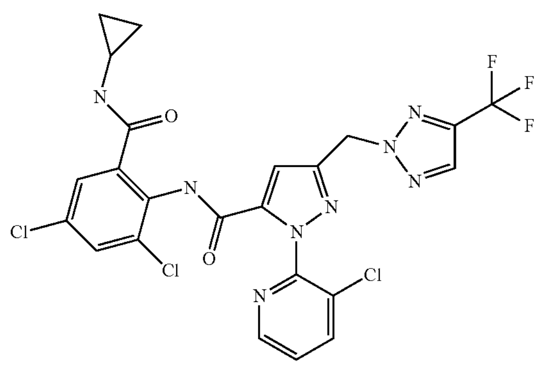 | 3.18 | 599 | 10.209, 2.66; 8.460, 4.33; 8.457, 4.62; 8.449, 4.82; 8.445, 5.59; 8.441, 5.52; 8.440, 5.45; 8.098, 5.61; 8.094, 5.60; 8.089, 1.88; 8.078, 4.95; 8.074, 4.61; 7.722, 5.32; 7.716, 5.53; 7.573, 4.76; 7.562, 4.55; 7.553, 4.39; 7.541, 4.52; 7.535, 0.38; 7.498, 0.35; 7.492, 0.37; 7.418, 5.55; 7.412, 5.40; 7.269, 7.98; 7.253, 0.32; 5.939, 0.33; 5.918, 16.00; 5.809, 0.38; 3.115, 199.39; 2.695, 0.38; 2.685, 0.81; 2.675, 1.09; 2.667, 1.85; 2.657, 2.26; 2.652, 0.84; 2.648, 1.25; 2.639, 0.83; 2.526, 2.03; 2.510, 1.28; 2.505, 1.74; 2.497, 26.83; 2.492, 56.07; 2.488, 79.55; 2.483, 55.87; 2.478, 26.85; 2.319, 0.37; 2.315, 0.49; 2.310, 0.35; 2.037, 0.33; 1.363, 1.41; 0.611, 1.15; 0.598, 3.10; 0.593, 4.13; 0.581, 4.16; 0.575, 3.19; 0.563, 1.48; 0.426, 1.64; 0.416, 4.27; 0.409, 4.14; 0.405, 3.71; 0.400, 3.75; 0.388, 1.20; −0.000, 1.45 |
| 149 | 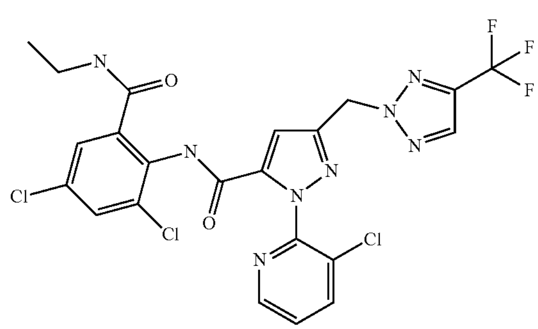 [SMILES: CCNC(=O)c1cc(Cl)cc(Cl)c1NC(=O)c1cc(Cn2ncc(C(F)(F)F)n2)nn1-c1ncccc1Cl] | 3.2 | 587 | 10.217, 1.02; 8.448, 3.48; 8.445, 3.77; 8.437, 4.10; 8.433, 6.54; 8.086, 2.71; 8.082, 2.77; 8.066, 3.00; 8.062, 2.93; 7.703, 1.56; 7.563, 3.11; 7.552, 3.08; 7.543, 2.98; 7.531, 2.95; 7.460, 2.86; 7.454, 2.77; 7.232, 1.35; 5.904, 13.20; 3.179, 0.35; 3.164, 1.33; 3.150, 1.85; 3.146, 3.91; 3.132, 4.99; 3.128, 5.96; 3.115, 314.76; 3.096, 2.86; 3.092, 2.42; 2.662, 0.34; 2.657, 0.49; 2.652, 0.35; 2.526, 0.47; 2.510, 1.28; 2.505, 1.82; 2.497, 26.59; 2.493, 54.72; 2.488, 77.02; 2.483, 53.75; 2.478, 25.63; 2.319, 0.34; 2.315, 0.48; 2.310, 0.33; 1.364, 0.50; 1.052, 0.36; 1.034, 0.72; 1.016, 0.36; 0.994, 7.55; 0.976, 16.00; 0.958, 7.31; −0.000, 2.52 |

-continued
| No. | Structure | logP | MH+ | NMR |
|---|---|---|---|---|
| 150 | 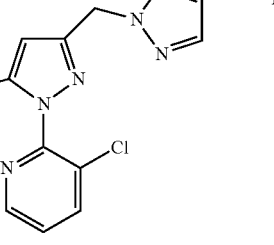 | 3.41 | 601 | 10.192, 0.61; 8.446, 2.02; 8.442, 2.18; 8.434, 4.56; 8.431, 2.44; 8.088, 1.96; 8.085, 2.03; 8.068, 2.22; 8.064, 2.08; 7.833, 0.47; 7.819, 0.46; 7.725, 2.46; 7.719, 2.60; 7.568, 2.28; 7.556, 2.22; 7.548, 2.14; 7.536, 2.18; 7.424, 3.14; 7.418, 3.07; 7.263, 2.97; 5.912, 7.89; 3.899, 0.59; 3.883, 0.86; 3.864, 0.84; 3.847, 0.58; 3.112, 94.97; 2.526, 1.11; 2.510, 0.67; 2.505, 0.94; 2.497, 14.35; 2.492, 29.95; 2.487, 42.41; 2.483, 29.71; 2.478, 14.21; 1.363, 1.33; 1.083, 0.86; 1.066, 0.83; 1.014, 16.00; 0.997, 15.85; −0.000, 2.55 |
| 151 | 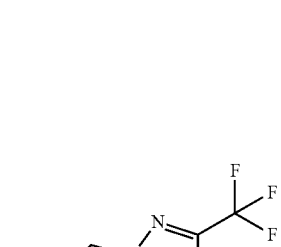 | 3.8 | 615 | 10.175, 0.60; 8.451, 0.50; 8.449, 0.57; 8.447, 0.58; 8.446, 0.55; 8.439, 0.59; 8.438, 0.72; 8.434, 1.34; 8.100, 0.47; 8.098, 0.53; 8.096, 0.52; 8.094, 0.48; 8.080, 0.53; 8.078, 0.59; 8.076, 0.53; 8.074, 0.50; 7.703, 0.75; 7.702, 0.77; 7.697, 0.81; 7.696, 0.77; 7.575, 0.54; 7.573, 0.56; 7.563, 0.53; 7.561, 0.55; 7.554, 0.51; 7.553, 0.52; 7.543, 0.52; 7.541, 0.52; 7.395, 0.97; 7.393, 1.05; 7.389, 1.00; 7.387, 1.04; 7.376, 0.53; 7.244, 1.24; 5.916, 2.85; 3.113, 33.24; 2.497, 4.40; 2.493, 8.17; 2.492, 8.51; 2.489, 11.60; 2.488, 11.46; 2.484, 8.57; 2.483, 8.00; 2.480, 4.36; 1.266, 0.53; 1.200, 15.52; 1.199, 16.00; −0.000, 0.33 |
| 152 | 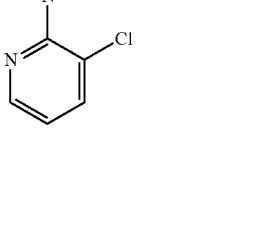 | 3.48 | 613 | 10.22, 3.070; 8.45, 4.020; 8.44, 4.360; 8.43, 8.500; 8.43, 7.120; 8.09, 5.040; 8.08, 5.490; 8.07, 5.200; 8.06, 4.660; 7.75, 0.430; 7.74, 5.550; 7.73, 5.810; 7.57, 4.590; 7.56, 4.450; 7.55, 4.280; 7.54, 4.320; 7.53, 0.520; 7.52, 0.410; 7.45, 6.850; 7.45, 6.630; 7.27, 7.570; 5.91, 16.000; 3.12, 153.420; 3.01, 4.070; 2.99, 5.200; 2.99, 5.200; 2.97, 4.130; 2.53, 1.420; 2.51, 0.910; 2.51, 1.240; 2.50, 18.640; 2.49, 38.740; 2.49, 54.820; 2.48, 38.350; 2.48, 18.360; 0.88, 0.380; 0.87, 0.420; 0.86, 0.770; 0.86, 0.840; 0.85, 0.780; 0.85, 0.650; 0.84, 1.470; 0.83, 0.670; 0.83, 0.840; 0.82, 0.830; 0.82, 0.910; 0.81, 0.410; 0.81, 0.470; 0.80, 0.360; 0.32, 1.510; 0.31, 3.980; 0.30, 4.290; 0.30, 1.890; 0.29, 2.170; 0.29, 4.320; 0.28, 3.610; 0.27, 1.810; 0.12, 1.600; 0.11, 4.290; 0.10, 4.080; 0.10, 3.720; 0.09, 4.400; 0.08, 1.110; 0.00, 1.120 |

-continued

| No. | Structure | logP | MH+ | NMR |
|---|---|---|---|---|
| 153 | 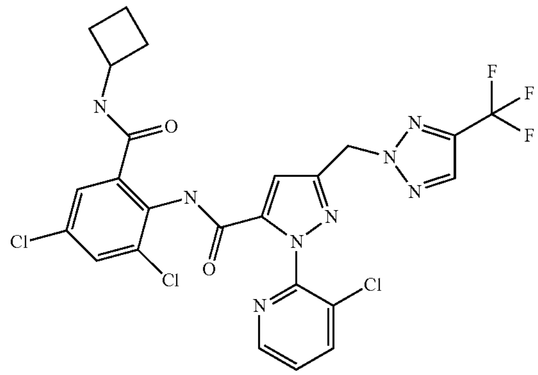 [SMILES: O=C(NC1CCC1)c1cc(Cl)cc(Cl)c1NC(=O)c1cc(Cn2ncc(C(F)(F)F)n2)nn1-c1ncccc1Cl] | 3.56 | 613 | 10.187, 0.51; 8.453, 4.08; 8.449, 4.47; 8.441, 4.50; 8.438, 4.81; 8.432, 5.35; 8.248, 0.89; 8.238, 0.88; 8.233, 0.93; 8.090, 3.88; 8.086, 3.99; 8.070, 4.42; 8.066, 4.17; 7.727, 5.39; 7.721, 5.67; 7.570, 4.68; 7.558, 4.50; 7.550, 4.29; 7.538, 4.32; 7.528, 0.40; 7.452, 6.52; 7.446, 6.36; 7.251, 6.80; 5.909, 16.00; 4.214, 0.90; 4.195, 1.64; 4.174, 1.60; 4.155, 0.86; 3.192, 0.42; 3.119, 493.75; 2.662, 0.42; 2.657, 0.69; 2.653, 0.46; 2.527, 0.91; 2.511, 1.61; 2.506, 2.32; 2.498, 32.80; 2.493, 67.52; 2.488, 94.88; 2.484, 66.09; 2.479, 31.39; 2.320, 0.38; 2.315, 0.54; 2.310, 0.38; 2.147, 0.69; 2.140, 0.75; 2.129, 1.22; 2.118, 1.78; 2.113, 1.68; 2.107, 1.68; 2.099, 1.93; 2.094, 1.69; 2.089, 1.65; 2.079, 0.89; 2.071, 0.82; 2.040, 0.38; 1.922, 0.47; 1.917, 0.42; 1.900, 1.68; 1.894, 1.25; 1.877, 2.27; 1.870, 1.95; 1.853, 1.64; 1.847, 1.88; 1.831, 0.58; 1.825, 0.56; 1.653, 1.27; 1.640, 1.20; 1.636, 1.64; 1.629, 1.92; 1.617, 2.03; 1.610, 2.62; 1.603, 0.87; 1.594, 0.95; 1.590, 0.93; 1.586, 1.27; 1.566, 0.48; 1.364, 0.67; 0.978, 0.58; −0.000, 3.40 |
| 154 | 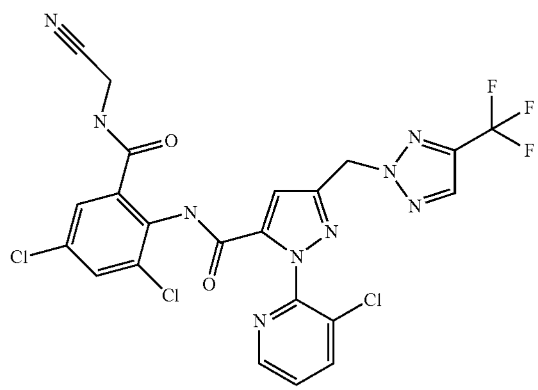 [SMILES: N#CCNC(=O)c1cc(Cl)cc(Cl)c1NC(=O)c1cc(Cn2ncc(C(F)(F)F)n2)nn1-c1ncccc1Cl] | 2.9 | 598 | 12.550, 0.67; 10.303, 4.69; 10.285, 0.82; 8.943, 2.47; 8.458, 4.04; 8.451, 3.50; 8.447, 4.49; 8.431, 6.29; 8.085, 3.78; 8.065, 4.06; 7.800, 4.87; 7.564, 2.91; 7.562, 2.79; 7.553, 3.00; 7.544, 3.29; 7.533, 2.67; 7.513, 4.94; 7.509, 5.99; 7.490, 0.55; 7.280, 6.90; 5.902, 16.00; 4.153, 7.55; 4.140, 7.92; 4.116, 0.53; 3.367, 0.55; 3.304, 0.54; 3.296, 0.59; 3.293, 0.65; 3.254, 0.77; 3.223, 0.82; 3.198, 1.10; 3.183, 1.70; 3.117, 848.83; 3.114, 737.58; 3.031, 0.56; 2.657, 1.71; 2.586, 0.83; 2.565, 0.72; 2.497, 75.60; 2.493, 165.68; 2.488, 250.34; 2.486, 224.89; 2.484, 226.38; 2.319, 1.11; 2.311, 1.59; 2.040, 1.79; 1.403, 0.50; 1.242, 0.69; 1.160, 0.52; −0.000, 10.91; −0.002, 9.39 |
| 155 | Chiral | 3.64 | 647 | 10.202, 0.93; 8.451, 1.75; 8.447, 1.89; 8.439, 2.02; 8.435, 2.37; 8.432, 2.50; 8.431, 2.49; 8.090, 1.64; 8.086, 1.60; 8.070, 1.84; 8.066, 1.68; 8.011, 0.65; 7.991, 0.66; 7.751, 0.46; 7.744, 2.53; 7.738, 2.49; 7.570, 1.82; 7.559, 1.77; 7.550, 1.71; 7.538, 1.69; 7.470, 0.40; 7.465, 0.40; 7.445, 2.69; 7.439, 2.59; 7.282, 3.16; 7.270, 0.64; 5.909, 7.14; 3.955, 0.49; 3.938, 0.62; 3.920, 0.50; 3.112, 93.12; 2.579, 0.80; 2.563, 0.78; 2.546, 1.24; 2.530, 1.25; 2.510, 0.73; 2.505, 1.07; 2.497, 14.58; 2.492, 29.93; 2.487, 42.06; 2.483, 29.48; 2.478, 14.18; 2.441, 1.27; 2.423, 1.24; 2.408, 0.81; 2.390, 0.78; 2.006, 1.13; 2.000, 16.00; 1.987, 2.36; 1.364, 0.50; 1.108, 0.92; 1.090, 1.04; 1.080, 5.49; 1.063, 5.42; 0.980, 0.44; 0.964, 0.39; −0.000, 0.58 |

| No. | Structure | logP | MH+ | NMR |
|---|---|---|---|---|
| 156 | 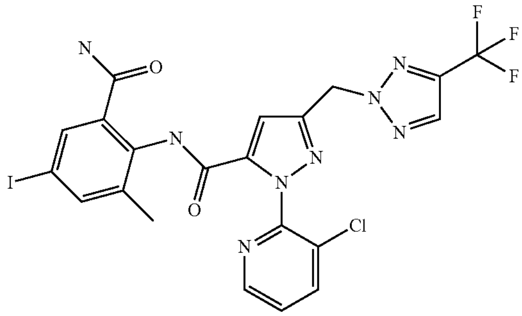 [SMILES: Cc1cc(I)cc(C(N)=O)c1NC(=O)c1cc(Cn2ncc(C(F)(F)F)n2)nn1-c1ncccc1Cl] | 2.89 | 631 | 10.156, 1.41; 8.462, 1.78; 8.458, 1.93; 8.450, 1.94; 8.447, 1.92; 8.430, 2.19; 8.428, 2.14; 8.102, 1.77; 8.098, 1.82; 8.082, 1.97; 8.078, 1.89; 7.709, 1.42; 7.707, 1.52; 7.704, 2.00; 7.702, 1.82; 7.679, 2.07; 7.678, 2.10; 7.674, 1.61; 7.568, 2.11; 7.557, 2.06; 7.548, 1.99; 7.536, 1.99; 7.186, 2.12; 6.874, 0.88; 6.401, 0.46; 5.900, 6.90; 3.117, 71.30; 2.510, 0.33; 2.505, 0.48; 2.497, 6.82; 2.492, 14.03; 2.488, 19.74; 2.483, 13.77; 2.478, 2.488, 6.56; 2.183, 1.45; 2.096, 9.46; 1.761, 0.39; 1.364, 16.00; −0.000, 1.11 |
| 157 | 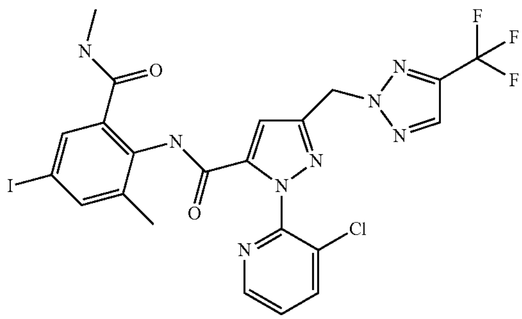 [SMILES: CNC(=O)c1cc(I)cc(C)c1NC(=O)c1cc(Cn2ncc(C(F)(F)F)n2)nn1-c1ncccc1Cl] | 3.26 | 645 | 10.083, 1.29; 8.456, 1.57; 8.452, 1.69; 8.444, 1.75; 8.440, 1.73; 8.432, 1.97; 8.431, 1.97; 8.103, 1.54; 8.099, 1.62; 8.082, 1.76; 8.079, 1.67; 7.982, 0.50; 7.975, 0.59; 7.971, 0.51; 7.700, 1.45; 7.696, 1.60; 7.601, 1.61; 7.596, 1.49; 7.569, 1.84; 7.557, 1.73; 7.549, 1.69; 7.537, 1.67; 7.185, 1.70; 6.872, 0.92; 6.403, 0.48; 5.906, 6.09; 3.118, 372.19; 2.660, 5.79; 2.649, 5.74; 2.527, 0.44; 2.510, 1.13; 2.506, 1.62; 2.497, 23.70; 2.493, 48.71; 2.488, 68.53; 2.483, 47.78; 2.479, 22.76; 2.315, 0.43; 2.182, 1.45; 2.103, 8.61; 2.040, 0.35; 1.363, 16.00; 1.174, 0.32; −0.000, 0.71 |
| 158 | 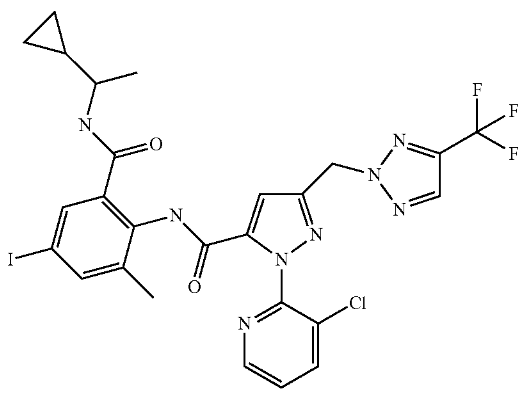 [SMILES: Cc1cc(I)cc(C(=O)NC(C)C2CC2)c1NC(=O)c1cc(Cn2ncc(C(F)(F)F)n2)nn1-c1ncccc1Cl] | 4.05 | 699 | 10.022, 1.59; 8.447, 3.00; 8.443, 3.26; 8.435, 3.37; 8.431, 3.56; 8.427, 3.99; 8.425, 3.89; 8.094, 3.07; 8.090, 3.10; 8.074, 3.47; 8.070, 3.22; 7.840, 1.19; 7.820, 1.20; 7.704, 2.76; 7.702, 2.93; 7.699, 3.16; 7.697, 2.89; 7.573, 3.15; 7.567, 5.84; 7.555, 3.47; 7.547, 3.30; 7.535, 3.24; 7.185, 3.46; 5.900, 11.89; 3.347, 0.64; 3.327, 1.21; 3.310, 1.27; 3.290, 0.65; 3.112, 80.97; 2.526, 1.25; 2.510, 0.82; 2.505, 1.14; 2.497, 16.27; 2.492, 33.67; 2.487, 47.48; 2.483, 33.20; 2.478, 15.83; 2.109, 16.00; 1.238, 0.61; 1.222, 0.58; 1.056, 10.12; 1.039, 9.96; 0.835, 0.64; 0.827, 0.93; 0.815, 1.34; 0.807, 0.74; 0.802, 0.82; 0.794, 1.31; 0.782, 0.74; 0.774, 0.51; 0.361, 0.50; 0.357, 0.58; 0.348, 1.11; 0.340, 1.03; 0.336, 0.99; 0.326, 1.20; 0.320, 0.59; 0.314, 0.69; 0.305, 0.62; 0.232, 0.45; 0.222, 0.77; 0.218, 0.70; 0.208, 1.01; 0.202, 1.08; 0.198, 0.91; 0.193, 0.77; 0.188, 1.41; 0.181, 1.07; 0.170, 1.12; 0.167, 1.14; 0.157, 1.50; 0.147, 1.23; 0.132, 1.03; 0.123, 0.90; 0.120, 1.13; 0.110, 1.26; 0.105, 0.66; 0.097, 0.84; 0.088, 0.49; −0.000, 2.50 |
| 159 | 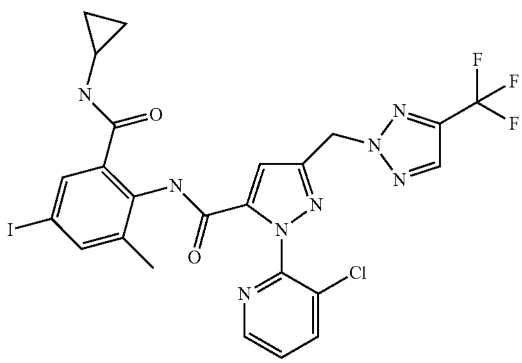 [SMILES: Cc1cc(I)cc(C(=O)NC2CC2)c1NC(=O)c1cc(Cn2ncc(C(F)(F)F)n2)nn1-c1ncccc1Cl] | 3.45 | 671 | 10.015, 2.95; 8.453, 2.68; 8.445, 2.51; 8.441, 3.06; 8.434, 4.52; 8.100, 1.89; 8.097, 2.41; 8.080, 2.13; 8.077, 2.64; 8.009, 1.80; 7.687, 3.86; 7.570, 2.08; 7.558, 2.28; 7.548, 4.92; 7.538, 3.49; 7.191, 3.56; 5.909, 10.67; 3.208, 0.42; 3.116, 406.00; 2.700, 0.64; 2.682, 1.27; 2.674, 1.37; 2.662, 1.38; 2.657, 1.39; 2.547, 0.42; 2.535, 0.57; 2.492, 76.10; 2.488, 113.38; 2.484, 98.47; 2.479, 61.74; 2.314, 0.65; 2.100, 16.00; 2.040, 0.67; 0.607, 0.82; 0.589, 3.23; 0.576, 2.93; 0.560, 1.17; 0.437, 1.13; 0.426, 3.52; 0.420, 3.83; 0.411, 3.42; 0.398, 0.91; −0.000, 1.44 |

| No. | Structure | logP | MH+ | NMR |
|---|---|---|---|---|
| 160 | 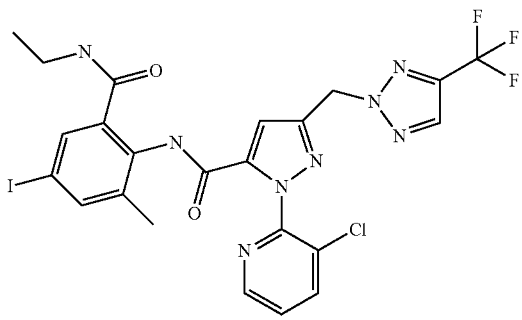 [SMILES: CCNC(=O)c1cc(I)cc(C)c1NC(=O)c1cc(Cn2ncc(C(F)(F)F)n2)nn1-c1ncccc1Cl] | 3.5 | 659 | 10.055, 2.49; 8.450, 3.05; 8.446, 3.31; 8.439, 3.39; 8.435, 3.49; 8.429, 3.86; 8.427, 3.76; 8.098, 3.08; 8.094, 3.07; 8.078, 3.49; 8.074, 3.21; 7.982, 0.65; 7.969, 1.13; 7.956, 0.65; 7.699, 2.76; 7.695, 3.00; 7.590, 3.04; 7.585, 2.82; 7.567, 3.57; 7.556, 3.42; 7.547, 3.30; 7.536, 3.23; 7.180, 3.31; 5.905, 11.68; 3.172, 0.98; 3.154, 3.03; 3.140, 3.61; 3.136, 3.90; 3.118, 187.21; 2.510, 0.63; 2.506, 0.92; 2.497, 13.20; 2.493, 27.16; 2.488, 38.17; 2.483, 26.62; 2.479, 12.68; 2.107, 16.00; 1.008, 5.82; 0.990, 12.32; 0.972, 5.61; −0.000, 0.96 |
| 161 | 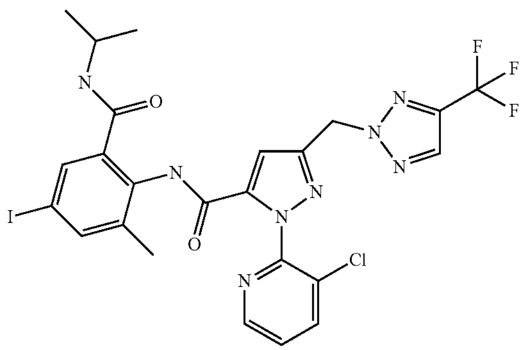 [SMILES: Cc1cc(I)cc(C(=O)NC(C)C)c1NC(=O)c1cc(Cn2ncc(C(F)(F)F)n2)nn1-c1ncccc1Cl] | 3.73 | 673 | 10.017, 1.73; 8.446, 2.06; 8.442, 2.25; 8.434, 2.71; 8.431, 4.74; 8.094, 2.14; 8.090, 2.18; 8.074, 2.44; 8.070, 2.30; 7.765, 0.78; 7.746, 0.80; 7.694, 1.98; 7.691, 2.15; 7.567, 4.36; 7.561, 2.07; 7.555, 2.57; 7.547, 2.34; 7.535, 2.32; 7.182, 2.23; 5.905, 8.23; 3.920, 0.59; 3.904, 0.85; 3.885, 0.84; 3.868, 0.58; 3.112, 135.84; 2.657, 0.36; 2.526, 1.47; 2.510, 0.93; 2.505, 1.25; 2.497, 19.03; 2.492, 39.58; 2.487, 55.98; 2.483, 39.16; 2.478, 18.68; 2.314, 0.34; 2.107, 11.15; 1.023, 16.00; 1.006, 15.84; −0.000, 3.05 |
| 162 | 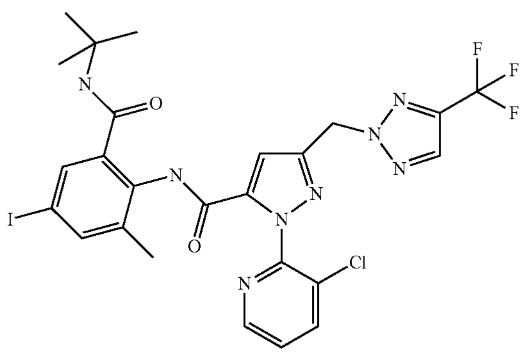 [SMILES: Cc1cc(I)cc(C(=O)NC(C)(C)C)c1NC(=O)c1cc(Cn2ncc(C(F)(F)F)n2)nn1-c1ncccc1Cl] | 4.11 | 687 | 9.701, 0.47; 8.449, 0.57; 8.445, 0.61; 8.438, 0.64; 8.434, 0.64; 8.083, 0.91; 7.969, 0.56; 7.965, 0.58; 7.948, 0.64; 7.944, 0.61; 7.588, 1.17; 7.585, 1.24; 7.489, 0.63; 7.478, 0.65; 7.469, 0.61; 7.457, 0.60; 7.169, 1.31; 6.562, 0.48; 5.818, 2.79; 2.491, 1.14; 2.146, 0.43; 2.052, 3.86; 2.039, 0.35; 1.950, 0.73; 1.944, 1.43; 1.938, 2.09; 1.931, 1.50; 1.925, 0.85; 1.270, 16.00; 1.257, 1.15; 1.216, 0.70; 1.199, 1.68; −0.000, 0.88 |
| 163 | 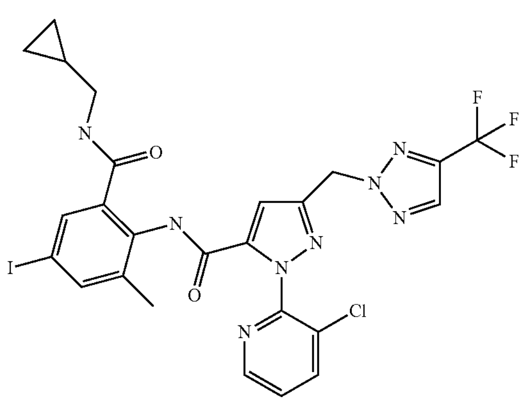 [SMILES: Cc1cc(I)cc(C(=O)NCC2CC2)c1NC(=O)c1cc(Cn2ncc(C(F)(F)F)n2)nn1-c1ncccc1Cl] | 3.8 | 685 | 10.06, 2.290; 8.45, 2.940; 8.44, 3.190; 8.43, 3.310; 8.43, 4.310; 8.43, 4.060; 8.43, 3.930; 8.10, 3.040; 8.09, 3.120; 8.07, 3.430; 8.07, 3.280; 8.05, 0.640; 8.03, 1.140; 8.02, 0.660; 7.71, 2.590; 7.71, 2.780; 7.70, 3.050; 7.60, 3.090; 7.60, 2.890; 7.57, 3.530; 7.55, 3.370; 7.55, 3.260; 7.53, 3.240; 7.19, 3.320; 5.90, 11.890; 3.11, 105.290; 3.01, 2.980; 3.00, 3.960; 2.98, 3.010; 2.66, 0.300; 2.53, 1.150; 2.51, 0.730; 2.51, 1.030; 2.50, 15.130; 2.49, 31.390; 2.49, 44.390; 2.48, 31.030; 2.48, 14.830; 2.11, 16.000; 0.88, 0.590; 0.87, 0.620; 0.87, 0.580; 0.87, 0.500; 0.86, 1.070; 0.85, 0.510; 0.84, 0.630; 0.84, 0.610; 0.84, 0.660; 0.82, 0.360; 0.32, 1.140; 0.31, 3.000; 0.31, 3.260; 0.30, 1.450; 0.30, 1.650; 0.29, 3.300; 0.29, 2.790; 0.28, 1.370; 0.12, 1.200; 0.11, 3.200; 0.11, 3.100; 0.10, 2.800; 0.10, 3.300; 0.09, 0.830; −0.00, 1.720 |

-continued

| No. | Structure | logP | MH+ | NMR |
|---|---|---|---|---|
| 164 | 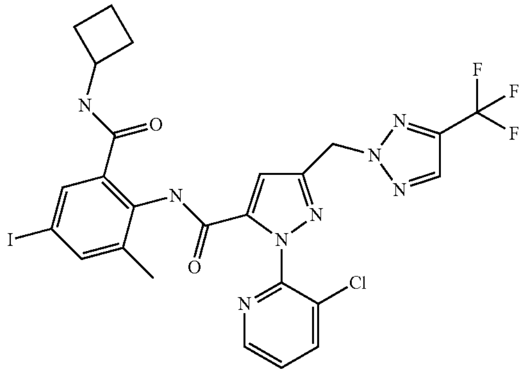 [SMILES: Cc1cc(I)cc(C(=O)NC2CCC2)c1NC(=O)c1cc(Cn2ncc(C(F)(F)F)n2)nn1-c1ncccc1Cl] | 3.89 | 685 | 10.012, 0.52; 8.452, 2.63; 8.448, 2.83; 8.440, 2.91; 8.436, 2.87; 8.428, 3.60; 8.427, 3.48; 8.185, 0.67; 8.169, 0.68; 8.095, 2.52; 8.091, 2.55; 8.075, 2.81; 8.071, 2.65; 7.700, 2.40; 7.698, 2.56; 7.695, 2.79; 7.592, 2.74; 7.588, 2.55; 7.568, 3.21; 7.556, 3.05; 7.547, 2.95; 7.536, 2.89; 7.169, 2.80; 5.904, 10.33; 4.239, 0.54; 4.220, 1.03; 4.200, 1.01; 4.180, 0.56; 3.119, 107.29; 3.095, 1.09; 2.510, 0.45; 2.505, 0.65; 2.497, 8.83; 2.493, 18.13; 2.488, 25.51; 2.483, 17.77; 2.478, 8.45; 2.150, 0.41; 2.141, 0.59; 2.131, 0.89; 2.122, 1.37; 2.116, 1.50; 2.104, 16.00; 2.093, 1.36; 2.082, 0.68; 2.075, 0.57; 1.941, 0.38; 1.917, 1.12; 1.911, 0.84; 1.893, 1.49; 1.886, 1.30; 1.870, 1.08; 1.864, 1.20; 1.848, 0.34; 1.842, 0.36; 1.652, 0.79; 1.641, 0.72; 1.635, 1.12; 1.628, 1.14; 1.618, 1.12; 1.609, 1.69; 1.602, 0.56; 1.595, 0.52; 1.589, 0.65; 1.584, 0.72; 0.990, 0.38 |
| 165 | 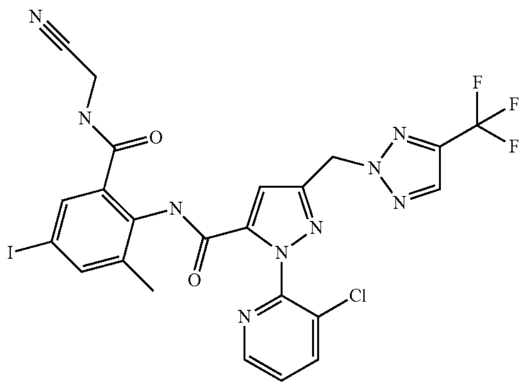 [SMILES: Cc1cc(I)cc(C(=O)NCC#N)c1NC(=O)c1cc(Cn2ncc(C(F)(F)F)n2)nn1-c1ncccc1Cl] | 3.11 | 670 | 10.050, 1.41; 8.838, 0.63; 8.826, 1.17; 8.813, 0.67; 8.456, 3.06; 8.452, 3.28; 8.444, 3.27; 8.441, 3.27; 8.425, 3.73; 8.423, 3.70; 8.093, 3.03; 8.089, 3.03; 8.073, 3.42; 8.069, 3.17; 7.768, 2.73; 7.767, 2.91; 7.763, 3.16; 7.762, 2.85; 7.632, 2.97; 7.628, 2.85; 7.562, 3.43; 7.550, 3.37; 7.542, 3.22; 7.530, 3.20; 7.216, 2.91; 5.894, 11.61; 4.146, 5.02; 4.132, 4.98; 3.484, 0.69; 3.121, 156.92; 2.658, 0.41; 2.527, 0.42; 2.511, 1.07; 2.506, 1.52; 2.498, 22.93; 2.493, 47.34; 2.488, 66.70; 2.484, 46.60; 2.479, 22.27; 2.315, 0.40; 2.126, 16.00; 2.095, 0.41; 2.073, 0.48; 1.404, 0.89; 1.364, 0.64; −0.000, 3.03 |
| 166 | Chiral | 3.98 | 719 | 10.032, 0.55; 10.009, 1.64; 8.449, 2.19; 8.447, 2.08; 8.438, 2.33; 8.434, 2.24; 8.426, 3.90; 8.095, 2.03; 8.094, 1.97; 8.075, 2.23; 7.930, 0.95; 7.910, 0.99; 7.705, 2.53; 7.617, 0.83; 7.596, 2.55; 7.569, 1.96; 7.557, 1.99; 7.549, 1.84; 7.537, 1.79; 7.195, 2.71; 5.901, 10.22; 3.998, 0.40; 3.980, 0.82; 3.964, 0.99; 3.946, 0.76; 3.928, 0.37; 3.339, 0.32; 3.306, 0.38; 3.115, 396.04; 3.078, 0.59; 2.657, 0.76; 2.586, 1.03; 2.569, 1.04; 2.553, 1.74; 2.536, 1.77; 2.526, 0.86; 2.497, 39.14; 2.493, 76.76; 2.488, 104.33; 2.483, 74.72; 2.459, 1.81; 2.441, 1.63; 2.426, 0.95; 2.408, 0.91; 2.315, 0.61; 2.184, 0.34; 2.112, 14.47; 2.040, 0.55; 1.997, 16.00; 1.988, 4.07; 1.404, 0.39; 1.363, 2.31; 1.246, 0.34; 1.112, 1.80; 1.089, 6.99; 1.072, 6.69; 0.992, 0.54; 0.975, 0.52; −0.000, 6.87 |
| 167 | 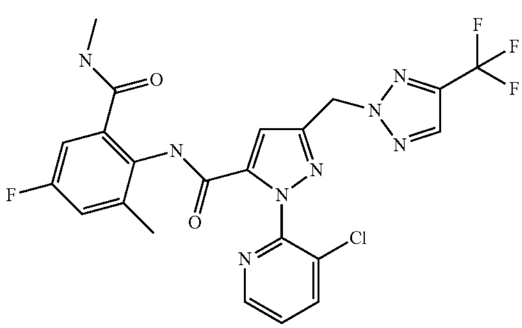 [SMILES: CNC(=O)c1cc(F)cc(C)c1NC(=O)c1cc(Cn2ncc(C(F)(F)F)n2)nn1-c1ncccc1Cl] | 2.63 | 537 | 10.004, 1.41; 8.458, 2.90; 8.454, 3.15; 8.446, 3.18; 8.443, 3.24; 8.434, 3.44; 8.103, 2.88; 8.099, 2.95; 8.083, 3.27; 8.079, 3.06; 7.916, 0.83; 7.906, 0.83; 7.569, 3.40; 7.557, 3.26; 7.548, 3.13; 7.537, 3.07; 7.192, 3.21; 7.185, 1.89; 7.167, 1.21; 7.161, 1.31; 7.103, 1.40; 7.096, 1.23; 7.081, 1.43; 7.074, 1.17; 5.908, 9.94; 3.123, 162.52; 2.672, 10.66; 2.660, 10.68; 2.527, 0.33; 2.511, 0.77; 2.506, 1.11; 2.498, 16.37; 2.493, 33.72; 2.488, 47.48; 2.484, 33.14; 2.479, 15.81; 2.147, 16.00; 2.040, 0.34; 1.364, 0.81; −0.000, 2.44 |

| No. | Structure | logP | MH+ | NMR |
|---|---|---|---|---|
| 168 | 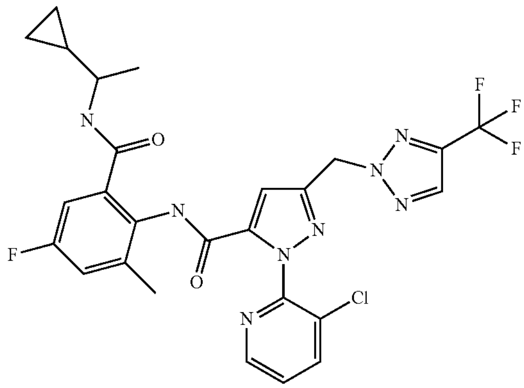 [SMILES: Cc1cc(F)cc(C(=O)NC(C)C2CC2)c1NC(=O)c1cc(Cn2ncc(C(F)(F)F)n2)nn1-c1ncccc1Cl] | 3.36 | 591 | 9.951, 0.93; 8.449, 2.96; 8.445, 3.19; 8.437, 3.30; 8.433, 3.31; 8.426, 3.76; 8.425, 3.74; 8.095, 2.98; 8.091, 3.02; 8.075, 3.35; 8.071, 3.11; 7.729, 1.02; 7.709, 1.03; 7.567, 3.48; 7.556, 3.37; 7.547, 3.23; 7.536, 3.22; 7.193, 3.76; 7.170, 1.34; 7.164, 1.39; 7.076, 1.41; 7.069, 1.26; 7.054, 1.43; 7.047, 1.20; 5.901, 10.59; 3.800, 0.67; 3.357, 0.64; 3.337, 1.23; 3.320, 1.27; 3.300, 0.67; 3.126, 237.28; 2.652, 0.77; 2.511, 0.96; 2.506, 1.36; 2.498, 19.61; 2.493, 40.52; 2.489, 57.21; 2.484, 40.07; 2.479, 19.19; 2.151, 16.00; 1.232, 0.58; 1.215, 0.55; 1.053, 9.82; 1.036, 9.66; 0.816, 0.63; 0.803, 1.12; 0.796, 0.64; 0.791, 0.78; 0.783, 1.19; 0.771, 0.72; 0.763, 0.51; 0.354, 0.52; 0.350, 0.56; 0.342, 1.05; 0.334, 1.00; 0.328, 1.00; 0.318, 1.27; 0.315, 0.62; 0.307, 0.68; 0.298, 0.65; 0.209, 0.78; 0.205, 0.67; 0.199, 0.49; 0.195, 1.07; 0.189, 1.60; 0.185, 0.89; 0.175, 2.05; 0.168, 1.12; 0.160, 0.82; 0.154, 2.11; 0.145, 1.16; 0.141, 1.06; 0.132, 1.24; 0.123, 0.99; 0.120, 1.10; 0.111, 1.17; 0.101, 0.82; 0.097, 0.77; 0.090, 0.49; −0.000, 0.82 |
| 169 | 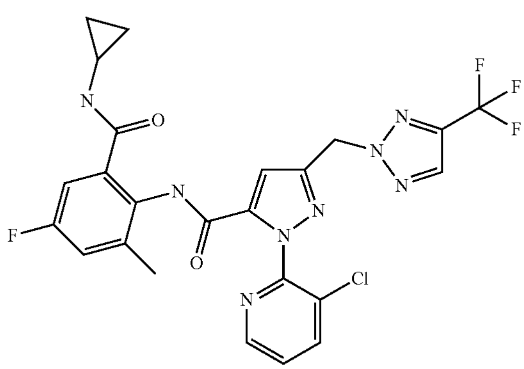 [SMILES: Cc1cc(F)cc(C(=O)NC2CC2)c1NC(=O)c1cc(Cn2ncc(C(F)(F)F)n2)nn1-c1ncccc1Cl] | 2.86 | 563 | 18.092, 0.70; 14.788, 0.72; 14.632, 0.69; 14.423, 0.67; 12.550, 2.01; 11.918, 0.68; 9.933, 1.30; 8.949, 0.77; 8.456, 1.43; 8.445, 1.29; 8.437, 1.92; 8.161, 0.70; 8.097, 1.31; 8.094, 1.09; 8.081, 0.95; 8.078, 1.33; 7.934, 0.82; 7.832, 2.12; 7.568, 1.01; 7.556, 0.93; 7.548, 0.89; 7.536, 0.87; 7.194, 1.40; 7.175, 0.94; 7.153, 0.95; 7.063, 0.82; 7.055, 0.80; 7.035, 0.96; 5.911, 4.25; 3.868, 0.68; 3.490, 0.71; 3.407, 0.75; 3.357, 0.76; 3.351, 0.84; 3.328, 0.81; 3.322, 0.83; 3.291, 1.13; 3.274, 1.18; 3.259, 1.19; 3.214, 1.66; 3.211, 1.97; 3.202, 1.98; 3.118, 1633.28; 3.115, 1714.72; 3.046, 1.02; 3.040, 1.01; 3.026, 0.85; 2.688, 1.00; 2.676, 1.00; 2.657, 2.92; 2.635, 0.82; 2.620, 0.80; 2.589, 0.93; 2.579, 1.03; 2.550, 1.50; 2.549, 1.58; 2.498, 143.77; 2.493, 300.36; 2.488, 430.51; 2.486, 395.53; 2.484, 338.54; 2.481, 266.37; 2.477, 120.41; 2.432, 0.95; 2.316, 2.43; 2.140, 6.71; 2.040, 1.73; 2.038, 1.53; 1.404, 16.00; 1.401, 14.97; 1.246, 1.05; 0.592, 1.53; 0.573, 1.40; 0.563, 0.71; 0.409, 1.58; −0.000, 11.50; −0.003, 10.47 |

-continued

| No. | Structure | logP | MH+ | NMR |
|---|---|---|---|---|
| 170 | 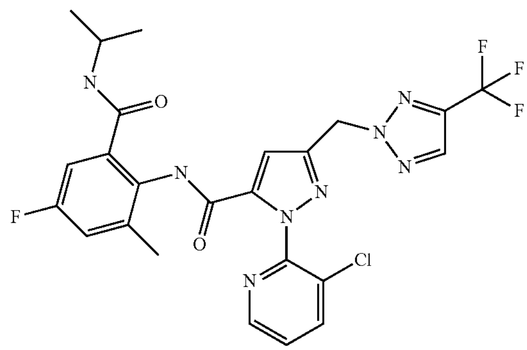 [SMILES: Cc1cc(F)cc(C(=O)NC(C)C)c1NC(=O)c1cc(Cn2ncc(C(F)(F)F)n2)nn1-c1ncccc1Cl] | 3.08 | 565 | 9.939, 0.59; 8.590, 0.40; 8.578, 0.38; 8.574, 0.40; 8.448, 2.08; 8.444, 2.21; 8.437, 2.49; 8.433, 4.28; 8.419, 0.50; 8.274, 0.35; 8.270, 0.34; 8.254, 0.38; 8.250, 0.35; 8.095, 2.14; 8.091, 2.22; 8.075, 2.43; 8.071, 2.27; 7.974, 0.42; 7.718, 0.44; 7.706, 0.45; 7.698, 0.49; 7.686, 0.45; 7.663, 0.62; 7.645, 0.77; 7.633, 0.35; 7.567, 2.56; 7.556, 2.63; 7.547, 2.47; 7.535, 2.33; 7.263, 1.00; 7.185, 2.80; 7.178, 1.42; 7.162, 0.95; 7.154, 1.02; 7.075, 1.01; 7.068, 0.90; 7.053, 1.09; 7.045, 0.92; 5.947, 1.59; 5.907, 7.61; 3.926, 0.56; 3.909, 0.88; 3.891, 0.84; 3.874, 0.62; 3.204, 0.34; 3.116, 703.49; 3.094, 4.37; 2.667, 0.34; 2.662, 0.69; 2.657, 1.01; 2.653, 0.71; 2.648, 0.34; 2.526, 1.01; 2.510, 2.59; 2.506, 3.69; 2.497, 51.80; 2.493, 106.27; 2.488, 149.27; 2.483, 103.85; 2.479, 49.33; 2.320, 0.65; 2.315, 0.88; 2.310, 0.70; 2.148, 11.99; 2.040, 0.50; 1.795, 2.01; 1.363, 0.55; 1.166, 0.37; 1.020, 16.00; 1.003, 15.85; −0.000, 0.39 |
| 171 | 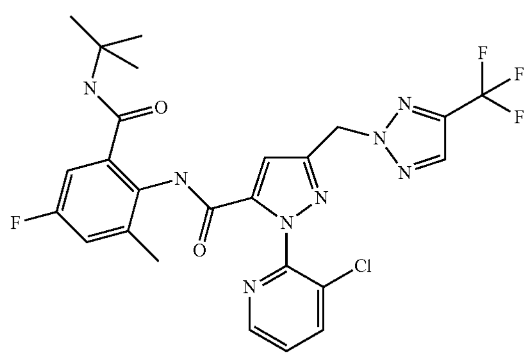 [SMILES: Cc1cc(F)cc(C(=O)NC(C)(C)C)c1NC(=O)c1cc(Cn2ncc(C(F)(F)F)n2)nn1-c1ncccc1Cl] | 4.02 | 579 | 8.590, 2.85; 8.587, 3.06; 8.578, 3.08; 8.575, 3.00; 8.418, 3.41; 8.417, 3.37; 8.274, 2.87; 8.271, 2.91; 8.254, 3.18; 8.250, 3.04; 7.719, 3.37; 7.707, 3.24; 7.699, 3.11; 7.687, 3.03; 7.652, 1.18; 7.645, 1.47; 7.644, 1.45; 7.633, 1.19; 7.631, 1.23; 7.625, 1.40; 7.624, 1.38; 7.581, 1.36; 7.579, 1.36; 7.574, 1.21; 7.572, 1.10; 7.557, 1.36; 7.556, 1.44; 7.550, 1.10; 7.548, 1.08; 7.264, 7.83; 5.948, 12.17; 3.128, 462.68; 2.659, 0.44; 2.654, 0.32; 2.528, 0.43; 2.512, 1.14; 2.507, 1.68; 2.499, 24.08; 2.495, 49.71; 2.490, 69.97; 2.485, 48.93; 2.480, 23.40; 2.317, 0.41; 2.296, 0.33; 2.142, 0.37; 1.795, 16.00; 1.364, 0.67; 1.253, 2.32; 1.206, 1.68; −0.000, 0.51 |
| 172 | 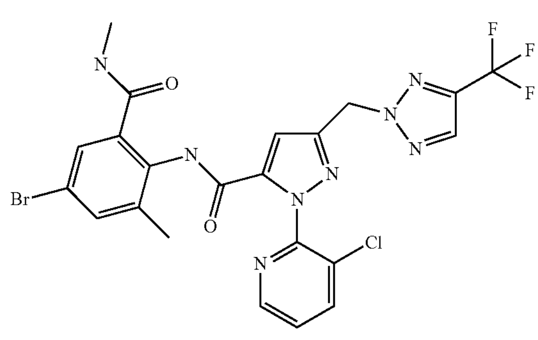 [SMILES: CNC(=O)c1cc(Br)cc(C)c1NC(=O)c1cc(Cn2ncc(C(F)(F)F)n2)nn1-c1ncccc1Cl] | 3.1 | 597/599 | 10.089, 1.33; 8.458, 2.87; 8.454, 3.06; 8.446, 3.13; 8.442, 3.14; 8.433, 3.54; 8.432, 3.46; 8.104, 2.87; 8.100, 2.93; 8.083, 3.20; 8.080, 3.04; 8.003, 0.85; 7.992, 0.86; 7.569, 3.35; 7.558, 3.22; 7.549, 3.20; 7.541, 2.62; 7.538, 4.82; 7.535, 3.05; 7.534, 2.72; 7.448, 2.82; 7.443, 2.55; 7.193, 2.83; 6.874, 0.48; 5.909, 10.89; 3.116, 102.20; 2.668, 10.19; 2.656, 10.27; 2.510, 0.69; 2.505, 1.00; 2.497, 13.38; 2.493, 27.38; 2.488, 38.33; 2.483, 26.71; 2.478, 12.69; 2.183, 0.80; 2.137, 16.00; 1.364, 8.57; −0.000, 2.05 |

| No. | Structure | logP | MH+ | NMR |
|---|---|---|---|---|
| 173 | 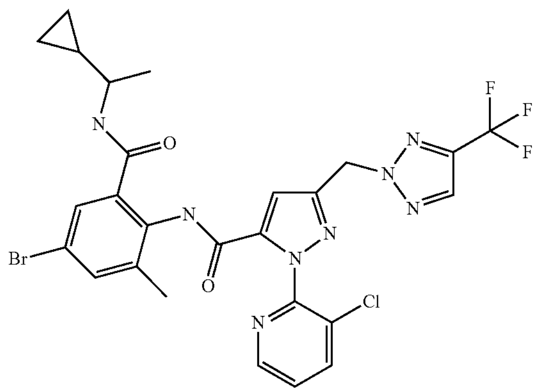 [SMILES: Cc1cc(Br)cc(C(=O)NC(C)C2CC2)c1NC(=O)c1cc(Cn2ncc(C(F)(F)F)n2)nn1-c1ncccc1Cl] | 3.87 | 651/653 | 10.022, 1.82; 8.449, 3.06; 8.445, 3.25; 8.438, 3.37; 8.434, 3.37; 8.426, 3.91; 8.425, 3.83; 8.096, 3.04; 8.092, 3.11; 8.076, 3.43; 8.072, 3.23; 7.852, 1.04; 7.832, 1.08; 7.569, 3.50; 7.557, 3.43; 7.549, 3.48; 7.543, 2.77; 7.542, 2.88; 7.537, 6.09; 7.417, 2.97; 7.412, 2.74; 7.188, 3.09; 5.902, 11.87; 3.353, 0.67; 3.333, 1.27; 3.316, 1.32; 3.296, 0.67; 3.126, 726.94; 2.663, 0.52; 2.659, 0.69; 2.654, 0.50; 2.528, 0.67; 2.512, 1.74; 2.507, 2.46; 2.499, 39.10; 2.494, 80.86; 2.489, 114.16; 2.485, 79.95; 2.480, 38.34; 2.316, 0.70; 2.312, 0.51; 2.142, 16.00; 1.404, 0.52; 1.059, 10.16; 1.042, 10.03; 0.828, 0.67; 0.816, 1.28; 0.808, 0.75; 0.803, 0.82; 0.795, 1.34; 0.783, 0.79; 0.775, 0.52; 0.363, 0.50; 0.358, 0.54; 0.350, 1.13; 0.342, 1.02; 0.337, 0.99; 0.327, 1.23; 0.321, 0.58; 0.316, 0.73; 0.306, 0.61; 0.223, 0.76; 0.220, 0.71; 0.214, 0.58; 0.209, 0.98; 0.203, 1.11; 0.199, 0.96; 0.189, 1.43; 0.183, 1.28; 0.178, 0.66; 0.173, 1.08; 0.168, 1.30; 0.160, 1.51; 0.150, 1.26; 0.136, 1.16; 0.127, 0.89; 0.123, 1.15; 0.114, 1.22; 0.108, 0.69; 0.100, 0.86 |
| 174 | 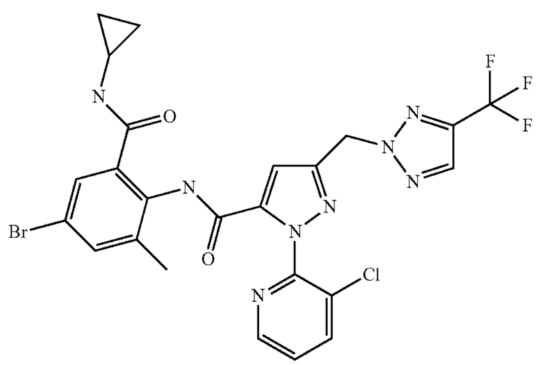 [SMILES: Cc1cc(Br)cc(C(=O)NC2CC2)c1NC(=O)c1cc(Cn2ncc(C(F)(F)F)n2)nn1-c1ncccc1Cl] | 3.28 | 623/625 | 10.021, 1.43; 8.584, 0.51; 8.572, 0.48; 8.458, 3.01; 8.455, 3.13; 8.447, 3.27; 8.443, 3.30; 8.435, 3.62; 8.416, 0.62; 8.269, 0.53; 8.249, 0.51; 8.102, 2.86; 8.098, 2.85; 8.082, 3.10; 8.078, 3.04; 8.028, 1.08; 7.996, 0.49; 7.975, 0.85; 7.864, 0.50; 7.859, 0.55; 7.717, 0.52; 7.706, 0.57; 7.571, 3.33; 7.560, 3.29; 7.551, 3.13; 7.539, 3.19; 7.529, 2.45; 7.525, 2.71; 7.398, 2.81; 7.394, 2.67; 7.277, 1.15; 7.198, 2.67; 5.948, 1.89; 5.912, 10.87; 5.688, 2.28; 3.219, 0.62; 3.213, 0.66; 3.119, 1894.43; 3.097, 10.92; 3.073, 1.13; 2.707, 0.54; 2.696, 0.84; 2.689, 1.13; 2.679, 1.13; 2.667, 1.13; 2.662, 1.68; 2.658, 2.17; 2.653, 1.50; 2.648, 0.83; 2.539, 0.58; 2.527, 1.92; 2.511, 5.06; 2.506, 7.56; 2.498, 109.36; 2.493, 225.40; 2.488, 317.36; 2.484, 221.73; 2.479, 105.84; 2.325, 0.61; 2.320, 1.39; 2.315, 1.97; 2.310, 1.50; 2.306, 0.64; 2.132, 16.00; 2.040, 0.73; 1.769, 2.59; 1.404, 6.57; 0.895, 0.56; 0.612, 0.62; 0.598, 1.93; 0.593, 2.69; 0.581, 2.62; 0.575, 2.00; 0.563, 0.93; 0.440, 1.19; 0.430, 3.16; 0.423, 2.94; 0.413, 2.74; 0.401, 0.91; −0.000, 0.93 |
| 175 | 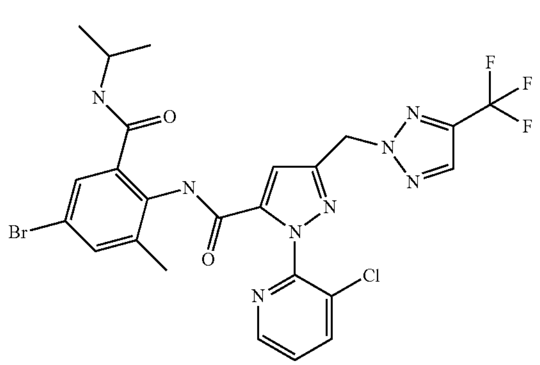 | 3.55 | 625/627 | 10.020, 0.66; 8.448, 0.84; 8.444, 0.94; 8.436, 1.02; 8.432, 1.65; 8.095, 0.91; 8.092, 0.89; 8.075, 1.02; 8.071, 0.92; 7.781, 0.37; 7.762, 0.35; 7.568, 1.02; 7.556, 1.02; 7.548, 0.92; 7.536, 1.25; 7.528, 0.84; 7.413, 0.86; 7.407, 0.79; 7.187, 0.87; 5.907, 3.40; 3.908, 0.35; 3.889, 0.33; 3.166, 0.48; 3.114, 494.66; 2.662, 0.57; 2.657, 0.87; 2.652, 0.63; 2.526, 0.85; 2.510, 2.25; 2.506, 3.10; 2.497, 44.71; 2.493, 92.00; 2.488, 129.41; 2.483, 90.10; 2.478, 42.83; 2.319, 0.56; 2.315, 0.74; 2.310, 0.54; 2.139, 4.63; 2.040, 0.42; 1.404, 16.00; 1.025, 6.58; 1.009, 6.51; −0.000, 2.63 |

-continued

| No. | Structure | logP | MH+ | NMR |
|---|---|---|---|---|
| 176 | 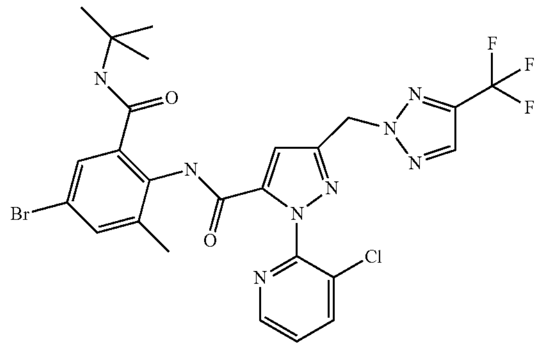 [SMILES: Cc1cc(Br)cc(C(=O)NC(C)(C)C)c1NC(=O)c1cc(Cn2ncc(C(F)(F)F)n2)nn1-c1ncccc1Cl] | 4.65 | 639/641 | 8.588, 2.81; 8.584, 3.01; 8.576, 2.99; 8.572, 2.98; 8.418, 3.34; 8.416, 3.30; 8.273, 2.78; 8.270, 2.90; 8.253, 3.20; 8.249, 2.97; 8.000, 2.40; 7.999, 2.42; 7.995, 2.62; 7.993, 2.59; 7.863, 2.66; 7.861, 2.81; 7.858, 2.66; 7.856, 2.42; 7.718, 3.22; 7.706, 3.17; 7.698, 3.06; 7.686, 2.99; 7.277, 7.92; 5.950, 11.70; 3.602, 0.56; 3.112, 192.17; 3.088, 1.59; 2.658, 0.44; 2.527, 0.47; 2.511, 1.17; 2.506, 1.65; 2.498, 22.86; 2.493, 46.84; 2.488, 65.81; 2.484, 45.92; 2.479, 21.87; 2.315, 0.39; 2.132, 0.34; 1.768, 16.00; 1.762, 1.56; 1.404, 1.43; 1.210, 1.79; −0.000, 3.22 |
| 177 | 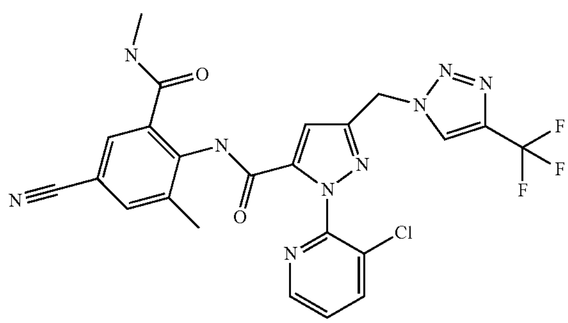 [SMILES: CNC(=O)c1cc(C#N)cc(C)c1NC(=O)c1cc(Cn2cc(C(F)(F)F)nn2)nn1-c1ncccc1Cl] | 2.28 | 543 | 10.134, 1.15; 8.468, 2.77; 8.464, 2.82; 8.456, 2.89; 8.452, 2.82; 8.398, 3.89; 8.396, 3.67; 7.991, 2.85; 7.987, 2.82; 7.971, 3.07; 7.967, 2.99; 7.725, 2.93; 7.724, 2.93; 7.721, 3.61; 7.684, 3.24; 7.682, 3.34; 7.679, 2.85; 7.677, 2.39; 7.513, 3.26; 7.501, 3.21; 7.492, 3.03; 7.481, 2.96; 7.126, 7.48; 7.047, 0.75; 7.041, 0.74; 5.791, 16.00; 2.799, 15.25; 2.787, 15.11; 2.183, 20.02; 2.145, 51.10; 1.963, 0.34; 1.957, 0.80; 1.952, 9.79; 1.946, 19.07; 1.939, 27.73; 1.933, 18.80; 1.927, 9.44; −0.000, 3.43 |
| 178 | 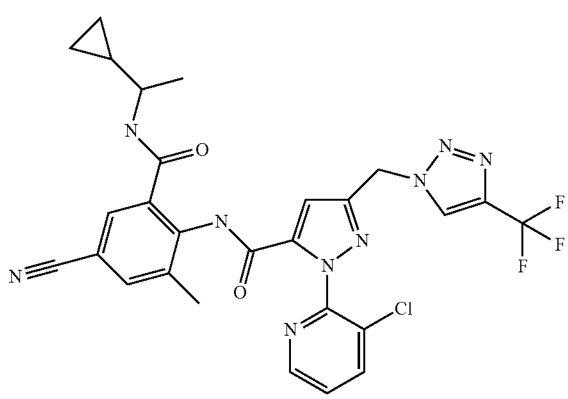 [SMILES: Cc1cc(C#N)cc(C(=O)NC(C)C2CC2)c1NC(=O)c1cc(Cn2cc(C(F)(F)F)nn2)nn1-c1ncccc1Cl] | 2.95 | 598 | 8.928, 4.00; 8.926, 3.98; 8.453, 3.04; 8.449, 3.31; 8.441, 3.30; 8.438, 3.28; 8.101, 3.18; 8.097, 3.20; 8.081, 3.59; 8.077, 3.41; 8.051, 0.49; 7.791, 2.69; 7.788, 2.88; 7.708, 3.08; 7.704, 2.88; 7.572, 3.47; 7.560, 3.33; 7.552, 3.22; 7.540, 3.17; 7.221, 5.53; 5.864, 13.51; 3.375, 0.76; 3.355, 1.31; 3.338, 1.31; 3.319, 0.70; 3.120, 124.73; 2.527, 1.01; 2.511, 0.76; 2.506, 1.07; 2.498, 14.08; 2.493, 28.82; 2.488, 40.41; 2.484, 28.15; 2.479, 13.41; 2.287, 1.48; 2.193, 16.00; 2.135, 1.46; 1.234, 0.58; 1.132, 0.95; 1.115, 0.98; 1.080, 10.31; 1.064, 10.21; 0.860, 0.51; 0.852, 0.69; 0.840, 1.30; 0.832, 0.81; 0.827, 0.92; 0.819, 1.35; 0.807, 0.76; 0.799, 0.51; 0.383, 0.60; 0.379, 0.66; 0.370, 1.27; 0.362, 1.09; 0.357, 1.13; 0.348, 1.24; 0.341, 0.65; 0.336, 0.77; 0.326, 0.63; 0.263, 0.58; 0.253, 0.90; 0.250, 0.83; 0.239, 1.14; 0.233, 1.17; 0.229, 1.03; 0.219, 1.90; 0.212, 0.72; 0.207, 1.17; 0.197, 1.48; 0.192, 0.67; 0.184, 1.55; 0.173, 1.31; 0.159, 1.16; 0.150, 1.08; 0.146, 1.29; 0.137, 1.33; 0.132, 0.78; 0.123, 0.94; 0.114, 0.54; −0.000, 2.07 |

| No. | Structure | logP | MH+ | NMR |
|---|---|---|---|---|
| 179 | 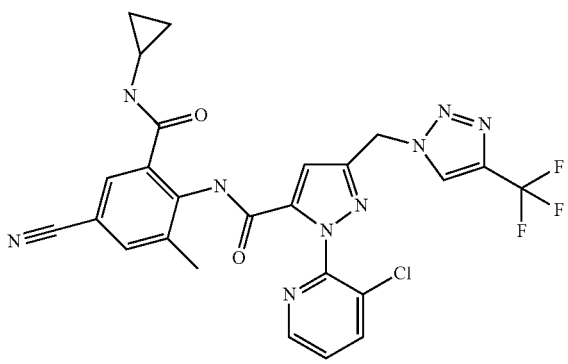 [SMILES: Cc1cc(C#N)cc(C(=O)NC2CC2)c1NC(=O)c1cc(Cn2cc(C(F)(F)F)nn2)nn1-c1ncccc1Cl] | 2.5 | 570 | 15.167, 0.56; 12.547, 0.97; 10.323, 3.21; 8.950, 4.51; 8.460, 2.88; 8.458, 2.40; 8.452, 2.39; 8.449, 3.09; 8.179, 1.99; 8.108, 2.70; 8.088, 2.89; 8.085, 2.38; 7.833, 1.14; 7.783, 4.25; 7.683, 3.69; 7.590, 0.56; 7.578, 2.10; 7.566, 2.19; 7.557, 2.21; 7.546, 1.84; 7.238, 5.50; 5.873, 10.73; 3.549, 0.57; 3.537, 0.52; 3.369, 0.53; 3.312, 0.67; 3.277, 0.72; 3.232, 1.08; 3.211, 1.29; 3.120, 1219.92; 3.117, 1065.70; 3.033, 0.94; 3.019, 0.69; 2.717, 1.08; 2.713, 1.28; 2.710, 1.23; 2.702, 1.52; 2.695, 1.66; 2.672, 0.95; 2.653, 1.79; 2.603, 0.58; 2.567, 0.84; 2.558, 0.80; 2.498, 82.21; 2.493, 181.47; 2.489, 276.52; 2.484, 255.35; 2.312, 1.60; 2.186, 16.00; 2.169, 0.72; 2.040, 1.84; 2.037, 1.59; 1.244, 0.70; 0.616, 3.58; 0.598, 3.35; 0.464, 1.48; 0.446, 4.17; 0.424, 1.07; −0.000, 2.72; −0.002, 2.17; −3.685, 0.52 |
| 180 | 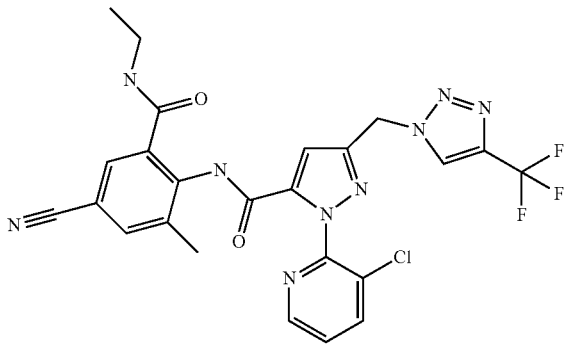 [SMILES: CCNC(=O)c1cc(C#N)cc(C)c1NC(=O)c1cc(Cn2cc(C(F)(F)F)nn2)nn1-c1ncccc1Cl] | 2.49 | 558 | 18.871, 0.78; 13.985, 0.70; 10.491, 0.74; 10.357, 2.97; 8.944, 4.18; 8.457, 3.00; 8.453, 2.86; 8.445, 2.64; 8.441, 2.73; 8.140, 1.32; 8.108, 2.49; 8.105, 2.69; 8.088, 3.05; 8.084, 2.57; 7.790, 3.08; 7.722, 3.40; 7.719, 3.01; 7.575, 2.88; 7.563, 3.19; 7.554, 3.04; 7.543, 2.85; 7.226, 6.61; 5.868, 12.82; 3.700, 1.85; 3.567, 0.77; 3.354, 0.80; 3.286, 0.94; 3.263, 1.06; 3.197, 2.21; 3.179, 4.67; 3.164, 5.49; 3.161, 5.32; 3.147, 7.20; 3.108, 1912.17; 2.695, 0.83; 2.661, 3.56; 2.657, 5.05; 2.652, 3.51; 2.647, 1.83; 2.616, 0.89; 2.605, 1.05; 2.575, 1.57; 2.551, 1.99; 2.526, 32.63; 2.510, 17.93; 2.505, 26.46; 2.497, 265.01; 2.492, 525.97; 2.487, 725.43; 2.483, 509.60; 2.478, 246.66; 2.324, 1.67; 2.319, 3.02; 2.314, 4.43; 2.310, 3.23; 2.305, 1.44; 2.191, 16.00; 2.040, 5.51; 2.037, 2.39; 1.420, 0.95; 1.404, 12.52; 1.296, 0.95; 1.245, 1.85; 1.164, 1.19; 1.082, 1.60; 1.030, 5.78; 1.012, 11.86; 0.994, 5.46; 0.008, 7.23; −0.000, 164.27; −0.008, 6.36; −0.149, 0.77 |
| 181 | 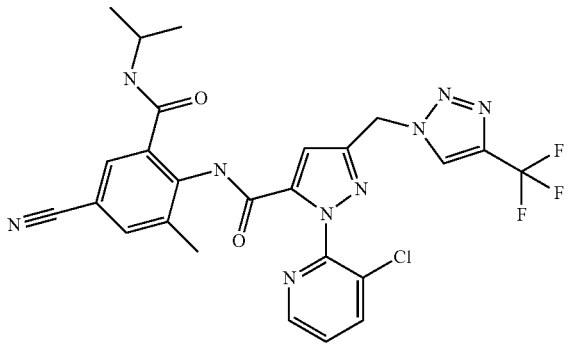 [SMILES: Cc1cc(C#N)cc(C(=O)NC(C)C)c1NC(=O)c1cc(Cn2cc(C(F)(F)F)nn2)nn1-c1ncccc1Cl] | 2.67 | 572 | 8.937, 2.75; 8.935, 2.72; 8.452, 2.02; 8.448, 2.18; 8.440, 2.21; 8.436, 2.20; 8.101, 2.08; 8.098, 2.11; 8.081, 2.34; 8.077, 2.22; 7.993, 0.38; 7.989, 0.43; 7.977, 0.35; 7.974, 0.56; 7.784, 1.89; 7.781, 2.04; 7.707, 2.16; 7.703, 2.01; 7.572, 2.40; 7.560, 2.31; 7.552, 2.20; 7.540, 2.17; 7.223, 3.96; 5.868, 9.35; 3.941, 0.66; 3.924, 0.93; 3.906, 0.88; 3.889, 0.60; 3.115, 130.21; 2.526, 0.96; 2.510, 0.70; 2.506, 0.99; 2.497, 14.00; 2.493, 28.79; 2.488, 40.50; 2.483, 28.35; 2.479, 13.61; 2.286, 1.01; 2.191, 11.43; 2.138, 1.07; 1.364, 0.40; 1.203, 0.40; 1.187, 0.45; 1.092, 1.53; 1.076, 1.59; 1.048, 16.00; 1.031, 15.92; −0.000, 4.75 |

-continued

| No. | Structure | logP | MH+ | NMR |
|---|---|---|---|---|
| 182 | 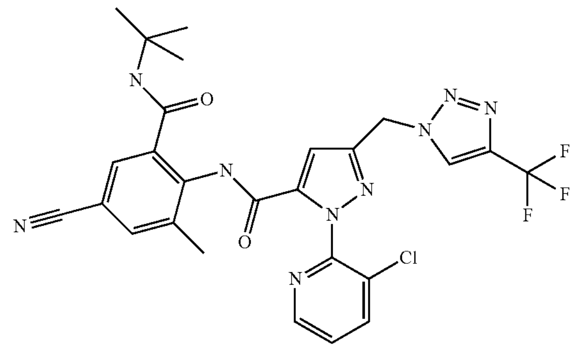 [SMILES: Cc1cc(C#N)cc(C(=O)NC(C)(C)C)c1NC(=O)c1cc(Cn2cc(C(F)(F)F)nn2)nn1-c1ncccc1Cl] | 2.97 | 586 | 8.920, 0.74; 8.918, 0.75; 8.454, 0.58; 8.451, 0.63; 8.443, 0.61; 8.439, 0.61; 8.106, 0.46; 8.102, 0.46; 8.086, 0.51; 8.082, 0.48; 7.747, 0.36; 7.679, 0.45; 7.573, 0.59; 7.561, 0.58; 7.553, 0.56; 7.541, 0.55; 7.182, 0.44; 5.868, 2.27; 3.117, 43.48; 2.497, 3.09; 2.493, 6.34; 2.488, 8.90; 2.483, 6.22; 2.479, 2.97; 2.179, 2.53; 1.364, 0.69; 1.273, 0.87; 1.232, 16.00; −0.000, 0.86 |
| 183 | Chiral | 2.95 | 619 | 8.932, 2.53; 8.456, 1.86; 8.452, 2.01; 8.444, 2.03; 8.440, 1.98; 8.101, 1.75; 8.097, 1.71; 8.081, 1.91; 8.077, 1.75; 7.791, 1.48; 7.723, 1.73; 7.720, 1.56; 7.572, 1.89; 7.561, 1.81; 7.552, 1.76; 7.540, 1.71; 7.230, 2.53; 7.221, 0.53; 5.864, 7.64; 4.002, 0.57; 3.985, 0.64; 3.966, 0.52; 3.167, 0.35; 3.115, 43.05; 2.605, 0.78; 2.589, 0.79; 2.577, 0.39; 2.572, 1.36; 2.556, 1.31; 2.526, 0.71; 2.510, 0.58; 2.505, 0.90; 2.497, 9.90; 2.493, 20.20; 2.488, 28.33; 2.483, 19.84; 2.478, 9.77; 2.458, 1.31; 2.442, 0.81; 2.424, 0.76; 2.291, 0.84; 2.194, 9.30; 2.138, 0.93; 2.090, 0.48; 2.007, 16.00; 1.998, 3.22; 1.246, 0.38; 1.164, 0.67; 1.148, 0.63; 1.133, 0.99; 1.112, 5.62; 1.096, 5.55; 1.015, 0.45; 0.999, 0.45; 0.858, 0.83; 0.842, 0.75; 0.835, 0.32; 0.827, 0.49; 0.811, 0.44; −0.000, 5.32 |
| 184 | 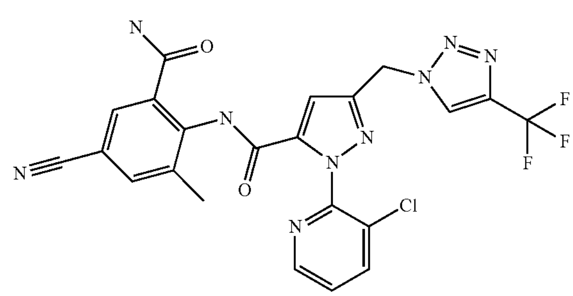 [SMILES: Cc1cc(C#N)cc(C(N)=O)c1NC(=O)c1cc(Cn2cc(C(F)(F)F)nn2)nn1-c1ncccc1Cl] | 2.12 | 530 | 10.483, 2.48; 8.950, 3.92; 8.470, 2.77; 8.466, 2.89; 8.458, 2.93; 8.454, 2.93; 8.115, 2.58; 8.111, 2.63; 8.094, 2.93; 8.091, 2.77; 7.806, 5.38; 7.671, 0.36; 7.577, 3.15; 7.565, 3.08; 7.557, 2.88; 7.545, 2.78; 7.448, 0.34; 7.432, 0.36; 7.226, 5.85; 5.863, 12.91; 3.188, 0.49; 3.173, 0.56; 3.110, 436.01; 2.667, 0.49; 2.661, 0.81; 2.657, 1.12; 2.652, 0.88; 2.647, 0.44; 2.566, 0.37; 2.526, 1.74; 2.510, 4.18; 2.505, 6.34; 2.497, 63.45; 2.492, 125.59; 2.488, 173.00; 2.483, 121.67; 2.478, 59.13; 2.319, 0.77; 2.315, 1.01; 2.310, 0.75; 2.174, 16.00; 2.040, 1.43; 1.247, 0.36; −0.000, 18.44; −0.009, 0.66 |

| No. | Structure | logP | MH+ | NMR |
|---|---|---|---|---|
| 185 | 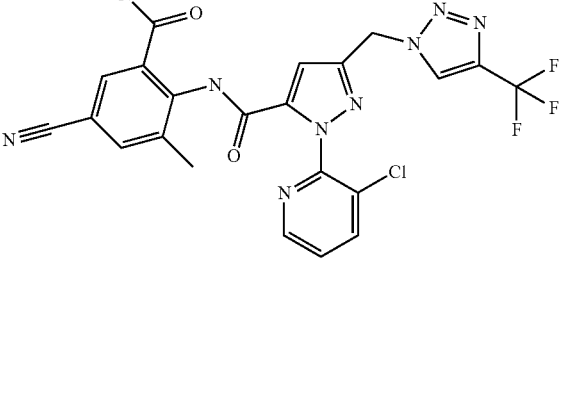 | 2.81 | 584 | 10.350, 0.75; 8.936, 4.15; 8.934, 4.09; 8.451, 3.00; 8.447, 3.23; 8.439, 3.25; 8.435, 3.24; 8.221, 0.60; 8.190, 0.34; 8.103, 2.87; 8.099, 2.93; 8.083, 3.19; 8.079, 3.06; 8.002, 0.32; 7.997, 0.32; 7.795, 2.55; 7.782, 0.47; 7.734, 3.10; 7.730, 2.81; 7.571, 3.27; 7.560, 3.18; 7.551, 3.10; 7.539, 3.01; 7.467, 0.37; 7.270, 0.39; 7.226, 4.32; 5.918, 0.58; 5.862, 13.72; 3.114, 225.99; 3.079, 0.58; 3.064, 0.54; 3.042, 3.28; 3.027, 4.28; 3.011, 3.24; 2.657, 0.37; 2.526, 1.32; 2.510, 1.08; 2.505, 1.55; 2.497, 20.18; 2.493, 41.13; 2.488, 57.54; 2.483, 40.22; 2.478, 19.26; 2.315, 0.36; 2.287, 1.50; 2.194, 16.00; 2.135, 1.50; 2.040, 0.43; 2.037, 0.39; 2.019, 0.68; 0.906, 0.37; 0.897, 0.65; 0.895, 0.75; 0.889, 0.66; 0.885, 0.59; 0.877, 1.16; 0.869, 0.59; 0.865, 0.68; 0.858, 1.24; 0.848, 0.40; 0.842, 0.79; 0.828, 0.40; 0.352, 1.23; 0.341, 3.09; 0.337, 3.28; 0.332, 1.69; 0.326, 1.71; 0.321, 3.32; 0.317, 2.84; 0.306, 1.30; 0.158, 0.38; 0.147, 1.58; 0.136, 3.49; 0.133, 3.35; 0.124, 3.02; 0.121, 3.46; 0.109, 0.89; −0.000, 8.09 |
| 186 | 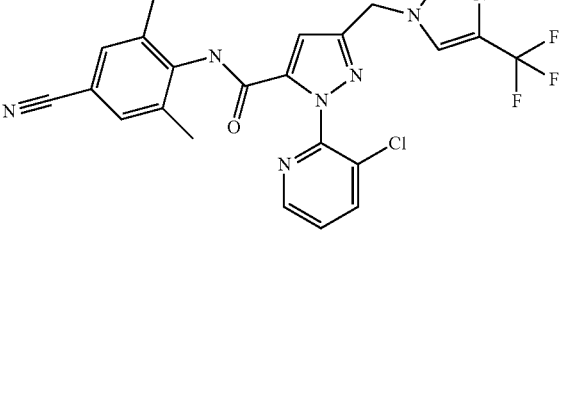 | 2.32 | 569 | 10.323, 0.99; 8.958, 0.92; 8.928, 4.94; 8.926, 4.94; 8.464, 3.95; 8.460, 4.31; 8.453, 4.33; 8.449, 4.25; 8.104, 3.21; 8.101, 3.34; 8.084, 3.65; 8.080, 3.41; 7.857, 2.49; 7.768, 3.32; 7.764, 3.21; 7.570, 3.93; 7.558, 3.77; 7.549, 3.65; 7.538, 3.52; 7.250, 3.85; 5.861, 15.65; 4.174, 5.24; 4.161, 5.01; 3.226, 0.38; 3.214, 0.45; 3.208, 0.42; 3.198, 0.57; 3.182, 0.75; 3.120, 1049.25; 3.063, 0.33; 2.667, 0.38; 2.662, 0.76; 2.658, 1.17; 2.653, 0.73; 2.648, 0.46; 2.527, 2.24; 2.511, 2.72; 2.506, 3.80; 2.498, 59.95; 2.493, 124.50; 2.488, 175.97; 2.484, 123.03; 2.479, 58.64; 2.324, 0.41; 2.320, 0.78; 2.315, 1.09; 2.311, 0.75; 2.306, 0.38; 2.213, 16.00; 2.040, 1.21; 1.404, 2.10; 1.245, 0.37; −0.000, 5.32 |
| 187 | 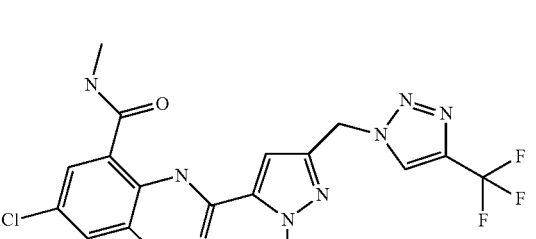 | 2.6 | 553 | 10.097, 1.57; 8.947, 3.47; 8.946, 3.42; 8.459, 2.78; 8.455, 2.93; 8.447, 2.99; 8.443, 2.92; 8.107, 2.78; 8.103, 2.84; 8.086, 3.15; 8.083, 2.95; 8.008, 0.83; 7.998, 0.84; 7.571, 3.22; 7.559, 3.12; 7.551, 3.03; 7.539, 2.95; 7.406, 2.28; 7.405, 2.38; 7.400, 2.76; 7.399, 2.58; 7.328, 2.83; 7.322, 2.48; 7.202, 3.27; 5.862, 11.90; 3.119, 120.42; 2.675, 10.15; 2.663, 10.08; 2.526, 0.61; 2.510, 0.47; 2.505, 0.67; 2.497, 8.69; 2.493, 17.77; 2.488, 24.89; 2.483, 17.36; 2.478, 8.28; 2.139, 16.00; −0.000, 2.99 |

| No. | Structure | logP | MH+ | NMR |
|---|---|---|---|---|
| 188 | 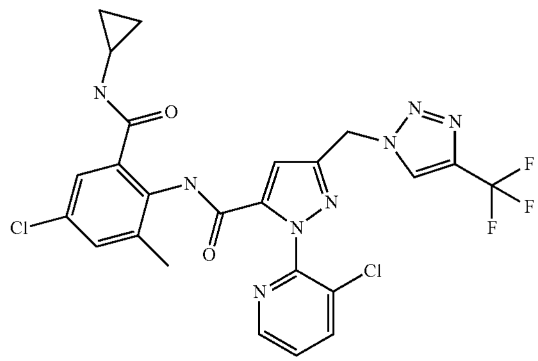 [SMILES: Cc1cc(Cl)cc(C(=O)NC2CC2)c1NC(=O)c1cc(Cn2cc(C(F)(F)F)nn2)nn1-c1ncccc1Cl] | 2.82 | 579 | 10.035, 1.43; 8.944, 3.58; 8.943, 3.54; 8.460, 2.87; 8.457, 3.02; 8.449, 3.12; 8.445, 3.03; 8.105, 2.80; 8.101, 2.88; 8.085, 3.16; 8.081, 2.98; 8.047, 1.04; 8.039, 1.05; 7.572, 3.29; 7.561, 3.18; 7.552, 3.04; 7.540, 2.99; 7.396, 2.34; 7.394, 2.45; 7.390, 2.65; 7.388, 2.50; 7.280, 2.89; 7.279, 2.91; 7.274, 2.67; 7.207, 3.29; 5.868, 11.43; 5.856, 0.51; 3.119, 186.83; 2.716, 0.47; 2.706, 0.68; 2.697, 1.02; 2.688, 1.03; 2.679, 0.69; 2.670, 0.52; 2.662, 0.34; 2.657, 0.32; 2.526, 0.85; 2.510, 0.61; 2.506, 0.90; 2.497, 12.10; 2.493, 24.79; 2.488, 34.79; 2.483, 24.30; 2.479, 11.62; 2.135, 16.00; 0.618, 0.66; 0.605, 1.94; 0.600, 2.52; 0.588, 2.50; 0.582, 1.97; 0.571, 0.86; 0.447, 1.15; 0.437, 3.00; 0.430, 2.78; 0.426, 2.53; 0.420, 2.50; 0.408, 0.82; −0.000, 2.64 |
| 189 | 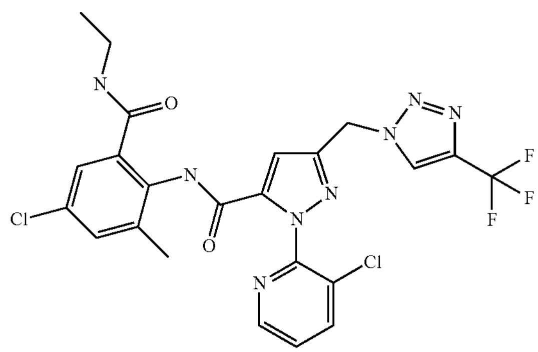 [SMILES: CCNC(=O)c1cc(Cl)cc(C)c1NC(=O)c1cc(Cn2cc(C(F)(F)F)nn2)nn1-c1ncccc1Cl] | 2.9 | 567 | 10.068, 1.14; 8.936, 3.55; 8.934, 3.49; 8.453, 2.76; 8.450, 2.88; 8.442, 2.95; 8.438, 2.87; 8.103, 2.75; 8.099, 2.77; 8.083, 3.09; 8.079, 2.88; 8.007, 0.60; 7.996, 0.99; 7.570, 3.17; 7.558, 3.06; 7.550, 2.95; 7.538, 2.87; 7.404, 2.40; 7.402, 2.48; 7.398, 2.79; 7.396, 2.64; 7.315, 2.86; 7.310, 2.54; 7.196, 3.32; 5.861, 12.17; 3.184, 1.03; 3.166, 2.98; 3.152, 3.51; 3.148, 3.71; 3.134, 6.11; 3.123, 211.00; 2.527, 0.75; 2.511, 0.61; 2.506, 0.90; 2.498, 11.34; 2.493, 23.06; 2.488, 32.16; 2.484, 22.49; 2.479, 10.79; 2.141, 16.00; 1.016, 5.48; 0.998, 11.50; 0.980, 5.28; −0.000, 2.07 |
| 190 | 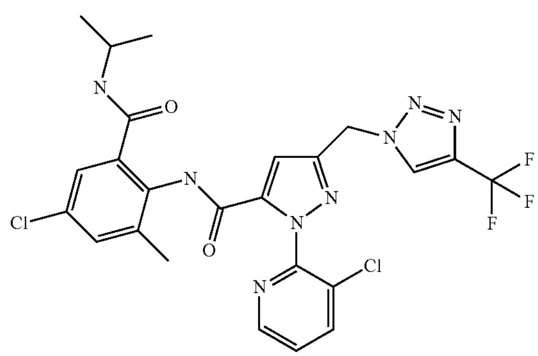 [SMILES: Cc1cc(Cl)cc(C(=O)NC(C)C)c1NC(=O)c1cc(Cn2cc(C(F)(F)F)nn2)nn1-c1ncccc1Cl] | 3.06 | 581 | 10.033, 1.62; 8.930, 2.66; 8.928, 2.66; 8.449, 2.03; 8.445, 2.17; 8.437, 2.17; 8.434, 2.16; 8.098, 2.11; 8.094, 2.17; 8.078, 2.38; 8.074, 2.26; 7.792, 0.75; 7.773, 0.76; 7.569, 2.45; 7.557, 2.35; 7.549, 2.27; 7.537, 2.23; 7.399, 1.82; 7.397, 1.89; 7.392, 2.12; 7.391, 2.00; 7.293, 2.10; 7.287, 1.92; 7.196, 2.38; 5.862, 9.22; 3.933, 0.58; 3.916, 0.89; 3.898, 0.87; 3.881, 0.60; 3.116, 162.75; 2.526, 0.81; 2.510, 0.59; 2.505, 0.84; 2.497, 11.65; 2.493, 23.90; 2.488, 33.54; 2.483, 23.47; 2.478, 11.28; 2.141, 11.60; 1.032, 16.00; 1.016, 15.80; −0.000, 2.56 |
| 191 | 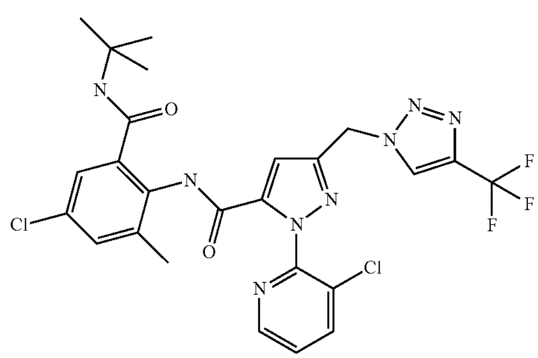 [SMILES: Cc1cc(Cl)cc(C(=O)NC(C)(C)C)c1NC(=O)c1cc(Cn2cc(C(F)(F)F)nn2)nn1-c1ncccc1Cl] | 3.44 | 595 | 9.993, 0.46; 8.914, 0.74; 8.453, 0.54; 8.449, 0.56; 8.441, 0.53; 8.438, 0.54; 8.109, 0.47; 8.105, 0.50; 8.089, 0.54; 8.085, 0.52; 7.576, 0.55; 7.564, 0.55; 7.555, 0.53; 7.543, 0.52; 7.376, 0.56; 7.370, 0.58; 7.306, 0.44; 7.247, 0.63; 7.240, 0.58; 7.168, 0.67; 5.865, 2.48; 3.131, 273.86; 2.511, 0.72; 2.499, 12.40; 2.494, 24.83; 2.489, 34.53; 2.484, 24.61; 2.480, 12.17; 2.132, 3.24; 2.040, 0.39; 1.215, 16.00 |

| No. | Structure | logP | MH+ | NMR |
|---|---|---|---|---|
| 192 | 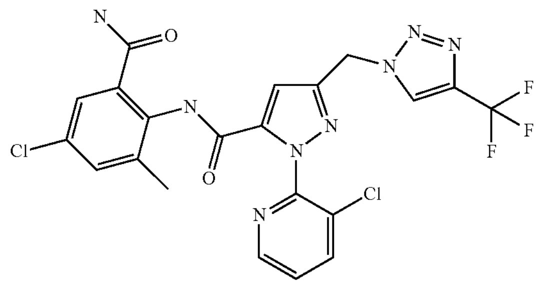 [SMILES: Cc1cc(Cl)cc(C(N)=O)c1NC(=O)c1cc(Cn2cc(C(F)(F)F)nn2)nn1-c1ncccc1Cl] | 2.44 | 539 | 10.163, 2.09; 8.942, 3.59; 8.941, 3.56; 8.466, 2.75; 8.462, 2.94; 8.454, 2.93; 8.450, 2.93; 8.107, 2.69; 8.104, 2.77; 8.087, 3.02; 8.083, 2.89; 7.572, 3.26; 7.560, 3.20; 7.551, 3.09; 7.540, 3.04; 7.412, 1.87; 7.408, 4.34; 7.406, 4.36; 7.402, 4.82; 7.401, 4.69; 7.396, 1.97; 7.204, 3.70; 5.856, 12.54; 5.686, 1.15; 3.129, 252.94; 2.511, 0.62; 2.506, 0.91; 2.498, 11.54; 2.494, 23.50; 2.489, 32.86; 2.484, 23.08; 2.480, 11.12; 2.131, 16.00; −0.000, 0.33 |
| 193 | 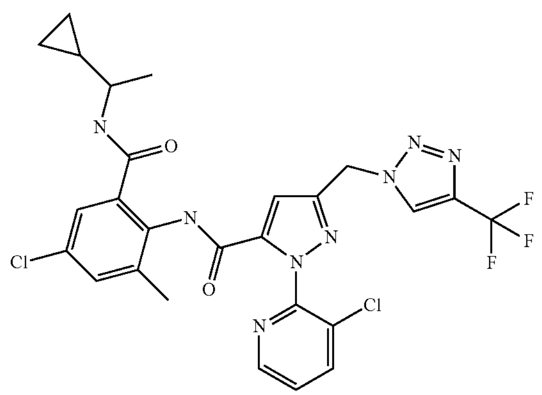 [SMILES: Cc1cc(Cl)cc(C(=O)NC(C)C2CC2)c1NC(=O)c1cc(Cn2cc(C(F)(F)F)nn2)nn1-c1ncccc1Cl] | 3.34 | 607 | 10.033, 1.62; 8.920, 3.69; 8.918, 3.66; 8.450, 3.01; 8.446, 3.17; 8.438, 3.18; 8.434, 3.09; 8.098, 3.00; 8.094, 3.03; 8.078, 3.34; 8.074, 3.10; 7.863, 1.07; 7.844, 1.10; 7.570, 3.45; 7.558, 3.38; 7.549, 3.22; 7.538, 3.16; 7.407, 2.61; 7.406, 2.72; 7.401, 3.03; 7.400, 2.86; 7.295, 2.93; 7.290, 2.67; 7.197, 3.51; 5.857, 12.89; 3.365, 0.67; 3.345, 1.24; 3.328, 1.27; 3.308, 0.67; 3.119, 249.49; 2.662, 0.57; 2.527, 1.19; 2.510, 0.90; 2.506, 1.28; 2.498, 17.13; 2.493, 35.13; 2.488, 49.32; 2.484, 34.45; 2.479, 16.46; 2.143, 16.00; 1.065, 9.95; 1.048, 9.84; 0.842, 0.58; 0.835, 0.74; 0.822, 1.28; 0.815, 0.79; 0.810, 0.87; 0.802, 1.30; 0.790, 0.73; 0.782, 0.49; 0.368, 0.52; 0.364, 0.55; 0.356, 1.09; 0.347, 1.02; 0.343, 0.99; 0.333, 1.25; 0.327, 0.57; 0.321, 0.67; 0.312, 0.62; 0.240, 0.45; 0.230, 0.78; 0.226, 0.73; 0.215, 1.04; 0.209, 1.14; 0.204, 1.03; 0.195, 1.49; 0.189, 1.29; 0.184, 0.70; 0.180, 1.09; 0.174, 1.28; 0.167, 1.49; 0.157, 1.24; 0.142, 1.03; 0.133, 0.90; 0.129, 1.11; 0.120, 1.21; 0.115, 0.66; 0.106, 0.81; 0.098, 0.48; −0.000, 3.83 |
| 194 | Chiral | 3.35 | 627 | 10.028, 0.74; 8.926, 2.64; 8.452, 1.97; 8.448, 2.04; 8.441, 2.07; 8.437, 2.05; 8.099, 1.90; 8.096, 1.80; 8.079, 2.13; 8.075, 1.87; 7.955, 0.54; 7.934, 0.55; 7.571, 2.10; 7.559, 2.03; 7.551, 1.96; 7.539, 1.89; 7.415, 1.63; 7.408, 1.69; 7.340, 0.42; 7.334, 0.39; 7.319, 1.83; 7.313, 1.63; 7.211, 2.05; 5.858, 8.26; 3.976, 0.65; 3.973, 0.65; 3.957, 0.57; 3.159, 0.40; 3.113, 174.32; 2.594, 0.82; 2.578, 0.80; 2.560, 1.31; 2.544, 1.29; 2.526, 1.07; 2.510, 0.87; 2.505, 1.22; 2.497, 15.27; 2.492, 31.10; 2.488, 43.54; 2.483, 30.41; 2.478, 14.56; 2.468, 1.61; 2.451, 1.32; 2.435, 0.83; 2.418, 0.78; 2.147, 11.31; 2.040, 0.36; 2.001, 16.00; 1.992, 3.86; 1.364, 2.15; 1.246, 0.35; 1.122, 1.50; 1.105, 1.77; 1.098, 5.82; 1.081, 5.69; 1.003, 0.42; 0.986, 0.41; 0.858, 0.35; 0.842, 0.33; 0.828, 0.42; 0.811, 0.38; 0.008, 0.36; −0.000, 10.66; −0.008, 0.33 |

| No. | Structure | logP | MH+ | NMR |
|---|---|---|---|---|
| 195 | 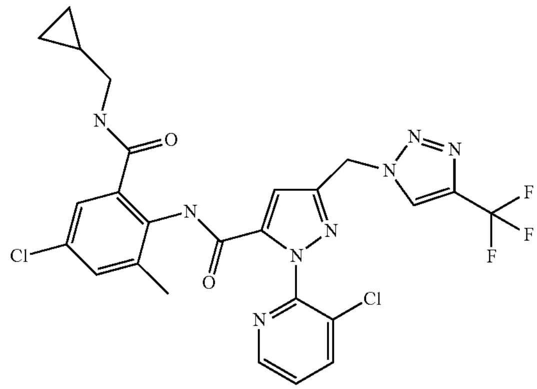 [SMILES: Cc1cc(Cl)cc(C(=O)NCC2CC2)c1NC(=O)c1cc(Cn2cc(C(F)(F)F)nn2)nn1-c1ncccc1Cl] | 3.22 | 593 | 10.070, 1.81; 8.929, 3.71; 8.448, 2.71; 8.444, 2.89; 8.436, 2.90; 8.433, 2.87; 8.099, 2.83; 8.095, 2.87; 8.079, 3.30; 8.075, 3.17; 8.067, 0.70; 8.054, 1.10; 8.040, 0.66; 7.568, 3.21; 7.556, 3.08; 7.548, 2.98; 7.536, 2.93; 7.412, 2.53; 7.407, 2.91; 7.326, 3.00; 7.320, 2.68; 7.200, 3.51; 5.855, 12.78; 3.114, 173.42; 3.029, 2.98; 3.013, 4.02; 2.998, 2.94; 2.526, 0.99; 2.510, 0.83; 2.505, 1.22; 2.497, 15.01; 2.492, 30.45; 2.488, 42.52; 2.483, 29.82; 2.478, 14.37; 2.145, 16.00; 0.894, 0.35; 0.885, 0.58; 0.882, 0.61; 0.878, 0.59; 0.874, 0.54; 0.865, 1.07; 0.858, 0.69; 0.853, 0.68; 0.849, 0.63; 0.845, 0.66; 0.842, 0.45; 0.834, 0.43; 0.828, 0.47; 0.332, 1.06; 0.321, 2.93; 0.317, 3.12; 0.312, 1.46; 0.306, 1.58; 0.301, 3.12; 0.296, 2.70; 0.286, 1.25; 0.132, 1.18; 0.121, 3.21; 0.118, 3.13; 0.110, 2.83; 0.106, 3.25; 0.095, 0.80; −0.000, 8.10 |
| 196 | 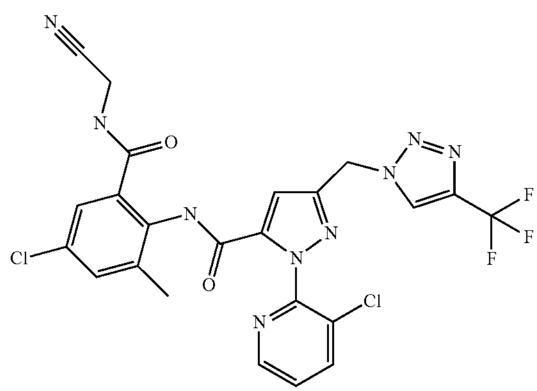 [SMILES: Cc1cc(Cl)cc(C(=O)NCC#N)c1NC(=O)c1cc(Cn2cc(C(F)(F)F)nn2)nn1-c1ncccc1Cl] | 2.61 | 578 | 10.070, 2.41; 8.921, 3.76; 8.861, 0.83; 8.848, 1.38; 8.835, 0.81; 8.460, 2.73; 8.456, 2.92; 8.448, 2.94; 8.444, 2.90; 8.099, 2.77; 8.095, 2.71; 8.079, 3.01; 8.075, 2.83; 7.565, 3.09; 7.553, 2.99; 7.545, 2.86; 7.533, 2.76; 7.474, 2.74; 7.470, 3.05; 7.362, 2.96; 7.335, 2.77; 7.224, 3.24; 5.852, 12.73; 4.160, 5.54; 4.147, 5.49; 3.180, 0.64; 3.173, 0.63; 3.110, 526.34; 3.057, 0.54; 3.052, 0.46; 2.661, 0.95; 2.657, 1.35; 2.652, 0.88; 2.567, 0.41; 2.561, 0.42; 2.526, 1.86; 2.510, 4.53; 2.497, 72.18; 2.492, 143.80; 2.488, 198.70; 2.483, 140.35; 2.478, 68.56; 2.325, 0.50; 2.319, 0.93; 2.315, 1.25; 2.310, 0.89; 2.305, 0.50; 2.161, 16.00; 2.040, 1.63; 1.246, 0.50; 0.008, 0.93; −0.000, 23.24; −0.008, 0.92 |
| 197 | 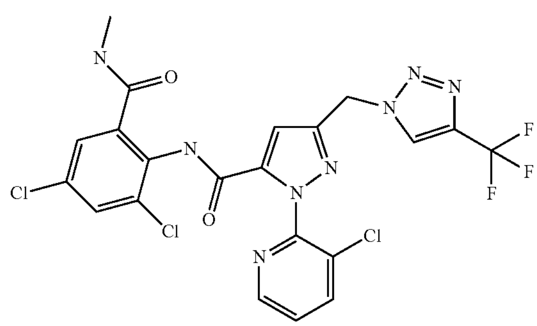 [SMILES: CNC(=O)c1cc(Cl)cc(Cl)c1NC(=O)c1cc(Cn2cc(C(F)(F)F)nn2)nn1-c1ncccc1Cl] | 2.59 | 573 | 10.251, 3.70; 8.954, 4.88; 8.952, 4.83; 8.460, 3.26; 8.457, 3.51; 8.448, 3.62; 8.445, 3.48; 8.101, 3.34; 8.097, 3.30; 8.080, 3.76; 8.077, 3.60; 8.036, 1.28; 7.974, 0.54; 7.731, 4.33; 7.726, 4.58; 7.572, 3.79; 7.560, 3.72; 7.552, 3.50; 7.540, 3.43; 7.463, 5.50; 7.457, 5.34; 7.257, 7.59; 5.862, 16.00; 5.841, 0.35; 3.109, 476.00; 2.658, 14.02; 2.646, 13.52; 2.621, 0.42; 2.565, 0.55; 2.526, 2.45; 2.510, 5.64; 2.497, 83.95; 2.492, 165.43; 2.487, 226.74; 2.483, 158.68; 2.478, 76.61; 2.324, 0.48; 2.319, 0.95; 2.314, 1.38; 2.309, 0.93; 2.040, 2.14; 1.974, 1.00; 1.245, 0.52; 1.177, 0.65; 1.160, 0.33; 0.008, 0.85; −0.000, 19.70; −0.008, 0.83 |

-continued

| No. | Structure | logP | MH+ | NMR |
|---|---|---|---|---|
| 198 | 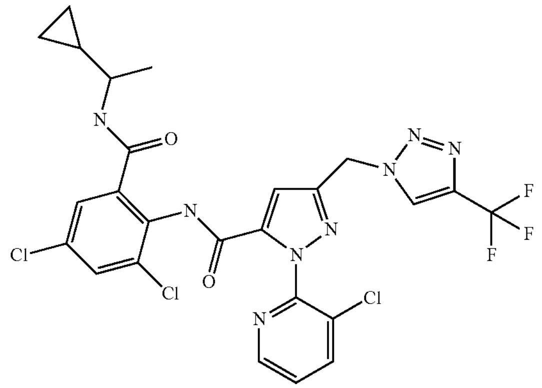 [SMILES: CC(NC(=O)c1cc(Cl)cc(Cl)c1NC(=O)c1cc(Cn2cc(C(F)(F)F)nn2)nn1-c1ncccc1Cl)C1CC1] | 3.38 | 627 | 10.178, 0.57; 8.927, 4.67; 8.925, 4.62; 8.448, 3.61; 8.444, 3.75; 8.436, 3.83; 8.432, 3.71; 8.090, 3.53; 8.087, 3.58; 8.070, 3.99; 8.066, 3.73; 7.916, 1.06; 7.896, 1.08; 7.733, 5.37; 7.727, 5.61; 7.569, 4.07; 7.557, 3.94; 7.549, 3.76; 7.537, 3.71; 7.425, 5.98; 7.419, 5.81; 7.262, 7.61; 5.861, 16.00; 3.333, 0.83; 3.313, 1.59; 3.296, 1.57; 3.277, 0.83; 3.115, 143.27; 2.526, 1.04; 2.510, 0.84; 2.505, 1.20; 2.497, 15.52; 2.493, 31.62; 2.488, 44.22; 2.483, 30.86; 2.478, 14.77; 1.048, 12.55; 1.031, 12.35; 0.826, 0.62; 0.818, 0.85; 0.813, 0.50; 0.805, 1.58; 0.798, 0.93; 0.793, 1.00; 0.785, 1.64; 0.773, 0.93; 0.765, 0.63; 0.372, 0.53; 0.363, 0.66; 0.360, 0.72; 0.351, 1.77; 0.343, 1.29; 0.338, 1.21; 0.330, 1.55; 0.322, 0.75; 0.317, 0.83; 0.308, 0.78; 0.235, 0.59; 0.225, 0.94; 0.221, 0.94; 0.211, 1.30; 0.205, 1.30; 0.201, 1.15; 0.191, 2.08; 0.184, 0.84; 0.179, 1.44; 0.170, 1.92; 0.165, 0.79; 0.157, 1.97; 0.147, 1.76; 0.144, 1.41; 0.140, 1.41; 0.134, 1.19; 0.131, 1.28; 0.127, 1.62; 0.118, 1.53; 0.113, 0.83; 0.105, 1.09; 0.096, 0.59; −0.000, 5.38 |
| 199 | 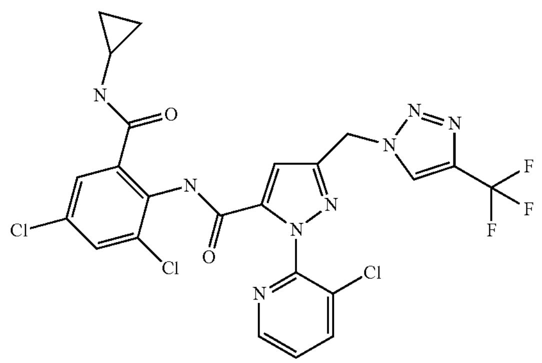 [SMILES: O=C(NC1CC1)c1cc(Cl)cc(Cl)c1NC(=O)c1cc(Cn2cc(C(F)(F)F)nn2)nn1-c1ncccc1Cl] | 2.89 | 599 | 10.193, 0.62; 8.950, 5.19; 8.948, 5.08; 8.461, 3.71; 8.458, 4.03; 8.450, 4.01; 8.446, 3.97; 8.099, 4.24; 8.095, 4.14; 8.079, 4.14; 8.075, 3.97; 7.726, 0.59; 7.719, 4.54; 7.713, 4.58; 7.574, 4.15; 7.562, 4.02; 7.553, 3.90; 7.542, 3.87; 7.532, 0.37; 7.499, 0.33; 7.493, 0.34; 7.423, 4.82; 7.417, 4.63; 7.264, 7.28; 7.252, 0.45; 5.870, 16.00; 3.602, 0.59; 3.115, 166.02; 2.690, 0.72; 2.680, 1.03; 2.672, 1.54; 2.662, 1.74; 2.653, 1.18; 2.644, 0.75; 2.526, 0.99; 2.510, 0.78; 2.505, 1.16; 2.497, 15.29; 2.492, 31.20; 2.488, 43.65; 2.483, 30.65; 2.478, 14.78; 2.040, 0.37; 1.761, 0.71; 1.364, 0.58; 0.632, 0.32; 0.615, 1.17; 0.602, 3.01; 0.597, 3.84; 0.584, 3.83; 0.579, 2.96; 0.567, 1.30; 0.431, 1.59; 0.420, 4.16; 0.414, 4.03; 0.410, 3.60; 0.404, 3.59; 0.392, 1.13; 0.008, 0.34; −0.000, 9.62; −0.008, 0.34 |
| 200 | 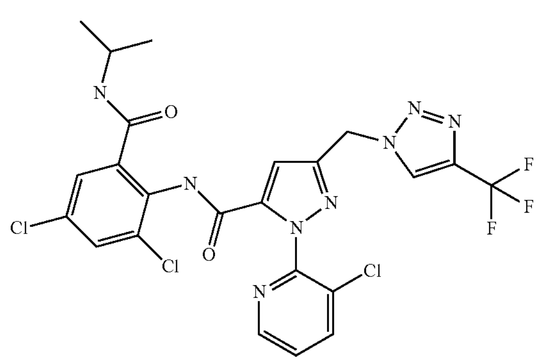 [SMILES: CC(C)NC(=O)c1cc(Cl)cc(Cl)c1NC(=O)c1cc(Cn2cc(C(F)(F)F)nn2)nn1-c1ncccc1Cl] | 3.1 | 601 | 10.189, 0.57; 8.935, 2.86; 8.447, 1.89; 8.444, 1.99; 8.436, 2.03; 8.432, 1.95; 8.090, 1.89; 8.087, 1.90; 8.070, 2.10; 8.067, 1.98; 7.852, 0.54; 7.836, 0.54; 7.723, 2.65; 7.717, 2.75; 7.569, 2.11; 7.557, 2.07; 7.549, 1.98; 7.537, 1.95; 7.427, 3.17; 7.421, 3.07; 7.259, 3.95; 5.865, 9.31; 3.903, 0.62; 3.887, 0.93; 3.868, 0.92; 3.852, 0.62; 3.120, 116.38; 2.526, 0.45; 2.510, 0.42; 2.497, 7.62; 2.493, 15.30; 2.488, 21.22; 2.483, 15.03; 2.479, 7.38; 1.364, 1.68; 1.084, 0.87; 1.067, 0.87; 1.018, 16.00; 1.002, 15.83; −0.000, 1.45 |

-continued

| No. | Structure | logP | MH+ | NMR |
|---|---|---|---|---|
| 201 | 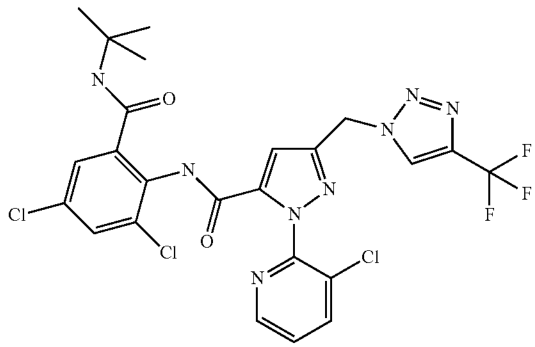 [SMILES: CC(C)(C)NC(=O)c1cc(Cl)cc(Cl)c1NC(=O)c1cc(Cn2cc(C(F)(F)F)nn2)nn1-c1ncccc1Cl] | 3.42 | 615 | 10.169, 0.54; 8.922, 0.73; 8.920, 0.72; 8.450, 0.56; 8.446, 0.60; 8.438, 0.60; 8.434, 0.59; 8.101, 0.56; 8.097, 0.56; 8.081, 0.62; 8.077, 0.59; 7.701, 0.79; 7.694, 0.82; 7.575, 0.62; 7.563, 0.60; 7.554, 0.59; 7.543, 0.58; 7.394, 1.28; 7.388, 1.05; 7.240, 1.10; 5.869, 2.51; 3.106, 32.13; 2.510, 0.36; 2.505, 0.55; 2.497, 6.76; 2.492, 13.72; 2.487, 19.15; 2.483, 13.39; 2.478, 6.42; 1.364, 0.74; 1.266, 0.47; 1.203, 16.00; −0.000, 1.51 |
| 202 | 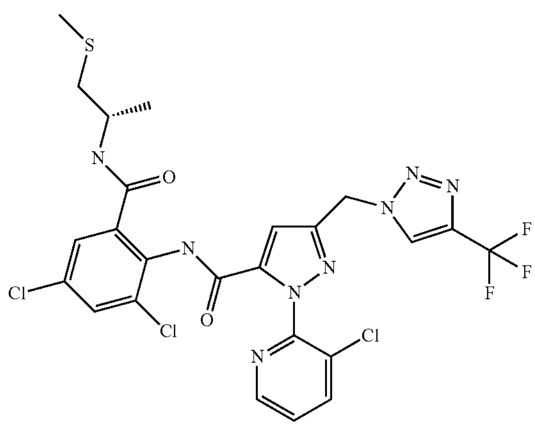 [SMILES: CSC[C@H](C)NC(=O)c1cc(Cl)cc(Cl)c1NC(=O)c1cc(Cn2cc(C(F)(F)F)nn2)nn1-c1ncccc1Cl] | 3.28 | 647 | 8.932, 2.47; 8.451, 1.80; 8.447, 1.85; 8.439, 1.90; 8.436, 1.82; 8.092, 1.62; 8.088, 1.53; 8.072, 1.79; 8.068, 1.61; 7.740, 1.48; 7.734, 1.46; 7.571, 1.75; 7.559, 1.69; 7.551, 1.66; 7.539, 1.58; 7.470, 0.32; 7.450, 2.19; 7.444, 2.05; 7.273, 2.21; 5.861, 7.69; 3.959, 0.52; 3.941, 0.65; 3.922, 0.49; 3.108, 191.26; 3.085, 2.23; 2.661, 0.37; 2.657, 0.49; 2.652, 0.40; 2.582, 0.82; 2.566, 0.86; 2.548, 1.29; 2.533, 1.39; 2.526, 0.74; 2.510, 1.49; 2.505, 2.20; 2.497, 27.62; 2.492, 56.17; 2.487, 78.48; 2.483, 54.98; 2.478, 26.44; 2.445, 1.28; 2.427, 1.26; 2.412, 0.84; 2.394, 0.77; 2.319, 0.32; 2.314, 0.47; 2.309, 0.34; 2.040, 0.58; 2.002, 16.00; 1.989, 2.35; 1.111, 0.89; 1.094, 1.04; 1.083, 5.51; 1.066, 5.42; 1.048, 0.34; 0.985, 0.49; 0.968, 0.44; −0.000, 7.39 |
| 203 | 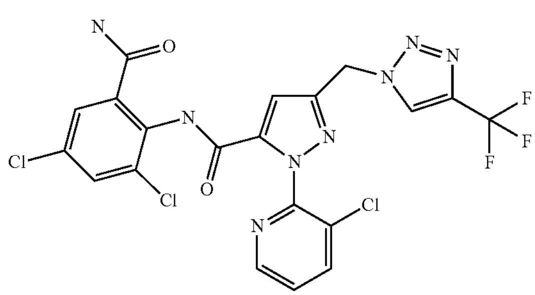 [SMILES: NC(=O)c1cc(Cl)cc(Cl)c1NC(=O)c1cc(Cn2cc(C(F)(F)F)nn2)nn1-c1ncccc1Cl] | 2.43 | 559 | 10.259, 0.86; 8.951, 3.02; 8.950, 3.00; 8.467, 2.27; 8.463, 2.48; 8.455, 2.43; 8.452, 2.40; 8.098, 2.25; 8.094, 2.25; 8.078, 2.52; 8.074, 2.36; 7.733, 3.22; 7.727, 3.43; 7.588, 0.38; 7.582, 0.39; 7.570, 2.71; 7.558, 2.64; 7.550, 2.59; 7.538, 2.67; 7.527, 4.83; 7.521, 4.60; 7.448, 0.37; 7.250, 5.05; 6.873, 0.93; 6.398, 0.53; 5.871, 0.77; 5.859, 10.48; 5.688, 0.51; 3.602, 0.40; 3.108, 134.46; 3.086, 1.42; 2.657, 0.36; 2.526, 0.43; 2.510, 1.09; 2.505, 1.63; 2.497, 20.45; 2.492, 41.60; 2.487, 58.20; 2.483, 40.79; 2.478, 19.60; 2.314, 0.34; 2.183, 1.53; 1.761, 0.50; 1.364, 16.00; −0.000, 6.90 |

-continued

| No. | Structure | logP | MH+ | NMR |
|---|---|---|---|---|
| 204 | 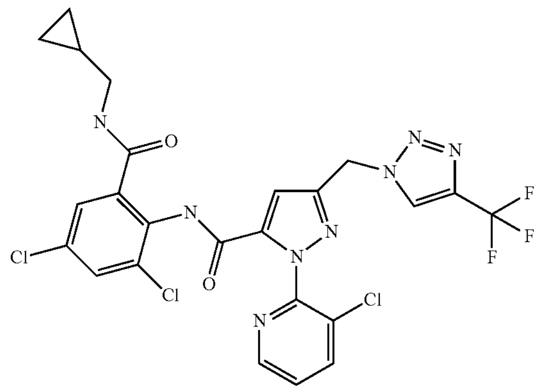 [SMILES: O=C(NCC1CC1)c1cc(Cl)cc(Cl)c1NC(=O)c1cc(Cn2cc(C(F)(F)F)nn2)nn1-c1ncccc1Cl] | 3.14 | 613 | 10.211, 1.24; 8.932, 4.93; 8.445, 3.75; 8.441, 3.90; 8.433, 3.97; 8.429, 4.02; 8.089, 3.76; 8.085, 3.83; 8.069, 3.73; 8.065, 3.59; 7.742, 0.75; 7.734, 2.19; 7.728, 2.23; 7.566, 3.60; 7.554, 3.54; 7.546, 3.34; 7.534, 3.42; 7.523, 0.57; 7.460, 3.80; 7.454, 3.83; 7.255, 3.53; 5.856, 16.00; 3.107, 518.29; 3.083, 6.73; 3.052, 0.62; 3.043, 0.41; 3.008, 3.95; 2.994, 5.22; 2.977, 3.97; 2.666, 0.50; 2.661, 0.92; 2.657, 1.27; 2.652, 1.00; 2.647, 0.49; 2.526, 1.53; 2.510, 3.95; 2.505, 5.75; 2.497, 75.10; 2.492, 152.74; 2.487, 213.53; 2.483, 149.53; 2.478, 71.93; 2.324, 0.47; 2.319, 0.88; 2.314, 1.28; 2.310, 0.85; 2.305, 0.48; 2.040, 4.30; 1.363, 1.80; 1.245, 0.48; 1.096, 0.42; 1.050, 0.65; 1.048, 0.59; 1.033, 0.45; 0.871, 0.51; 0.858, 0.91; 0.853, 0.85; 0.849, 0.97; 0.841, 1.49; 0.832, 0.89; 0.824, 0.94; 0.821, 0.88; 0.811, 0.53; 0.324, 1.52; 0.314, 3.88; 0.309, 4.06; 0.305, 1.88; 0.299, 2.06; 0.293, 4.05; 0.289, 3.49; 0.279, 1.60; 0.120, 1.61; 0.109, 4.31; 0.106, 4.12; 0.098, 3.70; 0.094, 4.21; 0.083, 1.10; 0.008, 0.78; −0.000, 21.39; −0.008, 0.66 |
| 205 | 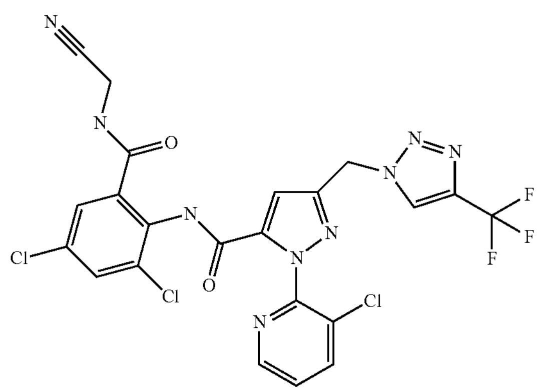 | 2.63 | 598 | 10.297, 0.46; 10.284, 0.53; 8.982, 0.35; 8.960, 0.59; 8.929, 5.32; 8.927, 5.27; 8.463, 4.15; 8.460, 4.45; 8.452, 4.47; 8.448, 4.38; 8.089, 3.24; 8.086, 3.31; 8.069, 3.66; 8.066, 3.45; 7.975, 0.61; 7.793, 1.83; 7.564, 3.99; 7.552, 3.74; 7.544, 3.72; 7.532, 3.80; 7.521, 4.16; 7.515, 3.96; 7.267, 2.67; 5.854, 16.00; 4.154, 4.59; 3.200, 0.50; 3.117, 1089.75; 3.061, 0.41; 2.667, 0.44; 2.662, 0.88; 2.657, 1.34; 2.653, 0.82; 2.648, 0.42; 2.526, 2.41; 2.510, 2.91; 2.506, 4.09; 2.497, 69.40; 2.493, 144.37; 2.488, 204.48; 2.483, 142.92; 2.479, 68.41; 2.449, 0.38; 2.324, 0.40; 2.320, 0.91; 2.315, 1.23; 2.310, 0.88; 2.305, 0.48; 2.040, 0.63; 1.404, 3.82; 1.263, 0.34; 1.246, 0.44; −0.000, 5.02 |
| 206 | 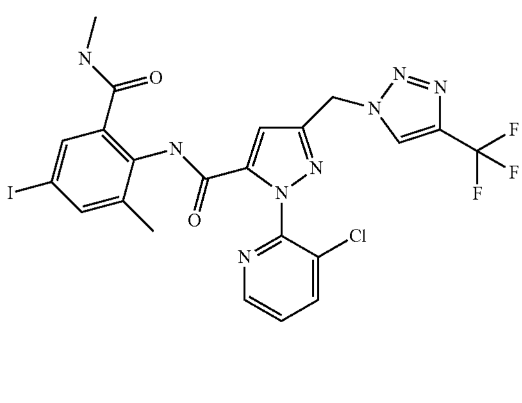 [SMILES: CNC(=O)c1cc(I)cc(C)c1NC(=O)c1cc(Cn2cc(C(F)(F)F)nn2)nn1-c1ncccc1Cl] | 2.86 | 645 | 8.945, 3.49; 8.943, 3.47; 8.456, 2.68; 8.452, 2.96; 8.444, 2.93; 8.440, 2.92; 8.105, 2.78; 8.084, 3.04; 8.081, 2.90; 7.999, 0.87; 7.988, 0.91; 7.973, 0.41; 7.703, 2.51; 7.701, 2.68; 7.698, 2.96; 7.607, 2.93; 7.603, 2.75; 7.569, 3.17; 7.558, 3.00; 7.549, 2.96; 7.537, 2.86; 7.196, 4.11; 5.857, 11.95; 3.108, 156.09; 2.841, 1.42; 2.665, 9.73; 2.653, 9.85; 2.589, 0.58; 2.576, 0.64; 2.526, 0.62; 2.510, 1.46; 2.505, 2.10; 2.497, 26.74; 2.492, 54.46; 2.487, 76.20; 2.483, 53.40; 2.478, 25.77; 2.384, 2.09; 2.319, 0.34; 2.314, 0.44; 2.309, 0.33; 2.102, 16.00; 2.040, 0.40; 1.364, 1.10; −0.000, 7.34 |

-continued

| No. | Structure | logP | MH+ | NMR |
|---|---|---|---|---|
| 207 | 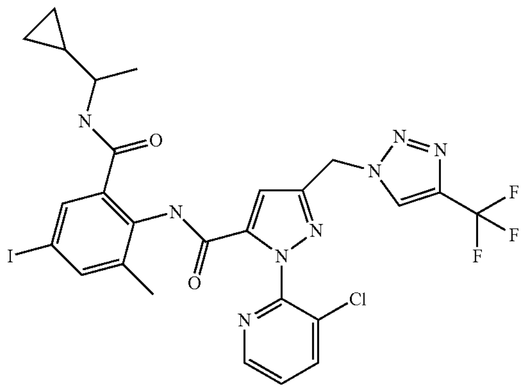 [SMILES: Cc1cc(I)cc(C(=O)NC(C)C2CC2)c1NC(=O)c1cc(Cn2cc(C(F)(F)F)nn2)nn1-c1ncccc1Cl] | 3.69 | 699 | , 8.918, 3.74; 8.917, 3.72; 8.448, 2.88; 8.444, 3.08; 8.436, 3.10; 8.432, 3.01; 8.096, 2.86; 8.092, 2.93; 8.076, 3.20; 8.072, 3.06; 7.870, 1.20; 7.850, 1.18; 7.704, 2.75; 7.702, 2.95; 7.699, 3.22; 7.697, 2.91; 7.578, 3.10; 7.574, 3.04; 7.568, 3.73; 7.556, 3.25; 7.548, 3.11; 7.536, 3.03; 7.198, 4.14; 5.853, 12.70; 3.355, 0.66; 3.336, 1.23; 3.319, 1.24; 3.299, 0.69; 3.115, 136.92; 2.884, 1.57; 2.526, 1.35; 2.510, 0.97; 2.505, 1.30; 2.497, 16.41; 2.493, 33.51; 2.488, 46.97; 2.483, 32.87; 2.478, 15.76; 2.107, 16.00; 1.364, 0.95; 1.240, 2.09; 1.223, 2.00; 1.186, 0.66; 1.169, 0.67; 1.062, 9.71; 1.045, 9.55; 0.858, 0.69; 0.842, 0.90; 0.836, 0.99; 0.827, 0.81; 0.823, 1.37; 0.815, 0.93; 0.811, 1.29; 0.803, 1.30; 0.790, 0.74; 0.354, 1.11; 0.346, 1.04; 0.342, 1.03; 0.332, 1.20; 0.320, 0.71; 0.310, 0.68; 0.228, 0.79; 0.224, 0.74; 0.214, 1.05; 0.208, 1.11; 0.204, 0.94; 0.198, 0.83; 0.194, 1.43; 0.188, 1.09; 0.176, 1.16; 0.173, 1.15; 0.163, 1.45; 0.153, 1.21; 0.138, 0.97; 0.128, 0.91; 0.125, 1.13; 0.116, 1.21; 0.110, 0.66; 0.102, 0.84 |
| 208 | 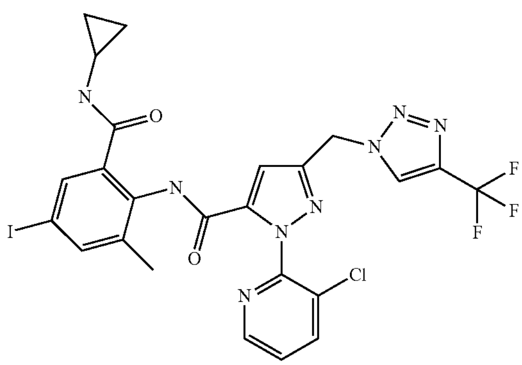 [SMILES: Cc1cc(I)cc(C(=O)NC2CC2)c1NC(=O)c1cc(Cn2cc(C(F)(F)F)nn2)nn1-c1ncccc1Cl] | 3.15 | 671 | 8.942, 3.62; 8.940, 3.59; 8.458, 2.81; 8.454, 3.04; 8.446, 3.09; 8.442, 2.99; 8.103, 2.77; 8.099, 2.84; 8.083, 3.13; 8.079, 3.00; 8.049, 1.07; 8.040, 1.08; 7.694, 2.62; 7.692, 2.75; 7.689, 2.94; 7.687, 2.66; 7.571, 3.26; 7.559, 3.66; 7.556, 3.42; 7.555, 3.51; 7.551, 6.01; 7.539, 3.03; 7.206, 3.99; 5.865, 11.57; 3.121, 101.58; 2.905, 0.67; 2.709, 0.45; 2.700, 0.69; 2.691, 0.97; 2.681, 1.00; 2.672, 0.68; 2.662, 0.67; 2.658, 0.40; 2.653, 0.43; 2.527, 0.97; 2.511, 0.76; 2.506, 1.09; 2.498, 14.12; 2.493, 28.86; 2.488, 40.47; 2.484, 28.34; 2.479, 13.57; 2.099, 16.00; 2.040, 0.33; 1.901, 0.47; 0.612, 0.69; 0.600, 1.96; 0.594, 2.54; 0.582, 2.49; 0.576, 2.00; 0.565, 0.85; 0.446, 1.15; 0.435, 2.96; 0.428, 2.77; 0.425, 2.52; 0.419, 2.48; 0.407, 0.94; −0.000, 4.27 |
| 209 | 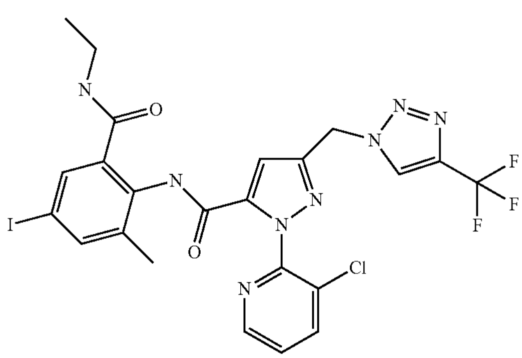 [SMILES: CCNC(=O)c1cc(I)cc(C)c1NC(=O)c1cc(Cn2cc(C(F)(F)F)nn2)nn1-c1ncccc1Cl] | 3.04 | 659 | 10.060, 0.47; 8.934, 3.54; 8.932, 3.53; 8.450, 2.70; 8.447, 2.96; 8.439, 2.93; 8.435, 2.93; 8.101, 2.74; 8.097, 2.76; 8.080, 3.10; 8.077, 2.86; 7.990, 1.11; 7.978, 0.66; 7.974, 0.67; 7.699, 2.73; 7.696, 2.99; 7.594, 2.93; 7.590, 2.79; 7.569, 3.26; 7.557, 3.12; 7.549, 3.03; 7.537, 2.92; 7.190, 4.07; 5.857, 12.21; 3.175, 1.12; 3.157, 3.19; 3.143, 3.84; 3.139, 4.11; 3.113, 411.87; 2.852, 0.56; 2.846, 0.41; 2.827, 0.43; 2.661, 0.50; 2.657, 0.71; 2.652, 0.56; 2.526, 0.80; 2.510, 2.10; 2.505, 3.01; 2.497, 38.05; 2.493, 77.41; 2.488, 108.43; 2.483, 75.99; 2.478, 36.60; 2.319, 0.49; 2.315, 0.62; 2.310, 0.45; 2.104, 16.00; 2.040, 0.33; 1.974, 0.56; 1.364, 0.43; 1.177, 0.40; 1.171, 0.65; 1.153, 1.22; 1.135, 0.61; 1.013, 5.43; 0.995, 11.44; 0.977, 5.21; −0.000, 6.61 |

-continued

| No. | Structure | logP | MH+ | NMR |
|---|---|---|---|---|
| 210 | 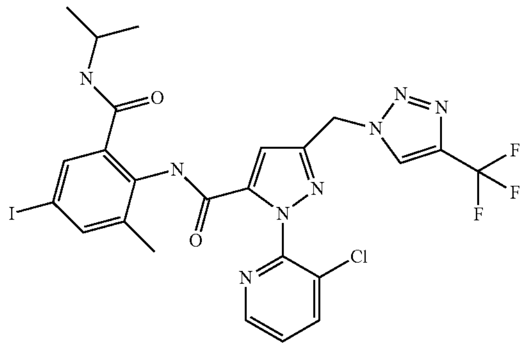 [SMILES: Cc1cc(I)cc(C(=O)NC(C)C)c1NC(=O)c1cc(Cn2cc(C(F)(F)F)nn2)nn1-c1ncccc1Cl] | 3.38 | 673 | 10.042, 0.44; 8.928, 2.71; 8.926, 2.70; 8.447, 2.05; 8.443, 2.17; 8.435, 2.21; 8.431, 2.15; 8.096, 2.10; 8.092, 2.16; 8.076, 2.36; 8.072, 2.25; 7.799, 0.82; 7.780, 0.85; 7.696, 2.04; 7.695, 2.18; 7.691, 2.36; 7.689, 2.13; 7.571, 2.42; 7.568, 4.43; 7.556, 2.45; 7.548, 2.31; 7.536, 2.25; 7.199, 2.94; 5.859, 9.32; 3.927, 0.59; 3.910, 0.88; 3.891, 0.87; 3.875, 0.59; 3.115, 107.65; 2.865, 0.37; 2.526, 0.63; 2.510, 0.48; 2.505, 0.70; 2.497, 9.94; 2.493, 20.40; 2.488, 28.68; 2.483, 20.09; 2.478, 9.65; 2.105, 12.04; 1.364, 2.07; 1.196, 2.63; 1.179, 2.57; 1.132, 0.35; 1.115, 0.35; 1.029, 16.00; 1.013, 15.84; −0.000, 6.14 |
| 211 | 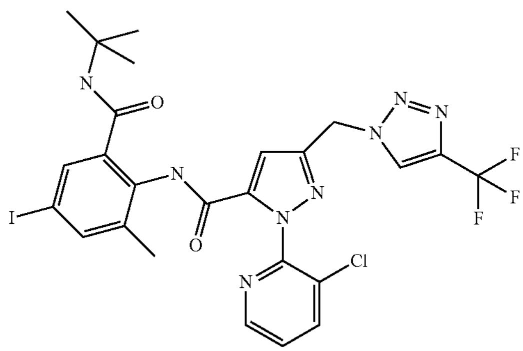 [SMILES: Cc1cc(I)cc(C(=O)NC(C)(C)C)c1NC(=O)c1cc(Cn2cc(C(F)(F)F)nn2)nn1-c1ncccc1Cl] | 3.72 | 687 | 8.966, 3.58; 8.964, 3.60; 8.910, 0.47; 8.583, 2.71; 8.579, 2.93; 8.571, 2.90; 8.567, 2.91; 8.451, 0.39; 8.447, 0.32; 8.435, 0.38; 8.269, 2.72; 8.265, 2.73; 8.249, 3.00; 8.245, 2.93; 8.174, 2.43; 8.173, 2.59; 8.169, 2.74; 8.168, 2.71; 8.107, 0.34; 8.087, 0.39; 8.083, 0.36; 8.017, 2.66; 8.015, 3.07; 8.012, 2.99; 8.010, 2.55; 7.714, 3.13; 7.702, 3.08; 7.693, 3.05; 7.681, 2.96; 7.670, 0.49; 7.573, 0.41; 7.562, 0.41; 7.554, 0.36; 7.542, 0.36; 7.523, 0.42; 7.371, 7.93; 7.162, 0.49; 5.884, 12.89; 5.862, 1.51; 5.688, 7.70; 3.602, 0.56; 3.112, 582.21; 2.905, 0.49; 2.667, 0.43; 2.662, 0.75; 2.657, 1.04; 2.652, 0.77; 2.648, 0.40; 2.526, 1.20; 2.510, 3.00; 2.506, 4.45; 2.497, 55.63; 2.493, 113.22; 2.488, 158.61; 2.484, 111.12; 2.479, 53.40; 2.320, 0.63; 2.315, 0.97; 2.310, 0.65; 2.306, 0.37; 2.293, 1.51; 2.098, 1.86; 2.040, 0.68; 1.771, 0.33; 1.762, 0.76; 1.736, 16.00; 1.407, 0.39; 1.363, 1.53; 1.269, 1.56; 1.260, 11.61; 1.244, 0.45; 1.212, 9.40; −0.000, 3.64 |
| 212 | Chiral | 3.59 | 719 | 8.923, 2.67; 8.450, 1.96; 8.446, 2.10; 8.439, 2.09; 8.435, 2.08; 8.097, 1.92; 8.094, 1.83; 8.080, 0.71; 8.077, 2.17; 8.073, 1.89; 7.958, 0.66; 7.938, 0.68; 7.710, 1.76; 7.708, 1.79; 7.705, 1.91; 7.703, 1.77; 7.624, 0.56; 7.619, 0.54; 7.601, 1.84; 7.597, 1.75; 7.570, 2.14; 7.558, 2.08; 7.549, 2.01; 7.538, 1.97; 7.212, 2.50; 7.202, 0.78; 5.855, 8.33; 3.987, 0.57; 3.970, 0.64; 3.967, 0.63; 3.950, 0.56; 3.194, 0.54; 3.178, 0.74; 3.119, 62.42; 2.913, 1.75; 2.897, 0.47; 2.591, 0.80; 2.575, 1.60; 2.558, 2.11; 2.542, 1.25; 2.527, 0.94; 2.510, 0.73; 2.506, 1.09; 2.498, 13.86; 2.493, 28.41; 2.488, 39.92; 2.484, 27.99; 2.479, 13.48; 2.466, 1.53; 2.449, 1.36; 2.433, 0.84; 2.415, 0.78; 2.183, 0.37; 2.111, 11.63; 2.089, 3.85; 2.085, 1.94; 2.053, 0.45; 2.040, 0.36; 2.037, 0.32; 1.999, 16.00; 1.990, 4.29; 1.364, 3.48; 1.209, 0.73; 1.193, 0.92; 1.183, 1.48; 1.167, 1.46; 1.122, 0.83; 1.117, 1.75; 1.105, 0.98; 1.100, 2.21; 1.095, 5.78; 1.078, 5.59; 0.999, 0.47; 0.982, 0.44; −0.000, 3.43 |

| No. | Structure | logP | MH+ | NMR |
|---|---|---|---|---|
| 213 | 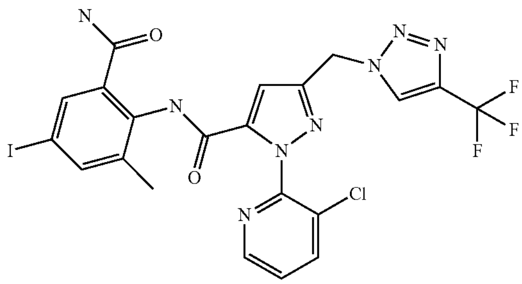 [SMILES: Cc1cc(I)cc(C(N)=O)c1NC(=O)c1cc(Cn2cc(C(F)(F)F)nn2)nn1-c1ncccc1Cl] | 2.64 | 631 | 10.172, 0.76; 10.164, 0.99; 8.941, 3.53; 8.473, 0.33; 8.462, 2.73; 8.459, 2.95; 8.451, 2.96; 8.447, 2.83; 8.106, 2.80; 8.102, 2.68; 8.086, 3.09; 8.082, 2.60; 7.974, 0.52; 7.708, 2.69; 7.704, 3.33; 7.680, 3.61; 7.676, 2.61; 7.570, 3.17; 7.559, 3.11; 7.550, 3.01; 7.538, 2.90; 7.526, 0.35; 7.518, 0.35; 7.504, 0.45; 7.477, 0.46; 7.400, 0.33; 7.312, 0.37; 7.291, 0.44; 7.274, 0.32; 7.195, 4.66; 5.873, 0.38; 5.851, 12.52; 5.688, 2.42; 3.256, 0.40; 3.238, 0.42; 3.221, 0.43; 3.213, 0.54; 3.191, 0.77; 3.182, 0.76; 3.109, 1022.01; 3.050, 0.36; 2.902, 2.54; 2.666, 0.69; 2.661, 1.53; 2.657, 2.06; 2.652, 1.64; 2.648, 0.72; 2.534, 0.80; 2.526, 2.34; 2.510, 5.87; 2.505, 8.68; 2.497, 118.85; 2.492, 243.30; 2.487, 341.62; 2.483, 240.95; 2.478, 117.21; 2.324, 0.70; 2.319, 1.67; 2.314, 2.12; 2.310, 1.47; 2.093, 16.00; 2.040, 3.63; 1.420, 0.41; 1.246, 0.64; 0.008, 0.46; −0.000, 15.48 |
| 214 | 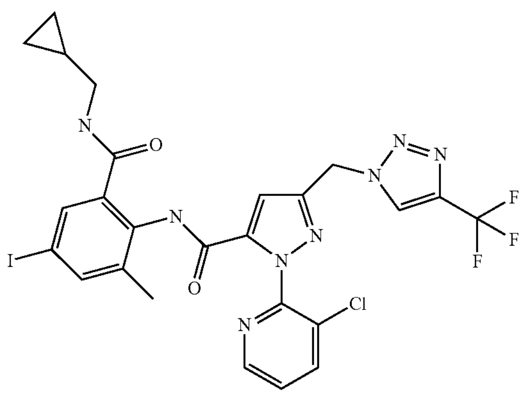 [SMILES: Cc1cc(I)cc(C(=O)NCC2CC2)c1NC(=O)c1cc(Cn2cc(C(F)(F)F)nn2)nn1-c1ncccc1Cl] | 3.45 | 685 | 10.075, 1.77; 8.927, 3.78; 8.925, 3.76; 8.446, 2.73; 8.442, 2.91; 8.434, 2.95; 8.430, 2.92; 8.097, 2.84; 8.093, 2.92; 8.077, 3.47; 8.073, 3.60; 8.057, 1.31; 8.043, 0.74; 7.708, 2.89; 7.705, 3.16; 7.608, 3.14; 7.603, 2.96; 7.567, 3.22; 7.555, 3.15; 7.547, 3.04; 7.535, 2.96; 7.200, 4.29; 5.852, 12.87; 3.115, 179.39; 3.020, 2.93; 3.005, 4.07; 2.989, 2.93; 2.868, 0.49; 2.831, 0.65; 2.813, 0.63; 2.695, 0.38; 2.677, 0.36; 2.526, 1.04; 2.510, 0.90; 2.505, 1.29; 2.497, 16.00; 2.493, 32.43; 2.488, 45.22; 2.483, 31.72; 2.478, 15.34; 2.109, 16.00; 2.040, 0.34; 1.099, 0.36; 0.896, 0.35; 0.884, 0.58; 0.881, 0.64; 0.876, 0.62; 0.864, 1.06; 0.859, 0.67; 0.856, 0.65; 0.852, 0.67; 0.847, 0.65; 0.844, 0.67; 0.835, 0.36; 0.832, 0.35; 0.599, 0.38; 0.583, 0.37; 0.359, 0.43; 0.355, 0.44; 0.347, 0.42; 0.343, 0.51; 0.331, 1.20; 0.320, 3.18; 0.316, 3.30; 0.311, 1.64; 0.305, 1.84; 0.300, 3.20; 0.295, 2.80; 0.285, 1.27; 0.130, 1.19; 0.119, 3.26; 0.116, 3.18; 0.107, 2.84; 0.103, 3.25; 0.092, 0.82; −0.000, 7.48 |
| 215 | 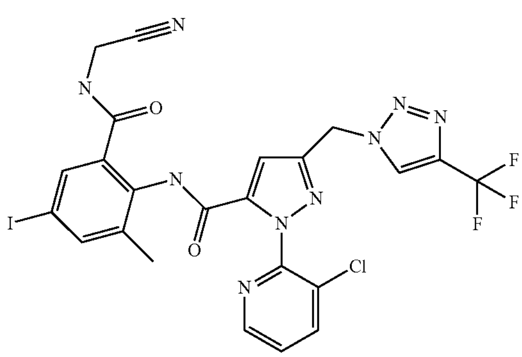 [SMILES: Cc1cc(I)cc(C(=O)NCC#N)c1NC(=O)c1cc(Cn2cc(C(F)(F)F)nn2)nn1-c1ncccc1Cl] | 2.82 | 670 | 10.050, 1.39; 8.933, 0.32; 8.917, 3.69; 8.826, 1.10; 8.818, 0.70; 8.457, 2.91; 8.453, 3.11; 8.445, 3.07; 8.441, 3.13; 8.096, 2.88; 8.092, 2.92; 8.076, 3.19; 8.072, 3.01; 7.974, 0.51; 7.767, 2.96; 7.764, 3.17; 7.634, 3.03; 7.630, 2.93; 7.563, 3.30; 7.552, 3.30; 7.543, 3.16; 7.531, 3.03; 7.370, 0.32; 7.217, 3.75; 7.171, 0.39; 5.884, 0.54; 5.849, 13.30; 5.688, 0.52; 4.150, 4.96; 4.136, 5.17; 4.061, 0.34; 3.993, 0.80; 3.979, 0.76; 3.687, 4.17; 3.671, 4.83; 3.621, 0.41; 3.479, 6.59; 3.292, 0.39; 3.238, 0.38; 3.112, 465.09; 2.992, 5.15; 2.902, 0.52; 2.666, 0.48; 2.662, 1.06; 2.657, 1.48; 2.652, 0.96; 2.647, 0.57; 2.526, 1.65; 2.510, 4.26; 2.505, 6.05; 2.497, 80.57; 2.493, 164.71; 2.488, 231.19; 2.483, 162.39; 2.478, 78.49; 2.324, 0.59; 2.319, 0.90; 2.315, 1.27; 2.310, 0.93; 2.305, 0.44; 2.125, 16.00; 2.092, 0.60; 2.040, 1.39; 1.736, 0.56; 1.404, 2.16; 1.363, 0.34; 1.257, 0.56; 1.245, 0.63; 1.219, 0.41; 1.119, 0.39; 1.109, 0.35; 1.091, 0.34; 1.048, 0.88; 1.033, 0.84; 0.008, 0.50; −0.000, 11.71; −0.008, 0.40 |

| No. | Structure | logP | MH+ | NMR |
|---|---|---|---|---|
| 216 | 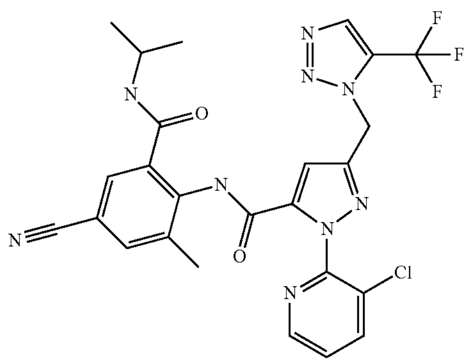 [SMILES: Cc1cc(C#N)cc(C(=O)NC(C)C)c1NC(=O)c1cc(Cn2nncc2C(F)(F)F)nn1-c1ncccc1Cl] | 2.63 | 572 | 10.294, 1.31; 8.444, 2.64; 8.441, 2.67; 8.433, 1.43; 8.429, 1.36; 8.087, 1.30; 8.084, 1.33; 8.067, 1.45; 8.064, 1.37; 7.913, 0.48; 7.893, 0.50; 7.784, 1.33; 7.781, 1.37; 7.692, 1.44; 7.688, 1.27; 7.565, 1.53; 7.553, 1.47; 7.545, 1.40; 7.533, 1.38; 7.179, 2.82; 6.872, 0.92; 6.399, 0.43; 5.920, 5.07; 5.756, 0.40; 3.932, 0.40; 3.916, 0.55; 3.897, 0.54; 3.881, 0.37; 3.108, 185.71; 2.661, 0.36; 2.657, 0.56; 2.652, 0.40; 2.526, 0.61; 2.510, 1.58; 2.505, 2.28; 2.497, 30.13; 2.492, 61.26; 2.487, 85.68; 2.483, 59.94; 2.478, 28.80; 2.319, 0.39; 2.314, 0.50; 2.310, 0.36; 2.187, 7.35; 2.040, 0.50; 1.539, 0.51; 1.363, 16.00; 1.179, 0.61; 1.163, 0.61; 1.092, 0.38; 1.075, 0.38; 1.042, 10.21; 1.025, 10.18; −0.000, 8.27 |
| 217 | 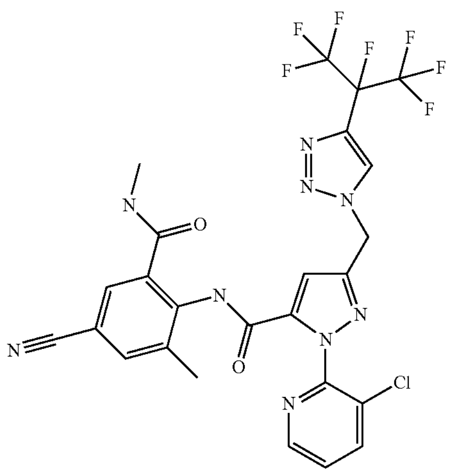 [SMILES: CNC(=O)c1cc(C#N)cc(C)c1NC(=O)c1cc(Cn2cc(C(F)(C(F)(F)F)C(F)(F)F)nn2)nn1-c1ncccc1Cl] | 3.03 | 644 | 10.514, 4.43; 9.052, 7.52; 8.478, 3.36; 8.474, 3.56; 8.466, 3.53; 8.462, 3.30; 8.321, 1.78; 8.309, 1.78; 8.242, 0.31; 8.156, 2.57; 8.136, 2.81; 7.850, 3.87; 7.739, 4.07; 7.600, 2.42; 7.587, 2.30; 7.580, 2.18; 7.567, 2.04; 7.280, 4.46; 5.946, 0.31; 5.939, 0.36; 5.906, 10.67; 3.722, 0.34; 3.708, 0.36; 3.699, 0.35; 3.655, 0.36; 3.636, 0.34; 3.627, 0.33; 3.609, 0.39; 3.535, 0.59; 3.524, 0.63; 3.496, 0.72; 3.446, 1.14; 3.309, 2108.66; 3.194, 0.99; 3.179, 0.83; 3.147, 0.68; 3.132, 0.51; 3.126, 0.47; 3.114, 0.47; 3.019, 0.37; 3.003, 0.36; 2.944, 0.36; 2.931, 0.31; 2.785, 0.39; 2.741, 0.36; 2.734, 0.39; 2.721, 0.40; 2.693, 0.66; 2.669, 3.91; 2.660, 12.48; 2.648, 11.60; 2.631, 1.03; 2.539, 14.96; 2.505, 2 80.95; 2.500, 352.51; 2.496, 247.60; 2.392, 0.79; 2.366, 0.58; 2.347, 0.66; 2.331, 2.04; 2.327, 2.54; 2.322, 2.07; 2.278, 0.35; 2.267, 0.47; 2.238, 0.45; 2.190, 15.00; 2.089, 0.34; 2.069, 1.07; 2.059, 0.34; 2.057, 0.30; 2.049, 0.92; 2.042, 0.33; 2.025, 0.36; 1.958, 0.31; 1.908, 0.47;1.292, 0.48; 1.237, 0.57; 1.159, 0.31; 0.890, 0.70; −0.000, 5.44 |
| 218 | 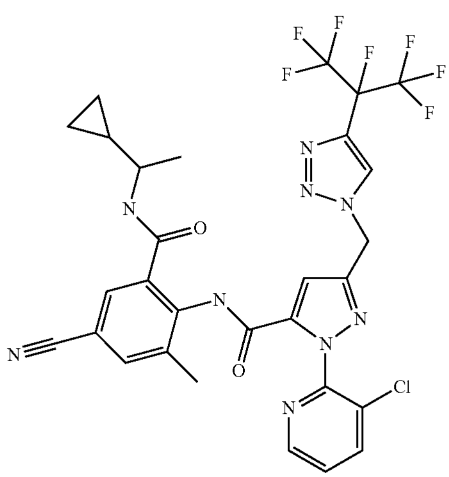 [SMILES: Cc1cc(C#N)cc(C(=O)NC(C)C2CC2)c1NC(=O)c1cc(Cn2cc(C(F)(C(F)(F)F)C(F)(F)F)nn2)nn1-c1ncccc1Cl] | 3.73 | 699 | 10.442, 4.07; 9.027, 7.16; 8.687, 0.73; 8.467, 3.68; 8.463, 3.82; 8.455, 3.97; 8.451, 3.59; 8.380, 0.42; 8.205, 2.15; 8.185, 2.31; 8.142, 2.92; 8.139, 2.86; 8.122, 3.07; 8.119, 2.88; 8.042, 0.38; 7.850, 3.84; 7.700, 4.14; 7.595, 2.85; 7.583, 3.01; 7.575, 2.65; 7.563, 2.41; 7.351, 0.51; 7.285, 4.51; 6.737, 0.41; 5.901, 11.42; 5.759, 1.35; 3.465, 0.41; 3.432, 0.69; 3.385, 1.28; 3.304, 955.43; 3.253, 1.82; 3.193, 0.46; 2.669, 1.58; 2.664, 1.23; 2.633, 0.38; 2.621, 0.40; 2.539, 9.59; 2.508, 102.44; 2.504, 178.81; 2.500, 223.33; 2.496, 155.92; 2.331, 1.30; 2.327, 1.57; 2.322, 1.22; 2.199, 15.00; 2.160, 0.40; 2.069, 1.29; 2.049, 0.58; 1.378, 1.51; 1.270, 0.93; 1.256, 1.00; 1.236, 0.56; 1.053, 11.97; 1.036, 11.74; 0.825, 1.01; 0.814, 1.53; 0.801, 1.29; 0.793, 1.55; 0.781, 0.96; 0.761, 0.37; 0.374, 0.77; 0.363, 1.01; 0.354, 1.74; 0.341, 1.68; 0.332, 1.77; 0.312, 0.81; 0.242, 0.65; 0.231, 1.11; 0.218, 1.43; 0.210, 1.59; 0.198, 1.70; 0.179, 1.73; 0.169, 1.71; 0.157, 2 .44; 0.146, 2.33; 0.126, 2.13; 0.117, 2.02; 0.104, 1.46; 0.095, 0.88; −0.000, 14.99 |

-continued

| No. | Structure | logP | MH+ | NMR |
|---|---|---|---|---|
| 219 | 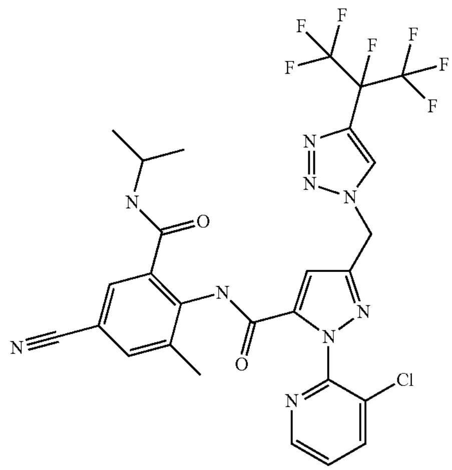 [SMILES: Cc1cc(C#N)cc(C(=O)NC(C)C)c1NC(=O)c1cc(Cn2cc(C(F)(C(F)(F)F)C(F)(F)F)nn2)nn1-c1ncccc1Cl] | 3.44 | 672 | 10.473, 0.59; 10.466, 0.66; 10.461, 0.67; 10.458, 0.79; 10.446, 0.74; 10.434, 0.77; 9.031, 4.91; 8.462, 3.22; 8.459, 3.15; 8.451, 3.06; 8.447, 2.87; 8.153, 0.82; 8.134, 2.56; 8.116, 2.50; 8.089, 0.49; 7.831, 1.25; 7.714, 1.52; 7.589, 1.69; 7.577, 1.84; 7.570, 1.73; 7.558, 1.52; 7.278, 1.06; 7.261, 0.64; 7.252, 0.55; 5.900, 6.54; 3.926, 0.56; 3.909, 1.21; 3.894, 1.83; 3.876, 1.82; 3.862, 0.91; 3.859, 1.29; 3.842, 0.58; 3.632, 0.56; 3.617, 0.47; 3.586, 0.67; 3.564, 0.64; 3.551, 0.63; 3.525, 0.77; 3.515, 0.79; 3.481, 0.94; 3.458, 1.20; 3.304, 2420.87; 3.207, 0.96; 3.183, 0.69; 3.171, 0.57; 3.146, 0.55; 2.732, 0.48; 2.691, 0.57; 2.674, 2.55; 2.669, 3.33; 2.665, 2.55; 2.649, 0.75; 2.621, 0.83; 2.539, 20.41; 2.508, 212.20; 2.504, 372.20; 2.500, 466.02; 2.496, 323.99; 2.420, 1.23; 2.370, 0.83; 2.331, 2.57; 2.327, 3.34; 2.322, 2.58; 2.289, 0.54; 2.189, 5.89; 2.132, 0.57; 2.069, 2.45; 2.049, 1.27; 1.956, 0.49; 1.907, 0.57; 1.292, 0.77; 1.237, 0.79; 1.209, 0.64; 1.069, 0.51; 1.048, 0.50; 1.011, 15.00; 0.994, 14.82; 0.890, 0.93; 0.854, 0.61; −0.000, 21.13 |
| 220 | 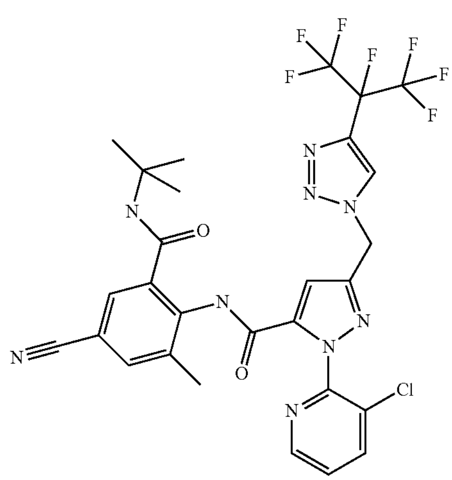 [SMILES: Cc1cc(C#N)cc(C(=O)NC(C)(C)C)c1NC(=O)c1cc(Cn2cc(C(F)(C(F)(F)F)C(F)(F)F)nn2)nn1-c1ncccc1Cl] | 3.75 | 686 | 10.382, 1.04; 9.012, 1.70; 8.453, 1.45; 8.151, 0.94; 8.127, 0.97; 7.813, 1.43; 7.713, 1.27; 7.676, 1.35; 7.582, 1.09; 7.567, 0.89; 7.253, 1.26; 6.871, 0.56; 5.907, 2.85; 3.708, 0.66; 3.682, 0.71; 3.670, 0.73; 3.636, 0.75; 3.609, 0.86; 3.602, 0.88; 3.565, 1.00; 3.533, 1.12; 3.525, 1.14; 3.505, 1.29; 3.471, 1.66; 3.441, 2.22; 3.419, 2.71; 3.301, 6584.73; 3.278, 52.58; 3.172, 0.95; 3.165, 0.95; 3.147, 0.88; 3.139, 0.71; 3.125, 0.69; 3.116, 0.68; 3.067, 0.62; 2.769, 0.61; 2.738, 0.64; 2.702, 0.84; 2.673, 8.28; 2.669, 10.81; 2.664, 7.88; 2.660, 4.31; 2.645, 1.28; 2.539, 23.80; 2.522, 51.12; 2.509, 628.82; 2.504, 1150.23; 2.500, 1479.51; 2.495, 1017.04; 2.491, 492.15; 2.410, 2.29; 2.336, 4.47; 2.331, 7.91; 2.326, 10.61; 2.322, 7.74; 2.280, 1.38; 2.260, 0.73; 2.241, 0.71; 2.229, 0.78; 2.184, 4.74; 2.126, 1.26; 2.091, 0.65; 2.069, 4.98; 2.049, 4.32; 1.986, 1.11; 1.961, 0.59; 1.907, 0.72; 1.422, 1.03; 1.356, 6.61; 1.292, 0.59; 1.261, 2.95; 1.239, 3.24; 1.201, 15.00; 1.159, 1.55; 1.149, 1.42; 1.128, 0.89; 1.114, 0.65; 0.890, 0.65; −0.000, 39.46; −0.009, 1.91 |

| No. | Structure | logP | MH+ | NMR |
|---|---|---|---|---|
| 221 | 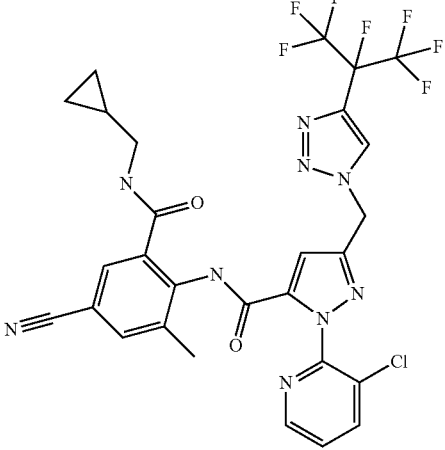 | 3.52 | 684 | 10.483, 2.83; 9.050, 0.76; 9.034, 9.21; 8.462, 4.93; 8.459, 4.94; 8.451, 4.98; 8.447, 4.70; 8.391, 2.05; 8.141, 3.43; 8.122, 3.65; 7.852, 3.45; 7.821, 0.46; 7.764, 0.49; 7.735, 4.20; 7.605, 0.54; 7.592, 3.03; 7.580, 3.11; 7.572, 2.96; 7.560, 2.58; 7.284, 3.50; 5.898, 12.99; 3.731, 0.46; 3.709, 0.49; 3.685, 0.50; 3.654, 0.51; 3.643, 0.50; 3.633, 0.52; 3.610, 0.64; 3.602, 0.57; 3.579, 0.59; 3.486, 0.98; 3.480, 0.98; 3.466, 1.15; 3.459, 1.19; 3.422, 1.70; 3.420, 1.75; 3.305, 2095.54; 3.193, 0.84; 3.168, 0.61; 3.147, 0.70; 3.006, 5.27; 2.990, 7.97; 2.975, 5.18; 2.944, 0.59; 2.731, 0.46; 2.694, 0.65; 2.691, 0.69; 2.674, 2.60; 2.669, 3.27; 2.665, 2.76; 2.639, 0.73; 2.635, 0.75; 2.539, 19.10; 2.504, 363.66; 2.500, 458.69; 2.496, 323.23; 2.377, 0.86; 2.336, 1.56; 2.331, 2.49; 2.327, 3.29; 2.322, 2.52; 2.235, 0.61; 2.196, 15.00; 2.142, 0.84; 2.069, 1.43; 2.049, 1.18; 1.292, 0.78; 1.237, 0.63; 1.159, 0.54; 0.862, 1.49; 0.856, 1.97; 0.846, 2.18; 0.833, 1.82; 0.829, 1.73; 0.313, 5.02; 0.296, 4.81; 0.122, 2.11; 0.112, 6.53; 0.098, 6.08; −0.000, 19.87 |
| 222 | 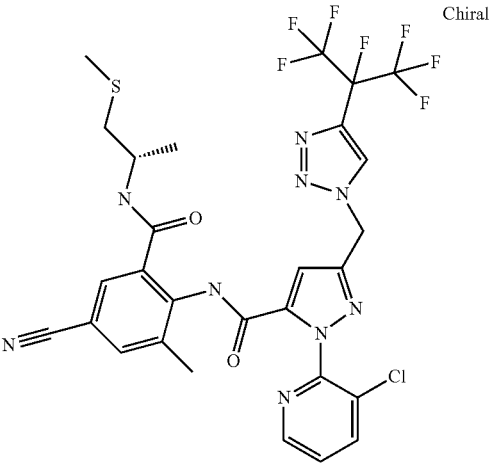 [SMILES: CSC[C@H](C)NC(=O)c1cc(C#N)cc(C)c1NC(=O)c1cc(Cn2cc(C(F)(C(F)(F)F)C(F)(F)F)nn2)nn1-c1ncccc1Cl] | 3.63 | 719 | 10.446, 1.91; 9.033, 2.99; 8.470, 1.48; 8.467, 1.54; 8.459, 1.58; 8.455, 1.48; 8.272, 0.93; 8.251, 0.95; 8.145, 1.18; 8.141, 1.16; 8.125, 1.34; 8.121, 1.22; 7.864, 1.70; 7.712, 1.74; 7.709, 1.67; 7.598, 1.19; 7.587, 1.18; 7.578, 1.14; 7.567, 1.07; 7.306, 2.21; 7.292, 0.32; 5.905, 5.10; 3.973, 0.60; 3.956, 0.70; 3.937, 0.58; 3.387, 0.69; 3.310, 409.40; 3.257, 0.39; 2.674, 0.40; 2.670, 0.51; 2.665, 0.37; 2.568, 1.08; 2.552, 1.36; 2.539, 3.19; 2.535, 2.36; 2.509, 28.10; 2.505, 48.11; 2.500, 59.25; 2.496, 40.57; 2.439, 1.05; 2.421, 1.04; 2.405, 0.68; 2.388, 0.62; 2.327, 0.39; 2.207, 6.87; 1.994, 15.00; 1.108, 0.48; 1.080, 4.34; 1.063, 4.19; −0.000, 0.53 |

-continued

| No. | Structure | logP | MH+ | NMR |
|---|---|---|---|---|
| 223 | 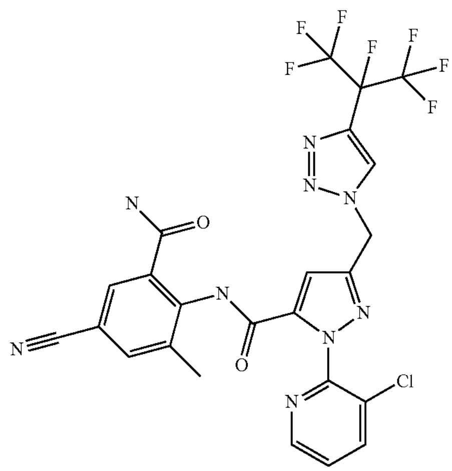 [SMILES: Cc1cc(C#N)cc(C(N)=O)c1NC(=O)c1cc(Cn2cc(C(F)(C(F)(F)F)C(F)(F)F)nn2)nn1-c1ncccc1Cl] | 2.84 | 630 | 10.576, 2.32; 9.051, 3.56; 9.036, 1.44; 8.485, 1.70; 8.482, 1.59; 8.474, 1.63; 8.470, 1.58; 8.157, 1.40; 8.154, 1.44; 8.137, 1.59; 8.133, 1.47; 7.852, 3.37; 7.814, 2.29; 7.600, 1.68; 7.589, 1.54; 7.580, 1.58; 7.569, 1.58; 7.546, 1.38; 7.283, 3.05; 6.871, 1.16; 6.613, 0.77; 5.899, 6.34; 3.708, 1.15; 3.677, 0.61; 3.654, 0.65; 3.618, 0.91; 3.601, 1.60; 3.584, 1.03; 3.575, 0.89; 3.569, 1.01; 3.491, 1.37; 3.449, 2.07; 3.434, 2.35; 3.307, 6601.26; 3.283, 39.16; 3.201, 1.40; 3.191, 0.87; 3.183, 0.95; 3.171, 0.94; 3.147, 1.05; 2.944, 0.67; 2.784, 0.63; 2.678, 2.87; 2.674, 5.52; 2.669, 7.15; 2.665, 5.18; 2.660, 2.83; 2.637, 0.84; 2.539, 22.48; 2.522, 33.76; 2.509, 415.53; 2.505, 757.58; 2.500, 972.41; 2.496, 663.98; 2.491, 317.90; 2.436, 2.65; 2.365, 0.91; 2.358, 0.91; 2.336, 2.96; 2.332, 5.44; 2.327, 6.96; 2.322, 5.09; 2.296, 0.65; 2.289, 0.70; 2.270, 1.21; 2.183, 2.66; 2.173, 8.81; 2.156, 0.75; 2.130, 1.10; 2.069, 5.86; 2.049, 3.15; 1.761, 0.97; 1.671, 3.13; 1.356, 15.00; 1.243, 0.76; 1.237, 1.27; 1.181, 0.82; 0.890, 1.28; −0.000, 23.21; −0.009, 1.13 |
| 224 | 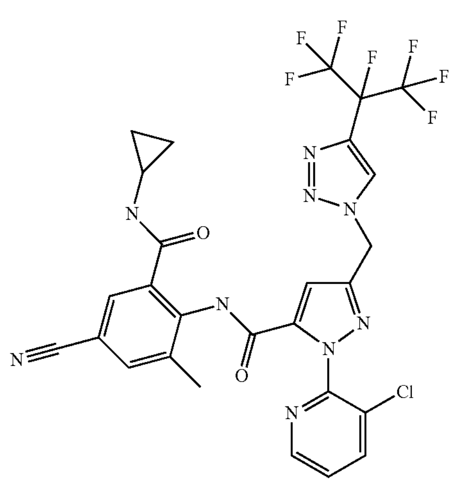 [SMILES: Cc1cc(C#N)cc(C(=O)NC2CC2)c1NC(=O)c1cc(Cn2cc(C(F)(C(F)(F)F)C(F)(F)F)nn2)nn1-c1ncccc1Cl] | 3.24 | 670 | 10.463, 2.19; 9.052, 3.22; 9.028, 1.34; 8.474, 1.63; 8.463, 1.58; 8.353, 1.39; 8.344, 1.71; 8.332, 0.80; 8.328, 0.78; 8.294, 0.81; 8.288, 1.24; 8.268, 0.71; 8.264, 0.54; 8.151, 1.33; 8.134, 1.45; 7.905, 0.84; 7.841, 2.15; 7.695, 2.13; 7.601, 1.22; 7.589, 1.27; 7.581, 1.25; 7.569, 1.53; 7.558, 0.55; 7.550, 0.56; 7.538, 0.53; 7.390, 1.67; 7.299, 2.55; 6.870, 1.23; 6.613, 0.59; 5.935, 2.49; 5.913, 5.41; 3.618, 0.56; 3.601, 1.13; 3.581, 0.57; 3.516, 0.53; 3.490, 0.56; 3.299, 1968.96; 3.275, 47.61; 2.673, 4.38; 2.669, 5.17; 2.664, 4.07; 2.539, 9.88; 2.522, 22.95; 2.508, 272.29; 2.504, 492.90; 2.500, 630.66; 2.495, 437.61; 2.491, 215.68; 2.405, 0.95; 2.363, 0.63; 2.353, 0.60; 2.331, 3.35; 2.326, 4.56; 2.322, 3.43; 2.317, 1.85; 2.282, 1.28; 2.192, 8.30; 2.184, 3.54; 2.134, 1.26; 2.069, 2.20; 2.049, 1.68; 1.862, 3.24; 1.760, 0.96; 1.755, 0.64; 1.742, 0.61; 1.356, 15.00; 1.236, 0.70; 0.987, 0.71; 0.971, 0.68; 0.743, 0.67; 0.615, 0.79; 0.601, 1.77; 0.598, 2.19; 0.585, 2.16; 0.568, 0.87; 0.430, 2.11; 0.421, 2.33; 0.402, 0.74; 0.008, 1.88; −0.000, 41.93 |

| No. | Structure | logP | MH+ | NMR |
|---|---|---|---|---|
| 225 | 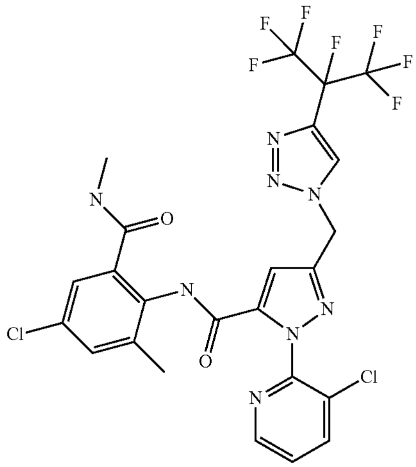 [SMILES: CNC(=O)c1cc(Cl)cc(C)c1NC(=O)c1cc(Cn2cc(C(F)(C(F)(F)F)C(F)(F)F)nn2)nn1-c1ncccc1Cl] | 3.36 | 653 | 10.243, 3.68; 9.063, 0.50; 9.049, 5.38; 8.474, 2.85; 8.470, 2.82; 8.462, 2.89; 8.458, 2.70; 8.195, 1.59; 8.184, 1.57; 8.172, 0.72; 8.151, 2.69; 8.148, 2.58; 8.131, 2.86; 8.127, 2.59; 7.595, 2.67; 7.583, 2.70; 7.575, 2.49; 7.563, 2.45; 7.446, 2.94; 7.441, 3.05; 7.321, 3.48; 7.315, 3.05; 7.250, 6.28; 6.871, 1.12; 6.612, 0.64; 5.942, 0.50; 5.898, 9.53; 3.680, 0.99; 3.601, 0.53; 3.587, 0.37; 3.579, 0.53; 3.520, 0.36; 3.496, 0.44; 3.472, 0.51; 3.457, 0.60; 3.302, 2094.75; 3.278, 17.08; 3.178, 0.38; 3.169, 0.35; 2.691, 0.34; 2.674, 2.69; 2.669, 3.73; 2.664, 2.79; 2.659, 1.83; 2.648, 9.83; 2.636, 9.75; 2.620, 0.64; 2.539, 7.51; 2.522, 16.22; 2.509, 203.01; 2.504, 370.96; 2.500, 477.73; 2.495, 328.61; 2.491, 158.99; 2.394, 0.68; 2.377, 0.56; 2.359, 0.54; 2.331, 2.64; 2.326, 3.48; 2.322, 2.62; 2.183, 1.82; 2.163, 0.34; 2.138, 15.00; 2.069, 1.72; 2.049, 1.33; 1.899, 0.63; 1.760, 0.44; 1.356, 13.15; 1.243, 0.40; 1.237, 0.58; 1.181, 1.07; 1.169, 0.35; 0.008, 0.94; −0.000, 23.80; −0.008, 1.21 |
| 226 | 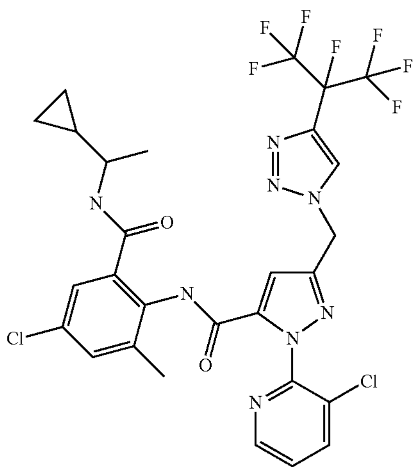 [SMILES: Cc1cc(Cl)cc(C(=O)NC(C)C2CC2)c1NC(=O)c1cc(Cn2cc(C(F)(C(F)(F)F)C(F)(F)F)nn2)nn1-c1ncccc1Cl] | 4.15 | 707 | 10.179, 3.43; 9.019, 5.52; 8.465, 2.74; 8.461, 2.91; 8.453, 2.90; 8.449, 2.79; 8.140, 2.70; 8.136, 2.63; 8.120, 2.91; 8.116, 2.68; 8.061, 1.81; 8.041, 1.81; 7.593, 2.79; 7.581, 2.73; 7.572, 2.59; 7.561, 2.54; 7.447, 3.02; 7.442, 3.20; 7.281, 3.49; 7.275, 3.29; 7.255, 6.68; 5.894, 9.90; 3.312, 548.01; 3.288, 3.99; 3.266, 1.29; 3.250, 0.52; 2.674, 0.39; 2.670, 0.52; 2.665, 0.39; 2.539, 3.98; 2.523, 2.48; 2.509, 29.56; 2.505, 53.55; 2.500, 68.36; 2.496, 46.95; 2.492, 22.64; 2.332, 0.36; 2.327, 0.46; 2.322, 0.35; 2.145, 15.00; 2.069, 0.39; 2.049, 0.32; 1.357, 0.31; 1.089, 0.32; 1.044, 8.78; 1.027, 8.62; 0.822, 0.50; 0.814, 0.65; 0.801, 1.23; 0.793, 0.80; 0.789, 0.87; 0.781, 1.22; 0.769, 0.71; 0.761, 0.50; 0.362, 0.37; 0.354, 0.54; 0.350, 0.59; 0.341, 1.25; 0.333, 1.04; 0.329, 1.07; 0.319, 1.27; 0.313, 0.60; 0.307, 0.67; 0.298, 0.54; 0.220, 0.42; 0.209, 0.73; 0.206, 0.73; 0.196, 1.00; 0.189, 1.10; 0.175, 1.45; 0.164, 1.17; 0.155, 1.50; 0.143, 1.66; 0.133, 1.38; 0.123, 1.30; 0.110, 1.36; 0.101, 1.35; 0.089, 0.94; 0.079, 0.54; −0.000, 2.53 |
| 227 | 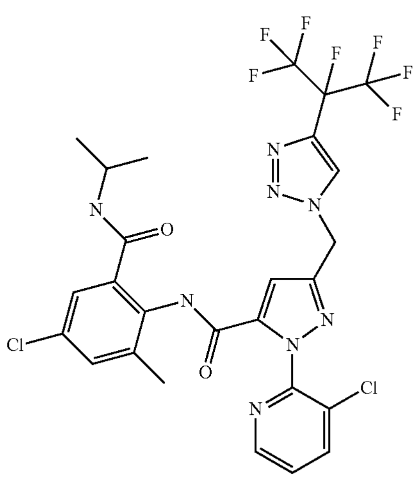 [SMILES: Cc1cc(Cl)cc(C(=O)NC(C)C)c1NC(=O)c1cc(Cn2cc(C(F)(C(F)(F)F)C(F)(F)F)nn2)nn1-c1ncccc1Cl] | 3.85 | 681 | 10.184, 1.99; 9.029, 4.02; 8.463, 1.99; 8.459, 2.15; 8.451, 2.20; 8.448, 2.13; 8.140, 1.95; 8.136, 1.95; 8.120, 2.18; 8.116, 2.03; 7.997, 1.18; 7.978, 1.18; 7.592, 2.08; 7.580, 2.02; 7.572, 1.98; 7.560, 1.94; 7.437, 2.19; 7.432, 2.37; 7.281, 2.55; 7.275, 2.44; 7.255, 4.84; 6.872, 0.38; 5.900, 7.27; 3.911, 0.61; 3.895, 0.93; 3.876, 0.91; 3.859, 0.60; 3.311, 215.71; 2.539, 1.81; 2.509, 13.39; 2.505, 24.32; 2.500, 31.04; 2.496, 21.31; 2.492, 10.27; 2.184, 0.68; 2.145, 11.29; 1.357, 4.82; 1.005, 15.00; 0.988, 14.82; −0.000, 1.26 |

| No. | Structure | logP | MH+ | NMR |
|---|---|---|---|---|
| 228 | 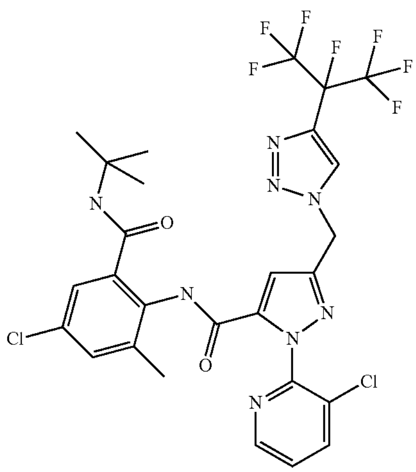 [SMILES: Cc1cc(Cl)cc(C(=O)NC(C)(C)C)c1NC(=O)c1cc(Cn2cc(C(F)(C(F)(F)F)C(F)(F)F)nn2)nn1-c1ncccc1Cl] | 4.19 | 695 | 10.148, 0.94; 9.007, 1.35; 8.469, 0.71; 8.465, 0.72; 8.457, 0.73; 8.453, 0.68; 8.153, 0.64; 8.149, 0.66; 8.133, 0.71; 8.129, 0.67; 7.598, 0.67; 7.587, 0.69; 7.578, 0.65; 7.566, 0.62; 7.517, 0.89; 7.412, 0.87; 7.406, 0.77; 7.239, 0.85; 7.233, 0.83; 7.223, 1.76; 6.871, 0.30; 5.902, 2.47; 3.299, 329.05; 3.276, 4.35; 2.673, 0.57; 2.669, 0.74; 2.664, 0.57; 2.659, 0.31; 2.539, 1.68; 2.522, 3.66; 2.508, 43.57; 2.504, 79.42; 2.500, 101.92; 2.495, 70.40; 2.491, 34.48; 2.331, 0.54; 2.326, 0.71; 2.322, 0.54; 2.183, 0.50; 2.132, 3.65; 2.069, 0.57; 1.724, 0.33; 1.356, 3.72; 1.245, 0.85; 1.190, 15.00; 0.008, 0.35; −0.000, 7.80; −0.008, 0.38 |
| 229 | 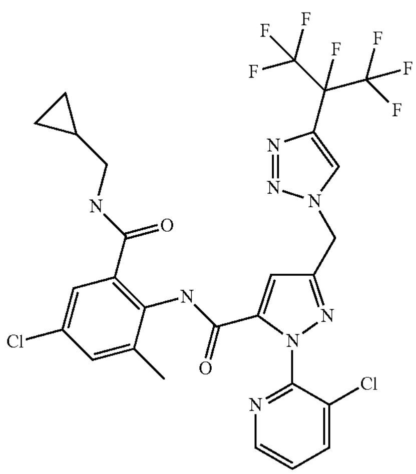 [SMILES: Cc1cc(Cl)cc(C(=O)NCC2CC2)c1NC(=O)c1cc(Cn2cc(C(F)(C(F)(F)F)C(F)(F)F)nn2)nn1-c1ncccc1Cl] | 3.91 | 693 | 10.218, 3.82; 9.028, 6.01; 8.461, 3.09; 8.457, 3.19; 8.449, 3.22; 8.445, 3.02; 8.268, 1.21; 8.254, 2.05; 8.239, 0.99; 8.141, 2.60; 8.138, 2.40; 8.121, 2.75; 8.118, 2.46; 7.590, 2.60; 7.579, 2.54; 7.570, 2.41; 7.558, 2.39; 7.452, 3.11; 7.447, 3.13; 7.313, 3.54; 7.308, 3.08; 7.254, 5.77; 5.891, 10.03; 3.612, 0.30; 3.455, 0.60; 3.431, 0.80; 3.418, 0.90; 3.301, 1845.99; 3.278, 14.14; 2.997, 3.27; 2.981, 4.91; 2.966, 3.26; 2.673, 2.29; 2.669, 3.03; 2.664, 2.29; 2.644, 0.36; 2.539, 6.87; 2.522, 14.74; 2.509, 177.59; 2.504, 324.53; 2.500, 417.41; 2.495, 286.20; 2.491, 138.07; 2.411, 0.53; 2.335, 1.27; 2.331, 2.20; 2.326, 2.94; 2.322, 2.12; 2.182, 0.49; 2.145, 15.00; 2.069, 1.18; 2.049, 1.15; 1.983, 0.30; 1.356, 2.06; 1.236, 0.50; 0.891, 0.31; 0.858, 0.84; 0.854, 0.87; 0.841, 1.35; 0.829, 0.91; 0.824, 1.02; 0.809, 0.58; 0.310, 1.03; 0.299, 3.15; 0.294, 3.50; 0.284, 1.93; 0.278, 3.31; 0.275, 3.16; 0.264, 1.39; 0.112, 1.35; 0.100, 4.07; 0.087, 3.99; 0.076, 1.06; 0.008, 0.55; −0.000, 12.30 |
| 230 | Chiral | 4.04 | 727 | 10.205, 0.42; 10.188, 1.49; 9.040, 0.32; 9.027, 3.16; 8.466, 1.69; 8.462, 1.65; 8.454, 1.76; 8.451, 1.59; 8.150, 1.10; 8.141, 1.82; 8.137, 1.78; 8.130, 1.16; 8.120, 1.82; 8.117, 1.60; 7.594, 1.61; 7.582, 1.54; 7.574, 1.52; 7.562, 1.43; 7.457, 1.64; 7.451, 1.70; 7.308, 1.81; 7.302, 1.69; 7.274, 3.62; 7.260, 0.48; 6.871, 0.66; 6.613, 0.36; 5.897, 5.82; 3.973, 0.54; 3.956, 0.62; 3.936, 0.52; 3.376, 0.33; 3.305, 299.87; 2.674, 0.34; 2.669, 0.46; 2.664, 0.35; 2.653, 0.32; 2.559, 0.85; 2.539, 3.55; 2.526, 2.08; 2.523, 2.11; 2.509, 24.86; 2.504, 44.18; 2.500, 56.85; 2.496, 39.16; 2.491, 19.01; 2.453, 0.44; 2.441, 1.27; 2.423, 1.24; 2.408, 0.83; 2.390, 0.75; 2.331, 0.37; 2.327, 0.45; 2.322, 0.34; 2.183, 1.20; 2.151, 8.38; 2.106, 0.44; 2.069, 0.57; 2.059, 0.50; 2.047, 1.01; 2.040, 0.38; 1.990, 15.00; 1.985, 3.11; 1.357, 8.57; 1.122, 0.30; 1.105, 0.34; 1.101, 0.38; 1.096, 0.73; 1.084, 0.48; 1.079, 0.92; 1.068, 4.62; 1.051, 4.57; 0.970, 0.53; 0.953, 0.49; −0.000, 4.36 |

| No. | Structure | logP | MH+ | NMR |
|---|---|---|---|---|
| 231 | 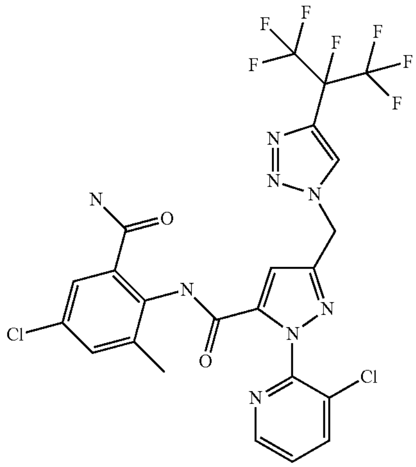 [SMILES: Cc1cc(Cl)cc(C(N)=O)c1NC(=O)c1cc(Cn2cc(C(F)(C(F)(F)F)C(F)(F)F)nn2)nn1-c1ncccc1Cl] | 3.16 | 639 | 10.284, 3.09; 9.047, 4.28; 8.481, 2.35; 8.477, 2.45; 8.469, 2.45; 8.465, 2.35; 8.152, 2.22; 8.148, 2.22; 8.132, 2.49; 8.128, 2.29; 7.704, 1.55; 7.595, 2.45; 7.584, 2.34; 7.575, 2.21; 7.564, 2.17; 7.467, 0.38; 7.451, 3.65; 7.446, 4.17; 7.391, 3.07; 7.385, 2.50; 7.261, 4.95; 6.870, 1.20; 6.613, 0.71; 5.891, 8.00; 3.618, 0.33; 3.601, 0.49; 3.555, 0.31; 3.541, 0.31; 3.511, 0.36; 3.491, 0.43; 3.481, 0.43; 3.447, 0.61; 3.423, 0.84; 3.306, 1805.85; 2.678, 0.86; 2.674, 1.58; 2.669, 2.06; 2.664, 1.60; 2.539, 6.55; 2.522, 9.90; 2.509, 121.78; 2.504, 222.59; 2.500, 286.57; 2.496, 196.70; 2.491, 95.08; 2.412, 0.42; 2.403, 0.40; 2.393, 0.34; 2.331, 1.51; 2.327, 2.05; 2.322, 1.47; 2.183, 1.95; 2.127, 12.62; 2.069, 1.33; 2.049, 0.87; 1.760, 0.43; 1.356, 15.00; 1.237, 0.41; 0.008, 0.36; −0.000, 8.14; −0.009, 0.39 |
| 232 | 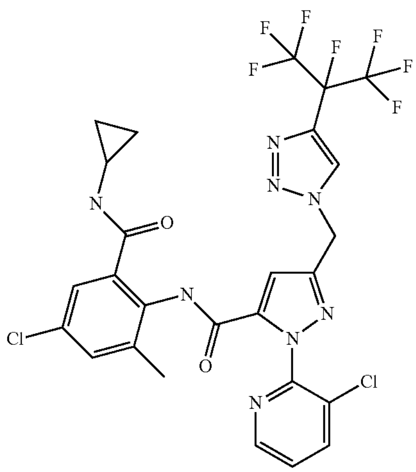 [SMILES: Cc1cc(Cl)cc(C(=O)NC2CC2)c1NC(=O)c1cc(Cn2cc(C(F)(C(F)(F)F)C(F)(F)F)nn2)nn1-c1ncccc1Cl] | 3.61 | 679 | 10.194, 4.02; 9.045, 5.62; 8.470, 2.97; 8.462, 2.82; 8.459, 2.45; 8.240, 2.47; 8.230, 2.36; 8.149, 2.46; 8.129, 2.60; 7.596, 2.31; 7.584, 2.45; 7.576, 2.25; 7.564, 2.04; 7.436, 3.27; 7.430, 3.28; 7.267, 8.73; 5.904, 9.64; 3.734, 0.64; 3.708, 0.51; 3.663, 0.54; 3.609, 0.56; 3.593, 0.64; 3.580, 0.67; 3.568, 0.66; 3.533, 0.77; 3.524, 0.73; 3.510, 0.87; 3.453, 1.30; 3.299, 3144.94; 3.275, 71.01; 3.193, 0.59; 2.725, 0.49; 2.715, 0.57; 2.710, 0.69; 2.678, 3.96; 2.673, 6.34; 2.668, 8.43; 2.664, 6.42; 2.660, 4.45; 2.642, 1.56; 2.634, 1.30; 2.539, 16.09; 2.522, 36.29; 2.508, 429.35; 2.504, 777.02; 2.500, 994.59; 2.495, 689.60; 2.491, 339.86; 2.427, 2.21; 2.392, 1.13; 2.375, 0.89; 2.362, 0.77; 2.357, 0.77; 2.331, 5.38; 2.326, 6.99; 2.322, 5.29; 2.289, 1.11; 2.281, 0.63; 2.198, 0.58; 2.182, 0.58; 2.167, 0.52; 2.136, 15.00; 2.069, 3.99; 2.049, 2.68; 2.027, 0.55; 1.356, 0.73; 1.237, 1.05; 1.088, 0.60; 0.600, 0.94; 0.583, 3.61; 0.571, 3.49; 0.564, 3.13; 0.554, 1.31; 0.427, 1.47; 0.415, 3.61; 0.410, 3.89; 0.402, 3.26; 0.008, 3.45; −0.000, 79.62; −0.009, 4.05 |
| 233 | 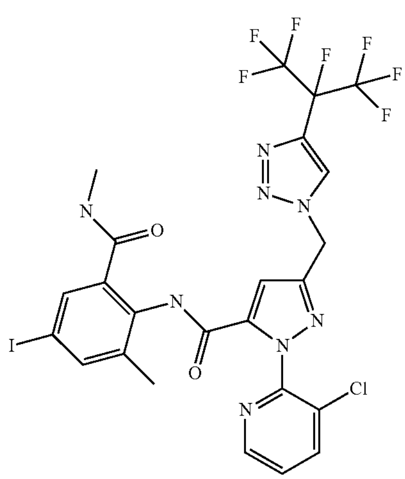 [SMILES: CNC(=O)c1cc(I)cc(C)c1NC(=O)c1cc(Cn2cc(C(F)(C(F)(F)F)C(F)(F)F)nn2)nn1-c1ncccc1Cl] | 3.59 | 745 | 10.230, 3.70; 9.061, 0.59; 9.045, 6.07; 8.471, 3.14; 8.467, 3.27; 8.460, 3.27; 8.456, 3.01; 8.175, 1.74; 8.163, 1.77; 8.149, 3.03; 8.146, 2.70; 8.129, 2.85; 8.125, 2.55; 7.729, 3.29; 7.726, 3.29; 7.593, 4.89; 7.586, 3.81; 7.581, 3.47; 7.573, 2.49; 7.561, 2.36; 7.308, 0.36; 7.243, 5.30; 6.872, 0.80; 6.612, 0.55; 5.939, 0.57; 5.894, 9.97; 3.671, 0.98; 3.602, 0.42; 3.469, 0.32; 3.423, 0.49; 3.301, 1191.95; 3.277, 9.73; 2.673, 1.66; 2.669, 2.21; 2.664, 1.74; 2.639, 10.96; 2.628, 10.95; 2.595, 0.45; 2.539, 4.55; 2.522, 9.64; 2.509, 121.34; 2.504, 221.86; 2.500, 285.75; 2.495, 196.41; 2.491, 95.07; 2.375, 0.39; 2.336, 0.87; 2.331, 1.57; 2.326, 2.07; 2.322, 1.58; 2.317, 0.90; 2.183, 1.42; 2.100, 15.00; 2.069, 1.06; 2.049, 0.87; 1.857, 0.69; 1.760, 0.37; 1.356, 10.85; 1.269, 0.32; 1.236, 0.33; 1.181, 1.14; 1.170, 0.75; 0.008, 0.46; −0.000, 10.89 |

| No. | Structure | logP | MH+ | NMR |
|---|---|---|---|---|
| 234 | 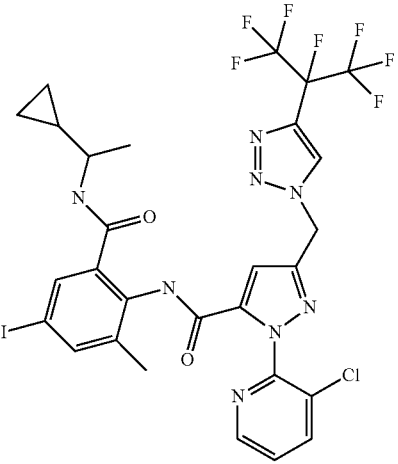 [SMILES: Cc1cc(I)cc(C(=O)NC(C)C2CC2)c1NC(=O)c1cc(Cn2cc(C(F)(C(F)(F)F)C(F)(F)F)nn2)nn1-c1ncccc1Cl] | 4.38 | 799 | 10.164, 2.75; 9.016, 5.52; 8.462, 2.78; 8.459, 2.96; 8.451, 3.00; 8.447, 2.88; 8.138, 2.76; 8.134, 2.67; 8.118, 3.01; 8.114, 2.77; 8.052, 1.65; 8.031, 1.67; 7.729, 3.22; 7.726, 3.39; 7.591, 2.87; 7.580, 2.83; 7.571, 2.76; 7.559, 3.22; 7.554, 3.66; 7.549, 3.44; 7.248, 6.15; 5.890, 9.84; 3.313, 657.73; 3.275, 2.57; 3.255, 1.23; 3.239, 0.52; 2.674, 0.42; 2.670, 0.56; 2.665, 0.43; 2.540, 4.48; 2.523, 2.59; 2.509, 32.46; 2.505, 59.14; 2.501, 75.83; 2.496, 51.99; 2.492, 25.00; 2.332, 0.41; 2.327, 0.54; 2.323, 0.38; 2.108, 15.00; 2.069, 0.56; 1.088, 0.47; 1.041, 8.96; 1.024, 8.67; 0.840, 0.33; 0.822, 0.58; 0.813, 0.70; 0.809, 0.54; 0.801, 1.26; 0.793, 0.83; 0.789, 0.89; 0.781, 1.29; 0.768, 0.74; 0.760, 0.49; 0.363, 0.38; 0.354, 0.54; 0.350, 0.59; 0.342, 1.27; 0.333, 1.04; 0.329, 1.09; 0.320, 1.28; 0.313, 0.62; 0.308, 0.70; 0.298, 0.54; 0.221, 0.43; 0.211, 0.74; 0.208, 0.72; 0.197, 1.01; 0.190, 1.08; 0.176, 1.45; 0.161, 0.99; 0.152, 1.21; 0.139, 1.61; 0.129, 1.40; 0.118, 1.28; 0.106, 1.36; 0.097, 1.37; 0.084, 0.99; 0.075, 0.56; −0.000, 4.47 |
| 235 | 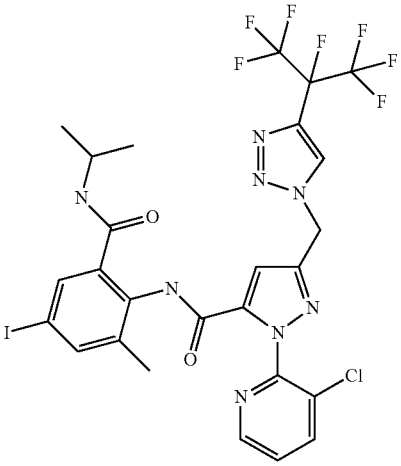 [SMILES: Cc1cc(I)cc(C(=O)NC(C)C)c1NC(=O)c1cc(Cn2cc(C(F)(C(F)(F)F)C(F)(F)F)nn2)nn1-c1ncccc1Cl] | 4.09 | 773 | 10.169, 2.79; 9.026, 4.05; 8.460, 2.02; 8.457, 2.13; 8.449, 2.21; 8.445, 2.13; 8.138, 2.01; 8.134, 2.00; 8.118, 2.23; 8.114, 2.08; 7.984, 1.47; 7.964, 1.49; 7.721, 2.40; 7.718, 2.54; 7.591, 2.14; 7.579, 2.08; 7.571, 2.04; 7.559, 2.09; 7.548, 2.66; 7.543, 2.55; 7.249, 4.83; 6.872, 0.75; 6.613, 0.45; 5.896, 7.25; 3.904, 0.63; 3.887, 0.92; 3.869, 0.91; 3.852, 0.61; 3.307, 3.66.21; 2.669, 0.41; 2.539, 3.18; 2.522, 1.82; 2.509, 23.14; 2.505, 42.14; 2.500, 53.93; 2.496, 36.93; 2.491, 17.68; 2.327, 0.38; 2.183, 1.22; 2.107, 11.14; 2.069, 0.41; 1.357, 9.50; 1.182, 0.36; 1.170, 0.34; 1.002, 15.00; 0.985, 14.80; −0.000, 4.08 |
| 236 | 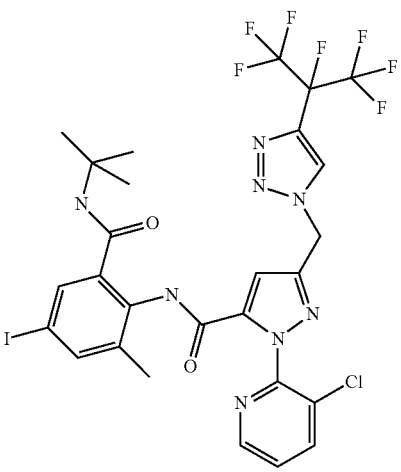 [SMILES: Cc1cc(I)cc(C(=O)NC(C)(C)C)c1NC(=O)c1cc(Cn2cc(C(F)(C(F)(F)F)C(F)(F)F)nn2)nn1-c1ncccc1Cl] | 4.43 | 787 | 10.129, 0.91; 9.069, 0.53; 9.003, 1.47; 8.466, 0.73; 8.462, 0.76; 8.455, 0.71; 8.451, 0.77; 8.164, 0.37; 8.148, 0.65; 8.131, 0.59; 8.127, 0.65; 8.032, 0.38; 7.748, 0.31; 7.697, 0.89; 7.597, 0.67; 7.585, 0.83; 7.577, 0.65; 7.565, 0.64; 7.502, 1.72; 7.401, 0.77; 7.215, 1.64; 6.871, 0.49; 5.917, 1.02; 5.897, 2.45; 5.880, 0.33; 5.747, 1.22; 3.601, 0.51; 3.498, 0.32; 3.467, 0.42; 3.448, 0.44; 3.395, 0.93; 3.300, 1661.86; 3.277, 36.18; 3.191, 0.56; 3.183, 0.42; 3.170, 0.42; 3.146, 0.41; 3.137, 0.32; 2.678, 1.43; 2.673, 2.55; 2.669, 3.27; 2.664, 2.41; 2.660, 1.32; 2.539, 7.28; 2.522, 15.98; 2.508, 191.35; 2.504, 346.86; 2.500, 444.04; 2.495, 305.85; 2.491, 148.40; 2.388, 0.56; 2.336, 1.36; 2.331, 2.38; 2.326, 3.18; 2.322, 2.31; 2.183, 0.91; 2.096, 3.71; 2.069, 1.91; 2.049, 1.20; 1.990, 0.39; 1.987, 0.41; 1.760, 0.48; 1.686, 1.42; 1.612, 0.54; 1.356, 6.57; 1.237, 0.63; 1.186, 15.00; 1.150, 0.34; 0.713, 0.42; 0.647, 0.41; 0.008, 2.29; −0.000, 47.20; −0.008, 2.22 |

| No. | Structure | logP | MH+ | NMR |
|---|---|---|---|---|
| 237 | 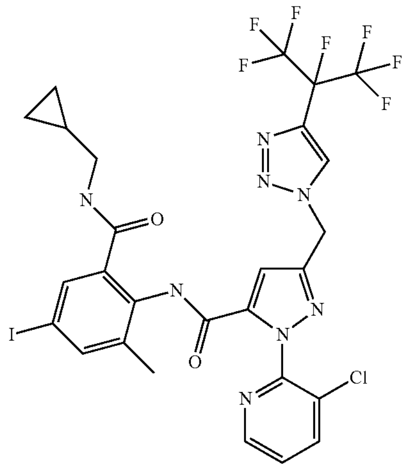 [SMILES: Cc1cc(I)cc(C(=O)NCC2CC2)c1NC(=O)c1cc(Cn2cc(C(F)(C(F)(F)F)C(F)(F)F)nn2)nn1-c1ncccc1Cl] | 4.14 | 785 | 10.204, 3.92; 9.026, 5.45; 8.459, 2.85; 8.455, 2.92; 8.447, 2.96; 8.443, 2.75; 8.255, 1.15; 8.242, 2.10; 8.228, 1.03; 8.140, 2.75; 8.136, 2.65; 8.120, 3.01; 8.116, 2.69; 7.735, 3.31; 7.732, 3.36; 7.589, 3.88; 7.585, 4.01; 7.578, 4.26; 7.569, 2.68; 7.558, 2.58; 7.248, 6.40; 6.871, 1.19; 6.612, 0.71; 5.888, 9.80; 4.039, 0.45; 4.021, 0.49; 3.493, 0.37; 3.302, 1390.16; 3.279, 10.41; 3.227, 0.43; 2.988, 2.78; 2.973, 4.14; 2.957, 2.80; 2.674, 1.69; 2.669, 2.23; 2.664, 1.61; 2.628, 0.36; 2.599, 0.46; 2.539, 4.89; 2.522, 10.59; 2.509, 128.49; 2.504, 234.30; 2.500, 300.73; 2.495, 206.46; 2.491, 99.69; 2.331, 1.58; 2.326, 2.10; 2.322, 1.54; 2.183, 1.91; 2.108, 15.00; 2.069, 1.28; 2.049, 0.87; 1.987, 1.90; 1.356, 14.79; 1.236, 0.49; 1.193, 0.57; 1.175, 1.07; 1.157, 0.60; 0.870, 0.43; 0.858, 0.73; 0.852, 0.72; 0.850, 0.71; 0.840, 1.20; 0.829, 0.76; 0.824, 0.77; 0.808, 0.43; 0.312, 0.99; 0.301, 2.95; 0.297, 3.23; 0.287, 1.74; 0.281, 3.12; 0.277, 2.99; 0.267, 1.27; 0.111, 1.30; 0.100, 3.61; 0.097, 3.68; 0.089, 3.35; 0.085, 3.71; 0.074, 1.01; −0.000, 8.65 |
| 238 | Chiral | 4.26 | 819 | 10.171, 1.12; 9.036, 0.34; 9.024, 3.11; 8.464, 1.66; 8.460, 1.68; 8.452, 1.78; 8.448, 1.60; 8.139, 1.92; 8.135, 2.24; 8.124, 0.64; 8.118, 2.05; 8.115, 2.23; 7.737, 1.74; 7.733, 1.82; 7.605, 0.37; 7.593, 1.78; 7.581, 3.20; 7.573, 1.85; 7.561, 1.47; 7.267, 3.44; 7.253, 0.46; 5.893, 5.74; 3.967, 0.52; 3.950, 0.62; 3.930, 0.52; 3.310, 408.48; 2.674, 0.37; 2.669, 0.47; 2.665, 0.36; 2.637, 0.33; 2.625, 0.35; 2.556, 0.95; 2.539, 4.22; 2.522, 3.13; 2.509, 25.47; 2.505, 46.70; 2.500, 58.98; 2.496, 40.28; 2.492, 19.29; 2.439, 1.19; 2.422, 1.18; 2.406, 0.76; 2.388, 0.69; 2.331, 0.34; 2.327, 0.44; 2.322, 0.34; 2.113, 8.42; 2.069, 0.54; 2.059, 0.47; 2.049, 0.48; 2.047, 0.51; 2.004, 0.53; 1.987, 15.00; 1.356, 0.87; 1.120, 0.39; 1.104, 0.35; 1.090, 0.72; 1.073, 0.98; 1.064, 4.56; 1.047, 4.48; 0.967, 0.49; 0.950, 0.45; −0.000, 3.97 |
| 239 | 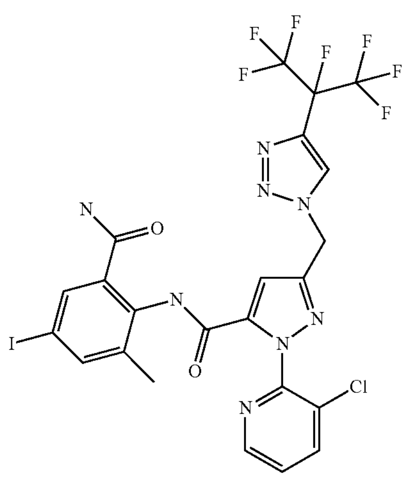 [SMILES: Cc1cc(I)cc(C(N)=O)c1NC(=O)c1cc(Cn2cc(C(F)(C(F)(F)F)C(F)(F)F)nn2)nn1-c1ncccc1Cl] | 3.35 | 731 | 10.274, 2.71; 9.044, 4.36; 8.478, 2.33; 8.475, 2.46; 8.467, 2.49; 8.463, 2.33; 8.150, 2.30; 8.146, 2.24; 8.130, 2.53; 8.126, 2.31; 7.733, 2.66; 7.730, 2.86; 7.686, 1.68; 7.661, 3.21; 7.656, 2.79; 7.594, 2.46; 7.582, 2.28; 7.574, 2.23; 7.562, 2.19; 7.412, 1.53; 7.254, 4.66; 6.871, 1.17; 5.888, 7.99; 3.708, 0.41; 3.618, 0.45; 3.601, 0.78; 3.591, 0.46; 3.584, 0.48; 3.512, 0.48; 3.505, 0.49; 3.497, 0.48; 3.465, 0.67; 3.439, 0.82; 3.307, 2250.97; 3.284, 13.80; 3.223, 0.70; 3.184, 0.35; 3.147, 0.40; 2.674, 1.84; 2.669, 2.45; 2.665, 1.81; 2.660, 0.98; 2.635, 0.30; 2.539, 7.69; 2.522, 11.66; 2.509, 142.97; 2.504, 260.67; 2.500, 334.84; 2.496, 229.02; 2.491, 110.00; 2.390, 0.37; 2.375, 0.31; 2.331, 1.79; 2.327, 2.35; 2.322, 1.78; 2.318, 0.93; 2.183, 2.01; 2.089, 12.48; 2.069, 1.41; 2.049, 1.10; 1.769, 0.33; 1.760, 0.67; 1.356, 15.00; 1.237, 0.49; 1.181, 0.43; 0.890, 0.31; 0.008, 0.52; −0.000, 11.45; −0.009, 0.53 |

-continued
| No. | Structure | logP | MH+ | NMR |
|---|---|---|---|---|
| 240 | 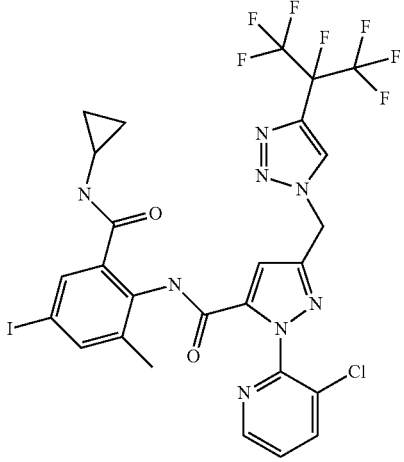 [SMILES: Cc1cc(I)cc(C(=O)NC2CC2)c1NC(=O)c1cc(Cn2cc(C(F)(C(F)(F)F)C(F)(F)F)nn2)nn1-c1ncccc1Cl] | 3.83 | 771 | 10.177, 3.77; 9.042, 5.53; 8.472, 2.85; 8.468, 2.94; 8.460, 2.98; 8.456, 2.77; 8.222, 2.14; 8.211, 2.05; 8.147, 2.68; 8.144, 2.64; 8.127, 2.95; 8.123, 2.69; 7.720, 3.23; 7.716, 3.32; 7.595, 2.84; 7.583, 2.80; 7.575, 2.59; 7.563, 2.57; 7.531, 3.49; 7.527, 3.27; 7.261, 6.27; 6.870, 1.08; 6.611, 0.64; 5.901, 9.67; 3.618, 0.46; 3.601, 0.76; 3.585, 0.43; 3.580, 0.42; 3.573, 0.34; 3.478, 0.44; 3.469, 0.40; 3.464, 0.39; 3.416, 0.68; 3.298, 1379.63; 3.274, 35.50; 2.673, 3.43; 2.668, 4.05; 2.664, 3.81; 2.653, 1.79; 2.643, 1.24; 2.635, 1.00; 2.623, 0.70; 2.611, 0.60; 2.539, 7.67; 2.522, 17.07; 2.508, 205.22; 2.504, 373.01; 2.500, 478.39; 2.495, 330.67; 2.491, 161.30; 2.374, 0.50; 2.366, 0.49; 2.335, 1.40; 2.331, 2.60; 2.326, 3.47; 2.322, 2.53; 2.198, 0.58; 2.183, 1.95; 2.100, 15.00; 2.069, 1.81; 2.049, 1.35; 1.760, 0.70; 1.754, 0.42; 1.741, 0.52; 1.356, 13.74; 1.235, 0.57; 0.597, 0.95; 0.584, 2.74; 0.579, 3.59; 0.567, 3.39; 0.561, 2.80; 0.549, 1.23; 0.425, 1.24; 0.414, 3.45; 0.408, 3.31; 0.399, 2.94; 0.387, 0.99; 0.008, 2.32; −0.000, 51.96; −0.008, 2.60 |
| 241 | 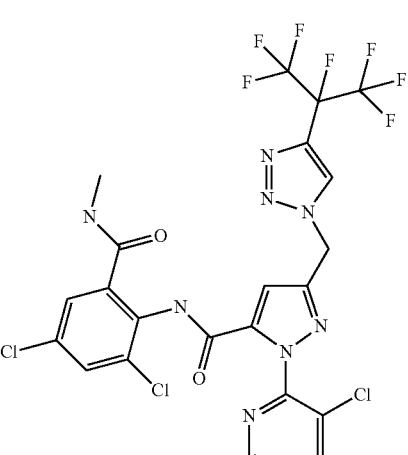 | 3.31 | 673 | 10.450, 2.33; 9.052, 3.63; 8.476, 1.76; 8.472, 1.84; 8.465, 1.84; 8.461, 1.70; 8.364, 0.39; 8.361, 0.38; 8.353, 0.44; 8.349, 0.42; 8.259, 0.98; 8.248, 0.93; 8.182, 0.40; 8.178, 0.40; 8.161, 0.44; 8.157, 0.44; 8.145, 1.74; 8.141, 1.63; 8.125, 1.91; 8.121, 1.69; 8.032, 0.47; 8.026, 0.83; 8.014, 0.84; 8.009, 0.43; 7.803, 2.57; 7.797, 2.58; 7.596, 1.80; 7.584, 1.85; 7.576, 1.66; 7.564, 1.59; 7.533, 0.36; 7.522, 0.36; 7.513, 0.41; 7.502, 0.36; 7.473, 3.08; 7.467, 2.89; 7.331, 1.21; 7.314, 2.59; 6.871, 1.19; 6.612, 0.65; 5.950, 1.46; 5.900, 6.60; 3.671, 2.89; 3.299, 656.49; 2.688, 0.54; 2.673, 1.50; 2.669, 1.85; 2.664, 1.41; 2.660, 0.85; 2.636, 6.02; 2.624, 6.29; 2.539, 3.94; 2.522, 8.63; 2.508, 104.48; 2.504, 189.97; 2.500, 243.42; 2.495, 168.23; 2.491, 82.33; 2.387, 0.31; 2.374, 0.30; 2.335, 0.73; 2.331, 1.35; 2.326, 1.74; 2.322, 1.32; 2.317, 0.71; 2.183, 1.95; 2.069, 1.09; 2.049, 0.67; 1.356, 15.00; 1.235, 0.34; 1.182, 0.30; 0.008, 0.96; −0.000, 22.27; −0.008, 1.15 |

| No. | Structure | logP | MH+ | NMR |
|---|---|---|---|---|
| 242 | 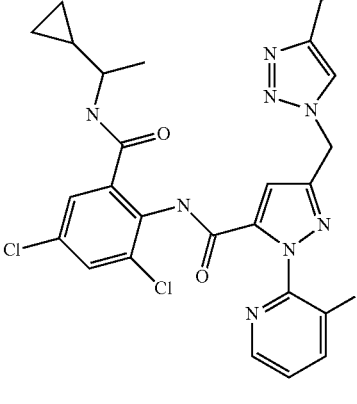 | 4.08 | 727 | 10.380, 1.01; 9.023, 8.53; 8.462, 4.12; 8.458, 4.33; 8.450, 4.44; 8.447, 4.23; 8.132, 4.79; 8.128, 4.78; 8.112, 5.02; 8.108, 4.60; 7.801, 3.65; 7.795, 3.70; 7.777, 0.42; 7.771, 0.41; 7.592, 4.05; 7.580, 4.09; 7.572, 3.77; 7.560, 3.67; 7.419, 5.34; 7.414, 5.19; 7.325, 4.21; 5.897, 15.00; 5.765, 0.38; 3.309, 356.15; 3.272, 3.02; 3.255, 2.54; 3.235, 1.33; 3.218, 0.49; 2.669, 0.47; 2.539, 3.61; 2.523, 2.10; 2.509, 27.22; 2.505, 49.71; 2.500, 63.69; 2.496, 43.93; 2.492, 21.33; 2.327, 0.46; 2.069, 0.39; 1.232, 0.38; 1.122, 0.66; 1.106, 0.66; 1.089, 0.43; 1.029, 13.05; 1.012, 12.88; 0.817, 0.36; 0.805, 0.68; 0.797, 0.96; 0.785, 1.78; 0.777, 1.22; 0.773, 1.31; 0.765, 1.85; 0.752, 1.09; 0.744, 0.76; 0.732, 0.38; 0.356, 0.61; 0.350, 0.92; 0.346, 0.92; 0.337, 1.69; 0.329, 1.63; 0.324, 1.66; 0.316, 1.93; 0.308, 0.96; 0.303, 1.06; 0.294, 0.89; 0.215, 0.70; 0.205, 1.11; 0.202, 1.12; 0.192, 1.62; 0.185, 1.62; 0.172, 2.07; 0.155, 1.58; 0.146, 1.78; 0.133, 2.65; 0.123, 3.23; 0.111, 2.90; 0.102, 2.10; 0.089, 1.33; 0.080, 0.79; 0.067, 0.38; −0.000, 4.63 |
| 243 | 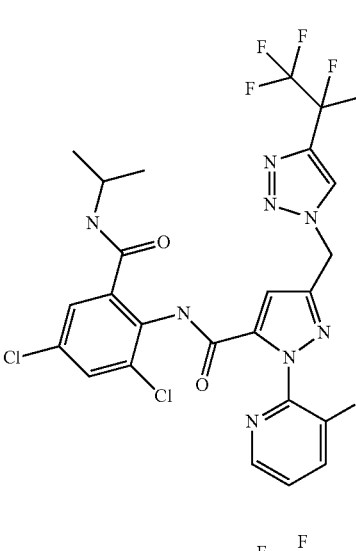 | 3.79 | 701 | 10.396, 0.94; 9.031, 4.18; 8.461, 2.10; 8.457, 2.23; 8.449, 2.27; 8.445, 2.17; 8.133, 2.03; 8.129, 2.00; 8.113, 2.27; 8.109, 2.10; 8.073, 0.75; 8.055, 0.74; 7.794, 2.37; 7.788, 2.39; 7.593, 2.13; 7.581, 2.10; 7.573, 2.00; 7.561, 1.92; 7.425, 3.29; 7.419, 3.16; 7.325, 2.58; 5.902, 7.54; 3.883, 0.64; 3.866, 0.96; 3.848, 0.94; 3.831, 0.62; 3.318, 332.58; 2.540, 2.22; 2.523, 1.25; 2.510, 16.09; 2.505, 29.28; 2.501, 37.53; 2.497, 25.66; 2.492, 12.31; 1.072, 0.83; 1.056, 0.83; 0.992, 15.00; 0.976, 14.84; −0.000, 2.99 |
| 244 | 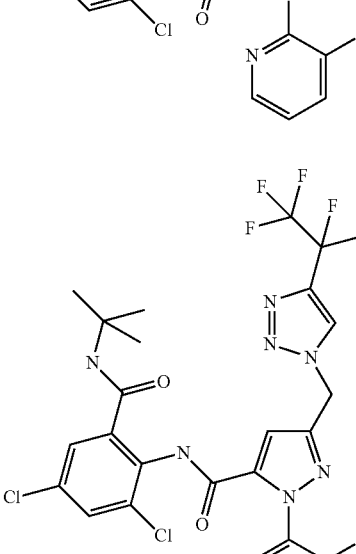 | 4.13 | 715 | 10.367, 0.40; 9.009, 1.35; 8.465, 0.67; 8.461, 0.70; 8.453, 0.70; 8.449, 0.67; 8.145, 0.50; 8.142, 0.50; 8.125, 0.52; 8.121, 0.47; 7.762, 0.51; 7.635, 0.47; 7.597, 0.54; 7.586, 0.54; 7.577, 0.51; 7.566, 0.45; 7.398, 0.56; 7.304, 0.61; 5.903, 1.98; 3.299, 257.80; 3.275, 6.28; 2.673, 0.46; 2.669, 0.61; 2.664, 0.44; 2.539, 1.35; 2.522, 3.02; 2.508, 36.20; 2.504, 65.75; 2.500, 84.37; 2.495, 58.50; 2.491, 28.82; 2.331, 0.45; 2.326, 0.60; 2.322, 0.45; 2.069, 0.30; 1.356, 0.58; 1.254, 0.67; 1.244, 0.45; 1.178, 15.00; 0.008, 0.32; −0.000, 7.18; −0.008, 0.36 |

-continued
| No. | Structure | logP | MH+ | NMR |
|---|---|---|---|---|
| 245 | 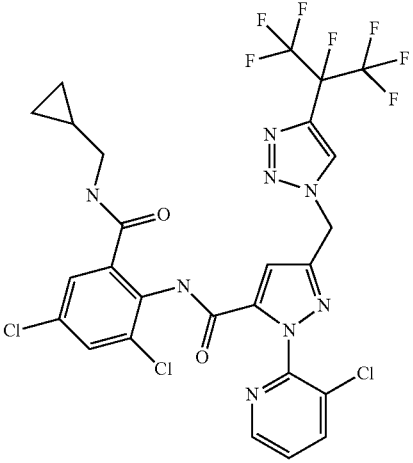 [SMILES: O=C(NCC1CC1)c1cc(Cl)cc(Cl)c1NC(=O)c1cc(Cn2cc(C(F)(C(F)(F)F)C(F)(F)F)nn2)nn1-c1ncccc1Cl] | 3.84 | 713 | 10.414, 2.15; 9.033, 3.45; 8.458, 2.02; 8.455, 1.73; 8.447, 1.77; 8.315, 1.19; 8.133, 1.55; 8.113, 1.53; 7.811, 2.12; 7.804, 2.40; 7.590, 1.46; 7.579, 1.35; 7.570, 1.40; 7.558, 1.61; 7.455, 2.48; 7.449, 2.32; 7.323, 2.35; 5.894, 5.70; 3.899, 1.06; 3.822, 1.03; 3.773, 1.07; 3.759, 0.98; 3.741, 0.99; 3.729, 1.04; 3.711, 1.15; 3.708, 1.08; 3.701, 1.08; 3.685, 1.04; 3.642, 1.30; 3.637, 1.33; 3.613, 1.42; 3.580, 1.39; 3.575, 1.55; 3.559, 1.60; 3.545, 1.69; 3.535, 1.84; 3.482, 2.51; 3.477, 2.52; 3.302, 9219.60; 3.278, 84.28; 3.146, 0.92; 2.977, 1.58; 2.961, 2.51; 2.947, 1.82; 2.722, 1.15; 2.720, 1.04; 2.708, 0.98; 2.673, 11.16; 2.669, 15.00; 2.664, 10.77; 2.539, 33.08; 2.522, 71.16; 2.509, 861.72; 2.504, 1572.12; 2.500, 2019.99; 2.495, 1387.30; 2.491, 669.75; 2.422, 3.44; 2.396, 2.14; 2.387, 1.81; 2.373, 1.67; 2.362, 1.69; 2.331, 10.73; 2.326, 14.39; 2.322, 10.40; 2.182, 1.44; 2.069, 8.34; 2.049, 5.31; 1.356, 7.88; 1.237, 2.36; 0.890, 1.03; 0.294, 1.90; 0.285, 1.21; 0.274, 1.98; 0.104, 0.89; 0.093, 2.24; 0.078, 2.22; 0.008, 4.35; −0.000, 100.72; −0.008, 4.71 |
| 246 | 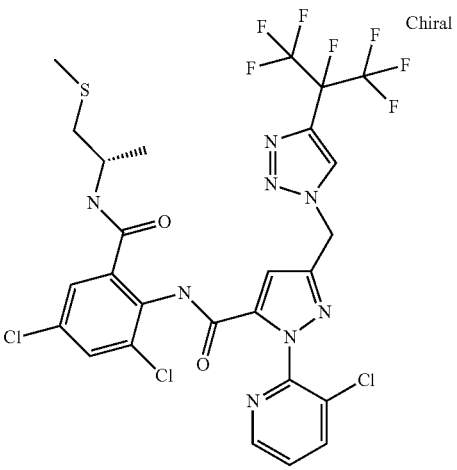 [SMILES: CSC[C@H](C)NC(=O)c1cc(Cl)cc(Cl)c1NC(=O)c1cc(Cn2cc(C(F)(C(F)(F)F)C(F)(F)F)nn2)nn1-c1ncccc1Cl] Chiral | 4.02 | 747 | 9.030, 3.27; 8.466, 1.77; 8.462, 1.68; 8.454, 1.83; 8.450, 1.59; 8.247, 0.45; 8.229, 0.46; 8.135, 1.56; 8.131, 1.48; 8.115, 1.68; 8.111, 1.48; 7.815, 2.17; 7.810, 2.03; 7.595, 1.58; 7.584, 1.64; 7.575, 1.47; 7.564, 1.41; 7.508, 0.30; 7.479, 0.31; 7.446, 2.58; 7.440, 2.45; 7.345, 2.15; 5.901, 6.22; 3.941, 0.52; 3.923, 0.64; 3.905, 0.52; 3.319, 361.25; 3.207, 0.34; 3.192, 0.33; 3.147, 0.31; 2.670, 0.33; 2.649, 0.37; 2.642, 0.33; 2.549, 0.87; 2.540, 2.35; 2.533, 1.09; 2.510, 17.45; 2.506, 32.04; 2.501, 41.77; 2.497, 29.08; 2.493, 14.42; 2.418, 1.16; 2.400, 1.17; 2.385, 0.82; 2.367, 0.74; 2.332, 0.31; 2.328, 0.38; 2.323, 0.30; 2.297, 0.31; 2.105, 0.49; 2.069, 0.31; 2.060, 0.34; 2.048, 0.43; 1.999, 1.33; 1.992, 15.00; 1.983, 1.95; 1.357, 1.57; 1.236, 0.30; 1.143, 0.33; 1.127, 0.40; 1.123, 0.40; 1.106, 0.35; 1.084, 0.60; 1.066, 0.80; 1.056, 4.64; 1.039, 4.65; 0.954, 0.54; 0.937, 0.53; −0.000, 4.78 |

-continued

| No. | Structure | logP | MH+ | NMR |
|---|---|---|---|---|
| 247 | 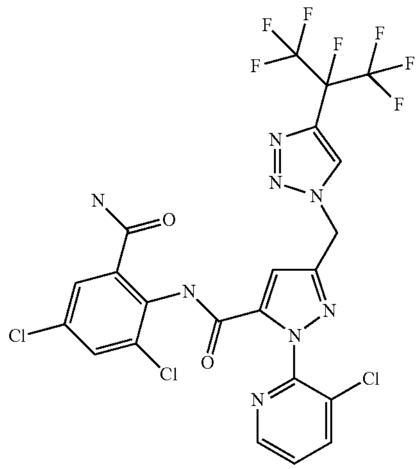 [SMILES: NC(=O)c1cc(Cl)cc(Cl)c1NC(=O)c1cc(Cn2cc(C(F)(C(F)(F)F)C(F)(F)F)nn2)nn1-c1ncccc1Cl] | 3.13 | 659 | 10.432, 3.33; 9.052, 4.69; 9.033, 0.64; 8.504, 0.36; 8.501, 0.42; 8.493, 0.49; 8.489, 0.61; 8.483, 2.36; 8.480, 2.41; 8.472, 2.44; 8.468, 2.30; 8.232, 0.31; 8.212, 0.33; 8.142, 2.25; 8.138, 2.21; 8.122, 2.49; 8.118, 2.27; 7.980, 0.36; 7.974, 0.52; 7.956, 0.31; 7.863, 0.31; 7.803, 3.65; 7.797, 3.67; 7.725, 1.68; 7.643, 0.35; 7.631, 0.31; 7.622, 0.34; 7.611, 0.40; 7.595, 2.58; 7.588, 0.89; 7.583, 2.66; 7.575, 2.43; 7.563, 2.41; 7.527, 5.36; 7.521, 4.45; 7.314, 3.29; 6.871, 1.17; 6.613, 0.68; 5.922, 1.27; 5.896, 8.56; 3.618, 0.42; 3.601, 0.79; 3.585, 0.44; 3.504, 0.30; 3.428, 0.57; 3.307, 1262.09; 3.221, 0.38; 2.674, 1.12; 2.669, 1.49; 2.665, 1.13; 2.660, 0.61; 2.585, 0.43; 2.539, 4.74; 2.522, 7.20; 2.509, 86.87; 2.504, 158.47; 2.500, 203.80; 2.496, 139.68; 2.491, 67.34; 2.332, 1.03; 2.327, 1.41; 2.322, 1.09; 2.183, 1.90; 2.069, 1.31; 2.049, 0.62; 1.768, 0.33; 1.760, 0.81; 1.752, 0.31; 1.356, 15.00; 1.181, 1.05; −0.000, 5.09 |
| 248 | 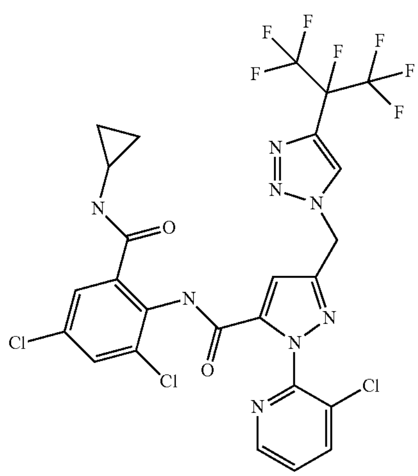 [SMILES: O=C(NC1CC1)c1cc(Cl)cc(Cl)c1NC(=O)c1cc(Cn2cc(C(F)(C(F)(F)F)C(F)(F)F)nn2)nn1-c1ncccc1Cl] | 3.56 | 699 | 10.417, 1.87; 9.046, 2.38; 8.463, 1.97; 8.327, 0.98; 8.314, 1.55; 8.308, 1.60; 8.147, 1.18; 8.144, 1.37; 8.121, 1.27; 7.969, 1.09; 7.791, 1.66; 7.597, 1.17; 7.581, 1.50; 7.424, 2.07; 7.374, 0.97; 7.334, 2.09; 7.319, 1.08; 5.934, 1.06; 5.906, 4.22; 5.887, 1.02; 3.860, 2.22; 3.708, 0.95; 3.698, 0.87; 3.692, 0.97; 3.630, 0.87; 3.610, 1.17; 3.592, 1.22; 3.578, 1.21; 3.569, 1.21; 3.563, 1.23; 3.532, 1.38; 3.496, 1.76; 3.441, 2.62; 3.298, 5978.54; 3.274, 142.29; 2.732, 0.91; 2.708, 1.09; 2.673, 11.28; 2.668, 15.00; 2.664, 11.39; 2.637, 2.56; 2.629, 2.44; 2.616, 2.56; 2.608, 2.65; 2.539, 32.23; 2.522, 71.29; 2.508, 863.33; 2.504, 1566.30; 2.500, 2007.05; 2.495, 1397.22; 2.491, 694.29; 2.431, 5.36; 2.414, 5.03; 2.385, 2.45; 2.335, 6.43; 2.331, 11.13; 2.326, 14.47; 2.322, 10.91; 2.294, 1.37; 2.282, 1.34; 2.243, 0.92; 2.215, 0.95; 2.198, 1.18; 2.193, 0.91; 2.116, 0.85; 2.069, 7.78; 2.049, 5.21; 1.906, 0.91; 1.237, 2.49; 0.890, 1.11; 0.599, 1.14; 0.583, 2.59; 0.565, 2.64; 0.551, 1.47; 0.397, 2.72; 0.365, 0.97; 0.008, 6.01; −0.000, 143.13; −0.008, 7.88; −0.064, 0.87 |

| No. | Structure | logP | MH+ | NMR |
|---|---|---|---|---|
| 249 | 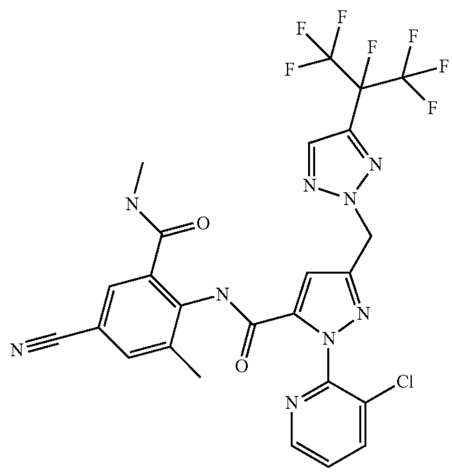 [SMILES: CNC(=O)c1cc(C#N)cc(C)c1NC(=O)c1cc(Cn2ncc(C(F)(C(F)(F)F)C(F)(F)F)n2)nn1-c1ncccc1Cl] | 3.39 | 644 | 10.526, 0.37; 10.498, 3.94; 8.516, 6.83; 8.478, 3.06; 8.475, 3.25; 8.467, 3.31; 8.463, 2.92; 8.309, 1.82; 8.298, 1.67; 8.151, 2.63; 8.147, 2.45; 8.131, 2.75; 8.127, 2.58; 7.848, 3.54; 7.735, 3.82; 7.598, 2.57; 7.587, 2.52; 7.578, 2.49; 7.566, 2.20; 7.246, 4.18; 5.978, 10.56; 3.708, 0.36; 3.684, 0.36; 3.638, 0.31; 3.623, 0.32; 3.619, 0.32; 3.605, 0.31; 3.588, 0.40; 3.575, 0.35; 3.544, 0.36; 3.530, 0.38; 3.509, 0.42; 3.496, 0.51; 3.453, 0.71; 3.435, 0.84; 3.388, 1.57; 3.303, 1380.08; 3.213, 0.86; 3.201, 0.65; 3.188, 0.51; 3.178, 0.54; 3.170, 0.47; 3.164, 0.44; 3.147, 0.40; 3.135, 0.33; 3.115, 0.31; 2.947, 0.30; 2.730, 0.33; 2.669, 2.78; 2.664, 2.76; 2.655, 11.09; 2.644, 11.11; 2.539, 13.13; 2.508, 134.31; 2.504, 240.60; 2.500, 305.77; 2.496, 215.11; 2.398, 0.68; 2.360, 0.59; 2.345, 0.62; 2.331, 1, 1.72; 2.326, 2.28; 2.322, 1.68; 2.289, 0.34; 2.235, 0.35; 2.228, 0.42; 2.221, 0.46; 2.188, 15.00; 2.140, 0.47; 2.069, 1.55; 2.049, 0.87; 1.907, 0.41; 1.292, 0.37; 1.236, 0.54; 1.228, 0.35; 0.891, 0.59; −0.000, 6.65 |
| 250 | 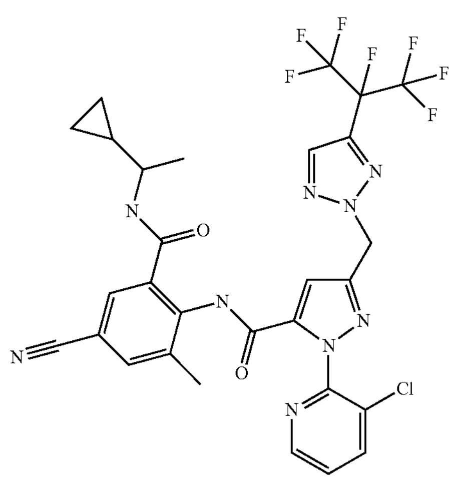 [SMILES: Cc1cc(C#N)cc(C(=O)NC(C)C2CC2)c1NC(=O)c1cc(Cn2ncc(C(F)(C(F)(F)F)C(F)(F)F)n2)nn1-c1ncccc1Cl] | 4.2 | 699 | 10.423, 3.17; 8.505, 9.63; 8.466, 4.68; 8.463, 5.48; 8.455, 4.76; 8.451, 4.25; 8.191, 2.48; 8.172, 2.24; 8.135, 3.50; 8.114, 3.46; 7.848, 3.99; 7.698, 4.26; 7.593, 3.00; 7.581, 3.17; 7.573, 2.93; 7.560, 2.72; 7.505, 1.34; 7.248, 4.18; 5.968, 12.35; 5.802, 2.98; 3.708, 1.74; 3.568, 2.84; 3.531, 2.36; 3.286, 81.17; 3.212, 3.03; 3.170, 1.44; 3.146, 1.84; 3.077, 1.54; 2.674, 9.73; 2.669, 12.62; 2.665, 9.40; 2.643, 1.66; 2.626, 1.90; 2.539, 38.42; 2.522, 62.64; 2.509, 766.25; 2.505, 1377.19; 2.500, 1748.21; 2.496, 1203.37; 2.443, 5.39; 2.332, 9.66; 2.327, 12.15; 2.322, 9.12; 2.318, 4.94; 2.284, 3.18; 2.196, 15.00; 2.124, 3.41; 2.069, 10.59; 2.049, 4.55; 1.908, 1.37; 1.437, 3.62; 1.398, 3.54; 1.237, 3.67; 1.230, 3.66; 1.213, 1.50; 1.128, 1.96; 1.107, 3.75; 1.048, 14.45; 1.032, 14.53; 0.890, 2.51; 0.808, 1.87; 0.797, 1.81; 0.789, 1.80; 0.786, 1.75; 0.353, 2.31; 0.343, 2.22; 0.331, 2.44; 0.319, 1.56; 0.228, 1.72; 0.209, 2.21; 0.195, 2.25; 0.176, 2.29; 0.164, 2.18; 0.152, 3.01; 0.142, 2.85; 0.131, 2.46; 0.121, 2.63; 0.111, 2.57; 0.098, 1.92; −0.000, 59.79 |

| No. | Structure | logP | MH+ | NMR |
|---|---|---|---|---|
| 251 | 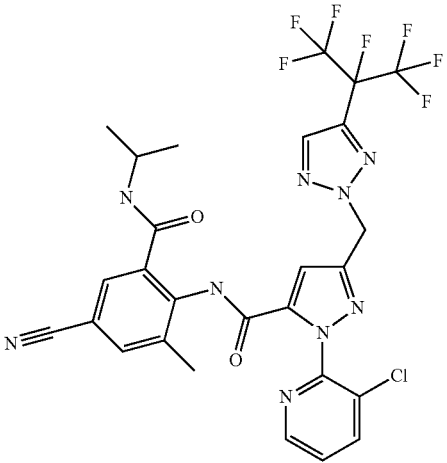 | 3.89 | 672 | 10.428, 2.83; 8.511, 4.69; 8.465, 2.03; 8.461, 2.47; 8.453, 2.06; 8.450, 1.92; 8.137, 2.17; 8.133, 2.00; 8.117, 3.32; 8.113, 3.06; 8.097, 1.41; 7.838, 2.37; 7.701, 2.68; 7.696, 2.37; 7.594, 2.11; 7.582, 1.95; 7.574, 1.78; 7.562, 1.76; 7.505, 0.58; 7.253, 3.32; 5.975, 7.36; 5.805, 0.82; 5.746, 1.09; 3.906, 0.87; 3.890, 1.23; 3.872, 1.19; 3.856, 0.83; 3.655, 0.64; 3.629, 0.65; 3.586, 0.63; 3.568, 0.87; 3.561, 0.78; 3.547, 0.79; 3.521, 0.97; 3.508, 0.98; 3.491, 1.12; 3.455, 1.62; 3.309, 4396.28; 3.223, 1.22; 3.209, 0.91; 3.201, 0.83; 3.191, 0.63; 2.674, 2.92; 2.669, 3.82; 2.665, 2.95; 2.610, 0.66; 2.539, 18.29; 2.522, 18.34; 2.509, 231.38; 2.505, 422.17; 2.500, 541.50; 2.496, 371.68; 2.492, 179.51; 2.336, 1.65; 2.331, 2.89; 2.327, 3.86; 2.322, 2.85; 2.285, 1.30; 2.197, 10.80; 2.184, 0.98; 2.126, 1.24; 2.069, 3.36; 2.049, 1.47; 2.005, 0.90; 1.987, 0.71; 1.600, 0.87; 1.583, 0.98; 1.473, 1.16; 1.356, 3.39; 1.237, 0.98; 1.193, 0.88; 1.175, 1.30; 1.159, 1.36; 1.080, 1.57; 1.070, 1.05; 1.064, 1.53; 1.013, 15.00; 0.996, 14.81; 0.890, 0.58; −0.000, 4.63 |
| 252 | 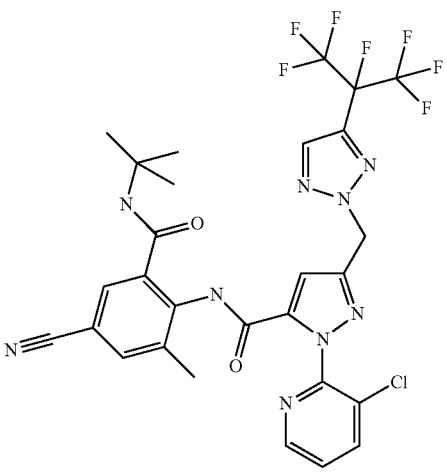 [SMILES: Cc1cc(C#N)cc(C(=O)NC(C)(C)C)c1NC(=O)c1cc(Cn2ncc(C(F)(C(F)(F)F)C(F)(F)F)n2)nn1-c1ncccc1Cl] | 4.21 | 686 | 10.368, 0.78; 8.506, 1.43; 8.470, 0.65; 8.467, 0.70; 8.459, 0.70; 8.455, 0.67; 8.147, 0.64; 8.143, 0.63; 8.127, 0.71; 8.123, 0.65; 7.813, 0.75; 7.810, 0.79; 7.693, 0.91; 7.679, 0.90; 7.674, 0.84; 7.598, 0.67; 7.586, 0.65; 7.578, 0.64; 7.566, 0.61; 7.217, 1.04; 5.975, 2.40; 3.307, 185.95; 2.539, 1.02; 2.522, 1.05; 2.509, 13.41; 2.504, 24.49; 2.500, 31.42; 2.496, 21.62; 2.491, 10.45; 2.184, 3.50; 2.128, 0.30; 1.262, 1.08; 1.245, 0.84; 1.202, 15.00 |

| No. | Structure | logP | MH+ | NMR |
|---|---|---|---|---|
| 253 | 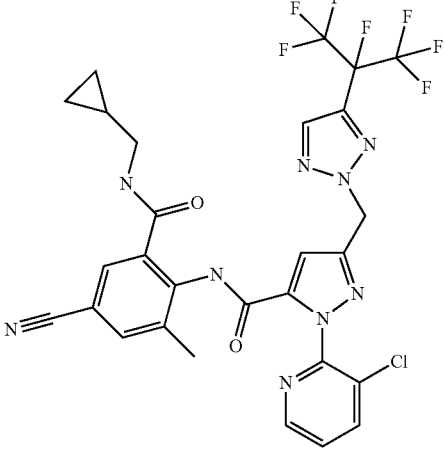 | 3.95 | 684 | 10.465, 3.93; 8.508, 6.67; 8.463, 3.00; 8.460, 2.88; 8.451, 2.66; 8.392, 1.21; 8.377, 1.96; 8.138, 2.47; 8.134, 2.52; 8.118, 2.66; 8.115, 2.61; 7.853, 3.79; 7.729, 3.83; 7.592, 2.27; 7.581, 2.37; 7.572, 2.14; 7.561, 1.91; 7.250, 4.57; 7.230, 1.73; 6.026, 2.27; 5.970, 9.71; 4.183, 1.19; 4.169, 1.14; 3.658, 1.53; 3.587, 1.21; 3.544, 1.36; 3.522, 1.52; 3.516, 1.57; 3.496, 1.68; 3.484, 1.92; 3.474, 2.02; 3.451, 2.46; 3.422, 3.34; 3.300, 7370.71; 3.277, 48.68; 3.001, 3.09; 2.985, 4.56; 2.969, 2.94; 2.673, 8.32; 2.669, 11.26; 2.664, 8.27; 2.659, 4.58; 2.645, 1.48; 2.643, 1.51; 2.539, 54.06; 2.522, 53.79; 2.508, 654.02; 2.504, 1191.69; 2.500, 1527.80; 2.495, 1047.36; 2.491, 505.29; 2.417, 2.62; 2.335, 4.52; 2.331, 8.16; 2.326, 11.04; 2.322, 7.97; 2.284, 2.39; 2.197, 15.00; 2.123, 2.23; 2.069, 4.85; 2.049, 4.04; 1.992, 3.00; 1.356, 3.15; 1.292, 1.57; 1.238, 2.37; 1.159, 3.27; 1.111, 1.83; 1.070, 2.29; 0.891, 2.61; 0.855, 1.44; 0.842, 1.46; 0.839, 1.38; 0.312, 3.49; 0.297, 3.43; 0.282, 1.49; 0.276, 1.19; 0.122, 1.23; 0.109, 4.17; 0.100, 3.89; −0.000, 23.56 |
| 254 | 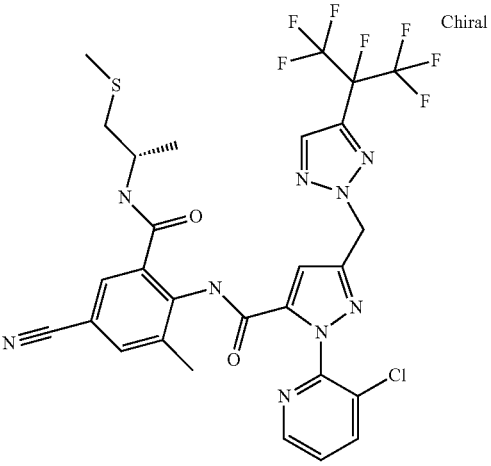 [SMILES: CSC[C@H](C)NC(=O)c1cc(C#N)cc(C)c1NC(=O)c1cc(Cn2ncc(C(F)(C(F)(F)F)C(F)(F)F)n2)nn1-c1ncccc1Cl] Chiral | 4.06 | 719 | 10.430, 0.45; 8.507, 3.48; 8.470, 1.63; 8.466, 1.64; 8.458, 1.76; 8.454, 1.58; 8.262, 0.45; 8.244, 0.45; 8.137, 1.30; 8.134, 1.22; 8.117, 1.34; 8.114, 1.23; 7.858, 1.18; 7.711, 1.36; 7.596, 1.24; 7.584, 1.31; 7.575, 1.18; 7.564, 1.09; 7.268, 1.08; 5.972, 5.15; 3.986, 0.30; 3.968, 0.54; 3.952, 0.66; 3.933, 0.52; 3.299, 716.11; 3.275, 17.68; 3.222, 0.36; 3.219, 0.35; 2.673, 1.35; 2.668, 1.78; 2.664, 1.35; 2.634, 0.41; 2.621, 0.56; 2.605, 0.49; 2.568, 1.40; 2.551, 1.90; 2.539, 4.27; 2.534, 3.82; 2.508, 105.34; 2.504, 190.91; 2.500, 244.42; 2.495, 169.43; 2.491, 83.40; 2.433, 1.54; 2.414, 1.41; 2.399, 1.02; 2.381, 0.87; 2.331, 1.30; 2.326, 1.77; 2.322, 1.31; 2.317, 0.76; 2.291, 0.87; 2.203, 5.81; 2.127, 0.95; 2.103, 0.70; 2.069, 0.86; 2.049, 1.03; 1.997, 15.00; 1.990, 2.19; 1.239, 0.39; 1.208, 0.31; 1.152, 0.52; 1.135, 0.51; 1.119, 0.33; 1.102, 0.71; 1.074, 4.38; 1.058, 4.35; 0.972, 0.49; 0.954, 0.47; 0.008, 0.92; −0.000, 20.91; −0.008, 1.08 |

-continued
| No. | Structure | logP | MH+ | NMR |
|---|---|---|---|---|
| 255 | 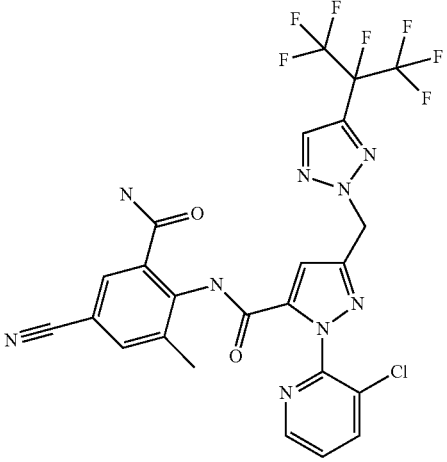 [SMILES: Cc1cc(C#N)cc(C(N)=O)c1NC(=O)c1cc(Cn2ncc(C(F)(C(F)(F)F)C(F)(F)F)n2)nn1-c1ncccc1Cl] | 3.19 | 630 | 10.558, 3.61; 10.207, 0.49; 8.534, 1.14; 8.531, 1.22; 8.514, 7.94; 8.486, 2.80; 8.482, 2.90; 8.474, 2.95; 8.470, 2.60; 8.248, 1.13; 8.225, 0.75; 8.150, 2.61; 8.146, 2.57; 8.130, 2.90; 8.126, 2.55; 8.039, 0.55; 7.898, 0.69; 7.850, 4.69; 7.811, 4.28; 7.669, 0.77; 7.658, 0.77; 7.649, 0.71; 7.637, 0.69; 7.598, 2.69; 7.587, 2.78; 7.578, 2.71; 7.567, 2.84; 7.546, 2.06; 7.512, 0.56; 7.244, 4.30; 7.019, 0.53; 6.871, 0.86; 6.613, 0.55; 5.978, 4.65; 5.970, 10.97; 3.708, 0.59; 3.641, 0.52; 3.629, 0.56; 3.619, 0.66; 3.608, 0.68; 3.601, 0.82; 3.585, 0.66; 3.568, 0.74; 3.451, 1.34; 3.427, 1.94; 3.409, 2.23; 3.306, 3560.21; 3.283, 23.85; 3.218, 0.84; 3.147, 0.56; 3.077, 1.13; 2.674, 3.04; 2.669, 4.28; 2.664, 3.21; 2.651, 0.52; 2.639, 0.51; 2.625, 0.67; 2.610, 0.77; 2.539, 12.95; 2.522, 20.73; 2.509, 256.29; 2.505, 461.41; 2.500, 586.23; 2.496, 404.94; 2.365, 0.56; 2.332, 3.28; 2.327, 4.22; 2.322, 3.04; 2.270, 2.06; 2.171, 15.00; 2.131, 1.99; 2.069, 1.71; 2.049, 1.64; 1.667, 5.93; 1.356, 10.99; 1.237, 0.97; 1.182, 0.58; 1.107, 3.59; 0.891, 0.81; −0.000, 18.16 |
| 256 | 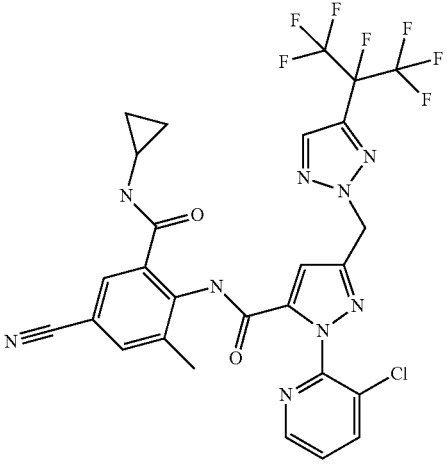 | 3.63 | 670 | 10.441, 3.84; 8.516, 6.07; 8.492, 2.22; 8.478, 2.66; 8.475, 2.78; 8.467, 2.92; 8.463, 2.81; 8.340, 3.17; 8.329, 2.99; 8.283, 1.24; 8.262, 0.98; 8.148, 2.76; 8.145, 2.60; 8.128, 2.89; 8.124, 2.63; 7.907, 1.22; 7.904, 1.37; 7.840, 3.36; 7.691, 3.91; 7.686, 3.44; 7.600, 2.73; 7.588, 2.60; 7.580, 2.56; 7.568, 3.10; 7.292, 2.93; 7.268, 4.46; 6.871, 1.15; 5.998, 3.66; 5.982, 10.04; 3.616, 1.02; 3.601, 1.07; 3.540, 1.24; 3.523, 1.22; 3.501, 1.44; 3.305, 6468.41; 3.190, 1.04; 3.180, 1.02; 3.171, 0.99; 2.695, 1.01; 2.674, 6.27; 2.669, 8.16; 2.664, 6.51; 2.660, 3.82; 2.649, 1.74; 2.639, 1.34; 2.592, 1.74; 2.539, 34.60; 2.522, 34.80; 2.509, 437.06; 2.504, 797.94; 2.500, 1022.93; 2.496, 704.00; 2.491, 341.28; 2.331, 5.63; 2.327, 7.25; 2.322, 5.37; 2.282, 2.13; 2.191, 15.00; 2.135, 1.85; 2.069, 8.40; 2.049, 2.68; 1.870, 4.95; 1.356, 13.79; 1.292, 1.12; 1.237, 1.79; 1.159, 1.98; 1.070, 1.38; 0.950, 0.97; 0.738, 0.98; 0.612, 1.07; 0.599, 2.81; 0.594, 3.44; 0.582, 3.56; 0.576, 2.93; 0.566, 1.22; 0.434, 1.25; 0.425, 3.50; 0.418, 3.43; 0.410, 2.96; −0.000, 9.47 |

-continued

| No. | Structure | logP | MH+ | NMR |
|---|---|---|---|---|
| 257 | 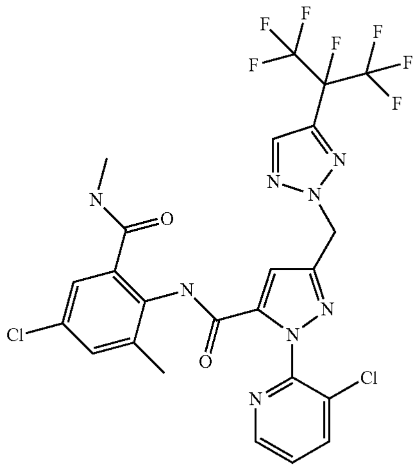 | 3.76 | 653 | 10.226, 3.61; 8.513, 5.32; 8.502, 0.48; 8.474, 2.71; 8.471, 2.79; 8.463, 2.81; 8.459, 2.66; 8.181, 1.54; 8.169, 1.51; 8.159, 0.65; 8.146, 2.68; 8.142, 2.53; 8.125, 2.88; 8.122, 2.61; 7.593, 2.71; 7.581, 2.66; 7.573, 2.48; 7.561, 2.46; 7.444, 2.87; 7.438, 3.05; 7.316, 3.37; 7.310, 3.01; 7.216, 6.14; 6.012, 0.50; 5.968, 9.25; 3.655, 1.00; 3.451, 0.30; 3.446, 0.30; 3.415, 0.44; 3.299, 952.85; 3.275, 22.35; 2.673, 1.92; 2.669, 2.51; 2.664, 1.98; 2.644, 9.09; 2.632, 9.55; 2.539, 5.12; 2.522, 11.53; 2.508, 139.91; 2.504, 254.04; 2.500, 325.64; 2.495, 225.42; 2.491, 110.55; 2.402, 0.53; 2.372, 0.39; 2.363, 0.35; 2.356, 0.33; 2.331, 1.84; 2.326, 2.37; 2.322, 1.79; 2.182, 0.55; 2.135, 15.00; 2.069, 1.11; 2.049, 0.87; 1.904, 0.70; 1.356, 3.56; 1.237, 0.51; 0.856, 0.56; 0.839, 0.56; 0.834, 0.33; 0.008, 1.27; −0.000, 28.23; −0.008, 1.41 |
| 258 | 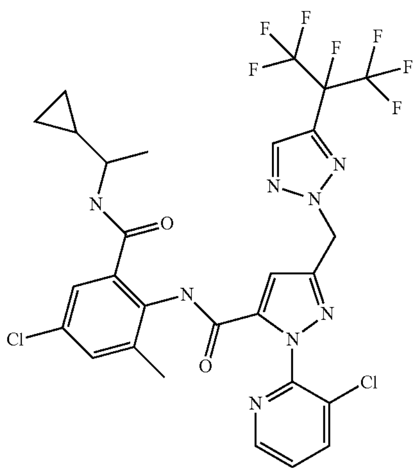 [SMILES: Cc1cc(Cl)cc(C(=O)NC(C)C2CC2)c1NC(=O)c1cc(Cn2ncc(C(F)(C(F)(F)F)C(F)(F)F)n2)nn1-c1ncccc1Cl] | 4.61 | 707 | 10.159, 3.96; 8.503, 5.29; 8.464, 2.54; 8.461, 2.84; 8.452, 2.94; 8.449, 2.71; 8.134, 2.86; 8.130, 2.77; 8.113, 3.10; 8.110, 2.78; 8.041, 1.97; 8.021, 1.78; 7.591, 2.86; 7.579, 2.79; 7.570, 2.54; 7.559, 2.56; 7.445, 3.16; 7.440, 3.31; 7.277, 3.43; 7.271, 3.26; 7.219, 6.82; 5.959, 9.58; 3.779, 1.04; 3.755, 1.09; 3.708, 1.72; 3.700, 1.13; 3.694, 1.15; 3.682, 1.34; 3.666, 1.25; 3.649, 1.39; 3.634, 1.52; 3.599, 1.68; 3.569, 1.95; 3.517, 2.54; 3.500, 2.98; 3.188, 1.83; 3.158, 1.18; 3.147, 1.46; 2.679, 4.18; 2.674, 7.65; 2.670, 10.04; 2.665, 7.54; 2.660, 4.09; 2.581, 3.28; 2.540, 32.68; 2.523, 48.89; 2.509, 585.73; 2.505, 1067.22; 2.500, 1370.00; 2.496, 936.93; 2.492, 450.29; 2.387, 1.07; 2.336, 4.11; 2.332, 7.34; 2.327, 9.62; 2.323, 6.91; 2.318, 3.62; 2.143, 15.00; 2.069, 6.58; 2.049, 4.10; 1.237, 1.68; 1.039, 8.89; 1.022, 8.47; 0.890, 1.16; 0.795, 1.13; 0.776, 1.48; 0.339, 1.30; 0.330, 1.05; 0.318, 1.19; 0.193, 1.13; 0.173, 1.67; 0.161, 1.17; 0.153, 1.49; 0.139, 1.59; 0.129, 1.52; 0.117, 1.36; 0.106, 1.33; 0.094, 1.26; −0.000, 46.59; −0.008, 2.14 |
| 259 | 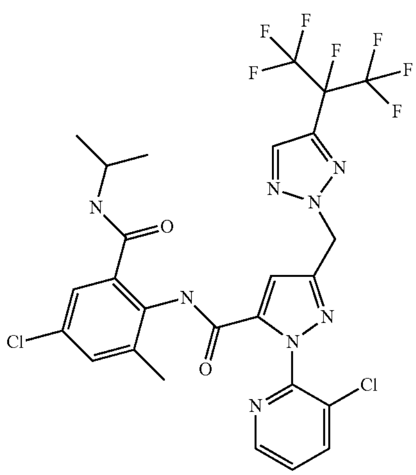 | 4.3 | 681 | 10.162, 2.90; 8.509, 4.23; 8.463, 2.14; 8.459, 2.14; 8.451, 2.12; 8.447, 2.03; 8.134, 2.00; 8.130, 1.96; 8.114, 2.15; 8.110, 2.00; 7.971, 1.45; 7.952, 1.48; 7.590, 2.14; 7.578, 1.97; 7.570, 1.97; 7.558, 1.86; 7.436, 2.26; 7.431, 2.30; 7.276, 2.58; 7.270, 2.28; 7.219, 5.08; 5.966, 7.17; 3.921, 0.36; 3.904, 0.78; 3.888, 1.04; 3.869, 1.02; 3.853, 0.74; 3.837, 0.41; 3.708, 0.32; 3.651, 0.33; 3.643, 0.34; 3.563, 0.46; 3.511, 0.57; 3.481, 0.76; 3.437, 1.05; 3.305, 2835.88; 3.282, 17.78; 3.229, 1.09; 3.200, 0.50; 3.188, 0.44; 3.176, 0.39; 3.163, 0.33; 3.145, 0.33; 2.694, 0.35; 2.674, 2.28; 2.669, 3.10; 2.664, 2.22; 2.642, 0.42; 2.640, 0.38; 2.539, 14.26; 2.522, 14.27; 2.509, 179.02; 2.504, 326.63; 2.500, 419.89; 2.496, 288.60; 2.491, 139.80; 2.386, 0.45; 2.382, 0.45; 2.362, 0.39; 2.358, 0.40; 2.331, 2.29; 2.327, 2.95; 2.322, 2.22; 2.301, 0.31; 2.141, 11.38; 2.069, 2.33; 2.049, 1.04; 1.292, 0.33; 1.236, 0.67; 1.159, 0.87; 1.070, 0.58; 1.000, 15.00; 0.983, 14.87; −0.000, 1.96 |

-continued
| No. | Structure | logP | MH+ | NMR |
|---|---|---|---|---|
| 260 | 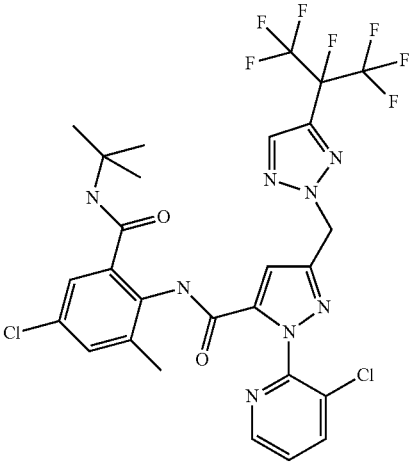 [SMILES: Cc1cc(Cl)cc(C(=O)NC(C)(C)C)c1NC(=O)c1cc(Cn2ncc(C(F)(C(F)(F)F)C(F)(F)F)n2)nn1-c1ncccc1Cl] | 4.64 | 695 | 10.133, 1.03; 8.504, 1.42; 8.469, 0.65; 8.465, 0.69; 8.457, 0.73; 8.453, 0.69; 8.146, 0.62; 8.142, 0.63; 8.126, 0.70; 8.122, 0.66; 7.596, 0.64; 7.584, 0.64; 7.576, 0.61; 7.564, 0.60; 7.485, 1.01; 7.411, 0.77; 7.406, 0.80; 7.239, 0.87; 7.233, 0.81; 7.187, 1.77; 5.967, 2.45; 3.310, 206.36; 2.539, 1.26; 2.509, 13.15; 2.505, 22.85; 2.500, 28.47; 2.496, 19.80; 2.130, 3.80; 1.187, 15.00 |
| 261 | 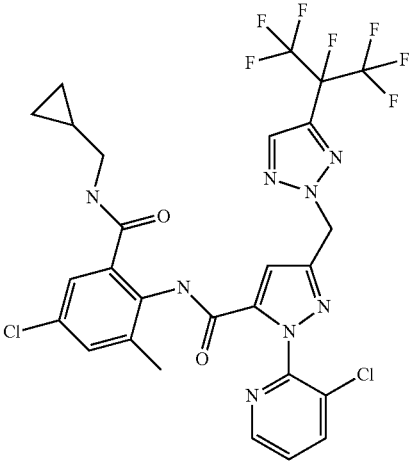 [SMILES: Cc1cc(Cl)cc(C(=O)NCC2CC2)c1NC(=O)c1cc(Cn2ncc(C(F)(C(F)(F)F)C(F)(F)F)n2)nn1-c1ncccc1Cl] | 4.34 | 693 | 10.194, 3.70; 8.496, 5.46; 8.461, 2.66; 8.457, 2.82; 8.449, 2.97; 8.445, 2.73; 8.238, 1.01; 8.223, 1.93; 8.209, 0.98; 8.132, 2.62; 8.128, 2.61; 8.112, 2.97; 8.108, 2.73; 7.587, 2.80; 7.575, 2.66; 7.567, 2.59; 7.555, 2.56; 7.449, 2.90; 7.443, 3.16; 7.312, 3.44; 7.306, 3.15; 7.218, 6.21; 5.957, 9.51; 3.364, 0.56; 3.346, 0.86; 3.294, 618.99; 3.171, 0.72; 2.994, 2.78; 2.980, 4.09; 2.963, 2.77; 2.673, 0.67; 2.668, 0.90; 2.664, 0.71; 2.538, 1.50; 2.521, 3.83; 2.508, 52.51; 2.504, 101.23; 2.499, 133.71; 2.494, 94.81; 2.490, 44.82; 2.335, 0.37; 2.331, 0.62; 2.326, 0.86; 2.321, 0.61; 2.144, 15.00; 2.067, 0.87; 0.871, 0.40; 0.856, 0.71; 0.852, 0.68; 0.839, 1.11; 0.831, 0.67; 0.827, 0.73; 0.822, 0.72; 0.808, 0.38; 0.309, 1.02; 0.298, 2.98; 0.294, 3.09; 0.283, 1.64; 0.277, 3.01; 0.273, 2.80; 0.263, 1.12; 0.110, 1.27; 0.099, 3.60; 0.088, 3.16; 0.084, 3.50; 0.073, 0.85; −0.000, 7.27; −0.008, 0.31 |
| 262 | 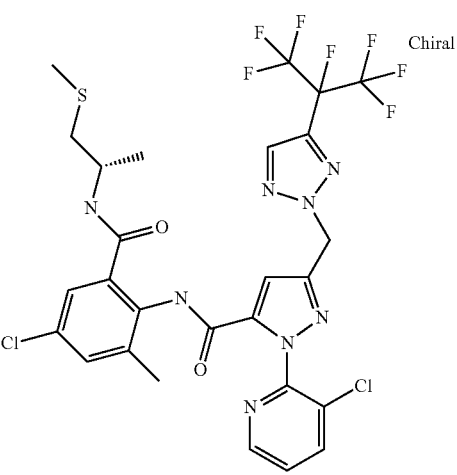 [SMILES: CSC[C@H](C)NC(=O)c1cc(Cl)cc(C)c1NC(=O)c1cc(Cn2ncc(C(F)(C(F)(F)F)C(F)(F)F)n2)nn1-c1ncccc1Cl] Chiral | 4.45 | 727 | 10.165, 0.94; 8.504, 3.51; 8.466, 1.61; 8.462, 1.68; 8.454, 1.77; 8.450, 1.68; 8.134, 2.19; 8.130, 1.97; 8.114, 2.42; 8.110, 2.00; 7.591, 1.51; 7.580, 1.51; 7.571, 1.45; 7.560, 1.40; 7.454, 1.58; 7.448, 1.65; 7.304, 1.77; 7.299, 1.66; 7.236, 2.77; 7.223, 0.45; 6.871, 0.47; 5.963, 5.77; 5.747, 0.39; 3.968, 0.56; 3.951, 0.67; 3.931, 0.56; 3.300, 524.60; 3.276, 12.34; 3.233, 0.40; 2.673, 0.99; 2.669, 1.21; 2.664, 0.98; 2.579, 0.59; 2.558, 1.58; 2.539, 3.24; 2.522, 6.68; 2.508, 71.03; 2.504, 125.40; 2.500, 158.73; 2.495, 108.88; 2.491, 52.50; 2.435, 1.32; 2.418, 1.23; 2.402, 0.79; 2.384, 0.73; 2.336, 0.45; 2.331, 0.85; 2.326, 1.08; 2.322, 0.81; 2.317, 0.41; 2.183, 0.85; 2.148, 8.40; 2.085, 0.66; 2.069, 0.81; 2.059, 0.32; 2.049, 0.64; 2.013, 0.31; 1.992, 15.00; 1.988, 2.63; 1.356, 5.79; 1.236, 0.31; 1.091, 0.61; 1.074, 0.89; 1.063, 4.74; 1.046, 4.64; 0.963, 0.42; 0.947, 0.39; 0.008, 0.67; −0.000, 11.95; −0.008, 0.48 |

-continued

| No. | Structure | logP | MH+ | NMR |
|---|---|---|---|---|
| 263 | 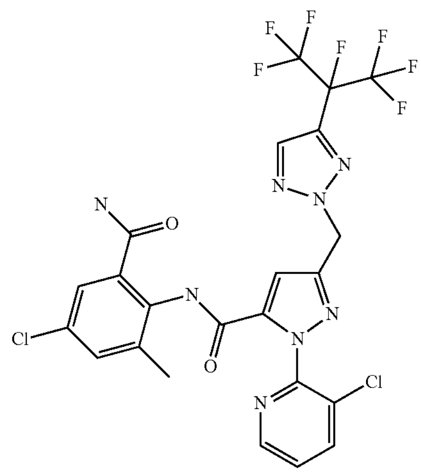 [SMILES: Cc1cc(Cl)cc(C(N)=O)c1NC(=O)c1cc(Cn2ncc(C(F)(C(F)(F)F)C(F)(F)F)n2)nn1-c1ncccc1Cl] | 3.48 | 639 | 10.266, 3.61; 8.512, 5.26; 8.481, 2.72; 8.477, 2.80; 8.470, 2.87; 8.466, 2.74; 8.145, 2.59; 8.141, 2.59; 8.125, 2.87; 8.121, 2.66; 7.687, 1.89; 7.594, 2.81; 7.582, 2.72; 7.573, 2.60; 7.562, 2.55; 7.449, 4.63; 7.445, 4.64; 7.387, 3.62; 7.381, 3.01; 7.224, 5.72; 6.871, 0.41; 5.961, 9.12; 3.304, 1017.33; 3.281, 6.89; 2.673, 0.92; 2.669, 1.25; 2.664, 0.92; 2.539, 5.85; 2.522, 5.96; 2.509, 72.57; 2.504, 131.93; 2.500, 168.91; 2.496, 116.00; 2.491, 56.02; 2.331, 0.90; 2.327, 1.20; 2.322, 0.86; 2.183, 0.70; 2.125, 15.00; 2.069, 1.57; 2.049, 0.47; 1.356, 5.08; 1.236, 0.32; 1.159, 0.32; −0.000, 1.22 |
| 264 | 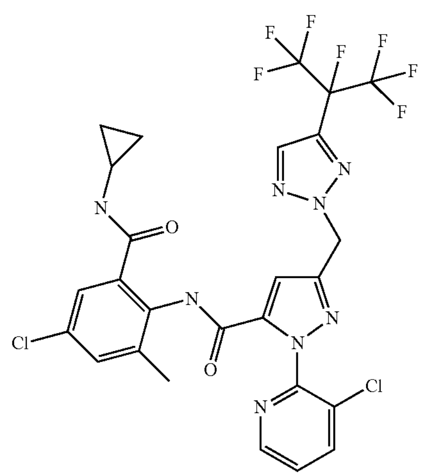 | 4.01 | 679745 | 10.172, 1.73; 8.513, 2.45; 8.474, 1.13; 8.459, 1.27; 8.211, 1.19; 8.143, 1.60; 8.122, 1.16; 7.594, 1.33; 7.582, 1.14; 7.435, 1.28; 7.265, 1.45; 7.259, 1.33; 7.235, 2.73; 5.972, 4.03; 3.708, 1.50; 3.690, 1.26; 3.676, 1.45; 3.657, 1.22; 3.622, 1.46; 3.607, 1.62; 3.578, 1.68; 3.556, 1.74; 3.541, 2.00; 3.526, 2.18; 3.488, 2.43; 3.466, 2.97; 3.300, 9732.98; 3.276, 64.90; 3.216, 2.62; 3.207, 1.62; 3.176, 1.18; 3.162, 1.17; 2.709, 1.15; 2.673, 11.72; 2.669, 15.00; 2.664, 12.00; 2.659, 6.72; 2.628, 2.23; 2.616, 2.32; 2.605, 3.08; 2.602, 3.13; 2.581, 4.70; 2.539, 72.90; 2.522, 71.01; 2.508, 878.87; 2.504, 1601.13; 2.500, 2052.56; 2.495, 1402.08; 2.491, 673.02; 2.400, 2.47; 2.394, 2.41; 2.367, 1.87; 2.349, 2.20; 2.335, 6.10; 2.331, 11.16; 2.326, 14.80; 2.322, 10.64; 2.317, 5.90; 2.301, 1.25; 2.279, 1.15; 2.134, 6.52; 2.069, 6.22; 2.049, 5.60; 1.987, 1.52; 1.907, 1.87; 1.398, 1.73; 1.292, 2.13; 1.237, 3.07; 1.192, 1.26; 1.175, 1.14; 1.159, 4.27; 1.111, 1.77; 1.070, 2.93; 0.890, 3.05; 0.581, 1.40; 0.568, 1.44; 0.410, 1.45; 0.405, 1.77; 0.008, 1.37; −0.000, 32.23 |
| 265 | 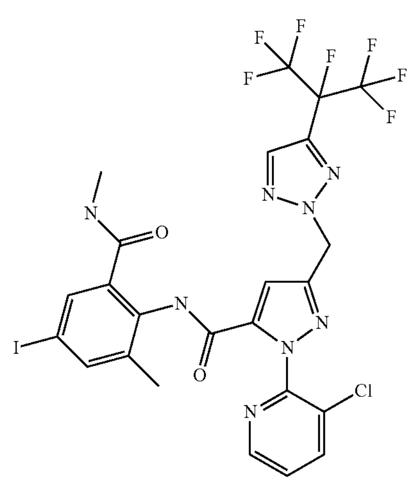 [SMILES: CNC(=O)c1cc(I)cc(C)c1NC(=O)c1cc(Cn2ncc(C(F)(C(F)(F)F)C(F)(F)F)n2)nn1-c1ncccc1Cl] | 4 | 799 | 10.213, 3.75; 8.510, 5.67; 8.502, 0.51; 8.472, 2.86; 8.468, 2.88; 8.460, 2.96; 8.457, 2.72; 8.175, 0.64; 8.159, 1.92; 8.144, 3.42; 8.140, 3.11; 8.123, 3.01; 8.120, 2.64; 7.727, 3.21; 7.723, 3.28; 7.592, 3.30; 7.584, 4.07; 7.580, 5.96; 7.572, 2.67; 7.560, 2.45; 7.222, 0.81; 7.208, 5.89; 6.870, 0.94; 6.613, 0.57; 6.007, 0.77; 5.965, 9.29; 3.645, 1.40; 3.618, 0.30; 3.601, 0.52; 3.585, 0.33; 3.303, 1328.22; 3.279, 10.21; 2.674, 1.50; 2.669, 2.05; 2.664, 1.54; 2.635, 9.83; 2.624, 9.78; 2.539, 4.08; 2.522, 9.03; 2.509, 114.99; 2.504, 209.98; 2.500, 269.90; 2.496, 185.71; 2.491, 89.83; 2.408, 0.51; 2.378, 0.35; 2.367, 0.35; 2.336, 0.89; 2.331, 1.57; 2.327, 1.97; 2.322, 1.46; 2.183, 1.61; 2.098, 15.00; 2.069, 1.15; 2.049, 0.84; 1.862, 0.98; 1.760, 0.57; 1.356, 11.95; 1.237, 0.36; 1.181, 0.88; 1.170, 0.45; 0.008, 0.48; −0.000, 12.40 |

| No. | Structure | logP | MH+ | NMR |
|---|---|---|---|---|
| 266 | 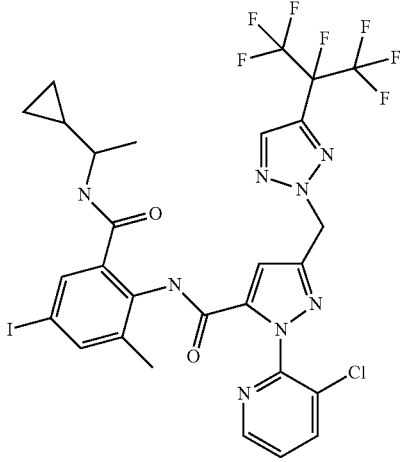 [SMILES: Cc1cc(I)cc(C(=O)NC(C)C2CC2)c1NC(=O)c1cc(Cn2ncc(C(F)(C(F)(F)F)C(F)(F)F)n2)nn1-c1ncccc1Cl] | 4.86 | 799 | 10.146, 3.94; 8.501, 5.71; 8.462, 2.86; 8.458, 2.81; 8.450, 3.04; 8.447, 2.71; 8.132, 2.93; 8.128, 2.69; 8.112, 3.05; 8.108, 2.69; 8.032, 1.95; 8.011, 2.00; 7.729, 3.33; 7.725, 3.37; 7.589, 2.84; 7.578, 2.61; 7.569, 2.70; 7.557, 3.02; 7.550, 3.68; 7.546, 3.33; 7.211, 6.49; 5.956, 9.56; 3.708, 0.93; 3.591, 0.85; 3.579, 0.88; 3.478, 1.68; 3.467, 1.72; 3.307, 6378.64; 3.285, 38.54; 3.174, 0.76; 3.170, 0.69; 3.147, 0.93; 2.678, 2.81; 2.674, 5.01; 2.669, 6.73; 2.665, 4.90; 2.629, 0.91; 2.604, 1.25; 2.539, 21.19; 2.522, 31.68; 2.509, 394.72; 2.505, 719.52; 2.500, 923.16; 2.496, 631.04; 2.491, 302.66; 2.361, 0.88; 2.331, 5.05; 2.327, 6.63; 2.322, 4.92; 2.318, 2.66; 2.106, 15.00; 2.069, 6.75; 2.049, 2.87; 1.908, 0.76; 1.399, 1.43; 1.237, 1.13; 1.036, 8.64; 1.020, 8.55; 0.890, 1.09; 0.816, 0.66; 0.808, 0.69; 0.796, 1.33; 0.788, 0.93; 0.775, 1.28; 0.340, 1.05; 0.329, 1.05; 0.319, 1.14; 0.210, 0.70; 0.189, 1.15; 0.175, 1.26; 0.156, 1.12; 0.148, 1.29; 0.136, 1.64; 0.124, 1.28; 0.113, 1.35; 0.101, 1.31; 0.091, 1.34; 0.079, 1.04; −0.000, 14.47; −0.009, 0.85 |
| 267 | 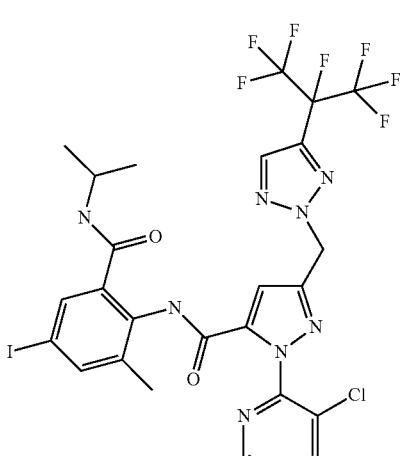 | 4.51 | 773 | 10.148, 2.94; 8.506, 4.15; 8.460, 2.05; 8.457, 2.17; 8.449, 2.14; 8.445, 2.07; 8.132, 1.96; 8.128, 1.99; 8.112, 2.07; 8.108, 1.99; 7.959, 1.51; 7.940, 1.39; 7.720, 2.42; 7.716, 2.49; 7.589, 2.10; 7.577, 2.13; 7.569, 2.04; 7.557, 2.06; 7.543, 2.72; 7.539, 2.41; 7.212, 4.86; 5.962, 7.15; 3.898, 0.84; 3.882, 1.05; 3.863, 1.12; 3.847, 0.80; 3.831, 0.46; 3.775, 0.34; 3.751, 0.38; 3.708, 0.47; 3.690, 0.37; 3.682, 0.39; 3.657, 0.69; 3.625, 0.48; 3.601, 0.54; 3.593, 0.56; 3.557, 0.58; 3.541, 0.63; 3.522, 0.74; 3.469, 1.01; 3.424, 1.64; 3.305, 3482.64; 3.209, 0.72; 3.188, 0.48; 3.176, 0.47; 3.170, 0.41; 3.153, 0.33; 2.693, 0.37; 2.678, 1.53; 2.674, 2.81; 2.669, 3.86; 2.664, 2.84; 2.660, 1.53; 2.641, 0.44; 2.604, 0.73; 2.539, 18.29; 2.522, 17.88; 2.509, 225.37; 2.504, 412.72; 2.500, 531.64; 2.496, 364.55; 2.491, 175.94; 2.374, 0.60; 2.357, 0.49; 2.331, 2.90; 2.327, 3.76; 2.322, 2.86; 2.318, 1.55; 2.104, 11.25; 2.069, 3.12; 2.049, 1.47; 1.398, 0.47; 1.292, 0.51; 1.236, 0.99; 1.159, 1.00; 1.070, 0.74; 0.997, 15.00; 0.981, 14.83; 0.890, 0.60; −0.000, 3.68 |

| No. | Structure | logP | MH+ | NMR |
|---|---|---|---|---|
| 268 | 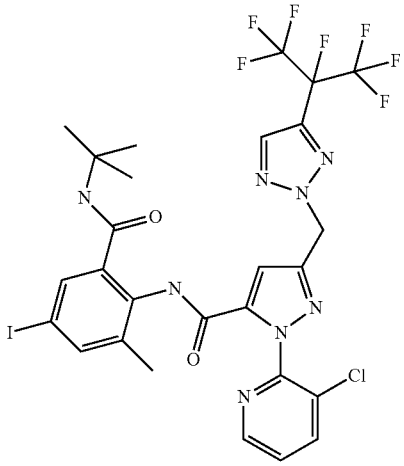 [SMILES: Cc1cc(I)cc(C(=O)NC(C)(C)C)c1NC(=O)c1cc(Cn2ncc(C(F)(C(F)(F)F)C(F)(F)F)n2)nn1-c1ncccc1Cl] | 4.9 | 787 | 10.114, 1.00; 8.502, 1.45; 8.466, 0.66; 8.463, 0.70; 8.455, 0.67; 8.451, 0.66; 8.144, 0.62; 8.141, 0.59; 8.124, 0.71; 8.121, 0.60; 7.697, 0.83; 7.693, 0.85; 7.595, 0.65; 7.583, 0.64; 7.575, 0.60; 7.563, 0.59; 7.502, 0.92; 7.498, 0.87; 7.470, 1.00; 7.179, 1.65; 5.963, 2.35; 3.304, 357.76; 2.673, 0.44; 2.669, 0.53; 2.664, 0.43; 2.539, 3.32; 2.508, 33.44; 2.504, 59.97; 2.500, 76.36; 2.496, 53.73; 2.331, 0.41; 2.326, 0.54; 2.322, 0.44; 2.094, 3.72; 2.069, 0.33; 1.182, 15.00; −0.000, 4.86 |
| 269 | 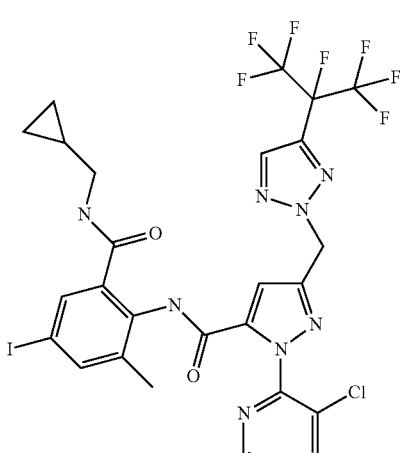 | 4.58 | 785 | 10.187, 4.15; 8.502, 5.61; 8.459, 2.76; 8.455, 2.99; 8.447, 3.01; 8.444, 2.93; 8.238, 1.16; 8.224, 2.19; 8.210, 1.17; 8.133, 2.67; 8.130, 2.82; 8.113, 3.21; 8.109, 2.76; 7.733, 3.22; 7.730, 3.35; 7.588, 3.33; 7.581, 4.03; 7.576, 6.03; 7.568, 2.86; 7.556, 2.62; 7.212, 6.51; 5.956, 9.61; 3.625, 0.74; 3.587, 0.73; 3.543, 0.82; 3.527, 0.87; 3.510, 1.03; 3.494, 1.12; 3.480, 1.18; 3.468, 1.43; 3.305, 4882.39; 3.281, 31.89; 3.199, 0.94; 3.176, 0.71; 3.077, 0.72; 2.983, 2.86; 2.967, 4.23; 2.951, 2.90; 2.678, 2.35; 2.673, 4.19; 2.669, 5.61; 2.664, 4.12; 2.660, 2.28; 2.648, 0.78; 2.539, 26.50; 2.522, 26.05; 2.509, 322.71; 2.504, 588.74; 2.500, 756.65; 2.496, 518.47; 2.491, 250.04; 2.380, 0.74; 2.336, 2.37; 2.331, 4.21; 2.327, 5.33; 2.322, 3.86; 2.106, 15.00; 2.069, 5.29; 2.049, 1.95; 1.292, 0.75; 1.235, 1.33; 1.159, 1.49; 1.070, 1.10; 1.051, 1.26; 0.853, 0.97; 0.849, 0.83; 0.836, 1.32; 0.819, 0.80; 0.309, 0.91; 0.298, 3.00; 0.294, 3.24; 0.283, 1.69; 0.278, 3.21; 0.273, 2.93; 0.263, 1.14; 0.106, 1.22; 0.093, 3.68; 0.081, 3.79; 0.069, 1.08; −0.000, 5.48 |
| 270 | 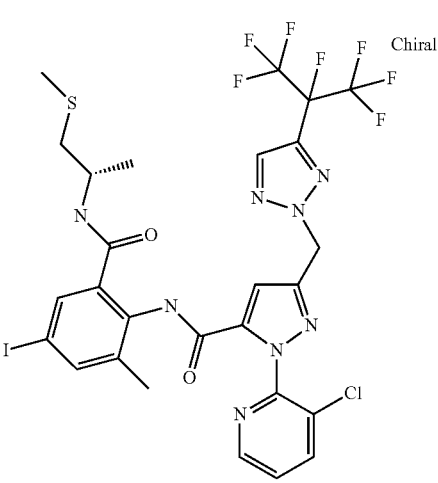 [SMILES: CSC[C@H](C)NC(=O)c1cc(I)cc(C)c1NC(=O)c1cc(Cn2ncc(C(F)(C(F)(F)F)C(F)(F)F)n2)nn1-c1ncccc1Cl] Chiral | 4.73 | 819 | 10.167, 0.51; 10.148, 2.04; 8.502, 3.48; 8.464, 1.70; 8.460, 1.69; 8.452, 1.75; 8.448, 1.56; 8.132, 1.68; 8.129, 1.59; 8.112, 2.25; 8.108, 1.75; 8.095, 1.05; 7.735, 1.79; 7.731, 1.82; 7.591, 1.71; 7.579, 3.33; 7.571, 2.34; 7.559, 1.43; 7.229, 3.43; 7.216, 0.42; 5.959, 5.67; 3.962, 0.57; 3.944, 0.72; 3.926, 0.57; 3.483, 0.34; 3.307, 1140.04; 3.222, 0.38; 2.674, 1.12; 2.669, 1.53; 2.664, 1.04; 2.660, 0.56; 2.582, 0.42; 2.554, 1.42; 2.539, 4.73; 2.522, 7.32; 2.509, 79.70; 2.504, 146.36; 2.500, 187.54; 2.496, 129.09; 2.491, 62.70; 2.434, 1.47; 2.417, 1.37; 2.401, 0.90; 2.383, 0.80; 2.336, 0.55; 2.331, 1.03; 2.327, 1.37; 2.322, 1.00; 2.111, 8.45; 2.069, 1.16; 2.049, 0.74; 1.990, 15.00; 1.986, 3.02; 1.237, 0.32; 1.086, 0.70; 1.069, 0.90; 1.059, 4.63; 1.042, 4.62; 0.959, 0.43; 0.943, 0.42; −0.000, 5.61 |

-continued
| No. | Structure | logP | MH+ | NMR |
|---|---|---|---|---|
| 271 | 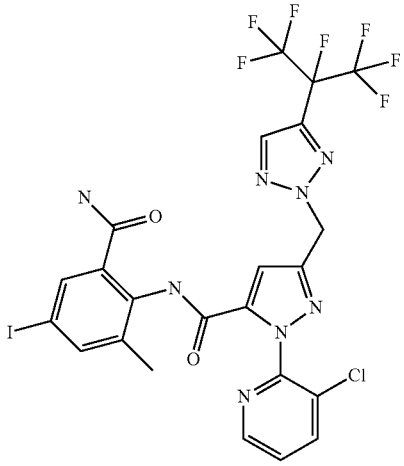 [SMILES: Cc1cc(I)cc(C(N)=O)c1NC(=O)c1cc(Cn2ncc(C(F)(C(F)(F)F)C(F)(F)F)n2)nn1-c1ncccc1Cl] | 3.7 | 731 | 10.257, 3.64; 8.509, 5.47; 8.479, 2.65; 8.475, 2.79; 8.467, 2.86; 8.463, 2.75; 8.143, 2.58; 8.139, 2.61; 8.123, 2.87; 8.119, 2.69; 7.732, 3.16; 7.728, 3.49; 7.669, 2.13; 7.658, 4.24; 7.653, 3.69; 7.592, 2.71; 7.5 80, 2.69; 7.572, 2.59; 7.560, 2.54; 7.414, 1.91; 7.217, 5.47; 6.871, 1.16; 6.613, 0.70; 5.979, 0.42; 5.958, 9.28; 3.304, 568.77; 2.677, 0.32; 2.674, 0.57; 2.669, 0.75; 2.664, 0.58; 2.539, 3.41; 2.522, 3.61; 2.509, 43.91; 2.504, 79.37; 2.500, 100.97; 2.496, 69.40; 2.491, 33.53; 2.331, 0.56; 2.327, 0.72; 2.322, 0.53; 2.183, 1.88; 2.088, 15.00; 2.069, 1.05; 2.049, 0.31; 1.629, 0.31; 1.356, 14.25; 1.182, 0.60; −0.000, 1.95 |
| 272 | 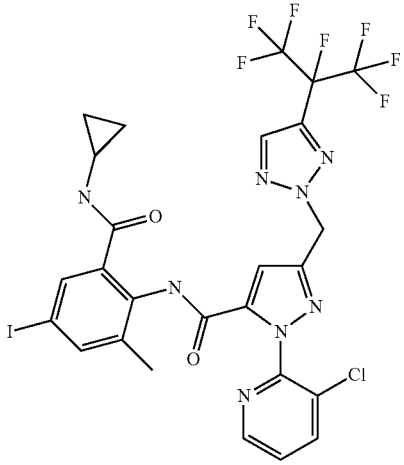 [SMILES: Cc1cc(I)cc(C(=O)NC2CC2)c1NC(=O)c1cc(Cn2ncc(C(F)(C(F)(F)F)C(F)(F)F)n2)nn1-c1ncccc1Cl] | 4.26 | 771 | 10.157, 3.87; 8.511, 5.71; 8.472, 2.83; 8.468, 3.03; 8.460, 3.09; 8.457, 2.98; 8.206, 2.26; 8.196, 2.25; 8.141, 2.70; 8.137, 2.73; 8.120, 3.05; 8.117, 2.82; 7.717, 3.19; 7.714, 3.32; 7.593, 2.87; 7.581, 2.92; 7.573, 2.75; 7.561, 2.72; 7.528, 3.49; 7.523, 3.36; 7.229, 6.49; 5.969, 9.37; 3.300, 637.07; 3.276, 4.93; 2.674, 1.22; 2.668, 1.74; 2.658, 1.65; 2.648, 1.48; 2.638, 1.09; 2.629, 0.81; 2.539, 5.33; 2.522, 5.13; 2.508, 63.99; 2.504, 117.14; 2.500, 150.74; 2.495, 103.21; 2.491, 49.68; 2.335, 0.49; 2.331, 0.83; 2.326, 1.11; 2.322, 0.86; 2.198, 0.34; 2.098, 15.00; 2.069, 0.66; 2.049, 0.49; 1.159, 0.32; 0.593, 0.96; 0.581, 2.59; 0.575, 3.47; 0.563, 3.29; 0.557, 2.73; 0.546, 1.13; 0.419, 1.20; 0.409, 3.41; 0.403, 3.25; 0.399, 3.05; 0.393, 2.85; 0.381, 0.92; −0.000, 1.94 |
| 273 | 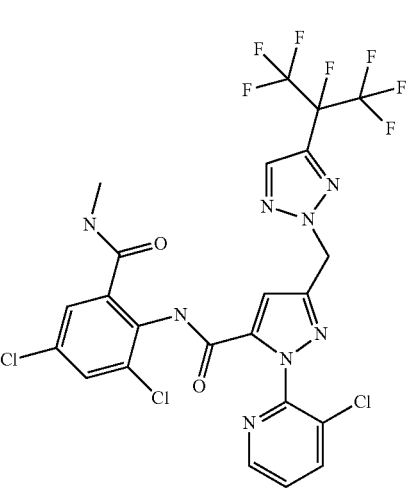 [SMILES: CNC(=O)c1cc(Cl)cc(Cl)c1NC(=O)c1cc(Cn2ncc(C(F)(C(F)(F)F)C(F)(F)F)n2)nn1-c1ncccc1Cl] | 3.69 | 673 | 10.502, 0.34; 10.485, 0.35; 10.435, 2.64; 8.567, 0.30; 8.548, 0.48; 8.513, 9.10; 8.476, 4.21; 8.472, 4.12; 8.464, 4.25; 8.460, 3.76; 8.268, 0.76; 8.247, 1.57; 8.240, 1.50; 8.136, 3.10; 8.133, 3.01; 8.116, 3.27; 7.853, 0.36; 7.838, 0.32; 7.797, 2.45; 7.719, 0.34; 7.614, 0.35; 7.592, 3.19; 7.580, 3.29; 7.572, 2.91; 7.560, 2.81; 7.504, 0.31; 7.473, 3.77; 7.286, 2.34; 5.969, 12.91; 3.558, 0.34; 3.517, 0.43; 3.502, 0.44; 3.442, 0.73; 3.413, 1.09; 3.305, 1315.00; 3.194, 0.52; 3.175, 0.41; 3.153, 0.35; 2.688, 0.92; 2.674, 1.82; 2.669, 2.19; 2.665, 1.77; 2.635, 15.00; 2.624, 14.92; 2.596, 0.77; 2.575, 0.93; 2.539, 11.28; 2.508, 118.81; 2.504, 215.25; 2.500, 276.20; 2.496, 197.25; 2.367, 0.55; 2.359, 0.56; 2.331, 1.64; 2.326, 2.16; 2.322, 1.69; 2.301, 0.44; 2.282, 0.35; 2.273, 0.38; 2.252, 0.38; 2.208, 0.32; 2.190, 0.34; 2.069, 1.90; 2.049, 0.80; 1.293, 0.36; 1.236, 0.51; −0.000, 23.20; −0.036, 0.32 |

| No. | Structure | logP | MH+ | NMR |
|---|---|---|---|---|
| 274 | 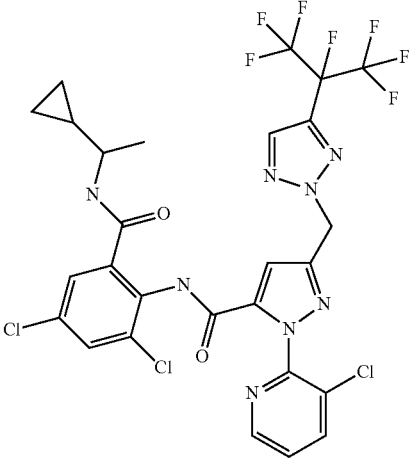 [SMILES: CC(NC(=O)c1cc(Cl)cc(Cl)c1NC(=O)c1cc(Cn2ncc(C(F)(C(F)(F)F)C(F)(F)F)n2)nn1-c1ncccc1Cl)C1CC1] | 4.49 | 727 | 10.358, 5.77; 8.505, 9.07; 8.461, 4.28; 8.458, 4.25; 8.449, 4.50; 8.446, 4.12; 8.126, 4.23; 8.123, 4.16; 8.111, 3.77; 8.106, 5.45; 8.103, 4.59; 8.091, 3.04; 7.805, 6.20; 7.799, 6.19; 7.590, 4.13; 7.579, 3.84; 7.570, 3.70; 7.558, 3.39; 7.413, 6.98; 7.408, 6.56; 7.303, 6.52; 5.964, 15.00; 3.708, 1.21; 3.589, 1.06; 3.584, 1.06; 3.578, 1.01; 3.572, 1.08; 3.505, 1.59; 3.453, 2.35; 3.450, 2.40; 3.305, 7002.88; 3.282, 44.95; 3.248, 5.81; 3.232, 3.33; 3.147, 1.08; 2.674, 6.35; 2.669, 8.40; 2.664, 6.21; 2.539, 26.44; 2.522, 40.67; 2.509, 497.73; 2.504, 904.67; 2.500, 1156.39; 2.496, 790.53; 2.491, 378.91; 2.331, 6.01; 2.327, 8.22; 2.322, 6.19; 2.069, 6.12; 2.049, 3.30; 1.245, 1.09; 1.237, 1.34; 1.122, 1.15; 1.106, 1.18; 1.026, 13.44; 1.009, 13.19; 0.891, 1.24; 0.795, 1.04; 0.782, 1.75; 0.773, 1.40; 0.761, 2.05; 0.750, 1.17; 0.336, 1.89; 0.324, 1.72; 0.315, 1.94; 0.302, 1.12; 0.205, 1.33; 0.193, 1.72; 0.185, 1.81; 0.173, 2.17; 0.165, 1.47; 0.153, 1.99; 0.143, 1.95; 0.131, 2.85; 0.119, 3.35; 0.107, 2.90; 0.098, 2.19; 0.086, 1.46; −0.000, 29.03; −0.008, 1.45 |
| 275 | 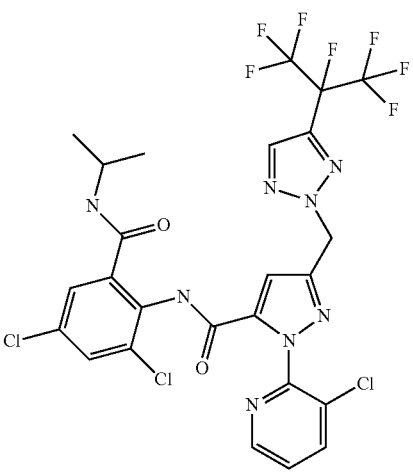 | 4.17 | 701 | 10.373, 2.78; 8.510, 4.27; 8.460, 2.18; 8.456, 2.15; 8.448, 2.11; 8.444, 1.92; 8.127, 1.93; 8.123, 1.98; 8.107, 2.26; 8.103, 2.00; 8.050, 1.59; 8.031, 1.45; 7.795, 3.12; 7.789, 3.15; 7.590, 2.21; 7.579, 2.02; 7.570, 1.97; 7.559, 1.72; 7.504, 0.52; 7.420, 3.69; 7.415, 3.47; 7.300, 3.39; 6.037, 0.66; 5.969, 7.53; 3.901, 0.53; 3.895, 0.70; 3.879, 0.95; 3.862, 1.37; 3.844, 1.22; 3.827, 0.95; 3.810, 0.62; 3.768, 0.57; 3.699, 0.64; 3.681, 0.60; 3.678, 0.62; 3.653, 0.68; 3.639, 0.64; 3.624, 0.81; 3.577, 0.80; 3.566, 0.85; 3.499, 1.23; 3.492, 1.32; 3.486, 1.38; 3.448, 1.79; 3.303, 5311.79; 3.281, 33.06; 3.235, 2.18; 3.176, 0.72; 3.146, 0.53; 2.693, 0.79; 2.673, 4.80; 2.669, 6.30; 2.664, 5.01; 2.660, 2.51; 2.539, 30.18; 2.522, 30.54; 2.509, 376.54; 2.504, 686.81; 2.500, 881.84; 2.495, 605.89; 2.491, 293.18; 2.405, 1.24; 2.331, 4.52; 2.326, 6.21; 2.322, 4.49; 2.298, 0.52; 2.151, 3.47; 2.069, 5.14; 2.049, 2.27; 1.998, 2.75; 1.907, 0.55; 1.292, 0.81; 1.237, 1.49; 1.159, 1.66; 1.070, 1.97; 1.055, 0.94; 0.990, 15.00; 0.973, 14.84; 0.890, 0.91; −0.000, 5.44 |

-continued
| No. | Structure | logP | MH+ | NMR |
|---|---|---|---|---|
| 276 | 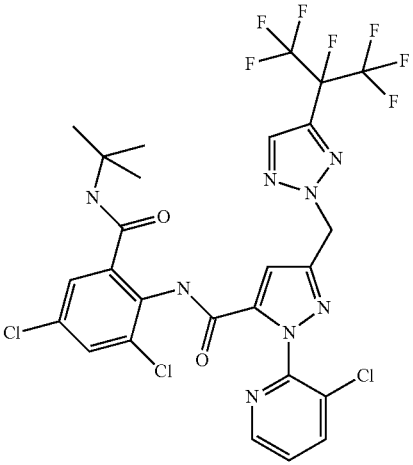 [SMILES: CC(C)(C)NC(=O)c1cc(Cl)cc(Cl)c1NC(=O)c1cc(Cn2ncc(C(F)(C(F)(F)F)C(F)(F)F)n2)nn1-c1ncccc1Cl] | 4.53 | 715 | 10.346, 0.77; 8.506, 1.47; 8.461, 0.77; 8.453, 0.71; 8.139, 0.60; 8.118, 0.59; 7.765, 0.81; 7.760, 0.78; 7.605, 0.98; 7.595, 0.66; 7.583, 0.56; 7.576, 0.51; 7.564, 0.50; 7.396, 0.86; 7.390, 0.76; 7.278, 1.01; 5.971, 2.12; 3.677, 0.32; 3.653, 0.37; 3.606, 0.38; 3.557, 0.49; 3.530, 0.50; 3.509, 0.56; 3.476, 0.76; 3.427, 1.19; 3.304, 2729.22; 3.280, 17.41; 3.176, 0.51; 3.162, 0.41; 3.158, 0.32; 2.678, 1.34; 2.673, 2.48; 2.669, 3.25; 2.664, 2.50; 2.659, 1.25; 2.632, 0.44; 2.610, 0.54; 2.539, 15.43; 2.522, 15.31; 2.509, 190.94; 2.504, 348.68; 2.500, 448.43; 2.495, 307.98; 2.491, 148.94; 2.331, 2.48; 2.326, 3.20; 2.322, 2.32; 2.069, 2.67; 2.049, 1.20; 1.292, 0.42; 1.253, 0.69; 1.236, 0.90; 1.176, 15.00; 1.159, 1.28; 1.070, 0.71; 0.890, 0.52; −0.000, 3.58 |
| 277 | 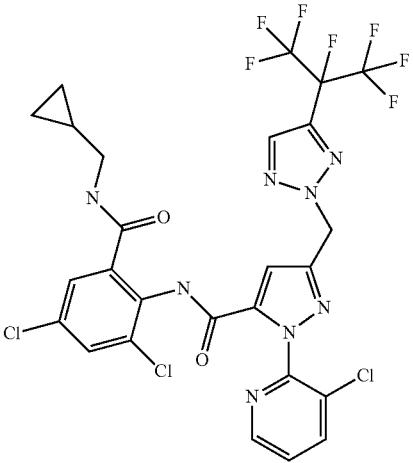 [SMILES: O=C(NCC1CC1)c1cc(Cl)cc(Cl)c1NC(=O)c1cc(Cn2ncc(C(F)(C(F)(F)F)C(F)(F)F)n2)nn1-c1ncccc1Cl] | 4.23 | 713 | 10.387, 5.59; 10.174, 0.44; 8.498, 8.55; 8.458, 4.07; 8.454, 4.25; 8.446, 4.46; 8.442, 4.17; 8.301, 1.57; 8.287, 3.01; 8.273, 1.45; 8.123, 3.95; 8.120, 3.90; 8.103, 4.45; 8.099, 3.98; 7.865, 0.42; 7.860, 0.45; 7.804, 6.48; 7.798, 6.52; 7.761, 0.45; 7.755, 0.47; 7.586, 4.23; 7.575, 4.07; 7.566, 3.82; 7.555, 3.76; 7.531, 0.56; 7.525, 0.51; 7.453, 7.52; 7.447, 7.12; 7.298, 5.87; 5.961, 15.00; 3.293, 538.05; 3.240, 0.45; 3.231, 0.40; 3.035, 0.49; 2.978, 4.16; 2.963, 5.96; 2.947, 4.08; 2.673, 0.72; 2.668, 0.88; 2.663, 0.65; 2.659, 0.37; 2.538, 1.61; 2.521, 4.20; 2.508, 54.25; 2.503, 103.66; 2.499, 136.25; 2.494, 95.97; 2.490, 44.80; 2.330, 0.70; 2.326, 0.87; 2.321, 0.62; 2.067, 1.13; 1.238, 0.39; 0.854, 0.49; 0.847, 0.57; 0.835, 1.07; 0.830, 1.04; 0.818, 1.68; 0.806, 1.06; 0.798, 1.04; 0.786, 0.56; 0.341, 0.39; 0.337, 0.43; 0.321, 0.48; 0.305, 1.63; 0.294, 4.52; 0.290, 4.78; 0.280, 2.55; 0.274, 4.59; 0.270, 4.16; 0.259, 1.69; 0.150, 0.46; 0.135, 0.44; 0.103, 1.92; 0.092, 5.39; 0.090, 5.26; 0.081, 4.73; 0.077, 5.22; 0.066, 1.25; −0.000, 6.97 |

-continued
| No. | Structure | logP | MH+ | NMR |
|---|---|---|---|---|
| 278 | 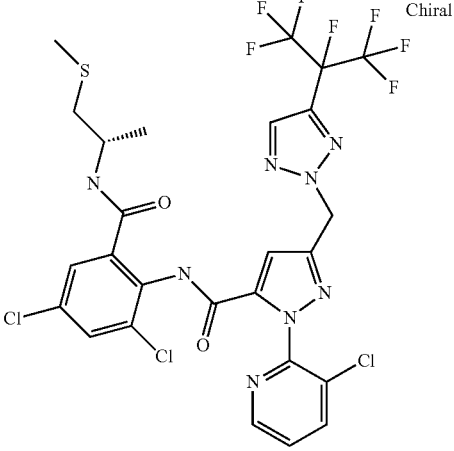 | 4.38 | 747 | 10.389, 2.15; 10.380, 0.37; 8.506, 3.49; 8.465, 1.67; 8.461, 1.60; 8.453, 1.79; 8.450, 1.57; 8.220, 1.04; 8.201, 1.08; 8.129, 1.47; 8.125, 1.47; 8.108, 1.57; 8.105, 1.56; 7.818, 2.49; 7.812, 2.31; 7.594, 1.60; 7.582, 1.48; 7.573, 1.40; 7.562, 1.39; 7.440, 2.51; 7.434, 2.43; 7.320, 2.18; 5.968, 5.74; 3.953, 0.43; 3.935, 0.70; 3.918, 0.81; 3.899, 0.70; 3.881, 0.43; 3.708, 0.64; 3.644, 0.43; 3.632, 0.42; 3.626, 0.46; 3.584, 0.53; 3.554, 0.58; 3.549, 0.67; 3.507, 0.83; 3.491, 0.93; 3.485, 0.94; 3.472, 1.05; 3.465, 1.08; 3.309, 3314.19; 3.190, 0.65; 3.147, 0.71; 2.944, 0.43; 2.731, 0.40; 2.726, 0.37; 2.678, 1.75; 2.674, 2.93; 2.669, 3.77; 2.665, 2.84; 2.539, 12.22; 2.522, 18.42; 2.509, 213.15; 2.505, 387.16; 2.500, 497.21; 2.496, 340.21; 2.491, 163.79; 2.415, 1.40; 2.396, 1.28; 2.381, 0.90; 2.363, 0.87; 2.336, 1.34; 2.331, 2.71; 2.327, 3.46; 2.322, 2.45; 2.318, 1.32; 2.109, 0.37; 2.069, 2.22; 2.049, 1.56; 1.994, 15.00; 1.985, 1.80; 1.236, 0.57; 1.144, 0.46; 1.081, 0.52; 1.053, 4.46; 1.036, 4.36; 0.949, 0.45; 0.932, 0.41; 0.890, 0.39; −0.000, 15.28 |
| 279 | 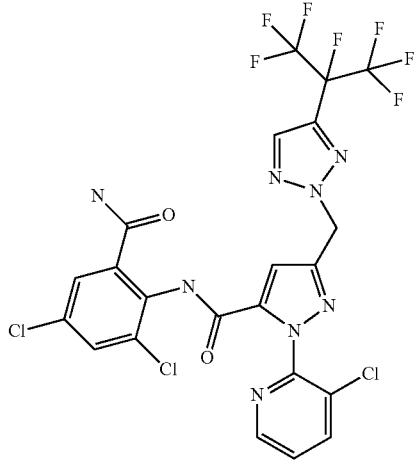 | 3.46 | 659 | 10.415, 5.66; 10.184, 0.91; 8.514, 8.80; 8.498, 0.75; 8.483, 4.22; 8.479, 4.32; 8.471, 4.29; 8.467, 4.00; 8.135, 4.02; 8.131, 3.90; 8.115, 4.43; 8.111, 4.08; 7.863, 1.36; 7.856, 1.39; 7.802, 6.42; 7.797, 6.33; 7.767, 1.10; 7.762, 1.13; 7.711, 2.98; 7.612, 0.67; 7.593, 5.34; 7.588, 2.87; 7.581, 5.27; 7.573, 4.23; 7.561, 4.20; 7.535, 3.28; 7.523, 8.19; 7.517, 7.39; 7.287, 5.10; 6.871, 0.77; 6.613, 0.48; 6.541, 1.03; 5.981, 1.89; 5.966, 15.00; 3.730, 0.44; 3.708, 0.47; 3.682, 0.46; 3.647, 0.50; 3.636, 0.51; 3.631, 0.49; 3.602, 0.77; 3.582, 0.58; 3.553, 0.71; 3.535, 0.77; 3.511, 0.95; 3.507, 0.92; 3.457, 1.31; 3.306, 4398.92; 3.283, 25.25; 3.178, 0.66; 3.163, 0.52; 2.674, 3.34; 2.669, 4.35; 2.665, 3.42; 2.660, 1.85; 2.631, 0.69; 2.539, 21.27; 2.522, 21.21; 2.509, 258.75; 2.504, 471.10; 2.500, 603.56; 2.496, 411.92; 2.491, 197.37; 2.373, 0.55; 2.331, 3.24; 2.327, 4.22; 2.322, 3.17; 2.183, 1.33; 2.069, 1.82; 2.049, 1.58; 1.987, 0.56; 1.612, 0.58; 1.356, 10.07; 1.293, 0.50; 1.236, 1.15; 1.159, 1.33; 1.070, 0.91; 0.890, 0.80; 0.713, 0.55; −0.000, 7.54 |

-continued

| No. | Structure | logP | MH+ | NMR |
|---|---|---|---|---|
| 280 | 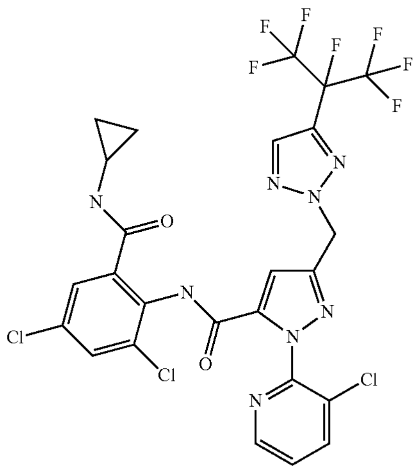 [SMILES: O=C(NC1CC1)c1cc(Cl)cc(Cl)c1NC(=O)c1cc(Cn2ncc(C(F)(C(F)(F)F)C(F)(F)F)n2)nn1-c1ncccc1Cl] | 3.92 | 699 | 10.398, 3.52; 8.514, 9.74; 8.475, 4.57; 8.471, 4.68; 8.463, 4.69; 8.460, 4.25; 8.302, 2.77; 8.293, 2.53; 8.138, 3.86; 8.134, 3.75; 8.118, 4.15; 8.114, 3.69; 7.852, 0.43; 7.790, 4.23; 7.785, 3.90; 7.740, 0.52; 7.734, 0.47; 7.597, 4.45; 7.585, 3.98; 7.576, 3.78; 7.565, 3.56; 7.508, 0.47; 7.425, 5.46; 7.419, 4.90; 7.308, 4.57; 6.525, 0.50; 5.975, 15.00; 3.593, 0.44; 3.495, 0.48; 3.453, 0.68; 3.303, 2385.48; 3.280, 17.43; 2.673, 2.30; 2.669, 3.19; 2.664, 2.56; 2.660, 2.07; 2.652, 1.66; 2.642, 2.37; 2.633, 2.40; 2.624, 1.69; 2.615, 1.27; 2.605, 0.68; 2.539, 13.55; 2.522, 12.89; 2.509, 174.43; 2.504, 321.71; 2.500, 415.96; 2.495, 287.27; 2.491, 140.51; 2.422, 1.17; 2.396, 0.81; 2.331, 2.48; 2.326, 3.09; 2.322, 2.38; 2.198, 0.51; 2.069, 3.28; 2.049, 1.14; 1.908, 0.72; 1.236, 0.76; 1.186, 1.46; 1.159, 0.84; 1.070, 0.67; 0.628, 0.47; 0.616, 0.53; 0.610, 0.49; 0.600, 1.57; 0.587, 4.27; 0.582, 5.73; 0.570, 5.53; 0.564, 4.76; 0.552, 1.97; 0.480, 0.46; 0.473, 0.47; 0.407, 1.72; 0.396, 5.04; 0.390, 5.17; 0.381, 4.58; 0.369, 1.51; 0.357, 0.46; −0.000, 4.49 |
| 281 | 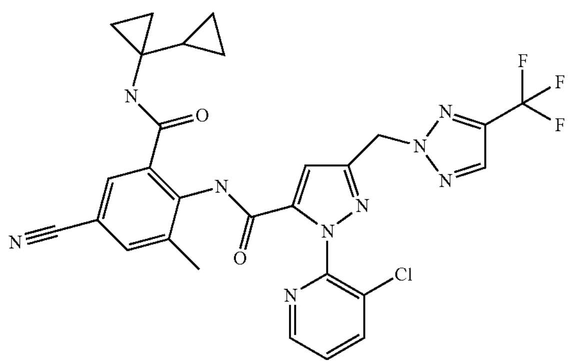 [SMILES: Cc1cc(C#N)cc(C(=O)NC2(C3CC3)CC2)c1NC(=O)c1cc(Cn2ncc(C(F)(F)F)n2)nn1-c1ncccc1Cl] | 3.37 | 610 | 10.365, 0.59; 8.524, 2.90; 8.465, 2.25; 8.462, 2.28; 8.453, 2.07; 8.450, 1.92; 8.141, 1.39; 8.138, 1.41; 8.121, 1.44; 8.118, 1.33; 7.826, 1.19; 7.661, 1.49; 7.594, 1.31; 7.582, 1.32; 7.574, 1.27; 7.562, 1.22; 7.259, 1.01; 6.871, 1.30; 6.612, 0.74; 5.951, 5.48; 3.303, 148.12; 3.279, 2.70; 2.668, 0.62; 2.539, 0.73; 2.504, 31.63; 2.500, 39.17; 2.496, 27.89; 2.326, 0.32; 2.192, 6.28; 2.184, 3.61; 1.398, 0.63; 1.357, 15.00; 1.241, 0.59; 1.234, 0.66; 1.221, 1.00; 1.208, 0.65; 1.200, 0.61; 1.187, 0.37; 1.182, 0.45; 0.538, 0.84; 0.520, 2.58; 0.510, 1.23; 0.476, 0.38; 0.439, 1.37; 0.428, 2.68; 0.410, 0.81; 0.227, 0.62; 0.216, 1.79; 0.212, 1.95; 0.201, 1.13; 0.196, 1.81; 0.191, 1.83; 0.181, 0.78; 0.076, 0.82; 0.063, 2.29; 0.053, 2.04; 0.050, 2.05; 0.038, 0.57; −0.000, 2.88 |
| 282 | 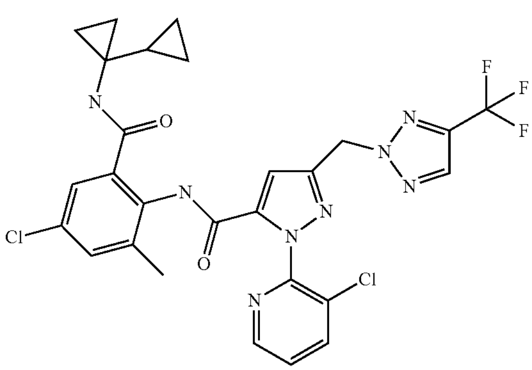 [SMILES: Cc1cc(Cl)cc(C(=O)NC2(C3CC3)CC2)c1NC(=O)c1cc(Cn2ncc(C(F)(F)F)n2)nn1-c1ncccc1Cl] | 3.78 | 619 | 10.111, 2.01; 8.523, 3.53; 8.502, 0.39; 8.495, 0.31; 8.479, 0.38; 8.464, 1.96; 8.460, 2.05; 8.453, 2.05; 8.449, 1.95; 8.327, 2.64; 8.140, 1.91; 8.137, 1.86; 8.120, 2.04; 8.116, 1.89; 7.592, 1.98; 7.581, 1.94; 7.572, 1.83; 7.560, 1.73; 7.444, 0.42; 7.425, 2.25; 7.420, 2.36; 7.299, 0.52; 7.225, 7.12; 6.871, 1.29; 6.612, 0.74; 5.981, 0.74; 5.943, 7.52; 3.303, 285.79; 3.279, 5.21; 2.673, 0.47; 2.669, 0.62; 2.664, 0.47; 2.539, 1.35; 2.504, 57.02; 2.500, 70.60; 2.496, 49.97; 2.434, 0.34; 2.331, 0.45; 2.327, 0.55; 2.183, 2.11; 2.137, 10.94; 2.103, 0.53; 2.069, 0.51; 2.044, 0.56; 1.728, 0.92; 1.356, 15.00; 1.249, 0.39; 1.237, 0.84; 1.229, 0.87; 1.217, 1.26; 1.204, 0.81; 1.196, 0.79; 1.182, 0.55; 0.525, 1.02; 0.507, 3.19; 0.497, 1.56; 0.469, 0.43; 0.458, 0.42; 0.431, 1.63; 0.421, 3.12; 0.402, 0.98; 0.214, 0.76; 0.203, 2.07; 0.199, 2.32; 0.188, 1.31; 0.183, 2.11; 0.178, 2.12; 0.168, 0.86; 0.068, 1.02; 0.054, 2.73; 0.045, 2.40; 0.041, 2.42; 0.030, 0.69; −0.000, 3.27 |

| No. | Structure | logP | MH+ | NMR |
|---|---|---|---|---|
| 283 | 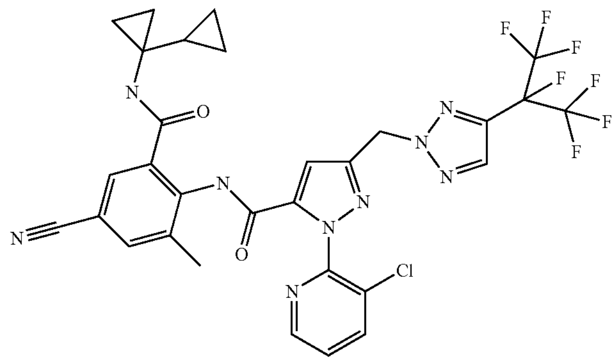 [SMILES: Cc1cc(C#N)cc(C(=O)NC2(C3CC3)CC2)c1NC(=O)c1cc(Cn2ncc(C(F)(C(F)(F)F)C(F)(F)F)n2)nn1-c1ncccc1Cl] | 4.12 | 711 | 10.394, 0.92; 8.508, 3.71; 8.486, 0.72; 8.478, 0.64; 8.464, 2.75; 8.461, 2.85; 8.453, 2.16; 8.449, 1.87; 8.140, 1.54; 8.136, 1.47; 8.119, 1.64; 8.116, 1.53; 7.832, 1.96; 7.663, 2.20; 7.660, 2.08; 7.593, 1.66; 7.582, 1.65; 7.573, 1.55; 7.562, 1.43; 7.261, 2.12; 7.128, 0.36; 6.871, 1.27; 6.612, 0.76; 5.975, 6.40; 3.433, 0.34; 3.409, 0.45; 3.301, 438.29; 3.277, 7.64; 3.223, 0.45; 2.668, 0.88; 2.664, 0.71; 2.539, 2.28; 2.504, 93.77; 2.500, 116.57; 2.496, 81.87; 2.331, 0.74; 2.327, 0.86; 2.283, 0.35; 2.190, 8.88; 2.126, 0.36; 2.069, 1.26; 1.668, 1.02; 1.398, 0.64; 1.378, 0.48; 1.356, 15.00; 1.254, 0.31; 1.242, 0.70; 1.234, 0.84; 1.221, 1.08; 1.209, 0.71; 1.201, 0.66; 1.187, 0.46; 1.182, 0.49; 1.169, 0.49; 1.136, 0.41; 0.890, 0.34; 0.540, 0.88; 0.522, 2.74; 0.511, 1.29; 0.474, 0.49; 0.436, 1.40; 0.425, 2.73; 0.407, 0.86; 0.226, 0.62; 0.214, 1.79; 0.210, 1.94; 0.200, 1.11; 0.194, 1.80; 0.190, 1.81; 0.179, 0.77; 0.077, 0.82; 0.064, 2.37; 0.054, 2.07; 0.051, 2.13; 0.039, 0.63; −0.000, 8.10 |
| 284 | 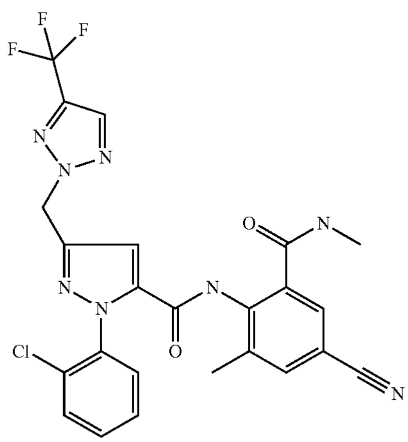 [SMILES: CNC(=O)c1cc(C#N)cc(C)c1NC(=O)c1cc(Cn2ncc(C(F)(F)F)n2)nn1-c1ccccc1Cl] | 3.10 | 543 | 16.003, 0.34; 10.391, 4.34; 8.526, 4.53; 8.340, 1.70; 8.328, 1.44; 8.318, 0.76; 7.847, 3.38; 7.844, 3.33; 7.732, 3.66; 7.728, 3.31; 7.571, 1.79; 7.567, 1.27; 7.551, 2.87; 7.547, 1.72; 7.531, 0.32; 7.527, 0.31; 7.496, 1.66; 7.489, 2.69; 7.474, 5.71; 7.457, 4.41; 7.452, 3.49; 7.443, 1.34; 7.434, 1.61; 7.420, 0.47; 7.416, 0.34; 7.214, 5.69; 5.933, 10.41; 3.720, 0.35; 3.669, 0.33; 3.661, 0.36; 3.648, 0.35; 3.634, 0.37; 3.615, 0.44; 3.608, 0.51; 3.600, 0.47; 3.583, 0.46; 3.566, 0.47; 3.527, 0.57; 3.510, 0.61; 3.489, 0.79; 3.454, 0.95; 3.438, 1.15; 3.381, 2.77; 3.309, 2519.00; 3.206, 0.90; 3.181, 0.52; 3.163, 0.49; 3.150, 0.40; 3.069, 0.30; 2.674, 2.65; 2.669, 3.49; 2.665, 2.73; 2.648, 9.73; 2.637, 9.75; 2.624, 0.76; 2.522, 15.33; 2.509, 193.86; 2.505, 357.03; 2.500, 461.13; 2.496, 320.77; 2.492, 155.57; 2.402, 0.75; 2.390, 0.54; 2.359, 0.52; 2.336, 1.43; 2.332, 2.50; 2.327, 3.12; 2.322, 2.42; 2.266, 0.33; 2.252, 0.33; 2.193, 15.00; 2.069, 2.84; 1.907, 0.30; 1.235, 0.40; 0.145, 0.36; 0.008, 2.67; −0.000, 61.09; −0.008, 3.10; −0.037, 0.32 |
| 285 | 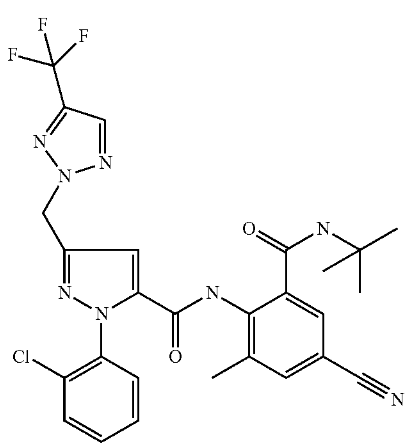 [SMILES: Cc1cc(C#N)cc(C(=O)NC(C)(C)C)c1NC(=O)c1cc(Cn2ncc(C(F)(F)F)n2)nn1-c1ccccc1Cl] | 3.93 | 585 | 10.261, 0.99; 8.520, 1.09; 7.810, 0.76; 7.807, 0.80; 7.731, 0.95; 7.683, 0.87; 7.679, 0.82; 7.567, 0.40; 7.553, 0.34; 7.549, 0.72; 7.546, 0.47; 7.482, 0.36; 7.475, 0.62; 7.471, 0.35; 7.468, 0.43; 7.457, 1.62; 7.456, 1.70; 7.451, 1.02; 7.440, 0.46; 7.184, 1.44; 5.936, 2.37; 3.309, 89.16; 2.522, 0.68; 2.509, 8.25; 2.505, 15.08; 2.500, 19.40; 2.496, 13.46; 2.492, 6.50; 2.185, 3.54; 2.069, 0.40; 1.199, 15.00; −0.000, 2.27 |

| No. | Structure | logP | MH+ | NMR |
|---|---|---|---|---|
| 286 | 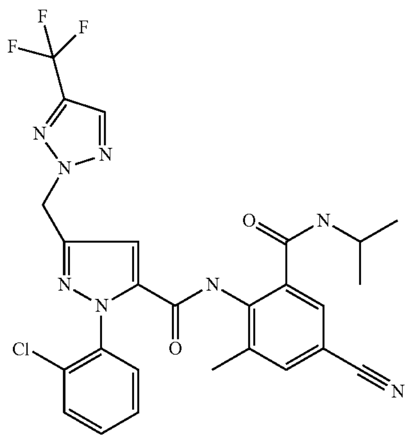 [SMILES: Cc1cc(C#N)cc(C(=O)NC(C)C)c1NC(=O)c1cc(Cn2ncc(C(F)(F)F)n2)nn1-c1ccccc1Cl] | 3.59 | 571 | 10.327, 3.34; 8.524, 3.62; 8.157, 1.46; 8.138, 1.49; 7.838, 2.60; 7.835, 2.67; 7.703, 2.93; 7.699, 2.72; 7.559, 1.52; 7.555, 0.98; 7.549, 0.60; 7.539, 2.09; 7.535, 1.49; 7.491, 0.85; 7.485, 1.03; 7.475, 1.41; 7.469, 2.43; 7.465, 1.39; 7.457, 2.97; 7.452, 4.25; 7.447, 2.65; 7.443, 2.33; 7.431, 1.42; 7.427, 0.88; 7.411, 0.39; 7.407, 0.32; 7.219, 4.66; 5.934, 8.11; 3.905, 0.66; 3.888, 1.01; 3.870, 1.00; 3.853, 0.70; 3.309, 432.31; 2.674, 0.51; 2.669, 0.64; 2.665, 0.49; 2.560, 0.39; 2.509, 39.22; 2.505, 70.24; 2.500, 88.64; 2.496, 61.23; 2.332, 0.50; 2.327, 0.63; 2.322, 0.46; 2.197, 11.82; 2.069, 0.49; 1.206, 0.36; 1.013, 15.00; 0.997, 14.86; 0.008, 0.58; −0.000, 11.07; −0.008, 0.49 |
| 287 | 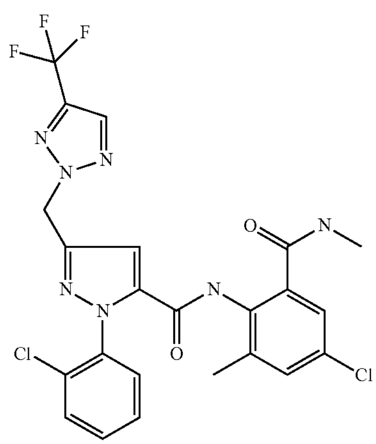 [SMILES: CNC(=O)c1cc(Cl)cc(C)c1NC(=O)c1cc(Cn2ncc(C(F)(F)F)n2)nn1-c1ccccc1Cl] | 3.45 | 552 | 10.117, 3.64; 8.524, 4.38; 8.219, 1.48; 8.207, 1.43; 7.568, 2.09; 7.563, 1.40; 7.557, 0.92; 7.549, 2.33; 7.544, 1.97; 7.490, 1.37; 7.485, 1.63; 7.480, 2.01; 7.469, 4.95; 7.466, 5.03; 7.462, 3.07; 7.452, 4.96; 7.447, 4.08; 7.443, 3.73; 7.437, 3.82; 7.430, 1.47; 7.416, 0.44; 7.411, 0.40; 7.316, 3.45; 7.310, 3.03; 7.183, 5.87; 5.924, 9.78; 3.308, 1072.11; 2.674, 1.25; 2.669, 1.53; 2.665, 1.17; 2.639, 9.58; 2.628, 9.70; 2.582, 0.44; 2.522, 6.64; 2.509, 89.94; 2.505, 164.52; 2.500, 211.41; 2.496, 146.87; 2.492, 71.65; 2.332, 1.14; 2.327, 1.53; 2.322, 1.13; 2.139, 15.00; 2.069, 0.64; 0.008, 1.06; −0.000, 24.82; −0.008, 1.28 |
| 288 | 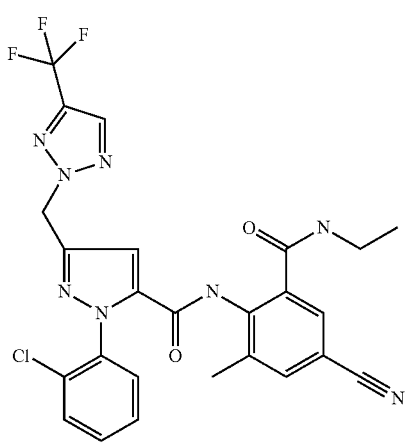 [SMILES: CCNC(=O)c1cc(C#N)cc(C)c1NC(=O)c1cc(Cn2ncc(C(F)(F)F)n2)nn1-c1ccccc1Cl] | 3.30 | 557 | 10.370, 4.47; 9.034, 0.97; 8.523, 6.11; 8.331, 2.18; 7.842, 4.20; 7.784, 0.37; 7.753, 0.35; 7.725, 4.20; 7.585, 0.33; 7.565, 2.76; 7.545, 3.56; 7.541, 3.16; 7.522, 0.43; 7.493, 1.79; 7.486, 2.81; 7.480, 3.30; 7.465, 6.16; 7.462, 5.06; 7.451, 5.27; 7.435, 1.77; 7.430, 1.94; 7.415, 0.77; 7.212, 4.37; 5.954, 0.50; 5.931, 11.18; 5.867, 1.60; 3.589, 0.31; 3.570, 0.33; 3.563, 0.39; 3.550, 0.32; 3.518, 0.38; 3.507, 0.46; 3.484, 0.52; 3.433, 0.81; 3.414, 1.08; 3.406, 1.29; 3.398, 1.55; 3.311, 1479.81; 3.210, 0.65; 3.160, 1.45; 3.143, 4.04; 3.129, 4.92; 3.125, 4.82; 3.111, 3.97; 3.092, 1.36; 2.673, 1.23; 2.669, 1.48; 2.665, 1.29; 2.608, 0.42; 2.540, 2.70; 2.505, 165.45; 2.500, 215.43; 2.497, 166.64; 2.403, 0.42; 2.398, 0.42; 2.384, 0.40; 2.378, 0.42; 2.359, 0.32; 2.349, 0.35; 2.332, 1.16; 2.327, 1.52; 2.281, 0.56; 2.224, 0.53; 2.193, 15.00; 2.146, 0.39; 2.128, 0.58; 2.069, 1.46; 1.237, 0.67; 1.034, 0.40; 0.995, 6.44; 0.977, 12.76; 0.959, 6.27; 0.941, 0.49; −0.000, 10.27 |

| No. | Structure | logP | MH+ | NMR |
|---|---|---|---|---|
| 289 | 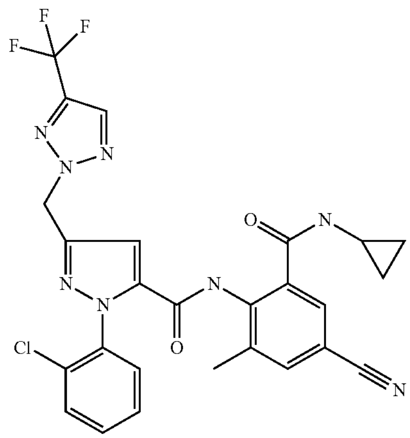 [SMILES: Cc1cc(C#N)cc(C(=O)NC2CC2)c1NC(=O)c1cc(Cn2ncc(C(F)(F)F)n2)nn1-c1ccccc1Cl] | 3.30 | 569 | 10.334, 4.19; 8.528, 4.63; 8.363, 2.21; 8.353, 2.11; 7.836, 3.47; 7.690, 3.79; 7.686, 3.53; 7.569, 1.80; 7.564, 1.34; 7.549, 2.76; 7.545, 1.79; 7.497, 1.68; 7.490, 2.53; 7.476, 6.11; 7.459, 4.81; 7.454, 3.08; 7.446, 1.35; 7.437, 1.58; 7.423, 0.45; 7.419, 0.42; 7.227, 5.38; 5.939, 10.16; 3.732, 0.39; 3.480, 0.83; 3.431, 1.05; 3.418, 1.31; 3.309, 1489.15; 3.155, 0.63; 3.134, 0.51; 3.111, 0.39; 3.067, 0.33; 2.986, 0.33; 2.670, 2.68; 2.664, 2.58; 2.653, 1.68; 2.644, 1.24; 2.635, 0.94; 2.625, 0.59; 2.605, 0.51; 2.539, 4.40; 2.504, 207.87; 2.500, 259.70; 2.496, 187.43; 2.357, 0.50; 2.351, 0.54; 2.331, 1.59; 2.327, 2.00; 2.323, 1.62; 2.300, 0.41; 2.287, 0.33; 2.249, 0.33; 2.193, 15.00; 2.125, 0.37; 2.069, 3.25; 2.049, 0.52; 1.265, 0.34; 1.237, 0.60; 0.890, 0.30; 0.616, 0.88; 0.604, 2.71; 0.599, 3.47; 0.586, 3.44; 0.581, 2.87; 0.570, 1.14; 0.429, 1.24; 0.419, 3.61; 0.412, 3.56; 0.403, 3.06; 0.391, 0.98; −0.000, 22.02 |
| 290 | 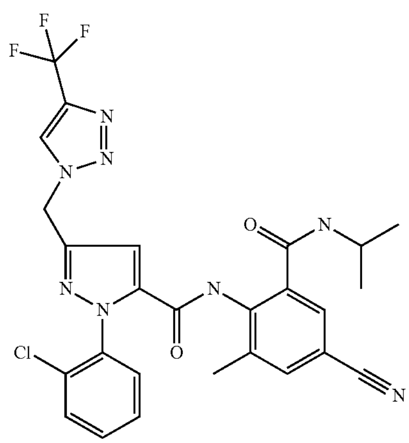 [SMILES: Cc1cc(C#N)cc(C(=O)NC(C)C)c1NC(=O)c1cc(Cn2cc(C(F)(F)F)nn2)nn1-c1ccccc1Cl] | 3.17 | 571 | 10.344, 3.27; 10.317, 0.33; 9.031, 3.56; 9.029, 3.49; 8.181, 1.45; 8.162, 1.48; 7.840, 2.57; 7.837, 2.79; 7.711, 2.80; 7.707, 2.70; 7.561, 1.32; 7.556, 1.05; 7.540, 2.21; 7.537, 1.55; 7.531, 0.56; 7.496, 1.16; 7.489, 1.31; 7.487, 1.49; 7.472, 4.88; 7.455, 2.57; 7.452, 2.68; 7.448, 2.59; 7.440, 0.78; 7.436, 0.86; 7.430, 1.50; 7.416, 0.52; 7.412, 0.52; 7.408, 0.40; 7.231, 4.83; 7.190, 0.36; 5.933, 0.68; 5.870, 8.45; 3.911, 0.62; 3.894, 0.98; 3.876, 0.99; 3.859, 0.65; 3.308, 507.32; 2.674, 0.52; 2.669, 0.69; 2.665, 0.48; 2.522, 3.25; 2.509, 40.80; 2.505, 73.83; 2.500, 93.89; 2.496, 64.58; 2.492, 30.96; 2.332, 0.51; 2.327, 0.67; 2.322, 0.50; 2.192, 11.94; 2.069, 1.24; 1.079, 0.31; 1.062, 0.34; 1.020, 15.00; 1.004, 14.98; 0.992, 1.65; 0.008, 0.48; −0.000, 9.27; −0.008, 0.37 |
| 291 | 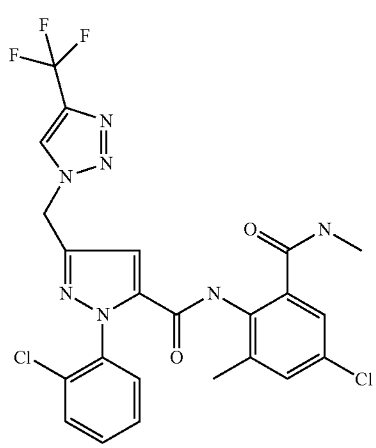 [SMILES: CNC(=O)c1cc(Cl)cc(C)c1NC(=O)c1cc(Cn2cc(C(F)(F)F)nn2)nn1-c1ccccc1Cl] | 3.08 | 552 | 10.122, 3.58; 10.107, 0.63; 9.038, 4.10; 8.519, 0.44; 8.233, 1.45; 8.222, 1.48; 8.210, 0.69; 7.569, 1.65; 7.564, 1.98; 7.559, 0.50; 7.552, 1.87; 7.550, 2.25; 7.547, 2.38; 7.504, 1.30; 7.499, 1.25; 7.497, 1.28; 7.492, 1.12; 7.486, 3.04; 7.481, 3.47; 7.473, 3.43; 7.467, 2.02; 7.455, 4.49; 7.451, 3.67; 7.448, 3.01; 7.444, 3.54; 7.438, 5.02; 7.434, 2.85; 7.423, 0.81; 7.419, 0.96; 7.415, 0.87; 7.323, 3.37; 7.317, 3.19; 7.307, 0.56; 7.197, 5.86; 7.157, 0.68; 5.922, 1.02; 5.860, 10.14; 3.365, 0.71; 3.311, 600.28; 3.224, 0.45; 2.674, 0.68; 2.669, 0.87; 2.665, 0.74; 2.661, 0.52; 2.643, 9.71; 2.631, 9.94; 2.522, 3.38; 2.509, 44.03; 2.505, 80.60; 2.500, 103.73; 2.496, 71.60; 2.491, 34.68; 2.331, 0.57; 2.327, 0.76; 2.322, 0.57; 2.136, 15.00; 2.069, 0.46; 0.008, 0.51; −0.000, 10.73; −0.008, 0.41 |

| No. | Structure | logP | MH+ | NMR |
|---|---|---|---|---|
| 292 | 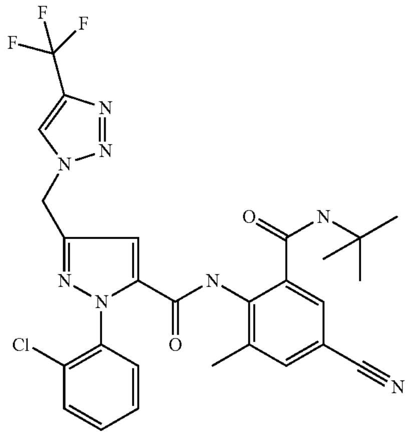 [SMILES: Cc1cc(C#N)cc(C(=O)NC(C)(C)C)c1NC(=O)c1cc(Cn2cc(C(F)(F)F)nn2)nn1-c1ccccc1Cl] | 3.48 | 585 | 10.271, 0.99; 9.016, 1.08; 9.014, 1.06; 8.092, 1.45; 7.812, 0.78; 7.809, 0.86; 7.764, 0.91; 7.690, 0.85; 7.686, 0.82; 7.571, 0.44; 7.568, 0.31; 7.552, 0.54; 7.548, 0.48; 7.494, 0.34; 7.489, 0.44; 7.478, 1.13; 7.475, 1.22; 7.471, 0.79; 7.462, 1.14; 7.456, 0.88; 7.450, 0.32; 7.439, 0.41; 7.199, 1.50; 7.159, 1.53; 6.208, 2.33; 6.004, 0.34; 5.874, 2.49; 3.861, 4.29; 3.851, 0.75; 3.845, 0.83; 3.309, 29.62; 2.523, 1.32; 2.509, 16.20; 2.505, 29.55; 2.500, 37.94; 2.496, 26.18; 2.492, 12.64; 2.246, 0.49; 2.181, 3.66; 2.069, 0.88; 1.243, 0.38; 1.206, 15.00; 1.193, 1.72; 0.008, 0.35; −0.000, 6.93 |
| 293 | 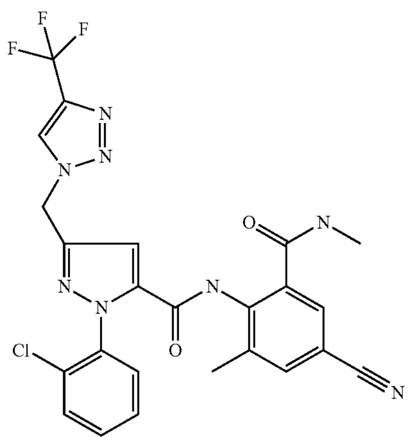 [SMILES: CNC(=O)c1cc(C#N)cc(C)c1NC(=O)c1cc(Cn2cc(C(F)(F)F)nn2)nn1-c1ccccc1Cl] | 2.63 | 543 | 10.393, 0.53; 9.042, 4.54; 8.523, 0.40; 8.353, 0.90; 7.844, 3.22; 7.742, 3.49; 7.738, 3.35; 7.573, 1.68; 7.568, 1.99; 7.553, 2.14; 7.550, 2.63; 7.541, 0.45; 7.515, 1.45; 7.509, 1.32; 7.508, 1.28; 7.497, 2.89; 7.491, 4.41; 7.478, 3.05; 7.472, 2.08; 7.461, 4.01; 7.456, 3.03; 7.448, 0.95; 7.443, 1.99; 7.439, 2.01; 7.425, 0.93; 7.421, 0.66; 7.227, 4.82; 7.187, 0.40; 5.931, 0.91; 5.869, 10.82; 3.321, 436.58; 3.298, 5.08; 3.281, 1.00; 2.675, 0.54; 2.670, 0.74; 2.654, 9.49; 2.643, 9.60; 2.621, 0.58; 2.523, 2.08; 2.510, 23.70; 2.506, 43.02; 2.501, 54.68; 2.497, 37.82; 2.493, 18.28; 2.328, 0.38; 2.189, 15.00; 2.069, 0.47; −0.000, 5.19 |
| 294 | 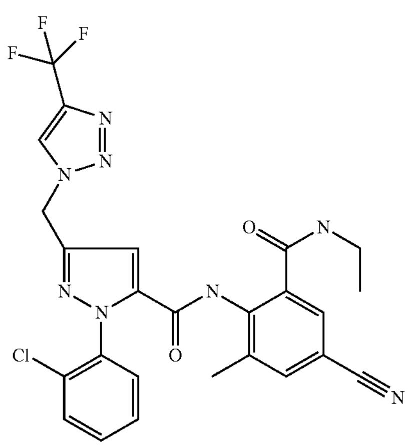 [SMILES: CCNC(=O)c1cc(C#N)cc(C)c1NC(=O)c1cc(Cn2cc(C(F)(F)F)nn2)nn1-c1ccccc1Cl] | 2.92 | 557 | 10.380, 4.15; 10.355, 0.44; 9.036, 4.51; 9.034, 4.27; 8.523, 0.45; 8.361, 1.02; 8.347, 1.94; 8.334, 0.98; 8.315, 0.31; 7.846, 3.27; 7.843, 3.52; 7.734, 3.60; 7.729, 3.31; 7.716, 0.48; 7.567, 1.73; 7.562, 1.96; 7.547, 2.43; 7.545, 2.35; 7.533, 0.51; 7.505, 1.54; 7.500, 1.47; 7.495, 1.20; 7.488, 2.61; 7.482, 3.60; 7.476, 3.50; 7.470, 1.86; 7.457, 4.29; 7.451, 3.76; 7.439, 1.54; 7.434, 1.76; 7.420, 0.91; 7.226, 6.11; 7.185, 0.55; 5.931, 1.03; 5.868, 10.67; 3.601, 0.45; 3.503, 0.35; 3.492, 0.33; 3.481, 0.35; 3.308, 1051.70; 3.254, 1.31; 3.193, 0.35; 3.164, 1.02; 3.147, 2.63; 3.132, 2.97; 3.128, 3.00; 3.115, 2.74; 3.096, 0.94; 2.674, 1.00; 2.669, 1.31; 2.665, 0.98; 2.608, 0.32; 2.559, 0.83; 2.539, 2.25; 2.522, 6.27; 2.509, 75.55; 2.505, 136.92; 2.500, 175.21; 2.496, 119.75; 2.491, 57.51; 2.331, 0.96; 2.327, 1.25; 2.322, 0.95; 2.291, 0.34; 2.282, 0.46; 2.190, 15.00; 2.128, 0.47; 2.069, 1.44; 1.760, 0.36; 1.237, 0.32; 1.035, 0.43; 1.016, 0.39; 1.004, 5.74; 0.986, 12.27; 0.968, 5.63; 0.954, 0.73; −0.000, 1.68 |

| No. | Structure | logP | MH+ | NMR |
|---|---|---|---|---|
| 295 | 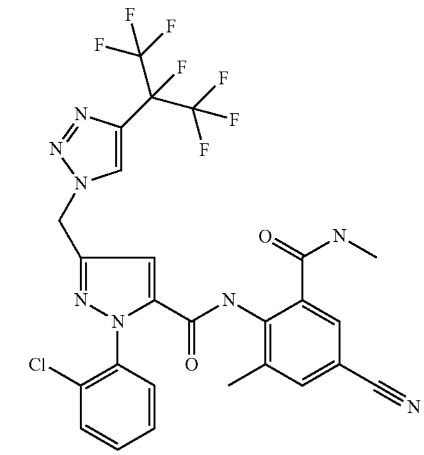 [SMILES: CNC(=O)c1cc(C#N)cc(C)c1NC(=O)c1cc(Cn2cc(C(F)(C(F)(F)F)C(F)(F)F)nn2)nn1-c1ccccc1Cl] | 3.46 | 643 | 10.440, 4.12; 9.032, 5.85; 8.471, 0.45; 8.352, 1.69; 8.340, 1.64; 7.849, 3.30; 7.846, 3.44; 7.736, 3.81; 7.736, 3.47; 7.576, 1.81; 7.571, 1.89; 7.556, 2.40; 7.522, 0.48; 7.505, 1.78; 7.498, 2.00; 7.492, 2.19; 7.488, 2.66; 7.483, 4.23; 7.478, 4.07; 7.472, 1.94; 7.461, 4.80; 7.456, 3.10; 7.444, 1.47; 7.439, 1.48; 7.425, 0.53; 7.421, 0.45; 7.242, 5.59; 7.230, 0.58; 5.887, 10.57; 3.311, 325.89; 3.177, 0.38; 3.163, 0.33; 2.674, 0.79; 2.670, 0.98; 2.664, 1.03; 2.649, 9.55; 2.638, 9.44; 2.540, 4.44; 2.505, 69.64; 2.500, 86.55; 2.496, 61.36; 2.437, 0.36; 2.332, 0.54; 2.327, 0.65; 2.191, 15.00; 2.122, 0.56; 2.069, 0.45; −0.000, 2.85 |
| 296 | 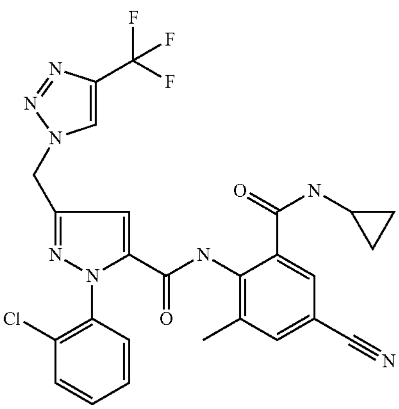 [SMILES: Cc1cc(C#N)cc(C(=O)NC2CC2)c1NC(=O)c1cc(Cn2cc(C(F)(F)F)nn2)nn1-c1ccccc1Cl] | 2.93 | 269 | 10.349, 4.27; 9.043, 4.67; 8.379, 2.24; 8.369, 2.17; 7.836, 3.50; 7.697, 3.79; 7.693, 3.48; 7.571, 1.71; 7.567, 1.89; 7.551, 2.18; 7.548, 2.61; 7.516, 1.45; 7.510, 1.42; 7.498, 2.75; 7.493, 4.15; 7.479, 2.97; 7.473, 1.99; 7.463, 3.54; 7.458, 2.84; 7.446, 1.78; 7.442, 1.38; 7.427, 0.51; 7.423, 0.37; 7.237, 5.67; 5.875, 10.76; 3.786, 0.63; 3.496, 0.37; 3.483, 0.41; 3.464, 0.49; 3.458, 0.53; 3.311, 1111.68; 3.207, 0.75; 3.153, 0.38; 3.143, 0.37; 3.116, 0.30; 2.725, 0.37; 2.713, 0.37; 2.688, 0.79; 2.679, 1.53; 2.670, 2.65; 2.660, 2.00; 2.652, 1.17; 2.642, 0.90; 2.632, 0.49; 2.539, 3.01; 2.505, 141.63; 2.500, 177.31; 2.496, 127.52; 2.410, 0.52; 2.401, 0.46; 2.331, 1.11; 2.327, 1.34; 2.323, 1.08; 2.300, 0.60; 2.241, 0.55; 2.189, 15.00; 2.069, 2.02; 2.049, 0.35; 1.238, 0.31; 0.622, 0.89; 0.609, 2.68; 0.604, 3.51; 0.592, 3.36; 0.586, 2.90; 0.575, 1.19; 0.438, 1.19; 0.427, 3.51; 0.421, 3.48; 0.412, 3.12; 0.399, 1.03; −0.000, 15.55 |
| 297 | 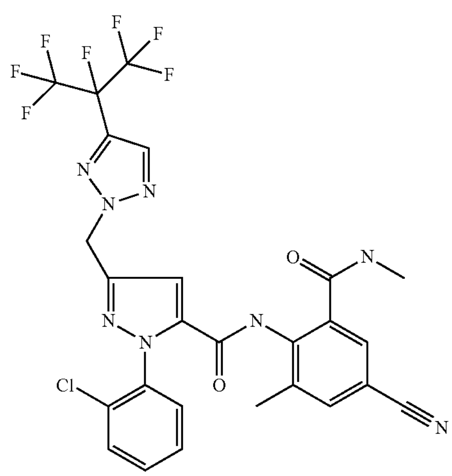 [SMILES: CNC(=O)c1cc(C#N)cc(C)c1NC(=O)c1cc(Cn2ncc(C(F)(C(F)(F)F)C(F)(F)F)n2)nn1-c1ccccc1Cl] | 3.88 | 643 | 10.424, 4.11; 8.510, 8.88; 8.338, 1.90; 7.876, 0.42; 7.845, 3.88; 7.789, 0.37; 7.776, 0.36; 7.735, 4.26; 7.569, 2.66; 7.550, 3.43; 7.546, 2.67; 7.494, 1.54; 7.486, 1.97; 7.472, 4.47; 7.461, 6.73; 7.455, 10.23; 7.441, 2.26; 7.419, 0.62; 7.193, 4.09; 5.957, 11.89; 3.763, 0.40; 3.744, 0.53; 3.713, 0.35; 3.710, 0.33; 3.664, 0.45; 3.646, 0.42; 3.640, 0.42; 3.630, 0.43; 3.618, 0.44; 3.593, 0.55; 3.582, 0.57; 3.557, 0.60; 3.536, 0.69; 3.517, 0.76; 3.509, 0.97; 3.485, 0.99; 3.476, 1.01; 3.443, 1.39; 3.309, 1997.77; 3.165, 0.56; 3.147, 0.53; 3.139, 0.54; 3.131, 0.44; 3.126, 0.40; 3.108, 0.44; 2.806, 0.36; 2.733, 0.37; 2.728, 0.34; 2.719, 0.39; 2.697, 0.63; 2.669, 2.79; 2.665, 2.45; 2.647, 15.00; 2.635, 14.92; 2.585, 1.13; 2.539, 15.02; 2.505, 271.69; 2.500, 338.78; 2.496, 241.66; 2.363, 0.57; 2.327, 2.65; 2.322, 1.95; 2.294, 0.59; 2.286, 0.76; 2.274, 0.49; 2.187, 14.75; 2.134, 0.69; 2.118, 0.43; 2.088, 0.44; 2.069, 1.59; 2.049, 0.92; 1.987, 0.42; 1.908, 0.44; 1.293, 0.54; 1.237, 1.02; 1.195, 0.59; 1.160, 0.46; 1.071, 0.48; 0.891, 0.55; −0.000, 12.54 |

| No. | Structure | logP | MH+ | NMR |
|---|---|---|---|---|
| 298 | 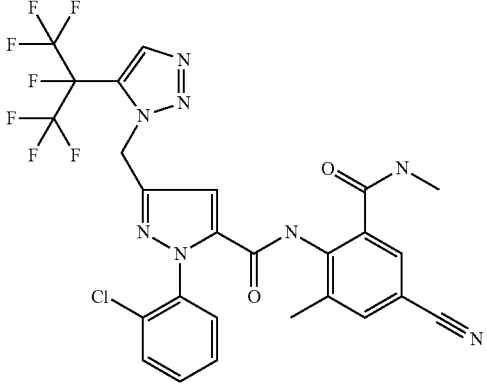 [SMILES: CNC(=O)c1cc(C#N)cc(C)c1NC(=O)c1cc(Cn2nncc2C(F)(C(F)(F)F)C(F)(F)F)nn1-c1ccccc1Cl] | 3.46 | 643 | 10.461, 0.05; 10.409, 0.01; 9.063, 0.08; 8.575, 0.01; 8.567, 0.01; 8.510, 0.05; 8.498, 0.40; 8.479, 0.01; 8.394, 0.01; 8.387, 0.02; 8.380, 0.02; 8.371, 0.01; 7.861, 0.05; 7.742, 0.05; 7.740, 0.05; 7.732, 0.01; 7.636, 0.12; 7.622, 0.18; 7.584, 0.02; 7.575, 0.03; 7.571, 0.03; 7.562, 0.03; 7.550, 0.06; 7.547, 0.07; 7.535, 0.13; 7.525, 0.13; 7.523, 0.13; 7.514, 0.19; 7.505, 0.03; 7.502, 0.03; 7.492, 0.17; 7.480, 0.17; 7.467, 0.07; 7.460, 0.03; 7.458, 0.03; 7.448, 0.04; 7.440, 0.04; 7.437, 0.04; 7.428, 0.01; 7.403, 0.01; 7.400, 0.01; 7.250, 0.06; 7.167, 0.01; 6.953, 0.07; 6.938, 0.19; 5.984, 0.01; 5.910, 0.58; 5.892, 0.22; 3.669, 0.01; 3.660, 0.01; 3.618, 0.01; 3.595, 0.01; 3.543, 0.02; 3.362, 13.50; 3.172, 0.03; 3.164, 0.03; 3.142, 0.01; 3.134, 0.01; 3.047, 0.01; 2.696, 0.01; 2.641, 0.13; 2.633, 0.15; 2.623, 0.10; 2.619, 0.05; 2.616, 0.06; 2.543, 0.14; 2.525, 0.11; 2.522, 0.14; 2.519, 0.15; 2.507, 7.14; 2.504, 9.36; 2.502, 7.04; 2.388, 0.06; 2.192, 0.22; 2.181, 0.03; 2.076, 0.02; 1.910, 0.03; 1.235, 0.02 |
| 299 | 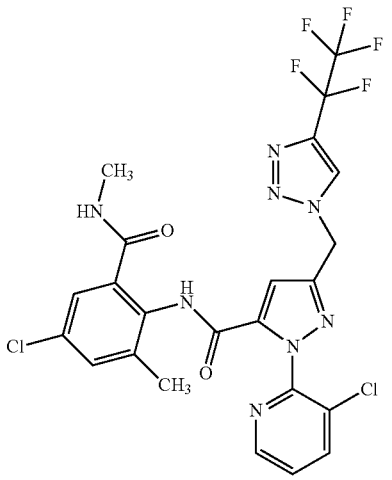 [SMILES: CNC(=O)c1cc(Cl)cc(C)c1NC(=O)c1cc(Cn2cc(C(F)(F)C(F)(F)F)nn2)nn1-c1ncccc1Cl] | 3.02 | 603 | (10.22; 2.29), (9.10; 4.51), (8.47; 2.68), (8.47; 2.77), (8.46; 2.84), (8.46; 2.69), (8.19; 1.27), (8.17; 1.23), (8.15; 2.60), (8.14; 2.59), (8.13; 2.86), (8.12; 2.66), (7.59; 2.69), (7.58; 2.62), (7.57; 2.53), (7.56; 2.48), (7.44; 2.72), (7.44; 2.92), (7.32; 3.28), (7.32; 3.01), (7.24; 5.37), (5.90; 9.86), (4.40; 0.40), (3.37; 0.51), (3.35; 0.58), (3.34; 0.53), (3.29; 489.01), (3.26; 3.49), (2.67; 0.88), (2.67; 1.20), (2.66; 1.11), (2.65; 9.66), (2.64; 9.53), (2.55; 1.27), (2.54; 1.65), (2.54; 1.64), (2.52; 3.88), (2.51; 57.78), (2.50; 112.98), (2.50; 150.45), (2.49; 106.87), (2.49; 50.89), (2.33; 0.42), (2.33; 0.76), (2.33; 1.01), (2.32; 0.73), (2.14; 15.00), (2.10; 0.34), (2.08; 0.48), (2.07; 1.54), (2.06; 0.36), (1.62; 0.33), (0.01; 0.80), (0.00; 16.70), (−0.01; 0.63) |

| No. | Structure | logP | MH+ | NMR |
|---|---|---|---|---|
| 300 | 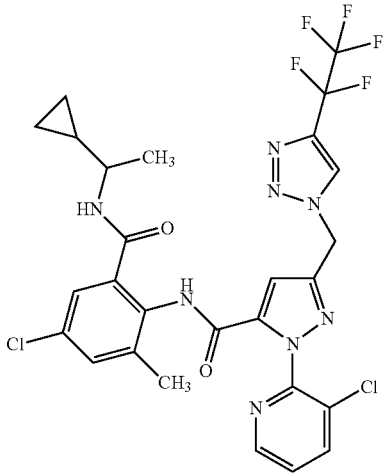 [SMILES: Cc1cc(Cl)cc(C(=O)NC(C)C2CC2)c1NC(=O)c1cc(Cn2cc(C(F)(F)C(F)(F)F)nn2)nn1-c1ncccc1Cl] | 3.79 | 657 | (10.15; 0.62), (9.07; 4.70), (8.46; 2.74), (8.46; 2.91), (8.45; 2.91), (8.45; 2.79), (8.14; 2.65), (8.13; 2.59), (8.12; 2.92), (8.11; 2.69), (8.06; 0.79), (8.04; 0.80), (7.59; 2.77), (7.58; 2.68), (7.57; 2.61), (7.56; 2.52), (7.44; 2.76), (7.44; 2.92), (7.28; 3.22), (7.28; 3.01), (7.24; 5.21), (6.87; 0.51), (5.89; 10.08), (3.36; 0.37), (3.32; 1.51), (3.29; 367.87), (3.26; 2.79), (2.68; 0.34), (2.67; 0.66), (2.67; 0.86), (2.66; 0.64), (2.66; 0.35), (2.56; 0.33), (2.54; 1.31), (2.52; 3.53), (2.51; 47.02), (2.50; 91.28), (2.50; 121.11), (2.49; 85.57), (2.49; 40.17), (2.33; 0.56), (2.33; 0.75), (2.32; 0.54), (2.18; 0.88), (2.14; 15.00), (2.07; 0.60), (1.36; 6.60), (1.22; 0.35), (1.20; 0.35), (1.05; 8.86), (1.03; 8.68), (0.86; 0.70), (0.84; 0.67), (0.83; 0.55), (0.82; 0.69), (0.81; 0.76), (0.81; 0.81), (0.80; 1.20), (0.79; 0.78), (0.79; 0.83), (0.78; 1.20), (0.77; 0.69), (0.76; 0.47), (0.37; 0.42), (0.36; 0.57), (0.35; 0.60), (0.34; 1.27), (0.34; 1.02), (0.33; 1.06), (0.32; 1.28), (0.32; 0.61), (0.31; 0.66), (0.30; 0.52), (0.22; 0.40), (0.21; 0.69), (0.21; 0.68), (0.20; 0.98), (0.19; 1.05), (0.19; 1.00), (0.18; 1.37), (0.17; 1.09), (0.16; 1.27), (0.15; 1.76), (0.14; 1.42), (0.13; 1.21), (0.11; 1.36), (0.11; 1.30), (0.10; 0.74), (0.09; 0.88), (0.08; 0.51), (0.01; 0.96), (0.00; 19.56), (−0.01; 0.66) |
| 301 | 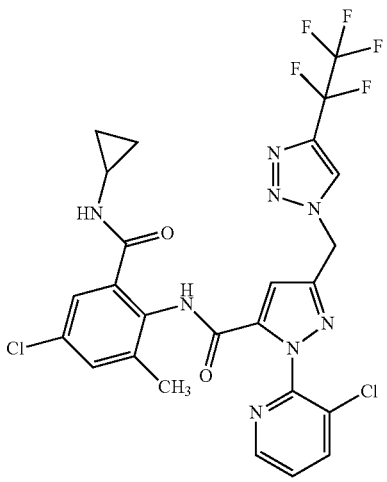 | 3.26 | 629 | (10.16; 2.50), (9.10; 4.84), (8.47; 2.80), (8.47; 2.94), (8.46; 2.99), (8.46; 2.86), (8.23; 1.68), (8.22; 1.65), (8.14; 2.64), (8.14; 2.61), (8.12; 2.90), (8.12; 2.70), (7.59; 2.82), (7.58; 2.74), (7.57; 2.64), (7.56; 2.58), (7.43; 2.80), (7.43; 2.93), (7.27; 3.30), (7.26; 3.17), (7.25; 5.27), (5.90; 10.18), (4.50; 0.41), (4.49; 0.85), (4.47; 0.44), (3.61; 0.37), (3.60; 0.48), (3.59; 0.79), (3.59; 0.49), (3.58; 0.78), (3.58; 0.52), (3.57; 0.47), (3.56; 0.40), (3.29; 523.10), (3.26; 3.31), (2.70; 0.31), (2.69; 0.76), (2.68; 1.09), (2.67; 2.20), (2.67; 1.68), (2.66; 2.20), (2.65; 1.07), (2.64; 0.78), (2.63; 0.39), (2.60; 0.33), (2.59; 0.35), (2.58; 0.37), (2.57; 0.45), (2.54; 1.78), (2.52; 4.65), (2.51; 62.16), (2.50; 120.43), (2.50; 159.53), (2.49; 112.46), (2.49; 52.67), (2.33; 0.75), (2.33; 1.00), (2.32; 0.69), (2.22; 0.60), (2.20; 1.19), (2.18; 0.76), (2.16; 0.70), (2.14; 15.00), (2.07; 1.83), (1.75; 0.92), (1.74; 1.06), (0.61; 0.98), (0.59; 2.73), (0.59; 3.73), (0.58; 3.47), (0.57; 2.94), (0.56; 1.21), (0.43; 1.20), (0.42; 3.43), (0.41; 3.26), (0.40; 2.84), (0.39; 0.88), (0.37; 0.32), (0.36; 0.35), (0.36; 0.38), (0.01; 1.06), (0.00; 21.55), (−0.01; 0.71) |

-continued

| No. | Structure | logP | MH+ | NMR |
|---|---|---|---|---|
| 302 | 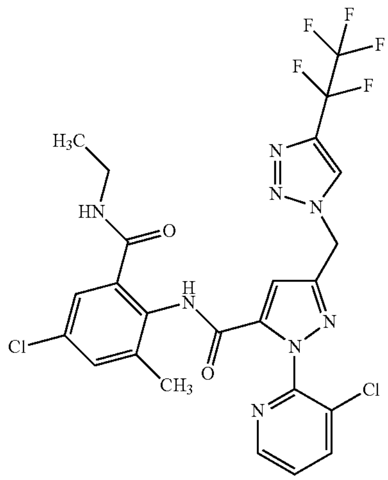 [SMILES: CCNC(=O)c1cc(Cl)cc(C)c1NC(=O)c1cc(Cn2cc(C(F)(F)C(F)(F)F)nn2)nn1-c1ncccc1Cl] | 3.26 | 617 | (10.19; 2.03), (9.09; 4.63), (8.47; 2.72), (8.46; 2.89), (8.46; 2.93), (8.45; 2.83), (8.19; 0.78), (8.17; 1.39), (8.14; 2.65), (8.14; 2.59), (8.12; 2.90), (8.12; 2.72), (7.59; 2.72), (7.58; 2.64), (7.57; 2.55), (7.56; 2.53), (7.44; 2.67), (7.43; 2.86), (7.31; 3.19), (7.30; 2.92), (7.24; 4.81), (6.87; 0.54), (6.60; 0.34), (5.89; 9.99), (3.34; 0.61), (3.29; 645.87), (3.27; 3.78), (3.25; 0.64), (3.24; 0.46), (3.16; 0.85), (3.14; 2.62), (3.13; 2.96), (3.12; 2.94), (3.11; 2.65), (3.09; 0.86), (2.67; 0.67), (2.67; 0.87), (2.66; 0.62), (2.54; 1.30), (2.52; 3.41), (2.51; 49.31), (2.50; 96.15), (2.50; 128.09), (2.49; 91.07), (2.49; 43.25), (2.33; 0.66), (2.33; 0.83), (2.32; 0.59), (2.18; 0.97), (2.14; 15.00), (2.07; 1.24), (1.36; 6.84), (1.24; 0.35), (0.99; 5.62), (0.97; 12.05), (0.96; 5.46), (0.89; 0.32), (0.00; 1.51) |
| 303 | 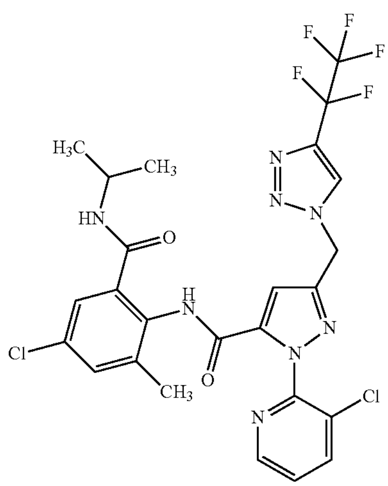 [SMILES: Cc1cc(Cl)cc(C(=O)NC(C)C)c1NC(=O)c1cc(Cn2cc(C(F)(F)C(F)(F)F)nn2)nn1-c1ncccc1Cl] | 3.5 | 631 | (10.15; 1.21), (9.08; 3.45), (8.46; 1.98), (8.46; 2.11), (8.45; 2.13), (8.45; 2.05), (8.14; 1.92), (8.13; 1.89), (8.12; 2.15), (8.11; 1.95), (7.99; 0.86), (7.97; 0.87), (7.59; 2.03), (7.58; 1.99), (7.57; 1.91), (7.56; 1.87), (7.43; 2.01), (7.43; 2.12), (7.28; 2.33), (7.28; 2.16), (7.24; 3.76), (5.90; 7.46), (3.91; 0.58), (3.90; 0.91), (3.88; 0.90), (3.86; 0.60), (3.28; 385.16), (3.26; 2.97), (2.67; 0.71), (2.67; 0.94), (2.66; 0.68), (2.54; 1.29), (2.52; 3.77), (2.51; 53.40), (2.50; 103.92), (2.50; 137.84), (2.49; 97.57), (2.49; 45.85), (2.33; 0.35), (2.33; 0.68), (2.33; 0.90), (2.32; 0.63), (2.32; 0.32), (2.14; 11.00), (2.07; 0.94), (1.01; 15.00), (0.99; 14.79), (0.01; 1.03), (0.00; 21.32), (−0.01; 0.76) |
| 304 | 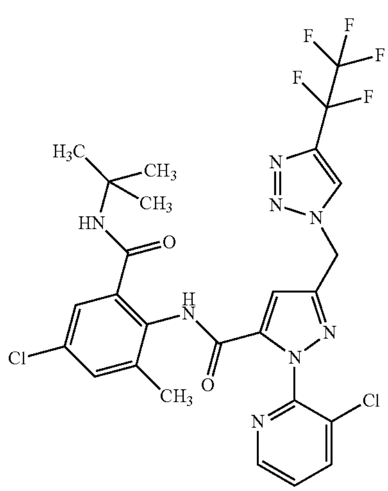 [SMILES: Cc1cc(Cl)cc(C(=O)NC(C)(C)C)c1NC(=O)c1cc(Cn2cc(C(F)(F)C(F)(F)F)nn2)nn1-c1ncccc1Cl] | 3.85 | 645 | (10.12; 0.87), (9.06; 1.16), (8.47; 0.70), (8.46; 0.70), (8.46; 0.72), (8.45; 0.68), (8.15; 0.62), (8.15; 0.62), (8.13; 0.70), (8.13; 0.64), (7.60; 0.66), (7.58; 0.65), (7.58; 0.63), (7.56; 0.61), (7.51; 0.86), (7.41; 0.71), (7.40; 0.76), (7.24; 0.85), (7.23; 0.77), (7.20; 1.66), (5.90; 2.51), (3.29; 63.65), (3.27; 0.48), (2.52; 0.57), (2.51; 7.99), (2.50; 15.48), (2.50; 20.42), (2.49; 14.47), (2.49; 6.81), (2.18; 0.43), (2.13; 3.63), (2.07; 0.48), (1.36; 3.37), (1.25; 0.57), (1.20; 15.00), (0.00; 1.45) |

| No. | Structure | logP | MH+ | NMR |
|---|---|---|---|---|
| 305 | 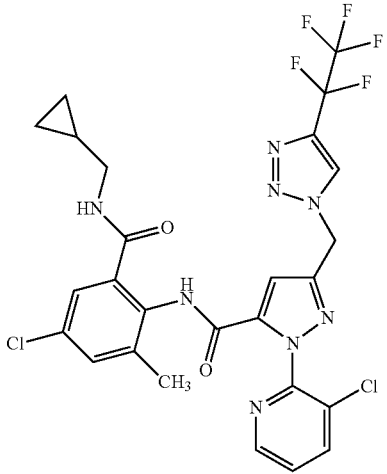 [SMILES: Cc1cc(Cl)cc(C(=O)NCC2CC2)c1NC(=O)c1cc(Cn2cc(C(F)(F)C(F)(F)F)nn2)nn1-c1ncccc1Cl] | 3.55 | 643 | (10.184; 1.05), (9.089; 0.30), (9.076; 4.74), (8.459; 2.72), (8.455; 2.89), (8.448; 2.92), (8.444; 2.84), (8.241; 1.07), (8.228; 0.76), (8.135; 2.61), (8.131; 2.60), (8.115; 2.89), (8.111; 2.62), (7.587; 2.73), (7.576; 2.60), (7.567; 2.49), (7.555; 2.44), (7.447; 2.71), (7.441; 2.88), (7.313; 3.22), (7.308; 2.99), (7.239; 4.73), (5.886; 10.27), (3.455; 0.32), (3.436; 0.45), (3.414; 0.58), (3.398; 0.63), (3.381; 0.89), (3.299; 1515.35), (3.276; 7.53), (3.230; 0.45), (3.221; 0.42), (3.214; 0.32), (3.207; 0.34), (2.999; 2.87), (2.983; 4.22), (2.967; 2.86), (2.672; 0.97), (2.667; 1.30), (2.663; 0.86), (2.537; 2.00), (2.520; 5.29), (2.507; 72.61), (2.503; 140.42), (2.498; 185.43), (2.494; 131.18), (2.489; 61.61), (2.330; 0.88), (2.325; 1.15), (2.320; 0.84), (2.143; 15.00), (2.065; 1.40), (2.047; 0.32), (0.889; 0.51), (0.877; 0.31), (0.871; 0.42), (0.860; 0.72), (0.853; 0.77), (0.841; 1.10), (0.829; 0.69), (0.824; 0.72), (0.811; 0.42), (0.311; 1.07), (0.300; 2.99), (0.296; 3.20), (0.286; 1.68), (0.280; 3.11), (0.276; 2.84), (0.266; 1.12), (0.115; 1.28), (0.101; 3.62), (0.092; 3.19), (0.089; 3.55), (0.077; 0.83), (−0.002; 0.82) |
| 306 | 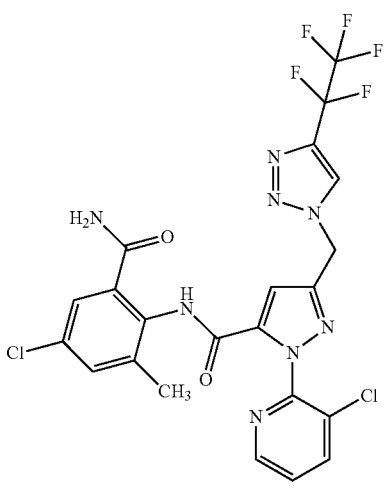 [SMILES: Cc1cc(Cl)cc(C(N)=O)c1NC(=O)c1cc(Cn2cc(C(F)(F)C(F)(F)F)nn2)nn1-c1ncccc1Cl] | 2.78 | 589 | (10.26; 1.59), (9.09; 3.78), (8.48; 2.27), (8.48; 2.38), (8.47; 2.45), (8.47; 2.32), (8.15; 2.21), (8.14; 2.21), (8.13; 2.47), (8.12; 2.27), (7.69; 1.40), (7.59; 2.34), (7.58; 2.28), (7.57; 2.18), (7.56; 2.17), (7.45; 3.04), (7.44; 4.03), (7.39; 3.10), (7.39; 2.60), (7.24; 4.68), (6.87; 1.20), (6.60; 0.71), (5.89; 8.41), (5.74; 0.30), (3.37; 0.38), (3.35; 0.60), (3.30; 432.79), (3.28; 1.92), (2.67; 0.35), (2.54; 0.54), (2.52; 1.41), (2.51; 19.51), (2.50; 37.80), (2.50; 49.98), (2.50; 35.39), (2.49; 16.65), (2.33; 0.31), (2.18; 1.91), (2.13; 12.87), (2.07; 0.37), (1.36; 15.00) |

-continued
| No. | Structure | logP | MH+ | NMR |
|---|---|---|---|---|
| 307 | 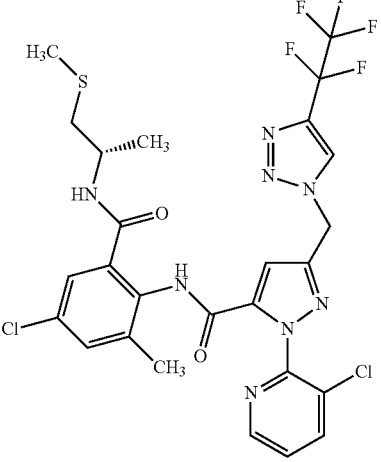 Chiral | 3.66 | 677 | (9.08; 2.72), (8.47; 1.63), (8.46; 1.64), (8.45; 1.73), (8.45; 1.59), (8.16; 0.99), (8.14; 1.14), (8.14; 1.70), (8.13; 1.54), (8.12; 1.69), (8.11; 1.52), (7.59; 1.54), (7.58; 1.51), (7.57; 1.45), (7.56; 1.40), (7.45; 1.71), (7.45; 1.78), (7.33; 0.32), (7.33; 0.31), (7.31; 1.94), (7.30; 1.80), (7.28; 3.54), (7.26; 0.49), (5.89; 5.99), (3.97; 0.55), (3.96; 0.64), (3.94; 0.54), (3.51; 0.32), (3.50; 0.32), (3.46; 0.31), (3.44; 0.32), (3.30; 36.15), (3.25; 1.57), (3.20; 0.34), (3.18; 0.34), (3.17; 0.30), (3.16; 0.35), (3.15; 0.32), (2.87; 0.44), (2.85; 0.35), (2.68; 0.42), (2.67; 0.37), (2.66; 0.39), (2.64; 0.99), (2.63; 1.01), (2.62; 2.13), (2.60; 2.32), (2.58; 0.39), (2.56; 0.82), (2.55; 0.87), (2.54; 0.64), (2.53; 1.55), (2.51; 16.90), (2.50; 32.50), (2.50; 42.73), (2.50; 30.33), (2.49; 14.28), (2.44; 1.08), (2.42; 1.08), (2.41; 0.69), (2.39; 0.64), (2.30; 0.34), (2.15; 8.78), (2.10; 8.86), (2.07; 0.31), (2.06; 0.31), (2.04; 0.32), (2.04; 0.40), (1.99; 15.00), (1.99; 2.79), (1.25; 0.58), (1.24; 0.77), (1.24; 0.78), (1.23; 4.02), (1.21; 3.36), (1.13; 1.75), (1.11; 1.67), (1.10; 0.70), (1.08; 1.04), (1.07; 4.77), (1.06; 4.65), (0.98; 0.43), (0.96; 0.41) |
| 308 | 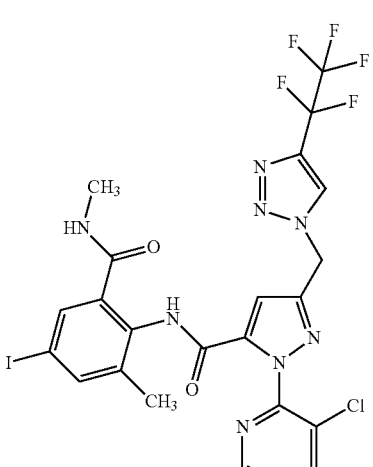 | 3.23 | 695 | (10.20; 1.18), (9.09; 4.70), (8.47; 2.80), (8.47; 2.90), (8.46; 2.92), (8.46; 2.80), (8.16; 1.09), (8.15; 1.20), (8.14; 3.12), (8.14; 3.00), (8.12; 2.98), (8.12; 2.75), (7.73; 2.84), (7.72; 2.88), (7.59; 5.87), (7.58; 2.90), (7.57; 2.64), (7.56; 2.50), (7.23; 4.12), (5.93; 0.40), (5.89; 10.03), (3.68; 0.78), (3.47; 0.30), (3.47; 0.31), (3.42; 0.42), (3.42; 0.51), (3.38; 0.94), (3.37; 1.08), (3.36; 1.18), (3.35; 1.44), (3.33; 4.95), (3.30; 1349.09), (3.28; 6.25), (3.27; 1.53), (3.26; 0.82), (3.25; 0.89), (3.24; 0.61), (3.24; 0.52), (2.67; 0.95), (2.67; 1.23), (2.66; 0.97), (2.64; 10.01), (2.63; 9.71), (2.58; 0.33), (2.57; 0.37), (2.55; 0.74), (2.54; 2.05), (2.52; 4.72), (2.51; 63.72), (2.50; 122.30), (2.50; 160.99), (2.50; 113.09), (2.49; 52.95), (2.33; 0.79), (2.33; 1.00), (2.32; 0.72), (2.10; 15.00), (2.07; 2.54), (1.86; 0.48), (0.89; 0.35), (0.00; 0.96) |

| No. | Structure | logP | MH+ | NMR |
|---|---|---|---|---|
| 309 | 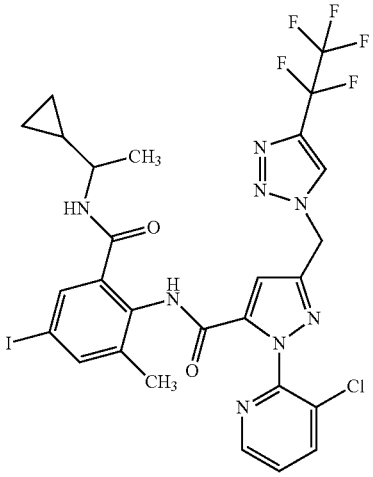 [SMILES: Cc1cc(I)cc(C(=O)NC(C)C2CC2)c1NC(=O)c1cc(Cn2cc(C(F)(F)C(F)(F)F)nn2)nn1-c1ncccc1Cl] | 4.03 | 749 | (10.137; 2.97), (9.068; 4.79), (8.462; 2.74), (8.458; 2.90), (8.450; 2.98), (8.447; 2.88), (8.134; 2.70), (8.131; 2.73), (8.114; 3.05), (8.111; 2.76), (8.044; 1.71), (8.023; 1.71), (7.727; 3.23), (7.724; 3.35), (7.590; 2.98), (7.579; 2.75), (7.570; 2.74), (7.558; 3.96), (7.556; 3.87), (7.551; 3.38), (7.234; 5.98), (5.888; 10.29), (3.349; 0.81), (3.335; 1.47), (3.293; 824.71), (3.270; 5.12), (2.678; 0.45), (2.674; 0.87), (2.669; 1.09), (2.665; 0.80), (2.539; 1.71), (2.509; 62.59), (2.504; 121.12), (2.500; 160.28), (2.495; 113.43), (2.491; 53.39), (2.331; 0.76), (2.327; 1.03), (2.322; 0.70), (2.318; 0.40), (2.184; 0.60), (2.108; 15.00), (2.068; 3.60), (1.358; 4.57), (1.046; 9.00), (1.029; 8.79), (0.824; 0.50), (0.816; 0.68), (0.803; 1.24), (0.795; 0.82), (0.791; 0.87), (0.783; 1.20), (0.770; 0.70), (0.763; 0.47), (0.358; 0.58), (0.354; 0.62), (0.346; 1.31), (0.338; 1.05), (0.333; 1.07), (0.325; 1.31), (0.318; 0.66), (0.312; 0.70), (0.302; 0.51), (0.222; 0.42), (0.212; 0.72), (0.209; 0.76), (0.200; 1.02), (0.192; 1.07), (0.189; 1.04), (0.178; 1.57), (0.166; 1.06), (0.155; 1.23), (0.142; 1.63), (0.132; 1.41 ), (0.124; 1.21), (0.112; 1.39), (0.102; 1.31), (0.090; 0.93), (0.080; 0.53), (0.001; 1.34) |
| 310 | 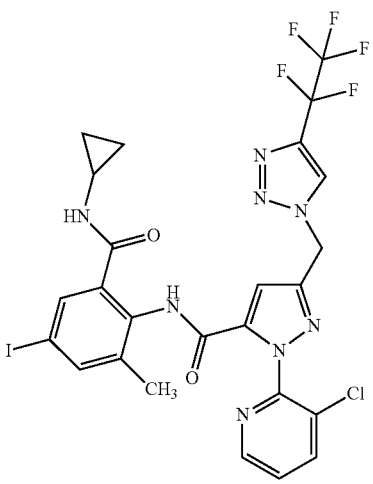 [SMILES: Cc1cc(I)cc(C(=O)NC2CC2)c1NC(=O)c1cc(Cn2cc(C(F)(F)C(F)(F)F)nn2)nn1-c1ncccc1Cl] | 3.49 | 721 | (10.15; 2.04), (9.09; 4.92), (8.47; 2.77), (8.47; 2.97), (8.46; 3.01), (8.46; 2.91), (8.21; 1.56), (8.20; 1.57), (8.14; 2.62), (8.14; 2.64), (8.12; 2.94), (8.12; 2.75), (7.72; 3.02), (7.71; 3.13), (7.59; 2.79), (7.58; 2.79), (7.57; 2.65), (7.56; 2.62), (7.53; 3.29), (7.53; 3.14), (7.24; 4.80), (5.90; 10.27), (4.49; 0.39), (3.59; 0.32), (3.58; 0.36), (3.29; 607.33), (3.26; 4.24), (2.69; 0.32), (2.68; 0.72), (2.67; 1.59), (2.67; 2.25), (2.66; 1.60), (2.65; 1.00), (2.64; 0.76), (2.63; 0.32), (2.54; 1.72), (2.52; 4.63), (2.51; 69.59), (2.50; 136.46), (2.50; 181.82), (2.49; 129.13), (2.49; 61.29), (2.45; 0.33), (2.33; 0.48), (2.33; 0.91), (2.33; 1.19), (2.32; 0.86), (2.22; 0.30), (2.20; 0.54), (2.18; 0.45), (2.17; 0.31), (2.10; 15.00), (2.07; 1.64), (1.75; 0.34), (1.74; 0.61), (1.36; 0.62), (1.24; 0.32), (0.60; 0.97), (0.59; 2.77), (0.58; 3.76), (0.57; 3.52), (0.56; 2.94), (0.55; 1.18), (0.43; 1.22), (0.42; 3.44), (0.41; 3.26), (0.40; 2.85), (0.39; 0.90), (0.01; 1.04), (0.00; 23.17), (−0.01; 0.80) |

|No.|Structure|logP|MH+|NMR|
|---|---|---|---|---|
|311| 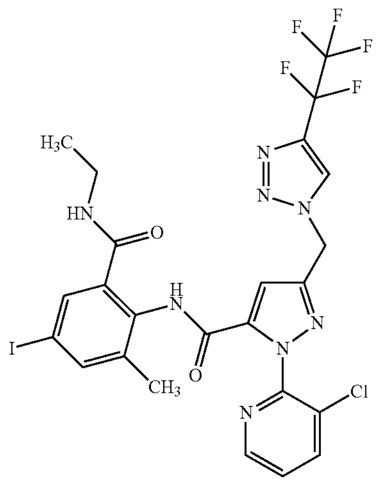 [SMILES: CCNC(=O)c1cc(I)cc(C)c1NC(=O)c1cc(Cn2cc(C(F)(F)C(F)(F)F)nn2)nn1-c1ncccc1Cl] |3.49|709|(10.18; 2.26), (9.08; 4.64), (8.46; 2.69), (8.46; 2.86), (8.45; 2.92), (8.45; 2.82), (8.17; 0.85), (8.16; 1.51), (8.14; 3.00), (8.14; 2.80), (8.12; 2.96), (8.12; 2.73), (7.72; 3.01), (7.72; 3.15), (7.59; 2.82), (7.58; 4.39), (7.58; 4.07), (7.57; 5.55), (7.56; 2.60), (7.23; 5.07), (5.89; 10.09), (3.38; 0.36), (3.38; 0.41), (3.36; 0.61), (3.29; 866.72), (3.27; 5.16), (3.25; 1.10), (3.23; 0.40), (3.19; 0.32), (3.15; 0.85), (3.13; 2.60), (3.12; 2.95), (3.12; 2.96), (3.10; 2.62), (3.08; 0.81), (2.67; 0.83), (2.67; 1.12), (2.66; 0.81), (2.57; 0.36), (2.54; 1.66), (2.52; 4.55), (2.51; 64.82), (2.50; 125.76), (2.50; 166.60), (2.49; 118.31), (2.49; 55.83), (2.33; 0.84), (2.33; 1.11), (2.32; 0.80), (2.10; 15.00), (2.07; 1.07), (1.36; 0.35), (1.24; 0.40), (0.99; 5.69), (0.97; 12.13), (0.95; 5.45), (0.89; 0.38), (0.00; 1.33)|
|312| 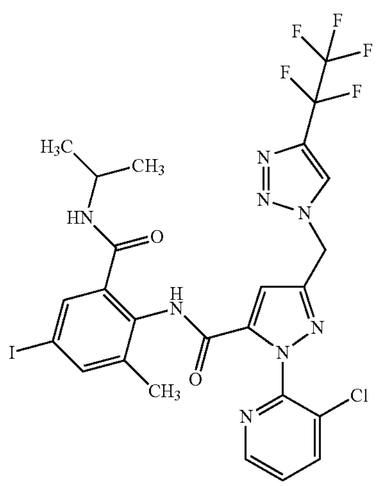 [SMILES: Cc1cc(I)cc(C(=O)NC(C)C)c1NC(=O)c1cc(Cn2cc(C(F)(F)C(F)(F)F)nn2)nn1-c1ncccc1Cl] |3.73|723|(10.14; 1.44), (9.08; 3.46), (8.46; 1.99), (8.46; 2.11), (8.45; 2.15), (8.44; 2.08), (8.13; 1.92), (8.13; 1.96), (8.11; 2.18), (8.11; 2.01), (7.97; 1.05), (7.95; 1.06), (7.72; 2.31), (7.71; 2.42), (7.59; 2.06), (7.58; 2.04), (7.57; 1.97), (7.56; 2.12), (7.55; 2.57), (7.54; 2.43), (7.23; 4.17), (5.89; 7.45), (3.91; 0.58), (3.89; 0.91), (3.87; 0.89), (3.85; 0.60), (3.37; 0.44), (3.36; 0.50), (3.34; 1.11), (3.30; 712.51), (3.27; 3.95), (3.25; 0.69), (3.24; 0.45), (3.23; 0.32), (2.67; 0.49), (2.67; 0.65), (2.66; 0.50), (2.54; 1.02), (2.52; 2.73), (2.51; 38.56), (2.50; 75.22), (2.50; 100.25), (2.49; 71.22), (2.49; 33.81), (2.33; 0.49), (2.33; 0.67), (2.32; 0.45), (2.11; 11.05), (2.07; 2.35), (1.09; 0.35), (1.01; 15.00), (0.99; 14.80), (0.00; 0.64)|
|313| 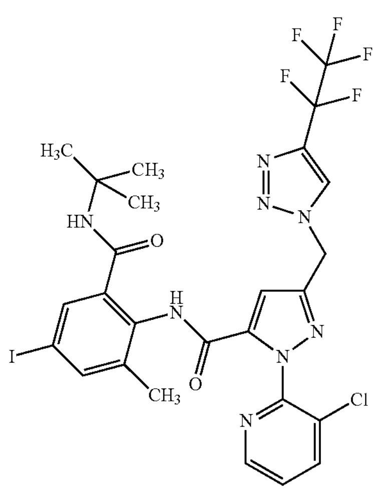 [SMILES: Cc1cc(I)cc(C(=O)NC(C)(C)C)c1NC(=O)c1cc(Cn2cc(C(F)(F)C(F)(F)F)nn2)nn1-c1ncccc1Cl] |4.09|737|(10.177; 1.04), (9.076; 4.71), (8.459; 2.68), (8.455; 2.80), (8.447; 2.90), (8.443; 2.77), (8.233; 1.28), (8.221; 0.78), (8.135; 2.66), (8.131; 2.63), (8.115; 2.96), (8.111; 2.70), (7.732; 3.11), (7.729; 3.28), (7.588; 6.15), (7.584; 3.67), (7.576; 2.90), (7.568; 2.61), (7.556; 2.52), (7.235; 5.50), (5.886; 10.16), (3.400; 0.34), (3.387; 0.37), (3.331; 0.66), (3.291; 347.93), (3.267; 2.12), (2.992; 2.77), (2.977; 4.12), (2.961; 2.77), (2.673; 0.40), (2.668; 0.53), (2.664; 0.40), (2.538; 0.86), (2.521; 2.13), (2.508; 30.61), (2.504; 59.30), (2.499; 78.30), (2.495; 55.54), (2.490; 26.18), (2.330; 0.36), (2.326; 0.49), (2.322; 0.35), (2.108; 15.00), (2.067; 1.04), (1.357; 0.32), (0.891; 0.31), (0.872; 0.36), (0.861; 0.68), (0.855; 0.72), (0.843; 1.15), (0.835; 0.65), (0.831; 0.70), (0.826; 0.73), (0.811; 0.40), (0.315; 1.05), (0.305; 3.05), (0.301; 3.25), (0.290; 1.72), (0.285; 3.13), (0.280; 2.89), (0.270; 1.17), (0.115; 1.27), (0.105; 3.63), (0.102; 3.57), (0.093; 3.21), (0.090; 3.56), (0.078; 0.86), (0.000; 0.90)|

| No. | Structure | logP | MH+ | NMR |
|---|---|---|---|---|
| 314 | 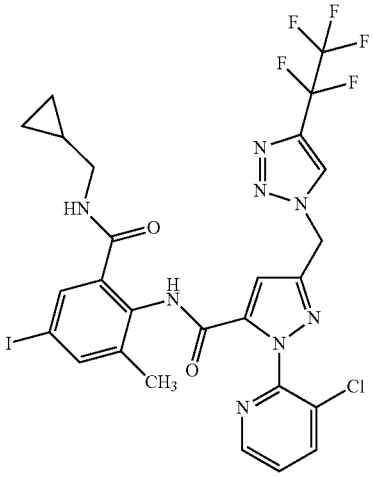 [SMILES: Cc1cc(I)cc(C(=O)NCC2CC2)c1NC(=O)c1cc(Cn2cc(C(F)(F)C(F)(F)F)nn2)nn1-c1ncccc1Cl] | 3.8 | 735 | (10.10; 0.45), (9.06; 1.14), (8.47; 0.70), (8.46; 0.71), (8.45; 0.72), (8.45; 0.69), (8.15; 0.65), (8.14; 0.63), (8.13; 0.71), (8.12; 0.64), (7.69; 0.74), (7.69; 0.77), (7.60; 0.67), (7.58; 0.69), (7.58; 0.70), (7.56; 0.62), (7.50; 0.89), (7.50; 0.95), (7.49; 0.66), (7.20; 1.50), (5.90; 2.47), (3.30; 337.82), (3.28; 1.44), (2.54; 0.71), (2.52; 1.27), (2.51; 16.56), (2.50; 31.46), (2.50; 40.98), (2.50; 28.78), (2.49; 13.42), (2.18; 0.44), (2.10; 3.62), (1.36; 3.47), (1.24; 0.41), (1.19; 15.00), (0.00; 0.31) |
| 315 | 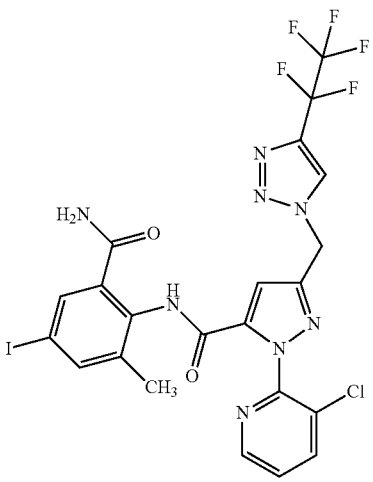 [SMILES: Cc1cc(I)cc(C(N)=O)c1NC(=O)c1cc(Cn2cc(C(F)(F)C(F)(F)F)nn2)nn1-c1ncccc1Cl] | 2.98 | 681 | (10.25; 2.83), (9.09; 4.60), (9.08; 0.33), (8.48; 2.76), (8.47; 2.90), (8.47; 2.91), (8.46; 2.79), (8.15; 2.66), (8.14; 2.65), (8.13; 2.99), (8.12; 2.74), (7.73; 3.21), (7.73; 3.50), (7.67; 1.83), (7.66; 4.10), (7.66; 3.66), (7.59; 2.82), (7.58; 2.75), (7.57; 2.66), (7.56; 2.61), (7.40; 1.73), (7.24; 5.29), (6.87; 1.02), (6.60; 0.60), (5.91; 0.68), (5.89; 10.15), (5.74; 0.76), (3.36; 0.37), (3.29; 443.33), (3.27; 2.38), (3.25; 0.30), (2.67; 0.50), (2.67; 0.67), (2.66; 0.46), (2.54; 1.18), (2.52; 2.89), (2.51; 38.43), (2.50; 73.64), (2.50; 96.92), (2.49; 68.16), (2.49; 31.69), (2.33; 0.45), (2.33; 0.59), (2.32; 0.43), (2.18; 1.63), (2.09; 15.00), (2.07; 0.76), (1.64; 0.74), (1.36; 13.21), (0.00; 0.98) |

| No. | Structure | logP | MH+ | NMR |
|---|---|---|---|---|
| 316 | 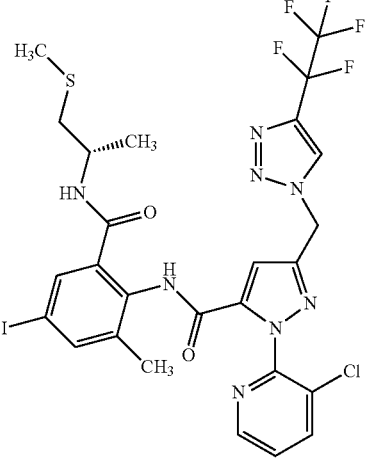 | 3.91 | 769 | (10.16; 0.53), (9.08; 2.79), (8.46; 1.65), (8.46; 1.65), (8.45; 1.74), (8.45; 1.59), (8.13; 2.39), (8.13; 2.20), (8.11; 2.51), (8.11; 2.29), (7.73; 1.85), (7.73; 1.95), (7.69; 0.30), (7.64; 0.53), (7.62; 0.52), (7.62; 0.62), (7.61; 0.77), (7.60; 0.74), (7.59; 1.98), (7.58; 2.66), (7.58; 3.21), (7.57; 1.80), (7.56; 1.56), (7.26; 3.28), (7.25; 0.62), (5.89; 6.04), (5.25; 0.31), (5.24; 0.54), (3.97; 0.53), (3.95; 0.62), (3.93; 0.53), (3.53; 0.34), (3.52; 0.31), (3.51; 0.47), (3.50; 0.31), (3.39; 0.40), (3.37; 0.56), (3.36; 0.75), (3.34; 1.12), (3.33; 1.87), (3.29; 337.54), (3.27; 3.25), (3.19; 0.32), (3.18; 0.32), (3.17; 0.41), (3.16; 0.36), (2.93; 0.31), (2.69; 0.40), (2.68; 0.66), (2.67; 0.78), (2.67; 1.03), (2.66; 0.93), (2.66; 1.45), (2.65; 1.92), (2.64; 2.85), (2.64; 1.31), (2.62; 1.10), (2.60; 0.46), (2.59; 0.47), (2.56; 0.95), (2.54; 1.32), (2.54; 1.65), (2.52; 4.31), (2.51; 53.27), (2.50; 102.77), (2.50; 136.81), (2.49; 97.47), (2.49; 46.00), (2.44; 1.15), (2.42; 1.13), (2.41; 0.69), (2.39; 0.62), (2.33; 0.32), (2.33; 0.63), (2.33; 0.86), (2.32; 0.63), (2.30; 0.38), (2.11; 9.33), (2.11; 11.79), (2.07; 1.96), (2.06; 0.40), (2.05; 0.40), (2.01; 0.31), (1.99; 15.00), (1.99; 3.73), (1.31; 0.91), (1.30; 0.82), (1.29; 0.93), (1.29; 0.82), (1.24; 3.72), (1.23; 3.60), (1.15; 0.30), (1.13; 2.67), (1.11; 2.63), (1.09; 1.02), (1.08; 1.34), (1.07; 4.67), (1.05; 4.53), (0.97; 0.45), (0.95; 0.41), (0.01; 1.28), (0.00; 27.89), (−0.01; 1.00) |
| 317 | 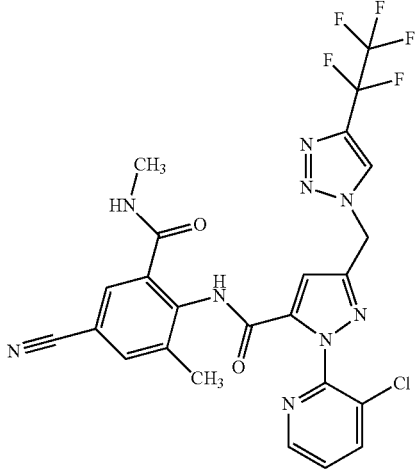 [SMILES: CNC(=O)c1cc(C#N)cc(C)c1NC(=O)c1cc(Cn2cc(C(F)(F)C(F)(F)F)nn2)nn1-c1ncccc1Cl] | 2.68 | 594 | (10.49; 2.97), (9.11; 8.25), (9.03; 0.35), (8.48; 4.42), (8.47; 4.75), (8.47; 4.84), (8.46; 4.59), (8.34; 0.61), (8.32; 1.41), (8.15; 3.21), (8.15; 3.28), (8.13; 3.50), (8.13; 3.26), (7.85; 3.04), (7.74; 3.86), (7.60; 3.29), (7.59; 3.28), (7.58; 3.14), (7.57; 3.13), (7.29; 0.34), (7.27; 3.54), (5.90; 13.99), (3.57; 0.35), (3.57; 0.42), (3.56; 0.34), (3.55; 0.32), (3.53; 0.33), (3.50; 0.35), (3.49; 0.48), (3.48; 0.44), (3.43; 0.62), (3.42; 0.64), (3.39; 1.03), (3.38; 1.09), (3.37; 1.21), (3.37; 1.25), (3.35; 1.94), (3.30; 3488.51), (3.28; 16.86), (3.26; 1.46), (3.25; 0.73), (3.25; 0.74), (2.69; 0.67), (2.68; 1.83), (2.67; 3.64), (2.67; 5.28), (2.66; 15.70), (2.65; 14.48), (2.63; 1.20), (2.58; 0.64), (2.57; 0.70), (2.54; 6.26), (2.52; 12.12), (2.52; 18.67), (2.51; 229.90), (2.50; 449.22), (2.50; 605.45), (2.50; 412.04), (2.49; 191.59), (2.34; 1.24), (2.33; 2.96), (2.33; 3.91), (2.32; 2.88), (2.19; 16.00), (2.07; 5.39), (2.05; 0.93), (1.38; 1.20), (1.24; 0.94), (1.15; 0.33), (0.89; 0.64), (0.87; 0.35), (0.01; 2.25), (0.00; 62.31), (−0.01; 2.02) |

-continued

| No. | Structure | logP | MH+ | NMR |
|---|---|---|---|---|
| 318 | 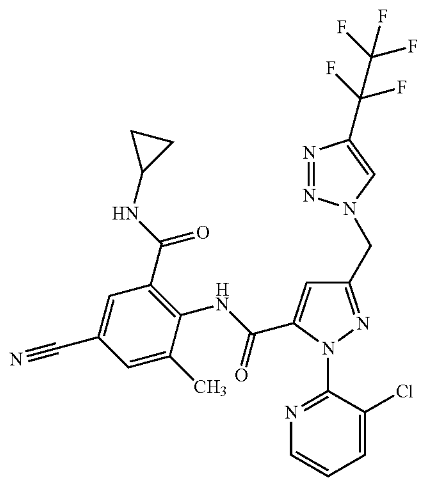 [SMILES: Cc1cc(C#N)cc(C(=O)NC2CC2)c1NC(=O)c1cc(Cn2cc(C(F)(F)C(F)(F)F)nn2)nn1-c1ncccc1Cl] | 2.89 | 620 | (10.44; 3.90), (9.11; 6.90), (8.48; 3.64), (8.48; 4.00), (8.47; 4.08), (8.46; 3.92), (8.35; 2.31), (8.34; 2.33), (8.15; 2.93), (8.15; 3.04), (8.13; 3.37), (8.13; 3.15), (7.84; 3.73), (7.71; 0.57), (7.69; 3.91), (7.69; 3.71), (7.60; 3.20), (7.59; 3.16), (7.58; 3.14), (7.57; 2.99), (7.28; 5.20), (6.49; 0.34), (5.91; 12.72), (3.35; 1.70), (3.31; 2929.50), (3.29; 13.03), (3.26; 1.21), (3.25; 1.05), (3.24; 0.86), (3.20; 0.47), (3.18; 0.37), (3.17; 0.34), (2.69; 0.89), (2.68; 1.38), (2.67; 3.40), (2.67; 3.08), (2.66; 3.13), (2.66; 1.23), (2.65; 0.82), (2.54; 3.18), (2.52; 5.92), (2.52; 9.33), (2.51; 129.50), (2.51; 256.07), (2.50; 347.52), (2.50; 238.47), (2.49; 112.33), (2.34; 0.87), (2.33; 1.78), (2.33; 2.43), (2.32; 1.79), (2.19; 16.00), (2.07; 2.16), (2.05; 0.56), (1.40; 1.62), (1.25; 0.50), (1.24; 0.59), (0.89; 0.62), (0.62; 1.29), (0.61; 3.36), (0.60; 4.55), (0.59; 4.29), (0.58; 3.62), (0.57; 1.42), (0.44; 1.22), (0.43; 3.77), (0.42; 3.76), (0.41; 3.31), (0.40; 1.08), (0.01; 0.43), (0.00; 13.44), (−0.01; 0.41) |
| 319 | 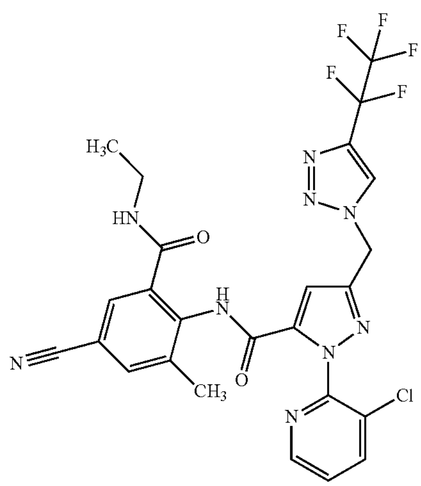 [SMILES: CCNC(=O)c1cc(C#N)cc(C)c1NC(=O)c1cc(Cn2cc(C(F)(F)C(F)(F)F)nn2)nn1-c1ncccc1Cl] | 2.89 | 608 | (10.47; 4.23), (9.10; 5.69), (8.47; 3.13), (8.47; 3.39), (8.46; 3.47), (8.46; 3.35), (8.32; 1.00), (8.31; 2.02), (8.30; 1.04), (8.15; 3.13), (8.15; 3.18), (8.13; 3.59), (8.13; 3.32), (7.85; 3.27), (7.85; 3.52), (7.73; 3.73), (7.73; 3.56), (7.60; 3.41), (7.59; 3.32), (7.58; 3.21), (7.57; 3.20), (7.27; 5.88), (5.90; 11.77), (3.36; 0.41), (3.30; 800.24), (3.17; 0.82), (3.15; 2.76), (3.14; 2.98), (3.13; 2.99), (3.12; 2.82), (3.10; 0.82), (2.68; 0.37), (2.67; 0.76), (2.67; 1.05), (2.66; 0.75), (2.54; 1.53), (2.52; 2.98), (2.52; 4.56), (2.51; 57.90), (2.50; 113.76), (2.50; 153.97), (2.50; 105.22), (2.49; 49.16), (2.34; 0.34), (2.33; 0.74), (2.33; 1.05), (2.32; 0.73), (2.32; 0.39), (2.19; 16.00), (2.07; 1.93), (1.00; 6.66), (0.98; 14.70), (0.97; 6.42), (0.00; 8.36) |
| 320 | 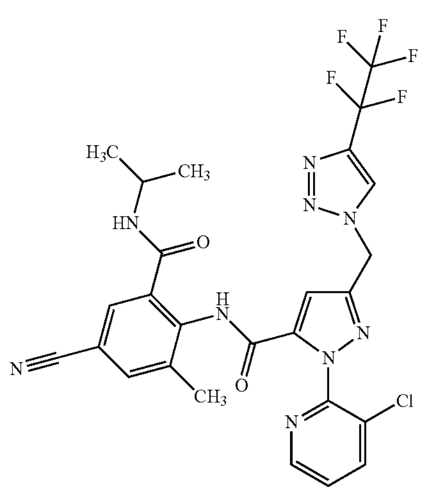 [SMILES: Cc1cc(C#N)cc(C(=O)NC(C)C)c1NC(=O)c1cc(Cn2cc(C(F)(F)C(F)(F)F)nn2)nn1-c1ncccc1Cl] | 3.11 | 622 | (10.43; 2.98), (9.10; 3.99), (8.47; 2.14), (8.46; 2.29), (8.45; 2.38), (8.45; 2.28), (8.14; 2.46), (8.14; 3.15), (8.12; 2.87), (8.12; 3.48), (7.84; 2.32), (7.84; 2.45), (7.70; 2.64), (7.70; 2.53), (7.60; 2.25), (7.58; 2.18), (7.57; 2.11), (7.56; 2.10), (7.28; 4.00), (5.91; 8.23), (3.91; 0.62), (3.90; 0.92), (3.88; 0.91), (3.86; 0.62), (3.34; 0.50), (3.30; 616.48), (3.28; 2.94), (2.67; 0.56), (2.67; 0.79), (2.66; 0.57), (2.54; 1.10), (2.52; 2.15), (2.52; 3.31), (2.51; 43.84), (2.50; 85.74), (2.50; 115.36), (2.50; 78.83), (2.49; 36.80), (2.33; 0.55), (2.33; 0.79), (2.32; 0.55), (2.20; 11.07), (2.07; 1.48), (1.02; 16.00), (1.00; 15.88), (0.01; 0.34), (0.00; 9.53) |

-continued
| No. | Structure | logP | MH+ | NMR |
|---|---|---|---|---|
| 321 | 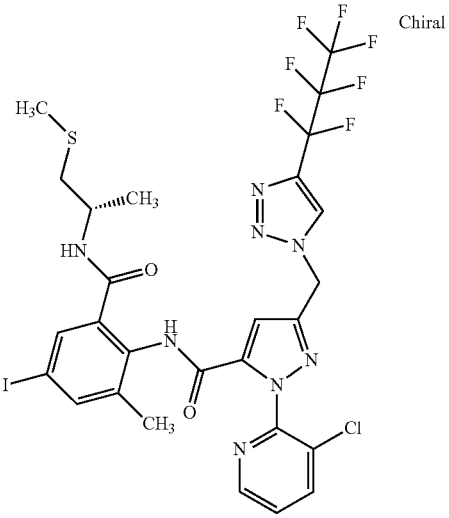 [SMILES: CSC[C@H](C)NC(=O)c1cc(I)cc(C)c1NC(=O)c1cc(Cn2cc(C(F)(F)C(F)(F)C(F)(F)F)nn2)nn1-c1ncccc1Cl] Chiral | 4.27 | 819 | (9.07; 2.72), (8.46; 1.62), (8.46; 1.64), (8.45; 1.75), (8.45; 1.59), (8.15; 1.01), (8.13; 1.78), (8.13; 1.89), (8.13; 1.16), (8.12; 0.63), (8.11; 1.80), (8.11; 1.57), (7.73; 1.74), (7.73; 1.81), (7.61; 0.34), (7.60; 0.34), (7.59; 1.82), (7.58; 2.09), (7.58; 3.15), (7.57; 1.57), (7.56; 1.47), (7.27; 3.31), (7.25; 0.57), (5.90; 5.65), (3.97; 0.51), (3.95; 0.60), (3.93; 0.51), (3.49; 0.35), (3.30; 46.18), (3.18; 0.42), (3.17; 0.39), (3.16; 0.45), (3.15; 0.41), (3.15; 0.35), (3.14; 0.31), (2.87; 0.51), (2.85; 0.45), (2.68; 0.35), (2.67; 0.38), (2.66; 0.47), (2.65; 0.95), (2.63; 0.95), (2.62; 2.32), (2.60; 2.62), (2.59; 0.37), (2.57; 0.42), (2.56; 0.73), (2.54; 0.80), (2.54; 0.65), (2.53; 1.55), (2.52; 1.57), (2.51; 19.29), (2.50; 37.04), (2.50; 48.68), (2.50; 34.54), (2.49; 16.33), (2.44; 1.12), (2.42; 1.12), (2.41; 0.74), (2.39; 0.65), (2.33; 0.34), (2.30; 0.33), (2.11; 8.74), (2.10; 9.79), (2.07; 0.98), (2.06; 0.34), (1.99; 15.00), (1.99; 2.89), (1.26; 0.70), (1.25; 0.90), (1.24; 0.82), (1.23; 3.68), (1.21; 3.38), (1.14; 0.36), (1.13; 2.28), (1.11; 2.13), (1.09; 0.79), (1.08; 1.22), (1.07; 4.61), (1.05; 4.50), (0.97; 0.44), (0.96; 0.42), (0.00; 0.35) |
| 322 | 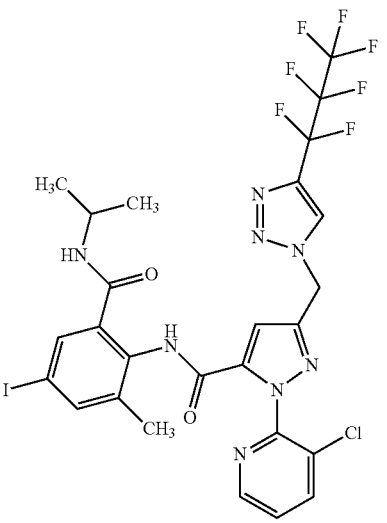 [SMILES: Cc1cc(I)cc(C(=O)NC(C)C)c1NC(=O)c1cc(Cn2cc(C(F)(F)C(F)(F)C(F)(F)F)nn2)nn1-c1ncccc1Cl] | 4.07 | 773 | (10.15; 1.34), (9.08; 3.61), (8.46; 2.00), (8.46; 2.10), (8.45; 2.17), (8.44; 2.04), (8.13; 1.94), (8.13; 1.90), (8.11; 2.14), (8.11; 1.97), (7.98; 0.96), (7.96; 0.98), (7.72; 2.25), (7.71; 2.33), (7.59; 2.03), (7.58; 2.02), (7.57; 1.98), (7.56; 2.25), (7.55; 2.52), (7.55; 2.36), (7.23; 3.69), (5.90; 7.13), (3.91; 0.65), (3.89; 0.93), (3.87; 0.92), (3.85; 0.60), (3.34; 0.71), (3.29; 501.35), (3.27; 2.64), (3.25; 0.54), (3.25; 0.37), (2.67; 0.55), (2.67; 0.73), (2.66; 0.53), (2.54; 1.18), (2.52; 3.09), (2.51; 41.81), (2.50; 80.95), (2.50; 107.27), (2.49; 75.78), (2.49; 35.70), (2.33; 0.50), (2.33; 0.67), (2.32; 0.48), (2.10; 10.96), (2.07; 0.81), (1.36; 0.30), (1.09; 0.31), (1.04; 0.31), (1.01; 15.00), (0.99; 14.73), (0.00; 0.95) |

US 8,536,202 B2
261	262
-continued
| No. | Structure | logP | MH+ | NMR |
|---|---|---|---|---|
| 323 | 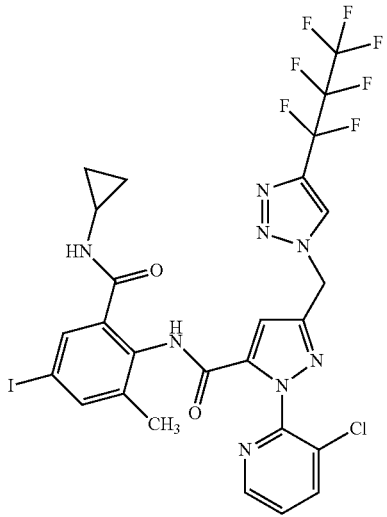 [SMILES: Cc1cc(I)cc(C(=O)NC2CC2)c1NC(=O)c1cc(Cn2cc(C(F)(F)C(F)(F)C(F)(F)F)nn2)nn1-c1ncccc1Cl] | 3.82 | 771 | (10.15; 1.44), (9.09; 5.11), (8.47; 2.88), (8.47; 3.03), (8.46; 3.06), (8.46; 2.92), (8.21; 1.36), (8.20; 1.38), (8.14; 2.67), (8.14; 2.60), (8.12; 2.96), (8.12; 2.70), (7.80; 0.32), (7.71; 3.02), (7.59; 2.77), (7.58; 2.80), (7.57; 2.64), (7.56; 2.64), (7.53; 3.17), (7.53; 3.07), (7.24; 4.08), (5.90; 9.91), (4.50; 0.76), (4.49; 1.54), (4.48; 0.77), (3.61; 0.39), (3.60; 0.75), (3.59; 0.89), (3.59; 1.47), (3.58; 0.94), (3.58; 0.67), (3.57; 1.40), (3.57; 0.53), (3.56; 0.64), (3.41; 0.33), (3.41; 0.42), (3.40; 0.38), (3.39; 0.44), (3.38; 0.48), (3.37; 0.64), (3.36; 0.97), (3.34; 1.41), (3.29; 1015.60), (3.27; 5.45), (3.24; 0.50), (3.22; 0.33), (2.69; 0.39), (2.68; 0.81), (2.67; 1.68), (2.67; 2.10), (2.66; 1.67), (2.65; 1.11), (2.64; 0.82), (2.61; 0.43), (2.61; 0.62), (2.60; 0.73), (2.59; 0.61), (2.58; 0.61), (2.57; 0.62), (2.54; 1.93), (2.52; 5.04), (2.51; 70.00), (2.50; 135.19), (2.50; 178.94), (2.49; 126.39), (2.49; 59.53), (2.45; 0.31), (2.33; 0.85), (2.33; 1.17), (2.32; 0.83), (2.22; 0.63), (2.20; 1.27), (2.18; 1.51), (2.17; 2.24), (2.15; 1.09), (2.10; 15.00), (2.07; 1.81), (2.05; 0.32), (1.76; 0.56), (1.74; 4.17), (1.36; 0.97), (1.24; 0.36), (0.89; 0.49), (0.60; 1.32), (0.59; 3.53), (0.58; 4.83), (0.57; 4.34), (0.56; 3.85), (0.55; 1.45), (0.43; 1.27), (0.42; 3.51), (0.41; 3.45), (0.40; 2.98), (0.39; 1.03), (0.37; 1.20), (0.37; 1.08), (0.36; 1.27), (0.36; 1.34), (0.35; 0.70), (0.34; 0.74), (0.00; 1.57) |
| 324 | 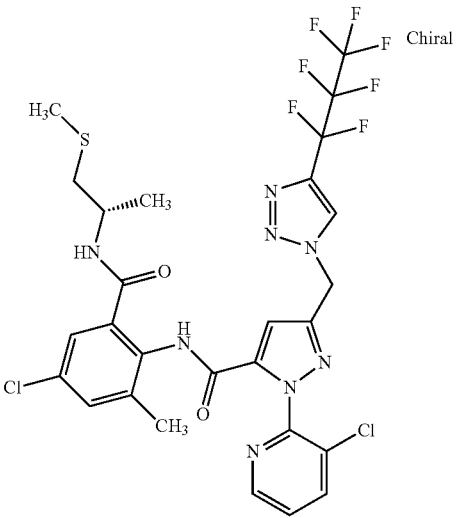 [SMILES: CSC[C@H](C)NC(=O)c1cc(Cl)cc(C)c1NC(=O)c1cc(Cn2cc(C(F)(F)C(F)(F)C(F)(F)F)nn2)nn1-c1ncccc1Cl] | 3.99 | 727 | (10.20; 0.37), (9.08; 2.93), (8.47; 1.80), (8.46; 1.71), (8.45; 1.82), (8.45; 1.54), (8.46; 1.15), (8.14; 1.63), (8.14; 2.00), (8.13; 1.62), (8.12; 1.78), (8.11; 1.47), (7.66; 0.35), (7.65; 0.36), (7.59; 1.76), (7.58; 1.68), (7.57; 1.59), (7.56; 1.47), (7.45; 1.97), (7.45; 1.87), (7.33; 0.33), (7.33; 0.33), (7.31; 2.10), (7.30; 1.79), (7.27; 3.53), (7.26; 0.48), (5.90; 6.14), (3.99; 0.30), (3.97; 0.62), (3.96; 0.73), (3.94; 0.57), (3.51; 0.33), (3.39; 0.40), (3.29; 102.83), (3.19; 0.35), (3.18; 0.33), (3.17; 0.39), (3.16; 0.37), (2.93; 0.31), (2.71; 0.32), (2.69; 0.33), (2.67; 1.10), (2.65; 0.96), (2.65; 1.54), (2.64; 2.01), (2.62; 0.78), (2.60; 0.40), (2.59; 0.42), (2.56; 0.92), (2.55; 1.15), (2.53; 2.40), (2.51; 27.87), (2.50; 47.39), (2.50; 57.97), (2.50; 39.82), (2.49; 18.24), (2.44; 1.20), (2.42; 1.15), (2.41; 0.74), (2.39; 0.67), (2.33; 0.32), (2.33; 0.38), (2.30; 0.38), (2.22; 0.46), (2.15; 9.32), (2.11; 7.81), (2.07; 0.71), (2.06; 0.31), (2.05; 0.33), (1.99; 15.00), (1.99; 2.67), (1.31; 1.13), (1.29; 1.14), (1.25; 2.96), (1.23; 2.82), (1.16; 0.30), (1.14; 0.74), (1.13; 2.17), (1.11; 2.09), (1.10; 0.83), (1.07; 4.94), (1.06; 4.73), (0.98; 0.48), (0.96; 0.45), (0.00; 0.47) |

| No. | Structure | logP | MH+ | NMR |
|---|---|---|---|---|
| 325 | 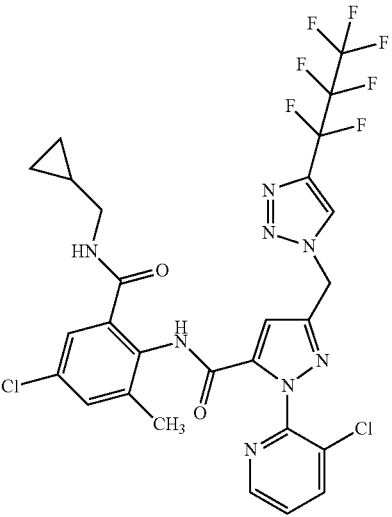 [SMILES: Cc1cc(Cl)cc(C(=O)NCC2CC2)c1NC(=O)c1cc(Cn2cc(C(F)(F)C(F)(F)C(F)(F)F)nn2)nn1-c1ncccc1Cl] | 3.9 | 693 | (10.197; 1.25), (9.078; 4.80), (8.462; 2.66), (8.458; 2.80), (8.450; 2.86), (8.446; 2.72), (8.246; 1.21 ), (8.138; 2.54), (8.134; 2.54), (8.118; 2.85), (8.114; 2.61), (7.590; 2.77), (7.578; 2.58), (7.570; 2.50), (7.558; 2.46), (7.450; 2.80), (7.445; 2.99), (7.317; 3.31), (7.311; 3.07), (7.238; 5.27), (5.896; 9.63), (3.401; 0.41), (3.394; 0.34), (3.388; 0.46), (3.365; 0.37), (3.295; 472.37), (3.271; 2.75), (3.035; 0.34), (3.001; 2.79), (2.986; 4.12), (2.970; 2.79), (2.674; 0.50), (2.670; 0.65), (2.665; 0.44), (2.540; 1.04), (2.523; 2.77), (2.510; 35.61), (2.505; 68.50), (2.501; 90.32), (2.496; 64.00), (2.492; 30.22), (2.332; 0.46), (2.328; 0.56), (2.323; 0.43), (2.221; 1.00), (2.145; 15.00), (2.104; 1.03), (2.068; 1.51), (1.359; 0.38), (0.892; 0.31), (0.883; 0.31), (0.876; 0.39), (0.866; 0.74), (0.858; 0.71), (0.846; 1.13), (0.834; 0.72), (0.829; 0.69), (0.827; 0.71), (0.815; 0.38), (0.318; 1.18), (0.307; 3.04), (0.303; 3.19), (0.292; 1.69), (0.287; 3.08), (0.283; 2.89), (0.272; 1.21), (0.146; 0.32), (0.134; 0.32), (0.119; 1.28), (0.108; 3.60), (0.096; 3.19), (0.093; 3.50), (0.082; 0.88), (0.001; 0.68) |
| 326 | 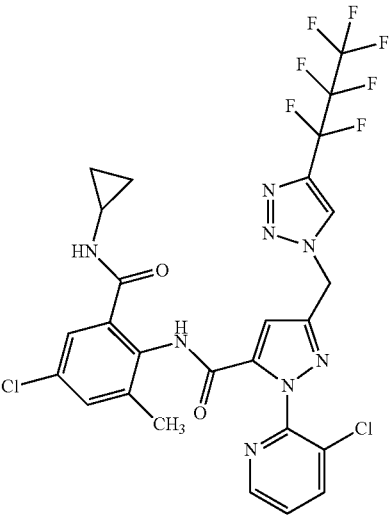 [SMILES: Cc1cc(Cl)cc(C(=O)NC2CC2)c1NC(=O)c1cc(Cn2cc(C(F)(F)C(F)(F)C(F)(F)F)nn2)nn1-c1ncccc1Cl] | 3.57 | 679 | (10.17; 3.48), (9.09; 4.89), (8.47; 2.73), (8.47; 2.84), (8.46; 2.93), (8.46; 2.76), (8.23; 2.05), (8.22; 2.03), (8.14; 2.60), (8.14; 2.58), (8.12; 2.89), (8.12; 2.66), (7.59; 2.76), (7.58; 2.88), (7.57; 2.69), (7.56; 2.54), (7.43; 2.94), (7.43; 3.13), (7.27; 3.45), (7.26; 3.25), (7.25; 6.27), (5.91; 9.58), (4.50; 0.37), (4.49; 0.77), (4.48; 0.39), (3.60; 0.37), (3.60; 0.46), (3.59; 0.50), (3.59; 0.72), (3.58; 0.48), (3.58; 0.35), (3.57; 0.70), (3.57; 0.44), (3.56; 0.32), (3.35; 0.43), (3.29; 374.68), (3.27; 2.13), (2.70; 0.32), (2.69; 0.73), (2.68; 1.00), (2.67; 1.77), (2.67; 1.12), (2.66; 1.75), (2.66; 0.97), (2.65; 0.70), (2.64; 0.32), (2.61; 0.32), (2.60; 0.34), (2.59; 0.37), (2.58; 0.34), (2.57; 0.32), (2.55; 0.32), (2.54; 0.83), (2.52; 2.35), (2.51; 31.33), (2.50; 60.30), (2.50; 79.32), (2.49; 55.98), (2.49; 26.21), (2.33; 0.40), (2.33; 0.53), (2.32; 0.38), (2.21; 1.12), (2.20; 0.72), (2.18; 0.95), (2.17; 1.29), (2.15; 1.06), (2.14; 15.00), (2.11; 1.20), (2.07; 0.37), (1.76; 0.52), (1.74; 2.43), (1.36; 1.58), (0.62; 0.37), (0.61; 0.46), (0.61; 1.06), (0.60; 0.83), (0.59; 2.89), (0.59; 3.85), (0.58; 3.53), (0.57; 3.11), (0.56; 1.32), (0.48; 0.32), (0.47; 0.37), (0.43; 1.24), (0.42; 3.47), (0.41; 3.27), (0.40; 2.88), (0.39; 1.01), (0.38; 0.40), (0.37; 0.65), (0.37; 0.60), (0.36; 0.66), (0.36; 0.72), (0.34; 0.43), (0.01; 0.30), (0.00; 5.79) |

| No. | Structure | logP | MH+ | NMR |
|---|---|---|---|---|
| 327 | 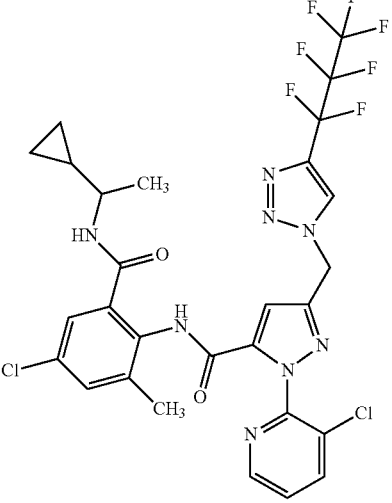 | 4.15 | 707 | (10.155; 3.65), (9.067; 4.86), (8.463; 2.72), (8.459; 2.87), (8.451; 2.87), (8.447; 2.72), (8.135; 2.66), (8.131; 2.54), (8.115; 2.94), (8.111; 2.62), (8.053; 1.83), (8.033; 1.86), (7.590; 2.77), (7.578; 2.72), (7.570; 2.55), (7.558; 2.50), (7.444; 3.03), (7.438; 3.20), (7.281; 3.41), (7.275; 3.17), (7.236; 6.39), (5.896; 9.83), (3.362; 0.56), (3.293; 655.88), (3.269; 4.14), (2.672; 0.67), (2.668; 0.86), (2.664; 0.60), (2.538; 1.31), (2.521; 3.52), (2.508; 47.64), (2.503; 91.90), (2.499; 121.53), (2.494; 86.01), (2.490; 40.61), (2.330; 0.58), (2.326; 0.76), (2.321; 0.58), (2.218; 0.87), (2.142; 15.00), (2.102; 0.91), (2.066; 1.83), (1.357; 0.87), (1.114; 0.61), (1.097; 0.61), (1.048; 8.90), (1.031; 8.75), (0.824; 0.58), (0.816; 0.68), (0.803; 1.17), (0.796; 0.80), (0.791; 0.84), (0.783; 1.23), (0.771; 0.76), (0.763; 0.47), (0.358; 0.61), (0.354; 0.65), (0.345; 1.32), (0.337; 1.06), (0.333; 1.11), (0.324; 1.27), (0.317; 0.60), (0.311; 0.64), (0.302; 0.55), (0.224; 0.49), (0.211; 0.78), (0.200; 1.06), (0.194; 1.08), (0.190; 1.08), (0.180; 1.52), (0.168; 1.18), (0.159; 1.56), (0.146; 1.68), (0.136; 1.41), (0.126; 1.30), (0.113; 1.34), (0.104; 1.30), (0.092; 0.90), (0.082; 0.59), (−0.000; 1.34) |
| 328 | 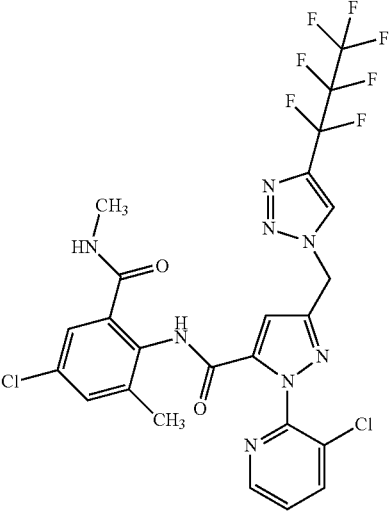 [SMILES: CNC(=O)c1cc(Cl)cc(C)c1NC(=O)c1cc(Cn2cc(C(F)(F)C(F)(F)C(F)(F)F)nn2)nn1-c1ncccc1Cl] | 3.38 | 653 | (10.22; 1.17), (9.10; 4.68), (8.47; 2.61), (8.47; 2.72), (8.46; 2.78), (8.46; 2.65), (8.19; 1.09), (8.18; 1.03), (8.15; 2.60), (8.14; 2.52), (8.13; 2.83), (8.12; 2.57), (7.59; 2.61), (7.58; 2.57), (7.57; 2.49), (7.56; 2.57), (7.44; 2.71), (7.44; 2.92), (7.32; 3.32), (7.32; 3.02), (7.23; 5.01), (6.87; 0.57), (6.60; 0.31), (5.90; 9.40), (3.68; 0.39), (3.29; 296.16), (3.26; 1.96), (2.68; 0.61), (2.67; 1.08), (2.67; 0.89), (2.66; 0.86), (2.65; 9.53), (2.64; 9.37), (2.54; 0.88), (2.52; 2.44), (2.51; 34.35), (2.50; 66.53), (2.50; 87.81), (2.49; 62.06), (2.49; 29.26), (2.33; 0.42), (2.33; 0.56), (2.32; 0.40), (2.22; 0.78), (2.18; 0.94), (2.14; 15.00), (2.11; 0.86), (2.07; 0.54), (1.36; 7.03), (0.01; 1.08), (0.00; 21.12), (−0.01; 0.75) |

| No. | Structure | logP | MH+ | NMR |
|---|---|---|---|---|
| 329 | 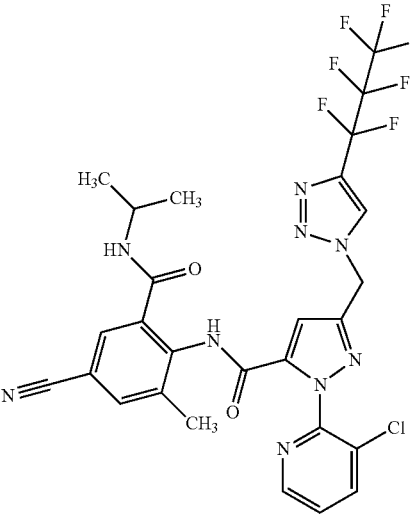 | 3.42 | 672 | (10.43; 2.98), (9.10; 4.02), (8.46; 2.11), (8.46; 2.31), (8.45; 2.36), (8.45; 2.32), (8.14; 2.55), (8.14; 3.48), (8.12; 3.02), (8.12; 3.62), (7.84; 2.29), (7.84; 2.47), (7.71; 2.60), (7.70; 2.51), (7.59; 2.26), (7.58; 2.17), (7.57; 2.10), (7.56; 2.12), (7.27; 4.00), (5.91; 7.83), (3.91; 0.60), (3.90; 0.92), (3.88; 0.91), (3.86; 0.61), (3.30; 582.58), (3.28; 2.70), (2.67; 0.50), (2.67; 0.70), (2.66; 0.53), (2.54; 0.92), (2.52; 1.80), (2.52; 2.75), (2.51; 37.73), (2.50; 75.03), (2.50; 102.31), (2.50; 70.70), (2.49; 33.51), (2.33; 0.50), (2.33; 0.68), (2.32; 0.49), (2.20; 11.03), (2.07; 0.51), (1.02; 16.00), (1.00; 15.86), (0.00; 3.29) |
| 330 | 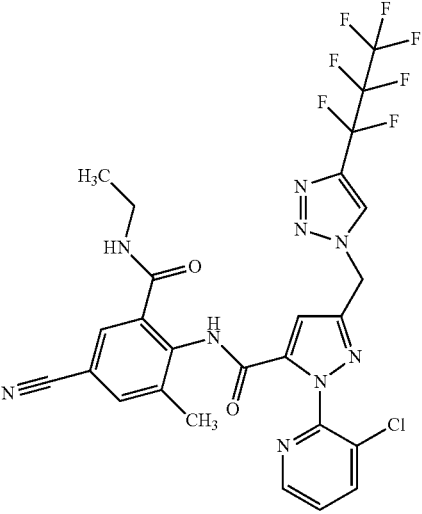 [SMILES: CCNC(=O)c1cc(C#N)cc(C)c1NC(=O)c1cc(Cn2cc(C(F)(F)C(F)(F)C(F)(F)F)nn2)nn1-c1ncccc1Cl] | 3.24 | 658 | (15.12; 0.91), (11.98; 0.87), (10.47; 2.28), (9.10; 2.75), (8.50; 0.85), (8.47; 1.86), (8.46; 1.95), (8.31; 1.11), (8.29; 1.08), (8.15; 1.09), (8.13; 1.59), (7.85; 2.26), (7.84; 2.09), (7.73; 1.94), (7.60; 1.08), (7.58; 1.29), (7.58; 1.12), (7.57; 1.13), (7.26; 2.32), (6.36; 0.84), (5.91; 5.05), (5.75; 1.54), (3.57; 0.92), (3.51; 0.96), (3.51; 0.92), (3.48; 0.92), (3.43; 1.20), (3.42; 0.94), (3.41; 0.93), (3.40; 0.93), (3.37; 2.69), (3.36; 4.08), (3.35; 9.01), (3.28; 49.12), (3.26; 7.66), (3.23; 2.92), (3.19; 1.82), (3.18; 2.01), (3.17; 1.98), (3.15; 2.46), (3.13; 2.45), (3.12; 2.66), (3.10; 1.27), (3.09; 1.06), (3.07; 1.16), (3.05; 0.88), (3.02; 0.97), (3.00; 0.98), (2.99; 0.86), (2.94; 0.93), (2.92; 0.81), (2.89; 2.66), (2.78; 0.89), (2.73; 1.74), (2.70; 1.60), (2.68; 4.36), (2.67; 9.33), (2.67; 13.22), (2.66; 9.80), (2.66; 4.55), (2.56; 1.20), (2.55; 1.68), (2.54; 16.89), (2.52; 34.61), (2.52; 51.65), (2.51; 701.17), (2.50; 1396.14), (2.50; 1907.75), (2.50; 1320.31), (2.49; 627.43), (2.43; 1.44), (2.42; 1.50), (2.41; 1.50), (2.39; 1.25), (2.36; 1.24), (2.34; 4.82), (2.33; 9.65), (2.33; 13.31), (2.32; 9.43), (2.32; 4.77), (2.31; 0.95), (2.29; 0.86), (2.23; 0.94), (2.19; 7.77), (2.18; 1.48), (2.16; 1.04), (2.13; 0.84), (2.10; 0.99), (2.07; 16.00), (2.05; 3.03), (1.96; 0.90), (1.88; 1.03), (1.76; 0.84), (1.74; 0.82), (1.36; 0.85), (1.24; 4.74), (1.20; 1.01), (1.16; 0.82), (1.15; 1.22), (1.14; 1.14), (1.01; 1.16), (1.00; 2.77), (0.98; 5.39), (0.97; 3.00), (0.89; 1.82), (0.85; 1.07), (0.83; 0.81), (0.81; 0.92), (0.01; 1.96), (0.00; 60.97), (−0.01; 1.94) |

-continued
| No. | Structure | logP | MH+ | NMR |
|---|---|---|---|---|
| 331 | 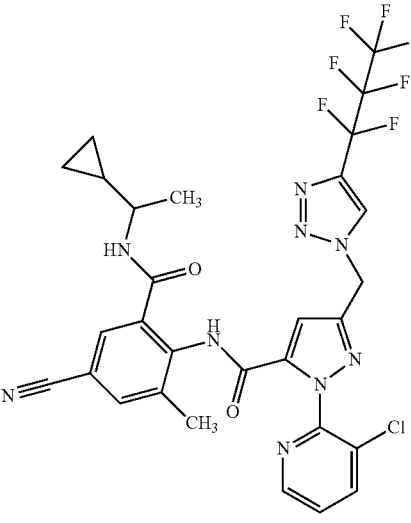 | 3.71 | 699 | (10.43; 4.37), (9.09; 5.88), (8.76; 0.53), (8.47; 3.21), (8.46; 3.45), (8.46; 3.54), (8.45; 3.41), (8.21; 2.17), (8.19; 2.26), (8.14; 3.30), (8.14; 3.33), (8.12; 3.72), (8.12; 3.43), (7.85; 3.41), (7.85; 3.59), (7.70; 3.78), (7.70; 3.68), (7.60; 3.76), (7.58; 3.36), (7.58; 3.27), (7.56; 3.27), (7.35; 0.33), (7.27; 6.11), (5.91; 11.40), (5.76; 1.02), (3.41; 0.38), (3.39; 0.64), (3.38; 0.72), (3.31; 1144.64), (3.27; 1.31), (3.25; 0.55), (2.68; 0.56), (2.67; 1.12), (2.67; 1.55), (2.66; 1.15), (2.66; 0.55), (2.54; 2.26), (2.52; 4.15), (2.52; 6.11), (2.51; 82.30), (2.50; 163.22), (2.50; 222.93), (2.50; 153.21), (2.49; 72.09), (2.34; 0.47), (2.33; 1.08), (2.33; 1.55), (2.32; 1.03), (2.32; 0.48), (2.20; 16.00), (2.07; 3.76), (2.05; 0.35), (1.40; 1.56), (1.38; 0.74), (1.27; 0.51), (1.25; 0.54), (1.24; 0.60), (1.09; 0.49), (1.07; 0.40), (1.06; 10.07), (1.04; 9.93), (0.89; 0.42), (0.84; 0.50), (0.83; 0.64), (0.82; 1.31), (0.81; 0.78), (0.80; 0.87), (0.80; 1.35), (0.78; 0.76), (0.77; 0.49), (0.38; 0.44), (0.37; 0.65), (0.36; 1.48), (0.35; 1.08), (0.34; 1.10), (0.34; 1.36), (0.33; 0.61), (0.32; 0.69), (0.31; 0.58), (0.25; 0.50), (0.24; 0.69), (0.23; 0.70), (0.22; 1.10), (0.21; 1.01), (0.20; 1.34), (0.19; 0.85), (0.18; 1.24), (0.17; 1.17), (0.16; 1.71), (0.15; 1.54), (0.14; 1.17), (0.13; 1.14), (0.13; 1.48), (0.12; 1.37), (0.11; 1.03), (0.10; 0.50), (0.00; 4.28) |
| 332 | 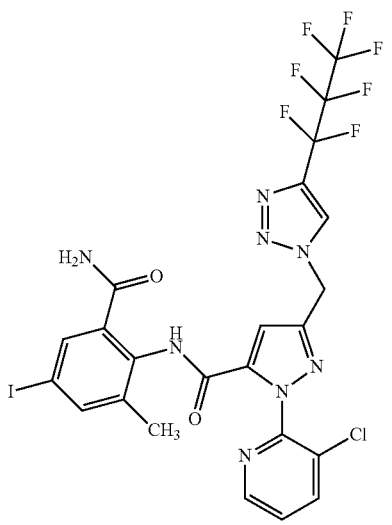 [SMILES: Cc1cc(I)cc(C(N)=O)c1NC(=O)c1cc(Cn2cc(C(F)(F)C(F)(F)C(F)(F)F)nn2)nn1-c1ncccc1Cl] | 3.35 | 731 | (10.25; 1.78), (9.09; 4.71), (8.48; 2.64), (8.47; 2.84), (8.47; 2.84), (8.46; 2.76), (8.14; 2.61), (8.14; 2.60), (8.12; 2.91), (8.12; 2.69), (7.73; 3.12), (7.73; 3.44), (7.68; 1.69), (7.66; 4.06), (7.66; 3.58), (7.59; 2.73), (7.58; 2.67), (7.57; 2.57), (7.56; 2.54), (7.40; 1.72), (7.23; 4.93), (6.87; 0.84), (6.60; 0.49), (5.89; 9.65), (5.74; 0.68), (3.41; 0.34), (3.41; 0.37), (3.41; 0.36), (3.39; 0.46), (3.38; 0.63), (3.37; 0.91), (3.31; 812.69), (3.29; 4.10), (3.26; 0.48), (3.25; 0.40), (3.24; 0.37), (2.67; 0.38), (2.67; 0.50), (2.67; 0.37), (2.54; 0.80), (2.52; 2.04), (2.51; 28.66), (2.51; 55.66), (2.50; 73.78), (2.50; 52.35), (2.49; 24.68), (2.33; 0.34), (2.33; 0.46), (2.32; 0.34), (2.18; 1.38), (2.09; 15.00), (2.07; 1.47), (1.36; 10.81), (0.00; 0.41) |

| No. | Structure | logP | MH+ | NMR |
|---|---|---|---|---|
| 333 | 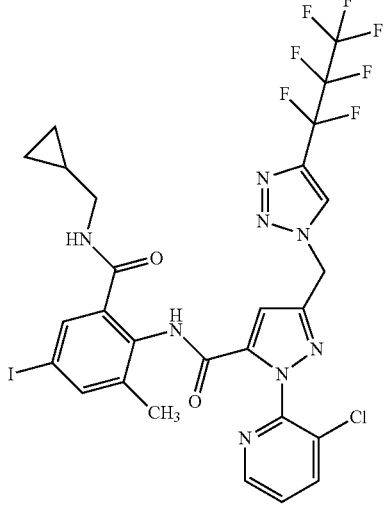 | 4.13 | 785 | (10.169; 0.79), (10.144; 0.31), (9.074; 5.41), (8.459; 2.96), (8.456; 3.13), (8.448; 3.27), (8.444; 3.07), (8.240; 0.71), (8.135; 2.71), (8.131; 2.62), (8.115; 3.04), (8.111; 2.74), (7.727; 2.65), (7.588; 4.85), (7.576; 2.86), (7.568; 2.66), (7.556; 2.47), (7.226; 2.98), (5.891; 10.23), (3.402; 0.79), (3.394; 0.75), (3.388; 0.96), (3.364; 1.22), (3.299; 1178.38), (3.276; 6.15), (3.253; 0.91), (2.993; 3.14), (2.978; 4.62), (2.962; 3.11), (2.675; 0.91), (2.671; 1.16), (2.666; 0.91), (2.632; 0.44), (2.540; 2.06), (2.524; 5.20), (2.510; 68.31), (2.506; 130.71), (2.501; 171.95), (2.497; 120.91), (2.493; 56.69), (2.337; 0.48), (2.333; 0.83), (2.328; 1.05), (2.324; 0.73), (2.185; 0.47), (2.106; 15.00), (2.069; 2.61), (1.359; 3.29), (1.070; 0.39), (1.053; 0.38), (0.892; 0.50), (0.882; 0.44), (0.862; 0.83), (0.857; 0.88), (0.844; 1.29), (0.832; 0.84), (0.828; 0.80), (0.812; 0.44), (0.318; 1.10), (0.307; 3.30), (0.303; 3.47), (0.293; 1.92), (0.287; 3.23), (0.283; 3.07), (0.273; 1.28), (0.115; 1.43), (0.105; 4.04), (0.093; 3.5 8), (0.090; 3.90), (0.078; 0.92), (0.002; 1.02) |
| 334 | 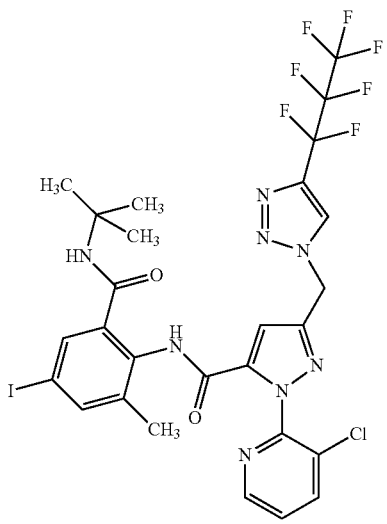 [SMILES: Cc1cc(I)cc(C(=O)NC(C)(C)C)c1NC(=O)c1cc(Cn2cc(C(F)(F)C(F)(F)C(F)(F)F)nn2)nn1-c1ncccc1Cl] | 4.42 | 787 | (10.10; 0.36), (9.05; 1.19), (8.47; 0.66), (8.46; 0.70), (8.45; 0.72), (8.45; 0.68), (8.15; 0.59), (8.14; 0.58), (8.13; 0.67), (8.12; 0.61), (7.69; 0.70), (7.59; 0.64), (7.58; 0.64), (7.57; 0.60), (7.56; 0.59), (7.50; 0.84), (7.19; 1.02), (5.90; 2.28), (3.35; 0.36), (3.30; 311.12), (2.54; 0.41), (2.52; 1.15), (2.51; 15.10), (2.50; 28.99), (2.50; 38.21), (2.50; 26.95), (2.49; 12.64), (2.18; 0.30), (2.09; 3.43), (2.07; 0.72), (1.36; 2.43), (1.24; 0.41), (1.19; 15.00) |

| No. | Structure | logP | MH+ | NMR |
|---|---|---|---|---|
| 335 | 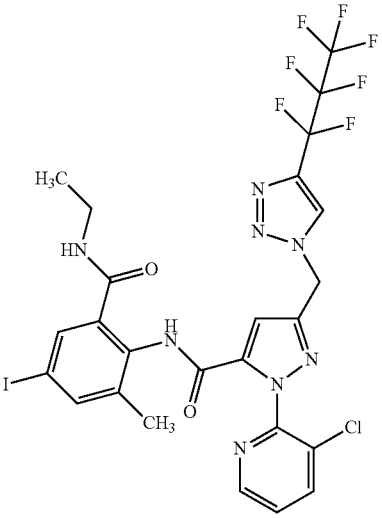 [SMILES: CCNC(=O)c1cc(I)cc(C)c1NC(=O)c1cc(Cn2cc(C(F)(F)C(F)(F)C(F)(F)F)nn2)nn1-c1ncccc1Cl] | 3.83 | 759 | (10.18; 1.62), (9.08; 4.78), (8.46; 2.74), (8.46; 2.82), (8.45; 2.79), (8.45; 2.67), (8.17; 0.86), (8.16; 1.41), (8.14; 2.93), (8.14; 2.68), (8.12; 2.90), (8.12; 2.55), (7.72; 3.06), (7.59; 2.84), (7.58; 5.26), (7.57; 4.72), (7.56; 2.50), (7.22; 4.73), (6.87; 0.96), (6.60; 0.61), (5.90; 9.67), (3.62; 0.47), (3.62; 0.43), (3.60; 0.91), (3.59; 0.50), (3.57; 0.32), (3.50; 0.38), (3.47; 0.41), (3.46; 0.48), (3.43; 0.63), (3.42; 0.56), (3.41; 0.79), (3.39; 1.12), (3.36; 1.79), (3.30; 1834.41), (3.27; 8.24), (3.25; 1.02), (3.24; 0.72), (3.22; 0.56), (3.20; 0.31), (3.15; 0.77), (3.13; 2.55), (3.12; 2.90), (3.12; 2.86), (3.10; 2.67), (3.08; 0.79), (2.67; 1.43), (2.67; 1.84), (2.66; 1.42), (2.63; 0.31), (2.54; 3.15), (2.51; 108.99), (2.50; 206.56), (2.50; 270.32), (2.49; 190.18), (2.49; 89.41), (2.33; 1.34), (2.33; 1.58), (2.32; 1.18), (2.18; 1.51), (2.10; 15.00), (2.07; 1.64), (2.05; 0.39), (1.78; 0.38), (1.77; 0.38), (1.76; 0.94), (1.75; 0.39), (1.36; 12.07), (1.24; 0.38), (1.18; 0.43), (0.99; 5.65), (0.97; 11.92), (0.95; 5.33), (0.89; 0.54), (0.00; 1.52) |
| 336 | 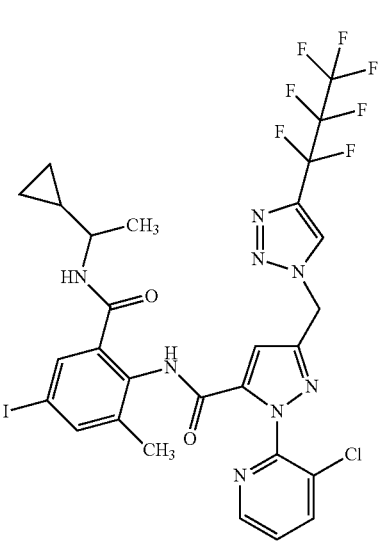 [SMILES: Cc1cc(I)cc(C(=O)NC(C)C2CC2)c1NC(=O)c1cc(Cn2cc(C(F)(F)C(F)(F)C(F)(F)F)nn2)nn1-c1ncccc1Cl] | 4.36 | 799 | (10.141; 1.04), (9.064; 5.09), (8.460; 2.82), (8.457; 3.00), (8.449; 3.08), (8.445; 2.96), (8.133; 2.79), (8.129; 2.64), (8.113; 2.94), (8.109; 2.72), (8.045; 0.91), (8.026; 0.97), (7.722; 2.90), (7.588; 2.82), (7.576; 2.82), (7.568; 2.87), (7.556; 5.69), (7.227; 4.15), (6.870; 0.66), (6.598; 0.43), (5.891; 9.81), (3.395; 0.42), (3.371; 0.65), (3.359; 0.80), (3.293; 896.12), (3.269; 5.88), (3.218; 0.38), (2.677; 0.53), (2.673; 0.92), (2.668; 1.23), (2.664; 0.92), (2.538; 1.99), (2.521; 5.12), (2.508; 71.03), (2.504; 138.25), (2.499; 183.30), (2.494; 129.65), (2.490; 61.17), (2.331; 0.89), (2.326; 1.19), (2.321; 0.79), (2.183; 1.15), (2.105; 15.00), (2.067; 1.69), (1.357; 9.08), (1.044; 9.03), (1.028; 8.85), (0.891; 0.49), (0.823; 0.58), (0.815; 0.65), (0.802; 1.17), (0.794; 0.90), (0.790; 0.91), (0.782; 1.29), (0.770; 0.67), (0.762; 0.49), (0.367; 0.42), (0.354; 0.66), (0.345; 1.32), (0.337; 1.08), (0.333; 1.11), (0.324; 1.30), (0.317; 0.66), (0.311; 0.72), (0.302; 0.58), (0.225; 0.44), (0.212; 0.74), (0.202; 1.00), (0.194; 1.06), (0.181; 1.35), (0.164; 1.02), (0.155; 1.19), (0.143; 1.63), (0.132; 1.49), (0.120; 1.32), (0.109; 1.36), (0.100; 1.39), (0.087; 0.96), (0.077; 0.54), (−0.000; 1.53) |

-continued

| No. | Structure | logP | MH+ | NMR |
|---|---|---|---|---|
| 337 | 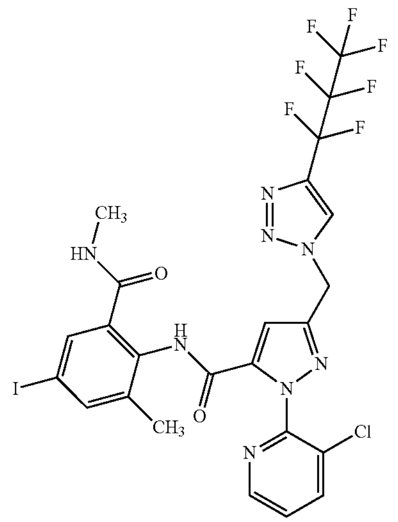 [SMILES: CNC(=O)c1cc(I)cc(C)c1NC(=O)c1cc(Cn2cc(C(F)(F)C(F)(F)C(F)(F)F)nn2)nn1-c1ncccc1Cl] | 3.59 | 745 | (10.21; 2.00), (9.09; 4.91), (8.47; 2.81), (8.47; 2.93), (8.46; 3.05), (8.46; 2.85), (8.16; 1.21), (8.15; 1.31), (8.14; 3.19), (8.14; 3.09), (8.12; 3.00), (8.12; 2.76), (7.73; 2.96), (7.72; 2.98), (7.59; 5.65), (7.58; 2.89), (7.57; 2.67), (7.56; 2.58), (7.23; 4.31), (6.87; 1.05), (6.60; 0.56), (5.94; 0.41), (5.90; 9.67), (3.67; 0.68), (3.36; 0.46), (3.35; 0.50), (3.34; 0.67), (3.29; 547.15), (3.27; 2.76), (3.25; 0.31), (2.68; 0.48), (2.67; 0.64), (2.67; 0.94), (2.66; 0.75), (2.66; 0.58), (2.64; 10.01), (2.63; 9.82), (2.54; 1.26), (2.51; 42.63), (2.50; 82.61), (2.50; 109.04), (2.49; 76.97), (2.49; 35.92), (2.33; 0.51), (2.33; 0.68), (2.32; 0.48), (2.18; 1.67), (2.10; 15.00), (2.07; 1.23), (1.86; 0.46), (1.36; 13.27), (0.00; 1.15) |
| 338 | 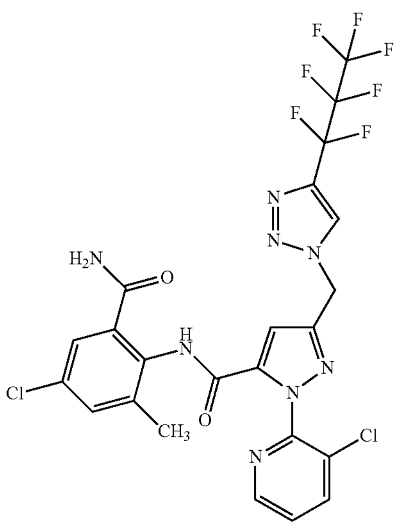 [SMILES: Cc1cc(Cl)cc(C(N)=O)c1NC(=O)c1cc(Cn2cc(C(F)(F)C(F)(F)C(F)(F)F)nn2)nn1-c1ncccc1Cl] | 3.13 | 639 | (10.26; 2.14), (9.09; 4.56), (8.48; 2.66), (8.48; 2.81), (8.47; 2.84), (8.46; 2.73), (8.15; 2.55), (8.14; 2.54), (8.13; 2.80), (8.12; 2.63), (7.69; 1.55), (7.59; 2.75), (7.58; 2.65), (7.57; 2.55), (7.56; 2.49), (7.45; 3.41), (7.44; 4.44), (7.39; 3.59), (7.39; 3.01), (7.24; 5.01), (6.87; 0.89), (6.60; 0.53), (5.89; 9.50), (3.39; 0.42), (3.34; 1.32), (3.29; 933.54), (3.27; 4.34), (3.25; 0.64), (3.23; 0.35), (2.67; 0.86), (2.67; 1.08), (2.66; 0.84), (2.54; 1.85), (2.52; 4.65), (2.51; 63.22), (2.50; 123.48), (2.50; 164.31), (2.49; 117.20), (2.49; 55.60), (2.33; 0.77), (2.33; 1.00), (2.32; 0.70), (2.21; 0.87), (2.18; 1.48), (2.13; 15.00), (2.11; 1.16), (2.09; 0.37), (2.07; 2.34), (1.36; 11.47), (0.89; 0.38), (0.00; 1.53) |
| 339 | 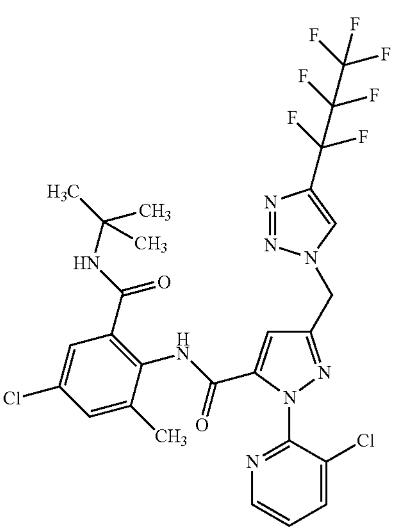 [SMILES: Cc1cc(Cl)cc(C(=O)NC(C)(C)C)c1NC(=O)c1cc(Cn2cc(C(F)(F)C(F)(F)C(F)(F)F)nn2)nn1-c1ncccc1Cl] | 4.21 | 695 | (10.13; 0.36), (9.06; 1.20), (8.47; 0.66), (8.46; 0.68), (8.46; 0.70), (8.45; 0.66), (8.15; 0.61), (8.14; 0.59), (8.13; 0.68), (8.12; 0.62), (7.60; 0.65), (7.58; 0.64), (7.58; 0.62), (7.56; 0.62), (7.51; 0.48), (7.41; 0.68), (7.40; 0.71), (7.24; 0.76), (7.24; 0.72), (7.20; 1.38), (5.90; 2.36), (3.29; 135.25), (3.27; 0.74), (2.54; 0.35), (2.52; 1.00), (2.51; 11.52), (2.50; 21.87), (2.50; 28.60), (2.49; 20.04), (2.49; 9.34), (2.13; 3.62), (1.36; 1.88), (1.25; 0.54), (1.24; 0.32), (1.20; 15.00) |

| No. | Structure | logP | MH+ | NMR |
|---|---|---|---|---|
| 340 | 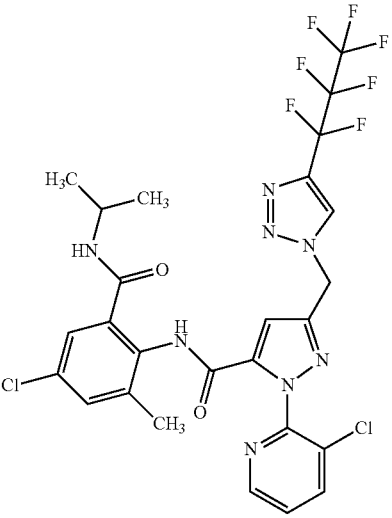 [SMILES: Cc1cc(Cl)cc(C(=O)NC(C)C)c1NC(=O)c1cc(Cn2cc(C(F)(F)C(F)(F)C(F)(F)F)nn2)nn1-c1ncccc1Cl] | 3.8 | 681 | (10.16; 1.41), (9.08; 3.59), (8.46; 1.99), (8.46; 2.10), (8.45; 2.14), (8.45; 2.00), (8.14; 1.89), (8.13; 1.88), (8.12; 2.12), (8.11; 1.93), (7.99; 0.97), (7.97; 0.94), (7.59; 2.11), (7.58; 1.91), (7.57; 1.87), (7.56; 1.86), (7.43; 2.07), (7.43; 2.17), (7.28; 2.36), (7.28; 2.21), (7.23; 3.73), (5.90; 7.19), (3.91; 0.62), (3.90; 0.94), (3.88; 0.93), (3.86; 0.67), (3.38; 0.35), (3.36; 0.54), (3.34; 0.78), (3.29; 567.85), (3.27; 3.18), (2.67; 0.68), (2.67; 0.85), (2.66; 0.59), (2.55; 0.48), (2.54; 1.25), (2.52; 3.34), (2.51; 46.60), (2.50; 90.39), (2.50; 119.71), (2.49; 84.81), (2.49; 40.07), (2.34; 0.31), (2.33; 0.55), (2.33; 0.74), (2.32; 0.53), (2.22; 0.80), (2.14; 11.08), (2.11; 0.79), (2.07; 0.99), (1.09; 0.34), (1.07; 1.06), (1.05; 1.06), (1.04; 0.34), (1.01; 15.00), (0.99; 14.80), (0.89; 0.31), (0.00; 1.14) |
| 341 | 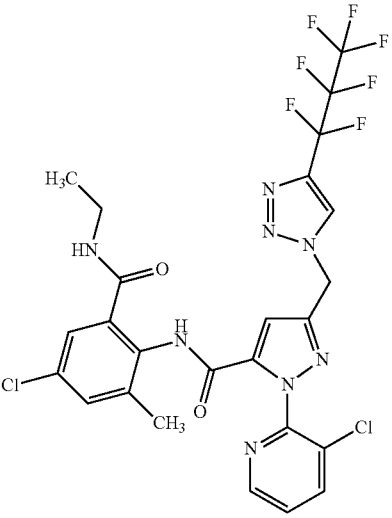 [SMILES: CCNC(=O)c1cc(Cl)cc(C)c1NC(=O)c1cc(Cn2cc(C(F)(F)C(F)(F)C(F)(F)F)nn2)nn1-c1ncccc1Cl] | 3.62 | 667 | (10.19; 3.06), (9.80; 0.31), (9.08; 4.71), (8.47; 2.80), (8.46; 2.95), (8.45; 3.00), (8.45; 2.85), (8.19; 0.93), (8.17; 1.75), (8.16; 0.96), (8.14; 2.67), (8.14; 2.62), (8.12; 2.96), (8.12; 2.64), (7.59; 2.82), (7.58; 2.91), (7.57; 2.71), (7.56; 2.53), (7.44; 2.87), (7.43; 2.97), (7.31; 3.30), (7.30; 3.04), (7.23; 5.73), (6.21; 0.31), (5.90; 9.53), (3.50; 0.31), (3.49; 0.40), (3.48; 0.35), (3.47; 0.35), (3.45; 0.36), (3.44; 0.37), (3.43; 0.39), (3.41; 0.51), (3.38; 0.83), (3.34; 1.65), (3.29; 1606.24), (3.27; 8.41), (3.25; 1.27), (3.23; 0.73), (3.21; 0.38), (3.19; 0.34), (3.18; 0.40), (3.16; 0.97), (3.14; 2.50), (3.13; 2.90), (3.12; 2.88), (3.11; 2.59), (3.09; 0.78), (2.70; 0.36), (2.68; 0.88), (2.67; 1.48), (2.67; 1.95), (2.66; 1.46), (2.66; 0.80), (2.59; 0.45), (2.58; 0.48), (2.54; 2.99), (2.52; 8.59), (2.51; 114.17), (2.50; 219.82), (2.50; 289.62), (2.49; 204.00), (2.49; 95.14), (2.33; 1.40), (2.33; 1.83), (2.32; 1.32), (2.22; 1.17), (2.14; 15.00), (2.11; 1.20), (2.07; 2.21), (2.05; 0.42), (1.91; 0.32), (1.24; 0.49), (1.09; 0.33), (1.04; 0.48), (1.03; 0.91), (1.01; 0.55), (0.99; 5.66), (0.97; 12.11), (0.96; 5.34), (0.89; 0.76), (0.00; 3.23) |

-continued

| No. | Structure | logP | MH+ | NMR |
|---|---|---|---|---|
| 342 | 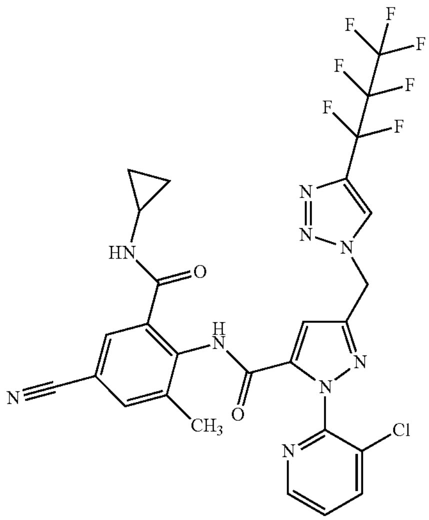 [SMILES: Cc1cc(C#N)cc(C(=O)NC2CC2)c1NC(=O)c1cc(Cn2cc(C(F)(F)C(F)(F)C(F)(F)F)nn2)nn1-c1ncccc1Cl] | 3.22 | 670 | (10.45; 4.44), (9.11; 6.06), (8.48; 3.12), (8.48; 3.30), (8.47; 3.40), (8.46; 3.32), (8.35; 2.31), (8.34; 2.32), (8.15; 3.00), (8.15; 3.02), (8.13; 3.38), (8.13; 3.16), (7.84; 3.36), (7.84; 3.58), (7.70; 3.80), (7.69; 3.67), (7.60; 3.14), (7.59; 3.07), (7.58; 2.97), (7.57; 3.04), (7.28; 5.77), (5.92; 11.47), (3.37; 0.38), (3.30; 1046.87), (3.28; 5.05), (2.69; 0.78), (2.68; 1.10), (2.67; 2.45), (2.67; 1.81), (2.66; 2.33), (2.66; 1.07), (2.65; 0.78), (2.54; 1.79), (2.52; 3.60), (2.52; 5.53), (2.51; 70.71), (2.50; 137.99), (2.50; 185.26), (2.50; 126.79), (2.49; 59.29), (2.34; 0.43), (2.33; 0.90), (2.33; 1.27), (2.32; 0.90), (2.19; 16.00), (2.07; 0.74), (1.24; 0.35), (0.62; 1.03), (0.61; 2.80), (0.60; 3.88), (0.59; 3.63), (0.58; 2.96), (0.57; 1.23), (0.44; 1.28), (0.43; 3.69), (0.43; 3.36), (0.42; 3.00), (0.40; 0.98), (0.00; 3.59) |
| 343 | 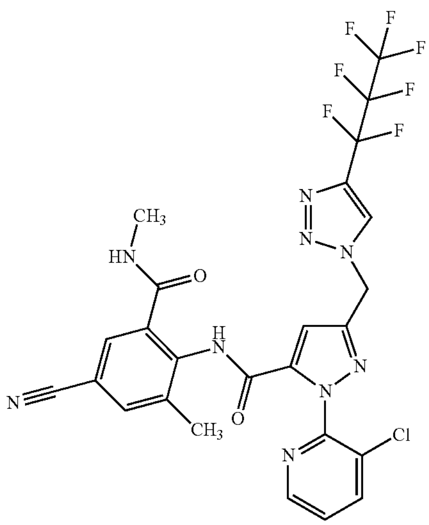 [SMILES: CNC(=O)c1cc(C#N)cc(C)c1NC(=O)c1cc(Cn2cc(C(F)(F)C(F)(F)C(F)(F)F)nn2)nn1-c1ncccc1Cl] | 3.04 | 644 | (10.50; 4.17), (9.11; 5.68), (8.48; 3.07), (8.47; 3.39), (8.47; 3.40), (8.46; 3.32), (8.32; 1.63), (8.31; 1.61), (8.16; 3.02), (8.15; 3.13), (8.14; 3.43), (8.13; 3.36), (7.85; 3.26), (7.85; 3.58), (7.74; 3.74), (7.74; 3.58), (7.60; 3.30), (7.59; 3.24), (7.58; 3.17), (7.57; 3.13), (7.27; 5.64), (5.91; 11.25), (3.50; 0.37), (3.50; 0.39), (3.48; 0.38), (3.46; 0.40), (3.46; 0.42), (3.43; 0.55), (3.41; 0.63), (3.41; 0.66), (3.38; 1.31), (3.35; 2.21), (3.35; 2.90), (3.31; 3054.47), (3.26; 0.77), (3.24; 0.37), (2.70; 0.46), (2.68; 1.26), (2.67; 2.34), (2.67; 3.44), (2.66; 3.49), (2.66; 11.65), (2.65; 10.76), (2.63; 0.48), (2.60; 0.35), (2.59; 0.36), (2.56; 0.63), (2.54; 4.35), (2.52; 8.35), (2.52; 12.65), (2.51; 163.89), (2.50; 322.84), (2.50; 437.97), (2.50; 300.44), (2.49; 140.77), (2.33; 2.11), (2.33; 2.90), (2.32; 1.99), (2.32; 0.93), (2.19; 16.00), (2.07; 4.28), (2.05; 0.68), (1.24; 0.64), (0.89; 0.88), (0.00; 3.67) |
| 344 | 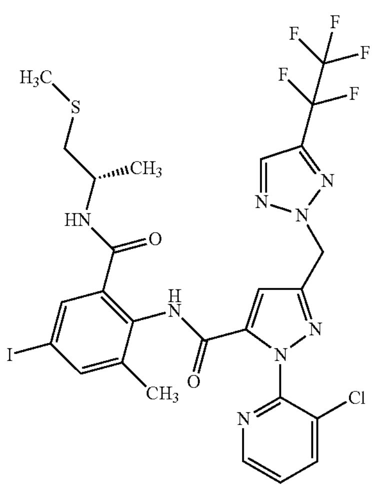 | 4.34 | 769 | (10.14; 0.45), (8.55; 3.00), (8.46; 1.63), (8.46; 1.61), (8.45; 1.70), (8.45; 1.58), (8.13; 1.57), (8.13; 1.54), (8.11; 2.28), (8.11; 1.77), (8.09; 1.00), (7.73; 1.74), (7.73; 1.83), (7.60; 0.44), (7.59; 1.71), (7.58; 3.45), (7.57; 2.23), (7.57; 1.99), (7.56; 1.57), (7.24; 3.27), (7.23; 0.45), (5.96; 5.53), (5.24; 0.37), (3.96; 0.54), (3.95; 0.64), (3.93; 0.57), (3.53; 0.32), (3.51; 0.37), (3.42; 0.36), (3.41; 0.35), (3.40; 0.38), (3.38; 0.67), (3.37; 0.90), (3.30; 599.03), (3.25; 0.73), (3.23; 0.39), (2.67; 0.70), (2.67; 0.93), (2.66; 0.76), (2.64; 0.88), (2.64; 1.30), (2.63; 2.12), (2.61; 0.79), (2.60; 0.31), (2.58; 0.37), (2.56; 1.06), (2.54; 2.16), (2.52; 4.72), (2.51; 49.75), (2.50; 96.12), (2.50; 126.57), (2.49; 89.21), (2.49; 41.94), (2.43; 1.03), (2.42; 1.02), (2.40; 0.70), (2.38; 0.60), (2.33; 0.56), (2.33; 0.77), (2.32; 0.56), (2.11; 8.53), (2.10; 7.54), (2.07; 2.38), (2.05; 0.46), (1.99; 15.00), (1.99; 2.76), (1.28; 0.91), (1.27; 0.89), (1.25; 0.81), (1.24; 2.61), (1.22; 2.37), (1.13; 1.75), (1.11; 1.73), (1.09; 0.75), (1.06; 4.58), (1.05; 4.49), (0.96; 0.39), (0.95; 0.41), (0.89; 0.35), (0.00; 1.18) |

-continued
| No. | Structure | logP | MH+ | NMR |
|---|---|---|---|---|
| 345 | 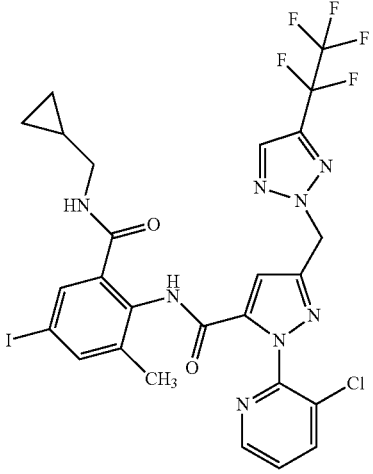 [SMILES: Cc1cc(I)cc(C(=O)NCC2CC2)c1NC(=O)c1cc(Cn2ncc(C(F)(F)C(F)(F)F)n2)nn1-c1ncccc1Cl] | 4.22 | 735 | (10.165; 2.88), (8.549; 5.03), (8.458; 2.76), (8.454; 2.89), (8.446; 3.01), (8.443; 2.80), (8.223; 0.97), (8.210; 1.77), (8.197; 0.91), (8.131; 2.66), (8.127; 2.65), (8.111; 3.05), (8.107; 2.72), (7.731; 3.15), (7.727; 3.21), (7.587; 3.63), (7.582; 3.86), (7.575; 4.68), (7.566; 2.78), (7.555; 2.65), (7.220; 5.25), (5.954; 9.64), (5.742; 0.32), (3.408; 0.32), (3.384; 0.45), (3.374; 0.51), (3.360; 0.66), (3.351; 0.80), (3.289; 1139.59), (3.265; 6.62), (3.232; 0.75), (3.220; 0.45), (3.187; 0.34), (2.986; 2.92), (2.970; 4.24), (2.955; 2.85), (2.672; 1.23), (2.668; 1.70), (2.663; 1.26), (2.538; 2.77), (2.521; 7.35), (2.508; 99.38), (2.503; 191.75), (2.499; 252.68), (2.494; 178.47), (2.490; 83.48), (2.330; 1.25), (2.326; 1.58), (2.321; 1.17), (2.136; 0.30), (2.108; 15.00), (2.067; 2.48), (2.048; 0.48), (1.238; 0.38), (0.891; 0.62), (0.866; 0.39), (0.854; 0.76), (0.847; 0.74), (0.835; 1.19), (0.824; 0.75), (0.818; 0.75), (0.803; 0.49), (0.798; 0.35), (0.307; 1.03), (0.296; 3.07), (0.292; 3.27), (0.282; 1.72), (0.276; 3.05), (0.272; 2.87), (0.262; 1.16), (0.108; 1.25), (0.097; 3.70), (0.086; 3.32), (0.082; 3.65), (0.071; 0.91), (−0.000; 3.02) |
| 346 | 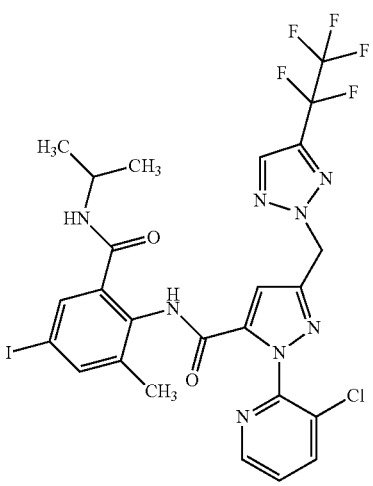 [SMILES: Cc1cc(I)cc(C(=O)NC(C)C)c1NC(=O)c1cc(Cn2ncc(C(F)(F)C(F)(F)F)n2)nn1-c1ncccc1Cl] | 4.15 | 723 | (10.13; 2.35), (8.55; 3.65), (8.46; 1.99), (8.46; 2.12), (8.45; 2.16), (8.44; 2.05), (8.13; 1.95), (8.13; 1.91), (8.11; 2.18), (8.11; 1.96), (7.95; 1.25), (7.93; 1.31), (7.72; 2.29), (7.71; 2.41), (7.59; 2.05), (7.58; 1.99), (7.57; 1.92), (7.56; 2.00), (7.54; 2.57), (7.54; 2.45), (7.22; 4.11), (5.96; 6.97), (3.90; 0.64), (3.88; 0.96), (3.87; 0.97), (3.85; 0.63), (3.46; 0.32), (3.45; 0.31), (3.44; 0.34), (3.43; 0.53), (3.42; 0.49), (3.40; 0.51), (3.39; 0.64), (3.37; 0.92), (3.36; 1.32), (3.30; 1128.75), (3.28; 5.15), (3.26; 0.75), (3.25; 0.36), (3.24; 0.31), (2.67; 0.68), (2.67; 0.89), (2.66; 0.63), (2.54; 1.54), (2.52; 3.76), (2.51; 51.71), (2.50; 100.03), (2.50; 132.37), (2.50; 93.45), (2.49; 43.87), (2.33; 0.61), (2.33; 0.79), (2.32; 0.58), (2.11; 10.90), (2.07; 0.64), (1.00; 15.00), (0.98; 14.72), (0.00; 0.55) |

| No. | Structure | logP | MH+ | NMR |
|---|---|---|---|---|
| 347 | 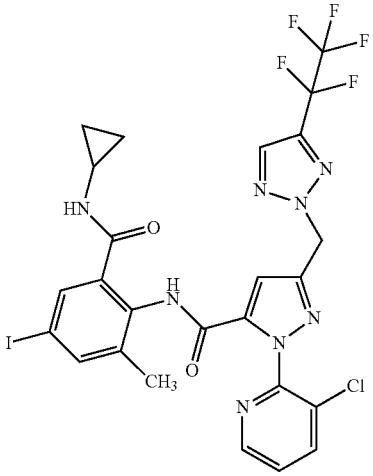 [SMILES: Cc1cc(I)cc(C(=O)NC2CC2)c1NC(=O)c1cc(Cn2ncc(C(F)(F)C(F)(F)F)n2)nn1-c1ncccc1Cl] | 3.86 | 721 | (10.13; 1.61), (8.56; 5.09), (8.47; 2.84), (8.47; 3.01), (8.46; 3.04), (8.46; 2.88), (8.20; 1.43), (8.19; 1.41), (8.14; 2.69), (8.13; 2.67), (8.12; 2.98), (8.11; 2.71), (7.71; 3.05), (7.71; 3.07), (7.59; 2.80), (7.58; 2.79), (7.57; 2.66), (7.56; 2.64), (7.53; 3.31), (7.53; 3.11), (7.23; 4.45), (5.97; 9.56), (4.49; 0.40), (3.60; 0.46), (3.58; 0.42), (3.40; 0.32), (3.39; 0.35), (3.39; 0.35), (3.37; 0.55), (3.35; 1.06), (3.30; 750.42), (3.28; 3.32), (3.25; 0.54), (3.25; 0.38), (3.24; 0.34), (2.68; 0.91), (2.67; 1.61), (2.66; 1.06), (2.66; 1.67), (2.65; 1.47), (2.64; 0.97), (2.63; 0.72), (2.54; 1.15), (2.52; 3.06), (2.51; 39.16), (2.50; 75.05), (2.50; 98.85), (2.49; 69.42), (2.49; 32.45), (2.33; 0.46), (2.33; 0.61), (2.32; 0.44), (2.22; 0.31), (2.20; 0.62), (2.18; 0.37), (2.17; 0.33), (2.10; 15.00), (2.07; 0.92), (1.76; 0.46), (0.60; 0.98), (0.58; 2.90), (0.58; 3.61), (0.57; 3.56), (0.56; 2.78), (0.55; 1.11), (0.42; 1.25), (0.41; 3.51), (0.40; 3.30), (0.39; 2.83), (0.38; 0.87), (0.00; 0.60) |
| 348 | 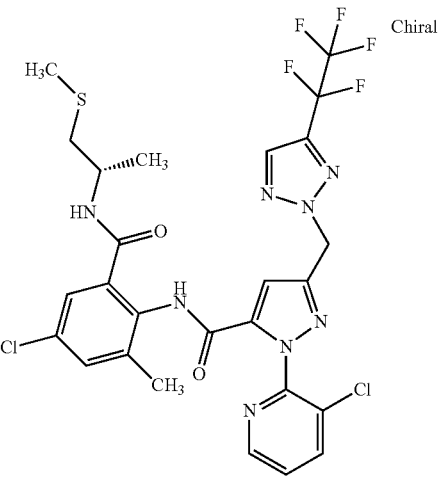 [SMILES: CSC[C@H](C)NC(=O)c1cc(Cl)cc(C)c1NC(=O)c1cc(Cn2ncc(C(F)(F)C(F)(F)F)n2)nn1-c1ncccc1Cl] Chiral | 4.1 | 677 | (10.18; 0.99), (8.59; 3.11), (8.47; 0.28), (8.47; 1.44), (8.47; 1.52), (8.46; 1.65), (8.46; 1.59), (8.18; 0.67), (8.17; 0.67), (8.14; 1.38), (8.14; 1.40), (8.13; 1.56), (8.13; 1.48), (7.59; 1.47), (7.59; 1.41), (7.58; 1.39), (7.57; 1.49), (7.47; 1.25), (7.46; 1.33), (7.30; 1.37), (7.29; 1.31), (7.26; 3.08), (7.25; 0.39), (7.24; 0.47), (5.97; 4.59), (3.95; 0.47), (3.94; 0.53), (3.93; 0.67), (3.84; 0.38), (3.53; 0.43), (3.51; 0.51), (3.45; 0.66), (3.39; 4.65), (3.36; 6263.01), (3.34; 24.10), (2.63; 0.45), (2.62; 1.99), (2.62; 4.34), (2.62; 6.13), (2.61; 4.73), (2.61; 2.76), (2.60; 0.72), (2.54; 0.88), (2.53; 1.28), (2.53; 12.17), (2.52; 15.57), (2.52; 14.26), (2.51; 314.55), (2.51; 702.34), (2.50; 990.70), (2.50; 721.05), (2.50; 324.21), (2.42; 0.76), (2.40; 0.79), (2.39; 2.35), (2.39; 4.23), (2.39; 5.87), (2.39; 4.23), (2.38; 2.17), (2.29; 0.40), (2.15; 6.65), (2.14; 0.74), (2.10; 5.24), (2.08; 7.26), (2.07; 0.47), (1.99; 13.50), (1.99; 2.44), (1.91; 1.25), (1.23; 1.56), (1.21; 1.17), (1.20; 1.11), (1.15; 0.36), (1.11; 1.23), (1.10; 1.18), (1.08; 0.63), (1.07; 0.63), (1.05; 3.57), (1.04; 3.57), (0.95; 0.37), (0.94; 0.35), (0.89; 2.13), (0.00; 8.19) |

| No. | Structure | logP | MH+ | NMR |
|---|---|---|---|---|
| 349 | 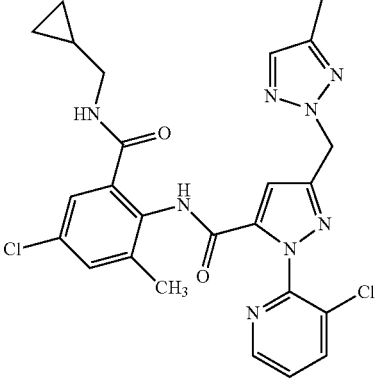 | 3.96 | 643 | (10.179; 1.22), (8.552; 4.81), (8.461; 2.69), (8.458; 2.84), (8.450; 2.90), (8.446; 2.74), (8.225; 1.27), (8.212; 0.74), (8.134; 2.59), (8.130; 2.57), (8.113; 2.94), (8.110; 2.69), (7.588; 2.71), (7.576; 2.64), (7.568; 2.52), (7.556; 2.50), (7.448; 2.79), (7.442; 3.02), (7.311; 3.34), (7.305; 3.11), (7.228; 5.50), (5.958; 9.40), (3.400; 0.32), (3.392; 0.32), (3.386; 0.38), (3.367; 0.34), (3.359; 0.32), (3.293; 520.84), (3.269; 2.97), (3.246; 0.34), (2.996; 2.80), (2.980; 4.08), (2.964; 2.76), (2.673; 0.54), (2.669; 0.68), (2.664; 0.54), (2.538; 1.07), (2.522; 2.72), (2.509; 38.29), (2.504; 74.25), (2.499; 98.32), (2.495; 69.73), (2.490; 32.82), (2.331; 0.49), (2.326; 0.62), (2.322; 0.46), (2.146; 15.00), (2.067; 1.78), (0.891; 0.31), (0.867; 0.36), (0.854; 0.69), (0.849; 0.65), (0.845; 0.61), (0.837; 1.12), (0.828; 0.60), (0.825; 0.72), (0.820; 0.69), (0.817; 0.68), (0.805; 0.35), (0.306; 1.04), (0.295; 2.96), (0.291; 3.18), (0.281; 1.62), (0.275; 3.03), (0.271; 2.78), (0.261; 1.08), (0.111; 1.23), (0.100; 3.57), (0.089; 3.14), (0.085; 3.47), (0.074; 0.87), (0.000; 0.81) |
| 350 | 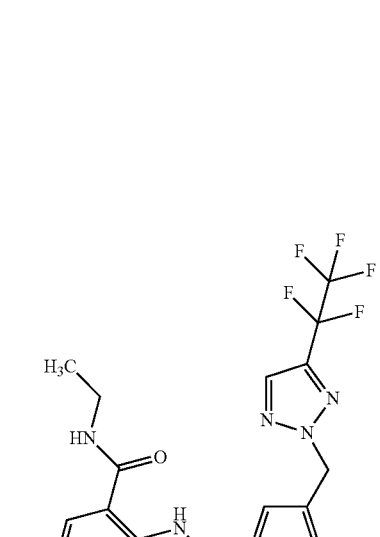 | 3.66 | 617 | (10.18; 1.82), (8.56; 4.65), (8.47; 2.66), (8.46; 2.82), (8.46; 2.85), (8.45; 2.75), (8.17; 0.80), (8.16; 1.48), (8.14; 2.95), (8.13; 2.78), (8.12; 2.86), (8.11; 2.67), (7.59; 2.70), (7.58; 2.64), (7.57; 2.53), (7.56; 2.47), (7.44; 2.83), (7.43; 2.98), (7.30; 3.25), (7.30; 3.05), (7.22; 5.59), (5.96; 9.22), (3.37; 0.39), (3.32; 1.67), (3.29; 550.48), (3.27; 3.30), (3.24; 0.30), (3.16; 0.81), (3.14; 2.55), (3.12; 2.86), (3.12; 2.80), (3.11; 2.51), (3.09; 0.74), (2.67; 0.63), (2.67; 0.87), (2.66; 0.63), (2.54; 1.29), (2.52; 3.41), (2.51; 47.20), (2.50; 91.18), (2.50; 120.47), (2.49; 85.05), (2.49; 39.92), (2.33; 0.58), (2.33; 0.74), (2.32; 0.54), (2.14; 15.00), (2.07; 1.12), (1.36; 0.35), (0.99; 5.52), (0.97; 11.68), (0.95; 5.26), (0.89; 0.32), (0.00; 1.34) |

| No. | Structure | logP | MH+ | NMR |
|---|---|---|---|---|
| 351 | 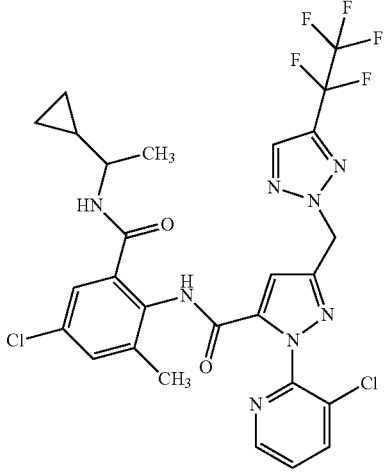 [SMILES: Cc1cc(Cl)cc(C(=O)NC(C)C2CC2)c1NC(=O)c1cc(Cn2ncc(C(F)(F)C(F)(F)F)n2)nn1-c1ncccc1Cl] | 4.21 | 657 | (10.135; 2.11), (8.547; 4.91), (8.462; 2.73), (8.459; 2.86), (8.451; 2.92), (8.447; 2.83), (8.130; 2.58), (8.126; 2.55), (8.109; 2.93), (8.106; 2.65), (8.026; 1.46), (8.007; 1.38), (7.588; 2.83), (7.577; 2.69), (7.568; 2.53), (7.556; 2.60), (7.440; 2.74), (7.435; 2.90), (7.275; 3.25), (7.269; 3.02), (7.221; 5.09), (5.955; 9.55), (3.600; 0.62), (3.482; 0.68), (3.462; 0.75), (3.437; 1.17), (3.422; 1.23), (3.416; 1.34), (3.401; 2.30), (3.391; 2.24), (3.382; 3.66), (3.374; 4.59), (3.319; 3994.80), (3.260; 2.98), (3.250; 2.52), (3.243; 2.40), (3.227; 1.45), (3.192; 1.04), (3.173; 0.71), (3.162; 0.65), (2.673; 1.39), (2.668; 1.98), (2.664; 1.53), (2.538; 2.99), (2.522; 7.86), (2.508; 111.26), (2.504; 216.69), (2.499; 287.77), (2.495; 204.41), (2.490; 96.79), (2.331; 1.45), (2.326; 1.90), (2.321; 1.38), (2.318; 0.72), (2.143; 15.00), (2.064; 1.35), (1.039; 8.94), (1.023; 8.72), (0.793; 1.18), (0.780; 0.87), (0.772; 1.16), (0.760; 0.69), (0.337; 1.26), (0.329; 1.03), (0.326; 1.10), (0.316; 1.28), (0.303; 0.68), (0.196; 0.73), (0.186; 1.00), (0.180; 1.13), (0.166; 1.40), (0.158; 1.14), (0.148; 1.33), (0.136; 1.72), (0.126; 1.49), (0.118; 1.26), (0.105; 1.32), (0.097; 1.29), (0.084; 0.88), (−0.002; 1.03) |
| 352 | 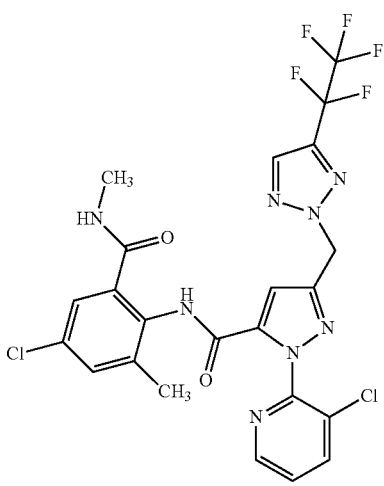 [SMILES: CNC(=O)c1cc(Cl)cc(C)c1NC(=O)c1cc(Cn2ncc(C(F)(F)C(F)(F)F)n2)nn1-c1ncccc1Cl] | 3.4 | 603 | (10.20; 1.66), (8.56; 4.62), (8.47; 2.64), (8.47; 2.76), (8.46; 2.85), (8.46; 2.70), (8.17; 1.17), (8.16; 1.23), (8.14; 2.77), (8.14; 2.68), (8.12; 2.87), (8.12; 2.66), (7.59; 2.71), (7.58; 2.62), (7.57; 2.55), (7.56; 2.49), (7.44; 2.77), (7.44; 2.95), (7.32; 3.37), (7.31; 3.05), (7.23; 5.44), (5.97; 9.11), (3.60; 0.33), (3.38; 0.38), 3.25(3.37; 0.52), (3.37; 0.58), (3.29; 698.78), (3.27; 4.03), (2.67; 0.92), (2.67; 1.20), (2.66; 0.99), (2.65; 9.67), (2.64; 9.54), (2.55; 0.66), (2.54; 1.63), (2.52; 3.99), (2.51; 56.41), (2.50; 109.33), (2.50; 144.57), (2.49; 102.16), (2.49; 48.14), (2.33; 0.38), (2.33; 0.71), (2.33; 0.92), (2.32; 0.68), (2.14; 15.00), (2.07; 2.87), (1.76; 0.33), (0.89; 0.32), (0.00; 1.13) |

-continued

| No. | Structure | logP | MH+ | NMR |
|---|---|---|---|---|
| 353 | 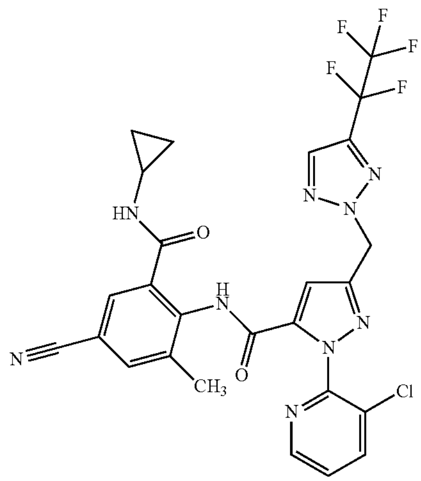 [SMILES: Cc1cc(C#N)cc(C(=O)NC2CC2)c1NC(=O)c1cc(Cn2ncc(C(F)(F)C(F)(F)F)n2)nn1-c1ncccc1Cl] | 3.25 | 620 | (10.43; 4.18), (8.57; 5.88), (8.48; 3.09), (8.48; 3.40), (8.47; 3.45), (8.46; 3.33), (8.34; 2.30), (8.33; 2.34), (8.15; 3.09), (8.15; 3.17), (8.13; 3.56), (8.13; 3.29), (7.84; 3.32), (7.84; 3.48), (7.69; 3.77), (7.69; 3.65), (7.60; 3.36), (7.59; 3.24), (7.58; 3.11), (7.57; 3.14), (7.27; 5.23), (5.98; 10.88), (3.38; 0.50), (3.31; 915.45), (3.26; 0.36), (2.69; 0.48), (2.69; 0.79), (2.67; 1.88), (2.67; 2.35), (2.66; 1.68), (2.65; 1.00), (2.64; 0.77), (2.63; 0.33), (2.54; 2.36), (2.52; 4.40), (2.52; 6.66), (2.51; 85.57), (2.50; 167.96), (2.50; 226.80), (2.50; 154.73), (2.49; 72.10), (2.34; 0.49), (2.33; 1.08), (2.33; 1.54), (2.32; 1.08), (2.19; 16.00), (2.07; 2.63), (2.05; 0.34), (1.24; 0.46), (0.61; 0.99), (0.60; 2.71), (0.60; 3.74), (0.58; 3.56), (0.58; 2.84), (0.57; 1.23), (0.43; 1.23), (0.42; 3.61), (0.42; 3.25), (0.41; 2.98), (0.41; 2.96), (0.40; 0.96), (0.01; 0.67), (0.00; 19.83), (−0.01; 0.56) |
| 354 | 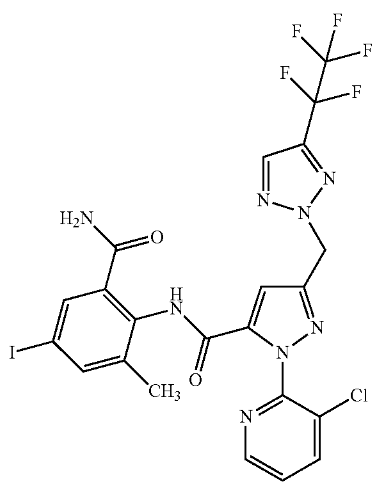 [SMILES: Cc1cc(I)cc(C(N)=O)c1NC(=O)c1cc(Cn2ncc(C(F)(F)C(F)(F)F)n2)nn1-c1ncccc1Cl] | 3.33 | 681 | (10.24; 2.62), (8.56; 4.84), (8.48; 2.67), (8.47; 2.85), (8.47; 2.92), (8.46; 2.78), (8.14; 2.60), (8.14; 2.58), (8.12; 2.85), (8.12; 2.69), (7.73; 3.02), (7.73; 3.26), (7.66; 5.10), (7.65; 4.26), (7.59; 2.72), (7.58; 2.67), (7.57; 2.56), (7.56; 2.53), (7.40; 1.67), (7.22; 4.52), (6.87; 0.40), (5.96; 9.44), (5.74; 0.54), (3.37; 0.38), (3.29; 770.53), (3.27; 4.16), (3.25; 0.60), (3.24; 0.62), (3.23; 0.53), (3.23; 0.44), (3.21; 0.31), (2.67; 0.75), (2.67; 0.95), (2.66; 0.70), (2.54; 1.55), (2.52; 3.85), (2.51; 55.28), (2.50; 108.13), (2.50; 143.95), (2.49; 102.65), (2.49; 48.93), (2.34; 0.40), (2.33; 0.70), (2.33; 0.89), (2.32; 0.68), (2.18; 0.67), (2.09; 15.00), (2.07; 2.33), (1.36; 5.24), (0.89; 0.36), (0.00; 1.41) |
| 355 | 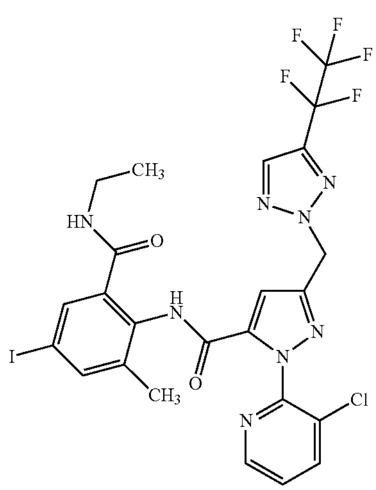 [SMILES: CCNC(=O)c1cc(I)cc(C)c1NC(=O)c1cc(Cn2ncc(C(F)(F)C(F)(F)F)n2)nn1-c1ncccc1Cl] | 3.89 | 709 | (10.16; 3.37), (8.55; 4.84), (8.47; 2.67), (8.46; 2.83), (8.45; 2.88), (8.45; 2.74), (8.15; 1.02), (8.14; 3.49), (8.13; 3.20), (8.12; 3.05), (8.11; 2.73), (7.72; 3.15), (7.72; 3.25), (7.59; 2.74), (7.58; 3.05), (7.57; 5.88), (7.57; 3.78), (7.56; 2.65), (7.21; 5.53), (5.96; 9.46), (3.39; 0.30), (3.37; 0.42), (3.36; 0.66), (3.29; 620.60), (3.27; 3.20), (3.15; 0.79), (3.13; 2.58), (3.12; 2.94), (3.11; 2.86), (3.10; 2.61), (3.08; 0.77), (2.67; 0.55), (2.67; 0.72), (2.66; 0.53), (2.54; 1.16), (2.51; 41.51), (2.50; 79.87), (2.50; 105.45), (2.49; 74.59), (2.49; 35.21), (2.33; 0.52), (2.33; 0.67), (2.32; 0.47), (2.10; 15.00), (2.07; 0.61), (1.36; 0.85), (0.98; 5.68), (0.97; 11.94), (0.95; 5.39), (0.00; 0.52) |

| No. | Structure | logP | MH+ | NMR |
|---|---|---|---|---|
| 356 | 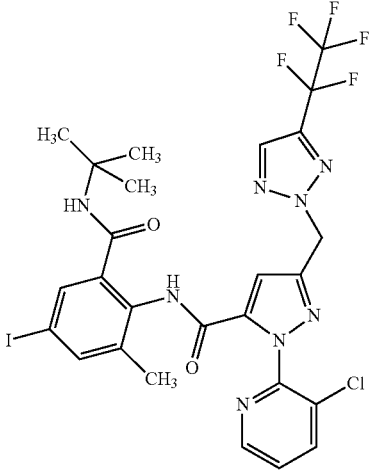 [SMILES: Cc1cc(I)cc(C(=O)NC(C)(C)C)c1NC(=O)c1cc(Cn2ncc(C(F)(F)C(F)(F)F)n2)nn1-c1ncccc1Cl] | 4.47 | 737 | (10.09; 0.89), (8.55; 1.19), (8.47; 0.63), (8.46; 0.71), (8.45; 0.68), (8.45; 0.67), (8.14; 0.63), (8.14; 0.64), (8.12; 0.69), (8.12; 0.63), (7.69; 0.77), (7.69; 0.81), (7.59; 0.66), (7.58; 0.65), (7.57; 0.62), (7.56; 0.64), (7.50; 0.83), (7.50; 0.79), (7.46; 0.90), (7.18; 1.56), (5.96; 2.32), (3.33; 1.14), (3.29; 446.29), (3.27; 2.24), (3.26; 0.44), (3.25; 0.45), (2.67; 0.37), (2.67; 0.49), (2.66; 0.36), (2.54; 0.80), (2.52; 2.11), (2.51; 28.69), (2.50; 55.45), (2.50; 73.43), (2.49; 51.85), (2.49; 24.45), (2.33; 0.36), (2.33; 0.47), (2.32; 0.33), (2.10; 3.54), (2.07; 1.42), (1.36; 0.92), (1.19; 15.00), (0.00; 0.70) |
| 357 | 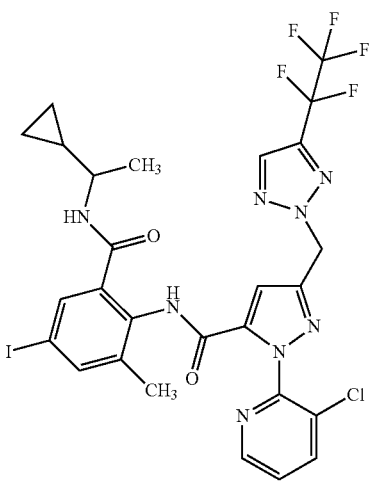 [SMILES: Cc1cc(I)cc(C(=O)NC(C)C2CC2)c1NC(=O)c1cc(Cn2ncc(C(F)(F)C(F)(F)F)n2)nn1-c1ncccc1Cl] | 4.45 | 749 | (10.124; 1.43), (8.548; 5.12), (8.462; 2.81), (8.458; 2.97), (8.450; 2.98), (8.447; 2.84), (8.130; 2.69), (8.126; 2.58), (8.110; 2.92), (8.106; 2.72), (8.021; 1.13), (8.002; 1.14), (7.725; 3.02), (7.722; 3.11), (7.589; 2.79), (7.577; 2.80), (7.569; 2.70), (7.557; 3.35), (7.552; 3.52), (7.548; 3.24), (7.216; 4.66), (5.955; 9.64), (3.424; 0.48), (3.408; 0.58), (3.379; 1.14), (3.370; 1.18), (3.305; 1313.97), (3.282; 7.09), (3.270; 3.22), (3.250; 1.40), (3.238; 0.64), (2.674; 0.73), (2.670; 0.99), (2.665; 0.73), (2.539; 1.62), (2.523; 4.26), (2.509; 58.25), (2.505; 113.12), (2.500; 149.86), (2.496; 106.15), (2.491; 50.12), (2.332; 0.75), (2.327; 0.95), (2.322; 0.68), (2.109; 15.00), (2.067; 1.54), (1.039; 9.05), (1.022; 8.74), (0.815; 0.48), (0.808; 0.64), (0.795; 1.23), (0.787; 0.82), (0.783; 0.85), (0.775; 1.20), (0.762; 0.71), (0.754; 0.48), (0.352; 0.57), (0.349; 0.60), (0.340; 1.28), (0.331; 1.07), (0.328; 1.10), (0.319; 1.25), (0.312; 0.59), (0.306; 0.66), (0.297; 0.54), (0.204; 0.67), (0.191; 1.01), (0.183; 1.09), (0.170; 1.62), (0.158; 1.14), (0.148; 1.38), (0.135; 1.67), (0.125; 1.46), (0.117; 1.17), (0.112; 1.06), (0.104; 1.41), (0.096; 1.35), (0.083; 0.91), (0.073; 0.54), (0.000; 0.84) |

-continued

| No. | Structure | logP | MH+ | NMR |
|---|---|---|---|---|
| 358 | 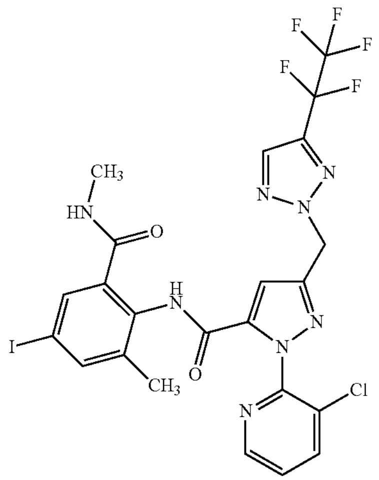 [SMILES: CNC(=O)c1cc(I)cc(C)c1NC(=O)c1cc(Cn2ncc(C(F)(F)C(F)(F)F)n2)nn1-c1ncccc1Cl] | 3.64 | 695 | (11.65; 0.48), (10.19; 2.16), (8.56; 4.88), (8.47; 2.71), (8.47; 2.84), (8.46; 2.91), (8.46; 2.77), (8.15; 1.40), (8.14; 3.74), (8.14; 3.65), (8.12; 3.13), (8.12; 2.78), (7.72; 3.03), (7.72; 3.14), (7.59; 3.51), (7.59; 3.79), (7.58; 4.60), (7.57; 2.68), (7.56; 2.51), (7.22; 4.86), (6.87; 0.97), (6.60; 0.58), (5.96; 9.23), (3.66; 0.44), (3.60; 0.31), (3.46; 0.33), (3.44; 0.33), (3.42; 0.42), (3.41; 0.45), (3.38; 0.64), (3.35; 1.15), (3.34; 1.95), (3.30; 929.55), (3.28; 4.68), (3.25; 0.71), (2.68; 0.46), (2.67; 0.74), (2.67; 0.96), (2.66; 0.79), (2.64; 9.78), (2.63; 9.58), (2.55; 0.66), (2.54; 1.50), (2.52; 3.59), (2.51; 50.08), (2.50; 97.06), (2.50; 128.57), (2.49; 91.08), (2.49; 42.94), (2.33; 0.58), (2.33; 0.80), (2.32; 0.58), (2.18; 1.50), (2.10; 15.00), (2.07; 0.65), (1.36; 12.06), (0.00; 0.62) |
| 359 | 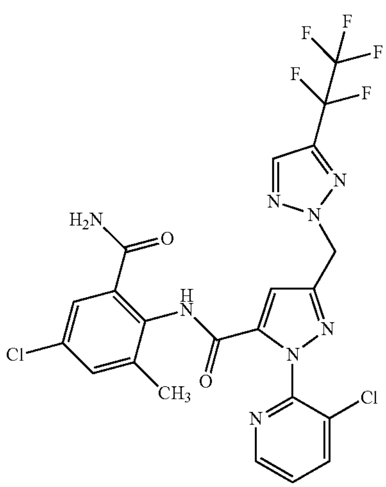 [SMILES: Cc1cc(Cl)cc(C(N)=O)c1NC(=O)c1cc(Cn2ncc(C(F)(F)C(F)(F)F)n2)nn1-c1ncccc1Cl] | 3.12 | 589 | (10.25; 1.70), (8.56; 4.54), (8.48; 2.59), (8.48; 2.75), (8.47; 2.81), (8.47; 2.68), (8.14; 2.52), (8.14; 2.52), (8.12; 2.80), (8.12; 2.61), (7.68; 1.63), (7.59; 2.73), (7.58; 2.61), (7.57; 2.56), (7.56; 2.49), (7.45; 3.77), (7.44; 4.84), (7.39; 3.60), (7.38; 3.04), (7.23; 5.37), (6.87; 0.91), (6.60; 0.53), (5.96; 9.03), (3.39; 0.34), (3.38; 0.39), (3.36; 0.78), (3.36; 0.76), (3.35; 1.01), (3.31; 563.32), (3.26; 0.53), (3.26; 0.37), (2.67; 0.33), (2.67; 0.43), (2.66; 0.31), (2.54; 0.72), (2.52; 1.71), (2.51; 24.30), (2.50; 47.01), (2.50; 62.14), (2.50; 43.99), (2.49; 20.75), (2.33; 0.39), (2.18; 1.48), (2.13; 15.00), (2.07; 0.40), (1.36; 11.49), (0.00; 0.31) |
| 360 | 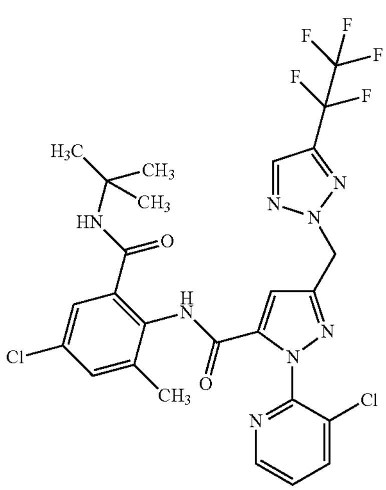 [SMILES: Cc1cc(Cl)cc(C(=O)NC(C)(C)C)c1NC(=O)c1cc(Cn2ncc(C(F)(F)C(F)(F)F)n2)nn1-c1ncccc1Cl] | 4.27 | 645 | (10.11; 0.36), (8.55; 1.19), (8.47; 0.67), (8.46; 0.71), (8.46; 0.73), (8.45; 0.69), (8.15; 0.63), (8.14; 0.64), (8.12; 0.69), (8.12; 0.64), (7.60; 0.68), (7.58; 0.64), (7.58; 0.64), (7.56; 0.61), (7.48; 0.54), (7.41; 0.70), (7.40; 0.74), (7.24; 0.80), (7.23; 0.74), (7.19; 1.55), (5.97; 2.39), (3.29; 153.58), (3.27; 0.79), (2.54; 0.31), (2.52; 0.83), (2.51; 11.14), (2.50; 21.59), (2.50; 28.63), (2.49; 20.27), (2.49; 9.60), (2.13; 3.67), (2.07; 0.32), (1.36; 1.27), (1.24; 0.61), (1.19; 15.00), (0.00; 0.32) |

| No. | Structure | logP | MH+ | NMR |
|---|---|---|---|---|
| 361 | 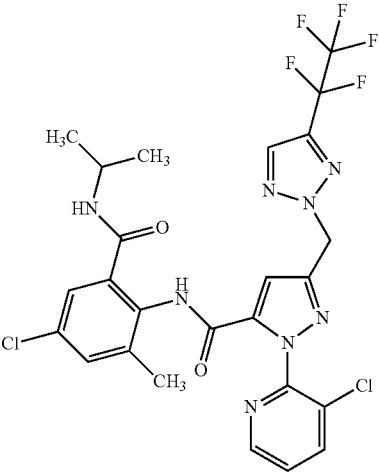 [SMILES: Cc1cc(Cl)cc(C(=O)NC(C)C)c1NC(=O)c1cc(Cn2ncc(C(F)(F)C(F)(F)F)n2)nn1-c1ncccc1Cl] | 3.89 | 631 | (10.14; 1.46), (8.56; 3.56), (8.46; 1.97), (8.46; 2.07), (8.45; 2.14), (8.45; 1.98), (8.13; 1.87), (8.13; 1.84), (8.11; 2.08), (8.11; 1.94), (7.96; 0.97), (7.94; 1.01), (7.59; 2.02), (7.58; 1.92), (7.57; 1.86), (7.56; 1.81), (7.43; 2.10), (7.43; 2.15), (7.28; 2.45), (7.27; 2.27), (7.22; 3.90), (5.96; 7.05), (3.91; 0.64), (3.89; 0.99), (3.87; 0.92), (3.85; 0.63), (3.43; 0.31), (3.42; 0.32), (3.40; 0.40), (3.39; 0.45), (3.39; 0.46), (3.38; 0.54), (3.37; 0.67), (3.30; 868.33), (3.27; 3.97), (3.26; 1.20), (3.25; 0.47), (3.24; 0.33), (3.23; 0.31), (2.67; 0.70), (2.67; 0.93), (2.66; 0.64), (2.54; 1.46), (2.52; 3.78), (2.51; 51.09), (2.50; 98.41), (2.50; 129.31), (2.49; 91.39), (2.49; 42.86), (2.33; 0.55), (2.33; 0.77), (2.32; 0.56), (2.14; 11.17), (2.07; 1.37), (1.36; 0.41), (1.00; 15.00), (0.99; 14.75), (0.00; 1.82) |
| 362 | 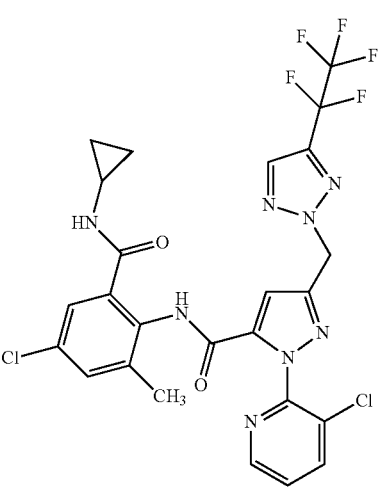 [SMILES: Cc1cc(Cl)cc(C(=O)NC2CC2)c1NC(=O)c1cc(Cn2ncc(C(F)(F)C(F)(F)F)n2)nn1-c1ncccc1Cl] | 3.62 | 629 | (10.17; 0.32), (10.15; 2.42), (8.56; 5.05), (8.47; 2.82), (8.47; 2.91), (8.46; 3.18), (8.46; 2.88), (8.21; 1.76), (8.20; 1.76), (8.14; 2.66), (8.14; 2.58), (8.12; 2.92), (8.12; 2.75), (7.59; 2.79), (7.58; 2.77), (7.57; 2.61), (7.56; 2.57), (7.43; 2.87), (7.42; 2.88), (7.27; 3.40), (7.26; 3.10), (7.24; 5.16), (5.99; 0.31), (5.97; 9.57), (4.51; 0.49), (4.49; 0.89), (4.48; 0.45), (3.61; 0.59), (3.59; 0.96), (3.59; 0.72), (3.58; 0.97), (3.57; 0.65), (3.56; 0.44), (3.53; 0.39), (3.51; 0.50), (3.48; 0.46), (3.46; 0.60), (3.45; 0.61), (3.44; 0.71), (3.43; 0.74), (3.40; 0.83), (3.38; 1.39), (3.37; 1.71), (3.30; 2100.27), (3.27; 8.73), (3.24; 0.67), (3.23; 0.61), (3.22; 0.40), (2.69; 0.60), (2.68; 0.90), (2.67; 2.26), (2.67; 2.83), (2.66; 1.66), (2.65; 1.08), (2.64; 0.85), (2.63; 0.58), (2.62; 0.41), (2.54; 3.33), (2.52; 8.54), (2.51; 113.71), (2.50; 219.38), (2.50; 289.65), (2.49; 204.34), (2.49; 95.57), (2.33; 1.33), (2.33; 1.76), (2.32; 1.26), (2.22; 0.56), (2.20; 1.26), (2.18; 0.74), (2.17; 0.66), (2.14; 15.00), (2.07; 1.25), (2.05; 0.44), (1.76; 1.10), (1.74; 0.90), (1.36; 0.60), (1.24; 0.39), (1.09; 0.57), (0.89; 0.55), (0.60; 1.14), (0.59; 2.96), (0.58; 3.88), (0.57; 3.66), (0.57; 3.06), (0.55; 1.25), (0.42; 1.21), (0.41; 3.49), (0.40; 3.28), (0.39; 2.90), (0.38; 0.98), (0.37; 0.42), (0.36; 0.47), (0.00; 1.23) |

-continued

| No. | Structure | logP | MH+ | NMR |
|---|---|---|---|---|
| 363 | 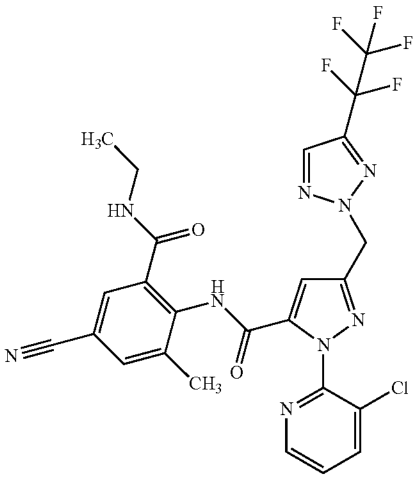 [SMILES: CCNC(=O)c1cc(C#N)cc(C)c1NC(=O)c1cc(Cn2ncc(C(F)(F)C(F)(F)F)n2)nn1-c1ncccc1Cl] | 3.26 | 608 | (10.45; 4.11), (8.57; 6.68), (8.47; 3.49), (8.47; 3.70), (8.46; 3.75), (8.46; 3.68), (8.31; 1.00), (8.30; 1.84), (8.28; 1.01), (8.15; 2.85), (8.14; 2.84), (8.13; 3.17), (8.12; 3.02), (7.84; 3.28), (7.72; 3.64), (7.72; 3.49), (7.60; 3.00), (7.59; 2.97), (7.58; 2.91), (7.56; 2.80), (7.26; 4.17), (5.98; 11.32), (3.38; 0.34), (3.31; 1039.92), (3.28; 4.70), (3.16; 0.93), (3.15; 3.26), (3.13; 3.57), (3.13; 3.56), (3.11; 3.36), (3.10; 0.99), (2.68; 0.47), (2.67; 0.88), (2.67; 1.21), (2.66; 0.89), (2.66; 0.42), (2.54; 1.70), (2.52; 3.56), (2.52; 5.54), (2.51; 67.30), (2.50; 131.06), (2.50; 175.92), (2.50; 120.37), (2.49; 55.83), (2.33; 0.88), (2.33; 1.15), (2.32; 0.85), (2.20; 15.12), (2.07; 2.03), (1.24; 0.48), (1.00; 7.42), (0.98; 16.00), (0.96; 7.12), (0.01; 0.34), (0.00; 9.09) |
| 364 | 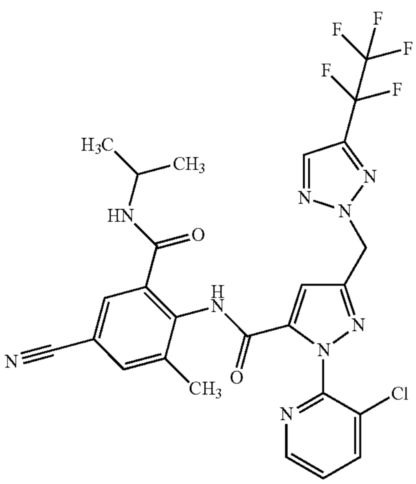 [SMILES: Cc1cc(C#N)cc(C(=O)NC(C)C)c1NC(=O)c1cc(Cn2ncc(C(F)(F)C(F)(F)F)n2)nn1-c1ncccc1Cl] | 3.52 | 622 | (10.41; 2.92), (8.57; 4.07), (8.47; 2.18), (8.46; 2.36), (8.45; 2.40), (8.45; 2.34), (8.14; 2.10), (8.13; 2.16), (8.12; 3.72), (8.11; 2.76), (8.10; 1.42), (7.84; 2.27), (7.84; 2.45), (7.70; 2.59), (7.70; 2.49), (7.59; 2.27), (7.58; 2.19), (7.57; 2.10), (7.56; 2.09), (7.26; 3.69), (5.98; 7.50), (3.91; 0.63), (3.89; 0.93), (3.87; 0.94), (3.86; 0.62), (3.35; 0.36), (3.34; 0.58), (3.30; 769.77), (3.28; 3.53), (2.68; 0.33), (2.67; 0.68), (2.67; 0.97), (2.66; 0.69), (2.54; 1.32), (2.52; 2.64), (2.52; 3.98), (2.51; 51.24), (2.50; 100.74), (2.50; 136.20), (2.50; 93.21), (2.49; 43.61), (2.33; 0.68), (2.33; 0.92), (2.32; 0.66), (2.20; 10.96), (2.07; 1.22), (1.30; 0.47), (1.01; 16.00), (1.00; 15.87), (0.01; 0.36), (0.00; 10.58), (−0.01; 0.32) |
| 365 | 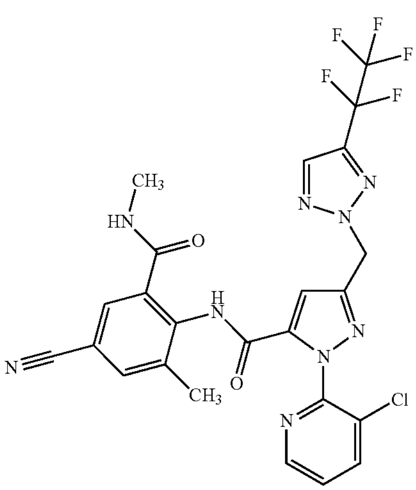 [SMILES: CNC(=O)c1cc(C#N)cc(C)c1NC(=O)c1cc(Cn2ncc(C(F)(F)C(F)(F)F)n2)nn1-c1ncccc1Cl] | 3.04 | 594 | (10.48; 3.74), (8.57; 6.22), (8.48; 3.26), (8.48; 3.53), (8.47; 3.67), (8.46; 3.52), (8.31; 1.59), (8.30; 1.59), (8.29; 0.66), (8.15; 2.89), (8.15; 2.91), (8.13; 3.26), (8.13; 2.99), (7.85; 3.42), (7.85; 3.55), (7.73; 3.86), (7.73; 3.60), (7.60; 3.16), (7.59; 3.04), (7.58; 2.86), (7.57; 2.90), (7.26; 4.76), (5.98; 11.23), (3.48; 0.37), (3.46; 0.39), (3.42; 0.45), (3.41; 0.61), (3.40; 0.68), (3.39; 0.69), (3.34; 2.15), (3.34; 2.35), (3.30; 2388.92), (3.28; 11.36), (2.69; 0.42), (2.68; 1.30), (2.67; 2.44), (2.67; 3.36), (2.66; 2.92), (2.66; 11.62), (2.64; 11.44), (2.60; 0.38), (2.57; 0.53), (2.54; 4.50), (2.52; 8.82), (2.52; 13.46), (2.51; 166.52), (2.50; 323.59), (2.50; 433.44), (2.50; 295.17), (2.49; 137.25), (2.34; 0.91), (2.33; 2.03), (2.33; 2.82), (2.32; 1.98), (2.19; 16.00), (2.07; 3.78), (2.05; 0.58), (1.24; 0.83), (0.01; 1.30), (0.00; 35.72), (−0.01; 1.02) |

-continued
| No. | Structure | logP | MH+ | NMR |
|---|---|---|---|---|
| 366 | 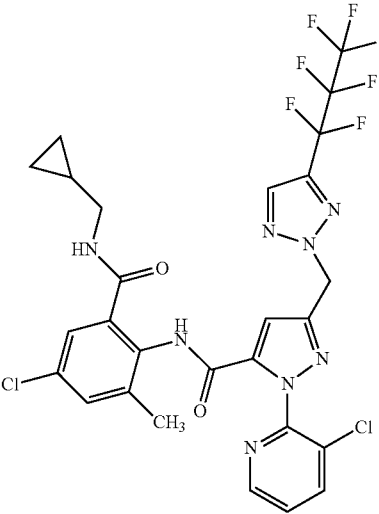 | 4.34 | 693 | (10.181; 2.40), (8.551; 5.12), (8.461; 2.83), (8.457; 2.83), (8.449; 2.94), (8.446; 2.84), (8.238; 0.86), (8.224; 1.63), (8.208; 0.83), (8.133; 2.69), (8.129; 2.64), (8.113; 2.98), (8.109; 2.71), (7.588; 2.78), (7.576; 2.74), (7.568; 2.60), (7.556; 2.60), (7.449; 2.86), (7.443; 3.07), (7.310; 3.33), (7.304; 3.16), (7.220; 5.65), (5.964; 9.24), (3.400; 0.52), (3.386; 0.64), (3.356; 0.58), (3.290; 986.83), (3.267; 5.86), (3.247; 0.97), (3.227; 0.53), (2.994; 2.86), (2.979; 4.11), (2.963; 2.80), (2.673; 0.98), (2.668; 1.40), (2.664; 1.00), (2.580; 0.32), (2.565; 0.43), (2.538; 2.15), (2.521; 5.95), (2.508; 79.83), (2.504; 152.66), (2.499; 200.41), (2.495; 140.50), (2.490; 65.05), (2.336; 0.56), (2.330; 0.99), (2.326; 1.27), (2.322; 0.97), (2.143; 15.00), (2.120; 0.30), (2.067; 2.24), (0.891; 0.55), (0.856; 0.74), (0.850; 0.71), (0.838; 1.13), (0.825; 0.75), (0.809; 0.39), (0.310; 1.06), (0.299; 2.96), (0.294; 3.15), (0.284; 1.73), (0.278; 3.06), (0.274; 2.80), (0.264; 1.09), (0.111; 1.26), (0.100; 3.63), (0.088; 3.26), (0.085; 3.50), (0.074; 0.87), (0.000; 2.42) |
| 367 | 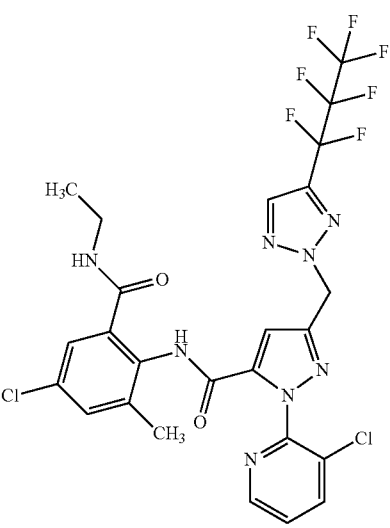 [SMILES: CCNC(=O)c1cc(Cl)cc(C)c1NC(=O)c1cc(Cn2ncc(C(F)(F)C(F)(F)C(F)(F)F)n2)nn1-c1ncccc1Cl] | 4.03 | 667 | (10.18; 3.10), (8.55; 4.98), (8.47; 2.70), (8.46; 2.83), (8.46; 2.89), (8.45; 2.67), (8.17; 0.95), (8.15; 1.84), (8.14; 3.13), (8.13; 2.82), (8.12; 2.89), (8.11; 2.71), (7.59; 2.75), (7.58; 2.65), (7.57; 2.55), (7.56; 2.53), (7.44; 2.79), (7.43; 3.09), (7.30; 3.34), (7.30; 3.07), (7.21; 5.90), (5.97; 9.08), (3.45; 0.33), (3.42; 0.42), (3.41; 0.44), (3.38; 0.77), (3.37; 0.75), (3.36; 1.14), (3.30; 1652.59), (3.28; 6.97), (3.26; 2.32), (3.24; 1.20), (3.23; 0.78), (3.22; 0.50), (3.21; 0.50), (3.20; 0.46), (3.20; 0.38), (3.19; 0.44), (3.17; 0.39), (3.15; 0.92), (3.14; 2.73), (3.12; 2.88), (3.12; 2.83), (3.10; 2.59), (3.09; 0.85), (2.67; 0.97), (2.67; 1.30), (2.66; 0.93), (2.58; 0.30), (2.54; 2.11), (2.52; 5.87), (2.51; 76.88), (2.50; 148.19), (2.50; 195.39), (2.50; 138.09), (2.49; 64.87), (2.33; 0.94), (2.33; 1.28), (2.32; 0.90), (2.18; 0.39), (2.14; 15.00), (2.07; 1.17), (1.36; 2.42), (0.99; 5.54), (0.97; 11.76), (0.95; 5.29), (0.89; 0.46), (0.00; 1.45) |

| No. | Structure | logP | MH+ | NMR |
|---|---|---|---|---|
| 368 | 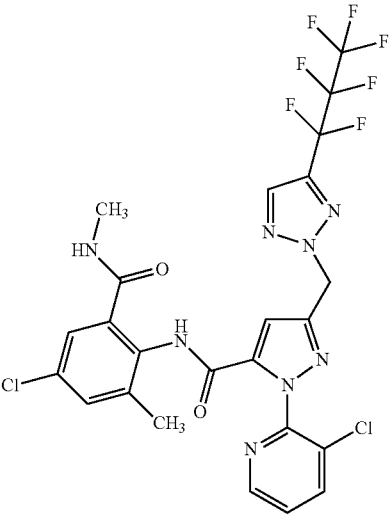 [SMILES: CNC(=O)c1cc(Cl)cc(C)c1NC(=O)c1cc(Cn2ncc(C(F)(F)C(F)(F)C(F)(F)F)n2)nn1-c1ncccc1Cl] | 3.76 | 653 | (10.21; 1.49), (8.56; 4.48), (8.47; 2.46), (8.47; 2.55), (8.46; 2.62), (8.46; 2.47), (8.17; 1.20), (8.16; 1.24), (8.14; 2.52), (8.14; 2.45), (8.12; 2.67), (8.12; 2.42), (7.59; 2.50), (7.58; 2.45), (7.57; 2.34), (7.56; 2.29), (7.44; 2.60), (7.44; 2.81), (7.32; 3.09), (7.31; 2.84), (7.24; 0.32), (7.22; 5.21), (6.87; 1.17), (6.60; 0.72), (6.01; 0.35), (5.97; 8.19), (3.66; 0.59), (3.38; 0.34), (3.37; 0.60), (3.35; 0.66), (3.29; 502.78), (3.27; 2.77), (3.26; 0.52), (2.86; 0.34), (2.67; 0.75), (2.67; 0.88), (2.66; 0.77), (2.66; 0.69), (2.65; 8.82), (2.63; 8.64), (2.58; 0.39), (2.57; 0.37), (2.55; 0.87), (2.54; 1.32), (2.52; 3.10), (2.51; 40.59), (2.50; 77.99), (2.50; 102.76), (2.49; 72.32), (2.49; 33.84), (2.33; 0.47), (2.33; 0.62), (2.32; 0.47), (2.18; 1.91), (2.13; 13.80), (2.07; 0.75), (1.91; 0.47), (1.36; 15.00), (0.00; 0.88) |
| 369 | 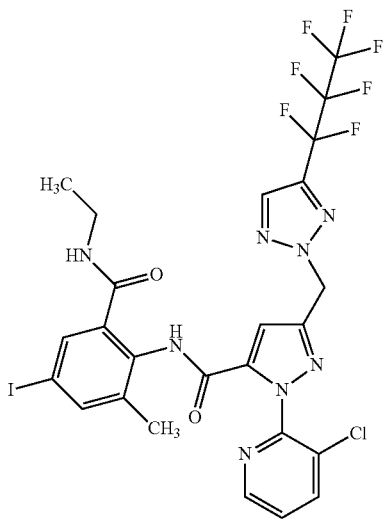 [SMILES: CCNC(=O)c1cc(I)cc(C)c1NC(=O)c1cc(Cn2ncc(C(F)(F)C(F)(F)C(F)(F)F)n2)nn1-c1ncccc1Cl] | 4.28 | 759 | (10.17; 3.25), (8.55; 5.12), (8.47; 2.74), (8.46; 2.84), (8.45; 2.93), (8.45; 2.74), (8.16; 1.04), (8.14; 2.13), (8.14; 3.26), (8.13; 3.39), (8.12; 3.04), (8.11; 2.73), (7.72; 3.19), (7.72; 3.36), (7.59; 2.84), (7.58; 3.15), (7.57; 5.38), (7.56; 2.69), (7.21; 5.92), (5.97; 9.22), (3.36; 0.31), (3.29; 349.78), (3.27; 1.74), (3.15; 0.80), (3.13; 2.55), (3.11; 2.86), (3.11; 2.78), (3.10; 2.56), (3.08; 0.79), (2.87; 0.43), (2.67; 0.43), (2.67; 0.55), (2.66; 0.41), (2.54; 0.86), (2.52; 2.31), (2.51; 31.53), (2.50; 60.88), (2.50; 80.27), (2.49; 56.48), (2.49; 26.45), (2.33; 0.38), (2.33; 0.51), (2.32; 0.36), (2.10; 15.00), (2.07; 0.46), (1.14; 0.30), (0.98; 5.63), (0.97; 11.98), (0.95; 5.38), (0.01; 0.77), (0.00; 15.60), (−0.01; 0.54) |

US 8,536,202 B2
303 304
-continued
| No. | Structure | logP | MH+ | NMR |
|---|---|---|---|---|
| 370 | 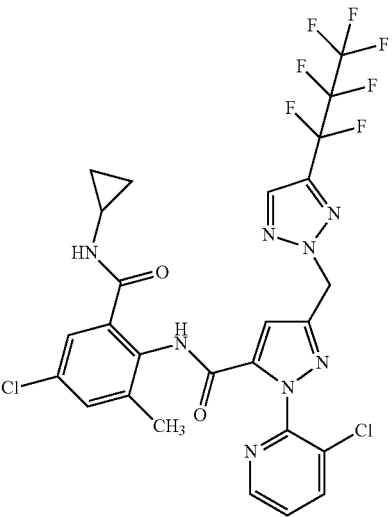 [SMILES: Cc1cc(Cl)cc(C(=O)NC2CC2)c1NC(=O)c1cc(Cn2ncc(C(F)(F)C(F)(F)C(F)(F)F)n2)nn1-c1ncccc1Cl] | 3.99 | 679 | (10.15; 1.97), (8.56; 5.07), (8.47; 2.72), (8.47; 2.81), (8.46; 2.86), (8.46; 2.82), (8.21; 1.70), (8.20; 1.68), (8.14; 2.56), (8.14; 2.51), (8.12; 2.77), (8.12; 2.63), (7.59; 2.70), (7.58; 2.64), (7.57; 2.49), (7.56; 2.50), (7.43; 2.86), (7.42; 3.03), (7.27; 3.40), (7.26; 3.19), (7.23; 6.03), (5.98; 9.05), (4.50; 0.50), (4.49; 0.98), (4.48; 0.51), (3.61; 0.31), (3.60; 0.49), (3.60; 0.63), (3.59; 0.67), (3.59; 0.91), (3.58; 0.65), (3.57; 0.92), (3.57; 0.59), (3.56; 0.44), (3.40; 0.44), (3.38; 0.57), (3.36; 0.73), (3.36; 0.76), (3.34; 1.35), (3.33; 2.03), (3.30; 786.43), (3.27; 4.30), (3.26; 0.81), (3.24; 0.36), (2.92; 0.52), (2.69; 0.42), (2.68; 0.75), (2.67; 1.36), (2.67; 1.84), (2.66; 1.47), (2.65; 1.00), (2.64; 0.72), (2.63; 0.38), (2.61; 0.41), (2.60; 0.45), (2.59; 0.43), (2.58; 0.40), (2.57; 0.41), (2.54; 1.32), (2.52; 3.54), (2.51; 48.21), (2.50; 93.10), (2.50; 123.23), (2.49; 87.24), (2.49; 41.09), (2.33; 0.61), (2.33; 0.80), (2.32; 0.58), (2.29; 0.30), (2.22; 0.49), (2.20; 0.88), (2.18; 0.98), (2.17; 1.56), (2.15; 1.19), (2.13; 15.00), (2.07; 2.62), (1.76; 0.43), (1.74; 1.81), (1.36; 0.65), (0.60; 1.10), (0.58; 3.84), (0.57; 3.72), (0.56; 3.00), (0.55; 1.21), (0.42; 1.23), (0.41; 3.46), (0.41; 3.26), (0.40; 2.87), (0.38; 1.15), (0.37; 0.77), (0.37; 0.72), (0.36; 0.76), (0.36; 0.81), (0.34; 0.45), (0.00; 0.81) |
| 371 | 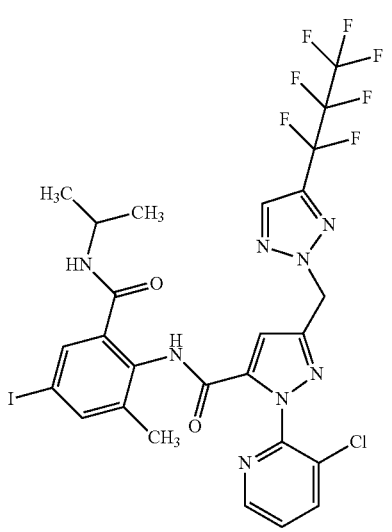 [SMILES: Cc1cc(I)cc(C(=O)NC(C)C)c1NC(=O)c1cc(Cn2ncc(C(F)(F)C(F)(F)C(F)(F)F)n2)nn1-c1ncccc1Cl] | 4.46 | 773 | (18.52; 0.31), (10.13; 1.32), (8.55; 3.94), (8.46; 1.95), (8.46; 2.15), (8.45; 2.24), (8.44; 2.18), (8.13; 1.87), (8.13; 1.79), (8.12; 0.42), (8.11; 2.10), (8.11; 1.89), (7.95; 1.00), (7.93; 1.03), (7.71; 2.25), (7.59; 2.02), (7.58; 2.04), (7.57; 1.97), (7.56; 2.21), (7.55; 2.41), (7.21; 3.08), (5.97; 6.87), (3.92; 0.31), (3.91; 0.30), (3.90; 0.65), (3.88; 0.95), (3.86; 0.85), (3.85; 0.74), (3.79; 0.30), (3.47; 0.39), (3.45; 0.56), (3.42; 0.73), (3.40; 0.63), (3.39; 0.90), (3.37; 1.46), (3.35; 2.50), (3.30; 2853.33), (3.27; 15.48), (3.26; 3.84), (3.23; 1.47), (3.21; 1.13), (3.20; 0.83), (3.19; 0.80), (3.17; 0.58), (3.14; 0.46), (3.12; 0.34), (2.91; 0.35), (2.89; 0.33), (2.88; 0.31), (2.72; 0.31), (2.71; 0.35), (2.70; 0.44), (2.67; 2.06), (2.67; 2.86), (2.66; 2.10), (2.64; 0.34), (2.63; 0.42), (2.62; 0.38), (2.54; 4.14), (2.52; 10.78), (2.51; 160.88), (2.50; 315.19), (2.50; 419.95), (2.49; 300.48), (2.49; 143.72), (2.41; 0.42), (2.40; 0.40), (2.33; 2.07), (2.33; 2.71), (2.32; 2.00), (2.32; 1.06), (2.29; 0.32), (2.10; 10.97), (2.07; 4.70), (2.06; 0.38), (2.05; 0.59), (1.91; 0.40), (1.36; 0.32), (1.36; 0.37), (1.24; 0.52), (1.23; 0.31), (1.15; 0.33), (1.09; 0.34), (1.04; 0.34), (1.00; 15.00), (0.98; 14.95), (0.89; 0.90), (0.84; 0.32), (0.00; 2.56) |

| No. | Structure | logP | MH+ | NMR |
|---|---|---|---|---|
| 372 | 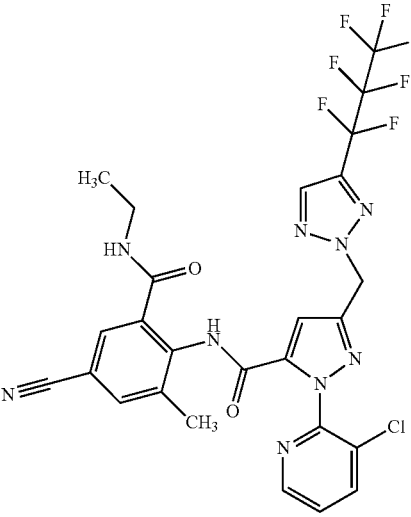 | 3.65 | 658 | (10.45; 4.18), (8.57; 6.00), (8.47; 3.08), (8.47; 3.39), (8.46; 3.37), (8.46; 3.33), (8.31; 1.07), (8.30; 2.07), (8.28; 1.05), (8.15; 3.14), (8.14; 3.14), (8.13; 3.59), (8.12; 3.28), (7.85; 3.28), (7.84; 3.49), (7.72; 3.75), (7.72; 3.62), (7.60; 3.34), (7.59; 3.24), (7.58; 3.12), (7.56; 3.15), (7.25; 5.36), (5.98; 10.60), (3.36; 0.52), (3.30; 1229.33), (3.16; 0.83), (3.14; 2.76), (3.13; 3.00), (3.13; 2.99), (3.11; 2.88), (3.09; 0.88), (2.68; 0.53), (2.67; 1.15), (2.67; 1.55), (2.66; 1.12), (2.66; 0.50), (2.54; 2.19), (2.52; 4.32), (2.52; 6.66), (2.51; 85.48), (2.50; 168.01), (2.50; 227.24), (2.50; 155.55), (2.49; 72.87), (2.34; 0.56), (2.33; 1.12), (2.33; 1.54), (2.32; 1.07), (2.32; 0.51), (2.19; 16.00), (2.07; 1.62), (1.40; 0.83), (1.24; 0.54), (1.00; 6.63), (0.98; 14.58), (0.96; 6.39), (0.89; 0.33), (0.01; 0.45), (0.00; 12.75), (−0.01; 0.43) |
| 373 | 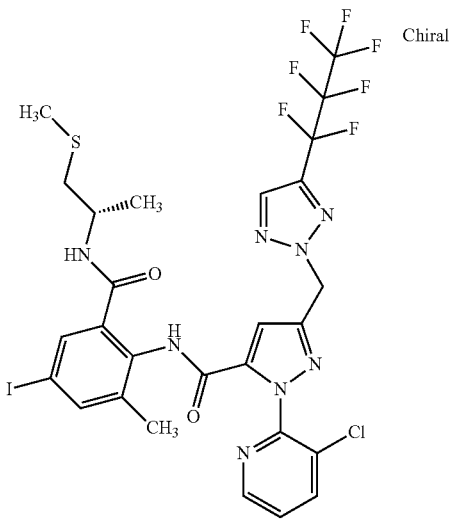 [SMILES: CSC[C@H](C)NC(=O)c1cc(I)cc(C)c1NC(=O)c1cc(Cn2ncc(C(F)(F)C(F)(F)C(F)(F)F)n2)nn1-c1ncccc1Cl] | 4.65 | 819 | (10.15; 0.38), (8.54; 3.22), (8.46; 1.60), (8.46; 1.65), (8.45; 1.72), (8.45; 1.61), (8.13; 1.74), (8.13; 1.94), (8.12; 1.27), (8.11; 1.94), (8.11; 1.97), (7.73; 1.97), (7.73; 2.06), (7.60; 0.45), (7.59; 1.76), (7.58; 3.38), (7.58; 2.28), (7.57; 1.89), (7.56; 1.55), (7.24; 3.27), (7.23; 0.42), (5.96; 5.46), (5.26; 0.52), (5.24; 0.30), (3.96; 0.56), (3.94; 0.66), (3.93; 0.55), (3.55; 0.42), (3.54; 0.52), (3.53; 0.40), (3.52; 0.48), (3.51; 0.71), (3.50; 0.57), (3.48; 0.37), (3.47; 0.47), (3.33; 595.63), (3.21; 0.64), (3.20; 0.54), (3.19; 0.74), (3.18; 0.68), (3.17; 0.80), (3.16; 0.69), (3.16; 0.59), (3.15; 0.53), (3.02; 0.30), (2.95; 0.39), (2.94; 0.45), (2.93; 0.44), (2.92; 0.37), (2.71; 0.46), (2.69; 0.44), (2.68; 0.63), (2.67; 1.73), (2.65; 2.83), (2.65; 2.78), (2.64; 1.37), (2.62; 1.21), (2.61; 0.49), (2.59; 0.48), (2.56; 0.85), (2.54; 1.36), (2.52; 4.25), (2.51; 30.17), (2.51; 59.49), (2.50; 77.92), (2.50; 55.51), (2.49; 26.34), (2.43; 1.11), (2.42; 1.12), (2.40; 0.76), (2.38; 0.69), (2.33; 0.43), (2.33; 0.57), (2.32; 0.40), (2.31; 0.60), (2.11; 9.26), (2.11; 13.80), (2.08; 0.41), (2.07; 0.48), (2.06; 0.38), (2.05; 0.42), (2.05; 0.38), (1.99; 15.00), (1.99; 2.42), (1.32; 1.20), (1.32; 1.06), (1.30; 1.23), (1.30; 1.09), (1.25; 4.37), (1.23; 4.30), (1.16; 0.39), (1.14; 0.49), (1.13; 3.73), (1.12; 3.65), (1.09; 0.70), (1.06; 4.64), (1.05; 4.55), (0.96; 0.43), (0.95; 0.40), (0.00; 0.31) |

| No. | Structure | logP | MH+ | NMR |
|---|---|---|---|---|
| 374 | 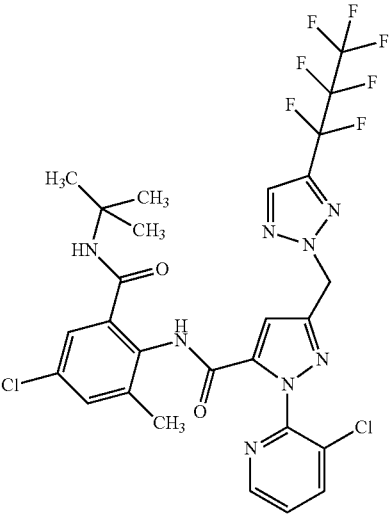 | 4.65 | 695 | (10.12; 0.34), (8.55; 1.26), (8.47; 0.68), (8.46; 0.72), (8.46; 0.74), (8.45; 0.70), (8.14; 0.64), (8.14; 0.65), (8.12; 0.69), (8.12; 0.65), (7.59; 0.67), (7.58; 0.65), (7.57; 0.65), (7.56; 0.61), (7.48; 0.53), (7.41; 0.71), (7.40; 0.75), (7.24; 0.80), (7.23; 0.76), (7.19; 1.50), (5.97; 2.40), (3.29; 221.78), (3.27; 1.27), (2.67; 0.33), (2.54; 0.51), (2.52; 1.30), (2.51; 17.81), (2.50; 34.63), (2.50; 45.91), (2.49; 32.59), (2.49; 15.51), (2.13; 3.69), (2.07; 0.71), (1.36; 0.58), (1.24; 0.78), (1.19; 15.00), (0.00; 0.46) |
| 375 | 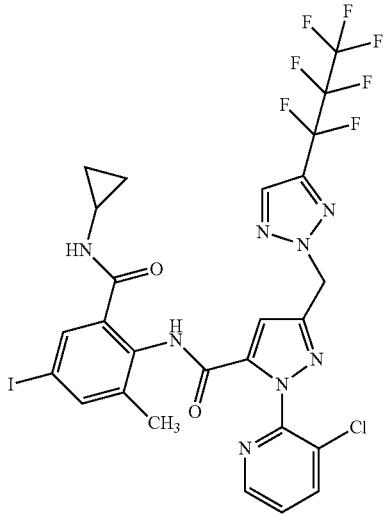 [SMILES: Cc1cc(I)cc(C(=O)NC2CC2)c1NC(=O)c1cc(Cn2ncc(C(F)(F)C(F)(F)C(F)(F)F)n2)nn1-c1ncccc1Cl] | 4.23 | 771 | (10.14; 2.07), (8.56; 5.18), (8.47; 2.70), (8.47; 2.86), (8.46; 2.89), (8.46; 2.70), (8.20; 1.73), (8.19; 1.72), (8.14; 2.58), (8.13; 2.52), (8.12; 2.89), (8.11; 2.61), (7.71; 3.14), (7.71; 3.24), (7.59; 2.67), (7.58; 2.65), (7.57; 2.52), (7.56; 2.50), (7.53; 3.44), (7.52; 3.32), (7.22; 5.61), (5.97; 9.09), (4.50; 0.56), (4.49; 1.22), (4.48; 0.61), (3.61; 0.37), (3.60; 0.63), (3.59; 0.72), (3.59; 1.16), (3.58; 0.76), (3.58; 0.64), (3.57; 1.15), (3.57; 0.74), (3.57; 0.47), (3.56; 0.56), (3.40; 0.38), (3.39; 0.39), (3.38; 0.44), (3.37; 0.51), (3.33; 1.76), (3.29; 938.45), (3.27; 4.89), (3.24; 0.54), (2.92; 0.68), (2.68; 1.14), (2.67; 2.11), (2.66; 1.82), (2.65; 1.49), (2.64; 1.03), (2.63; 0.77), (2.62; 0.49), (2.62; 0.43), (2.61; 0.47), (2.60; 0.53), (2.59; 0.54), (2.58; 0.57), (2.57; 0.57), (2.54; 2.00), (2.52; 5.23), (2.51; 71.32), (2.50; 137.64), (2.50; 181.64), (2.49; 128.49), (2.49; 60.55), (2.33; 0.89), (2.33; 1.14), (2.32; 0.84), (2.22; 0.55), (2.20; 1.00), (2.18; 1.14), (2.17; 1.85), (2.15; 0.88), (2.10; 15.00), (2.07; 3.09), (2.05; 0.33), (1.76; 0.51), (1.74; 2.65), (0.89; 0.51), (0.60; 0.52), (0.59; 1.12), (0.59; 1.24), (0.58; 3.36), (0.58; 3.83), (0.56; 3.99), (0.56; 2.92), (0.55; 1.16), (0.42; 1.27), (0.41; 3.53), (0.40; 3.32), (0.39; 2.94), (0.38; 1.15), (0.37; 1.00), (0.37; 0.87), (0.36; 0.92), (0.36; 0.98), (0.34; 0.64), (0.00; 1.40) |

| No. | Structure | logP | MH+ | NMR |
|---|---|---|---|---|
| 376 | 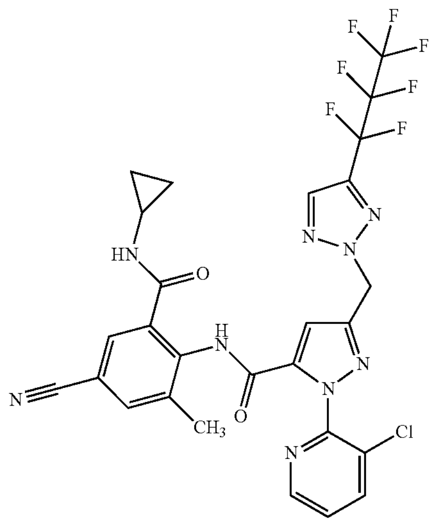 [SMILES: Cc1cc(C#N)cc(C(=O)NC2CC2)c1NC(=O)c1cc(Cn2ncc(C(F)(F)C(F)(F)C(F)(F)F)n2)nn1-c1ncccc1Cl] | 3.63 | 670 | (10.43; 4.63), (8.57; 8.58), (8.48; 3.86), (8.47; 3.93), (8.47; 4.05), (8.46; 3.95), (8.34; 2.59), (8.33; 2.53), (8.15; 2.85), (8.14; 2.90), (8.13; 3.13), (8.12; 3.05), (7.84; 3.92), (7.69; 4.03), (7.60; 2.77), (7.59; 2.80), (7.58; 2.73), (7.57; 2.66), (7.27; 4.91), (5.99; 11.72), (3.41; 0.38), (3.38; 0.50), (3.37; 0.99), (3.36; 1.65), (3.34; 5.12), (3.31; 3720.97), (3.29; 17.55), (3.27; 2.49), (3.24; 1.01), (3.23; 0.92), (3.22; 0.70), (3.20; 0.50), (3.19; 0.55), (3.18; 0.40), (3.16; 0.36), (3.12; 0.38), (2.89; 0.46), (2.73; 0.35), (2.70; 0.79), (2.69; 0.94), (2.67; 3.39), (2.67; 4.46), (2.67; 3.51), (2.66; 2.29), (2.65; 1.31), (2.64; 0.84), (2.63; 0.37), (2.54; 4.40), (2.52; 8.28), (2.52; 12.43), (2.51; 174.59), (2.51; 346.23), (2.50; 471.51), (2.50; 324.05), (2.49; 152.37), (2.41; 0.35), (2.39; 0.36), (2.34; 1.13), (2.33; 2.41), (2.33; 3.21), (2.32; 2.42), (2.32; 1.18), (2.19; 16.00), (2.07; 7.52), (2.05; 0.82), (1.40; 0.80), (1.24; 0.97), (0.89; 0.87), (0.61; 1.44), (0.60; 3.82), (0.59; 5.26), (0.58; 4.97), (0.58; 4.20), (0.56; 1.72), (0.43; 1.35), (0.42; 4.12), (0.42; 4.26), (0.41; 3.54), (0.40; 1.11), (0.00; 5.30) |
| 377 | 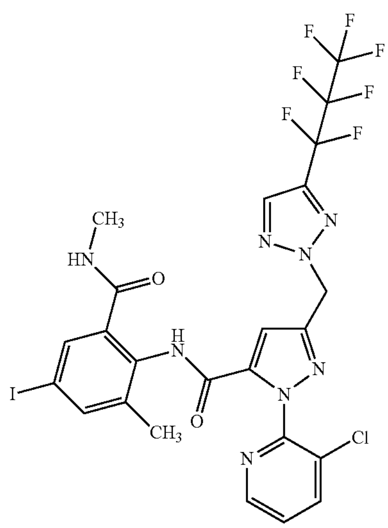 [SMILES: CNC(=O)c1cc(I)cc(C)c1NC(=O)c1cc(Cn2ncc(C(F)(F)C(F)(F)C(F)(F)F)n2)nn1-c1ncccc1Cl] | 4 | 745 | (10.19; 1.77), (8.56; 5.07), (8.47; 2.73), (8.47; 2.87), (8.46; 2.95), (8.46; 2.75), (8.15; 1.46), (8.14; 3.80), (8.14; 3.64), (8.12; 3.18), (8.12; 2.73), (7.72; 3.11), (7.72; 3.19), (7.59; 3.74), (7.59; 3.81), (7.58; 4.08), (7.57; 2.76), (7.56; 2.62), (7.23; 0.35), (7.21; 5.03), (6.87; 1.03), (6.60; 0.62), (6.01; 0.40), (5.97; 9.02), (3.65; 0.77), (3.60; 0.52), (3.39; 0.39), (3.38; 0.47), (3.34; 0.91), (3.34; 1.16), (3.33; 1.31), (3.29; 821.97), (3.27; 4.33), (3.24; 0.37), (3.23; 0.35), (3.23; 0.33), (2.86; 0.97), (2.68; 0.62), (2.67; 0.95), (2.67; 1.24), (2.66; 0.94), (2.64; 9.71), (2.63; 9.51), (2.58; 0.63), (2.57; 0.75), (2.54; 1.76), (2.52; 4.96), (2.51; 64.92), (2.50; 123.61), (2.50; 161.25), (2.49; 112.70), (2.49; 51.90), (2.33; 0.79), (2.33; 1.06), (2.32; 0.72), (2.18; 1.64), (2.10; 15.00), (2.07; 2.57), (1.86; 0.53), (1.76; 0.57), (1.36; 12.89), (1.24; 0.35), (0.89; 0.39), (0.00; 2.11) |
| 378 | 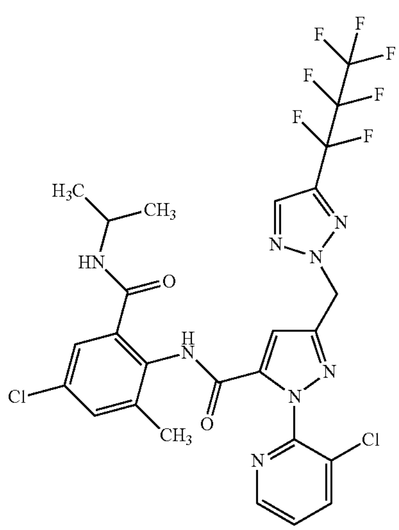 [SMILES: Cc1cc(Cl)cc(C(=O)NC(C)C)c1NC(=O)c1cc(Cn2ncc(C(F)(F)C(F)(F)C(F)(F)F)n2)nn1-c1ncccc1Cl] | 4.27 | 681 | (10.14; 1.63), (8.55; 3.71), (8.46; 2.04), (8.46; 2.11), (8.45; 2.12), (8.45; 2.03), (8.13; 1.85), (8.13; 1.82), (8.11; 2.11), (8.11; 1.93), (7.96; 1.06), (7.94; 1.06), (7.59; 2.05), (7.58; 1.98), (7.57; 1.90), (7.56; 1.83), (7.43; 2.12), (7.43; 2.21), (7.28; 2.44), (7.27; 2.25), (7.22; 3.90), (5.97; 6.84), (3.92; 0.31), (3.91; 0.68), (3.89; 1.06), (3.87; 0.97), (3.85; 0.64), (3.84; 0.35), (3.60; 0.41), (3.59; 0.35), (3.56; 0.30), (3.52; 0.42), (3.51; 0.36), (3.50; 0.43), (3.49; 0.44), (3.45; 0.59), (3.45; 0.65), (3.41; 1.16), (3.40; 1.65), (3.39; 2.01), (3.38; 2.08), (3.30; 1839.03), (3.28; 8.11), (3.26; 1.83), (3.26; 1.01), (3.24; 0.75), (3.23; 0.36), (2.67; 1.08), (2.67; 1.29), (2.66; 0.97), (2.61; 0.38), (2.59; 0.58), (2.54; 3.36), (2.52; 7.79), (2.51; 77.08), (2.50; 146.55), (2.50; 192.35), (2.50; 135.79), (2.49; 63.59), (2.33; 0.87), (2.33; 1.20), (2.32; 0.86), (2.14; 11.12), (2.07; 0.99), (1.05; 0.31), (1.00; 15.00), (0.99; 14.70), (0.89; 0.32), (0.00; 0.68) |

| No. | Structure | logP | MH+ | NMR |
|---|---|---|---|---|
| 379 | 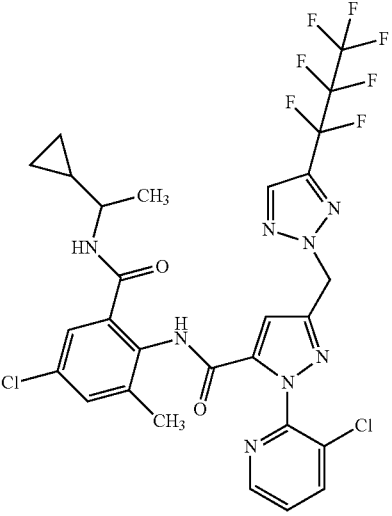 [SMILES: Cc1cc(Cl)cc(C(=O)NC(C)C2CC2)c1NC(=O)c1cc(Cn2ncc(C(F)(F)C(F)(F)C(F)(F)F)n2)nn1-c1ncccc1Cl] | 4.57 | 707 | (10.141; 1.52), (8.550; 5.10), (8.463; 2.65), (8.460; 2.83), (8.451; 2.90), (8.448; 2.74), (8.131; 2.56), (8.127; 2.48), (8.111; 2.81), (8.107; 2.63), (8.032; 1.20), (8.012; 1.27), (7.589; 2.72), (7.577; 2.66), (7.569; 2.52), 7.557; 2.51), (7.442; 2.84), (7.437; 3.02), (7.278; 3.35), (7.272; 3.06), (7.218; 5.48), (5.964; 9.27), (3.398; 0.47), (3.391; 0.45), (3.381; 0.63), (3.362; 1.00), (3.292; 950.88), (3.270; 6.46), (3.227; 0.50), (3.216; 0.41), (2.673; 1.01), (2.668; 1.27), (2.664; 0.98), (2.565; 0.69), (2.538; 2.76), (2.521; 6.69), (2.508; 76.44), (2.504; 146.15), (2.499; 191.98), (2.494; 136.19), (2.490; 64.25), (2.330; 0.94), (2.326; 1.22), (2.321; 0.85), (2.142; 15.00), (2.089; 0.58), (2.067; 1.11), (1.357; 0.44), (1.041; 8.81), (1.025; 8.51), (0.891; 0.50), (0.817; 0.49), (0.808; 0.68), (0.796; 1.25), (0.784; 0.86), (0.776; 1.17), (0.764; 0.70), (0.756; 0.51), (0.361; 0.46), (0.348; 0.60), (0.340; 1.23), (0.332; 1.01), (0.328; 1.09), (0.318; 1.20), (0.306; 0.70), (0.297; 0.58), (0.205; 0.76), (0.194; 0.99), (0.187; 1.09), (0.174; 1.50), (0.162; 1.18), (0.153; 1.52), (0.140; 1.63), (0.130; 1.40), (0.118; 1.29), (0.106; 1.34), (0.097; 1.31), (0.084; 0.98), (0.074; 0.53), (−0.000; 1.29) |
| 380 | 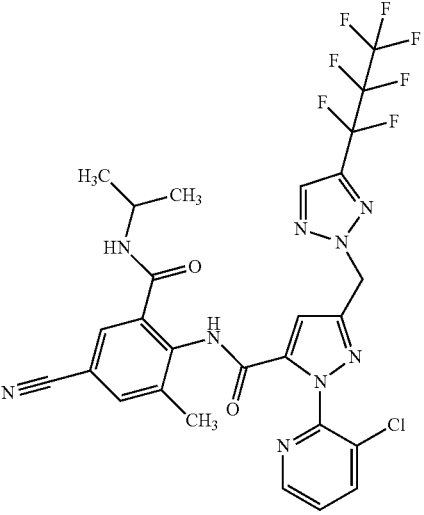 [SMILES: Cc1cc(C#N)cc(C(=O)NC(C)C)c1NC(=O)c1cc(Cn2ncc(C(F)(F)C(F)(F)C(F)(F)F)n2)nn1-c1ncccc1Cl] | 3.87 | 654 | (10.42; 2.15), (8.56; 4.73), (8.52; 0.32), (8.46; 2.45), (8.46; 2.69), (8.45; 2.78), (8.45; 2.70), (8.14; 1.79), (8.13; 1.95), (8.12; 2.71), (8.11; 2.33), (8.10; 1.09), (7.84; 1.95), (7.70; 2.15), (7.59; 1.93), (7.58; 1.86), (7.57; 1.80), (7.56; 1.74), (7.25; 2.30), (6.63; 0.36), (5.98; 6.66), (5.81; 0.50), (3.91; 0.75), (3.89; 1.15), (3.87; 1.09), (3.85; 0.75), (3.41; 0.60), (3.39; 1.41), (3.38; 1.58), (3.36; 1.35), (3.35; 1.68), (3.31; 1733.06), (3.29; 7.88), (2.68; 0.60), (2.67; 1.29), (2.67; 1.81), (2.66; 1.24), (2.66; 0.59), (2.55; 0.40), (2.54; 2.67), (2.52; 4.87), (2.52; 7.19), (2.51; 94.63), (2.50; 186.91), (2.50; 255.11), (2.50; 173.28), (2.49; 80.80), (2.34; 0.59), (2.33; 1.16), (2.33; 1.74), (2.32; 1.21), (2.32; 0.59), (2.20; 8.51), (2.07; 3.64), (2.05; 0.44), (1.47; 0.61), (1.24; 0.45), (1.20; 0.56), (1.18; 0.52), (1.11; 1.10), (1.09; 2.26), (1.07; 1.11), (1.01; 16.00), (1.00; 15.92), (0.89; 0.52), (0.00; 6.01) |

-continued
| No. | Structure | logP | MH+ | NMR |
|---|---|---|---|---|
| 381 | 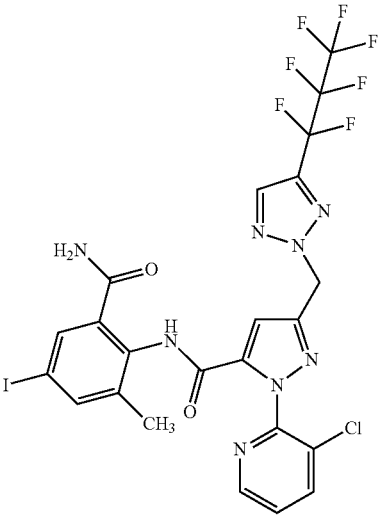 [SMILES: Cc1cc(I)cc(C(N)=O)c1NC(=O)c1cc(Cn2ncc(C(F)(F)C(F)(F)C(F)(F)F)n2)nn1-c1ncccc1Cl] | 3.7 | 731 | (10.24; 1.06), (8.55; 5.05), (8.48; 2.65), (8.47; 2.77), (8.47; 2.82), (8.46; 2.68), (8.14; 2.60), (8.14; 2.55), (8.12; 2.86), (8.12; 2.63), (7.73; 3.14), (7.73; 3.47), (7.66; 5.25), (7.66; 4.36), (7.59; 2.73), (7.58; 2.67), (7.57; 2.53), (7.56; 2.50), (7.40; 1.71), (7.22; 5.04), (6.87; 0.70), (6.60; 0.40), (5.96; 9.04), (5.74; 0.80), (3.62; 1.79), (3.62; 1.38), (3.61; 1.32), (3.61; 1.77), (3.60; 4.20), (3.60; 1.69), (3.59; 1.22), (3.59; 1.74), (3.29; 228.77), (3.27; 1.12), (2.91; 0.87), (2.67; 0.32), (2.54; 0.51), (2.51; 18.05), (2.50; 34.42), (2.50; 45.28), (2.49; 31.93), (2.49; 14.97), (2.18; 1.10), (2.09; 15.00), (2.07; 0.38), (1.78; 1.83), (1.77; 1.97), (1.76; 4.98), (1.76; 1.45), (1.75; 1.84), (1.74; 1.63), (1.63; 0.31), (1.36; 8.60), (1.14; 0.35) |
| 382 | 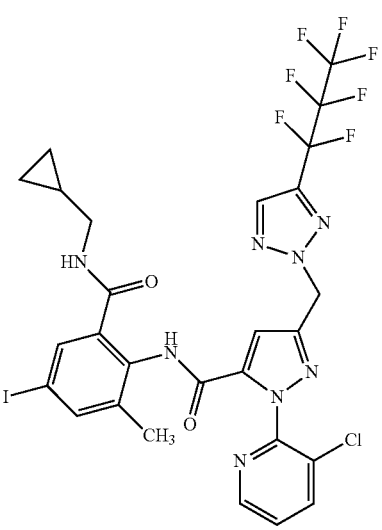 [SMILES: Cc1cc(I)cc(C(=O)NCC2CC2)c1NC(=O)c1cc(Cn2ncc(C(F)(F)C(F)(F)C(F)(F)F)n2)nn1-c1ncccc1Cl] | 4.59 | 785 | (10.171; 1.33), (8.548; 5.16), (8.459; 2.62), (8.455; 2.79), (8.447; 2.85), (8.443; 2.74), (8.228; 0.90), (8.215; 1.66), (8.201; 0.85), (8.130; 2.62), (8.127; 2.63), (8.110; 2.95), (8.107; 2.70), (7.731; 3.17), (7.727; 3.37), (7.586; 4.33), (7.584; 4.12), (7.579; 3.79), (7.575; 3.40), (7.566; 2.61), (7.554; 2.52), (7.213; 5.80), (5.960; 9.20), (3.400; 0.31), (3.386; 0.34), (3.359; 0.32), (3.289; 371.09), (3.266; 2.13), (2.986; 2.77), (2.970; 4.07), (2.954; 2.74), (2.673; 0.49), (2.668; 0.69), (2.663; 0.49), (2.538; 0.99), (2.521; 2.65), (2.508; 35.88), (2.503; 69.57), (2.499; 92.02), (2.494; 65.35), (2.490; 30.77), (2.330; 0.44), (2.326; 0.58), (2.321; 0.42), (2.106; 15.00), (2.067; 0.66), (1.357; 0.42), (0.867; 0.38), (0.855; 0.72), (0.849; 0.69), (0.845; 0.63), (0.837; 1.13), (0.829; 0.61), (0.825; 0.74), (0.820; 0.71), (0.817; 0.70), (0.806; 0.36), (0.311; 1.10), (0.300; 3.01), (0.296; 3.18), (0.285; 1.66), (0.280; 3.04), (0.276; 2.85), (0.266; 1.14), (0.109; 1.27), (0.098; 3.60), (0.095; 3.56), (0.086; 3.15), (0.083; 3.52), (0.072; 0.86), (−0.000; 0.91) |

| No. | Structure | logP | MH+ | NMR |
|---|---|---|---|---|
| 383 | 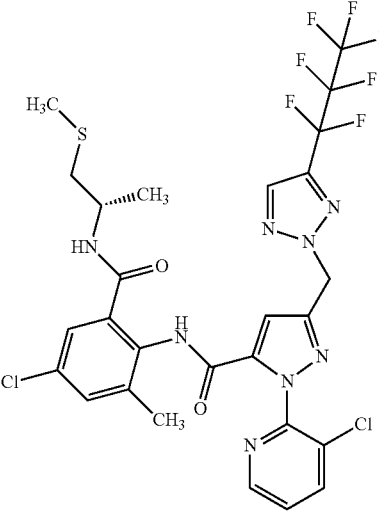 | 4.41 | 727 | (8.55; 3.11), (8.47; 1.57), (8.46; 1.63), (8.45; 1.70), (8.45; 1.57), (8.15; 0.91), (8.13; 1.90), (8.13; 2.28), (8.11; 1.73), (8.11; 1.53), (7.59; 1.50), (7.58; 1.49), (7.57; 1.41), (7.56; 1.41), (7.45; 1.63), (7.44; 1.70), (7.31; 1.82), (7.30; 1.71), (7.25; 3.27), (7.23; 0.37), (5.97; 5.45), (3.97; 0.53), (3.95; 0.65), (3.93; 0.52), (3.52; 0.35), (3.51; 0.41), (3.50; 0.50), (3.48; 0.51), (3.31; 74.24), (3.25; 3.96), (3.24; 3.13), (3.22; 2.51), (3.20; 1.58), (3.19; 0.95), (3.17; 0.78), (3.16; 0.73), (3.15; 0.75), (3.14; 0.66), (3.14; 0.59), (3.12; 0.50), (3.11; 0.38), (3.09; 0.33), (3.07; 0.31), (2.81; 0.45), (2.80; 0.47), (2.79; 0.36), (2.67; 0.38), (2.67; 0.50), (2.66; 0.36), (2.64; 0.32), (2.62; 0.33), (2.60; 1.85), (2.60; 2.00), (2.59; 2.13), (2.59; 1.87), (2.57; 3.09), (2.56; 0.85), (2.54; 0.93), (2.54; 1.00), (2.53; 1.73), (2.52; 1.94), (2.51; 27.22), (2.50; 52.37), (2.50; 69.83), (2.50; 49.94), (2.49; 23.95), (2.43; 1.22), (2.42; 1.20), (2.40; 0.80), (2.38; 0.74), (2.33; 0.39), (2.33; 0.51), (2.32; 0.40), (2.30; 0.55), (2.15; 8.44), (2.09; 14.83), (2.07; 1.44), (2.06; 0.44), (2.05; 0.44), (2.03; 0.76), (1.99; 15.00), (1.99; 2.21), (1.36; 1.38), (1.21; 1.14), (1.20; 5.90), (1.19; 1.31), (1.18; 5.80), (1.12; 2.29), (1.10; 2.28), (1.09; 0.67), (1.07; 4.67), (1.05; 4.61), (0.97; 0.43), (0.95; 0.41), (0.00; 0.37) |
| 384 | 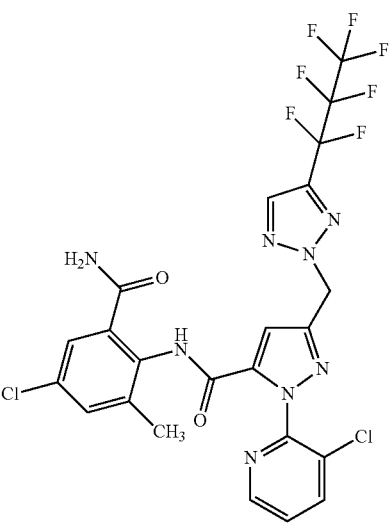 [SMILES: Cc1cc(Cl)cc(C(N)=O)c1NC(=O)c1cc(Cn2ncc(C(F)(F)C(F)(F)C(F)(F)F)n2)nn1-c1ncccc1Cl] | 3.5 | 639 | (10.25; 1.81), (8.56; 4.88), (8.48; 2.68), (8.48; 2.75), (8.47; 2.83), (8.47; 2.65), (8.14; 2.56), (8.14; 2.51), (8.12; 2.82), (8.12; 2.58), (7.68; 1.65), (7.59; 2.75), (7.58; 2.67), (7.57; 2.53), (7.56; 2.48), (7.45; 3.65), (7.44; 4.74), (7.39; 3.64), (7.38; 3.04), (7.22; 5.27), (6.87; 0.96), (6.60; 0.57), (5.97; 8.90), (3.60; 0.50), (3.29; 281.69), (3.27; 1.53), (3.26; 0.31), (2.67; 0.33), (2.67; 0.43), (2.66; 0.31), (2.54; 0.77), (2.52; 2.05), (2.51; 25.20), (2.50; 48.16), (2.50; 63.08), (2.49; 44.42), (2.49; 20.76), (2.33; 0.41), (2.18; 1.56), (2.15; 0.34), (2.12; 15.00), (2.07; 1.33), (1.76; 0.57), (1.36; 12.13), (0.00; 0.51) |

| No. | Structure | logP | MH+ | NMR |
|---|---|---|---|---|
| 385 | 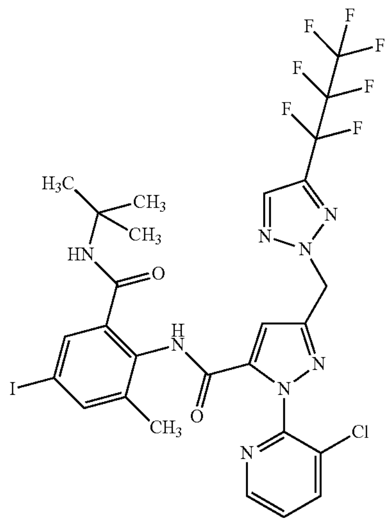 [SMILES: Cc1cc(I)cc(C(=O)NC(C)(C)C)c1NC(=O)c1cc(Cn2ncc(C(F)(F)C(F)(F)C(F)(F)F)n2)nn1-c1ncccc1Cl] | 4.89 | 787 | (8.55; 1.28), (8.47; 0.66), (8.46; 0.70), (8.45; 0.71), (8.45; 0.67), (8.14; 0.66), (8.14; 0.66), (8.12; 0.72), (8.12; 0.66), (7.69; 0.79), (7.69; 0.83), (7.59; 0.69), (7.58; 0.70), (7.57; 0.65), (7.56; 0.62), (7.51; 0.87), (7.50; 0.84), (7.47; 0.70), (7.18; 1.60), (5.97; 2.38), (3.30; 77.70), (2.52; 0.38), (2.51; 5.53), (2.50; 10.68), (2.50; 14.08), (2.50; 9.96), (2.49; 4.70), (2.09; 3.74), (1.36; 1.33), (1.26; 0.46), (1.24; 1.45), (1.19; 15.00) |
| 386 | 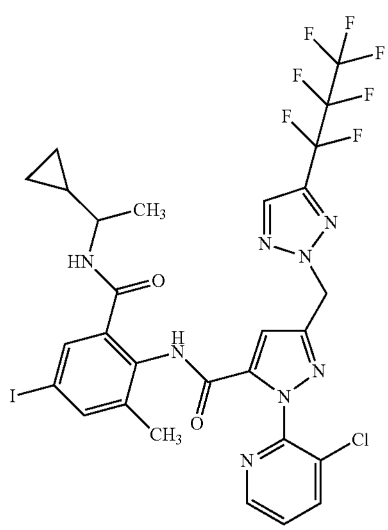 [SMILES: Cc1cc(I)cc(C(=O)NC(C)C2CC2)c1NC(=O)c1cc(Cn2ncc(C(F)(F)C(F)(F)C(F)(F)F)n2)nn1-c1ncccc1Cl] | 4.82 | 799 | (10.13; 1.77), (8.55; 5.24), (8.46; 2.87), (8.46; 2.96), (8.45; 2.98), (8.45; 2.86), (8.13; 2.73), (8.13; 2.63), (8.11; 3.02), (8.11; 2.73), (8.02; 1.35), (8.00; 1.26), (7.73; 3.14), (7.72; 3.29), (7.59; 2.84), (7.58; 2.80), (7.57; 2.68), (7.56; 3.44), (7.55; 3.69), (7.55; 3.38), (7.21; 5.43), (5.96; 9.42), (3.42; 0.32), (3.40; 0.35), (3.38; 0.36), (3.35; 1.03), (3.29; 962.51), (3.27; 6.89), (3.24; 0.76), (2.67; 1.17), (2.67; 1.51), (2.66; 1.09), (2.64; 0.30), (2.54; 2.37), (2.52; 5.96), (2.51; 85.61), (2.50; 166.12), (2.50; 219.81), (2.49; 155.53), (2.49; 73.00), (2.33; 1.00), (2.33; 1.36), (2.32; 0.99), (2.29; 0.33), (2.11; 15.00), (2.07; 2.99), (2.05; 0.43), (1.36; 0.55), (1.24; 1.00), (1.23; 0.31), (1.21; 0.32), (1.19; 0.37), (1.04; 8.90), (1.02; 8.70), (0.89; 0.60), (0.82; 0.51), (0.81; 0.74), (0.80; 1.15), (0.79; 0.81), (0.78; 0.90), (0.78; 1.25), (0.76; 0.73), (0.76; 0.50), (0.36; 0.39), (0.35; 0.61), (0.34; 1.22), (0.33; 1.06), (0.33; 1.12), (0.32; 1.24), (0.31; 0.64), (0.31; 0.67), (0.30; 0.52), (0.22; 0.43), (0.21; 0.75), (0.20; 1.01), (0.19; 1.06), (0.17; 1.34), (0.16; 0.95), (0.15; 1.16), (0.14; 1.58), (0.13; 1.38), (0.11; 1.34), (0.10; 1.32), (0.09; 1.32), (0.08; 1.01), (0.07; 0.59), (0.00; 2.23) |

| No. | Structure | logP | MH+ | NMR |
|---|---|---|---|---|
| 387 | 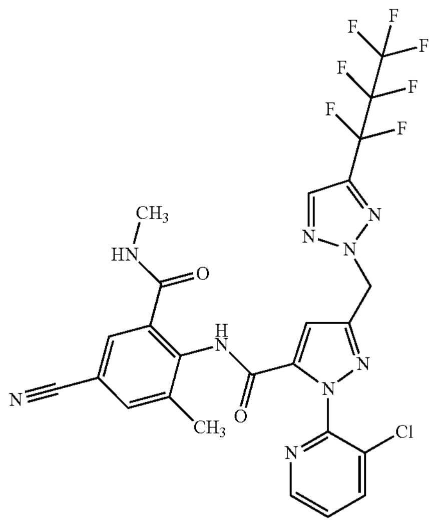 [SMILES: CNC(=O)c1cc(C#N)cc(C)c1NC(=O)c1cc(Cn2ncc(C(F)(F)C(F)(F)C(F)(F)F)n2)nn1-c1ncccc1Cl] | 3.39 | 644 | (10.48; 4.08), (8.57; 5.87), (8.48; 2.95), (8.48; 3.21), (8.47; 3.26), (8.46; 3.18), (8.31; 1.60), (8.30; 1.61), (8.15; 2.96), (8.15; 3.04), (8.13; 3.42), (8.13; 3.20), (7.85; 3.26), (7.85; 3.47), (7.73; 3.73), (7.73; 3.60), (7.60; 3.20), (7.59; 3.09), (7.58; 3.05), (7.57; 3.04), (7.25; 5.06), (5.98; 10.48), (3.82; 0.52), (3.75; 0.48), (3.57; 0.58), (3.31; 868.83), (2.67; 1.03), (2.67; 1.44), (2.66; 1.29), (2.65; 10.52), (2.64; 10.51), (2.54; 1.78), (2.52; 3.60), (2.52; 5.39), (2.51; 69.36), (2.50; 136.21), (2.50; 183.80), (2.50; 126.48), (2.49; 59.52), (2.34; 0.44), (2.33; 0.88), (2.33; 1.21), (2.32; 0.86), (2.32; 0.39), (2.19; 16.00), (2.07; 1.09), (1.40; 1.25), (1.24; 0.58), (0.01; 0.33), (0.00; 9.53) |
| 388 | Chiral | 4.64 | 787 | (8.47; 1.80), (8.47; 1.86), (8.46; 1.95), (8.45; 1.76), (8.14; 2.02), (8.14; 1.92), (8.12; 2.00), (8.12; 1.75), (7.74; 1.81), (7.73; 1.86), (7.60; 1.84), (7.59; 3.29), (7.58; 2.82), (7.57; 1.62), (7.32; 2.79), (6.09; 5.67), (3.96; 0.57), (3.95; 0.67), (3.93; 0.56), (3.31; 289.90), (3.09; 0.52), (3.08; 0.85), (3.06; 0.82), (3.04; 0.48), (2.68; 0.52), (2.67; 0.68), (2.67; 0.81), (2.67; 0.61), (2.66; 0.48), (2.56; 1.21), (2.55; 1.28), (2.54; 1.43), (2.54; 2.32), (2.53; 2.32), (2.52; 4.48), (2.51; 45.93), (2.51; 81.75), (2.50; 104.39), (2.50; 72.52), (2.49; 35.02), (2.48; 3.53), (2.47; 2.54), (2.46; 1.88), (2.45; 0.60), (2.43; 1.34), (2.41; 1.29), (2.39; 0.85), (2.38; 0.75), (2.34; 0.37), (2.33; 0.61), (2.33; 0.75), (2.32; 0.57), (2.12; 8.60), (2.07; 2.78), (2.07; 10.71), (2.03; 0.48), (2.03; 0.54), (2.00; 0.46), (1.98; 16.00), (1.98; 2.55), (1.36; 0.49), (1.23; 0.47), (1.13; 0.76), (1.12; 0.98), (1.11; 4.45), (1.09; 4.39), (1.08; 0.87), (1.08; 0.76), (1.06; 5.20), (1.04; 4.70), (0.96; 0.36), (0.94; 0.35), (0.00; 1.32) |
| 389 | 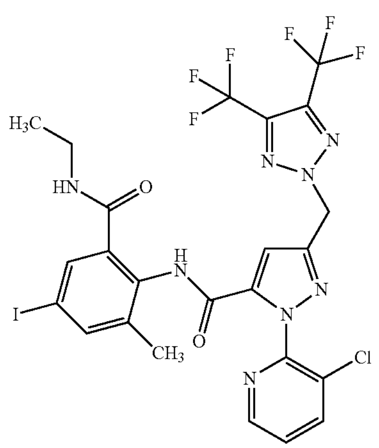 [SMILES: CCNC(=O)c1cc(I)cc(C)c1NC(=O)c1cc(Cn2nc(C(F)(F)F)c(C(F)(F)F)n2)nn1-c1ncccc1Cl] | 4.23 | 727 | (10.19; 1.49), (8.47; 3.17), (8.47; 3.34), (8.46; 3.44), (8.46; 3.27), (8.18; 1.35), (8.15; 3.11), (8.15; 3.07), (8.13; 3.34), (8.13; 3.10), (7.73; 3.21), (7.73; 3.27), (7.60; 3.16), (7.59; 3.40), (7.58; 4.48), (7.58; 4.05), (7.57; 3.89), (7.57; 4.12), (7.32; 0.38), (7.30; 4.86), (6.87; 0.37), (6.09; 9.92), (3.31; 671.65), (3.29; 11.80), (3.15; 1.00), (3.13; 2.87), (3.12; 3.22), (3.11; 3.14), (3.10; 2.88), (3.08; 0.93), (2.67; 0.57), (2.67; 0.72), (2.66; 0.56), (2.54; 1.11), (2.52; 3.62), (2.51; 42.71), (2.51; 78.07), (2.50; 101.02), (2.50; 70.09), (2.49; 33.64), (2.33; 0.55), (2.33; 0.74), (2.32; 0.53), (2.18; 0.67), (2.11; 16.00), (2.08; 0.44), (2.07; 1.42), (1.36; 4.83), (1.01; 0.47), (0.98; 6.15), (0.96; 13.06), (0.94; 5.90), (0.00; 1.07) |

| No. | Structure | logP | MH+ | NMR |
|---|---|---|---|---|
| 390 | 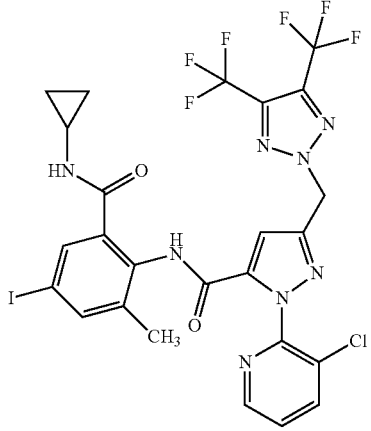 [SMILES: Cc1cc(I)cc(C(=O)NC2CC2)c1NC(=O)c1cc(Cn2nc(C(F)(F)F)c(C(F)(F)F)n2)nn1-c1ncccc1Cl] | 4.19 | 739 | (10.16; 2.61), (8.48; 3.19), (8.48; 3.31), (8.47; 3.45), (8.46; 3.21), (8.22; 1.91), (8.21; 1.85), (8.15; 2.95), (8.15; 2.91), (8.13; 3.30), (8.13; 3.00), (7.72; 3.43), (7.72; 3.46), (7.60; 3.08), (7.59; 3.11), (7.58; 3.05), (7.57; 2.92), (7.54; 3.65), (7.53; 3.49), (7.32; 5.91), (6.87; 0.74), (6.61; 0.38), (6.10; 9.99), (4.87; 0.34), (4.52; 0.60), (4.50; 1.28), (4.49; 0.63), (3.60; 0.58), (3.59; 0.53), (3.59; 0.75), (3.59; 1.12), (3.58; 0.57), (3.57; 1.11), (3.57; 0.68), (3.56; 0.32), (3.56; 0.54), (3.39; 0.57), (3.31; 758.47), (3.28; 8.98), (2.69; 0.46), (2.67; 1.27), (2.67; 1.87), (2.66; 1.84), (2.65; 1.65), (2.64; 1.18), (2.63; 0.93), (2.62; 0.48), (2.62; 0.40), (2.61; 0.55), (2.60; 0.59), (2.59; 0.59), (2.58; 0.61), (2.57; 0.61), (2.54; 1.69), (2.52; 5.63), (2.51; 59.84), (2.50; 106.77), (2.50; 136.12), (2.50; 93.82), (2.49; 44.86), (2.34; 0.43), (2.33; 0.75), (2.33; 0.97), (2.32; 0.71), (2.22; 0.35), (2.20; 0.68), (2.18; 1.92), (2.16; 1.80), (2.15; 0.95), (2.11; 16.00), (2.07; 1.03), (1.74; 2.49), (1.36; 9.58), (0.61; 0.33), (0.60; 0.50), (0.59; 1.89), (0.58; 1.73), (0.58; 3.34), (0.57; 4.70), (0.57; 2.15), (0.56; 3.93), (0.55; 3.23), (0.54; 1.28), (0.44; 0.33), (0.41; 1.44), (0.40; 3.88), (0.40; 3.71), (0.39; 3.23), (0.37; 1.28), (0.37; 0.94), (0.36; 0.98), (0.36; 0.95), (0.35; 0.49), (0.34; 0.60), (0.00; 0.86) |
| 391 | 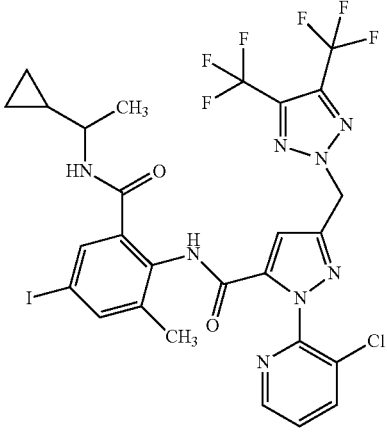 [SMILES: Cc1cc(I)cc(C(=O)NC(C)C2CC2)c1NC(=O)c1cc(Cn2nc(C(F)(F)F)c(C(F)(F)F)n2)nn1-c1ncccc1Cl] | 4.76 | 767 | (10.148; 1.55), (8.469; 3.29), (8.466; 3.43), (8.458; 3.50), (8.454; 3.32), (8.143; 2.92), (8.140; 2.82), (8.123; 3.18), (8.119; 2.95), (8.053; 1.24), (8.034; 1.19), (7.729; 3.30), (7.600; 3.01), (7.588; 3.02), (7.579; 3.10), (7.568; 3.20), (7.553; 3.44), (7.306; 4.16), (6.871; 0.43), (6.085; 10.41), (3.505; 0.41), (3.482; 0.48), (3.473; 0.50), (3.461; 0.58), (3.307; 1430.47), (3.283; 17.44), (3.263; 3.14), (2.674; 1.61), (2.669; 2.07), (2.664; 1.61), (2.539; 3.36), (2.509; 119.37), (2.504; 218.14), (2.500; 282.57), (2.496; 198.59), (2.491; 96.79), (2.336; 0.71), (2.331; 1.40), (2.327; 1.79), (2.322; 1.38), (2.183; 0.64), (2.116; 16.00), (2.084; 0.83), (2.069; 1.37), (1.356; 5.08), (1.080; 0.44), (1.064; 0.53), (1.036; 9.88), (1.020; 9.57), (0.890; 0.56), (0.808; 0.54), (0.801; 0.73), (0.788; 1.34), (0.777; 0.97), (0.768; 1.28), (0.756; 0.79), (0.748; 0.53), (0.342; 0.46), (0.334; 0.67), (0.322; 1.28), (0.314; 1.20), (0.310; 1.23), (0.300; 1.42), (0.289; 0.76), (0.280; 0.63), (0.189; 0.44), (0.179; 0.87), (0.175; 0.86), (0.165; 1.26), (0.159; 1.73), (0.145; 2.36), (0.135; 1.58), (0.124; 2.51), (0.113; 1.80), (0.105; 1.44), (0.093; 1.54), (0.084; 1.55), (0.074; 1.01), (0.063; 0.63), (−0.000; 1.62) |

| No. | Structure | logP | MH+ | NMR |
|---|---|---|---|---|
| 392 | 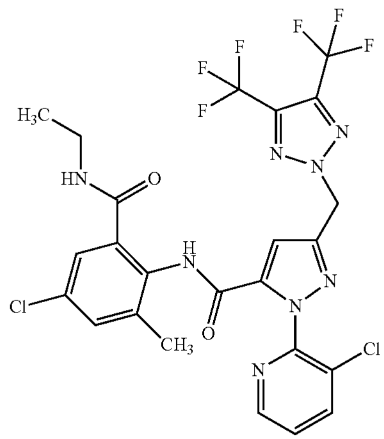 [SMILES: CCNC(=O)c1cc(Cl)cc(C)c1NC(=O)c1cc(Cn2nc(C(F)(F)F)c(C(F)(F)F)n2)nn1-c1ncccc1Cl] | 3.98 | 635 | (10.21; 2.59), (8.47; 3.00), (8.47; 3.15), (8.46; 3.23), (8.46; 3.04), (8.20; 1.01), (8.19; 1.75), (8.18; 0.97), (8.15; 2.86), (8.15; 2.83), (8.13; 3.17), (8.13; 2.90), (7.60; 2.97), (7.59; 2.91), (7.58; 2.86), (7.57; 2.77), (7.45; 3.07), (7.44; 3.28), (7.31; 7.64), (7.31; 5.00), (7.30; 3.60), (6.09; 9.82), (3.31; 1271.18), (3.29; 13.12), (3.19; 0.33), (3.16; 1.05), (3.14; 2.87), (3.12; 3.21), (3.12; 3.13), (3.11; 2.83), (3.09; 0.95), (2.87; 0.55), (2.67; 0.95), (2.67; 1.26), (2.67; 0.91), (2.54; 1.97), (2.52; 6.84), (2.51; 73.58), (2.51; 131.27), (2.50; 167.20), (2.50; 115.44), (2.49; 55.35), (2.34; 0.51), (2.33; 0.92), (2.33; 1.19), (2.32; 0.88), (2.18; 0.42), (2.15; 16.00), (2.07; 0.48), (1.36; 1.90), (1.01; 0.35), (0.98; 5.87), (0.97; 12.38), (0.95; 5.59), (0.89; 0.35), (0.00; 0.78) |
| 393 | 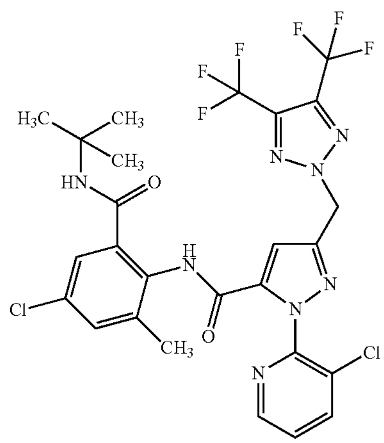 [SMILES: Cc1cc(Cl)cc(C(=O)NC(C)(C)C)c1NC(=O)c1cc(Cn2nc(C(F)(F)F)c(C(F)(F)F)n2)nn1-c1ncccc1Cl] | 4.59 | 663 | (8.48; 0.71), (8.47; 0.78), (8.47; 0.79), (8.46; 0.76), (8.16; 0.66), (8.15; 0.67), (8.14; 0.74), (8.13; 0.69), (7.76; 0.35), (7.61; 0.72), (7.60; 0.72), (7.59; 0.71), (7.58; 0.69), (7.53; 0.32), (7.44; 0.64), (7.41; 0.72), (7.41; 0.76), (7.27; 1.35), (7.25; 0.81), (7.24; 0.76), (6.11; 0.86), (6.10; 2.45), (3.32; 447.15), (3.30; 4.16), (2.54; 0.47), (2.52; 1.51), (2.51; 17.86), (2.51; 32.92), (2.50; 42.92), (2.50; 30.21), (2.49; 14.73), (2.18; 0.34), (2.14; 3.88), (1.73; 1.16), (1.36; 2.38), (1.24; 0.62), (1.18; 16.00) |
| 394 | 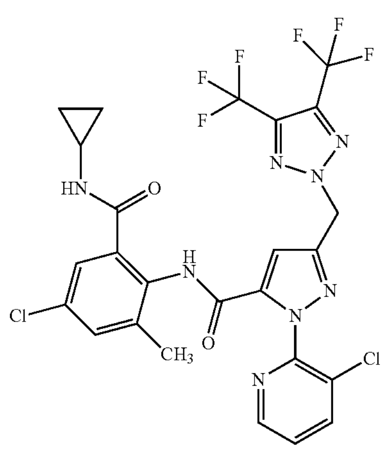 [SMILES: Cc1cc(Cl)cc(C(=O)NC2CC2)c1NC(=O)c1cc(Cn2nc(C(F)(F)F)c(C(F)(F)F)n2)nn1-c1ncccc1Cl] | 3.96 | 647 | (10.18; 1.41), (8.48; 3.01), (8.48; 3.19), (8.47; 3.26), (8.47; 3.10), (8.25; 1.64), (8.24; 1.61), (8.15; 2.80), (8.15; 2.83), (8.13; 3.14), (8.13; 2.94), (7.61; 3.01), (7.59; 2.94), (7.59; 2.87), (7.57; 2.78), (7.44; 3.08), (7.43; 3.24), (7.34; 0.34), (7.33; 6.80), (7.27; 3.56), (7.27; 3.31), (6.10; 9.75), (4.52; 0.40), (4.51; 0.86), (4.50; 0.44), (3.60; 0.43), (3.59; 0.42), (3.59; 0.57), (3.59; 0.84), (3.58; 0.47), (3.57; 0.83), (3.57; 0.52), (3.56; 0.43), (3.32; 907.08), (3.30; 8.05), (2.92; 0.59), (2.69; 0.37), (2.68; 0.82), (2.67; 1.50), (2.67; 1.28), (2.67; 1.96), (2.66; 1.57), (2.65; 1.08), (2.64; 0.82), (2.63; 0.39), (2.61; 0.37), (2.60; 0.42), (2.59; 0.42), (2.58; 0.43), (2.57; 0.42), (2.54; 1.11), (2.52; 3.38), (2.51; 39.02), (2.51; 70.99), (2.50; 91.50), (2.50; 63.37), (2.49; 30.28), (2.33; 0.49), (2.33; 0.65), (2.32; 0.48), (2.20; 0.52), (2.18; 1.18), (2.17; 1.62), (2.15; 16.00), (2.07; 0.69), (1.74; 2.07), (1.36; 3.31), (1.18; 0.40), (1.16; 0.40), (0.60; 0.51), (0.59; 1.21), (0.59; 1.05), (0.58; 3.16), (0.58; 3.87), (0.56; 3.83), (0.56; 2.97), (0.55; 1.23), (0.42; 1.39), (0.41; 3.69), (0.40; 3.55), (0.40; 3.26), (0.39; 3.06), (0.38; 1.08), (0.37; 0.84), (0.37; 0.66), (0.36; 0.73), (0.36; 0.71), (0.34; 0.46), (0.00; 0.71) |

-continued
| No. | Structure | logP | MH+ | NMR |
|---|---|---|---|---|
| 395 | 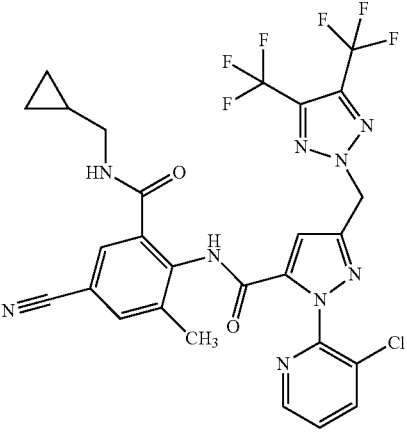 [SMILES: Cc1cc(C#N)cc(C(=O)NCC2CC2)c1NC(=O)c1cc(Cn2nc(C(F)(F)F)c(C(F)(F)F)n2)nn1-c1ncccc1Cl] | 3.89 | 652 | |
| 396 | 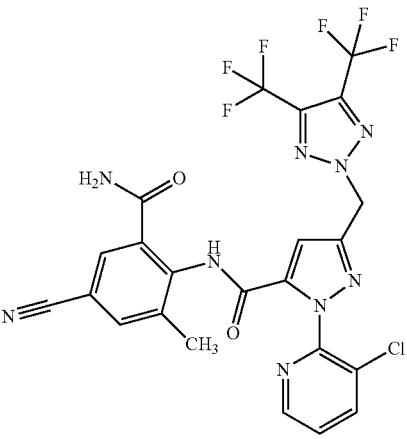 [SMILES: Cc1cc(C#N)cc(C(N)=O)c1NC(=O)c1cc(Cn2nc(C(F)(F)F)c(C(F)(F)F)n2)nn1-c1ncccc1Cl] | 3.21 | 598 | (10.57; 1.59), (10.55; 0.42), (8.86; 0.41), (8.85; 0.37), (8.57; 0.55), (8.54; 0.99), (8.53; 1.07), (8.52; 1.06), (8.52; 1.00), (8.49; 3.19), (8.49; 3.35), (8.48; 3.50), (8.48; 3.26), (8.24; 1.12), (8.23; 1.05), (8.16; 3.02), (8.16; 2.96), (8.14; 3.41), (8.14; 3.15), (8.07; 0.60), (7.90; 0.56), (7.86; 4.82), (7.82; 4.44), (7.81; 3.82), (7.67; 0.90), (7.66; 0.90), (7.65; 0.85), (7.64; 0.94), (7.61; 3.20), (7.60; 3.07), (7.59; 3.13), (7.58; 3.05), (7.55; 2.25), (7.51; 0.40), (7.46; 0.37), (7.35; 3.38), (7.22; 0.33), (7.21; 0.45), (6.49; 0.48), (6.09; 13.75), (4.87; 0.37), (3.68; 0.33), (3.65; 0.34), (3.62; 0.43), (3.60; 0.46), (3.56; 0.62), (3.46; 1.35), (3.44; 1.91), (3.32; 6382.56), (3.29; 61.19), (3.20; 1.84), (3.19; 1.55), (3.16; 1.25), (3.15; 1.15), (3.11; 0.81), (3.08; 0.72), (3.04; 0.63), (3.00; 0.57), (2.98; 0.45), (2.97; 0.50), (2.93; 0.45), (2.93; 0.45), (2.91; 0.48), (2.89; 0.46), (2.86; 0.37), (2.80; 0.38), (2.74; 0.40), (2.72; 0.47), (2.70; 0.65), (2.67; 3.85), (2.67; 4.91), (2.67; 3.74), (2.66; 1.95), (2.63; 3.72), (2.54; 7.75), (2.52; 26.94), (2.51; 294.25), (2.51; 526.14), (2.50; 671.26), (2.50; 462.75), (2.49; 221.75), (2.34; 2.12), (2.33; 3.72), (2.33; 4.85), (2.32; 3.53), (2.32; 1.89), (2.30; 0.47), (2.30; 0.48), (2.27; 0.72), (2.24; 0.39), (2.18; 16.00), (2.13; 0.67), (2.11; 1.10), (2.09; 0.37), (2.07; 2.89), (2.01; 0.33), (1.91; 0.86), (1.67; 6.01), (1.36; 0.62), (1.24; 0.74), (1.22; 0.41), (1.18; 0.33), (1.16; 0.36), (1.09; 0.35), (0.89; 1.40), (0.00; 3.75) |

-continued

| No. | Structure | logP | MH+ | NMR |
|-----|-----------|------|-----|-----|
| 397 | 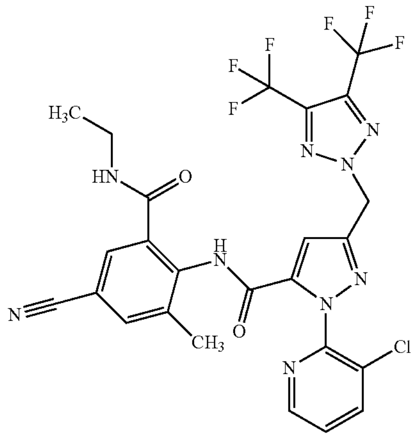 [SMILES: CCNC(=O)c1cc(C#N)cc(C)c1NC(=O)c1cc(Cn2nc(C(F)(F)F)c(C(F)(F)F)n2)nn1-c1ncccc1Cl] | 3.61 | 626 | |
| 398 | 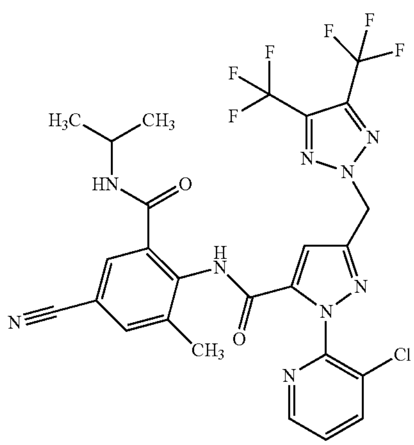 [SMILES: Cc1cc(C#N)cc(C(=O)NC(C)C)c1NC(=O)c1cc(Cn2nc(C(F)(F)F)c(C(F)(F)F)n2)nn1-c1ncccc1Cl] | 3.84 | 640 | (8.57; 0.39), (8.47; 2.91), (8.46; 3.04), (8.46; 3.20), (8.45; 3.00), (8.39; 0.41), (8.38; 0.50), (8.14; 2.07), (8.13; 2.14), (8.12; 2.26), (8.07; 0.93), (8.05; 0.48), (7.88; 0.33), (7.88; 0.38), (7.86; 0.44), (7.82; 0.71), (7.81; 0.87), (7.77; 0.42), (7.76; 0.45), (7.73; 1.54), (7.66; 0.42), (7.64; 0.39), (7.60; 2.00), (7.58; 2.03), (7.58; 1.93), (7.56; 1.85), (7.55; 0.37), (7.53; 0.37), (7.53; 0.40), (7.40; 0.65), (7.39; 0.41), (7.37; 0.61), (7.33; 0.50), (7.31; 0.60), (7.20; 0.39), (7.19; 0.49), (6.87; 0.98), (6.62; 0.55), (6.14; 0.38), (6.09; 7.03), (5.92; 0.67), (3.93; 0.61), (3.91; 1.08), (3.89; 1.56), (3.87; 1.48), (3.86; 1.03), (3.84; 0.47), (3.64; 0.38), (3.60; 0.48), (3.55; 0.61), (3.51; 0.93), (3.45; 1.69), (3.32; 5159.37), (3.20; 1.60), (3.14; 0.94), (3.11; 0.79), (3.03; 0.54), (2.98; 0.45), (2.97; 0.44), (2.95; 0.42), (2.95; 0.40), (2.88; 0.36), (2.85; 0.34), (2.83; 0.32), (2.81; 0.34), (2.80; 0.35), (2.77; 0.35), (2.69; 0.56), (2.68; 1.74), (2.68; 3.01), (2.67; 3.96), (2.67; 3.01), (2.66; 1.63), (2.63; 2.61), (2.60; 0.76), (2.54; 5.68), (2.52; 18.82), (2.51; 223.08), (2.51; 409.87), (2.50; 532.20), (2.50; 373.22), (2.49; 181.22), (2.37; 0.55), (2.34; 1.69), (2.33; 2.95), (2.33; 3.82), (2.32; 2.84), (2.32; 1.55), (2.29; 0.43), (2.28; 0.63), (2.27; 0.37), (2.26; 0.42), (2.19; 6.87), (2.13; 0.59), (2.07; 3.92), (2.00; 0.61), (1.91; 0.43), (1.63; 0.63), (1.61; 0.59), (1.46; 0.87), (1.36; 11.81), (1.24; 0.64), (1.22; 0.90), (1.21; 1.24), (1.19; 1.23), (1.18; 1.27), (1.17; 1.57), (1.15; 1.18), (1.09; 0.50), (1.08; 0.64), (1.06; 0.63), (1.05; 0.79), (1.03; 0.87), (1.00; 16.00), (0.99; 15.76), (0.89; 0.33), (0.00; 2.91) |

| No. | Structure | logP | MH+ | NMR |
|---|---|---|---|---|
| 399 | 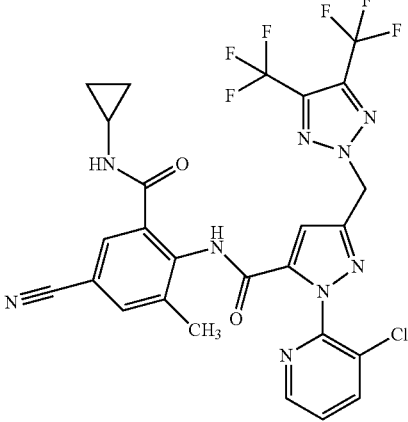 | 3.59 | 638 | |
| 400 | 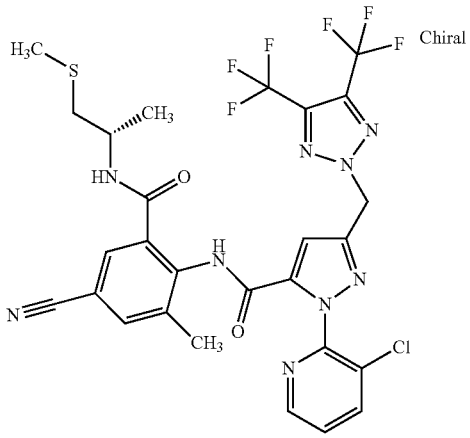 [SMILES: CSC[C@H](C)NC(=O)c1cc(C#N)cc(C)c1NC(=O)c1cc(Cn2nc(C(F)(F)F)c(C(F)(F)F)n2)nn1-c1ncccc1Cl] | 4.05 | 687 | (10.43; 1.63), (8.48; 1.53), (8.47; 1.64), (8.47; 1.66), (8.46; 1.56), (8.27; 0.87), (8.25; 0.88), (8.15; 1.27), (8.15; 1.24), (8.13; 1.41), (8.13; 1.27), (7.87; 1.62), (7.71; 1.67), (7.71; 1.61), (7.61; 1.26), (7.60; 1.27), (7.59; 1.21), (7.58; 1.16), (7.37; 1.98), (6.10; 4.94), (3.97; 0.53), (3.95; 0.65), (3.93; 0.53), (3.31; 402.90), (3.29; 4.24), (2.67; 0.33), (2.67; 0.44), (2.67; 0.33), (2.56; 0.88), (2.55; 1.10), (2.54; 1.08), (2.53; 2.08), (2.52; 2.42), (2.51; 25.07), (2.51; 45.93), (2.50; 59.98), (2.50; 42.74), (2.49; 21.26), (2.43; 1.14), (2.41; 1.13), (2.40; 0.78), (2.38; 0.73), (2.33; 0.35), (2.33; 0.44), (2.32; 0.33), (2.22; 6.72), (2.07; 0.54), (1.99; 16.00), (1.10; 0.55), (1.08; 4.48), (1.06; 4.35), (0.01; 0.33), (0.00; 6.46) |

-continued
| No. | Structure | logP | MH+ | NMR |
|---|---|---|---|---|
| 401 | 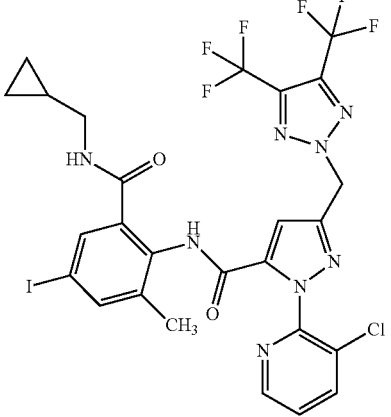 | 4.52 | 753 | (8.38; 0.39), (8.37; 0.41), (8.37; 0.43), (8.36; 0.39), (8.06; 0.36), (8.05; 0.36), (8.04; 0.41), (8.03; 0.37), (7.65; 0.43), (7.65; 0.43), (7.51; 0.43), (7.50; 0.82), (7.49; 0.47), (7.48; 0.36), (7.23; 0.65), (6.00; 1.32), (3.22; 104.51), (3.20; 1.08), (2.90; 0.42), (2.88; 0.60), (2.87; 0.40), (2.42; 6.94), (2.42; 12.50), (2.41; 16.00), (2.41; 11.17), (2.40; 5.38), (2.03; 2.07), (1.27; 0.75), (0.19; 0.44), (0.18; 0.46), (0.17; 0.43), (0.16; 0.40), (0.00; 0.53), (−0.01; 0.47), (−0.02; 0.50) |
| 402 | 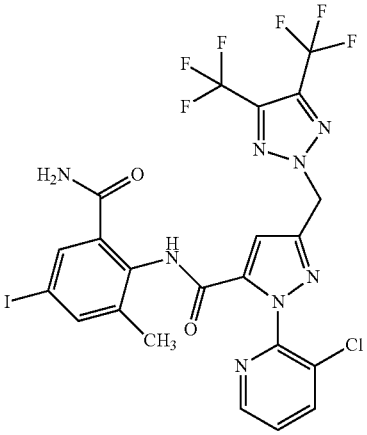 [SMILES: Cc1cc(I)cc(C(N)=O)c1NC(=O)c1cc(Cn2nc(C(F)(F)F)c(C(F)(F)F)n2)nn1-c1ncccc1Cl] | 3.67 | 699 | (10.27; 1.51), (8.49; 2.95), (8.48; 3.14), (8.47; 3.16), (8.47; 2.99), (8.15; 2.84), (8.15; 2.81), (8.13; 3.15), (8.13; 2.90), (7.74; 3.50), (7.73; 3.75), (7.70; 1.82), (7.67; 4.06), (7.66; 3.67), (7.60; 2.93), (7.59; 2.89), (7.58; 2.78), (7.57; 2.71), (7.41; 1.99), (7.32; 5.65), (6.87; 1.12), (6.62; 0.65), (6.08; 9.75), (4.86; 0.35), (3.60; 0.40), (3.31; 272.29), (3.29; 2.76), (2.67; 0.35), (2.54; 0.64), (2.51; 20.51), (2.51; 36.72), (2.50; 46.78), (2.50; 32.48), (2.49; 15.49), (2.18; 1.80), (2.11; 1.16), (2.10; 16.00), (2.08; 0.34), (1.76; 0.40), (1.36; 13.94) |
| 403 | 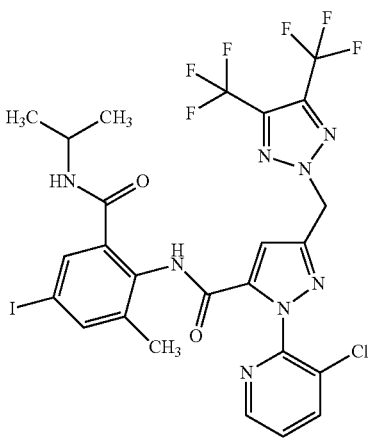 [SMILES: Cc1cc(I)cc(C(=O)NC(C)C)c1NC(=O)c1cc(Cn2nc(C(F)(F)F)c(C(F)(F)F)n2)nn1-c1ncccc1Cl] | 4.47 | 741 | (10.15; 2.19), (8.47; 2.32), (8.46; 2.45), (8.46; 2.51), (8.45; 2.35), (8.14; 2.15), (8.14; 2.11), (8.12; 2.40), (8.12; 2.18), (7.98; 1.21), (7.97; 1.20), (7.73; 2.46), (7.72; 2.46), (7.60; 2.30), (7.59; 2.27), (7.58; 2.20), (7.57; 2.21), (7.55; 2.65), (7.55; 2.49), (7.31; 4.01), (6.87; 0.55), (6.61; 0.32), (6.09; 7.43), (3.90; 0.70), (3.88; 1.05), (3.87; 1.00), (3.85; 0.66), (3.31; 460.96), (3.28; 5.67), (2.67; 0.53), (2.67; 0.68), (2.66; 0.50), (2.54; 1.14), (2.52; 3.63), (2.51; 39.35), (2.50; 70.68), (2.50; 90.08), (2.50; 61.71), (2.49; 29.05), (2.33; 0.45), (2.33; 0.59), (2.32; 0.42), (2.18; 0.91), (2.12; 11.67), (2.07; 0.87), (1.36; 7.04), (1.04; 0.67), (1.03; 0.75), (1.00; 16.00), (0.98; 15.69), (0.00; 3.15) |

| No. | Structure | logP | MH+ | NMR |
|---|---|---|---|---|
| 404 | 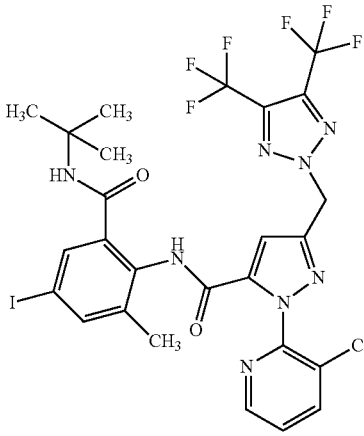 | 4.84 | 755 | (10.12; 1.06), (8.48; 0.72), (8.47; 0.77), (8.46; 0.78), (8.46; 0.73), (8.16; 0.68), (8.15; 0.70), (8.14; 0.78), (8.13; 0.72), (7.70; 0.85), (7.70; 0.87), (7.61; 0.75), (7.59; 0.72), (7.59; 0.71), (7.57; 0.69), (7.51; 1.90), (7.26; 1.87), (6.10; 2.45), (3.35; 0.95), (3.31; 307.13), (2.67; 0.33), (2.67; 0.42), (2.66; 0.32), (2.54; 0.80), (2.51; 23.55), (2.50; 43.18), (2.50; 56.16), (2.50; 39.57), (2.49; 19.26), (2.33; 0.35), (2.11; 3.84), (1.18; 16.00), (0.00; 6.26) |
| 405 | 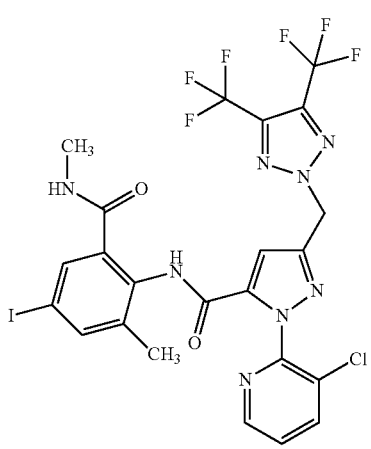 [SMILES: CNC(=O)c1cc(I)cc(C)c1NC(=O)c1cc(Cn2nc(C(F)(F)F)c(C(F)(F)F)n2)nn1-c1ncccc1Cl] | 4.03 | 713 | (10.22; 2.89), (8.48; 3.05), (8.47; 3.19), (8.47; 3.32), (8.46; 3.07), (8.19; 1.56), (8.17; 1.55), (8.16; 0.79), (8.15; 3.05), (8.15; 2.98), (8.13; 3.27), (8.13; 2.97), (7.73; 3.37), (7.73; 3.42), (7.60; 3.38), (7.59; 6.12), (7.58; 3.40), (7.57; 2.87), (7.31; 5.84), (6.09; 9.78), (3.31; 1222.63), (3.28; 16.43), (3.17; 0.34), (2.67; 1.30), (2.67; 1.67), (2.66; 1.48), (2.66; 1.06), (2.64; 10.36), (2.63; 10.21), (2.54; 2.13), (2.52; 7.53), (2.51; 87.08), (2.50; 156.59), (2.50; 199.80), (2.50; 138.40), (2.49; 66.45), (2.33; 1.18), (2.33; 1.47), (2.32; 1.13), (2.11; 16.00), (2.07; 2.90), (0.00; 4.77) |
| 406 | 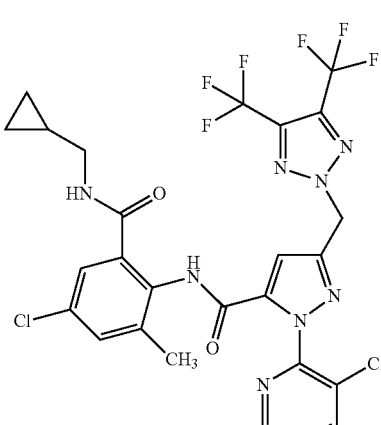 | 4.29 | 661 | (8.38; 0.64), (8.37; 0.67), (8.37; 0.69), (8.36; 0.65), (8.06; 0.62), (8.05; 0.61), (8.04; 0.68), (8.03; 0.63), (7.51; 0.63), (7.50; 0.62), (7.49; 0.61), (7.48; 0.59), (7.37; 0.69), (7.36; 0.73), (7.23; 1.59), (7.23; 1.00), (7.22; 0.80), (6.00; 2.21), (3.22; 119.99), (3.20; 1.26), (2.90; 0.67), (2.89; 0.97), (2.87; 0.65), (2.42; 6.93), (2.41; 12.50), (2.41; 16.00), (2.41; 11.17), (2.40; 5.39), (2.06; 3.58), (1.27; 0.32), (0.18; 0.69), (0.18; 0.74), (0.17; 0.41), (0.16; 0.71), (0.16; 0.65), (0.00; 0.86), (−0.01; 0.76), (−0.01; 0.82) |

-continued

| No. | Structure | logP | MH+ | NMR |
|---|---|---|---|---|
| 407 | 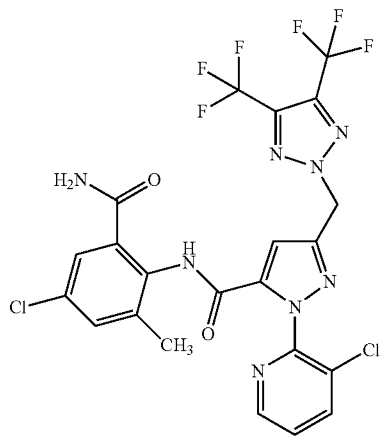 [SMILES: Cc1cc(Cl)cc(C(N)=O)c1NC(=O)c1cc(Cn2nc(C(F)(F)F)c(C(F)(F)F)n2)nn1-c1ncccc1Cl] | 3.49 | 607 | (10.28; 2.51), (8.49; 2.96), (8.48; 3.15), (8.48; 3.22), (8.47; 3.03), (8.16; 2.83), (8.15; 2.80), (8.14; 3.19), (8.13; 2.87), (7.72; 1.87), (7.60; 3.02), (7.59; 2.90), (7.58; 2.85), (7.57; 2.77), (7.45; 4.27), (7.45; 5.29), (7.39; 3.96), (7.39; 3.32), (7.32; 6.00), (6.09; 9.53), (3.41; 1.18), (3.39; 3.28), (3.38; 3.53), (3.36; 2.06), (3.31; 957.55), (3.28; 14.85), (3.20; 0.41), (2.91; 0.44), (2.67; 1.05), (2.67; 1.37), (2.66; 1.00), (2.54; 2.10), (2.51; 84.40), (2.50; 150.93), (2.50; 192.16), (2.50; 133.35), (2.49; 64.48), (2.34; 0.64), (2.33; 1.11), (2.33; 1.38), (2.32; 1.02), (2.13; 16.00), (2.07; 4.14), (1.36; 0.95), (1.11; 3.02), (1.09; 6.13), (1.07; 2.94), (0.00; 4.03) |
| 408 | Chiral | 4.4 | 695 | (8.47; 1.83), (8.47; 1.84), (8.46; 1.96), (8.46; 1.78), (8.16; 1.04), (8.15; 2.10), (8.14; 2.45), (8.13; 0.63), (8.13; 1.94), (8.12; 1.72), (7.60; 1.68), (7.59; 1.68), (7.58; 1.63), (7.57; 1.57), (7.46; 1.93), (7.46; 1.95), (7.34; 4.12), (7.33; 0.84), (7.31; 2.10), (7.30; 1.95), (6.09; 6.21), (3.97; 0.60), (3.95; 0.70), (3.93; 0.59), (3.31; 263.98), (3.29; 5.01), (2.67; 0.40), (2.67; 0.52), (2.67; 0.40), (2.62; 1.06), (2.62; 0.64), (2.61; 1.06), (2.60; 0.64), (2.55; 1.03), (2.54; 1.44), (2.52; 5.01), (2.51; 30.45), (2.50; 55.59), (2.50; 71.87), (2.50; 50.20), (2.49; 24.51), (2.43; 1.28), (2.41; 1.26), (2.40; 0.83), (2.38; 0.75), (2.33; 0.41), (2.33; 0.53), (2.32; 0.40), (2.16; 9.35), (2.10; 3.96), (2.07; 0.34), (2.03; 0.34), (1.98; 16.00), (1.98; 2.89), (1.25; 0.43), (1.24; 0.43), (1.23; 0.41), (1.22; 1.59), (1.21; 1.50), (1.12; 0.62), (1.10; 0.64), (1.09; 0.83), (1.06; 5.16), (1.05; 4.97), (0.96; 0.41), (0.95; 0.41), (0.00; 0.78) |
| 409 | 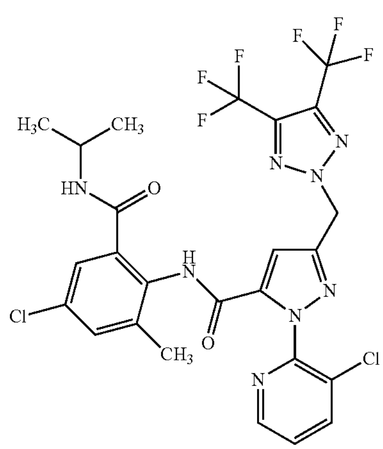 [SMILES: Cc1cc(Cl)cc(C(=O)NC(C)C)c1NC(=O)c1cc(Cn2nc(C(F)(F)F)c(C(F)(F)F)n2)nn1-c1ncccc1Cl] | 4.23 | 649 | (10.16; 0.47), (8.47; 2.34), (8.47; 2.48), (8.46; 2.53), (8.45; 2.37), (8.15; 2.12), (8.14; 2.09), (8.12; 2.36), (8.12; 2.17), (8.00; 0.63), (7.60; 2.29), (7.59; 2.27), (7.58; 2.18), (7.57; 2.15), (7.44; 2.05), (7.43; 2.11), (7.37; 0.44), (7.31; 2.88), (7.29; 2.45), (7.28; 2.29), (6.09; 7.45), (3.91; 0.68), (3.89; 1.03), (3.87; 1.02), (3.86; 0.96), (3.42; 0.41), (3.40; 0.55), (3.40; 0.60), (3.31; 1153.97), (3.28; 14.03), (2.88; 0.33), (2.68; 0.68), (2.67; 1.20), (2.67; 1.60), (2.66; 1.19), (2.66; 0.62), (2.54; 2.39), (2.52; 7.74), (2.51; 91.19), (2.50; 165.86), (2.50; 213.85), (2.50; 146.99), (2.49; 69.89), (2.44; 0.48), (2.34; 0.64), (2.33; 1.15), (2.33; 1.49), (2.32; 1.10), (2.18; 0.60), (2.15; 11.75), (2.07; 0.69), (1.36; 3.84), (1.04; 0.46), (1.03; 0.54), (1.00; 16.00), (0.98; 15.74), (0.89; 0.43), (0.00; 1.56) |

| No. | Structure | logP | MH+ | NMR |
|---|---|---|---|---|
| 410 | 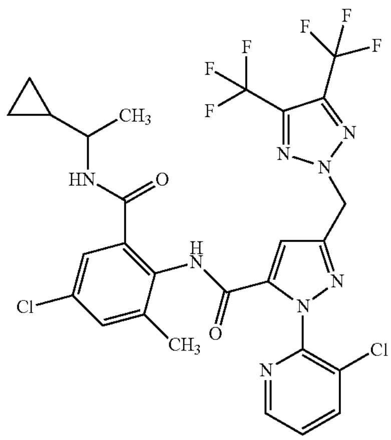 | 4.5 | 675 | (10.16; 1.95), (8.47; 3.20), (8.47; 3.37), (8.46; 3.52), (8.46; 3.22), (8.15; 2.83), (8.14; 2.71), (8.13; 3.20), (8.12; 2.85), (8.06; 1.40), (8.04; 1.40), (7.60; 2.93), (7.59; 2.90), (7.58; 2.77), (7.57; 2.69), (7.45; 2.99), (7.45; 2.95), (7.31; 4.62), (7.28; 3.29), (7.28; 3.07), (6.09; 10.29), (3.56; 0.42), (3.53; 0.47), (3.53; 0.54), (3.50; 0.69), (3.46; 0.87), (3.46; 0.91), (3.43; 1.13), (3.31; 3073.94), (3.28; 44.05), (3.14; 0.46), (3.13; 0.42), (3.11; 0.36), (2.90; 0.52), (2.74; 0.35), (2.67; 3.10), (2.67; 3.92), (2.66; 2.88), (2.63; 0.60), (2.54; 6.41), (2.51; 236.75), (2.50; 421.86), (2.50; 534.13), (2.50; 368.96), (2.49; 176.48), (2.37; 0.34), (2.33; 2.90), (2.33; 3.67), (2.32; 2.64), (2.18; 0.85), (2.15; 16.00), (2.08; 1.33), (2.07; 8.95), (1.36; 4.02), (1.24; 0.51), (1.14; 0.34), (1.12; 0.33), (1.08; 0.37), (1.07; 0.45), (1.04; 9.94), (1.03; 2.47), (1.02; 9.58), (0.82; 0.32), (0.81; 0.64), (0.80; 0.81), (0.79; 1.24), (0.78; 1.00), (0.77; 1.35), (0.76; 0.79), (0.75; 0.54), (0.34; 0.49), (0.33; 0.75), (0.32; 1.33), (0.31; 1.11), (0.31; 1.30), (0.30; 1.39), (0.29; 0.74), (0.28; 0.65), (0.19; 0.45), (0.18; 0.92), (0.16; 1.62), (0.14; 2.27), (0.13; 2.32), (0.12; 1.88), (0.11; 1.78), (0.10; 1.64), (0.09; 1.49), (0.08; 1.20), (0.07; 0.90), (0.07; 0.63), (0.01; 0.72), (0.00; 10.96), (−0.01; 0.50) |
| 411 | 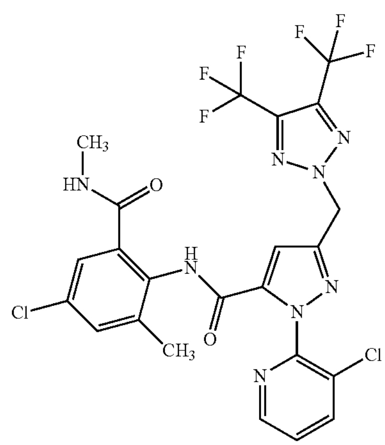 [SMILES: CNC(=O)c1cc(Cl)cc(C)c1NC(=O)c1cc(Cn2nc(C(F)(F)F)c(C(F)(F)F)n2)nn1-c1ncccc1Cl] | 3.78 | 621 | (10.24; 2.27), (8.48; 3.01), (8.48; 3.14), (8.47; 3.24), (8.47; 3.02), (8.21; 1.49), (8.20; 1.49), (8.16; 2.88), (8.15; 2.83), (8.14; 3.23), (8.13; 2.90), (7.60; 3.00), (7.59; 2.95), (7.58; 2.86), (7.57; 2.85), (7.45; 3.06), (7.45; 3.28), (7.32; 8.97), (6.13; 0.37), (6.09; 9.71), (3.69; 0.59), (3.31; 661.06), (3.29; 7.96), (2.86; 0.54), (2.67; 0.82), (2.67; 1.13), (2.66; 1.04), (2.65; 10.15), (2.64; 9.96), (2.58; 0.44), (2.57; 0.51), (2.54; 1.10), (2.52; 3.76), (2.51; 40.55), (2.51; 72.11), (2.50; 91.36), (2.50; 62.99), (2.49; 30.10), (2.33; 0.49), (2.33; 0.64), (2.32; 0.46), (2.15; 16.00), (2.07; 0.93), (1.90; 0.41), (0.00; 2.67) |
| 412 | 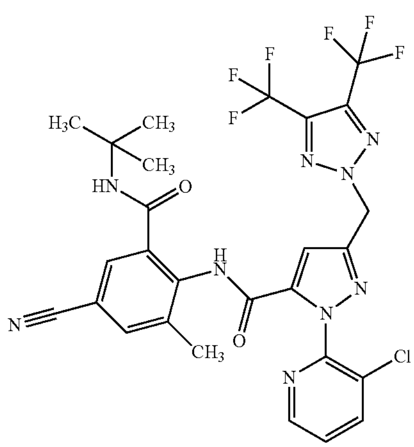 [SMILES: Cc1cc(C#N)cc(C(=O)NC(C)(C)C)c1NC(=O)c1cc(Cn2nc(C(F)(F)F)c(C(F)(F)F)n2)nn1-c1ncccc1Cl] | 4.16 | 654 | (8.48; 0.75), (8.47; 0.79), (8.47; 0.80), (8.46; 0.75), (8.16; 0.59), (8.15; 0.56), (8.14; 0.64), (8.13; 0.59), (7.81; 0.50), (7.69; 0.65), (7.61; 0.63), (7.60; 0.63), (7.59; 0.63), (7.58; 0.61), (7.30; 0.38), (6.10; 2.17), (3.31; 176.15), (2.62; 0.65), (2.54; 0.39), (2.51; 14.53), (2.51; 25.76), (2.50; 32.70), (2.50; 22.51), (2.49; 10.71), (2.19; 2.78), (2.07; 0.33), (1.40; 0.57), (1.36; 1.69), (1.24; 1.08), (1.20; 16.00), (0.00; 0.42) |

| No. | Structure | logP | MH+ | NMR |
|---|---|---|---|---|
| 413 | 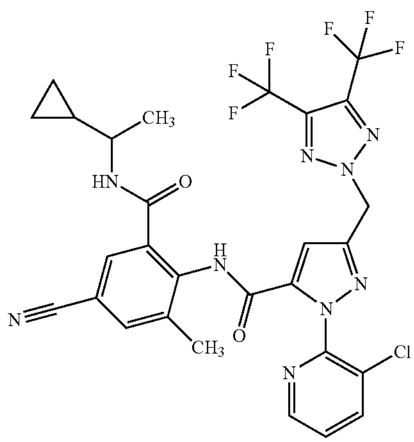 [SMILES: Cc1cc(C#N)cc(C(=O)NC(C)C2CC2)c1NC(=O)c1cc(Cn2nc(C(F)(F)F)c(C(F)(F)F)n2)nn1-c1ncccc1Cl] | 4.11 | 666 | |
| 414 | 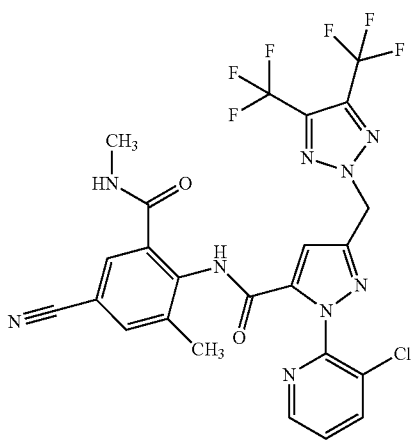 [SMILES: CNC(=O)c1cc(C#N)cc(C)c1NC(=O)c1cc(Cn2nc(C(F)(F)F)c(C(F)(F)F)n2)nn1-c1ncccc1Cl] | 3.43 | 612 | |

Analytical Methods

The determination of the log P values reported in the table below and in the preparation examples was carried out in accordance with EEC Directive 79/831 Annex V.A8 by HPLC (High Performance Liquid Chromatography) on reversed-phase columns (C 18), with the methods below:

Determination by LC-MS in the acidic range takes place at a pH of 2.7 using 0.1% aqueous formic acid and acetonitrile (containing 0.1% formic acid) as eluents, with a linear gradient from 10% acetonitrile to 95% acetonitrile.

Calibration was carried out using unbranched alkan-2-ones (having 3 to 16 carbon atoms) with known log P values (the log P values are determined from the retention times by linear interpolation between two successive alkanones).

The lambda-maX values were determined on the basis of the UV spectra from 200 nm to 400 nm in the maxima of the chromatographic signals.

The MH+ signals were determined using an Agilent MSD system with ESI and positive or negative ionization.

The NMR Spectra Were
a) determined with a Bruker Avance 400, equipped with a flow probe head (60 µl volume). The solvent used was $CD_3CN$ or $d_6$-DMSO, with tetramethylsilane (0.00 ppm) being employed as reference.
b) determined with a Bruker Avance II 600. The solvent used was $CD_3CN$ or $d_6$-DMSO, with tetramethylsilane (0.00 ppm) being employed as reference.

For all of the examples listed in the table above, $d_6$-DMSO was used as solvent, with the exception of Examples 121, 140, 162 and 177, for which $CD_3CN$ was used as solvent for producing the NMR spectra.

USE EXAMPLES

Example 1

*Boophilus Microplus* Test (BOOPMI Injection)

Solvent: dimethyl sulphoxide
An appropriate preparation of active compound is prepared by mixing 10 mg of active compound with 0.5 ml of solvent and diluting the concentrate with solvent to the desired concentration. The solution of active compound is injected into the abdomen (*Boophilus microplus*), and the animals are transferred to dishes and kept in a climatized room. Activity is assessed by deposition of fertile eggs.

After 7 days, the activity in % is assessed. Here, 100% means that none of the ticks has laid fertile eggs.

In this test, for example, the following compounds from the preparation examples exhibit an activity of 100% at an application rate of 20 µg/animal: 7, 70, 124, 128, 129, 134, 135, 136, 147, 151, 155, 162, 172, 174, 175, 218, 231, 232, 239, 241, 247, 263, 281, 282

Example 2

Lucilia Cuprina Test (LUCICU)

Solvent: dimethyl sulphoxide

An appropriate preparation of active compound is prepared by mixing 10 mg of active compound with 0.5 ml of dimethyl sulphoxide and diluting the concentrate with water to the desired concentration.

Vessels containing horse meat treated with the preparation of active compound at the desired concentration are populated with approximately 20 Lucilia cuprina larvae.

After 2 days, the kill in % is ascertained. Here, 100% means that all of the larvae have been killed; 0% means that no larvae have been killed.

In this test, for example, the following compounds from the preparation examples exhibit an activity of 100% at an application rate of 100 ppm: 7, 70, 124, 128, 129, 134, 135, 136, 147, 151, 155, 162, 172, 174, 175, 218, 231, 232, 239, 241, 247, 263, 281, 282

Example 3

Musca Domestica Test (MUSCDO)

Solvent: dimethyl sulphoxide

An appropriate preparation of active compound is prepared by mixing 10 mg of active compound with 0.5 ml of dimethyl sulphoxide and diluting the concentrate with water to the desired concentration. Vessels containing a sponge treated with the preparation of active compound at the desired concentration are populated with adult Musca domestica.

After 2 days, the kill in % is ascertained. Here, 100% means that all of the flies have been killed; 0% means that no flies have been killed.

In this test, for example, the following compounds from the preparation examples exhibit an activity of 100% at an application rate of 100 ppm: 134, 232, 239, 247, 263, 281

In this test, for example, the following compounds from the preparation examples exhibit an activity of 85% at an application rate of 100 ppm: 218

In this test, for example, the following compounds from the preparation examples exhibit an activity of 80% at an application rate of 100 ppm: 124, 128, 129, 172, 231, 241, 282

Example 4

Myzus Test (MYZUPE Spray Treatment)

Solvents: 78 parts by weight of acetone
1.5 parts by weight of dimethylformamide
Emulsifier: 0.5 part by weight of alkylaryl polyglycol ether
An appropriate preparation of active compound is prepared by mixing 1 part by weight of active compound with the stated amounts of solvents and emulsifier and diluting the concentrate with emulsifier-containing water to the desired concentration.

Leaf discs of Chinese cabbage (Brassica pekinensis) infested by all stages of the green peach aphid (Myzus persicae) are sprayed with a preparation of active compound at the desired concentration.

After 6 days, the activity in % is ascertained. Here, 100% means that all of the aphids have been killed; 0% means that no aphids have been killed.

In this test, for example, the following compounds from the preparation examples exhibit an activity of 100% at an application rate of 500 g/ha: 400

In this test, for example, the following compounds from the preparation examples exhibit an activity of 100% at an application rate of 100 g/ha: 5, 7, 9, 11, 12, 21, 70, 101, 121, 124, 125, 126, 128, 129, 130, 132, 134, 137, 143, 144, 146, 151, 155, 156, 157, 165, 166, 170, 172, 174, 177, 178, 182, 187, 192, 193, 194, 196, 201, 203, 212, 213, 217, 220, 222, 223, 225, 231, 238, 239, 241, 273, 281, 288, 289, 294, 303, 304, 305, 306, 307, 308, 313, 316, 317, 318, 319, 320, 321, 324, 325, 326, 327, 328, 329, 331, 332, 337, 338, 340, 341, 342, 343, 344, 353, 359, 363, 364, 365, 368, 372, 373, 381, 384, 387, 414

In this test, for example, the following compounds from the preparation examples exhibit an activity of 90% at an application rate of 100 g/ha: 6, 50, 110, 120, 127, 131, 133, 135, 139, 150, 181, 185, 197, 215, 300, 301, 315, 339, 393, 396, 408

In this test, for example, the following compounds from the preparation examples exhibit an activity of 80% at an application rate of 100 g/ha: 8, 53, 54, 189, 219, 221, 224, 228, 230, 232, 246, 249, 254, 255, 262, 263, 271, 282, 284, 286, 291, 293, 298, 299, 302, 309, 312, 314, 348, 349, 350, 352, 356, 358, 360, 361, 362, 383, 402, 412

In this test, for example, the following compounds from the preparation examples exhibit an activity of 100% at an application rate of 20 g/ha: 123, 180, 184

Example 5

Phaedon Test (PHAECO Spray Treatment)

Solvents: 78.0 parts by weight of acetone
1.5 parts by weight of dimethylformamide
Emulsifier: 0.5 part by weight of alkylaryl polyglycol ether
An appropriate preparation of active compound is prepared by mixing 1 part by weight of active compound with the stated amounts of solvent and emulsifier and diluting the concentrate with emulsifier-containing water to the desired concentration.

Leaf discs of Chinese cabbage (Brassica pekinensis) are sprayed with a preparation of active compound at the desired concentration and, after drying, are populated with larvae of the mustard beetle (Phaedon cochleariae).

After 7 days, the activity in % is ascertained. Here, 100% means that all of the beetle larvae have been killed; 0% means that no beetle larvae have been killed.

In this test, for example, the following compounds in the preparation examples exhibit an activity of 100% at an application rate of 500 g/ha: 180

In this test, for example, the following compounds in the preparation examples exhibit an activity of 100% at an application rate of 100 g/ha: 2, 3, 4, 5, 6, 7, 8, 9, 11, 12, 16, 17, 18, 19, 20, 21, 24, 25, 26, 27, 28, 29, 30, 31, 33, 34, 36, 37, 38, 40, 41, 42, 43, 44, 45, 46, 50, 53, 54, 55, 57, 61, 62, 63, 64, 65, 70, 71, 72, 74, 75, 77, 79, 81, 86, 87, 88, 89, 90, 91, 92, 94, 95, 96, 97, 98, 99, 100, 101, 102, 107, 108, 109, 110, 111, 112, 113, 114, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 172, 174, 175, 176, 177, 178, 182, 183, 184, 185, 186, 187, 189, 190, 192, 193, 194, 195, 196, 197, 198, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414

In this test, for example, the following compounds in the preparation examples exhibit an activity of 83% at an application rate of 100 g/ha: 14, 39

Example 6

*Spodoptera Frugiperda* Test (SPODFR Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration.

Leaf discs of maize (*Zea mays*) are sprayed with a preparation of active compound at the desired concentration and, after drying, are populated with caterpillars of the armyworm (*Spodoptera frugiperda*).

After 7 days, the activity in % is ascertained. Here, 100% means that all of the caterpillars have been killed; 0% means that no caterpillar has been killed.

In this test, for example, the following compounds from the preparation examples exhibit an activity of 100% at an application rate of 100 g/ha: 1, 2, 3, 4, 5, 6, 7, 8, 9, 10, 11, 12, 17, 18, 19, 20, 21, 22, 24, 25, 26, 27, 28, 32, 33, 34, 35, 36, 40, 41, 42, 43, 44, 45, 53, 54, 55, 58, 61, 62, 63, 64, 65, 66, 67, 68, 69, 70, 71, 72, 74, 75, 77, 78, 79, 80, 81, 82, 83, 84, 86, 87, 88, 89, 90, 91, 92, 94, 95, 96, 97, 98, 99, 100, 101, 102, 103, 106, 107, 108, 109, 110, 111, 112, 113, 114, 115, 117, 118, 119, 120, 121, 122, 123, 124, 125, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 165, 166, 167, 168, 169, 170, 171, 172, 174, 175, 176, 177, 178, 180, 181, 182, 183, 184, 185, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 221, 222, 224, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 273, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414

In this test, for example, the following compounds from the preparation examples exhibit an activity of 83% at an application rate of 100 g/ha: 16, 23, 50, 56, 57, 126

In this test, for example, the following compounds from the preparation examples exhibit an activity of 100% at an application rate of 20 g/ha: 220, 223, 225, 226, 270, 271, 272, 274

Example 7

*Tetranychus* Test, OP-Resistant (TETRUR Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvent and emulsifier and diluting the concentrate with emulsifier-containing water to the desired concentration. Leaf discs of French bean (*Phaseolus vulgaris*) infested by all stages of the two-spotted spider mite (*Tetranychus urticae*) are sprayed with a preparation of active compound at the desired concentration.

After 6 days, the activity in % is ascertained. Here, 100% means that all of the spider mites have been killed; 0% means that no spider mites have been killed.

In this test, for example, the following compounds from the preparation examples exhibit an activity of 90% at an application rate of 100 g/ha: 39, 321, 375

In this test, for example, the following compounds from the preparation examples exhibit an activity of 80% at an application rate of 100 g/ha: 50

Example 8

*Myzus* Test (MYZUPE Spray Treatment)

Solvents: 78.0 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvents and emulsifier and diluting the concentrate with emulsifier-containing water to the desired concentration.

Leaf discs of Chinese cabbage (*Brassica pekinensis*) infested by all stages of the green peach aphid (*Myzus persicae*) are sprayed with a preparation of active compound at the desired concentration. After the desired time, the activity in % is ascertained. Here, 100% means that all of the aphids have been killed; 0% means that no aphids have been killed.

In this test, for example, the following compounds from the preparation examples exhibit superior activity over the prior art: see table

| Substance | Structure | Subject | Concentration | % Activity |
|---|---|---|---|---|
| according to the invention | 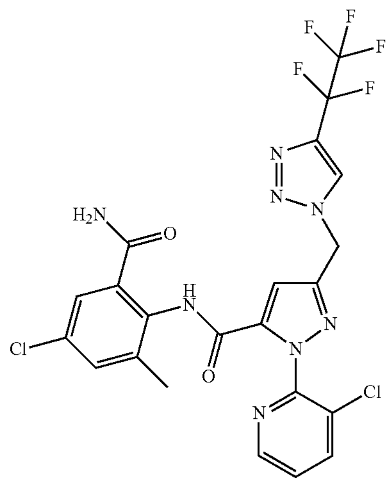 [SMILES: Cc1cc(Cl)cc(C(N)=O)c1NC(=O)c1cc(Cn2cc(C(F)(F)C(F)(F)F)nn2)nn1-c1ncccc1Cl] | MYZUPE | 100 g/ha | 100 6 d |
| known (WO 2007/144100) | 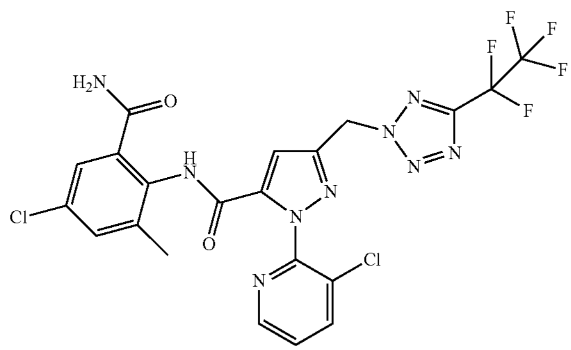 [SMILES: Cc1cc(Cl)cc(C(N)=O)c1NC(=O)c1cc(Cn2nnc(C(F)(F)C(F)(F)F)n2)nn1-c1ncccc1Cl] | MYZUPE | 100 g/ha | 80 6 d |

The invention claimed is:
1. An anthranilamide of formula (I),

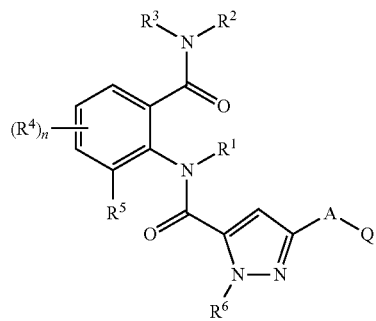

in which
R$^1$ is hydrogen, amino or hydroxyl or is C$_1$-C$_6$-alkyl, C$_2$-C$_6$-alkenyl, C$_2$-C$_6$-alkynyl or C$_3$-C$_6$-cycloalkyl each optionally substituted one or more times by identical or different substituents, the substituents being selectable independently of one another from halogen, cyano, nitro, hydroxyl, C$_1$-C$_4$-alkoxy, C$_1$-C$_4$-alkylthio, C$_1$-C$_4$-alkylsulphinyl, C$_1$-C$_4$-alkyl-sulphonyl, (C$_1$-C$_4$-alkoxy)carbonyl, C$_1$-C$_4$-alkylamino, di(C$_1$-C$_4$-alkyl)amino, C$_3$-C$_6$-cycloalkylamino or (C$_1$-C$_4$-alkyl)C$_3$-C$_6$-cycloalkylamino, R$^2$ is hydrogen, C$_1$-C$_6$-alkyl, C$_2$-C$_6$-alkenyl, C$_2$-C$_6$-alkynyl, C$_3$-C$_6$-cycloalkyl, C$_1$-C$_4$-alkoxy, C$_1$-C$_4$-alkylamino, di(C$_1$-C$_4$-alkyl)amino, C$_3$-C$_6$-cycloalkylamino, C$_2$-C$_6$-alkoxycarbonyl or C$_2$-C$_6$-alkylcarbonyl, R$^3$ is hydrogen or is C$_1$-C$_6$-alkyl, C$_1$-C$_6$-alkoxy, C$_2$-C$_6$-alkenyl or C$_2$-C$_6$-alkynyl each optionally substituted one or more times by identical or different substituents, the substituents being selectable independently of one another from halogen, cyano, nitro, hydroxyl, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-alkylsulphimino, C$_1$-C$_4$-alkylsulphimino-C$_1$-C$_4$-alkyl, C$_1$-C$_4$-alkylsulphimino-C$_2$-C$_5$-alkylcarbonyl, C$_1$-C$_4$-alkylsulphoximino, C$_1$-C$_4$-alkylsulphoximino-C$_1$-C$_4$-alkyl, C$_1$-C$_4$-alkylsulphoximino-C$_2$-C$_5$-alkylcarbonyl, C$_2$-C$_6$-alkoxycarbonyl, C$_2$-C$_6$-alkylcarbonyl or C$_3$-C$_6$-trialkylsilyl, or R$^3$ is C$_1$-C$_6$-alkyl, C$_1$-C$_6$-alkoxy, C$_2$-C$_6$-alkenyl, C$_2$-C$_6$-alkynyl each substituted one or more times by identical or different substituents, the substituents being selectable independently of one another from amino, C$_3$-C$_6$-cycloalkylamino or a 5- or 6-membered heteroaromatic ring, or R$^3$ is C$_3$-C$_{12}$-cycloalkyl, C$_3$-C$_{12}$-cycloalkyl-C$_1$-C$_6$-alkyl and C$_4$-C$_{12}$-bicycloalkyl, the substituents being selectable independently of one another from halogen, cyano, nitro, hydroxyl, amino, C$_1$-C$_6$-alkyl, C$_3$-C$_6$-cycloalkyl, C$_3$-C$_6$-cycloalkylamino, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$- alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, or $R^2$ and $R^3$ may be joined to one another via two to six carbon atoms and form a ring which optionally further comprises another nitrogen, sulphur or oxygen atom and may optionally be substituted one to four times by $C_1$-$C_2$-alkyl, halogen, cyano, amino or $C_1$-$C_2$-alkoxy, or $R^2$, $R^3$ together are $=S(C_1$-$C_4$-alkyl$)_2$, or $=S(O)(C_1$-$C_4$-alkyl$)_2$, $R^4$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two radicals $R^4$ form, via adjacent carbon atoms, a ring which is $-(CH_2)_3-$, $-(CH_2)_4-$, $-(CH_2)_5-$, $-(CH=CH-)_2-$, $-OCH_2O-$, $-O(CH_2)_2O-$, $-OCF_2O-$, $-(CF_2)_2O-$, $-O(CF_2)_2O-$, $-(CH=CH-CH=N)-$ or $-(CH=CH-N=CH)-$, or two radicals $R^4$, via adjacent carbon atoms, form one of the fused-on rings below, which are optionally substituted one or more times by identical or different substituents, the substituents being selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

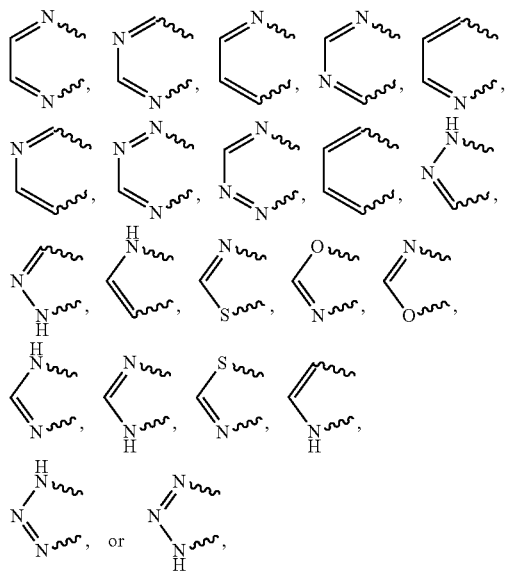

n is 0 to 3, $R^5$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

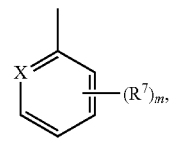

or $R^6$ is $C_3$-$C_6$-cycloalkoxy, $R^7$ independently at each occurrence is hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m is 0 to 4, X is N, CH, CF, CCl, CBr or CI, A is $-CH_2-$, $-CH_2O-$, $-CH_2OCH_2-$, $-CH_2S-$, $-CH_2SCH_2-$, $-CH_2N(C_1$-$C_6$-alkyl)-, $-CH_2N(C_1$-$C_6$-alkyl)$CH_2-$, $-CH[CO_2(C_1$-$C_6$-alkyl)]-, $-CH(CN)-$, $-CH(C_1$-$C_6$-alkyl)-, $-C(di$-$C_1$-$C_6$-alkyl)-, $-CH_2CH_2-$, or $-C=NO(C_1$-$C_6$-alkyl)-, Q is a triazole ring or an aromatic 9-membered fused-on heterobicyclic ring system, system comprising three nitrogens, the nitrogens in the triazole ring or ring system occupying adjacent positions; the ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, or where the substituents are selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents or an N-oxide or a salt of a compound of formula (I).

2. An anthranilamide or N-oxide or salt according to claim 1, in which $R^1$ is hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$- alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl, $R^2$ is hydrogen or $C_1$-$C_6$-alkyl, $R^3$ is hydrogen or is $C_1$-$C_6$-alkyl, $C_1$-$C_6$-alkoxy, $C_2$-$C_6$-alkenyl or $C_2$-$C_6$-alkynyl each optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, or $R^3$ is $C_3$-$C_{12}$-cycloalkyl and $C_4$-$C_{10}$-bicycloalkyl, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^4$ is hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio, or two adjacent radicals $R^4$ are —$(CH_2)_3$—, —$(CH_2)_4$—, —$(CH_2)_5$—, —$(CH=CH—)_2$—, —$OCH_2O$—, —$O(CH_2)_2O$—, —$OCF_2O$—, —$(CF_2)_2O$—, —$O(CF_2)_2$O—, —$(CH=CH—CH=N)$— or —$(CH=CH—N=CH)$—, n is 1, 2 or 3, $R^5$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ is $C_1$-$C_6$-alkyl or

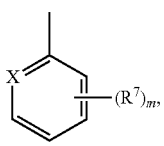

or $R^6$ is $C_3$-$C_6$-cycloalkoxy, $R^7$ independently at each occurrence is hydrogen, halogen, cyano, $C_1$-$C_4$-alkyl, $C_1$-$C_4$-alkoxy, $C_1$-$C_4$-haloalkyl or $C_1$-$C_4$-haloalkoxy, m is 1, 2 or 3, X is N, CH, CF, CCl, CBr or CI, A is —$CH_2$—, —$CH_2O$—, —$CH_2OCH_2$—, —$CH_2S$—, —$CH_2SCH_2$—, —$CH_2N(C_1$-$C_6$-alkyl)-, —$CH_2N(C_1$-$C_6$-alkyl)CH_2$—, —$CH(CN)$—, —$CH(C_1$-$C_6$-alkyl)-, —$C(di$-$C_1$-$C_6$-alkyl)-, —$CH_2CH_2$—, or —$C=NO(C_1$-$C_6$-alkyl)-, Q is a triazole ring or an aromatic 9-membered fused-on heterobicyclic ring system, system comprising three nitrogens and the nitrogens in the triazole ring or ring system occupying adjacent positions, and the bond of the ring or ring system to the radical A in formula (I) being either via nitrogen or carbon; the ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, or where the substituents may be selected independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy and/or $C_1$-$C_4$-haloalkoxy substituents.

3. An anthranilamide or N-oxide or salt according to claim 1, in which $R^1$ is hydrogen, methyl, cyclopropyl, cyanomethyl, methoxymethyl, methylthiomethyl, methylsulphinylmethyl or methylsulphonylmethyl, $R^2$ is hydrogen or methyl, $R^3$ is hydrogen or is $C_1$-$C_6$-alkyl or $C_1$-$C_6$-alkoxy each optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, or $R^3$ is $C_3$-$C_6$-cycloalkyl optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^4$ is hydrogen, $C_1$-$C_4$-alkyl, $C_1$-$C_2$-haloalkyl, halogen, cyano or $C_1$-$C_2$-haloalkoxy, or two adjacent radicals $R^4$ are —(CH$_2$)$_4$—, —(CH=CH—)$_2$—, —O(CH$_2$)$_2$O—, —O(CF$_2$)$_2$O—, —(CH=CH—CH=N)— or —(CH=CH—N=CH)—, n is 1 or 2, $R^5$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^6$ is methyl or

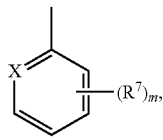

$R^7$ independently at each occurrence is hydrogen, halogen or $C_1$-$C_4$-haloalkyl, m is 1 or 2, X is N, CH, CF, CCl or CBr, A is —CH$_2$—, —CH(CH$_3$), C(CH$_3$)$_2$ or CH$_2$CH$_2$, or A is —CH(CN)—, Q is a triazole ring or an aromatic 9-membered fused-on heterobicyclic ring system, the ring or the ring system comprising three nitrogens and the nitrogens in the triazole ring or ring system occupying adjacent positions, and the bond of the ring or ring system to the radical A in formula (I) being via nitrogen; the ring or the ring system are optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, CO$_2$H, CO$_2$NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, or where the substituents may be selected independently of one another from phenyl or a 5- or 6-membered heteroaromatic ring, where phenyl or the ring may be optionally substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, NO$_2$, OH, $C_1$-$C_4$-alkoxy and/or $C_1$-$C_4$-haloalkoxy substituents.

4. The anthranilamide or N-oxide or salt according to claim 1, in which $R^1$ is H, $R^2$ is H, $R^3$ is isopropyl, $R^4$ is cyano, n is 1, $R^5$ is methyl, $R^6$ is

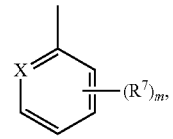

$R^7$ is Br,

X is N, m is 1,

A is —CH$_2$—, and

Q is

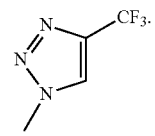

5. A mixture of compounds according to claim 1, the ring or the ring system Q being bonded to the radical (A) in each case via different carbon atoms or nitrogen atoms.

6. An agrochemical composition comprising at least one compound according to claim 1, and at least one extender and/or surfactant.

7. A composition according to claim 6 for controlling animal pests.

8. A composition comprising at least one compound according to claim 1, and at least one salt of formula (XI)

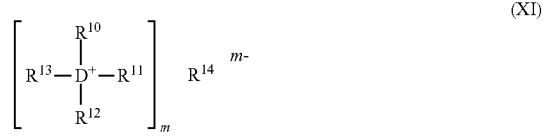

in which

D is nitrogen or phosphorus, $R^{10}$, $R^{11}$, $R^{12}$ and $R^{13}$ independently of one another are hydrogen or each optionally substituted $C_1$-$C_8$-alkyl or singly or multiply unsaturated, optionally substituted $C_1$-$C_8$-alkylene, the substituents being selectable from halogen, nitro and cyano, m is 1, 2, 3 or 4, $R^{14}$ is an inorganic or organic anion.

9. A composition comprising at least one compound according to claim 1, and at least one penetrant of formula (XII)

in which

R is straight-chain or branched alkyl having 4 to 20 carbon atoms,

R' is hydrogen, methyl, ethyl, n-propyl, isopropyl, n-butyl, isobutyl, tert-butyl, n-pentyl or n-hexyl, AO is an ethylene oxide radical, a propylene oxide radical, or a butylene oxide radical or is mixtures of ethylene oxide and propylene oxide radicals or butylene oxide radicals, and V is a number from 2 to 30.

10. A process for preparing a compound according to claim 1 comprising reacting:

(A) anilines of the formula (II)

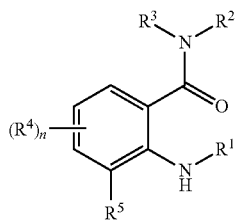
(II)

with carbonyl chlorides of the formula (III)

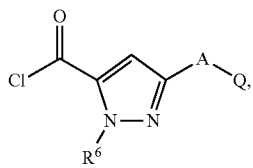
(III)

in the presence of an acid-binding agent, (B) anilines of the formula (II)

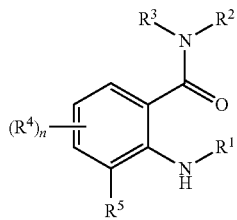
(II)

with a carboxylic acid of the formula (IV)

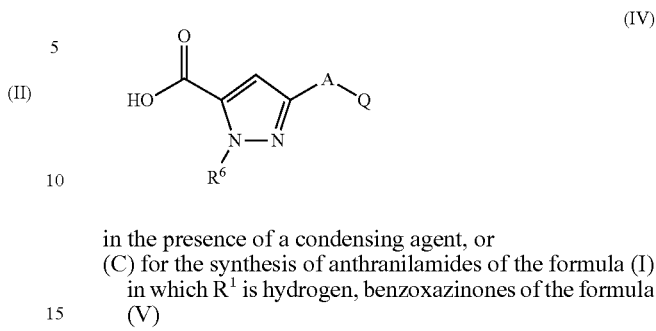
(IV)

in the presence of a condensing agent, or (C) for the synthesis of anthranilamides of the formula (I) in which $R^1$ is hydrogen, benzoxazinones of the formula (V)

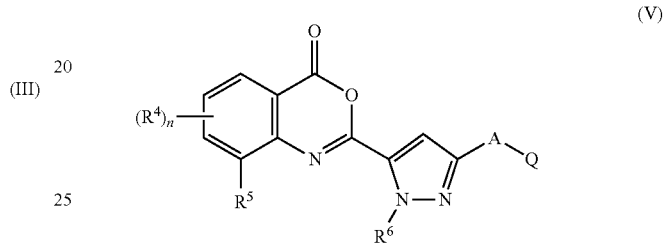
(V)

with an amine of the formula (VI)

(VI)

in the presence of a diluent.

11. A process for preparing an agrochemical composition, comprising mixing at least one compound according to claim 1 with at least one extender and/or surfactant.

12. A method for controlling animal pests, comprising causing a compound according to claim 1, to act on an animal pest and/or phytopathogenic fungi and/or their habitat and/or a seed.

\* \* \* \* \*